US011945832B2

(12) United States Patent
Clark

(10) Patent No.: US 11,945,832 B2
(45) Date of Patent: Apr. 2, 2024

(54) PSILOCYBIN AND O-ACETYLPSILOCIN, SALTS AND SOLID STATE FORMS THEREOF

(71) Applicant: Terran Biosciences Inc., New York, NY (US)

(72) Inventor: Samuel Clark, New York, NY (US)

( * ) Notice: Subject to any disclaimer, the term of this patent is extended or adjusted under 35 U.S.C. 154(b) by 0 days.

(21) Appl. No.: 18/468,583

(22) Filed: Sep. 15, 2023

(65) Prior Publication Data

US 2024/0010663 A1 Jan. 11, 2024

Related U.S. Application Data

(63) Continuation of application No. 18/147,066, filed on Dec. 28, 2022, which is a continuation of application No. PCT/US2022/079752, filed on Nov. 11, 2022.

(60) Provisional application No. 63/357,378, filed on Jun. 30, 2022, provisional application No. 63/357,512, filed on Jun. 30, 2022, provisional application No. 63/326,421, filed on Apr. 1, 2022, provisional application No. 63/326,713, filed on Apr. 1, 2022, provisional application No. 63/326,522, filed on Apr. 1, 2022, provisional application No. 63/326,364, filed on Apr. 1, 2022, provisional application No. 63/324,878, filed on Mar. 29, 2022, provisional application No. 63/321,593, filed on Mar. 18, 2022, provisional application No. 63/319,746, filed on Mar. 14, 2022, provisional application No. 63/316,952, filed on Mar. 4, 2022, provisional application No. 63/315,901, filed on Mar. 2, 2022, provisional application No. 63/311,878, filed on Feb. 18, 2022, provisional application No. 63/310,987, filed on Feb. 16, 2022, provisional application No. 63/310,984, filed on Feb. 16, 2022, provisional application No. 63/305,642, filed on Feb. 1, 2022, provisional application No. 63/305,643, filed on Feb. 1, 2022, provisional application No. 63/300,961, filed on Jan. 19, 2022, provisional application No. 63/300,957, filed on Jan. 19, 2022, provisional application No. 63/285,050, filed on Dec. 1, 2021, provisional application No. 63/280,294, filed on Nov. 17, 2021, provisional application No. 63/280,300, filed on Nov. 17, 2021, provisional application No. 63/279,005, filed on Nov. 12, 2021, provisional application No. 63/278,943, filed on Nov. 12, 2021.

(51) Int. Cl.
*C07F 9/572* (2006.01)

(52) U.S. Cl.
CPC ........ *C07F 9/5728* (2013.01); *C07B 2200/13* (2013.01)

(58) Field of Classification Search
CPC .......................... C07F 9/5728; C07B 2200/13
See application file for complete search history.

(56) References Cited

U.S. PATENT DOCUMENTS

| 3,075,992 | A | 1/1963 | Hofmann et al. |
| 3,182,071 | A | 5/1965 | Shavel, Jr. et al. |
| 11,723,894 | B2 | 8/2023 | Perez Castillo et al. |
| 2012/0289515 | A1 | 11/2012 | Migaly |
| 2014/0350064 | A1 | 11/2014 | Chen |
| 2015/0231126 | A1 | 8/2015 | Peters et al. |
| 2017/0281652 | A1 | 10/2017 | Altschul et al. |
| 2019/0105313 | A1 | 4/2019 | Stamets |
| 2019/0119310 | A1 | 4/2019 | Londesbrough et al. |
| 2019/0142851 | A1 | 5/2019 | Chadeayne |
| 2019/0350949 | A1 | 11/2019 | Kucuksen et al. |
| 2020/0179349 | A1 | 6/2020 | Yun et al. |
| 2021/0292278 | A1 | 9/2021 | Chadeayne |
| 2021/0403425 | A1 | 12/2021 | Bryson |
| 2022/0273680 | A1 | 9/2022 | Scott |
| 2023/0000885 | A1 | 1/2023 | Thompson |
| 2023/0151036 | A1 | 5/2023 | Duncton et al. |

FOREIGN PATENT DOCUMENTS

| GB | 941707 A | 11/1963 |
| WO | WO-2018135943 A1 | 7/2018 |
| WO | WO-2019081764 A1 | 5/2019 |
| WO | WO-2020157569 A1 | 8/2020 |
| WO | WO-2020212948 A1 | 10/2020 |
| WO | WO-2020212951 A1 | 10/2020 |
| WO | WO-2020212952 A1 | 10/2020 |
| WO | WO-2021030571 A1 | 2/2021 |
| WO | WO-2022212854 A1 | 10/2022 |
| WO | WO-2023023347 A1 | 2/2023 |
| WO | WO-2023043794 A1 | 3/2023 |

OTHER PUBLICATIONS

Al-Muhammed et al. In-vivo studies on dexamethasone sodium phosphate liposomes. J Microencapsul. 13(3):293-306 (1996).
Arnt et al. Facilitation of 8-OHDPAT-induced forepaw treading of rats by the 5-HT2 agonist DOI. Eur. J. Pharmacol., 161:45 (1989).
Balbach, et al. Pharmaceutical evaluation of early development candidates "the 100 mg-approach". Int J Pharm. 275(1-2):1-12 (2004).
Barrett et al. Emotions and brain function are altered up to one month after a single high dose of psilocybin. Sci. Rep. 10:2214 (2020).
Bartolucci et al., Observations concerning the synthesis of tryptamine homologues and branched tryptamine derivatives via the borrowing hydrogen process: synthesis of psilocin, bufotenin, and serotonin. Tetrahedron 72:2233-2238 (2016).

(Continued)

*Primary Examiner* — John M Mauro
(74) *Attorney, Agent, or Firm* — COOLEY LLP; Ivor R. Elrifi; Eric A. Owens

(57) ABSTRACT

Disclosed herein are salts and solid-state forms of psilocybin, including psilocybin HCl, and salts and solid forms of O-acetylpsilocin, including O-acetylpsilocin fumarate. Also disclosed are methods for making the salts and solid forms and methods for administering the salts and solid forms. The salts and solid forms disclosed herein are useful for treating neurological disease and/or a psychiatric disorder in a subject.

18 Claims, 90 Drawing Sheets

(56) References Cited

OTHER PUBLICATIONS

Beaton et al., A comparison of the behavioral effects of proteo- and deutero-N, N-dimethyltryptamine. Pharmacol Biochem Behav. 16(5):811-4 (1982).
Belmaker et al. Major depressive disorder. N Engl J Med 358:55-68 (2008).
Berge et al. Pharmaceutical Salts. Journal of Pharmaceutical Sciences 66(1):1-19 (Jan. 1977).
Billings et al. Social-environmental factors in unipolar depression; comparisons of depressed patients and nondepressed controls. J Abnormal Psychol 92:119-133 (1983).
Boldrini et al., Antidepressants increase neural progenitor cells in the human hippocampus. Neuropsychopharmacology. 34(11):2376-89 (2009).
Boulenguez et al. Modulation of dopamine release in the nucleus accumbens by 5-HT1E1 agonists: involvement of the hippocampo-accumbens pathway. Neuropharmacology 35:1521-1529 (1996).
Brandt et al., Characterization of the synthesis of N, N-dimethyltryptamine by reductive amination using gas chromatography ion trap mass spectrometry. Drug Test Anal 2(7):330-338 (2010).
Brun et al. Place cells and place recognition maintained by direct entorhinal-hippocampal circuitry. Science 296:2243-2246 (2002).
Bryson et al., Performed Mannich salts: a facile preparation of dimethyl(methylene)ammonium iodide. J Org Chem 45:524-525 (1980).
Bundgaard et al. Pro-drugs as drug delivery systems XIX. Bioreversiblf derivatization of aromatic amines by formation of N-Mannich bases with succinimide. Int'l J Pharm 8(3):183-192 (1981).
Burgdorf et al. Extinction of contextual cocaine memories requires $Ca(v)1.2$ within D1R-expressing cells and recruits hippocampal $Ca(v)1,2$-dependent signaling mechanisms. J Neurosci 37:11894-11911 (2017).
Burmeister et al. Differential roles of 5-HT receptor subtypes in cue and cocaine reinstatement of cocaine-seeking behavior in rats. Neuropsychopharmacology 29:660-668 (2004).
Cai et al. Local potentiation of excitatory synapses by serotonin and its alteration in rodent models of depression. Nat Neurosci 16:464-472 (2013).
Caira. Crystalline Polymorphism of Organic Compounds. Topics in Current Chemistry. 198:163-208 (Jan. 1998).
Canal et al. Head-twitch response in rodents induced by the hallucinogen 2,5-dimethoxy-4-iodoamphetamine: a comprehensive history, a re-evaluation of mechanisms, and its utility as a model. Drug Test Anal., 4:556-576 (2012).
Canel et al. Support for 5-HT2C receptor functional selectivity in vivo utilizing structurally diverse, selective 5-HT2C receptor ligands and the 2,5-dimethoxy-4-iodoamphetamine elicited head-twitch response model. Neuropharmacol 70:112-121 (2013).
Carhart-Harris et al. Psilocybin for treatment-resistant depression: fMRI-measured brain mechanisms. Sci. Rep. 7:13187 (2017).
Carhart-Harris et al.: Psilocybin with psychological support for treatment-resistant depression: an open-label feasibility study. Lancet Psychiatry 3: 619-627. Published Online May 17, 2016 (2016).
Carhart-Harris et al.: Psilocybin with psychological support for treatment-resistant depression: six-month follow-up. Psychopharmacology (Berl). 235(2):399-408 doi:10.1007/s00213-017-4771-x (2018).
Carr et al. The role of serotonin receptor subtypes in treating depression: a review of animal studies, Psychopharmacology (Berl.) 213:265-287 (2011).
Catlow et al. Effects of psilocybin on hippocampal neurogenesis and extinction of trace fear conditioning. Exper Brain Res 228(4):481-491 (2013).
Chan et al. Strained in Planning Your Mouse Background? Using the HPA Stress Axis as a Biological Readout for Backcrossing Strategies. Neuropsychopharmacology 42:1749-1751 (2017).
Chen et al., Antidepressant administration modulates neural stem cell survival and serotoninergic differentiation through bcl-2. Curr. Neurovasc. Res. 4(1):19-29 (2007).
Chonn et al. Recent advances in liposomal drug-delivery systems. Curr Opin Biotechnol. 6(6):698-708 (1995).
Compass Pathways. Compass Pathways Receives FDA Breakthrough Therapy Designation for Psilocybin Therapy for Treatment-resistant Depression. Available at https://www.prnewswire.com/news-releases/compass-pathways-receives-fda-breakthrough-therapy-designation-for-psilocybin-therapy-for-treatment-resistant-depression-834088100.html (Oct. 23, 2018).
Co-pending U.S. Appl. No. 17/945,865, inventor Clark; Sam, filed Sep. 15, 2022.
Cozzi et al. Receptor binding profiles and quantitative structure-affinity relationships of some 5-substituted-N,N-diallyltryptamines. Bioorg Med Chem Lett. 26(3):959-964 (2016).
Darmani et al., Do functional relationships exist between 5-HT1A and 5-HT2 receptors?. Pharmacol. Biochem. Behav., 36:901-606 (1990).
Di Vona et al., Ring-opening reactions. Part 4. The role of strain and stereochemical effects on the elimination and substitution reactions of small rings; the reactivity of 1, 1-dimethylaziridinium systems. Journal of The Chemical Society, Perkin Transactions II 12:1943-1946 (1980).
Dinis-Oliveira. Metabolism of psilocybin and psilocin: clinical and forensic toxicological relevance. Drug Metab. Rev., 49(1):84-91 (2017).
Dolen et al. Social reward requires coordinated activity of nucleus accumbens oxytocin and serotonin. Nature 501:179-184 (2013).
Drysdale et al. Resting-state connectivity biomarkers define neurophysiological subtypes of depression. Nature Med 23:28-38 (2017).
Duman et al. Altered connectivity in depression: GABA and glutamate neurotransmitter deficits and reversal by novel treatments. Neuron 102:75-90 (2019).
Engel et al. Identity of inhibitory presynaptic 5-hydroxytryptamine (5-1-IT) autoreceptors in the rat brain cortex with 5-HT1B binding sites Naunyn Schmiedebergs Arch Pharmacol 332:1-7 (1986).
Evans et al. Default mode connectivity in major depressive disorder measured up to 10 days after ketamine administration. Biol Psychiatry 84:582-590 (2018).
Eyles et al. Oral delivery and fate of poly(lactic acid) microsphere-encapsulated interferon in rats. J Pharm Pharmacol. 49(7):669-74 (1997).
Fava et al. Major depressive disorder. Neuron 28:335-341 (2000).
Fontanilla et al., The hallucinogen N,N-dimethyltryptamine (DMT) is an endogenous sigma-1 receptor regulator. Science 323(5916):934-7 (2009).
Frecksa et al., The Therapeutic Potentials of Ayahuasca: Possible Effects against Various Diseases of Civilization. Front. Pharmacol. 7:35 (2016).
Fricke et al., Production Options for Psilocybin: Making of the Magic. Chemistry 25:897-903 (2019).
Furay et al. 5-HT1B mRNA expression after chronic social stress. Behav Brain Res 224:350-357 (2011).
Gabriel. Risperidone, quetiapine, and olanzapine adjunctive treatments in major depression with psychotic features: a comparative study. Neuropsychiatr Dis Treat 9:485-492 (2013).
Gage. Mammalian neural stem cells. Science 287(5457):1433-8 (2000).
Gao et al.: Controlled release of a contraceptive steroid from biodegradable and injectable gel formulations: in vitro evaluation. Pharm Res. 12(6):857-863 (1995).
Gatch et al., Discriminative stimulus effects of substituted tryptamines in rats. ACS Pharmacology & Translational Science 4(2):467-471 (2021).
Gaynes et al. What did STAR*D teach US? Results from a large-scale, practical, clinical trial for patients with depression. Psychiart Serv. 60:1439-1445 (2009).
Gerfen et al. D1 and D2 dopamine receptor-regulated gene expression of striatonigral and striatopallidal neurons. Science 250(4986):1429-1432 (1990).
Gothert et al. Classification of serotonin receptors. J Cardiovasc Pharmacol 10 Suppl 3:S3-S7 (1987).
Halberstadt et al., Behavioral effects of $\alpha,\alpha$, $\beta,\beta$-tetradeutero-5-MeO-DMT in rats: comparison with 5-MeO-DMT administered in

(56) References Cited

OTHER PUBLICATIONS combination with a monoamine oxidase inhibitor. Psychopharmacology (Berl) 221(4):709-18 (2012).
Halberstadt et al. Multiple receptors contribute to the behavioral effects of indoleamine hallucinogens. Neuropharmacol 61:364-381 (2011).
Hall et al., Hydrogen-Borrowing Alkylation of 1,2-Amino Alcohols in the Synthesis of Enantioenriched γ-Aminobutyric Acids. Angew. Chem. Int. Ed., 60:6981-6985 (2021).
Hamet et al. Genetics and genomics of depression. Metabolism 54:10-15 (2005).
Hasler et al.: Determination of psilocin and 4-hydroxyindole-3-acetic acid in plasma by HPLC-ECD and pharmacokinetic profiles of oral and intravenous psilocybin in man. Pharm Acta Helv. 72(3):175-184 (1997).
Hayashi et al. Sigma-1 receptor chaperones at the ER-mitochondrion interface regulate Ca(2+) signaling and cell survival. Cell 131(3):596-610 (2007).
Heneka et al., Neuroinflammation in Alzheimer's Disease. Lancet Neural., 14(4):388-405 (2015).
Herrera-Arozamena et al., Recent Advances in Neurogenic Small Molecules as Innovative Treatments for Neurodegenerative Diseases. Molecules 21(9):1165 (2016).
Hibicke et al. Psychedelics, but Not Ketamine, Produce Persistent Antidepressant-like Effects in a Rodent Experimental System for the Study of Depression. ACS Chem Neurosci. 11(6):864-871 (2020).
Hofmann et al., Psilocybin und Psilocin, zwei psychotrope Wirkstoffe aus mexikanischen Rauschpilzen. Helvetica Chimica Acta 42(5):1557-72 (1959).
Hoyer et al. International Union of Pharmacology classification of receptors for 5-hydroxytryptamine (Serotonin). Pharmacol Rev 46:157-203 (1994).
Hubschle et al. ShelXle: a Qt graphical user interface for ShelX1. J. Appl. Cryst., 44:1281-1284 (2011).
Jefsen et al. Psilocybin lacks antidepressant-like effect in the Flinders Sensitive Line rat. Acta Neuropsychiatr. 31:213-219 (2019).
Johnson et al. The abuse potential of medical psilocybin according to the 8 factors of the Controlled Substances Act. Neuropharmacology 142:143-166 (2018).
Kallarackal et al. Chronic stress induces a selective decrease in AIVIPA receptor-mediated synaptic excitation at hippocampal temporoammonic-CA1 synapses. Neurosci 33:15669-15674 (2013).
Kargbo et al., Direct Phosphorylation of Psilocin Enables Optimized cGMP Kilogram-Scale Manufacture of Psilocybin. ACS Omega, 5:16959-16966 (2020).
Keller et al. Permanent alteration of behavior in mice by chemical and psychological means. Science 124:723 (1956).
Kennett et al., In vivo properties of SB 200646A, a 5-HT2C/2B receptor antagonist. J. Pharmacol., 111:797-802 (1994).
Kessler et al. Lifetime prevalence and age-of-onset distributions of DSM-IV disorders in the National Comorbidity Survey Replication. Arch Gen Psychiatry 62:593-602 (2005).
Kessler, et al. The epidemiology of major depressive disorder: results from the National Comorbidity Survey Replication (NCS-R). JAMA. Jun. 18, 2003;289(23):3095-105.
Kometer et al. Psilocybin Biases Facial Recognition, Goal-Directed Behavior, and Mood State Toward Positive Relative to Negative Emotions Through Different Serotonergic Subreceptors. Biol Psych 72(11):898-906 (2012).
Krause et al., Comparison of silver and molybdenum microfocus X-ray sources for single-crystal structure determination. J. Appl. Cryst. 48:3-10 (2015).
Lee et al. Specific roles of AMPA receptor subunit GluR1 (GluAl) phosphorylation sites in regulating synaptic plasticity in the CA1 region of hippocampus. J Neurephysiol 103:479-489 (2010).
Legates et al. Reward behaviour is regulated by the strength of hippocampus-nucleus accumbens synapses. Nature 564:258-262 (2018).
Legates et al. Sex differences in antidepressant efficacy. Neuropsychopharmacol 44:140-154 (2019).
Li et al. Synaptic potentiation onto habenula neurons in the learned helplessness model of depression. Nature 470:535-539 (2011).
Lim et al. Anhedonia requires MC4R-mediated synaptic adaptations in nucleus act umbens. Nature 87:183-189 (2012).
Ly et al., Psychedelics promote structural and functional neural plasticity. Cell Rep. 23(11):3170-3182 (2018).
Madsen et al.: Psychedelic effects of psilocybin correlate with serotonin 2A receptor occupancy and plasma psilocin levels. Neuropsychopharmacology 44(7):1328-1334 (2019).
Mathur et al. Serotonin induces long-term depression at corticostriatal synapses. J Neurosci 31:7402-7411 (2011).
Maura et al. Serotonin autoreceptor in rat hippocampus: pharmacological characterization as a subtype of the 5-HT1 receptor. Naunyn Schmiedebergs Arch Pharmacol 334:323-326 (1986).
McEwen. Stress and hippocampal plasticity. Ann Rev Neurosci 22:105-122 (1999).
McKenna et al., Differential interactions of indolealkylamines with 5-hydroxytryptamine receptor subtypes. Neuropharmacology 29(3):193-198 (1990).
Minto et al., Pharmacokinetics and pharmacodynamics of nandrolone esters in oil vehicle: effects of ester, injection site and injection vol. J. Pharmacol. Exp. Ther. 281:93-102 (1997).
Moda-Sava et al. Sustained rescue of prefrontal circuit dysfunction by antidepressant-induced spine formation. Science 364(6436):eaaat8078 (2019).
Morales-Garcia et al., Phosphodiesterase7 Inhibition Activates Adult Neurogenesis in Hippocampus and Subventricular Zone In Vitro and In Vivo. Stem Cells 35:458-472 (2017).
Mori et al., Sigma-1 receptor chaperone at the ER-mitochondrion interface mediates the mitochondrion-ER-nucleus signaling for cellular survival. PLoS One 8(10):e76941 (2013).
Mycophreak Journeyman 2003 (https://www.shroomery.org/forums/showflat.php/Number/1232164/fpart/all.
Nautiyal et al. Distinct circuits underlie the effects of 5-HT1B receptors on aggression and impulsivity. Neuron 86:813-826 (2015).
Nestler, et al. Neurobiology of depression. Neuron. Mar. 28, 2002;34(1):13-25.
Nestler et al. The mesolimbic dopamine reward circuit in depression. Biol Psychiatry 59:1151-1159 (2006).
Neumaier et al. Chronic fluoxetine reduces serotonin transporter mRNA and 5-HT1B mRNA in a sequential manner in the rat dorsal raphe nucleus. Neuropsychopharmacology 15:515-522 (1996).
Nichols., Hallucinogens. Pharmacol. Ther. 101(2):131-81 (2004).
Nichols. Psychedelics. Pharmacol Rev. 68:264-35 (2016).
Nutt et al. Independent Scientific Committee on Drugs. Drug harms in the UK: a multicriteria decision analysis. Lancet 376:1558-1565 (2010).
Nutt et al. Psychedelic Psychiatry's Brave New World. Cell 181:24-28 (2020).
Ociepa et al., Mild and Chemoselective Phosphorylation of Alcohols Using a ψ-Reagent. Org. Lett., 23:9337-9342 (2021).
Omi et al., Fluvoxamine alleviates ER stress via induction of Sigma-1 receptor. Cell Death Dis. 5:e1332 (2014).
Osorio et al., Antidepressant effects of a single dose of ayahuasca in patients with recurrent depression: a preliminary report. Revista Brasileira de Psiquiatria. 37(1):13-20 (2015).
Ostro et al. Use of Liposomes as Injectable-Drug Delivery Systems. Am J Hosp Pharm 46(8):1576-1587 (Aug. 1989).
Pal et al., The sigma-1 receptor protects against cellular oxidative stress and activates antioxidant response elements. Eur. J. Pharmacol. 682(1-3):12-20 (2012).
PCT/EP2018/079503 International Search Report and Written Opinion dated Feb. 1, 2019.
PCT/US2020/046149 International Search Report and Written Opinion dated Jan. 11, 2021.
PCT/US2022/023067 International Search Report and Written Opinion dated Jun. 21, 2022.
PCT/US2022/040922 International Invitation to Pay Additional Fees dated Oct. 19, 2022.
PCT/US2022/040922 International Search Report and Written Opinion dated Dec. 19, 2022.

(56) References Cited

OTHER PUBLICATIONS

PCT/US2022/043463 International Invitation to Pay Additional Fees dated Nov. 17, 2022.
PCT/US2022/043463 International Search Report and Written Opinion dated Feb. 3, 2023.
PCT/US2022/079752 International Search Report and Written Opinion dated Feb. 11, 2023.
Pfeil et al., Synthesis of Oxalactams (2-Morpholinones) from Aziridinium Tetrafluoroborates and Hydroxy Esters. Angewante Chemie International Edition in English 6:178 (1967).
Preller et al., The Fabric of Meaning and Subjective Effects in LSD-Induced States Depend on Serotonin 2A Receptor Activation. Curr. Biol. 27(3):451-457 (2017).
Rao. Recent developments of collagen-based materials for medical applications and drug delivery systems. J Biomater Sci Polym Ed. 7(7):623-45 (1995).
Ray., Psychedelics and the human receptorome. PLoS One 5(2):e9019 (2010).
Remondes et al. Role for a cortical input to hippocampal area CA1 in the consolidation of a long-term memory. Nature 431:699-703 (2004).
Repke et al., Psilocin analogs II. Synthesis of 3-[2-(dialkylamino)ethyl]-, 3-[2-(N-methyl-N-alkylamino)ethyl]-, and 3-[2-(cycloalkylamino)ethyl]indol-4-ols. Journal of Heterocyclic Chemistry, 18:175-178 (1981).
Repke et al., Psilocin analogs. III. Synthesis of 5-methoxy- and 5-hydroxy-1,2,3,4-tetrahydro-9H-pyrido[3,4-b]indoles. Journal of Heterocyclic Chemistry 19(4):845-848 (1982).
Riba et al., Human pharmacology of ayahuasca: subjective and cardiovascular effects, monoamine metabolite excretion, and pharmacokinetics. J. Pharmacol. Exp. Ther 306(1):73-83 (2003).
Rickli et al., Receptor interaction profiles of novel psychoactive tryptamines compared with classic hallucinogens. Eur Neuropharmacol. 26(8):1327-1337 (2016).
Rinehart et al., Eudistomins A-Q, .beta.-carbolines from the antiviral Caribbean tunicate Eudistoma olivaceum. J. Am. Chem. Soc., 109:3378-3387 (1987).
Rohatagi et al. Pharmacokinetic and pharmacodynamic evaluation of triamcinolone acetonide after intravenous, oral, and inhaled administration. J. Clin. Pharmacol. 35:1187-1193 (1995).
Roseman et al. Quality of Acute Psychedelic Experience Predicts Therapeutic Efficacy of Psilocybin for Treatment-Resistant Depression Front. Pharmacol. 8:974 (2018).
Roth et al. Serotonin 5-HT2A receptors: molecular biology and mechanisms of regulation. Crit Rev. Neurobiol 12:319-338 (1998).
Ruscher et al. The involvement of the sigma-1 receptor in neurodegeneration and neurorestoration. J. Pharmacol. Sci. 127(1):30-5 (2015).
Sachs et al. Chronic fluoxetine increases extra-hippocampal neurogenesis in adult mice. Int. J. Neuropsychopharmacol. 18(4):pyu029 (2015).
Sheldrick. SHELXT—Integrated space-group and crystal-structure determination. Acta crystallogr A Found Adv. 71(Pt.1):3-8 (2015).
Singhal et al. Drug polymorphism and Dosage from design: a practical perspective. Advanced Drug Deliver Reviews.56:335-347(2004).
Somei et al., The chemistry of indoles. CIII. Simple syntheses of serotonin, N-methylserotonin, bufotenine, 5-methoxy-N-methyltryptamine, bufobutanoic acid, N-(indol-3-yl)methyl-5-methoxy-N-methyltryptamine, and lespedamine based on 1-hydroxyindole chemistry. Chem Pharm Bull (Tokyo) 49(1):87-96 (2001).
Somei et al., The Chemistry of Indoles. CVII.1) A Novel Synthesis of 3,4,5,6-Tetrahydra-7-hydroxy-1H-azepina[5,4,3-cd]indoles and a New Finding on Pictet—Spengler Reaction. Chem Pharm Bull (Tokyo) 49(9):1159-1165 (2001).
Strassmann et al., Dose-response study of N, N-dimethyltryptamine in humans. II. Subjective effects and preliminary results of a new rating scale. Arch. Gen Psychiatry 51(2):98-108 (1994).
Sugihara et al., Studies on intestinal lymphatic absorption of drugs. I. Lymphatic absorption of alkyl ester derivatives and alpha-monoglyceride derivatives of drugs. J. Pharmacobiodyn. 11(5):369-376 (1988).
Svenningsson et al. Alterations in 5-HT(1B) receptor function by p11 in depression-like states. Science 311:77-80 (2006).
Szabo et al. Dimethyltryptamine (DMT): a biochemical Swiss Army knife in neuroinflammation and neuroprotection? Neural Regen. Res. 11(3):396-7 (2016).
Szabo et al., Psychedelic N,N-dimethyltryptamine and 5-methoxy-N,N-dimethyltryptamine modulate innate and adaptive inflammatory responses through the sigma-1 receptor of human monocyte-derived dendritic cells. PLoS One 9(8):e106533 (2014).
Szabo et al., The Endogenous Hallucinogen and Trace Amine N,N-Dimethyltryptamine (DMT) Displays Potent Protective Effects against Hypoxia via Sigma-1 Receptor Activation in Human Primary iPSC-Derived Cortical Neurons and Microglia-Like Immune Cells. Front. Neurosci. 10:423 (2016).
Temple., Stem cell plasticity—building the brain of our dreams. Nat. Rev. Neurosci. 2(7):513-20 (2001).
Thompson et al. An excitatory synapse hypothesis of depression. Trends Neurosci 38:279-294 (2015).
Tittarelli et al., Recreational use, analysis and toxicity of tryptamines. Cut Neuropharmacol. 13:26-46 (2015).
TJWA. Budesonide inhaled via Turbuhaler: a more effective treatment for asthma than beclomethasone dipropionate via Rotahaler. Ann. Allergy Asthma Immunol. 75:107-111, 1995.
Tye et al. Dopamine neurons modulate neural encoding and expression of depression-related behaviour. Nature 493:537-541 (2013).
Tyls et al. Sex differences and serotonergic mechanisms in the behavioural effects of psilocin. Behav Phamacol 27(4):309-320 (2016).
U.S. Appl. No. 18/147,066 Office Action dated May 5, 2023.
Valle et al. Inhibition of alpha oscillations through serotonin-2A receptor activation underlies the visual effects of ayahuasca in humans. Eur Neuropsychopharmacol 26(7):1161-75 (2016).
Van Dyke et al. Chronic fluoxetine treatment in vivo enhances excitatory synaptic transmission in the hippocampus. Neumpharmacology 150:38-45 (2019).
Vollenweider et al., Psilocybin induces schizophrenia-like psychosis in humans via a serotonin-2 agonist action. Neuroreport 9(17):3897-3902 (1998).
Weber et al., Crystal Structures of the Teonanacatl Hallucinogens. Part 1. Psilocybin C12H17N2O4P. J Chem Soc (8):942-6 (1974).
Weisstaub et al. Cortical 5-HT2A receptor signaling modulates anxiety-like behaviors in mice. Science 313:536-540 (2006).
Wiens et al., Concerning the preparation of 6-bromotryptamine. Tetrahedron 81:132055 (2021).
Willner. The chronic mild stress (CMS) model of depression: History, evaluation and usage. Neurobiol Stress 6:78-93 (2016).
Winter et al. Psilocybin-induced stimulus control in the rat. Pharmacol Biochem Behav. 87:472-480 (2007).
Wolfard et al., Synthesis of Chiral Tryptamines via a Regioselective Indole Alkylation. Org. Lett. 20:5431 (2018).
Xu et al., Synthesis of deuterium labeled standards of 5-methoxy-N,N-dimethyltryptamine (5-Meo-DMT). J. Label Compd Radiopharm. 49(10):897-902 (2006).
Yamada et al., Synthetic studies of psilocin analogs having either a formyl group or bromine atom at the 5- or 7-position. Chem. Pharm. Bull. 50(1):92-99 (2002).
Yuen et al. Repeated stress causes cognitive impairment by suppressing glutamate receptor expression and function in prefrontal cortex. Neuron 73:962-977 (2012).
Zhang et al. Direct Reductive Amination of Aldehydes with Nitroarenes using Bio-renewable Formic Acid as a Hydrogen Source. Green Chemistry 18(8):2507-2513 (2016).

PSILOCYBIN AND O-ACETYLPSILOCIN, SALTS AND SOLID STATE FORMS THEREOF

CROSS-REFERENCE TO RELATED APPLICATIONS

This application is a continuation of U.S. application Ser. No. 18/147,066, filed on Dec. 28, 2022, which is a continuation of International Application No. PCT/US2022/079752, filed Nov. 11, 2022, which claims the benefit of U.S. Provisional Application No. 63/278,943, filed on Nov. 12, 2021; U.S. Provisional Application No. 63/279,005, filed on Nov. 12, 2021; U.S. Provisional Application No. 63/280,294, filed on Nov. 17, 2021; U.S. Provisional Application No. 63/280,300, filed on Nov. 17, 2021; U.S. Provisional Application No. 63/285,050, filed on Dec. 1, 2021; U.S. Provisional Application No. 63/300,957, filed on Jan. 19, 2022; U.S. Provisional Application No. 63/300,961, filed on Jan. 19, 2022; U.S. Provisional Application No. 63/305,642, filed on Feb. 1, 2022; U.S. Provisional Application No. 63/305,643, filed on Feb. 1, 2022; U.S. Provisional Application No. 63/310,984, filed on Feb. 16, 2022; U.S. Provisional Application No. 63/310,987, filed on Feb. 16, 2022; U.S. Provisional Application No. 63/311,878, filed on Feb. 18, 2022; U.S. Provisional Application No. 63/315,901, filed on Mar. 2, 2022; U.S. Provisional Application No. 63/316,952, filed on Mar. 4, 2022; U.S. Provisional Application No. 63/319,746, filed on Mar. 14, 2022; U.S. Provisional Application No. 63/321,593, filed on Mar. 18, 2022; U.S. Provisional Application No. 63/324,878, filed on Mar. 29, 2022; U.S. Provisional Application No. 63/326,364, filed on Apr. 1, 2022; U.S. Provisional Application No. 63/326,421, filed on Apr. 1, 2022; U.S. Provisional Application No. 63/326,522, filed on Apr. 1, 2022; U.S. Provisional Application No. 63/326,713, filed on Apr. 1, 2022; U.S. Provisional Application No. 63/357,378, filed on Jun. 30, 2022; and U.S. Provisional Application No. 63/357,512, filed on Jun. 30, 2022; each of which is incorporated herein by reference in its entirety.

SUMMARY OF THE INVENTION

Described herein are solid state forms of psilocybin and O-acetylpsilocin, salts of psilocybin and O-acetylpsilocin, and solid state forms of said salts. Also disclosed herein are embodiments, of a pharmaceutical composition, comprising such solid state forms and salts, and a pharmaceutically acceptable excipient. Also disclosed is a method for administering the solid state forms and salts disclosed herein. In some embodiments, the method comprises administering to a subject an effective amount of a solid state form or salt disclosed herein, or a pharmaceutical composition thereof. In some embodiments, the subject has a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof. In some embodiments, administering the solid state form or salt disclosed herein comprises oral, intravenous, parenteral, or topical administration. In certain embodiments, oral administration is used, but in other particular embodiments, administration is by injection, inhalation, intraocular, intravaginal, intrarectal or transdermal routes.

In one aspect, disclosed herein are novel solid forms of psilocybin·HCl. The solid form of psilocybin·HCl may have at least one improved property compared to amorphous psilocybin·HCl and to previously known crystalline forms of psilocybin·HCl.

Also disclosed herein is a solid form of psilocybin·HCl that is made by the method described in Example 1. The solid form of psilocybin·HCl made by the disclosed method may have at least one improved property compared to amorphous psilocybin·HCl and previously known crystalline forms of psilocybin·HCl.

In any embodiments, the at least one improved property of the solid form of psilocybin·HCl may comprise a physical property, chemical property, pharmacokinetic property, or a combination thereof. In some embodiments, the at least one improved property comprises a melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof, that is improved compared to an amorphous sample of psilocybin·HCl and/or a previously known crystalline form of psilocybin·HCl.

In any embodiments, the solid form of psilocybin·HCl may be a solvate, such as a hydrate.

Also disclosed herein are embodiments, of a pharmaceutical composition, comprising a solid form of psilocybin·HCl, and a pharmaceutically acceptable excipient.

A method for administering the solid form of psilocybin·HCl also is disclosed herein. In some embodiments, the method comprises administering to a subject an effective amount of a solid form of psilocybin·HCl, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

In any embodiments, administering the solid form of psilocybin·HCl comprises oral, parenteral, or topical administration. In certain embodiments, oral administration is used, but in other particular embodiments, administration is by injection, inhalation, intraocular, intravaginal, intrarectal or transdermal routes.

In any embodiments, the psilocybin·HCl may be administered in a range about 10 milligram (mg) to 50 mg, such as about 25 mg to about 30 mg.

In another aspect, described herein are salts and solid forms of psilocybin, including salts of the solid forms, crystalline forms of the compound and salts, as well as polymorphs of solid forms. In some embodiments, the salt or solid form is not psilocybin·HCl. Also disclosed are methods for making the salts and solid forms and methods for using the forms of psilocybin. In some embodiments, a solid form of psilocybin is a polymorph of the free base form of the compound. The free base form of psilocybin may have a Form C as described herein, and/or have a an XRPD spectrum and/or NMR spectrum corresponding to Form C in FIG. 24 and FIG. 25, respectively.

In other embodiments, the psilocybin form is a salt form, such as a solid form of psilocybin, and may be a polymorph of the salt. The salt may be formed from an acid selected from galactaric (mucic) acid, naphthalene-1,5-disulfonic acid, citric acid, sulfuric acid, d-glucuronic acid, ethane-1, 2-disulfonic acid, lactobionic acid, p-toluenesulfonic acid, D-glucoheptonic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, ethanesulfonic acid 2-hydroxy, glutaric acid, L-aspartic acid, cinnamic acid, maleic acid, adipic acid, phosphoric acid, sebacic acid, ethanesulfonic acid, (+)-camphoric acid, glutamic acid, acetic acid, or a combination thereof. In some embodiments, the salt is an ethane-1,2-disulfonic acid salt.

In any embodiments, the solid form may be a crystalline solid. The crystalline solid may be substantially a single form, such as a polymorph form. And the polymorph may be selected to have one or more desired properties, particularly improved properties, such as physical properties, chemical properties, pharmacokinetic properties, or a combination thereof. The one or more desired properties may comprise melting point, glass transition temperature, flowability, thermal stability, mechanical stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

Also disclosed herein are embodiments, of a pharmaceutical composition, comprising a solid form of a disclosed compound, and a pharmaceutically acceptable excipient.

A method for administering the solid form of psilocybin also is disclosed herein. In some embodiments, the method comprises administering to a subject an effective amount of a solid form of psilocybin, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

In any embodiments, administering the solid form of the compound comprises oral, parenteral, or topical administration. In certain embodiments, oral administration is used, but in other particular embodiments, administration is by injection, inhalation, intraocular, intravaginal, intrarectal or transdermal routes.

In any embodiments, the solid form of psilocybin, including a salt form of psilocybin, may be administered in a range about 10 milligram (mg) to 50 mg, such as about 25 mg to about 30 mg.

In another aspect, disclosed herein are salts and solid forms of O-acetylpsilocin, including salts, crystalline forms of the compounds and salts, as well as polymorphs of solid forms. In some embodiments, the salt is not O-acetylpsilocin fumarate and the solid form does not comprise O-acetylpsilocin fumarate. Also disclosed are methods for making the salts and solid forms as well as methods for using the salts and solid forms of O-acetylpsilocin. In some embodiments, the solid form of O-acetylpsilocin is a polymorph of the free base form of the compound. In other embodiments, the solid form of O-acetylpsilocin is a salt, and may be a polymorph of the salt. Salts may be formed from an acid selected from hydrochloride, galactaric (mucic) acid, naphthalene-1,5-disulfonic acid, citric acid, sulfuric acid, d-glucuronic acid, ethane-1,2-disulfonic acid, lactobionic acid, p-toluenesulfonic acid, D-glucoheptonic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, ethanesulfonic acid 2-hydroxy, glutaric acid, L-aspartic acid, cinnamic acid, maleic acid, adipic acid, phosphoric acid, sebacic acid, ethanesulfonic acid, (+)-camphoric acid, glutamic acid, glycolic acid, acetic acid, or a combination thereof.

In any embodiments, the solid form may be a crystalline solid. The crystalline solid may be substantially a single form, such as a polymorph form. And the polymorph may be selected to have one or more desired properties, particularly improved properties, such as physical properties, chemical properties, pharmacokinetic properties, or a combination thereof. The one or more desired properties may comprise melting point, glass transition temperature, flowability, thermal stability, mechanical stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

Also disclosed herein are embodiments, of a pharmaceutical composition, comprising a salt and solid form of a disclosed compound, and a pharmaceutically acceptable excipient.

A method for administering the salt and solid form of O-acetylpsilocin also is disclosed herein. In some embodiments, the method comprises administering to a subject an effective amount of a salt form, a solid form of O-acetylpsilocin, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

In any embodiments, administering the form of the compound comprises oral, parenteral, or topical administration. In certain embodiments, oral administration is used, but in other particular embodiments, administration is by injection, inhalation, intraocular, intravaginal, intrarectal or transdermal routes.

In another aspect, disclosed herein are novel solid forms of O-acetylpsilocin fumarate. The solid form of O-acetylpsilocin fumarate may have at least one improved property compared to amorphous O-acetylpsilocin fumarate.

Also disclosed herein is a solid form of O-acetylpsilocin fumarate that is made by the method described in Example 12. The solid form of O-acetylpsilocin fumarate made by the disclosed method may have at least one improved property compared another solid form of O-acetylpsilocin. In one embodiment, the O-acetylpsilocin fumarate solid form disclosed herein is a crystalline form that has an improved property relative to amorphous O-acetylpsilocin fumarate. In one embodiment a crystalline form disclosed herein is a polymorph of O-acetylpsilocin fumarate. In certain embodiments, a disclosed polymorph of O-acetylpsilocin fumarate has an improved property over one or more other solid forms of O-acetylpsilocin fumarate.

In any embodiments, the at least one improved property of the solid form of O-acetylpsilocin fumarate disclosed herein may comprise a physical property, chemical property, pharmacokinetic property, or a combination thereof. In some embodiments, the at least one improved property comprises a melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof, that is improved compared to an amorphous sample of O-acetylpsilocin fumarate.

In any embodiments, the solid form of O-acetylpsilocin fumarate may be a solvate, such as a hydrate.

Also disclosed herein are embodiments, of a pharmaceutical composition, comprising a solid form of O-acetylpsilocin fumarate, and a pharmaceutically acceptable excipient.

A method for administering the solid form of and/or a previously known crystalline form of and/or a previously known crystalline form of and/or a previously known crystalline form of and/or a previously known crystalline form of O-acetylpsilocin fumarate also is disclosed herein. In some embodiments, the method comprises administering to a subject an effective amount of a solid form of O-acetylpsilocin fumarate, or a pharmaceutical composition thereof. In some embodiments, the subject has a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

In any embodiments, administering the solid form of O-acetylpsilocin fumarate comprises oral, intravenous, parenteral, or topical administration. In certain embodiments, oral administration is used, but in other particular embodiments, administration is by injection, inhalation, intraocular, intravaginal, intrarectal or transdermal routes The foregoing and other objects, features, and advantages of the invention will become more apparent from the following detailed description.

DETAILED DESCRIPTION

I. Definitions

Figure 1:
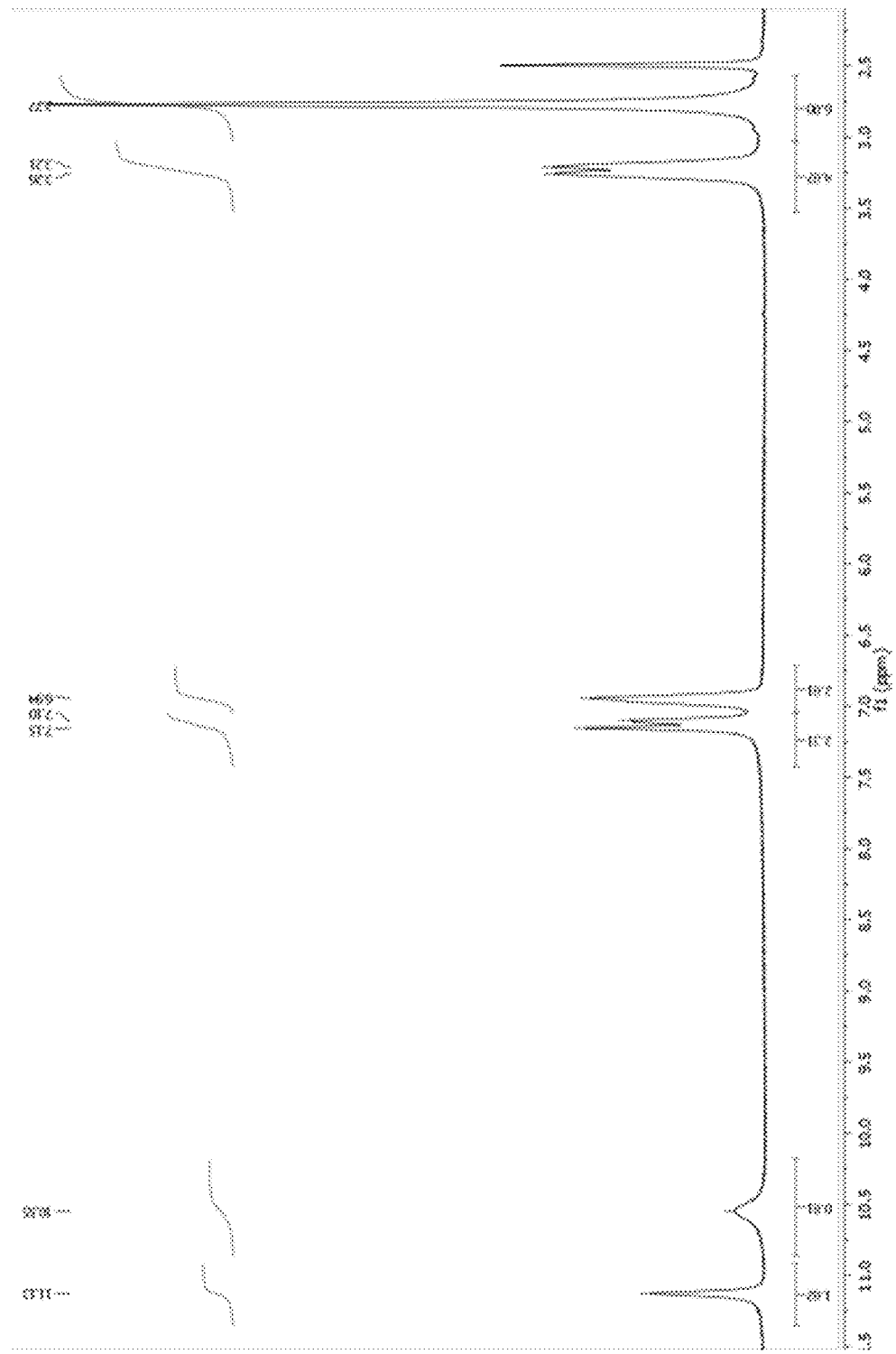
FIG. 1 provides an NMR spectrum of a non-crystalline solid form of psilocybin·HCl dissolved in DMSO-d6.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

"Administering" refers to any suitable mode of administration, including, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Subject" refers to an animal, such as a mammal, including, but not limited to, primates (e.g., humans), cows, sheep, goats, horses, dogs, cats, rabbits, rats, mice and the like. In certain embodiments, the subject is a human subject.

"Therapeutically effective amount" or "therapeutically sufficient amount" or "effective or sufficient amount" refers to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

"Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

"Combination therapy" refers to a method of treating a disease or disorder, wherein two or more different pharmaceutical agents are administered in overlapping regimens so that the subject is simultaneously exposed to both agents. For example, the compounds of the invention can be used in combination with other pharmaceutically active compounds. The compounds of the invention can be administered simultaneously (as a single preparation or separate preparation) or sequentially to the other drug therapy. In general, a combination therapy envisions administration of two or more drugs during a single cycle or course of therapy.

"Neurotrophic factors" refers to a family of soluble peptides or proteins which support the survival, growth, and differentiation of developing and mature neurons.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 mM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

"Composition" refers to a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

II. Compounds

Disclosed herein are solid forms of compounds that are useful to treat various disorders, such as brain disorders. Also disclosed are methods for making the solid forms of such compounds and method of administering the solid forms of the compounds.

In one aspect, the solid forms disclosed herein are solid forms of psilocybin·HCl. In another aspect, the solid forms disclosed herein are solid forms of psilocybin. In another aspect, the solid forms disclosed herein are solid forms of O-acetylpsilocin. In another aspect, the solid forms disclosed herein are solid forms of O-Acetylpsilocin fumarate.

In some embodiments, the solid form of the compound disclosed herein is a crystalline form of the compound. In some embodiments, the solid form of the compound is a polymorph of the compound, such as a novel polymorph that is not previously known in the art. In some embodiments, the solid form of the compound is a salt of the compound. In some embodiments, the solid form of the compound is a crystalline salt form of the compound, such as an acid addition salt form.

Psilocybin·HCl

Disclosed herein are solid forms of psilocybin·HCl that are useful to treat various disorders, such as brain disorders. Also disclosed are methods for making the solid forms of the compounds and method of administering the solid forms of the compounds.

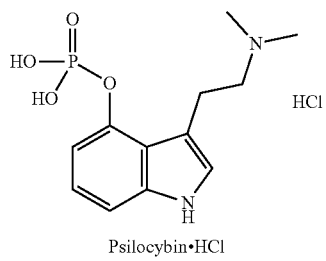 [SMILES: CN(C)CCc1c[nH]c2cccc(OP(=O)(O)O)c12 ; Cl]

Psilocybin•HCl

With reference to the formula for psilocybin·HCl, the middle dot, "·", represents that the compound is the acid addition salt of psilocybin. In some embodiments, the solid form of the compound is a crystalline form of the compound. In some embodiments, the solid form of the compound is a polymorph of the compound, such as a novel polymorph that is not previously known in the art.

Solid forms of Psilocybin·HCl

A solid form of a salt may be a crystalline form or an amorphous form. A person of ordinary skill in the art understands that solid forms of compounds, such as crystalline forms of psilocybin·HCl, may exist in more than one crystal form. Such different forms are referred to as polymorphs. In some embodiments, the disclosed compound is a novel polymorph of psilocybin·HCl.

In some embodiments, the solid form of psilocybin·HCl disclosed herein is selected to be a crystalline form, such as a particular polymorph of a crystalline form of psilocybin·HCl, that provides one or more desired properties. In one embodiment, the crystalline form offers advantages over the amorphous form of the molecule. In another embodiment, the disclosed polymorph offers improved properties as compared to another polymorph of the molecule. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques as described herein and also are known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of a compound are described herein and also are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

Psilocybin Salt and Solid Forms

Disclosed herein are solid forms of psilocybin that are useful to treat various disorders, such as brain disorders. Also disclosed are methods for making the solid forms of psilocybin and method of administering the solid forms of psilocybin.

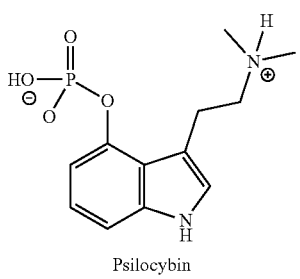 [SMILES: C[NH+](C)CCc1c[nH]c2cccc(OP(=O)([O-])O)c12]

Psilocybin

As is understood by those of skill in the art, the structure above illustrates the zwitterionic form of psilocybin. In some embodiments, the solid form of the compound is a crystalline form of psilocybin. In some embodiments, the solid form of psilocybin is a polymorph of psilocybin, such as a polymorph of the free base (zwitterionic) compound or a polymorph of the salt. In some embodiments, the solid form of the compound is a salt of the compound. In some embodiments, the solid form of the compound is a crystalline salt form of the compound, such as an acid addition salt form.

Salts of Psilocybin

In some embodiments, provided herein are novel salts of psilocybin. Also provided are solid forms of psilocybin, wherein the solid form of psilocybin comprises a salt of psilocybin. Suitable salts include a pharmaceutically acceptable salt of psilocybin. In some embodiments, the solid form of psilocybin is not, and does not comprise, psilocybin HCl.

In some embodiments, the salt of psilocybin may be formed from a suitable pharmaceutically acceptable acid, including, without limitation, inorganic acids such as hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like.

In other embodiments, the salt of psilocybin may be formed from a suitable pharmaceutically acceptable base, including, without limitation, inorganic bases such as sodium, potassium, lithium, ammonium, calcium, magnesium, iron, zinc, copper, manganese, aluminum salts and the like. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris (hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Additional information concerning pharmaceutically acceptable salts can be found in, for example, S. M. Berge, et al., "Pharmaceutical Salts," J. Pharm. Sci., 1977; 66:1-19 which is incorporated herein by reference.

In some embodiments, the salt may be formed using an acid from Table 1.

TABLE 1

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| fumaric acid | carbonic acid |
| galactaric (mucic) acid | |

The acid salts of psilocybin disclosed herein can have any suitable stoichiometric ratio of acid to psilocybin. In one embodiment, the molar ratio of acid is from about 0.4 molar equivalent to about 2.2 molar equivalent, such as forms wherein the salt has a stoichiometric ratio of from about 0.5 molar equivalent to about 2 molar equivalent, such as 0.5, 1 molar equivalent or 2 molar equivalents of acid.

Solid Forms of Psilocybin and Psilocybin Salts

Embodiments of psilocybin of the present disclosure are in a solid form. The solid form may be a crystalline form or an amorphous form. In some embodiments, the solid form is a crystalline form. In some embodiments, the solid form of psilocybin is a salt. And in certain embodiments, the solid form is a crystalline salt form of the compound. A person of ordinary skill in the art understands that solid forms of psilocybin, such as crystalline forms including salt and non-salt crystalline forms of psilocybin, may exist in more than one crystal form. Such different forms are referred to as polymorphs. In some embodiments, the disclosed compounds are particular polymorphs of psilocybin or psilocybin salts.

In some embodiments, the solid form of psilocybin disclosed herein is selected to be a crystalline form, such as a particular polymorph of a crystalline form of psilocybin that provides one or more desired properties. In one embodiment, the crystalline form offers advantages over the amorphous form of the molecule. In another embodiment, the disclosed polymorph offers improved properties as compared to another polymorph of psilocybin. The psilocybin may be a salt or free base compound. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of psilocybin are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

O-Acetylpsilocin

"O-Acetylpsilocin" refers to the compound [3-[2-(dimethylamino)ethyl]-1H-indol-4-yl]acetate. The compound may also be referred to as psilacetin, 4-acetoxy-DMT or 4-AcO-DMT.

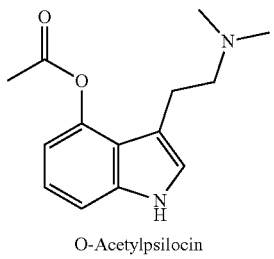 [SMILES: CC(=O)Oc1cccc2[nH]cc(CCN(C)C)c12]

O-Acetylpsilocin

Disclosed herein are solid forms of O-acetylpsilocin that are useful to treat various disorders, such as brain disorders. Also disclosed are methods for making the solid forms of O-acetylpsilocin and method of administering the solid forms of O-acetylpsilocin.

In some embodiments, the solid form of the compound is a crystalline form of O-acetylpsilocin. In some embodiments, the solid form of O-acetylpsilocin is a polymorph of O-acetylpsilocin, such as a polymorph of the free base (zwitterionic) compound or a polymorph of the salt. In some embodiments, the solid form of the compound is a salt of the compound. In some embodiments, the solid form of the compound is a crystalline salt form of the compound, such as an acid addition salt form.

Salts of O-acetylpsilocin

In some embodiments, salts of O-acetylpsilocin are disclosed, for example a solid form of O-acetylpsilocin comprises a salt of O-acetylpsilocin. Suitable salts include a pharmaceutically acceptable salt of O-acetylpsilocin. In some embodiments, the salt and solid forms of O-acetylpsilocin are not, and do not comprise, O-acetylpsilocin fumarate.

In some embodiments, the salt of O-acetylpsilocin may be formed from a suitable pharmaceutically acceptable acid, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like.

In other embodiments, the salt of O-acetylpsilocin may be formed from a suitable pharmaceutically acceptable base, including, without limitation, inorganic bases such as sodium, potassium, lithium, ammonium, calcium, magnesium, iron, zinc, copper, manganese, aluminum salts and the like. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris (hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Additional information concerning pharmaceutically acceptable salts can be found in, for example, S. M. Berge, et al., "Pharmaceutical Salts," J. Pharm. Sci., 1977; 66:1-19 which is incorporated herein by reference.

In some embodiments, the salt may be formed using an acid from Table 2.

TABLE 2

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| Hydrochloric acid | carbonic acid |
| galactaric (mucic) acid | |

The acid salts of O-acetylpsilocin disclosed herein can have any suitable stoichiometric ratio of acid to O-acetylpsilocin. In one embodiment, the molar ratio of acid to O-acetylpsilocin is from about 0.4 to about 2.2, such as forms wherein the salt has a stoichiometric ratio of acid to O-acetylpsilocin of from about 0.5 to about 2, such as about 0.5, about 1 or about 2.

Solid forms of O-acetylpsilocin

Embodiments of O-acetylpsilocin of the present disclosure are in a solid form. The solid form may be a crystalline form or an amorphous form. In some embodiments, the solid form is a crystalline form, such as a polymorph. In some embodiments, the solid form of O-acetylpsilocin is a salt. And in certain embodiments, the solid form is a crystalline salt form of the compound. A person of ordinary skill in the art understands that solid forms of O-acetylpsilocin, such as crystalline forms including salt and non-salt crystalline forms of O-acetylpsilocin, may exist in more than one crystal form. Such different forms are referred to as polymorphs. In some embodiments, the disclosed compounds are particular polymorphs of O-acetylpsilocin or O-acetylpsilocin salts.

In some embodiments, the solid form of O-acetylpsilocin disclosed herein is selected to be a crystalline form, such as a particular polymorph of a crystalline form of O-acetylpsilocin that provides one or more desired properties. In one embodiment, the crystalline form offers advantages over the amorphous form of the molecule. In another embodiment, the disclosed polymorph offers improved properties as compared to another polymorph of O-acetylpsilocin. The O-acetylpsilocin may be a salt or free base compound. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of O-acetylpsilocin are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

O-Acetylpsilocin Fumarate

"O-acetylpsilocin fumarate" refers to the fumarate salt of O-acetylpsilocin, which may also be referred to as O-acetylpsilocin fumarate or 4-acetoxy-DMT fumarate.

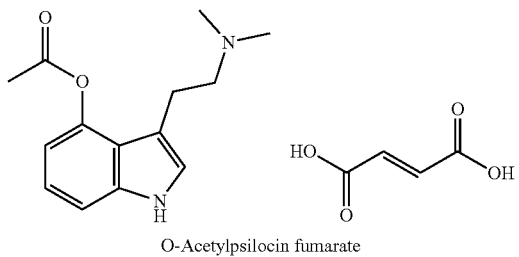 [SMILES: CC(=O)Oc1cccc2[nH]cc(CCN(C)C)c12 ; O=C(O)/C=C/C(=O)O]

O-Acetylpsilocin fumarate

Disclosed herein are solid forms of O-acetylpsilocin fumarate that are useful to treat various disorders, such as brain disorders. Also disclosed are methods for making the solid forms of the compounds and method of administering the solid forms of the compounds.

In some embodiments, the solid form of the compound is a crystalline form of the compound. In some embodiments, the solid form of the compound is a polymorph of the compound, such as a novel polymorph that is not previously known in the art.

Solid Forms of O-Acetylpsilocin Fumarate

A solid form of a salt may be a crystalline form or an amorphous form. A person of ordinary skill in the art understands that solid forms of compounds, such as crystalline forms of O-acetylpsilocin fumarate, may exist in more than one crystal form. Such different forms are referred to as polymorphs. In some embodiments, the disclosed compound is a novel polymorph of O-acetylpsilocin fumarate.

In some embodiments, the solid form of O-acetylpsilocin fumarate disclosed herein is selected to be a crystalline form, such as a particular polymorph of a crystalline form of O-acetylpsilocin fumarate, that provides one or more desired properties. In one embodiment, the crystalline form offers advantages over the amorphous form of the molecule. In another embodiment, the disclosed polymorph offers improved properties as compared to another polymorph of the molecule. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques as described herein and also are known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of O-acetylpsilocin fumarate are described herein and also are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

Pharmaceutical Compositions and Formulations

In some embodiments, the present disclosure provides a pharmaceutical composition comprising one or more of the disclosed solid forms of a compound described herein, and a pharmaceutically acceptable excipient. Such compositions are suitable for administration to a subject, such as a human subject.

In some embodiments, the present disclosure provides a pharmaceutical composition comprising one or more of the disclosed solid forms of psilocybin·HCl, and a pharmaceutically acceptable excipient. Such compositions are suitable for administration to a subject, such as a human subject.

In some embodiments, the present disclosure provides a pharmaceutical composition comprising one or more of the solid forms of psilocybin, illustrated above, and a pharmaceutically acceptable excipient. Such compositions are suitable for administration to a subject, such as a human subject.

In some embodiments, the present disclosure provides a pharmaceutical composition comprising one or more of the solid forms of O-acetylpsilocin, illustrated above, and a pharmaceutically acceptable excipient. Such compositions are suitable for administration to a subject, such as a human subject.

In some embodiments, the present disclosure provides a pharmaceutical composition comprising one or more of the disclosed solid forms of O-acetylpsilocin fumarate, and a pharmaceutically acceptable excipient. Such compositions are suitable for administration to a subject, such as a human subject.

The presently disclosed pharmaceutical compositions can be prepared in a wide variety of oral, parenteral and topical dosage forms. Oral preparations include tablets, pills, powder, capsules, lozenges, cachets, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see *J. Clin. Pharmacol.* 35:1187-1193, 1995; *Ann. Allergy Asthma Immunol.* 75:107-111, 1995). Accordingly, the present disclosure also provides pharmaceutical compositions including a pharmaceutically acceptable carrier or excipient and the solid form of the compounds of the present disclosure.

For preparing pharmaceutical compositions from the compounds and forms disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% to 70% or 10% to 70% of the compounds of the present disclosure.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen.

If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include suspensions, for example, water or water/propylene glycol suspensions.

Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include suspensions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present disclosure can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In some embodiments, the pharmaceutical compositions of the present disclosure can be formulated for parenteral administration, such as intravenous (IV) administration or administration into a body cavity or lumen of an organ. The formulations for administration will commonly comprise a solution or suspension of the compositions of the present disclosure dissolved or suspended in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions or suspensions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present disclosure in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present disclosure can be delivered by the use of liposomes which fuse with the cellular membrane or are endocytosed, for example, by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Administration

The compositions of the present disclosure can be administered by any suitable means, including oral, parenteral and topical methods. Transdermal administration methods, by a topical route, can be formulated as applicator sticks, suspensions, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds of the present invention can be co-administered with a second active agent. In some embodiments, co-administration can be accomplished by co-formulation, such as by preparing a single pharmaceutical composition including both the compound of the present disclosure and a second active agent. In other embodiments, the compound of the present disclosure and the second active agent can be formulated separately. A composition comprising a solid form of the present invention can also contain other compatible therapeutic agents. The compounds described herein can be used in combination with one another, with other active agents known to be useful in modulating a receptor, or with adjunctive agents that may not be effective alone, but may contribute to the efficacy of the active agent.

The compound of the present invention can be present in any suitable amount, and can depend on various factors including, but not limited to, weight and age of the subject, state of the disease, and the like as is known to those of ordinary skill in the art.

In some embodiments, the psilocybin·HCl is provided in a range about 10 milligrams (mg) to 50 mg, about 20 mg to about 50 mg, or about 25 mg to about 30 mg. In some embodiments, the psilocybin·HCl is provided at about 10 mg, about 15 mg, about 20 mg, about 25 mg, about 30 mg, about 35 mg, about 40 mg, about 45 mg, or about 50 mg. In some embodiments, the amount of psilocybin·HCl is provided on a psilocybin basis.

In some embodiments, the salt or solid form of psilocybin is provided in a range about 10 milligrams (mg) to 50 mg, about 20 mg to about 50 mg, or about 25 mg to about 30 mg. In some embodiments, the salt or solid form of psilocybin is provided at about 10 mg, about 15 mg, about 20 mg, about 25 mg, about 30 mg, about 35 mg, about 40 mg, about 45 mg, or about 50 mg. In some embodiments, the amount of the salt or solid form of psilocybin is provided on a psilocybin basis.

In some embodiments, the O-acetylpsilocin salt is provided in a range about 1 milligram (mg) to 50 mg, about 20 mg to about 50 mg, or about 20 mg to about 40 mg. In some embodiments, the O-acetylpsilocin salt is provided, at about 10 mg, about 15 mg, about 20 mg, about 25 mg, about 30 mg, about 35 mg, about 40 mg, about 45 mg, or about 50 mg. In some embodiments, the amount of O-acetylpsilocin salt is provided on an O-acetylpsilocin basis.

In some embodiments, the O-acetylpsilocin fumarate is provided in a range of about 1 milligrams (mg) to 50 mg, about 20 mg to about 50 mg, about 20 mg to about 40 mg. In some embodiments, the O-acetylpsilocin fumarate is provided, at about 10 mg, about 15 mg, about 20 mg, about 25 mg, about 30 mg, about 35 mg, about 40 mg, about 45 mg, or about 50 mg. In some embodiments, the amount of O-acetylpsilocin fumarate is provided on an O-acetylpsilocin basis.

Methods of Treatment

The solid forms of the compounds of the present disclosure can be used for increasing neuronal plasticity. The compounds of the present disclosure can also be used to treat any brain disease. The solid forms of the present disclosure can also be used for increasing at least one of translation, transcription or secretion of neurotrophic factors.

In some embodiments, the methods described herein are for treating a disease or disorder that is a brain disease or disorder. In some embodiments, the methods described herein are for increasing at least one of translation, transcription or secretion of neurotrophic factors. In some embodiments, the compositions provided herein have, for example, anti-addictive properties, antidepressant properties, anxiolytic properties, or a combination thereof. In some embodiments, the brain disorder is a neuropsychiatric disease. In some embodiments, the methods described herein are for treating a disease or disorder that is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder for example alcohol abuse, opiate addition, or abuse), depression, and anxiety.

In some embodiments, the brain disease or disorder is a neurodegenerative disorder, Alzheimer's disease or Parkinson's disease. In some embodiments, the brain disease or disorder is psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the methods described herein are for treating a disease or disorder that is a neurological disease. For example, a compound provided herein can exhibit, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, hypoxic brain injury, Chronic traumatic encephalopathy (CTE), traumatic brain injury, dementia, and addiction (e.g., substance use disorder). In some embodiments, the neurological disease is a migraine or cluster headache. In some embodiments, the neurological disease is a neurodegenerative disorder, dementia, Alzheimer's disease, or Parkinson's disease. In some embodiments, the neurological disease is dementia. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety.

In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety.

In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, the methods described herein are for increasing neuronal plasticity and has, for example, anti-addictive properties, antidepressant properties, anxiolytic properties, or a combination thereof. In some embodiments, decreased neuronal plasticity is associated with a neuropsychiatric disease.

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity by treating a subject with one or more of the disclosed compounds can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present disclosure provides methods for increasing neuronal plasticity, comprising contacting a neuronal cell with a compound of the present disclosure. In some embodiments, increasing neuronal plasticity improves a brain disorder described herein.

In some embodiments, a compound of the present disclosure is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder).

In some embodiments, the experiment or assay to determine increased neuronal plasticity of any compound of the present disclosure is a phenotypic assay, a dendritogenesis assay, a spinogenesis assay, a synaptogenesis assay, a Sholl analysis, a concentration-response experiment, a 5-HT$_{2A}$ agonist assay, a 5-HT$_{2A}$ antagonist assay, a 5-HT$_{2A}$ binding assay, or a 5-HT$_{2A}$ blocking experiment (e.g., ketanserin blocking experiments). In some embodiments, the experiment or assay to determine the hallucinogenic potential of any compound of the present invention is a mouse head-twitch response (HTR) assay.

In some embodiments, the present disclosure provides a method for increasing neuronal plasticity, comprising contacting a neuronal cell with a compound disclosed herein.

In some embodiments, the present disclosure provides a method of treating a disease, including administering to a subject in need thereof, a therapeutically effective amount of a compound form of the present disclosure. In some embodiments, the disease is a musculoskeletal pain disorder including fibromyalgia, muscle pain, joint stiffness, osteoarthritis, rheumatoid arthritis, muscle cramps. In some embodiments, the present invention provides a method of treating a disease of women's reproductive health including premenstrual dysphoric disorder (PMDD), premenstrual syndrome (PMS), post-partum depression, and menopause.

Diseases of particular interest include depression and related conditions. Accordingly, in some embodiments, the disease or disorder treated herein is depression or a disease or disorder related to depression. In some embodiments, the depression is major depressive disorder, persistent depressive disorder, bipolar disorder, treatment resistant depression (TRD), postpartum depression, premenstrual dysphoric disorder, or seasonal affective disorder. In some embodiments, the disease or disorder related to depression is anxiety. In some embodiments, methods of treating depression or a disease or disorder related to depression comprise treating the symptoms associated with the depression or the disease or disorder related to depression.

Described herein are methods of treating depression or a disease or disorder related to depression in a subject in need thereof, the method comprising administering to the subject a psychedelic and a serotonin receptor modulator, wherein the serotonin receptor modulator is administered at most about 3 hours prior to the release of the psychedelic. In some embodiments, the depression is major depressive disorder, persistent depressive disorder, bipolar disorder, treatment resistant depression (TRD), postpartum depression, premenstrual dysphoric disorder, or seasonal affective disorder. In some embodiments, the disease or disorder related to depression is anxiety. In some embodiments, methods of treating depression or a disease or disorder related to depression comprise treating the symptoms associated with the depression or the disease or disorder related to depression.

In some embodiments, the compounds of the present disclosure have activity as $5\text{-}HT_{2A}$ modulators. In some embodiments, the compounds of the present disclosure elicit a biological response by activating the $5\text{-}HT_{2A}$ receptor (e.g., allosteric modulation or modulation of a biological target that activates the $5\text{-}HT_{2A}$ receptor). $5\text{-}HT_{2A}$ agonism has been correlated with the promotion of neural plasticity (Ly et al., 2018). $5\text{-}HT_{2A}$ antagonists abrogate the neuritogenesis and spinogenesis effects of hallucinogenic compounds with $5\text{-}HT_{2A}$ agonist activity, for example, DMT, LSD, and DOI. In some embodiments, the compounds of the present disclosure function as $5\text{-}HT_{2A}$ modulators and promote neural plasticity (e.g., cortical structural plasticity). In some embodiments, the compounds of the present disclosure are selective $5\text{-}HT_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the presently disclosed compound forms function as serotonin receptor modulators, such as modulators of serotonin receptor 2A ($5\text{-}HT_{2A}$ modulators, e.g., $5\text{-}HT_{2A}$ agonists), are used to treat a brain disorder. The presently disclosed compounds can function as $5\text{-}HT_{2A}$ agonists alone, or in combination with a second therapeutic agent that also is a $5\text{-}HT_{2A}$ modulator. In such cases the second therapeutic agent can be an agonist or an antagonist. In some instances, it may be helpful administer a $5\text{-}HT_{2A}$ antagonist in combination with a compound form of the present disclosure to mitigate undesirable effects of $5\text{-}HT_{2A}$ agonism, such as potential hallucinogenic effects. Thus, in some embodiments of combination therapy with the presently disclosed compounds, the second therapeutic agent is a serotonin receptor modulator.

In some embodiments, non-hallucinogenic $5\text{-}HT_{2A}$ modulators (e.g., $5\text{-}HT_{2A}$ agonists) are used to treat neurological diseases. In some embodiments, the neurological diseases comprise decreased neural plasticity, decreased cortical structural plasticity, decreased $5\text{-}HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, non-hallucinogenic $5\text{-}HT_{2A}$ modulators (e.g., $5\text{-}HT_{2A}$ agonists) are used for increasing neuronal plasticity. In some embodiments, non-hallucinogenic $5\text{-}HT_{2A}$ modulators (e.g., $5\text{-}HT_{2A}$ agonists) are used for treating a brain disorder. In some embodiments, non-hallucinogenic $5\text{-}HT_{2A}$ modulators (e.g., $5\text{-}FIT_{2A}$ agonists) are used for increasing at least one of translation, transcription, or secretion of neurotrophic factors.

In some embodiments, the present disclosure provides a method of treating a disease, including administering to a subject in need thereof, a therapeutically effective amount of an psilocybin·HCl form of the present disclosure. In some embodiments the disease is a brain disorder. By way of example and not limitation, brain disorders include, for example, migraines, addiction (e.g., substance use disorder), depression, and anxiety. Such disorders also may be considered neuropsychiatric disorders or neurological disorders. In some embodiments, neurological disorders that can be treated relate to other disease conditions. Such conditions that can be treated as described herein include those wherein the disease includes a musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause. In some embodiments, the present disclosure provides a method of treating a brain disorder, including administering to a subject in need thereof, a therapeutically effective amount of a compound of the present disclosure. In some embodiments, the present disclosure provides a method of treating a brain disorder with combination therapy, including administering to a subject in need thereof, a therapeutically effective amount of a compound of the present disclosure and at least one additional therapeutic agent.

In some embodiments, the present disclosure provides a method of treating a disease, including administering to a subject in need thereof, a therapeutically effective amount of an O-acetylpsilocin salt form of the present disclosure. In some embodiments the disease is a brain disorder. By way of example and not limitation, brain disorders include, for example, migraines, addiction (e.g., substance use disorder), depression, and anxiety. Such disorders also may be considered neuropsychiatric disorders or neurological disorders. In some embodiments, neurological disorders that can be treated relate to other disease conditions. Such conditions that can be treated as described herein include those wherein the disease includes a musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause. In some embodiments, the present disclosure provides a method of treating a brain disorder, including administering to a subject in need thereof, a therapeutically effective amount of a compound of the present disclosure. In some embodiments, the present disclosure provides a method of treating a brain disorder with combination therapy, including administering to a subject in need thereof, a therapeutically effective amount of a compound of the present disclosure and at least one additional therapeutic agent.

In some embodiments, 5-$HT_{2A}$ modulators (e.g., 5-$HT_{2A}$ agonists) are used to treat a brain disorder. In some embodiments, the brain disorders comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

Methods of Increasing at Least One of Translation, Transcription, or Secretion of Neurotrophic Factors Neurotrophic factors refers to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapse in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-$HT_{2A}$ modulators (e.g., 5-$HT_{2A}$ agonists) are used to increase at least one of translation, transcription, or secretion of neurotrophic factors. In some embodiments, a compound of the present disclosure is used to increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present disclosure provides a method for increasing at least one of translation, transcription or secretion of neurotrophic factors, comprising contacting a neuronal cell with a compound disclosed herein.

Combination Therapy

In particular embodiments of treating the disorders described above, combination therapy is used as described herein.

In some embodiments, the method further comprises administering one or more additional therapeutic agent that is lithium, olanzapine (ZYPREXA®), quetiapine (SEROQUEL®), risperidone (RISPERDAL®), ariprazole (ABILIFY®), ziprasidone (GEODON®), clozapine (CLOZARIL®), divalproex sodium (DEPAKOTE®), lamotrigine (LAMICTAL®), valproic acid (DEPAKENE®), carbamazepine (EQUETRO®), topiramate (TOPAMAX®), levomilnacipran (FETZIMA®), duloxetine (CYMBALTA®, YENTREVE®), venlafaxine (EFFEXOR®), citalopram (CELEXA®), fluvoxamine (LUVOX®), escitalopram (LEXAPRO®), fluoxetine (PROZAC®), paroxetine (PAXIL®), sertraline (ZOLOFT®), clomipramine (ANAFRANIL®), amitriptyline (ELAVIL®), desipramine (NORPRAMIN®), imipramine (TOFRANIL®), nortriptyline (PAMELOR®), phenelzine (NARDIL®), tranylcypromine (PARNATE®), diazepam (VALIUM®), alprazolam (XANAX®), or clonazepam (KLONOPIN®).

In certain embodiments of the method for treating a brain disorder with a solid form disclosed herein, a second therapeutic agent that is an empathogenic agent is administered. Examples of suitable empathogenic agents for use in combination with the present solid forms include phenethylamines, such as 3,4-methylene-dioxymethamphetamine (MDMA) and analogs thereof. Other suitable empathogenic agents for use in combination with the presently disclosed compounds include, without limitation, N-Allyl-3,4-methylenedioxy-amphetamine (MDAL); N-Butyl-3,4-methylenedioxyamphetamine (MDBU); N-Benzyl-3,4-methylenedioxyamphetamine (MDBZ); N-Cyclopropylmethyl-3,4-methylenedioxyamphetamine (MDCPM); N,N-Dimethyl-3,4-methylenedioxyamphetamine (MDDM); N-Ethyl-3,4-methylenedioxyamphetamine (MDE; MDEA); N-(2-Hydroxyethyl)-3,4-methylenedioxy amphetamine (MDHOET); N-Isopropyl-3,4-methylenedioxyamphetamine (MDIP); N-Methyl-3,4-ethylenedioxyamphetamine (MDMC); N-Methoxy-3,4-methylenedioxyamphetamine (MDMEO); N-(2-Methoxyethyl)-3,4-methylenedioxyamphetamine (MDMEOET); alpha,alpha,N-Trimethyl-3,4-methylenedioxyphenethylamine (MDMP; 3,4-Methylenedioxy-N-methylphentermine; N-Hydroxy-3,4-methylenedioxyamphetamine (MDOH); 3,4-Methylenedioxyphenethylamine (MDPEA); alpha,alpha-Dimethyl-3,4-methylenedioxyphenethylamine (MDPH; 3,4-methylenedioxyphentermine); N-Propargyl-3,4-methylenedioxyamphetamine (MDPL); Methylenedioxy-2-aminoindane (MDAI); 1,3-Benzodioxolyl-N-methylbutanamine MBDB; 3,4-methylenedioxy-N-methyl-α-ethylphenylethylamine; 3,4-Methylenedioxyamphetamine MDA; Methylone (also known as "3,4-methylenedioxy-N-methylcathinone); Ethylone, also known as 3,4-methylenedioxy-N-ethylcathinone; GHB or Gamma Hydroxybutyrate or sodium oxybate; N-Propyl-3,4-methylenedioxyamphetamine (MDPR), and the like.

In some embodiments, the compounds of the present disclosure are used in combination with the standard of care therapy for a neurological disease described herein. Non-limiting examples of the standard of care therapies, may include, for example, lithium, olanzapine, quetiapine, risperidone, ariprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Nonlimiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline. Additional examples of standard of care therapeutics are known to those of ordinary skill in the art.

Combinations with Serotonin Receptor Modulators

In one embodiment of such combination therapy a form described herein is administered in combination with a serotonin receptor modulator.

In another embodiment of such combination therapy, a form of psilocybin described herein is administered in combination with a serotonin receptor modulator. In one embodiment of such therapy a form of psilocybin·HCl described herein is administered in combination with a serotonin receptor modulator. In one embodiment of such therapy a form of O-acetylpsilocin salt described herein is administered in combination with a serotonin receptor modulator. In another embodiment of such combination therapy, a form of O-acetylpsilocin-fumarate described herein is administered in combination with a serotonin receptor modulator.

Serotonin receptor modulators useful as second therapeutic agents for combination therapy as described herein are known to those of skill in the art and include, without limitation, ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperiodone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl)piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV®), an extended-release form of quetiapine, an extended-release form of risperidone (e.g., RISPERDAL CONSTA®), an extended-release form of paliperidone (e.g., INVEGA SUSTENNA® and INVEGA TRINZA®), an extended-release form of fluphenazine decanoate including PROLIXIN DECANOATE®, an extended-release form of aripiprazole lauroxil including ARISTADA®, and an extended-release form of aripiprazole including ABILIFY MAINTENA®, or a pharmaceutically acceptable salt, solvate, metabolite, deuterated analog, derivative, prodrug, or combinations thereof.

In some embodiments, the serotonin receptor modulator for combination with the presently disclosed compounds is selected from glemanserin (MDL-11,939), eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, volinanserin (MDL-100,907), pimavanserin (ACO-103), nelotanserin, lorcaserin, flibanserin, roluperiodone or a pharmaceutically acceptable salt, solvate, metabolite, deuterated analogue, derivative, prodrug, or combinations thereof.

In certain embodiments the serotonin receptor modulator is selected from the group consisting of altanserin, blonanserin, eplivanserin, glemanserin, volinanserin, ketanserin, ritanserin, pimavanserin, nelotanserin, pruvanserin, and flibanserin. In one embodiment, the serotonin receptor modulator is selected from the group consisting of eplivanserin, volinanserin, ketanserin, ritanserin, pimavanserin, nelotanserin, pruvanserin, flibanserin, olanzapine, quetiapine, and risperidone.

In some embodiments, the serotonin receptor modulator is ketanserin or a pharmaceutically acceptable salt, solvate, metabolite, deuterated analogue, derivative, or prodrug thereof. In some embodiments, the serotonin receptor modulator is pimavanserin or a pharmaceutically acceptable salt, solvate, metabolite, deuterated analogue, derivative, or prodrug thereof. In some embodiments, the serotonin receptor modulator is eplivanserin or a pharmaceutically acceptable salt, solvate, metabolite, deuterated analogue, derivative, or prodrug thereof. In some embodiments, the serotonin receptor modulator is flibanserin or a pharmaceutically acceptable salt, solvate, metabolite, deuterated analogue, derivative, or prodrug thereof. In some embodiments, the serotonin receptor modulator is roluperiodone or a pharmaceutically acceptable salt, solvate, metabolite, deuterated analogue, derivative, or prodrug thereof.

In some embodiments, the serotonin receptor modulator is administered prior to a compound disclosed herein, such as from about one to about three hours prior to administration of a compound disclosed herein. In some embodiments, the serotonin receptor modulator is administered at most about one hour prior to the presently disclosed compound. Thus, in some embodiments of combination therapy with the presently disclosed compounds, the second therapeutic agent is a serotonin receptor modulator.

Combinations with Psilocybin HCl

In one embodiment of such combination therapy, a form of psilocybin·HCl described herein is administered in combination with a serotonin receptor modulator.

In some embodiments, the serotonin receptor modulator for use with the psilocybin HCl forms disclosed herein, including those described in Table 4, is eplivanserin, wherein the eplivanserin is administered in about 1 mg to about 40 mg, or about 5 mg to about 10 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl forms disclosed herein, including those described in Table 4, is volinanserin, wherein the volinanserin is administered in about 1 mg to about 60 mg, or about 5 mg to about 20 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl forms disclosed herein, including those described in Table 4, is ketanserin, wherein the ketanserin is administered in about 10 mg to about 80 mg, about 30 mg to about 50 mg, or about 40 mg and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl forms disclosed herein, including those described in Table 4, is ritanserin, wherein the ritanserin is administered in about 1 mg to about 40 mg, or about 2.5 mg to about 10 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator is pimavanserin and the psilocybin HCl form disclosed herein, including those described in Table 4, wherein the pimavanserin is administered in about 1 mg to about 60 mg, or about 17 mg to about 34 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is nelotanserin, wherein the nelotanserin is administered in about 1 mg to about 80 mg, or about 40 mg to about 80 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is pruvanserin, wherein the pruvanserin is administered in about 1 mg to about 40 mg, or about 3 mg to about 10 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is flibanserin, wherein the flibanserin is administered in about 10 mg to about 200 mg, or about 80 mg to about 120 mg, or about 100 mg and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is olanzapine, wherein the olanzapine is administered in about 2.5 mg to about 30 mg, or about 5 mg or about 10 mg, or about 20 mg or about 25 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is an extended-release of olanzapine such as ZYPREXA RELPREVV®, wherein the extended release olanzapine is administered in about 50 mg to about 450 mg, or about 150 mg or about 210 mg, or about 300 mg or about 405 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is quetiapine, wherein the quetiapine is administered in about 25 mg to about 800 mg, or about 50 mg to about 100 mg, or about 150 mg or about 200 mg or about 250 mg or about 300 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is an extended-release of quetiapine, wherein the extended-release of quetiapine is administered in about 50 mg to about 300 mg, or about 50 mg or about 100 mg or about 200 mg, or about 300 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the psilocybin·HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl form disclosed herein, including those described in Table 4, is an extended-release of risperidone including (RISPERDAL CONSTA®), wherein the extended-release of risperidone is administered in about 12.5 mg, or about 25 mg, or about 37.5 mg, or about 50 mg, and the psilocybin HCl form disclosed herein, including those described in Table 4, is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psilocybin HCl cocrystal Form A, is eplivanserin, wherein the eplivanserin is administered in about 1 mg to about 40 mg, or about 5 mg to about 10 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is volinanserin, wherein the volinanserin is administered in about 1 mg to about 60 mg, or about 5 mg to about 20 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is ketanserin, wherein the ketanserin is administered in about 10 mg to about 80 mg, about 30 mg to about 50 mg, or about 40 mg and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is ritanserin, wherein the ritanserin is administered in about 1 mg to about 40 mg, or about 2.5 mg to about 10 mg, and the psilocybin HCl cocrystal Form A, is administered between about 10 mg to about 50 mg, or about 25 mg to about 30 mg.

In some embodiments, the serotonin receptor modulator is pimavanserin and the psilocybin HCl cocrystal Form A, wherein the pimavanserin is administered in about 1 mg to about 60 mg, or about 17 mg to about 34 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is nelotanserin, wherein the nelotanserin is administered in about 1 mg to about 80 mg, or about 40 mg to about 80 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is pruvanserin, wherein the pruvanserin is administered in about 1 mg to about 40 mg, or about 3 mg to about 10 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is flibanserin, wherein the flibanserin is administered in about 10 mg to about 200 mg, or about 80 mg to about 120 mg, or about 100 mg and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is olanzapine, wherein the olanzapine is administered in about 2.5 mg to about 30 mg, or about 5 mg or about 10 mg, or about 20 mg or about 25 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is an extended-release of olanzapine such as ZYPREXA REL-PREVV®, wherein the extended release olanzapine is administered in about 50 mg to about 450 mg, or about 150 mg or about 210 mg, or about 300 mg or about 405 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is quetiapine, wherein the quetiapine is administered in about 25 mg to about 800 mg, or about 50 mg to about 100 mg, or about 150 mg or about 200 mg or about 250 mg or about 300 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is an extended-release of quetiapine, wherein the extended-release of quetiapine is administered in about 50 mg to about 300 mg, or about 50 mg or about 100 mg or about 200 mg, or about 300 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the psilocybin HCl cocrystal Form A, is administered between about 10 mg to about 50 mg, or about 25 mg to about 30 mg.

In some embodiments, the serotonin receptor modulator for use with the psilocybin HCl cocrystal Form A, is an extended-release of risperidone including (RISPERDAL CONSTA®), wherein the extended-release of risperidone is administered in about 12.5 mg, or about 25 mg, or about 37.5 mg, or about 50 mg, and the psilocybin HCl cocrystal Form A, is administered between about 10 mg to about 50 mg, or about 25 mg to about 30 mg.

In some embodiments, the serotonin receptor modulator for use with the psilocybin HCl Form A, is eplivanserin, wherein the eplivanserin is administered in about 1 mg to about 40 mg, or about 5 mg to about 10 mg, and the psilocybin HCl Form A, is administered between about 10 mg to about 50 mg, or about 25 mg to about 30 mg.

In some embodiments, the serotonin receptor modulator for use with the psilocybin HCl Form A, is volinanserin, wherein the volinanserin is administered in about 1 mg to about 60 mg, or about 5 mg to about 20 mg, and the psilocybin HCl Form A, is administered between about 10 mg to about 50 mg, or about 25 mg to about 30 mg.

In some embodiments, the serotonin receptor modulator for use with the psilocybin HCl Form A, is ketanserin, wherein the ketanserin is administered in about 10 mg to about 80 mg, about 30 mg to about 50 mg, or about 40 mg and the psilocybin HCl Form A, is administered between about 10 mg to about 50 mg, or about 25 mg to about 30 mg.

In some embodiments, the serotonin receptor modulator for use with the psilocybin HCl Form A, is ritanserin, wherein the ritanserin is administered in about 1 mg to about 40 mg, or about 2.5 mg to about 10 mg, and the psilocybin HCl Form A, is administered between about 10 mg to about 50 mg, or about 25 mg to about 30 mg.

In some embodiments, the serotonin receptor modulator is pimavanserin and the psilocybin HCl Form A, wherein the pimavanserin is administered in about 1 mg to about 60 mg, or about 17 mg to about 34 mg, and the psilocybin HCl Form A, is administered between about 10 mg to about 50 mg, or about 25 mg to about 30 mg.

In some embodiments, the serotonin receptor modulator for use with the psilocybin HCl Form A, is nelotanserin, wherein the nelotanserin is administered in about 1 mg to about 80 mg, or about 40 mg to about 80 mg, and the psilocybin HCl Form A, is administered between about 10 mg to about 50 mg, or about 25 mg to about 30 mg.

In some embodiments, the serotonin receptor modulator for use with the psilocybin HCl Form A, is pruvanserin, wherein the pruvanserin is administered in about 1 mg to about 40 mg, or about 3 mg to about 10 mg, and the psilocybin HCl Form A, is administered between about 10 mg to about 50 mg, or about 25 mg to about 30 mg.

In some embodiments, the serotonin receptor modulator for use with the psilocybin HCl Form A, is flibanserin, wherein the flibanserin is administered in about 10 mg to about 200 mg, or about 80 mg to about 120 mg, or about 100 mg and the psilocybin HCl Form A, is administered between about 10 mg to about 50 mg, or about 25 mg to about 30 mg.

In some embodiments, the serotonin receptor modulator for use with the psilocybin HCl Form A, is olanzapine, wherein the olanzapine is administered in about 2.5 mg to about 30 mg, or about 5 mg or about 10 mg, or about 20 mg or about 25 mg, and the psilocybin HCl Form A, is administered between about 10 mg to about 50 mg, or about 25 mg to about 30 mg.

In some embodiments, the serotonin receptor modulator for use with the psilocybin HCl Form A, is an extended-release of olanzapine such as ZYPREXA RELPREVV®, wherein the extended release olanzapine is administered in about 50 mg to about 450 mg, or about 150 mg or about 210 mg, or about 300 mg or about 405 mg, and the psilocybin HCl Form A, is administered between about 10 mg to about 50 mg, or about 25 mg to about 30 mg.

In some embodiments, the serotonin receptor modulator for use with the psilocybin HCl Form A, is quetiapine, wherein quetiapine is administered in about 25 mg to about 800 mg, or about 50 mg to about 100 mg, or about 150 mg or about 200 mg or about 250 mg or about 300 mg, and the psilocybin HCl Form A, is administered between about 10 mg to about 50 mg, or about 25 mg to about 30 mg.

In some embodiments, the serotonin receptor modulator for use with psilocybin HCl Form A, is an extended-release of quetiapine, wherein quetiapine is administered in about 50 mg to about 300 mg, about 50 mg, about 100 mg, about 200 mg, or about 300 mg, and psilocybin HCl Form A, is administered between about 10 mg to about 50 mg, or about 25 mg to about 30 mg.

In some embodiments, the serotonin receptor modulator for use with the psilocybin HCl Form A, is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the psilocybin HCl Form A, is administered between about 10 mg to about 50 mg, or about 25 mg to about 30 mg.

In some embodiments, the serotonin receptor modulator for use with the psilocybin HCl Form A, is an extended-release of risperidone including (RISPERDAL CONSTA®), wherein the extended-release of risperidone is administered in about 12.5 mg, or about 25 mg, or about 37.5 mg, or about 50 mg, and the psilocybin HCl Form A, is administered between about 10 mg to about 50 mg, or about 25 mg to about 30 mg.

In some embodiments, the serotonin receptor modulator for use with the psychedelic psilocybin HCl is eplivanserin, wherein the eplivanserin is administered in about 1 mg to about 40 mg, or about 5 mg to about 10 mg, and the psilocybin HCl is administered between about 10 mg to about 50 mg, or about 25 mg to about 30 mg. In some embodiments, the amount of psilocybin·HCl is provided on a psilocybin basis.

In some embodiments, the serotonin receptor modulator is volinanserin and the psychedelic is psilocybin·HCl, wherein the volinanserin is administered in about 1 mg to about 60 mg, or about 5 mg to about 20 mg, and the psilocybin·HCl is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psychedelic psilocybin·HCl is ketanserin, wherein the ketanserin is administered in about 10 mg to about 80 mg, about 30 mg to about 50 mg, or about 40 mg and the psilocybin·HCl is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psychedelic psilocybin·HCl is ritanserin, wherein the ritanserin is administered in about 1 mg to about 40 mg, or about 2.5 mg to about 10 mg, and the psilocybin·HCl is administered between about 10 mg to about 50 mg, or about 25 mg to about 30 mg. In some embodiments, the amount of psilocybin·HCl is provided on a psilocybin basis.

In some embodiments, the serotonin receptor modulator is pimavanserin and the psychedelic is psilocybin·HCl, wherein the pimavanserin is administered in about 1 mg to about 60 mg, or about 17 mg to about 34 mg, and the psilocybin·HCl is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psychedelic psilocybin·HCl is nelotanserin, wherein the nelotanserin is administered in about 1 mg to about 80 mg, or about 40 mg to about 80 mg, and the psilocybin·HCl is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psychedelic psilocybin·HCl is pruvanserin, wherein the pruvanserin is administered in about 1 mg to about 40 mg, or about 3 mg to about 10 mg, and the psilocybin·HCl is administered between about 10 mg to about 50 mg, or about 25 mg to about 30 mg. In some embodiments, the amount of psilocybin·HCl is provided on a psilocybin basis.

In some embodiments, the serotonin receptor modulator for use with the psychedelic psilocybin·HCl is flibanserin, wherein the flibanserin is administered in about 10 mg to about 200 mg, or about 80 mg to about 120 mg, or about 100 mg and the psilocybin·HCl is administered between about 10 mg to about 50 mg, or about 25 mg to about 30 mg. In some embodiments, the amount of psilocybin·HCl is provided on a psilocybin basis.

In certain embodiments, such as those described above a psilocybin·HCl form disclosed herein, including those described in Table 4, is co-administered with a serotonin receptor modulator in the same or in separate compositions. In one embodiment, the serotonin receptor modulator is administered prior to the psilocybin HCl form disclosed herein, including those described in Table 4. In one embodiment, the psilocybin HCl form disclosed herein, including those described in Table 4, is administered in a modified release formulation such that the subject is effectively pretreated with serotonin receptor modulator prior to release of an effective amount of the psilocybin HCl. In some embodiments the serotonin receptor modulator is part of a single fixed dose formulation that releases serotonin receptor modulator first followed by the psilocybin HCl on two different release profiles. In another embodiment the serotonin receptor modulator is administered first as a single dosage and after a length of time, the psilocybin HCl form disclosed herein, including those described in Table 4, is administered as a second dosage separate from the first dosage. Thus, in some embodiments, the serotonin receptor modulator is administered or released from a composition provided herein prior to the administration and/or release of the psychedelic. This allows pretreatment to attenuate activation of the serotonin receptor by the psychedelic. In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the psychedelic. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the psychedelic.

In a preferred embodiment, the serotonin receptor modulator is administered at about 1 hour to about 3 hours prior to the administration of the psychedelic.

In some embodiments, the serotonin receptor modulator is eplivanserin and the psychedelic is psilocybin HCl, wherein the eplivanserin is administered to pretreat at least 15 minutes prior to the administration of the psilocybin HCl form disclosed herein, including those described in Table 4. In some embodiments, the serotonin receptor modulator is eplivanserin and the psychedelic is psilocybin HCl, wherein the eplivanserin is administered to pretreat between at least 30 minutes prior and 360 minutes prior to the release or administration of the psilocybin HCl form disclosed herein, including those described in Table 4. In some embodiments, the serotonin receptor modulator is eplivanserin and the psychedelic is psilocybin HCl, wherein the eplivanserin is administered to pretreat between at least 60 minutes prior and 360 minutes prior to the release or administration of the psilocybin HCl form disclosed herein, including those described in Table 4. In some embodiments, the serotonin receptor modulator is eplivanserin and the psychedelic is psilocybin HCl, wherein the eplivanserin is administered to pretreat between at least 90 minutes and 240 minutes prior to the psilocybin HCl form disclosed herein, including those described in Table 4. In some embodiments, the serotonin receptor modulator is eplivanserin and the psychedelic is psilocybin HCl, wherein the eplivanserin is administered to pretreat at least 120 minutes prior to the psilocybin HCl form disclosed herein, including those described in Table 4.

In some embodiments, the serotonin receptor modulator is eplivanserin and the psychedelic is psilocybin HCl, wherein the eplivanserin is administered to pretreat at least 150 minutes prior to the psilocybin HCl form disclosed herein, including those described in Table 4 In some embodiments, the serotonin receptor modulator is eplivanserin and the psychedelic is psilocybin HCl, wherein the eplivanserin is administered to pretreat between about 15 minutes and about 150 minutes prior to the psilocybin HCl form disclosed herein, including those described in Table 4. In some embodiments, the serotonin receptor modulator is eplivanserin and the psychedelic is psilocybin HCl, wherein the eplivanserin is administered to pretreat at least 180 minutes prior to the psilocybin HCl form disclosed herein, including those described in Table 4. In some embodiments, the serotonin receptor modulator is eplivanserin and the psychedelic is psilocybin HCl, wherein the eplivanserin is administered to pretreat at least 210 minutes prior to the psilocybin HCl form disclosed herein, including those described in Table 4. In some embodiments, the serotonin receptor modulator is eplivanserin and the psychedelic is psilocybin HCl, wherein the eplivanserin is administered to pretreat at least 240 minutes prior to the psilocybin HCl form disclosed herein, including those described in Table 4.

In some embodiments, the serotonin receptor modulator is eplivanserin and the psychedelic is psilocybin HCl, wherein the eplivanserin is administered to pretreat at least 270 minutes prior to psilocybin HCl. In some embodiments, the serotonin receptor modulator is eplivanserin and the psychedelic is psilocybin HCl, wherein the eplivanserin is administered to pretreat at least 300 minutes prior to the psilocybin HCl form disclosed herein, including those described in Table 4. In some embodiments, the serotonin receptor modulator is eplivanserin and the psychedelic is psilocybin HCl, wherein the eplivanserin is administered to pretreat at least 330 minutes prior to the psilocybin HCl form disclosed herein, including those described in Table 4. In some embodiments, the serotonin receptor modulator is eplivanserin and the psychedelic is psilocybin HCl, wherein the eplivanserin is administered to pretreat at least 360 minutes prior to the psilocybin HCl form disclosed herein, including those described in Table 4.

In some preferred embodiments, the serotonin receptor modulator is eplivanserin and the psychedelic is psilocybin HCl, wherein eplivanserin is administered to pretreat between about 60 minutes and about 180 minutes prior to the administration of the psilocybin HCl form disclosed herein, including those described in Table 4.

In some embodiments, the serotonin receptor modulator is volinanserin and the psychedelic is psilocybin HCl, wherein the volinanserin is administered to pretreat a subject between at least 15 minutes and 360 minutes prior to the administration or release of the psilocybin HCl form disclosed herein, including those described in Table 4. In some embodiments, the serotonin receptor modulator is volinanserin and the psychedelic is psilocybin HCl, wherein the volinanserin is administered to pretreat between at least 30 minutes and 360 minutes prior to the administration or release of the psilocybin HCl form disclosed herein, including those described in Table 4. In some embodiments, the serotonin receptor modulator is volinanserin and the psychedelic is psilocybin HCl, wherein the volinanserin is administered to pretreat between at least 60 minutes and 240 minutes prior to the administration or release of the psilocybin HCl form disclosed herein, including those described in Table 4. In some embodiments, the serotonin receptor modulator is volinanserin and the psychedelic is psilocybin HCl, wherein the volinanserin is administered to pretreat at least 90 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat at least 120 minutes prior to the psilocybin HCl form disclosed herein, including those described in Table 4.

In some embodiments, the serotonin receptor modulator is volinanserin and the psychedelic is psilocybin HCl, wherein the volinanserin is administered to pretreat at least 150 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat between about 15 minutes and about 150 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat at least 180 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat at least 210 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat at least 240 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat at least 270 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat at least 300 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat at least 330 minutes prior to the psilocybin HCl form disclosed herein, including those described in Table 4. In some embodiments, the serotonin receptor modulator is volinanserin and the psychedelic is psilocybin HCl, wherein the volinanserin is administered to pretreat at least 360 minutes prior to the psilocybin HCl form disclosed herein, including those described in Table 4. In some preferred embodiments, the serotonin receptor modulator is volinanserin and the psychedelic is psilocybin HCl, wherein volinanserin is administered to pretreat between about 60 minutes and about 180 minutes prior to the administration of the psilocybin HCl form disclosed herein, including those described in Table 4.

In some embodiments, the serotonin receptor modulator is ketanserin and the psychedelic is psilocybin HCl, wherein the ketanserin is administered to pretreat at least 15 minutes prior to the administration of the psilocybin HCl form disclosed herein, including those described in Table 4. In some embodiments, the serotonin receptor modulator is ketanserin and the psychedelic is psilocybin HCl, wherein the ketanserin is administered to pretreat between at least 30 minutes and 360 minutes prior to the administration or release of the psilocybin HCl form disclosed herein, including those described in Table 4. In some embodiments, the serotonin receptor modulator is ketanserin and the psychedelic is psilocybin HCl, wherein the ketanserin is administered to pretreat between at least 60 minutes and 240 minutes prior to the administration or release of the psilocybin HCl form disclosed herein, including those described in Table 4. In some embodiments, the serotonin receptor modulator is ketanserin and the psychedelic is psilocybin HCl, wherein the ketanserin is administered to pretreat at least 90 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 120 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 150 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat between about 15 minutes and about 150 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 180 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 210 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 240 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 270 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 300 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 330 minutes prior to the psilocybin HCl form disclosed herein, including those described in Table 4. In some embodiments, the serotonin receptor modulator is ketanserin and the psychedelic is psilocybin HCl, wherein the ketanserin is administered to pretreat at least 360 minutes prior to the psilocybin HCl form disclosed herein, including those described in Table 4. In some preferred embodiments, the serotonin receptor modulator is ketanserin and the psychedelic is psilocybin HCl, wherein ketanserin is administered to pretreat between about 60 minutes and about 180 minutes prior to the administration of the psilocybin HCl form disclosed herein, including those described in Table 4.

In some embodiments, the serotonin receptor modulator is ritanserin and the psychedelic is psilocybin HCl, wherein the ritanserin is administered to pretreat at least 15 minutes prior to the administration of the psilocybin HCl form disclosed herein, including those described in Table 4. In some embodiments, the serotonin receptor modulator is ritanserin and the psychedelic is psilocybin HCl, wherein the ritanserin is administered to pretreat at least 30 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat between at least 60 minutes and 240 minutes prior to the administration or release of the psilocybin HCl form disclosed herein, including those described in Table 4. In some embodiments, the serotonin receptor modulator is ritanserin and the psychedelic is psilocybin HCl, wherein the ritanserin is administered to pretreat at least 90 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 120 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 150 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat between about 15 minutes and about 150 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 180 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 210 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 240 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 270 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 300 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 330 minutes prior to the psilocybin HCl form disclosed herein, including those described in Table 4. In some embodiments, the serotonin receptor modulator is ritanserin and the psychedelic is psilocybin HCl, wherein the ritanserin is administered to pretreat at least 360 minutes prior to the psilocybin HCl form disclosed herein, including those described in Table 4. In some preferred embodiments, the serotonin receptor modulator is ritanserin and the psychedelic is psilocybin HCl, wherein ritanserin is administered to pretreat between about 60 minutes and about 180 minutes prior to the administration of the psilocybin HCl form disclosed herein, including those described in Table 4.

In some embodiments, the serotonin receptor modulator is pimavanserin and the psychedelic is psilocybin HCl, wherein the pimavanserin is administered to pretreat at least 15 minutes prior to the administration of the psilocybin HCl form disclosed herein, including those described in Table 4. In some embodiments, the serotonin receptor modulator is pimavanserin and the psychedelic is psilocybin HCl, wherein the pimavanserin is administered to pretreat at least 30 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat between at least 60 minutes and 240 minutes prior to the administration or release of the psilocybin HCl form disclosed herein, including those described in Table 4. In some embodiments, the serotonin receptor modulator is pimavanserin and the psychedelic is psilocybin HCl, wherein the pimavanserin is administered to pretreat at least 90 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 120 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 150 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat between about 15 minutes and about 150 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 180 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 210 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 240 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 270 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 300 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 330 minutes prior to the psilocybin HCl form disclosed herein, including those described in Table 4. In some embodiments, the serotonin receptor modulator is pimavanserin and the psychedelic is psilocybin HCl, wherein the pimavanserin is administered to pretreat at least 360 minutes prior to the psilocybin HCl form disclosed herein, including those described in Table 4. In some preferred embodiments, the serotonin receptor modulator is pimavanserin and the psychedelic is psilocybin HCl, wherein pimavanserin is administered to pretreat between about 60 minutes and about 180 minutes prior to the administration of the psilocybin HCl form disclosed herein, including those described in Table 4.

In some embodiments, the serotonin receptor modulator is nelotanserin and the psychedelic is psilocybin HCl, wherein the nelotanserin is administered to pretreat at least 15 minutes prior to the administration of the psilocybin HCl form disclosed herein, including those described in Table 4. In some embodiments, the serotonin receptor modulator is nelotanserin and the psychedelic is psilocybin HCl, wherein the nelotanserin is administered to pretreat at least 30 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat between at least 60 minutes and 240 minutes prior to the administration or release of the psilocybin HCl form disclosed herein, including those described in Table 4. In some embodiments, the serotonin receptor modulator is nelotanserin and the psychedelic is psilocybin HCl, wherein the nelotanserin is administered to pretreat at least 90 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat at least 120 minutes prior to the psilocybin HCl form disclosed herein, including those described in Table 4.

In some embodiments, the serotonin receptor modulator is nelotanserin and the psychedelic is psilocybin HCl, wherein the nelotanserin is administered to pretreat at least 150 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat between about 15 minutes and about 150 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat at least 180 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat at least 210 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat at least 240 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat at least 270 minutes prior to the psilocybin HCl form disclosed herein, including those described in Table 4.

In some embodiments, the serotonin receptor modulator is nelotanserin and the psychedelic is psilocybin HCl, wherein the nelotanserin is administered to pretreat at least 300 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat at least 330 minutes prior to the psilocybin HCl form disclosed herein, including those described in Table 4. In some embodiments, the serotonin receptor modulator is nelotanserin and the psychedelic is psilocybin HCl, wherein the nelotanserin is administered to pretreat at least 360 minutes prior to the psilocybin HCl form disclosed herein, including those described in Table 4. In some preferred embodiments, the serotonin receptor modulator is nelotanserin and the psychedelic is psilocybin HCl, wherein nelotanserin is administered to pretreat between about 60 minutes and about 180 minutes prior to the administration of the psilocybin HCl form disclosed herein, including those described in Table 4.

In some embodiments, the serotonin receptor modulator is pruvanserin and the psychedelic is psilocybin HCl, wherein the pruvanserin is administered to pretreat at least 15 minutes prior to the administration of the psilocybin HCl form disclosed herein, including those described in Table 4. In some embodiments, the serotonin receptor modulator is pruvanserin and the psychedelic is psilocybin HCl, wherein the pruvanserin is administered to pretreat at least 30 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat between at least 60 minutes and 240 minutes prior to the administration or release of the psilocybin HCl form disclosed herein, including those described in Table 4. In some embodiments, the serotonin receptor modulator is pruvanserin and the psychedelic is psilocybin HCl, wherein the pruvanserin is administered to pretreat at least 90 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat at least 120 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat at least 150 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat between about 15 minutes and about 150 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat at least 180 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat at least 210 minutes prior to the psilocybin HCl form disclosed herein, including those described in Table 4.

In some embodiments, the serotonin receptor modulator is pruvanserin and the psychedelic is psilocybin HCl, wherein the pruvanserin is administered to pretreat at least 240 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat at least 270 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat at least 300 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat at least 330 minutes prior to the psilocybin HCl form disclosed herein, including those described in Table 4. In some embodiments, the serotonin receptor modulator is pruvanserin and the psychedelic is psilocybin HCl, wherein the pruvanserin is administered to pretreat at least 360 minutes prior to the psilocybin HCl form disclosed herein, including those described in Table 4. In some preferred embodiments, the serotonin receptor modulator is pruvanserin and the psychedelic is psilocybin HCl, wherein pruvanserin is administered to pretreat between about 60 minutes and about 180 minutes prior to the administration of the psilocybin HCl form disclosed herein, including those described in Table 4.

In some embodiments, the serotonin receptor modulator is flibanserin and the psychedelic is psilocybin HCl, wherein the flibanserin is administered to pretreat at least 15 minutes prior to the administration of the psilocybin HCl form disclosed herein, including those described in Table 4. In some embodiments, the serotonin receptor modulator is flibanserin and the psychedelic is psilocybin HCl, wherein the flibanserin is administered to pretreat at least 30 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat between at least 60 minutes and 240 minutes prior to the administration or release of the psilocybin HCl form disclosed herein, including those described in Table 4. In some embodiments, the serotonin receptor modulator is flibanserin and the psychedelic is psilocybin HCl, wherein the flibanserin is administered to pretreat at least 90 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat at least 120 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat at least 150 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat between about 15 minutes and about 150 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat at least 180 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat at least 210 minutes prior to the psilocybin HCl form disclosed herein, including those described in Table 4.

In some embodiments, the serotonin receptor modulator is flibanserin and the psychedelic is psilocybin HCl, wherein the flibanserin is administered to pretreat at least 240 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat at least 270 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat at least 300 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat at least 330 minutes prior to the psilocybin HCl form disclosed herein, including those described in Table 4. In some embodiments, the serotonin receptor modulator is flibanserin and the psychedelic is psilocybin HCl, wherein the flibanserin is administered to pretreat at least 360 minutes prior to the psilocybin HCl form disclosed herein, including those described in Table 4. In some preferred embodiments, the serotonin receptor modulator is flibanserin and the psychedelic is psilocybin HCl, wherein flibanserin is administered to pretreat between about 60 minutes and about 180 minutes prior to the administration of the psilocybin HCl form disclosed herein, including those described in Table 4.

In some embodiments, the serotonin receptor modulator is olanzapine and the psychedelic is psilocybin HCl, wherein the olanzapine is administered to pretreat at least 15 minutes prior to the administration of the psilocybin HCl form disclosed herein, including those described in Table 4. In some embodiments, the serotonin receptor modulator is olanzapine and the psychedelic is psilocybin HCl, wherein the olanzapine is administered to pretreat at least 30 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat between at least 60 minutes and 240 minutes prior to the administration or release of the psilocybin HCl form disclosed herein, including those described in Table 4. In some embodiments, the serotonin receptor modulator is olanzapine and the psychedelic is psilocybin HCl, wherein the olanzapine is administered to pretreat at least 90 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat at least 120 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat at least 150 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat between about 15 minutes and about 150 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat at least 180 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat at least 210 minutes prior to the psilocybin HCl form disclosed herein, including those described in Table 4.

In some embodiments, the serotonin receptor modulator is olanzapine and the psychedelic is psilocybin HCl, wherein the olanzapine is administered to pretreat at least 240 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat at least 270 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat at least 300 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat at least 330 minutes prior to the psilocybin HCl form disclosed herein, including those described in Table 4. In some embodiments, the serotonin receptor modulator is olanzapine and the psychedelic is psilocybin HCl, wherein the olanzapine is administered to pretreat at least 360 minutes prior to the psilocybin HCl form disclosed herein, including those described in Table 4. In some preferred embodiments, the serotonin receptor modulator is olanzapine and the psychedelic is psilocybin HCl, wherein olanzapine is administered to pretreat between about 60 minutes and about 180 minutes prior to the administration of the psilocybin HCl form disclosed herein, including those described in Table 4.

In some embodiments, the serotonin receptor modulator is risperidone and the psychedelic is psilocybin HCl, wherein the risperidone is administered to pretreat at least 15 minutes prior to the administration of the psilocybin HCl form disclosed herein, including those described in Table 4. In some embodiments, the serotonin receptor modulator is risperidone and the psychedelic is psilocybin HCl, wherein the risperidone is administered to pretreat at least 30 minutes prior to the psilocybin HCl form disclosed herein, including those described in Table 4. In some embodiments, the serotonin receptor modulator is risperidone and the psychedelic is psilocybin HCl, wherein the risperidone is administered to pretreat between at least 60 minutes and 240 minutes prior to the administration or release of the psilocybin HCl form disclosed herein, including those described in Table 4. In some embodiments, the serotonin receptor modulator is risperidone and the psychedelic is psilocybin HCl, wherein the risperidone is administered to pretreat at least 90 minutes prior to the psilocybin HCl form disclosed herein, including those described in Table 4. In some embodiments, the serotonin receptor modulator is risperidone and the psychedelic is psilocybin HCl, wherein the risperidone is administered to pretreat at least 120 minutes prior to the psilocybin HCl form disclosed herein, including those described in Table 4. In some embodiments, the serotonin receptor modulator is risperidone and the psychedelic is psilocybin HCl, wherein the risperidone is administered to pretreat at least 150 minutes prior to the psilocybin HCl form disclosed herein, including those described in Table 4. In some embodiments, the serotonin receptor modulator is risperidone and the psychedelic is psilocybin HCl, wherein the risperidone is administered to pretreat between about 15 minutes and about 150 minutes prior to the psilocybin HCl form disclosed herein, including those described in Table 4. In some embodiments, the serotonin receptor modulator is risperidone and the psychedelic is psilocybin HCl, wherein the risperidone is administered to pretreat at least 180 minutes prior to the psilocybin HCl form disclosed herein, including those described in Table 4. In some embodiments, the serotonin receptor modulator is risperidone and the psychedelic is psilocybin HCl, wherein the risperidone is administered to pretreat at least 210 minutes prior to the psilocybin HCl form disclosed herein, including those described in Table 4.

In some embodiments, the serotonin receptor modulator is risperidone and the psychedelic is psilocybin HCl, wherein the risperidone is administered to pretreat at least 240 minutes prior to the psilocybin HCl form disclosed herein, including those described in Table 4. In some embodiments, the serotonin receptor modulator is risperidone and the psychedelic is psilocybin HCl, wherein the risperidone is administered to pretreat at least 270 minutes prior to the psilocybin HCl form disclosed herein, including those described in Table 4. In some embodiments, the serotonin receptor modulator is risperidone and the psychedelic is psilocybin HCl, wherein the risperidone is administered to pretreat at least 300 minutes prior to the psilocybin HCl form disclosed herein, including those described in Table 4. In some embodiments, the serotonin receptor modulator is risperidone and the psychedelic is psilocybin HCl, wherein the risperidone is administered to pretreat at least 330 minutes prior to the psilocybin HCl form disclosed herein, including those described in Table 4. In some embodiments, the serotonin receptor modulator is risperidone and the psychedelic is psilocybin HCl, wherein the risperidone is administered to pretreat at least 360 minutes prior to the psilocybin HCl form disclosed herein, including those described in Table 4. In some preferred embodiments, the serotonin receptor modulator is risperidone and the psychedelic is psilocybin HCl, wherein risperidone is administered to pretreat between about 60 minutes and about 180 minutes prior to the administration of the psilocybin HCl form disclosed herein, including those described in Table 4.

In some embodiments, the serotonin receptor modulator is quetiapine and the psychedelic is psilocybin HCl, wherein the quetiapine is administered to pretreat at least 15 minutes prior to the administration of the psilocybin HCl form disclosed herein, including those described in Table 4. In some embodiments, the serotonin receptor modulator is quetiapine and the psychedelic is psilocybin HCl, wherein the quetiapine is administered to pretreat at least 30 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat between at least 60 minutes and 240 minutes prior to the administration or release of the psilocybin HCl form disclosed herein, including those described in Table 4. In some embodiments, the serotonin receptor modulator is quetiapine and the psychedelic is psilocybin HCl, wherein the quetiapine is administered to pretreat at least 90 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat at least 120 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat at least 150 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat between about 15 minutes and about 150 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat at least 180 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat at least 210 minutes prior to the psilocybin HCl form disclosed herein, including those described in Table 4.

In some embodiments, the serotonin receptor modulator is quetiapine and the psychedelic is psilocybin HCl, wherein the quetiapine is administered to pretreat at least 240 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat at least 270 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat at least 300 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat at least 330 minutes prior to the psilocybin HCl form disclosed herein, including those described in Table 4. In some embodiments, the serotonin receptor modulator is quetiapine and the psychedelic is psilocybin HCl, wherein the quetiapine is administered to pretreat at least 360 minutes prior to the psilocybin HCl form disclosed herein, including those described in Table 4. In some preferred embodiments, the serotonin receptor modulator is quetiapine and the psychedelic is psilocybin HCl, wherein quetiapine is administered to pretreat between about 60 minutes and about 180 minutes prior to the administration of the psilocybin HCl form disclosed herein, including those described in Table 4.

In some embodiments, the serotonin receptor modulator is eplivanserin and the psychedelic is psilocybin HCl cocrystal Form A, wherein the eplivanserin is administered to pretreat at least 15 minutes prior to the administration of the psilocybin HCl cocrystal Form A. In some embodiments, the serotonin receptor modulator is eplivanserin and the psychedelic is psilocybin HCl cocrystal Form A, wherein the eplivanserin is administered to pretreat between at least 30 minutes prior and 360 minutes prior to the release or administration of the psilocybin HCl cocrystal Form A. In some embodiments, the serotonin receptor modulator is eplivanserin and the psychedelic is psilocybin HCl cocrystal Form A, wherein the eplivanserin is administered to pretreat between at least 60 minutes prior and 360 minutes prior to the release or administration of the psilocybin HCl cocrystal Form A.

In some embodiments, the serotonin receptor modulator is eplivanserin and the psychedelic is psilocybin HCl cocrystal Form A, wherein the eplivanserin is administered to pretreat between at least 90 minutes and 240 minutes prior to the psilocybin HCl cocrystal Form A. In some embodiments, the serotonin receptor modulator is eplivanserin and the psychedelic is psilocybin HCl cocrystal Form A, wherein the eplivanserin is administered to pretreat at least 120 minutes prior to the psilocybin HCl cocrystal Form A.

In some embodiments, the serotonin receptor modulator is eplivanserin and the psychedelic is psilocybin HCl cocrystal Form A, wherein the eplivanserin is administered to pretreat at least 150 minutes prior to the psilocybin HCl cocrystal Form A In some embodiments, the serotonin receptor modulator is eplivanserin and the psychedelic is psilocybin HCl cocrystal Form A, wherein the eplivanserin is administered to pretreat between about 15 minutes and about 150 minutes prior to the psilocybin HCl cocrystal Form A. In some embodiments, the serotonin receptor modulator is eplivanserin and the psychedelic is psilocybin HCl cocrystal Form A, wherein the eplivanserin is administered to pretreat at least 180 minutes prior to the psilocybin HCl cocrystal Form A. In some embodiments, the serotonin receptor modulator is eplivanserin and the psychedelic is psilocybin HCl cocrystal Form A, wherein the eplivanserin is administered to pretreat at least 210 minutes prior to the psilocybin HCl cocrystal Form A. In some embodiments, the serotonin receptor modulator is eplivanserin and the psychedelic is psilocybin HCl cocrystal Form A, wherein the eplivanserin is administered to pretreat at least 240 minutes prior to the psilocybin HCl cocrystal Form A.

In some embodiments, the serotonin receptor modulator is eplivanserin and the psychedelic is psilocybin HCl cocrystal Form A, wherein the eplivanserin is administered to pretreat at least 270 minutes prior to psilocybin HCl. In some embodiments, the serotonin receptor modulator is eplivanserin and the psychedelic is psilocybin HCl cocrystal Form A, wherein the eplivanserin is administered to pretreat at least 300 minutes prior to the psilocybin HCl cocrystal Form A. In some embodiments, the serotonin receptor modulator is eplivanserin and the psychedelic is psilocybin HCl cocrystal Form A, wherein the eplivanserin is administered to pretreat at least 330 minutes prior to the psilocybin HCl cocrystal Form A. In some embodiments, the serotonin receptor modulator is eplivanserin and the psychedelic is psilocybin HCl cocrystal Form A, wherein the eplivanserin is administered to pretreat at least 360 minutes prior to the psilocybin HCl cocrystal Form A.

In some preferred embodiments, the serotonin receptor modulator is eplivanserin and the psychedelic is psilocybin HCl cocrystal Form A, wherein eplivanserin is administered to pretreat between about 60 minutes and about 180 minutes prior to the administration of the psilocybin HCl cocrystal Form A.

In some embodiments, the serotonin receptor modulator is volinanserin and the psychedelic is psilocybin HCl cocrystal Form A, wherein the volinanserin is administered to pretreat a subject between at least 15 minutes and 360 minutes prior to the administration or release of the psilocybin HCl cocrystal Form A. In some embodiments, the serotonin receptor modulator is volinanserin and the psychedelic is psilocybin HCl cocrystal Form A, wherein the volinanserin is administered to pretreat between at least 30 minutes and 360 minutes prior to the administration or release of the psilocybin HCl cocrystal Form A. In some embodiments, the serotonin receptor modulator is volinanserin and the psychedelic is psilocybin HCl cocrystal Form A, wherein the volinanserin is administered to pretreat between at least 60 minutes and 240 minutes prior to the administration or release of the psilocybin HCl cocrystal Form A. In some embodiments, the serotonin receptor modulator is volinanserin and the psychedelic is psilocybin HCl cocrystal Form A, wherein the volinanserin is administered to pretreat at least 90 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat at least 120 minutes prior to the psilocybin HCl cocrystal Form A.

In some embodiments, the serotonin receptor modulator is volinanserin and the psychedelic is psilocybin HCl cocrystal Form A, wherein the volinanserin is administered to pretreat at least 150 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat between about 15 minutes and about 150 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat at least 180 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat at least 210 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat at least 240 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat at least 270 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat at least 300 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat at least 330 minutes prior to the psilocybin HCl cocrystal Form A. In some embodiments, the serotonin receptor modulator is volinanserin and the psychedelic is psilocybin HCl cocrystal Form A, wherein the volinanserin is administered to pretreat at least 360 minutes prior to the psilocybin HCl cocrystal Form A. In some preferred embodiments, the serotonin receptor modulator is volinanserin and the psychedelic is psilocybin HCl cocrystal Form A, wherein volinanserin is administered to pretreat between about 60 minutes and about 180 minutes prior to the administration of the psilocybin HCl cocrystal Form A.

In some embodiments, the serotonin receptor modulator is ketanserin and the psychedelic is psilocybin HCl cocrystal Form A, wherein the ketanserin is administered to pretreat at least 15 minutes prior to the administration of the psilocybin HCl cocrystal Form A. In some embodiments, the serotonin receptor modulator is ketanserin and the psychedelic is psilocybin HCl cocrystal Form A, wherein the ketanserin is administered to pretreat between at least 30 minutes and 360 minutes prior to the administration or release of the psilocybin HCl cocrystal Form A. In some embodiments, the serotonin receptor modulator is ketanserin and the psychedelic is psilocybin HCl cocrystal Form A, wherein the ketanserin is administered to pretreat between at least 60 minutes and 240 minutes prior to the administration or release of the psilocybin HCl cocrystal Form A. In some embodiments, the serotonin receptor modulator is ketanserin and the psychedelic is psilocybin HCl cocrystal Form A, wherein the ketanserin is administered to pretreat at least 90 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 120 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 150 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat between about 15 minutes and about 150 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 180 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 210 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 240 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 270 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 300 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 330 minutes prior to the psilocybin HCl cocrystal Form A. In some embodiments, the serotonin receptor modulator is ketanserin and the psychedelic is psilocybin HCl cocrystal Form A, wherein the ketanserin is administered to pretreat at least 360 minutes prior to the psilocybin HCl cocrystal Form A. In some preferred embodiments, the serotonin receptor modulator is ketanserin and the psychedelic is psilocybin HCl cocrystal Form A, wherein ketanserin is administered to pretreat between about 60 minutes and about 180 minutes prior to the administration of the psilocybin HCl cocrystal Form A.

In some embodiments, the serotonin receptor modulator is ritanserin and the psychedelic is psilocybin HCl cocrystal Form A, wherein the ritanserin is administered to pretreat at least 15 minutes prior to the administration of the psilocybin HCl cocrystal Form A. In some embodiments, the serotonin receptor modulator is ritanserin and the psychedelic is psilocybin HCl cocrystal Form A, wherein the ritanserin is administered to pretreat at least 30 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat between at least 60 minutes and 240 minutes prior to the administration or release of the psilocybin HCl cocrystal Form A. In some embodiments, the serotonin receptor modulator is ritanserin and the psychedelic is psilocybin HCl cocrystal Form A, wherein the ritanserin is administered to pretreat at least 90 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 120 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 150 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat between about 15 minutes and about 150 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 180 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 210 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 240 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 270 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 300 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 330 minutes prior to the psilocybin HCl cocrystal Form A. In some embodiments, the serotonin receptor modulator is ritanserin and the psychedelic is psilocybin HCl cocrystal Form A, wherein the ritanserin is administered to pretreat at least 360 minutes prior to the psilocybin HCl cocrystal Form A. In some preferred embodiments, the serotonin receptor modulator is ritanserin and the psychedelic is psilocybin HCl cocrystal Form A, wherein ritanserin is administered to pretreat between about 60 minutes and about 180 minutes prior to the administration of the psilocybin HCl cocrystal Form A.

In some embodiments, the serotonin receptor modulator is pimavanserin and the psychedelic is psilocybin HCl cocrystal Form A, wherein the pimavanserin is administered to pretreat at least 15 minutes prior to the administration of the psilocybin HCl cocrystal Form A. In some embodiments, the serotonin receptor modulator is pimavanserin and the psychedelic is psilocybin HCl cocrystal Form A, wherein the pimavanserin is administered to pretreat at least 30 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat between at least 60 minutes and 240 minutes prior to the administration or release of the psilocybin HCl cocrystal Form A. In some embodiments, the serotonin receptor modulator is pimavanserin and the psychedelic is psilocybin HCl cocrystal Form A, wherein the pimavanserin is administered to pretreat at least 90 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 120 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 150 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat between about 15 minutes and about 150 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 180 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 210 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 240 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 270 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 300 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 330 minutes prior to the psilocybin HCl cocrystal Form A. In some embodiments, the serotonin receptor modulator is pimavanserin and the psychedelic is psilocybin HCl cocrystal Form A, wherein the pimavanserin is administered to pretreat at least 360 minutes prior to the psilocybin HCl cocrystal Form A. In some preferred embodiments, the serotonin receptor modulator is pimavanserin and the psychedelic is psilocybin HCl cocrystal Form A, wherein pimavanserin is administered to pretreat between about 60 minutes and about 180 minutes prior to the administration of the psilocybin HCl cocrystal Form A.

In some embodiments, the serotonin receptor modulator is nelotanserin and the psychedelic is psilocybin HCl cocrystal Form A, wherein the nelotanserin is administered to pretreat at least 15 minutes prior to the administration of the psilocybin HCl cocrystal Form A. In some embodiments, the serotonin receptor modulator is nelotanserin and the psychedelic is psilocybin HCl cocrystal Form A, wherein the nelotanserin is administered to pretreat at least 30 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat between at least 60 minutes and 240 minutes prior to the administration or release of the psilocybin HCl cocrystal Form A. In some embodiments, the serotonin receptor modulator is nelotanserin and the psychedelic is psilocybin HCl cocrystal Form A, wherein the nelotanserin is administered to pretreat at least 90 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat at least 120 minutes prior to the psilocybin HCl cocrystal Form A.

In some embodiments, the serotonin receptor modulator is nelotanserin and the psychedelic is psilocybin HCl cocrystal Form A, wherein the nelotanserin is administered to pretreat at least 150 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat between about 15 minutes and about 150 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat at least 180 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat at least 210 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat at least 240 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat at least 270 minutes prior to the psilocybin HCl cocrystal Form A.

In some embodiments, the serotonin receptor modulator is nelotanserin and the psychedelic is psilocybin HCl cocrystal Form A, wherein the nelotanserin is administered to pretreat at least 300 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat at least 330 minutes prior to the psilocybin HCl cocrystal Form A. In some embodiments, the serotonin receptor modulator is nelotanserin and the psychedelic is psilocybin HCl cocrystal Form A, wherein the nelotanserin is administered to pretreat at least 360 minutes prior to the psilocybin HCl cocrystal Form A. In some preferred embodiments, the serotonin receptor modulator is nelotanserin and the psychedelic is psilocybin HCl cocrystal Form A, wherein nelotanserin is administered to pretreat between about 60 minutes and about 180 minutes prior to the administration of the psilocybin HCl cocrystal Form A.

In some embodiments, the serotonin receptor modulator is pruvanserin and the psychedelic is psilocybin HCl cocrystal Form A, wherein the pruvanserin is administered to pretreat at least 15 minutes prior to the administration of the psilocybin HCl cocrystal Form A. In some embodiments, the serotonin receptor modulator is pruvanserin and the psychedelic is psilocybin HCl cocrystal Form A, wherein the pruvanserin is administered to pretreat at least 30 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat between at least 60 minutes and 240 minutes prior to the administration or release of the psilocybin HCl cocrystal Form A. In some embodiments, the serotonin receptor modulator is pruvanserin and the psychedelic is psilocybin HCl cocrystal Form A, wherein the pruvanserin is administered to pretreat at least 90 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat at least 120 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat at least 150 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat between about 15 minutes and about 150 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat at least 180 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat at least 210 minutes prior to the psilocybin HCl cocrystal Form A.

In some embodiments, the serotonin receptor modulator is pruvanserin and the psychedelic is psilocybin HCl cocrystal Form A, wherein the pruvanserin is administered to pretreat at least 240 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat at least 270 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat at least 300 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat at least 330 minutes prior to the psilocybin HCl cocrystal Form A. In some embodiments, the serotonin receptor modulator is pruvanserin and the psychedelic is psilocybin HCl cocrystal Form A, wherein the pruvanserin is administered to pretreat at least 360 minutes prior to the psilocybin HCl cocrystal Form A. In some preferred embodiments, the serotonin receptor modulator is pruvanserin and the psychedelic is psilocybin HCl cocrystal Form A, wherein pruvanserin is administered to pretreat between about 60 minutes and about 180 minutes prior to the administration of the psilocybin HCl cocrystal Form A.

In some embodiments, the serotonin receptor modulator is flibanserin and the psychedelic is psilocybin HCl cocrystal Form A, wherein the flibanserin is administered to pretreat at least 15 minutes prior to the administration of the psilocybin HCl cocrystal Form A. In some embodiments, the serotonin receptor modulator is flibanserin and the psychedelic is psilocybin HCl cocrystal Form A, wherein the flibanserin is administered to pretreat at least 30 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat between at least 60 minutes and 240 minutes prior to the administration or release of the psilocybin HCl cocrystal Form A. In some embodiments, the serotonin receptor modulator is flibanserin and the psychedelic is psilocybin HCl cocrystal Form A, wherein the flibanserin is administered to pretreat at least 90 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat at least 120 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat at least 150 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat between about 15 minutes and about 150 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat at least 180 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat at least 210 minutes prior to the psilocybin HCl cocrystal Form A.

In some embodiments, the serotonin receptor modulator is flibanserin and the psychedelic is psilocybin HCl cocrystal Form A, wherein the flibanserin is administered to pretreat at least 240 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat at least 270 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat at least 300 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat at least 330 minutes prior to the psilocybin HCl cocrystal Form A. In some embodiments, the serotonin receptor modulator is flibanserin and the psychedelic is psilocybin HCl cocrystal Form A, wherein the flibanserin is administered to pretreat at least 360 minutes prior to the psilocybin HCl cocrystal Form A. In some preferred embodiments, the serotonin receptor modulator is flibanserin and the psychedelic is psilocybin HCl cocrystal Form A, wherein flibanserin is administered to pretreat between about 60 minutes and about 180 minutes prior to the administration of the psilocybin HCl cocrystal Form A.

In some embodiments, the serotonin receptor modulator is olanzapine and the psychedelic is psilocybin HCl cocrystal Form A, wherein the olanzapine is administered to pretreat at least 15 minutes prior to the administration of the psilocybin HCl cocrystal Form A. In some embodiments, the serotonin receptor modulator is olanzapine and the psychedelic is psilocybin HCl cocrystal Form A, wherein the olanzapine is administered to pretreat at least 30 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat between at least 60 minutes and 240 minutes prior to the administration or release of the psilocybin HCl cocrystal Form A. In some embodiments, the serotonin receptor modulator is olanzapine and the psychedelic is psilocybin HCl cocrystal Form A, wherein the olanzapine is administered to pretreat at least 90 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat at least 120 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat at least 150 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat between about 15 minutes and about 150 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat at least 180 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat at least 210 minutes prior to the psilocybin HCl cocrystal Form A.

In some embodiments, the serotonin receptor modulator is olanzapine and the psychedelic is psilocybin HCl cocrystal Form A, wherein the olanzapine is administered to pretreat at least 240 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat at least 270 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat at least 300 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat at least 330 minutes prior to the psilocybin HCl cocrystal Form A. In some embodiments, the serotonin receptor modulator is olanzapine and the psychedelic is psilocybin HCl cocrystal Form A, wherein the olanzapine is administered to pretreat at least 360 minutes prior to the psilocybin HCl cocrystal Form A. In some preferred embodiments, the serotonin receptor modulator is olanzapine and the psychedelic is psilocybin HCl cocrystal Form A, wherein olanzapine is administered to pretreat between about 60 minutes and about 180 minutes prior to the administration of the psilocybin HCl cocrystal Form A.

In some embodiments, the serotonin receptor modulator is risperidone and the psychedelic is psilocybin HCl cocrystal Form A, wherein the risperidone is administered to pretreat at least 15 minutes prior to the administration of the psilocybin HCl cocrystal Form A. In some embodiments, the serotonin receptor modulator is risperidone and the psychedelic is psilocybin HCl cocrystal Form A, wherein the risperidone is administered to pretreat at least 30 minutes prior to the psilocybin HCl cocrystal Form A. In some embodiments, the serotonin receptor modulator is risperidone and the psychedelic is psilocybin HCl cocrystal Form A, wherein the risperidone is administered to pretreat between at least 60 minutes and 240 minutes prior to the administration or release of the psilocybin HCl cocrystal Form A. In some embodiments, the serotonin receptor modulator is risperidone and the psychedelic is psilocybin HCl cocrystal Form A, wherein the risperidone is administered to pretreat at least 90 minutes prior to the psilocybin HCl cocrystal Form A. In some embodiments, the serotonin receptor modulator is risperidone and the psychedelic is psilocybin HCl cocrystal Form A, wherein the risperidone is administered to pretreat at least 120 minutes prior to the psilocybin HCl cocrystal Form A. In some embodiments, the serotonin receptor modulator is risperidone and the psychedelic is psilocybin HCl cocrystal Form A, wherein the risperidone is administered to pretreat at least 150 minutes prior to the psilocybin HCl cocrystal Form A. In some embodiments, the serotonin receptor modulator is risperidone and the psychedelic is psilocybin HCl cocrystal Form A, wherein the risperidone is administered to pretreat between about 15 minutes and about 150 minutes prior to the psilocybin HCl cocrystal Form A. In some embodiments, the serotonin receptor modulator is risperidone and the psychedelic is psilocybin HCl cocrystal Form A, wherein the risperidone is administered to pretreat at least 180 minutes prior to the psilocybin HCl cocrystal Form A. In some embodiments, the serotonin receptor modulator is risperidone and the psychedelic is psilocybin HCl cocrystal Form A, wherein the risperidone is administered to pretreat at least 210 minutes prior to the psilocybin HCl cocrystal Form A.

In some embodiments, the serotonin receptor modulator is risperidone and the psychedelic is psilocybin HCl cocrystal Form A, wherein the risperidone is administered to pretreat at least 240 minutes prior to the psilocybin HCl cocrystal Form A. In some embodiments, the serotonin receptor modulator is risperidone and the psychedelic is psilocybin HCl cocrystal Form A, wherein the risperidone is administered to pretreat at least 270 minutes prior to the psilocybin HCl cocrystal Form A. In some embodiments, the serotonin receptor modulator is risperidone and the psychedelic is psilocybin HCl cocrystal Form A, wherein the risperidone is administered to pretreat at least 300 minutes prior to the psilocybin HCl cocrystal Form A. In some embodiments, the serotonin receptor modulator is risperidone and the psychedelic is psilocybin HCl cocrystal Form A, wherein the risperidone is administered to pretreat at least 330 minutes prior to the psilocybin HCl cocrystal Form A. In some embodiments, the serotonin receptor modulator is risperidone and the psychedelic is psilocybin HCl cocrystal Form A, wherein the risperidone is administered to pretreat at least 360 minutes prior to the psilocybin HCl cocrystal Form A. In some preferred embodiments, the serotonin receptor modulator is risperidone and the psychedelic is psilocybin HCl cocrystal Form A, wherein risperidone is administered to pretreat between about 60 minutes and about 180 minutes prior to the administration of the psilocybin HCl cocrystal Form A.

In some embodiments, the serotonin receptor modulator is quetiapine and the psychedelic is psilocybin HCl cocrystal Form A, wherein the quetiapine is administered to pretreat at least 15 minutes prior to the administration of the psilocybin HCl cocrystal Form A. In some embodiments, the serotonin receptor modulator is quetiapine and the psychedelic is psilocybin HCl cocrystal Form A, wherein the quetiapine is administered to pretreat at least 30 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat between at least 60 minutes and 240 minutes prior to the administration or release of the psilocybin HCl cocrystal Form A. In some embodiments, the serotonin receptor modulator is quetiapine and the psychedelic is psilocybin HCl cocrystal Form A, wherein the quetiapine is administered to pretreat at least 90 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat at least 120 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat at least 150 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat between about 15 minutes and about 150 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat at least 180 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat at least 210 minutes prior to the psilocybin HCl cocrystal Form A.

In some embodiments, the serotonin receptor modulator is quetiapine and the psychedelic is psilocybin HCl cocrystal Form A, wherein the quetiapine is administered to pretreat at least 240 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat at least 270 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat at least 300 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat at least 330 minutes prior to the psilocybin HCl cocrystal Form A. In some embodiments, the serotonin receptor modulator is quetiapine and the psychedelic is psilocybin HCl cocrystal Form A, wherein the quetiapine is administered to pretreat at least 360 minutes prior to the psilocybin HCl cocrystal Form A. In some preferred embodiments, the serotonin receptor modulator is quetiapine and the psychedelic is psilocybin HCl cocrystal Form A, wherein quetiapine is administered to pretreat between about 60 minutes and about 180 minutes prior to the administration of the psilocybin HCl cocrystal Form A.

In some embodiments, the serotonin receptor modulator is eplivanserin and the psychedelic is psilocybin HCl Form A, wherein the eplivanserin is administered to pretreat at least 15 minutes prior to the administration of the psilocybin HCl Form A. In some embodiments, the serotonin receptor modulator is eplivanserin and the psychedelic is psilocybin HCl Form A, wherein the eplivanserin is administered to pretreat between at least 30 minutes prior and 360 minutes prior to the release or administration of the psilocybin HCl Form A. In some embodiments, the serotonin receptor modulator is eplivanserin and the psychedelic is psilocybin HCl Form A, wherein eplivanserin is administered to pretreat between at least 60 minutes prior and 360 minutes prior to the release or administration of the psilocybin HCl Form A. In some embodiments, the serotonin receptor modulator is eplivanserin and the psychedelic is psilocybin HCl Form A, wherein eplivanserin is administered to pretreat between at least 90 minutes and 240 minutes prior to the psilocybin HCl Form A. In some embodiments, the serotonin receptor modulator is eplivanserin and the psychedelic is psilocybin HCl Form A, wherein eplivanserin is administered to pretreat at least 120 minutes prior to psilocybin HCl Form A.

In some embodiments, the serotonin receptor modulator is eplivanserin and the psychedelic is psilocybin HCl Form A, wherein the eplivanserin is administered to pretreat at least 150 minutes prior to the psilocybin HCl Form A In some embodiments, the serotonin receptor modulator is eplivanserin and the psychedelic is psilocybin HCl Form A, wherein the eplivanserin is administered to pretreat between about 15 minutes and about 150 minutes prior to the psilocybin HCl Form A. In some embodiments, the serotonin receptor modulator is eplivanserin and the psychedelic is psilocybin HCl Form A, wherein the eplivanserin is administered to pretreat at least 180 minutes prior to the psilocybin HCl Form A. In some embodiments, the serotonin receptor modulator is eplivanserin and the psychedelic is psilocybin HCl Form A, wherein the eplivanserin is administered to pretreat at least 210 minutes prior to the psilocybin HCl Form A. In some embodiments, the serotonin receptor modulator is eplivanserin and the psychedelic is psilocybin HCl Form A, wherein the eplivanserin is administered to pretreat at least 240 minutes prior to the psilocybin HCl Form A.

In some embodiments, the serotonin receptor modulator is eplivanserin and the psychedelic is psilocybin HCl Form A, wherein eplivanserin is administered to pretreat at least 270 minutes prior to psilocybin HCl. In some embodiments, the serotonin receptor modulator is eplivanserin and the psychedelic is psilocybin HCl Form A, wherein eplivanserin is administered to pretreat at least 300 minutes prior to the psilocybin HCl Form A. In some embodiments, the serotonin receptor modulator is eplivanserin and psychedelic is psilocybin HCl Form A, wherein the eplivanserin is administered to pretreat at least 330 minutes prior to the psilocybin HCl Form A. In some embodiments, the serotonin receptor modulator is eplivanserin and psychedelic is psilocybin HCl Form A, wherein eplivanserin is administered to pretreat at least 360 minutes prior to psilocybin HCl Form A.

In some preferred embodiments, the serotonin receptor modulator is eplivanserin and the psychedelic is psilocybin HCl Form A, wherein eplivanserin is administered to pretreat between about 60 minutes and about 180 minutes prior to the administration of the psilocybin HCl Form A.

In some embodiments, the serotonin receptor modulator is volinanserin and the psychedelic is psilocybin HCl Form A, wherein the volinanserin is administered to pretreat a subject between at least 15 minutes and 360 minutes prior to the administration or release of the psilocybin HCl Form A.

In some embodiments, the serotonin receptor modulator is volinanserin and the psychedelic is psilocybin HCl Form A, wherein the volinanserin is administered to pretreat between at least 30 minutes and 360 minutes prior to the administration or release of the psilocybin HCl Form A. In some embodiments, the serotonin receptor modulator is volinanserin and the psychedelic is psilocybin HCl Form A, wherein the volinanserin is administered to pretreat between at least 60 minutes and 240 minutes prior to the administration or release of the psilocybin HCl Form A. In some embodiments, the serotonin receptor modulator is volinanserin and the psychedelic is psilocybin HCl Form A, wherein the volinanserin is administered to pretreat at least 90 minutes prior to the psilocybin HCl Form A. In some embodiments, the serotonin receptor modulator is volinanserin and the psychedelic is psilocybin HCl Form A, wherein the volinanserin is administered to pretreat at least 120 minutes prior to the psilocybin HCl Form A.

In some embodiments, the serotonin receptor modulator is volinanserin and the psychedelic is psilocybin HCl Form A, wherein the volinanserin is administered to pretreat at least 150 minutes prior to the psilocybin HCl Form A. In some embodiments, the serotonin receptor modulator is volinanserin and the psychedelic is psilocybin HCl Form A, wherein the volinanserin is administered to pretreat between about 15 minutes and about 150 minutes prior to the psilocybin HCl Form A. In some embodiments, the serotonin receptor modulator is volinanserin and the psychedelic is psilocybin HCl Form A, wherein the volinanserin is administered to pretreat at least 180 minutes prior to the psilocybin HCl Form A. In some embodiments, the serotonin receptor modulator is volinanserin and the psychedelic is psilocybin HCl Form A, wherein the volinanserin is administered to pretreat at least 210 minutes prior to the psilocybin HCl Form A. In some embodiments, the serotonin receptor modulator is volinanserin and the psychedelic is psilocybin HCl Form A, wherein the volinanserin is administered to pretreat at least 240 minutes prior to the psilocybin HCl Form A. In some embodiments, the serotonin receptor modulator is volinanserin and the psychedelic is psilocybin HCl Form A, wherein the volinanserin is administered to pretreat at least 270 minutes prior to the psilocybin HCl Form A. In some embodiments, the serotonin receptor modulator is volinanserin and the psychedelic is psilocybin HCl Form A, wherein the volinanserin is administered to pretreat at least 300 minutes prior to the psilocybin HCl Form A. In some embodiments, the serotonin receptor modulator is volinanserin and psychedelic is psilocybin HCl Form A, wherein the volinanserin is administered to pretreat at least 330 minutes prior to the psilocybin HCl Form A. In some embodiments, the serotonin receptor modulator is volinanserin and the psychedelic is psilocybin HCl Form A, wherein volinanserin is administered to pretreat at least 360 minutes prior to the psilocybin HCl Form A. In some preferred embodiments, the serotonin receptor modulator is volinanserin and psychedelic is psilocybin HCl Form A, wherein volinanserin is administered to pretreat between about 60 minutes and about 180 minutes prior to the administration of the psilocybin HCl Form A.

In some embodiments, the serotonin receptor modulator is ketanserin and the psychedelic is psilocybin HCl Form A, wherein the ketanserin is administered to pretreat at least 15 minutes prior to the administration of the psilocybin HCl Form A. In some embodiments, the serotonin receptor modulator is ketanserin and the psychedelic is psilocybin HCl Form A, wherein the ketanserin is administered to pretreat between at least 30 minutes and 360 minutes prior to the administration or release of the psilocybin HCl Form A. In some embodiments, the serotonin receptor modulator is ketanserin and the psychedelic is psilocybin HCl Form A, wherein the ketanserin is administered to pretreat between at least 60 minutes and 240 minutes prior to the administration or release of the psilocybin HCl Form A. In some embodiments, the serotonin receptor modulator is ketanserin and the psychedelic is psilocybin HCl Form A, wherein the ketanserin is administered to pretreat at least 90 minutes prior to the psilocybin HCl Form A. In some embodiments, the serotonin receptor modulator is ketanserin and the psychedelic is psilocybin HCl Form A, wherein the ketanserin is administered to pretreat at least 120 minutes prior to the psilocybin HCl Form A. In some embodiments, the serotonin receptor modulator is ketanserin and the psychedelic is psilocybin HCl Form A, wherein the ketanserin is administered to pretreat at least 150 minutes prior to the psilocybin HCl Form A. In some embodiments, the serotonin receptor modulator is ketanserin and the psychedelic is psilocybin HCl Form A, wherein the ketanserin is administered to pretreat between about 15 minutes and about 150 minutes prior to the psilocybin HCl Form A. In some embodiments, the serotonin receptor modulator is ketanserin and the psychedelic is psilocybin HCl Form A, wherein the ketanserin is administered to pretreat at least 180 minutes prior to the psilocybin HCl Form A. In some embodiments, the serotonin receptor modulator is ketanserin and the psychedelic is psilocybin HCl Form A, wherein the ketanserin is administered to pretreat at least 210 minutes prior to the psilocybin HCl Form A. In some embodiments, the serotonin receptor modulator is ketanserin and the psychedelic is psilocybin HCl Form A, wherein the ketanserin is administered to pretreat at least 240 minutes prior to the psilocybin HCl Form A. In some embodiments, the serotonin receptor modulator is ketanserin and the psychedelic is psilocybin HCl Form A, wherein the ketanserin is administered to pretreat at least 270 minutes prior to the psilocybin HCl Form A. In some embodiments, the serotonin receptor modulator is ketanserin and the psychedelic is psilocybin HCl Form A, wherein the ketanserin is administered to pretreat at least 300 minutes prior to the psilocybin HCl Form A. In some embodiments, the serotonin receptor modulator is ketanserin and the psychedelic is psilocybin HCl Form A, wherein the ketanserin is administered to pretreat at least 330 minutes prior to the psilocybin HCl Form A. In some embodiments, the serotonin receptor modulator is ketanserin and the psychedelic is psilocybin HCl Form A, wherein the ketanserin is administered to pretreat at least 360 minutes prior to the psilocybin HCl Form A. In some preferred embodiments, the serotonin receptor modulator is ketanserin and the psychedelic is psilocybin HCl Form A, wherein ketanserin is administered to pretreat between about 60 minutes and about 180 minutes prior to the administration of the psilocybin HCl Form A.

In some embodiments, the serotonin receptor modulator is ritanserin and the psychedelic is psilocybin HCl Form A, wherein the ritanserin is administered to pretreat at least 15 minutes prior to the administration of the psilocybin HCl Form A. In some embodiments, the serotonin receptor modulator is ritanserin and the psychedelic is psilocybin HCl Form A, wherein the ritanserin is administered to pretreat at least 30 minutes prior to the psilocybin HCl Form A. In some embodiments, the serotonin receptor modulator is ritanserin and the psychedelic is psilocybin HCl Form A, wherein the ritanserin is administered to pretreat between at least 60 minutes and 240 minutes prior to the administration or release of the psilocybin HCl Form A. In some embodiments, the serotonin receptor modulator is ritanserin and the psychedelic is psilocybin HCl Form A, wherein the ritanserin is administered to pretreat at least 90 minutes prior to the psilocybin HCl Form A. In some embodiments, the serotonin receptor modulator is ritanserin and the psychedelic is psilocybin HCl Form A, wherein the ritanserin is administered to pretreat at least 120 minutes prior to the psilocybin HCl Form A. In some embodiments, the serotonin receptor modulator is ritanserin and the psychedelic is psilocybin HCl Form A, wherein the ritanserin is administered to pretreat at least 150 minutes prior to the psilocybin HCl Form A. In some embodiments, the serotonin receptor modulator is ritanserin and the psychedelic is psilocybin HCl Form A, wherein the ritanserin is administered to pretreat between about 15 minutes and about 150 minutes prior to the psilocybin HCl Form A. In some embodiments, the serotonin receptor modulator is ritanserin and the psychedelic is psilocybin HCl Form A, wherein the ritanserin is administered to pretreat at least 180 minutes prior to the psilocybin HCl Form A. In some embodiments, the serotonin receptor modulator is ritanserin and the psychedelic is psilocybin HCl Form A, wherein the ritanserin is administered to pretreat at least 210 minutes prior to the psilocybin HCl Form A. In some embodiments, the serotonin receptor modulator is ritanserin and the psychedelic is psilocybin HCl Form A, wherein the ritanserin is administered to pretreat at least 240 minutes prior to the psilocybin HCl Form A. In some embodiments, the serotonin receptor modulator is ritanserin and the psychedelic is psilocybin HCl Form A, wherein the ritanserin is administered to pretreat at least 270 minutes prior to the psilocybin HCl Form A. In some embodiments, the serotonin receptor modulator is ritanserin and the psychedelic is psilocybin HCl Form A, wherein the ritanserin is administered to pretreat at least 300 minutes prior to the psilocybin HCl Form A. In some embodiments, the serotonin receptor modulator is ritanserin and the psychedelic is psilocybin HCl Form A, wherein the ritanserin is administered to pretreat at least 330 minutes prior to the psilocybin HCl Form A. In some embodiments, the serotonin receptor modulator is ritanserin and the psychedelic is psilocybin HCl Form A, wherein the ritanserin is administered to pretreat at least 360 minutes prior to the psilocybin HCl Form A. In some preferred embodiments, the serotonin receptor modulator is ritanserin and the psychedelic is psilocybin HCl Form A, wherein ritanserin is administered to pretreat between about 60 minutes and about 180 minutes prior to the administration of the psilocybin HCl Form A.

In some embodiments, the serotonin receptor modulator is pimavanserin and the psychedelic is psilocybin HCl Form A, wherein the pimavanserin is administered to pretreat at least 15 minutes prior to the administration of the psilocybin HCl Form A. In some embodiments, the serotonin receptor modulator is pimavanserin and the psychedelic is psilocybin HCl Form A, wherein the pimavanserin is administered to pretreat at least 30 minutes prior to the psilocybin HCl Form A. In some embodiments, the serotonin receptor modulator is pimavanserin and the psychedelic is psilocybin HCl Form A, wherein the pimavanserin is administered to pretreat between at least 60 minutes and 240 minutes prior to the administration or release of the psilocybin HCl Form A. In some embodiments, the serotonin receptor modulator is pimavanserin and the psychedelic is psilocybin HCl Form A, wherein the pimavanserin is administered to pretreat at least 90 minutes prior to the psilocybin HCl Form A. In some embodiments, the serotonin receptor modulator is pimavanserin and the psychedelic is psilocybin HCl Form A, wherein the pimavanserin is administered to pretreat at least 120 minutes prior to the psilocybin HCl Form A. In some embodiments, the serotonin receptor modulator is pimavanserin and the psychedelic is psilocybin HCl Form A, wherein the pimavanserin is administered to pretreat at least 150 minutes prior to the psilocybin HCl Form A. In some embodiments, the serotonin receptor modulator is pimavanserin and the psychedelic is psilocybin HCl Form A, wherein the pimavanserin is administered to pretreat between about 15 minutes and about 150 minutes prior to the psilocybin HCl Form A. In some embodiments, the serotonin receptor modulator is pimavanserin and the psychedelic is psilocybin HCl Form A, wherein the pimavanserin is administered to pretreat at least 180 minutes prior to the psilocybin HCl Form A. In some embodiments, the serotonin receptor modulator is pimavanserin and the psychedelic is psilocybin HCl Form A, wherein the pimavanserin is administered to pretreat at least 210 minutes prior to the psilocybin HCl Form A. In some embodiments, the serotonin receptor modulator is pimavanserin and the psychedelic is psilocybin HCl Form A, wherein the pimavanserin is administered to pretreat at least 240 minutes prior to the psilocybin HCl Form A. In some embodiments, the serotonin receptor modulator is pimavanserin and the psychedelic is psilocybin HCl Form A, wherein the pimavanserin is administered to pretreat at least 270 minutes prior to the psilocybin HCl Form A. In some embodiments, the serotonin receptor modulator is pimavanserin and the psychedelic is psilocybin HCl Form A, wherein the pimavanserin is administered to pretreat at least 300 minutes prior to the psilocybin HCl Form A. In some embodiments, the serotonin receptor modulator is pimavanserin and the psychedelic is psilocybin HCl Form A, wherein the pimavanserin is administered to pretreat at least 330 minutes prior to the psilocybin HCl Form A. In some embodiments, the serotonin receptor modulator is pimavanserin and the psychedelic is psilocybin HCl Form A, wherein the pimavanserin is administered to pretreat at least 360 minutes prior to the psilocybin HCl Form A. In some preferred embodiments, the serotonin receptor modulator is pimavanserin and the psychedelic is psilocybin HCl Form A, wherein pimavanserin is administered to pretreat between about 60 minutes and about 180 minutes prior to the administration of the psilocybin HCl Form A.

In some embodiments, the serotonin receptor modulator is nelotanserin and the psychedelic is psilocybin HCl Form A, wherein the nelotanserin is administered to pretreat at least 15 minutes prior to the administration of the psilocybin HCl Form A. In some embodiments, the serotonin receptor modulator is nelotanserin and the psychedelic is psilocybin HCl Form A, wherein the nelotanserin is administered to pretreat at least 30 minutes prior to the psilocybin HCl Form A. In some embodiments, the serotonin receptor modulator is nelotanserin and the psychedelic is psilocybin HCl Form A, wherein the nelotanserin is administered to pretreat between at least 60 minutes and 240 minutes prior to the administration or release of the psilocybin HCl Form A. In some embodiments, the serotonin receptor modulator is nelotanserin and the psychedelic is psilocybin HCl Form A, wherein the nelotanserin is administered to pretreat at least 90 minutes prior to the psilocybin HCl Form A. In some embodiments, the serotonin receptor modulator is nelotanserin and the psychedelic is psilocybin HCl Form A, wherein the nelotanserin is administered to pretreat at least 120 minutes prior to the psilocybin HCl Form A.

In some embodiments, the serotonin receptor modulator is nelotanserin and the psychedelic is psilocybin HCl Form A, wherein the nelotanserin is administered to pretreat at least 150 minutes prior to the psilocybin HCl Form A. In some embodiments, the serotonin receptor modulator is nelotanserin and the psychedelic is psilocybin HCl Form A, wherein the nelotanserin is administered to pretreat between about 15 minutes and about 150 minutes prior to the psilocybin HCl Form A. In some embodiments, the serotonin receptor modulator is nelotanserin and the psychedelic is psilocybin HCl Form A, wherein the nelotanserin is administered to pretreat at least 180 minutes prior to the psilocybin HCl Form A. In some embodiments, the serotonin receptor modulator is nelotanserin and the psychedelic is psilocybin HCl Form A, wherein the nelotanserin is administered to pretreat at least 210 minutes prior to the psilocybin HCl Form A. In some embodiments, the serotonin receptor modulator is nelotanserin and the psychedelic is psilocybin HCl Form A, wherein the nelotanserin is administered to pretreat at least 240 minutes prior to the psilocybin HCl Form A. In some embodiments, the serotonin receptor modulator is nelotanserin and the psychedelic is psilocybin HCl Form A, wherein the nelotanserin is administered to pretreat at least 270 minutes prior to the psilocybin HCl Form A.

In some embodiments, the serotonin receptor modulator is nelotanserin and the psychedelic is psilocybin HCl Form A, wherein the nelotanserin is administered to pretreat at least 300 minutes prior to the psilocybin HCl Form A. In some embodiments, the serotonin receptor modulator is nelotanserin and the psychedelic is psilocybin HCl Form A, wherein the nelotanserin is administered to pretreat at least 330 minutes prior to the psilocybin HCl Form A. In some embodiments, the serotonin receptor modulator is nelotanserin and the psychedelic is psilocybin HCl Form A, wherein the nelotanserin is administered to pretreat at least 360 minutes prior to the psilocybin HCl Form A. In some preferred embodiments, the serotonin receptor modulator is nelotanserin and the psychedelic is psilocybin HCl Form A, wherein nelotanserin is administered to pretreat between about 60 minutes and about 180 minutes prior to the administration of the psilocybin HCl Form A.

In some embodiments, the serotonin receptor modulator is pruvanserin and the psychedelic is psilocybin HCl Form A, wherein the pruvanserin is administered to pretreat at least 15 minutes prior to the administration of the psilocybin HCl Form A. In some embodiments, the serotonin receptor modulator is pruvanserin and the psychedelic is psilocybin HCl Form A, wherein the pruvanserin is administered to pretreat at least 30 minutes prior to the psilocybin HCl Form A. In some embodiments, the serotonin receptor modulator is pruvanserin and the psychedelic is psilocybin HCl Form A, wherein the pruvanserin is administered to pretreat between at least 60 minutes and 240 minutes prior to the administration or release of the psilocybin HCl Form A. In some embodiments, the serotonin receptor modulator is pruvanserin and the psychedelic is psilocybin HCl Form A, wherein the pruvanserin is administered to pretreat at least 90 minutes prior to the psilocybin HCl Form A. In some embodiments, the serotonin receptor modulator is pruvanserin and the psychedelic is psilocybin HCl Form A, wherein the pruvanserin is administered to pretreat at least 120 minutes prior to the psilocybin HCl Form A. In some embodiments, the serotonin receptor modulator is pruvanserin and the psychedelic is psilocybin HCl Form A, wherein the pruvanserin is administered to pretreat at least 150 minutes prior to the psilocybin HCl Form A. In some embodiments, the serotonin receptor modulator is pruvanserin and the psychedelic is psilocybin HCl Form A, wherein the pruvanserin is administered to pretreat between about 15 minutes and about 150 minutes prior to the psilocybin HCl Form A. In some embodiments, the serotonin receptor modulator is pruvanserin and the psychedelic is psilocybin HCl Form A, wherein the pruvanserin is administered to pretreat at least 180 minutes prior to the psilocybin HCl Form A. In some embodiments, the serotonin receptor modulator is pruvanserin and the psychedelic is psilocybin HCl Form A, wherein the pruvanserin is administered to pretreat at least 210 minutes prior to the psilocybin HCl Form A.

In some embodiments, the serotonin receptor modulator is pruvanserin and the psychedelic is psilocybin HCl Form A, wherein the pruvanserin is administered to pretreat at least 240 minutes prior to the psilocybin HCl Form A. In some embodiments, the serotonin receptor modulator is pruvanserin and the psychedelic is psilocybin HCl Form A, wherein the pruvanserin is administered to pretreat at least 270 minutes prior to the psilocybin HCl Form A. In some embodiments, the serotonin receptor modulator is pruvanserin and the psychedelic is psilocybin HCl Form A, wherein the pruvanserin is administered to pretreat at least 300 minutes prior to the psilocybin HCl Form A. In some embodiments, the serotonin receptor modulator is pruvanserin and the psychedelic is psilocybin HCl Form A, wherein the pruvanserin is administered to pretreat at least 330 minutes prior to the psilocybin HCl Form A. In some embodiments, the serotonin receptor modulator is pruvanserin and the psychedelic is psilocybin HCl Form A, wherein the pruvanserin is administered to pretreat at least 360 minutes prior to the psilocybin HCl Form A. In some preferred embodiments, the serotonin receptor modulator is pruvanserin and the psychedelic is psilocybin HCl Form A, wherein pruvanserin is administered to pretreat between about 60 minutes and about 180 minutes prior to the administration of the psilocybin HCl Form A.

In some embodiments, the serotonin receptor modulator is flibanserin and the psychedelic is psilocybin HCl Form A, wherein the flibanserin is administered to pretreat at least 15 minutes prior to the administration of the psilocybin HCl Form A. In some embodiments, the serotonin receptor modulator is flibanserin and the psychedelic is psilocybin HCl Form A, wherein the flibanserin is administered to pretreat at least 30 minutes prior to the psilocybin HCl Form A. In some embodiments, the serotonin receptor modulator is flibanserin and the psychedelic is psilocybin HCl Form A, wherein the flibanserin is administered to pretreat between at least 60 minutes and 240 minutes prior to the administration or release of the psilocybin HCl Form A. In some embodiments, the serotonin receptor modulator is flibanserin and the psychedelic is psilocybin HCl Form A, wherein the flibanserin is administered to pretreat at least 90 minutes prior to the psilocybin HCl Form A. In some embodiments, the serotonin receptor modulator is flibanserin and the psychedelic is psilocybin HCl Form A, wherein the flibanserin is administered to pretreat at least 120 minutes prior to the psilocybin HCl Form A. In some embodiments, the serotonin receptor modulator is flibanserin and the psychedelic is psilocybin HCl Form A, wherein the flibanserin is administered to pretreat at least 150 minutes prior to the psilocybin HCl Form A. In some embodiments, the serotonin receptor modulator is flibanserin and the psychedelic is psilocybin HCl Form A, wherein the flibanserin is administered to pretreat between about 15 minutes and about 150 minutes prior to the psilocybin HCl Form A. In some embodiments, the serotonin receptor modulator is flibanserin and the psychedelic is psilocybin HCl Form A, wherein the flibanserin is administered to pretreat at least 180 minutes prior to the psilocybin HCl Form A. In some embodiments, the serotonin receptor modulator is flibanserin and the psychedelic is psilocybin HCl Form A, wherein the flibanserin is administered to pretreat at least 210 minutes prior to the psilocybin HCl Form A.

In some embodiments, the serotonin receptor modulator is flibanserin and the psychedelic is psilocybin HCl Form A, wherein the flibanserin is administered to pretreat at least 240 minutes prior to the psilocybin HCl Form A. In some embodiments, the serotonin receptor modulator is flibanserin and the psychedelic is psilocybin HCl Form A, wherein the flibanserin is administered to pretreat at least 270 minutes prior to the psilocybin HCl Form A. In some embodiments, the serotonin receptor modulator is flibanserin and the psychedelic is psilocybin HCl Form A, wherein the flibanserin is administered to pretreat at least 300 minutes prior to the psilocybin HCl Form A. In some embodiments, the serotonin receptor modulator is flibanserin and the psychedelic is psilocybin HCl Form A, wherein the flibanserin is administered to pretreat at least 330 minutes prior to the psilocybin HCl Form A. In some embodiments, the serotonin receptor modulator is flibanserin and the psychedelic is psilocybin HCl Form A, wherein the flibanserin is administered to pretreat at least 360 minutes prior to the psilocybin HCl Form A. In some preferred embodiments, the serotonin receptor modulator is flibanserin and the psychedelic is psilocybin HCl Form A, wherein flibanserin is administered to pretreat between about 60 minutes and about 180 minutes prior to the administration of the psilocybin HCl Form A.

In some embodiments, the serotonin receptor modulator is olanzapine and the psychedelic is psilocybin HCl Form A, wherein the olanzapine is administered to pretreat at least 15 minutes prior to the administration of the psilocybin HCl Form A. In some embodiments, the serotonin receptor modulator is olanzapine and the psychedelic is psilocybin HCl Form A, wherein the olanzapine is administered to pretreat at least 30 minutes prior to the psilocybin HCl Form A. In some embodiments, the serotonin receptor modulator is olanzapine and the psychedelic is psilocybin HCl Form A, wherein the olanzapine is administered to pretreat between at least 60 minutes and 240 minutes prior to the administration or release of the psilocybin HCl Form A. In some embodiments, the serotonin receptor modulator is olanzapine and the psychedelic is psilocybin HCl Form A, wherein the olanzapine is administered to pretreat at least 90 minutes prior to the psilocybin HCl Form A. In some embodiments, the serotonin receptor modulator is olanzapine and the psychedelic is psilocybin HCl Form A, wherein the olanzapine is administered to pretreat at least 120 minutes prior to the psilocybin HCl Form A. In some embodiments, the serotonin receptor modulator is olanzapine and the psychedelic is psilocybin HCl Form A, wherein the olanzapine is administered to pretreat at least 150 minutes prior to the psilocybin HCl Form A. In some embodiments, the serotonin receptor modulator is olanzapine and the psychedelic is psilocybin HCl Form A, wherein the olanzapine is administered to pretreat between about 15 minutes and about 150 minutes prior to the psilocybin HCl Form A. In some embodiments, the serotonin receptor modulator is olanzapine and the psychedelic is psilocybin HCl Form A, wherein the olanzapine is administered to pretreat at least 180 minutes prior to the psilocybin HCl Form A. In some embodiments, the serotonin receptor modulator is olanzapine and the psychedelic is psilocybin HCl Form A, wherein the olanzapine is administered to pretreat at least 210 minutes prior to the psilocybin HCl Form A.

In some embodiments, the serotonin receptor modulator is olanzapine and the psychedelic is psilocybin HCl Form A, wherein the olanzapine is administered to pretreat at least 240 minutes prior to the psilocybin HCl Form A. In some embodiments, the serotonin receptor modulator is olanzapine and the psychedelic is psilocybin HCl Form A, wherein the olanzapine is administered to pretreat at least 270 minutes prior to the psilocybin HCl Form A. In some embodiments, the serotonin receptor modulator is olanzapine and the psychedelic is psilocybin HCl Form A, wherein the olanzapine is administered to pretreat at least 300 minutes prior to the psilocybin HCl Form A. In some embodiments, the serotonin receptor modulator is olanzapine and the psychedelic is psilocybin HCl Form A, wherein the olanzapine is administered to pretreat at least 330 minutes prior to the psilocybin HCl Form A. In some embodiments, the serotonin receptor modulator is olanzapine and the psychedelic is psilocybin HCl Form A, wherein the olanzapine is administered to pretreat at least 360 minutes prior to the psilocybin HCl Form A. In some preferred embodiments, the serotonin receptor modulator is olanzapine and the psychedelic is psilocybin HCl Form A, wherein olanzapine is administered to pretreat between about 60 minutes and about 180 minutes prior to the administration of the psilocybin HCl Form A.

In some embodiments, the serotonin receptor modulator is risperidone and the psychedelic is psilocybin HCl Form A, wherein the risperidone is administered to pretreat at least 15 minutes prior to the administration of the psilocybin HCl Form A. In some embodiments, the serotonin receptor modulator is risperidone and the psychedelic is psilocybin HCl Form A, wherein the risperidone is administered to pretreat at least 30 minutes prior to the psilocybin HCl Form A. In some embodiments, the serotonin receptor modulator is risperidone and the psychedelic is psilocybin HCl Form A, wherein the risperidone is administered to pretreat between at least 60 minutes and 240 minutes prior to the administration or release of the psilocybin HCl Form A. In some embodiments, the serotonin receptor modulator is risperidone and the psychedelic is psilocybin HCl Form A, wherein the risperidone is administered to pretreat at least 90 minutes prior to the psilocybin HCl Form A. In some embodiments, the serotonin receptor modulator is risperidone and the psychedelic is psilocybin HCl Form A, wherein the risperidone is administered to pretreat at least 120 minutes prior to the psilocybin HCl Form A. In some embodiments, the serotonin receptor modulator is risperidone and the psychedelic is psilocybin HCl Form A, wherein the risperidone is administered to pretreat at least 150 minutes prior to the psilocybin HCl Form A. In some embodiments, the serotonin receptor modulator is risperidone and the psychedelic is psilocybin HCl Form A, wherein the risperidone is administered to pretreat between about 15 minutes and about 150 minutes prior to the psilocybin HCl Form A. In some embodiments, the serotonin receptor modulator is risperidone and the psychedelic is psilocybin HCl Form A, wherein the risperidone is administered to pretreat at least 180 minutes prior to the psilocybin HCl Form A. In some embodiments, the serotonin receptor modulator is risperidone and the psychedelic is psilocybin HCl Form A, wherein the risperidone is administered to pretreat at least 210 minutes prior to the psilocybin HCl Form A.

In some embodiments, the serotonin receptor modulator is risperidone and the psychedelic is psilocybin HCl Form A, wherein the risperidone is administered to pretreat at least 240 minutes prior to the psilocybin HCl Form A. In some embodiments, the serotonin receptor modulator is risperidone and the psychedelic is psilocybin HCl Form A, wherein the risperidone is administered to pretreat at least 270 minutes prior to the psilocybin HCl Form A. In some embodiments, the serotonin receptor modulator is risperidone and the psychedelic is psilocybin HCl Form A, wherein the risperidone is administered to pretreat at least 300 minutes prior to the psilocybin HCl Form A. In some embodiments, the serotonin receptor modulator is risperidone and the psychedelic is psilocybin HCl Form A, wherein the risperidone is administered to pretreat at least 330 minutes prior to the psilocybin HCl Form A. In some embodiments, the serotonin receptor modulator is risperidone and the psychedelic is psilocybin HCl Form A, wherein the risperidone is administered to pretreat at least 360 minutes prior to the psilocybin HCl Form A. In some preferred embodiments, the serotonin receptor modulator is risperidone and the psychedelic is psilocybin HCl Form A, wherein risperidone is administered to pretreat between about 60 minutes and about 180 minutes prior to the administration of the psilocybin HCl Form A.

In some embodiments, the serotonin receptor modulator is quetiapine and the psychedelic is psilocybin HCl Form A, wherein the quetiapine is administered to pretreat at least 15 minutes prior to the administration of the psilocybin HCl Form A. In some embodiments, the serotonin receptor modulator is quetiapine and the psychedelic is psilocybin HCl Form A, wherein the quetiapine is administered to pretreat at least 30 minutes prior to the psilocybin HCl Form A. In some embodiments, the serotonin receptor modulator is quetiapine and the psychedelic is psilocybin HCl Form A, wherein the quetiapine is administered to pretreat between at least 60 minutes and 240 minutes prior to the administration or release of the psilocybin HCl Form A. In some embodiments, the serotonin receptor modulator is quetiapine and the psychedelic is psilocybin HCl Form A, wherein the quetiapine is administered to pretreat at least 90 minutes prior to the psilocybin HCl Form A. In some embodiments, the serotonin receptor modulator is quetiapine and the psychedelic is psilocybin HCl Form A, wherein the quetiapine is administered to pretreat at least 120 minutes prior to the psilocybin HCl Form A. In some embodiments, the serotonin receptor modulator is quetiapine and the psychedelic is psilocybin HCl Form A, wherein the quetiapine is administered to pretreat at least 150 minutes prior to the psilocybin HCl Form A. In some embodiments, the serotonin receptor modulator is quetiapine and the psychedelic is psilocybin HCl Form A, wherein the quetiapine is administered to pretreat between about 15 minutes and about 150 minutes prior to the psilocybin HCl Form A. In some embodiments, the serotonin receptor modulator is quetiapine and the psychedelic is psilocybin HCl Form A, wherein the quetiapine is administered to pretreat at least 180 minutes prior to the psilocybin HCl Form A. In some embodiments, the serotonin receptor modulator is quetiapine and the psychedelic is psilocybin HCl Form A, wherein the quetiapine is administered to pretreat at least 210 minutes prior to the psilocybin HCl Form A.

In some embodiments, the serotonin receptor modulator is quetiapine and the psychedelic is psilocybin HCl Form A, wherein the quetiapine is administered to pretreat at least 240 minutes prior to the psilocybin HCl Form A. In some embodiments, the serotonin receptor modulator is quetiapine and the psychedelic is psilocybin HCl Form A, wherein the quetiapine is administered to pretreat at least 270 minutes prior to the psilocybin HCl Form A. In some embodiments, the serotonin receptor modulator is quetiapine and the psychedelic is psilocybin HCl Form A, wherein the quetiapine is administered to pretreat at least 300 minutes prior to the psilocybin HCl Form A. In some embodiments, the serotonin receptor modulator is quetiapine and the psychedelic is psilocybin HCl Form A, wherein the quetiapine is administered to pretreat at least 330 minutes prior to the psilocybin HCl Form A. In some embodiments, the serotonin receptor modulator is quetiapine and the psychedelic is psilocybin HCl Form A, wherein the quetiapine is administered to pretreat at least 360 minutes prior to the psilocybin HCl Form A. In some preferred embodiments, the serotonin receptor modulator is quetiapine and the psychedelic is psilocybin HCl Form A, wherein quetiapine is administered to pretreat between about 60 minutes and about 180 minutes prior to the administration of the psilocybin HCl Form A.

In some embodiments, the serotonin receptor modulator is eplivanserin and the psychedelic is psilocybin·HCl, wherein the eplivanserin is administered to pretreat at least 15 minutes prior to the administration of psilocybin·HCl. In some embodiments, the serotonin receptor modulator is eplivanserin and the psychedelic is psilocybin·HCl, wherein the eplivanserin is administered to pretreat between at least 30 minutes prior and 360 minutes prior to the release or administration of the psilocybin·HCl. In some embodiments, the serotonin receptor modulator is eplivanserin and the psychedelic is psilocybin·HCl, wherein the eplivanserin is administered to pretreat between at least 60 minutes prior and 360 minutes prior to the release or administration the psilocybin·HCl. In some embodiments, the serotonin receptor modulator is eplivanserin and the psychedelic is psilocybin·HCl, wherein the eplivanserin is administered to pretreat between at least 90 minutes and 240 minutes prior to the psilocybin·HCl. In some embodiments, the serotonin receptor modulator is eplivanserin and the psychedelic is psilocybin·HCl, wherein the eplivanserin is administered to pretreat at least 120 minutes prior to the psilocybin·HCl.

In some embodiments, the serotonin receptor modulator is eplivanserin and the psychedelic is psilocybin·HCl, wherein the eplivanserin is administered to pretreat at least 150 minutes prior to the psilocybin·HCl. In some embodiments, the serotonin receptor modulator is eplivanserin and the psychedelic is psilocybin HCl, wherein the volinanserin is administered to pretreat between about 15 minutes and about 150 minutes prior to the psilocybin HCl. In some embodiments, the serotonin receptor modulator is eplivanserin and the psychedelic is psilocybin·HCl, wherein the eplivanserin is administered to pretreat at least 180 minutes prior to the psilocybin·HCl. In some embodiments, the serotonin receptor modulator is eplivanserin and the psychedelic is psilocybin·HCl, wherein the eplivanserin is administered to pretreat at least 210 minutes prior to the psilocybin·HCl. In some embodiments, the serotonin receptor modulator is eplivanserin and the psychedelic is psilocybin·HCl, wherein the eplivanserin is administered to pretreat at least 240 minutes prior to the psilocybin·HCl.

In some embodiments, the serotonin receptor modulator is eplivanserin and the psychedelic is psilocybin·HCl, wherein the eplivanserin is administered to pretreat at least 270 minutes prior to psilocybin·HCl. In some embodiments, the serotonin receptor modulator is eplivanserin and the psychedelic is psilocybin·HCl, wherein the eplivanserin is administered to pretreat at least 300 minutes prior to the psilocybin·HCl. In some embodiments, the serotonin receptor modulator is eplivanserin and the psychedelic is psilocybin·HCl, wherein the eplivanserin is administered to pretreat at least 330 minutes prior to the psilocybin·HCl. In some embodiments, the serotonin receptor modulator is eplivanserin and the psychedelic is psilocybin·HCl, wherein the eplivanserin is administered to pretreat at least 360 minutes prior to the psilocybin·HCl.

In some preferred embodiments, the serotonin receptor modulator is eplivanserin and the psychedelic is psilocybin·HCl, wherein eplivanserin is administered to pretreat between about 60 minutes and about 180 minutes prior to the administration of psilocybin·HCl.

In some embodiments, the serotonin receptor modulator is volinanserin and the psychedelic is psilocybin·HCl, wherein the volinanserin is administered to pretreat a subject between at least 15 minutes and 360 minutes prior to the administration or release of psilocybin·HCl. In some embodiments, the serotonin receptor modulator is volinanserin and the psychedelic is psilocybin·HCl, wherein the volinanserin is administered to pretreat between at least 30 minutes and 360 minutes prior to the administration or release of psilocybin·HCl. In some embodiments, the serotonin receptor modulator is volinanserin and the psychedelic is psilocybin·HCl, wherein the volinanserin is administered to pretreat between at least 60 minutes and 240 minutes prior to the administration or release of psilocybin·HCl. In some embodiments, the serotonin receptor modulator is volinanserin and the psychedelic is psilocybin·HCl, wherein the volinanserin is administered to pretreat at least 90 minutes prior to psilocybin·HCl. In some embodiments, the serotonin receptor modulator is volinanserin and the psychedelic is psilocybin·HCl, wherein the volinanserin is administered to pretreat at least 120 minutes prior to the psilocybin·HCl.

In some embodiments, the serotonin receptor modulator is volinanserin and the psychedelic is psilocybin·HCl, wherein the volinanserin is administered to pretreat at least 150 minutes prior to the psilocybin·HCl. In some embodiments, the serotonin receptor modulator is volinanserin and the psychedelic is psilocybin·HCl, wherein the volinanserin is administered to pretreat between about 15 minutes and about 150 minutes prior to the psilocybin·HCl. In some embodiments, the serotonin receptor modulator is volinanserin and the psychedelic is psilocybin·HCl, wherein the volinanserin is administered to pretreat at least 180 minutes prior to the psilocybin·HCl. In some embodiments, the serotonin receptor modulator is volinanserin and the psychedelic is psilocybin·HCl, wherein the volinanserin is administered to pretreat at least 210 minutes prior to the psilocybin·HCl. In some embodiments, the serotonin receptor modulator is volinanserin and the psychedelic is psilocybin·HCl, wherein the volinanserin is administered to pretreat at least 240 minutes prior to the psilocybin·HCl. In some embodiments, the serotonin receptor modulator is volinanserin and the psychedelic is psilocybin·HCl, wherein the volinanserin is administered to pretreat at least 270 minutes prior to the psilocybin·HCl. In some embodiments, the serotonin receptor modulator is volinanserin and the psychedelic is psilocybin·HCl, wherein the volinanserin is administered to pretreat at least 300 minutes prior to the psilocybin·HCl. In some embodiments, the serotonin receptor modulator is volinanserin and the psychedelic is psilocybin·HCl, wherein the volinanserin is administered to pretreat at least 330 minutes prior to the psilocybin·HCl. In some embodiments, the serotonin receptor modulator is volinanserin and the psychedelic is psilocybin·HCl, wherein the volinanserin is administered to pretreat at least 360 minutes prior to the psilocybin·HCl. In some preferred embodiments, the serotonin receptor modulator is volinanserin and the psychedelic is psilocybin·HCl, wherein volinanserin is administered to pretreat between about 60 minutes and about 180 minutes prior to the administration of psilocybin·HCl.

In some embodiments, the serotonin receptor modulator is ketanserin and the psychedelic is psilocybin·HCl, wherein the ketanserin is administered to pretreat at least 15 minutes prior to the administration of psilocybin·HCl. In some embodiments, the serotonin receptor modulator is ketanserin and the psychedelic is psilocybin·HCl, wherein the ketanserin is administered to pretreat between at least 30 minutes and 360 minutes prior to the administration or release psilocybin·HCl. In some embodiments, the serotonin receptor modulator is ketanserin and the psychedelic is psilocybin·HCl, wherein the ketanserin is administered to pretreat between at least 60 minutes and 240 minutes prior to the administration or release of psilocybin·HCl. In some embodiments, the serotonin receptor modulator is ketanserin and the psychedelic is psilocybin·HCl, wherein the ketanserin is administered to pretreat at least 90 minutes prior to the psilocybin·HCl. In some embodiments, the serotonin receptor modulator is ketanserin and the psychedelic is psilocybin·HCl, wherein the ketanserin is administered to pretreat at least 120 minutes prior to the psilocybin·HCl. In some embodiments, the serotonin receptor modulator is ketanserin and the psychedelic is psilocybin·HCl, wherein the ketanserin is administered to pretreat at least 150 minutes prior to the psilocybin·HCl. In some embodiments, the serotonin receptor modulator is ketanserin and the psychedelic is psilocybin·HCl, wherein the ketanserin is administered to pretreat between about 15 minutes and about 150 minutes prior to the psilocybin·HCl. In some embodiments, the serotonin receptor modulator is ketanserin and the psychedelic is psilocybin·HCl, wherein the ketanserin is administered to pretreat at least 180 minutes prior to the psilocybin·HCl. In some embodiments, the serotonin receptor modulator is ketanserin and the psychedelic is psilocybin·HCl, wherein the ketanserin is administered to pretreat at least 210 minutes prior to the psilocybin·HCl. In some embodiments, the serotonin receptor modulator is ketanserin and the psychedelic is psilocybin·HCl, wherein the ketanserin is administered to pretreat at least 240 minutes prior to the psilocybin·HCl. In some embodiments, the serotonin receptor modulator is ketanserin and the psychedelic is psilocybin·HCl, wherein the ketanserin is administered to pretreat at least 270 minutes prior to the psilocybin·HCl. In some embodiments, the serotonin receptor modulator is ketanserin and the psychedelic is psilocybin·HCl, wherein the ketanserin is administered to pretreat at least 300 minutes prior to the psilocybin·HCl. In some embodiments, the serotonin receptor modulator is ketanserin and the psychedelic is psilocybin·HCl, wherein the ketanserin is administered to pretreat at least 330 minutes prior to the psilocybin·HCl. In some embodiments, the serotonin receptor modulator is ketanserin and the psychedelic is psilocybin·HCl, wherein the ketanserin is administered to pretreat at least 360 minutes prior to the psilocybin·HCl. In some preferred embodiments, the serotonin receptor modulator is ketanserin and the psychedelic is psilocybin·HCl, wherein ketanserin is administered to pretreat between about 60 minutes and about 180 minutes prior to the administration of psilocybin·HCl.

In some embodiments, the serotonin receptor modulator is ritanserin and the psychedelic is psilocybin·HCl, wherein the ritanserin is administered to pretreat at least 15 minutes prior to the administration of psilocybin·HCl. In some embodiments, the serotonin receptor modulator is ritanserin and the psychedelic is psilocybin·HCl, wherein the ritanserin is administered to pretreat at least 30 minutes prior to the psilocybin·HCl. In some embodiments, the serotonin receptor modulator is ritanserin and the psychedelic is psilocybin·HCl, wherein the ritanserin is administered to pretreat between at least 60 minutes and 240 minutes prior to the administration or release of psilocybin·HCl. In some embodiments, the serotonin receptor modulator is ritanserin and the psychedelic is psilocybin·HCl, wherein the ritanserin is administered to pretreat at least 90 minutes prior to the psilocybin·HCl. In some embodiments, the serotonin receptor modulator is ritanserin and the psychedelic is psilocybin·HCl, wherein the ritanserin is administered to pretreat at least 120 minutes prior to the psilocybin·HCl. In some embodiments, the serotonin receptor modulator is ritanserin and the psychedelic is psilocybin·HCl, wherein the ritanserin is administered to pretreat at least 150 minutes prior to the psilocybin·HCl. In some embodiments, the serotonin receptor modulator is ritanserin and the psychedelic is psilocybin·HCl, wherein the ritanserin is administered to pretreat between about 15 minutes and about 150 minutes prior to the psilocybin·HCl. In some embodiments, the serotonin receptor modulator is ritanserin and the psychedelic is psilocybin·HCl, wherein the ritanserin is administered to pretreat at least 180 minutes prior to the psilocybin·HCl. In some embodiments, the serotonin receptor modulator is ritanserin and the psychedelic is psilocybin·HCl, wherein the ritanserin is administered to pretreat at least 210 minutes prior to the psilocybin·HCl. In some embodiments, the serotonin receptor modulator is ritanserin and the psychedelic is psilocybin·HCl, wherein the ritanserin is administered to pretreat at least 240 minutes prior to the psilocybin·HCl. In some embodiments, the serotonin receptor modulator is ritanserin and the psychedelic is psilocybin·HCl, wherein the ritanserin is administered to pretreat at least 270 minutes prior to the psilocybin·HCl. In some embodiments, the serotonin receptor modulator is ritanserin and the psychedelic is psilocybin·HCl, wherein the ritanserin is administered to pretreat at least 300 minutes prior to the psilocybin·HCl. In some embodiments, the serotonin receptor modulator is ritanserin and the psychedelic is psilocybin·HCl, wherein the ritanserin is administered to pretreat at least 330 minutes prior to the psilocybin·HCl. In some embodiments, the serotonin receptor modulator is ritanserin and the psychedelic is psilocybin·HCl, wherein the ritanserin is administered to pretreat at least 360 minutes prior to the psilocybin·HCl. In some preferred embodiments, the serotonin receptor modulator is ritanserin and the psychedelic is psilocybin·HCl, wherein ritanserin is administered to pretreat between about 60 minutes and about 180 minutes prior to the administration of psilocybin·HCl.

In some embodiments, the serotonin receptor modulator is pimavanserin and the psychedelic is psilocybin·HCl, wherein the pimavanserin is administered to pretreat at least 15 minutes prior to the administration of psilocybin·HCl. In some embodiments, the serotonin receptor modulator is pimavanserin and the psychedelic is psilocybin·HCl, wherein the pimavanserin is administered to pretreat at least 30 minutes prior to the psilocybin·HCl. In some embodiments, the serotonin receptor modulator is pimavanserin and the psychedelic is psilocybin·HCl, wherein the pimavanserin is administered to pretreat between at least 60 minutes and 240 minutes prior to the administration or release of psilocybin·HCl. In some embodiments, the serotonin receptor modulator is pimavanserin and the psychedelic is psilocybin·HCl, wherein the pimavanserin is administered to pretreat at least 90 minutes prior to the psilocybin·HCl. In some embodiments, the serotonin receptor modulator is pimavanserin and the psychedelic is psilocybin·HCl, wherein the pimavanserin is administered to pretreat at least 120 minutes prior to the psilocybin·HCl. In some embodiments, the serotonin receptor modulator is pimavanserin and the psychedelic is psilocybin·HCl, wherein the pimavanserin is administered to pretreat at least 150 minutes prior to the psilocybin·HCl. In some embodiments, the serotonin receptor modulator is pimavanserin and the psychedelic is psilocybin·HCl, wherein the pimavanserin is administered to pretreat between about 15 minutes and about 150 minutes prior to the psilocybin·HCl. In some embodiments, the serotonin receptor modulator is pimavanserin and the psychedelic is psilocybin·HCl, wherein the pimavanserin is administered to pretreat at least 180 minutes prior to the psilocybin·HCl. In some embodiments, the serotonin receptor modulator is pimavanserin and the psychedelic is psilocybin·HCl, wherein the pimavanserin is administered to pretreat at least 210 minutes prior to the psilocybin·HCl. In some embodiments, the serotonin receptor modulator is pimavanserin and the psychedelic is psilocybin·HCl, wherein the pimavanserin is administered to pretreat at least 240 minutes prior to the psilocybin·HCl. In some embodiments, the serotonin receptor modulator is pimavanserin and the psychedelic is psilocybin·HCl, wherein the pimavanserin is administered to pretreat at least 270 minutes prior to the psilocybin·HCl. In some embodiments, the serotonin receptor modulator is pimavanserin and the psychedelic is psilocybin·HCl, wherein the pimavanserin is administered to pretreat at least 300 minutes prior to the psilocybin·HCl. In some embodiments, the serotonin receptor modulator is pimavanserin and the psychedelic is psilocybin·HCl, wherein the pimavanserin is administered to pretreat at least 330 minutes prior to the psilocybin·HCl. In some embodiments, the serotonin receptor modulator is pimavanserin and the psychedelic is psilocybin·HCl, wherein the pimavanserin is administered to pretreat at least 360 minutes prior to the psilocybin·HCl. In some preferred embodiments, the serotonin receptor modulator is pimavanserin and the psychedelic is psilocybin·HCl, wherein pimavanserin is administered to pretreat between about 60 minutes and about 180 minutes prior to the administration of psilocybin·HCl.

In some embodiments, the serotonin receptor modulator is nelotanserin and the psychedelic is psilocybin·HCl, wherein the nelotanserin is administered to pretreat at least 15 minutes prior to the administration of psilocybin·HCl. In some embodiments, the serotonin receptor modulator is nelotanserin and the psychedelic is psilocybin·HCl, wherein the nelotanserin is administered to pretreat at least 30 minutes prior to the psilocybin·HCl. In some embodiments, the serotonin receptor modulator is nelotanserin and the psychedelic is psilocybin·HCl, wherein the nelotanserin is administered to pretreat between at least 60 minutes and 240 minutes prior to the administration or release of psilocybin·HCl. In some embodiments, the serotonin receptor modulator is nelotanserin and the psychedelic is psilocybin·HCl, wherein the nelotanserin is administered to pretreat at least 90 minutes prior to the psilocybin·HCl. In some embodiments, the serotonin receptor modulator is nelotanserin and the psychedelic is psilocybin·HCl, wherein the nelotanserin is administered to pretreat at least 120 minutes prior to the psilocybin·HCl.

In some embodiments, the serotonin receptor modulator is nelotanserin and the psychedelic is psilocybin·HCl, wherein the nelotanserin is administered to pretreat at least 150 minutes prior to the psilocybin·HCl. In some embodiments, the serotonin receptor modulator is nelotanserin and the psychedelic is psilocybin·HCl, wherein the nelotanserin is administered to pretreat between about 15 minutes and about 150 minutes prior to the psilocybin·HCl. In some embodiments, the serotonin receptor modulator is nelotanserin and the psychedelic is psilocybin·HCl, wherein the nelotanserin is administered to pretreat at least 180 minutes prior to the psilocybin·HCl. In some embodiments, the serotonin receptor modulator is nelotanserin and the psychedelic is psilocybin·HCl, wherein the nelotanserin is administered to pretreat at least 210 minutes prior to the psilocybin·HCl. In some embodiments, the serotonin receptor modulator is nelotanserin and the psychedelic is psilocybin·HCl, wherein the nelotanserin is administered to pretreat at least 240 minutes prior to the psilocybin·HCl.

In some embodiments, the serotonin receptor modulator is nelotanserin and the psychedelic is psilocybin·HCl, wherein the nelotanserin is administered to pretreat at least 270 minutes prior to the psilocybin·HCl. In some embodiments, the serotonin receptor modulator is nelotanserin and the psychedelic is psilocybin·HCl, wherein the nelotanserin is administered to pretreat at least 300 minutes prior to the psilocybin·HCl. In some embodiments, the serotonin receptor modulator is nelotanserin and the psychedelic is psilocybin·HCl, wherein the nelotanserin is administered to pretreat at least 330 minutes prior to the psilocybin·HCl. In some embodiments, the serotonin receptor modulator is nelotanserin and the psychedelic is psilocybin·HCl, wherein the nelotanserin is administered to pretreat at least 360 minutes prior to the psilocybin·HCl. In some preferred embodiments, the serotonin receptor modulator is nelotanserin and the psychedelic is psilocybin·HCl, wherein nelotanserin is administered to pretreat between about 60 minutes and about 180 minutes prior to the administration of psilocybin·HCl.

In some embodiments, the serotonin receptor modulator is pruvanserin and the psychedelic is psilocybin·HCl, wherein the pruvanserin is administered to pretreat at least 15 minutes prior to the administration of psilocybin·HCl. In some embodiments, the serotonin receptor modulator is pruvanserin and the psychedelic is psilocybin·HCl, wherein the pruvanserin is administered to pretreat at least 30 minutes prior to the psilocybin·HCl. In some embodiments, the serotonin receptor modulator is pruvanserin and the psychedelic is psilocybin·HCl, wherein the pruvanserin is administered to pretreat between at least 60 minutes and 240 minutes prior to the administration or release of psilocybin·HCl. In some embodiments, the serotonin receptor modulator is pruvanserin and the psychedelic is psilocybin·HCl, wherein the pruvanserin is administered to pretreat at least 90 minutes prior to the psilocybin·HCl. In some embodiments, the serotonin receptor modulator is pruvanserin and the psychedelic is psilocybin·HCl, wherein the pruvanserin is administered to pretreat at least 120 minutes prior to the psilocybin·HCl. In some embodiments, the serotonin receptor modulator is pruvanserin and the psychedelic is psilocybin·HCl, wherein the pruvanserin is administered to pretreat at least 150 minutes prior to the psilocybin·HCl. In some embodiments, the serotonin receptor modulator is pruvanserin and the psychedelic is psilocybin·HCl, wherein the pruvanserin is administered to pretreat between about 15 minutes and about 150 minutes prior to the psilocybin·HCl. In some embodiments, the serotonin receptor modulator is pruvanserin and the psychedelic is psilocybin·HCl, wherein the pruvanserin is administered to pretreat at least 180 minutes prior to the psilocybin·HCl. In some embodiments, the serotonin receptor modulator is pruvanserin and the psychedelic is psilocybin·HCl, wherein the pruvanserin is administered to pretreat at least 210 minutes prior to the psilocybin·HCl.

In some embodiments, the serotonin receptor modulator is pruvanserin and the psychedelic is psilocybin·HCl, wherein the pruvanserin is administered to pretreat at least 240 minutes prior to the psilocybin·HCl. In some embodiments, the serotonin receptor modulator is pruvanserin and the psychedelic is psilocybin·HCl, wherein the pruvanserin is administered to pretreat at least 270 minutes prior to the psilocybin·HCl. In some embodiments, the serotonin receptor modulator is pruvanserin and the psychedelic is psilocybin·HCl, wherein the pruvanserin is administered to pretreat at least 300 minutes prior to the psilocybin·HCl. In some embodiments, the serotonin receptor modulator is pruvanserin and the psychedelic is psilocybin·HCl, wherein the pruvanserin is administered to pretreat at least 330 minutes prior to the psilocybin·HCl. In some embodiments, the serotonin receptor modulator is pruvanserin and the psychedelic is psilocybin·HCl, wherein the pruvanserin is administered to pretreat at least 360 minutes prior to the psilocybin·HCl. In some preferred embodiments, the serotonin receptor modulator is pruvanserin and the psychedelic is psilocybin·HCl, wherein pruvanserin is administered to pretreat between about 60 minutes and about 180 minutes prior to the administration of psilocybin·HCl.

In certain embodiments, such as those described above a psilocybin·HCl form disclosed herein, including those described in Table 4, is co-administered with a serotonin receptor modulator in the same or in separate compositions. In one embodiment, the serotonin receptor modulator is administered after the psilocybin HCl form disclosed herein, including those described in Table 4. In one embodiment, the psilocybin HCl form disclosed herein, including those described in Table 4, is administered in a modified release formulation such that the subject is effectively post-treated with serotonin receptor modulator post to release of an effective amount of the psilocybin HCl. In some embodiments, the serotonin receptor modulator is part of a single fixed dose formulation that releases the psilocybin HCl first followed by serotonin receptor modulator on two different release profiles. In another embodiment, the psilocybin HCl form disclosed herein, including those described in Table 4, is administered first as a single dosage and, after a length of time, serotonin receptor modulator is administered as a second dosage separate from the first dosage. Thus, in some embodiments, the serotonin receptor modulator is administered or released from a composition provided herein post to the administration and/or release of the psychedelic. This allows post-treatment to attenuate activation of the serotonin receptor by the psychedelic. In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours post to the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post to the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post to the release of the psychedelic.

In a preferred embodiment, the serotonin receptor modulator is administered at about 1 hour to about 3 hours post to the administration of the psychedelic.

In some embodiments, the serotonin receptor modulator is eplivanserin and the psychedelic is psilocybin HCl, wherein the eplivanserin is administered to post-treat at least 15 minutes after the administration of the psilocybin HCl form disclosed herein, including those described in Table 4. In some embodiments, the serotonin receptor modulator is eplivanserin and the psychedelic is psilocybin HCl, wherein the eplivanserin is administered to post-treat between at least 30 minutes after and 360 minutes after the release or administration of the psilocybin HCl form disclosed herein, including those described in Table 4. In some embodiments, the serotonin receptor modulator is eplivanserin and the psychedelic is psilocybin HCl, wherein the eplivanserin is administered to post-treat between at least 60 minutes after and 360 minutes after the release or administration of the psilocybin HCl form disclosed herein, including those described in Table 4. In some embodiments, the serotonin receptor modulator is eplivanserin and the psychedelic is psilocybin HCl, wherein the eplivanserin is administered to post-treat between at least 90 minutes and 240 minutes after the psilocybin HCl form disclosed herein, including those described in Table 4. In some embodiments, the serotonin receptor modulator is eplivanserin and the psychedelic is psilocybin HCl, wherein the eplivanserin is administered to post-treat at least 120 minutes after the psilocybin HCl form disclosed herein, including those described in Table 4.

In some embodiments, the serotonin receptor modulator is eplivanserin and the psychedelic is psilocybin HCl, wherein the eplivanserin is administered to post-treat at least 150 minutes after the psilocybin HCl form disclosed herein, including those described in Table 4. In some embodiments, the serotonin receptor modulator is eplivanserin and the psychedelic is psilocybin HCl, wherein the eplivanserin is administered to post-treat between about 15 minutes and about 150 minutes after the psilocybin HCl form disclosed herein, including those described in Table 4. In some embodiments, the serotonin receptor modulator is eplivanserin and the psychedelic is psilocybin HCl, wherein the eplivanserin is administered to post-treat at least 180 minutes after the psilocybin HCl form disclosed herein, including those described in Table 4. In some embodiments, the serotonin receptor modulator is eplivanserin and the psychedelic is psilocybin HCl, wherein the eplivanserin is administered to post-treat at least 210 minutes after the psilocybin HCl form disclosed herein, including those described in Table 4. In some embodiments, the serotonin receptor modulator is eplivanserin and the psychedelic is psilocybin HCl, wherein the eplivanserin is administered to post-treat at least 240 minutes after the psilocybin HCl form disclosed herein, including those described in Table 4.

In some embodiments, the serotonin receptor modulator is eplivanserin and the psychedelic is psilocybin HCl, wherein the eplivanserin is administered to post-treat at least 270 minutes after the psilocybin HCl form disclosed herein, including those described in Table 4. In some embodiments, the serotonin receptor modulator is eplivanserin and the psychedelic is psilocybin HCl, wherein the eplivanserin is administered to post-treat at least 300 minutes after the psilocybin HCl form disclosed herein, including those described in Table 4. In some embodiments, the serotonin receptor modulator is eplivanserin and the psychedelic is psilocybin HCl, wherein the eplivanserin is administered to post-treat at least 330 minutes after the psilocybin HCl form disclosed herein, including those described in Table 4. In some embodiments, the serotonin receptor modulator is eplivanserin and the psychedelic is psilocybin HCl, wherein the eplivanserin is administered to post-treat at least 360 minutes after the psilocybin HCl form disclosed herein, including those described in Table 4.

In some preferred embodiments, the serotonin receptor modulator is eplivanserin and the psychedelic is psilocybin HCl, wherein eplivanserin is administered to post-treat between about 60 minutes and about 180 minutes after the administration of the psilocybin HCl form disclosed herein, including those described in Table 4.

In some embodiments, the serotonin receptor modulator is volinanserin and the psychedelic is psilocybin HCl, wherein the volinanserin is administered to post-treat a subject between at least 15 minutes and 360 minutes after the administration or release of the psilocybin HCl form disclosed herein, including those described in Table 4. In some embodiments, the serotonin receptor modulator is volinanserin and the psychedelic is psilocybin HCl, wherein the volinanserin is administered to post-treat between at least 30 minutes and 360 minutes after the administration or release of the psilocybin HCl form disclosed herein, including those described in Table 4. In some embodiments, the serotonin receptor modulator is volinanserin and the psychedelic is psilocybin HCl, wherein the volinanserin is administered to post-treat between at least 60 minutes and 240 minutes after the administration or release of the psilocybin HCl form disclosed herein, including those described in Table 4. In some embodiments, the serotonin receptor modulator is volinanserin and the psychedelic is psilocybin HCl, wherein the volinanserin is administered to post-treat at least 90 minutes after psilocybin HCl. In some embodiments, the serotonin receptor modulator is volinanserin and the psychedelic is psilocybin HCl, wherein the volinanserin is administered to post-treat at least 120 minutes after the psilocybin HCl form disclosed herein, including those described in Table 4.

In some embodiments, the serotonin receptor modulator is volinanserin and the psychedelic is psilocybin HCl, wherein the volinanserin is administered to post-treat at least 150 minutes after the psilocybin HCl form disclosed herein, including those described in Table 4. In some embodiments, the serotonin receptor modulator is volinanserin and the psychedelic is psilocybin HCl, wherein the volinanserin is administered to post-treat between about 15 minutes and about 150 minutes after the psilocybin HCl form disclosed herein, including those described in Table 4. In some embodiments, the serotonin receptor modulator is volinanserin and the psychedelic is psilocybin HCl, wherein the volinanserin is administered to post-treat at least 180 minutes after the psilocybin HCl form disclosed herein, including those described in Table 4. In some embodiments, the serotonin receptor modulator is volinanserin and the psychedelic is psilocybin HCl, wherein the volinanserin is administered to post-treat at least 210 minutes after the psilocybin HCl form disclosed herein, including those described in Table 4. In some embodiments, the serotonin receptor modulator is volinanserin and the psychedelic is psilocybin HCl, wherein the volinanserin is administered to post-treat at least 240 minutes after the psilocybin HCl form disclosed herein, including those described in Table 4. In some embodiments, the serotonin receptor modulator is volinanserin and the psychedelic is psilocybin HCl, wherein the volinanserin is administered to post-treat at least 270 minutes after the psilocybin HCl form disclosed herein, including those described in Table 4. In some embodiments, the serotonin receptor modulator is volinanserin and the psychedelic is psilocybin HCl, wherein the volinanserin is administered to post-treat at least 300 minutes after the psilocybin HCl form disclosed herein, including those described in Table 4. In some embodiments, the serotonin receptor modulator is volinanserin and the psychedelic is psilocybin HCl, wherein the volinanserin is administered to post-treat at least 330 minutes after the psilocybin HCl form disclosed herein, including those described in Table 4. In some embodiments, the serotonin receptor modulator is volinanserin and the psychedelic is psilocybin HCl, wherein the volinanserin is administered to post-treat at least 360 minutes after the psilocybin HCl form disclosed herein, including those described in Table 4. In some preferred embodiments, the serotonin receptor modulator is volinanserin and the psychedelic is psilocybin HCl, wherein volinanserin is administered to post-treat between about 60 minutes and about 180 minutes after the administration of the ®-MDMA form.

In some embodiments, the serotonin receptor modulator is ketanserin and the psychedelic is psilocybin HCl, wherein the ketanserin is administered to post-treat at least 15 minutes after the administration of the psilocybin HCl form disclosed herein, including those described in Table 4. In some embodiments, the serotonin receptor modulator is ketanserin and the psychedelic is psilocybin HCl, wherein the ketanserin is administered to post-treat between at least 30 minutes and 360 minutes after the administration or release of the psilocybin HCl form disclosed herein, including those described in Table 4. In some embodiments, the serotonin receptor modulator is ketanserin and the psychedelic is psilocybin HCl, wherein the ketanserin is administered to post-treat between at least 60 minutes and 240 minutes after the administration or release of the psilocybin HCl form disclosed herein, including those described in Table 4. In some embodiments, the serotonin receptor modulator is ketanserin and the psychedelic is psilocybin HCl, wherein the ketanserin is administered to post-treat at least 90 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 120 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 150 minutes after the psilocybin HCl form disclosed herein, including those described in Table 4. In some embodiments, the serotonin receptor modulator is ketanserin and the psychedelic is psilocybin HCl, wherein the ketanserin is administered to post-treat between about 15 minutes and about 150 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 180 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 210 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 240 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 270 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 300 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 330 minutes after the psilocybin HCl form disclosed herein, including those described in Table 4. In some embodiments, the serotonin receptor modulator is ketanserin and the psychedelic is psilocybin HCl, wherein the ketanserin is administered to post-treat at least 360 minutes after the psilocybin HCl form disclosed herein, including those described in Table 4. In some preferred embodiments, the serotonin receptor modulator is ketanserin and the psychedelic is psilocybin HCl, wherein ketanserin is administered to post-treat between about 60 minutes and about 180 minutes after the administration of the psilocybin HCl form disclosed herein, including those described in Table 4.

In some embodiments, the serotonin receptor modulator is ritanserin and the psychedelic is psilocybin HCl, wherein the ritanserin is administered to post-treat at least 15 minutes after the administration of the psilocybin HCl form disclosed herein, including those described in Table 4. In some embodiments, the serotonin receptor modulator is ritanserin and the psychedelic is psilocybin HCl, wherein the ritanserin is administered to post-treat at least 30 minutes after the psilocybin HCl form disclosed herein, including those described in Table 4. In some embodiments, the serotonin receptor modulator is ritanserin and the psychedelic is psilocybin HCl, wherein the ritanserin is administered to post-treat between at least 60 minutes and 240 minutes after the administration or release of the psilocybin HCl form disclosed herein, including those described in Table 4. In some embodiments, the serotonin receptor modulator is ritanserin and the psychedelic is psilocybin HCl, wherein the ritanserin is administered to post-treat at least 90 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 120 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 150 minutes after the psilocybin HCl form disclosed herein, including those described in Table 4. In some embodiments, the serotonin receptor modulator is ritanserin and the psychedelic is psilocybin HCl, wherein the ritanserin is administered to post-treat between about 15 minutes and about 150 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 180 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 210 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 240 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 270 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 300 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 330 minutes after the psilocybin HCl form disclosed herein, including those described in Table 4. In some embodiments, the serotonin receptor modulator is ritanserin and the psychedelic is psilocybin HCl, wherein the ritanserin is administered to post-treat at least 360 minutes after the psilocybin HCl form disclosed herein, including those described in Table 4. In some preferred embodiments, the serotonin receptor modulator is ritanserin and the psychedelic is psilocybin HCl, wherein ritanserin is administered to post-treat between about 60 minutes and about 180 minutes after the administration of the psilocybin HCl form disclosed herein, including those described in Table 4.

In some embodiments, the serotonin receptor modulator is pimavanserin and the psychedelic is psilocybin HCl, wherein the pimavanserin is administered to post-treat at least 15 minutes after the administration of the psilocybin HCl form disclosed herein, including those described in Table 4. In some embodiments, the serotonin receptor modulator is pimavanserin and the psychedelic is psilocybin HCl, wherein the pimavanserin is administered to post-treat at least 30 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat between at least 60 minutes and 240 minutes after the administration or release of the psilocybin HCl form disclosed herein, including those described in Table 4. In some embodiments, the serotonin receptor modulator is pimavanserin and the psychedelic is psilocybin HCl, wherein the pimavanserin is administered to post-treat at least 90 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 120 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 150 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat between about 15 minutes and about 150 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 180 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 210 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 240 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 270 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 300 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 330 minutes after the psilocybin HCl form disclosed herein, including those described in Table 4. In some embodiments, the serotonin receptor modulator is pimavanserin and the psychedelic is psilocybin HCl, wherein the pimavanserin is administered to post-treat at least 360 minutes after the psilocybin HCl form disclosed herein, including those described in Table 4. In some preferred embodiments, the serotonin receptor modulator is pimavanserin and the psychedelic is psilocybin HCl, wherein pimavanserin is administered to post-treat between about 60 minutes and about 180 minutes after the administration of the psilocybin HCl form disclosed herein, including those described in Table 4.

In some embodiments, the serotonin receptor modulator is nelotanserin and the psychedelic is psilocybin HCl, wherein the nelotanserin is administered to post-treat at least 15 minutes after the administration of the psilocybin HCl form disclosed herein, including those described in Table 4. In some embodiments, the serotonin receptor modulator is nelotanserin and the psychedelic is psilocybin HCl, wherein the nelotanserin is administered to post-treat at least 30 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat between at least 60 minutes and 240 minutes after the administration or release of the psilocybin HCl form disclosed herein, including those described in Table 4. In some embodiments, the serotonin receptor modulator is nelotanserin and the psychedelic is psilocybin HCl, wherein the nelotanserin is administered to post-treat at least 90 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat at least 120 minutes after the psilocybin HCl form disclosed herein, including those described in Table 4.

In some embodiments, the serotonin receptor modulator is nelotanserin and the psychedelic is psilocybin HCl, wherein the nelotanserin is administered to post-treat at least 150 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat between about 15 minutes and about 150 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat at least 180 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat at least 210 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat at least 240 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat at least 270 minutes after the psilocybin HCl form disclosed herein, including those described in Table 4.

In some embodiments, the serotonin receptor modulator is nelotanserin and the psychedelic is psilocybin HCl, wherein the nelotanserin is administered to post-treat at least 300 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat at least 330 minutes after the psilocybin HCl form disclosed herein, including those described in Table 4. In some embodiments, the serotonin receptor modulator is nelotanserin and the psychedelic is psilocybin HCl, wherein the nelotanserin is administered to post-treat at least 360 minutes after the psilocybin HCl form disclosed herein, including those described in Table 4. In some preferred embodiments, the serotonin receptor modulator is nelotanserin and the psychedelic is psilocybin HCl, wherein nelotanserin is administered to post-treat between about 60 minutes and about 180 minutes after the administration of the psilocybin HCl form disclosed herein, including those described in Table 4.

In some embodiments, the serotonin receptor modulator is pruvanserin and the psychedelic is psilocybin HCl, wherein the pruvanserin is administered to post-treat at least 15 minutes after the administration of the psilocybin HCl form disclosed herein, including those described in Table 4. In some embodiments, the serotonin receptor modulator is pruvanserin and the psychedelic is psilocybin HCl, wherein the pruvanserin is administered to post-treat at least 30 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat between at least 60 minutes and 240 minutes after the administration or release of the psilocybin HCl form disclosed herein, including those described in Table 4. In some embodiments, the serotonin receptor modulator is pruvanserin and the psychedelic is psilocybin HCl, wherein the pruvanserin is administered to post-treat at least 90 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat at least 120 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat at least 150 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat between about 15 minutes and about 150 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat at least 180 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat at least 210 minutes after the psilocybin HCl form disclosed herein, including those described in Table 4.

In some embodiments, the serotonin receptor modulator is pruvanserin and the psychedelic is psilocybin HCl, wherein the pruvanserin is administered to post-treat at least 240 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat at least 270 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat at least 300 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat at least 330 minutes after the psilocybin HCl form disclosed herein, including those described in Table 4. In some embodiments, the serotonin receptor modulator is pruvanserin and the psychedelic is psilocybin HCl, wherein the pruvanserin is administered to post-treat at least 360 minutes after the psilocybin HCl form disclosed herein, including those described in Table 4. In some preferred embodiments, the serotonin receptor modulator is pruvanserin and the psychedelic is psilocybin HCl, wherein pruvanserin is administered to post-treat between about 60 minutes and about 180 minutes after the administration of the psilocybin HCl form disclosed herein, including those described in Table 4.

In some embodiments, the serotonin receptor modulator is flibanserin, wherein the flibanserin is administered to post-treat at least 15 minutes post to the administration of the psilocybin HCl form disclosed herein, including those described in Table 4. In some embodiments, the serotonin receptor modulator is flibanserin, wherein the flibanserin is administered to post-treat at least 30 minutes post to the psilocybin HCl form disclosed herein, including those described in Table 4. In some embodiments, the serotonin receptor modulator is flibanserin, wherein the flibanserin is administered to post-treat between at least 60 minutes and 240 minutes post to the administration or release of the psilocybin HCl form disclosed herein, including those described in Table 4. In some embodiments, the serotonin receptor modulator is flibanserin, wherein the flibanserin is administered to post-treat at least 90 minutes post to the psilocybin HCl form disclosed herein, including those described in Table 4. In some embodiments, the serotonin receptor modulator is flibanserin, wherein the flibanserin is administered to post-treat at least 120 minutes post to the psilocybin HCl form disclosed herein, including those described in Table 4. In some embodiments, the serotonin receptor modulator is flibanserin, wherein the flibanserin is administered to post-treat at least 150 minutes post to the psilocybin HCl form disclosed herein, including those described in Table 4. In some embodiments, the serotonin receptor modulator is flibanserin, wherein the flibanserin is administered to post-treat between about 15 minutes and about 150 minutes post to the psilocybin HCl form disclosed herein, including those described in Table 4. In some embodiments, the serotonin receptor modulator is flibanserin, wherein the flibanserin is administered to post-treat at least 180 minutes post to the psilocybin HCl form disclosed herein, including those described in Table 4. In some embodiments, the serotonin receptor modulator is flibanserin, wherein flibanserin is administered to post-treat at least 210 minutes post to the psilocybin HCl form disclosed herein, including those described in Table 4.

In some embodiments, the serotonin receptor modulator is flibanserin, wherein the flibanserin is administered to post-treat at least 240 minutes post to the psilocybin HCl form disclosed herein, including those described in Table 4. In some embodiments, the serotonin receptor modulator is flibanserin, wherein the flibanserin is administered to post-treat at least 270 minutes post to the psilocybin HCl form disclosed herein, including those described in Table 4. In some embodiments, the serotonin receptor modulator is flibanserin, wherein the flibanserin is administered to post-treat at least 300 minutes post to the psilocybin HCl form disclosed herein, including those described in Table 4. In some embodiments, the serotonin receptor modulator is flibanserin, wherein the flibanserin is administered to post-treat at least 330 minutes post to the psilocybin HCl form disclosed herein, including those described in Table 4. In some embodiments, the serotonin receptor modulator is flibanserin, wherein the flibanserin is administered to post-treat at least 360 minutes post to the psilocybin HCl form disclosed herein, including those described in Table 4. In some preferred embodiments, the serotonin receptor modulator is flibanserin, wherein flibanserin is administered to post-treat between about 60 minutes and about 180 minutes post to the administration of the psilocybin HCl form disclosed herein, including those described in Table 4.

In some embodiments, the serotonin receptor modulator is olanzapine, wherein the olanzapine is administered to post-treat at least 15 minutes post to the administration of the psilocybin HCl form disclosed herein, including those described in Table 4. In some embodiments, the serotonin receptor modulator is olanzapine, wherein the olanzapine is administered to post-treat at least 30 minutes post to the psilocybin HCl form disclosed herein, including those described in Table 4. In some embodiments, the serotonin receptor modulator is olanzapine, wherein the olanzapine is administered to post-treat between at least 60 minutes and 240 minutes post to the administration or release of the psilocybin HCl form disclosed herein, including those described in Table 4. In some embodiments, the serotonin receptor modulator is olanzapine, wherein the olanzapine is administered to post-treat at least 90 minutes post to the psilocybin HCl form disclosed herein, including those described in Table 4. In some embodiments, the serotonin receptor modulator is olanzapine, wherein the olanzapine is administered to post-treat at least 120 minutes post to the psilocybin HCl form disclosed herein, including those described in Table 4. In some embodiments, the serotonin receptor modulator is olanzapine, wherein the olanzapine is administered to post-treat at least 150 minutes post to the psilocybin HCl form disclosed herein, including those described in Table 4. In some embodiments, the serotonin receptor modulator is olanzapine, wherein the olanzapine is administered to post-treat between about 15 minutes and about 150 minutes post to the psilocybin HCl form disclosed herein, including those described in Table 4. In some embodiments, the serotonin receptor modulator is olanzapine, wherein the olanzapine is administered to post-treat at least 180 minutes post to the psilocybin HCl form disclosed herein, including those described in Table 4. In some embodiments, the serotonin receptor modulator is olanzapine, wherein the olanzapine is administered to post-treat at least 210 minutes post to the psilocybin HCl form disclosed herein, including those described in Table 4. In some embodiments, the serotonin receptor modulator is olanzapine, wherein the olanzapine is administered to post-treat at least 240 minutes post to the psilocybin HCl form disclosed herein, including those described in Table 4. In some embodiments, the serotonin receptor modulator is olanzapine, wherein the olanzapine is administered to post-treat at least 270 minutes post to the psilocybin HCl form disclosed herein, including those described in Table 4. In some embodiments, the serotonin receptor modulator is olanzapine, wherein the olanzapine is administered to post-treat at least 300 minutes post to the psilocybin HCl form disclosed herein, including those described in Table 4. In some embodiments, the serotonin receptor modulator is olanzapine, wherein the olanzapine is administered to post-treat at least 330 minutes post to the psilocybin HCl form disclosed herein, including those described in Table 4. In some embodiments, the serotonin receptor modulator is olanzapine, wherein the olanzapine is administered to post-treat at least 360 minutes post to the psilocybin HCl form disclosed herein, including those described in Table 4. In some preferred embodiments, the serotonin receptor modulator is olanzapine, wherein olanzapine is administered to post-treat between about 60 minutes and about 180 minutes post to the administration of the psilocybin HCl form disclosed herein, including those described in Table 4.

In some embodiments, the serotonin receptor modulator is quetiapine, wherein the quetiapine is administered to post-treat at least 15 minutes post to the administration of the psilocybin HCl form disclosed herein, including those described in Table 4. In some embodiments, the serotonin receptor modulator is quetiapine, wherein the quetiapine is administered to post-treat at least 30 minutes post to the psilocybin HCl form disclosed herein, including those described in Table 4. In some embodiments, the serotonin receptor modulator is quetiapine, wherein the quetiapine is administered to post-treat between at least 60 minutes and 240 minutes post to the administration or release of the psilocybin HCl form disclosed herein, including those described in Table 4. In some embodiments, the serotonin receptor modulator is quetiapine, wherein the quetiapine is administered to post-treat at least 90 minutes post to the psilocybin HCl form disclosed herein, including those described in Table 4. In some embodiments, the serotonin receptor modulator is quetiapine, wherein the quetiapine is administered to post-treat at least 120 minutes post to the psilocybin HCl form disclosed herein, including those described in Table 4. In some embodiments, the serotonin receptor modulator is quetiapine, wherein the quetiapine is administered to post-treat at least 150 minutes post to the psilocybin HCl form disclosed herein, including those described in Table 4. In some embodiments, the serotonin receptor modulator is quetiapine, wherein the quetiapine is administered to post-treat between about 15 minutes and about 150 minutes post to the psilocybin HCl form disclosed herein, including those described in Table 4. In some embodiments, the serotonin receptor modulator is quetiapine, wherein the quetiapine is administered to post-treat at least 180 minutes post to the psilocybin HCl form disclosed herein, including those described in Table 4. In some embodiments, the serotonin receptor modulator is quetiapine, wherein quetiapine is administered to post-treat at least 210 minutes post to the psilocybin HCl form disclosed herein, including those described in Table 4.

In some embodiments, the serotonin receptor modulator is quetiapine, wherein the quetiapine is administered to post-treat at least 240 minutes post to the psilocybin HCl form disclosed herein, including those described in Table 4. In some embodiments, the serotonin receptor modulator is quetiapine, wherein the quetiapine is administered to post-treat at least 270 minutes post to the psilocybin HCl form disclosed herein, including those described in Table 4. In some embodiments, the serotonin receptor modulator is quetiapine, wherein the quetiapine is administered to post-treat at least 300 minutes post to the psilocybin HCl form disclosed herein, including those described in Table 4. In some embodiments, the serotonin receptor modulator is quetiapine, wherein the quetiapine is administered to post-treat at least 330 minutes post to the psilocybin HCl form disclosed herein, including those described in Table 4. In some embodiments, the serotonin receptor modulator is quetiapine, wherein the quetiapine is administered to post-treat at least 360 minutes post to the psilocybin HCl form disclosed herein, including those described in Table 4. In some preferred embodiments, the serotonin receptor modulator is quetiapine, wherein quetiapine is administered to post-treat between about 60 minutes and about 180 minutes post to the administration of the psilocybin HCl form disclosed herein, including those described in Table 4.

In some embodiments, the serotonin receptor modulator is risperidone, wherein the risperidone is administered to post-treat at least 15 minutes post to the administration of the psilocybin HCl form disclosed herein, including those described in Table 4. In some embodiments, the serotonin receptor modulator is risperidone, wherein the risperidone is administered to post-treat at least 30 minutes post to the psilocybin HCl form disclosed herein, including those described in Table 4. In some embodiments, the serotonin receptor modulator is risperidone, wherein the risperidone is administered to post-treat between at least 60 minutes and 240 minutes post to the administration or release of the psilocybin HCl form disclosed herein, including those described in Table 4. In some embodiments, the serotonin receptor modulator is risperidone, wherein the risperidone is administered to post-treat at least 90 minutes post to the psilocybin HCl form disclosed herein, including those described in Table 4. In some embodiments, the serotonin receptor modulator is risperidone, wherein the risperidone is administered to post-treat at least 120 minutes post to the psilocybin HCl form disclosed herein, including those described in Table 4. In some embodiments, the serotonin receptor modulator is risperidone, wherein the risperidone is administered to post-treat at least 150 minutes post to the psilocybin HCl form disclosed herein, including those described in Table 4. In some embodiments, the serotonin receptor modulator is risperidone, wherein the risperidone is administered to post-treat between about 15 minutes and about 150 minutes post to the psilocybin HCl form disclosed herein, including those described in Table 4. In some embodiments, the serotonin receptor modulator is risperidone, wherein the risperidone is administered to post-treat at least 180 minutes post to the psilocybin HCl form disclosed herein, including those described in Table 4. In some embodiments, the serotonin receptor modulator is risperidone, wherein the risperidone is administered to post-treat at least 210 minutes post to the psilocybin HCl form disclosed herein, including those described in Table 4.

In some embodiments, the serotonin receptor modulator is risperidone, wherein the risperidone is administered to post-treat at least 240 minutes post to the psilocybin HCl form disclosed herein, including those described in Table 4. In some embodiments, the serotonin receptor modulator is risperidone, wherein the risperidone is administered to post-treat at least 270 minutes post to the psilocybin HCl form disclosed herein, including those described in Table 4. In some embodiments, the serotonin receptor modulator is risperidone, wherein the risperidone is administered to post-treat at least 300 minutes post to the psilocybin HCl form disclosed herein, including those described in Table 4. In some embodiments, the serotonin receptor modulator is risperidone, wherein the risperidone is administered to post-treat at least 330 minutes post to the psilocybin HCl form disclosed herein, including those described in Table 4. In some embodiments, the serotonin receptor modulator is risperidone, wherein the risperidone is administered to post-treat at least 360 minutes post to the psilocybin HCl form disclosed herein, including those described in Table 4. In some preferred embodiments, the serotonin receptor modulator is risperidone, wherein risperidone is administered to post-treat between about 60 minutes and about 180 minutes post to the administration of the psilocybin HCl form disclosed herein, including those described in Table 4.

In some embodiments, the serotonin receptor modulator is eplivanserin and the psychedelic is psilocybin HCl cocrystal Form A, wherein the eplivanserin is administered to post-treat at least 15 minutes after the administration of the psilocybin HCl cocrystal Form A. In some embodiments, the serotonin receptor modulator is eplivanserin and the psychedelic is psilocybin HCl cocrystal Form A, wherein the eplivanserin is administered to post-treat between at least 30 minutes after and 360 minutes after the release or administration of the psilocybin HCl cocrystal Form A. In some embodiments, the serotonin receptor modulator is eplivanserin and the psychedelic is psilocybin HCl cocrystal Form A, wherein the eplivanserin is administered to post-treat between at least 60 minutes after and 360 minutes after the release or administration of the psilocybin HCl cocrystal Form A. In some embodiments, the serotonin receptor modulator is eplivanserin and the psychedelic is psilocybin HCl cocrystal Form A, wherein the eplivanserin is administered to post-treat between at least 90 minutes and 240 minutes after the psilocybin HCl cocrystal Form A. In some embodiments, the serotonin receptor modulator is eplivanserin and the psychedelic is psilocybin HCl cocrystal Form A, wherein the eplivanserin is administered to post-treat at least 120 minutes after the psilocybin HCl cocrystal Form A.

In some embodiments, the serotonin receptor modulator is eplivanserin and the psychedelic is psilocybin HCl cocrystal Form A, wherein the eplivanserin is administered to post-treat at least 150 minutes after the psilocybin HCl cocrystal Form A. In some embodiments, the serotonin receptor modulator is eplivanserin and the psychedelic is psilocybin HCl cocrystal Form A, wherein the eplivanserin is administered to post-treat between about 15 minutes and about 150 minutes after the psilocybin HCl cocrystal Form A. In some embodiments, the serotonin receptor modulator is eplivanserin and the psychedelic is psilocybin HCl cocrystal Form A, wherein the eplivanserin is administered to post-treat at least 180 minutes after the psilocybin HCl cocrystal Form A. In some embodiments, the serotonin receptor modulator is eplivanserin and the psychedelic is psilocybin HCl cocrystal Form A, wherein the eplivanserin is administered to post-treat at least 210 minutes after the psilocybin HCl cocrystal Form A. In some embodiments, the serotonin receptor modulator is eplivanserin and the psychedelic is psilocybin HCl cocrystal Form A, wherein the eplivanserin is administered to post-treat at least 240 minutes after the psilocybin HCl cocrystal Form A.

In some embodiments, the serotonin receptor modulator is eplivanserin and the psychedelic is psilocybin HCl cocrystal Form A, wherein the eplivanserin is administered to post-treat at least 270 minutes after the psilocybin HCl cocrystal Form A. In some embodiments, the serotonin receptor modulator is eplivanserin and the psychedelic is psilocybin HCl cocrystal Form A, wherein the eplivanserin is administered to post-treat at least 300 minutes after the psilocybin HCl cocrystal Form A. In some embodiments, the serotonin receptor modulator is eplivanserin and the psychedelic is psilocybin HCl cocrystal Form A, wherein the eplivanserin is administered to post-treat at least 330 minutes after the psilocybin HCl cocrystal Form A. In some embodiments, the serotonin receptor modulator is eplivanserin and the psychedelic is psilocybin HCl cocrystal Form A, wherein eplivanserin is administered to post-treat at least 360 minutes after psilocybin HCl cocrystal Form A.

In some preferred embodiments, the serotonin receptor modulator is eplivanserin and the psychedelic is psilocybin HCl cocrystal Form A, wherein eplivanserin is administered to post-treat between about 60 min. and about 180 min. after administration of psilocybin HCl cocrystal Form A.

In some embodiments, the serotonin receptor modulator is volinanserin and the psychedelic is psilocybin HCl cocrystal Form A, wherein the volinanserin is administered to post-treat a subject between at least 15 minutes and 360 minutes after the administration or release of the psilocybin HCl cocrystal Form A. In some embodiments, the serotonin receptor modulator is volinanserin and the psychedelic is psilocybin HCl cocrystal Form A, wherein the volinanserin is administered to post-treat between at least 30 minutes and 360 minutes after the administration or release of the psilocybin HCl cocrystal Form A. In some embodiments, the serotonin receptor modulator is volinanserin and the psychedelic is psilocybin HCl cocrystal Form A, wherein the volinanserin is administered to post-treat between at least 60 minutes and 240 minutes after the administration or release of the psilocybin HCl cocrystal Form A. In some embodiments, the serotonin receptor modulator is volinanserin and the psychedelic is psilocybin HCl cocrystal Form A, wherein the volinanserin is administered to post-treat at least 90 minutes after psilocybin HCl. In some embodiments, the serotonin receptor modulator is volinanserin and the psychedelic is psilocybin HCl cocrystal Form A, wherein the volinanserin is administered to post-treat at least 120 minutes after the psilocybin HCl cocrystal Form A.

In some embodiments, the serotonin receptor modulator is volinanserin and the psychedelic is psilocybin HCl cocrystal Form A, wherein the volinanserin is administered to post-treat at least 150 minutes after the psilocybin HCl cocrystal Form A. In some embodiments, the serotonin receptor modulator is volinanserin and the psychedelic is psilocybin HCl cocrystal Form A, wherein the volinanserin is administered to post-treat between about 15 minutes and about 150 minutes after the psilocybin HCl cocrystal Form A. In some embodiments, the serotonin receptor modulator is volinanserin and the psychedelic is psilocybin HCl cocrystal Form A, wherein the volinanserin is administered to post-treat at least 180 minutes after the psilocybin HCl cocrystal Form A. In some embodiments, the serotonin receptor modulator is volinanserin and the psychedelic is psilocybin HCl cocrystal Form A, wherein the volinanserin is administered to post-treat at least 210 minutes after the psilocybin HCl cocrystal Form A. In some embodiments, the serotonin receptor modulator is volinanserin and the psychedelic is psilocybin HCl cocrystal Form A, wherein the volinanserin is administered to post-treat at least 240 minutes after the psilocybin HCl cocrystal Form A. In some embodiments, the serotonin receptor modulator is volinanserin and the psychedelic is psilocybin HCl cocrystal Form A, wherein the volinanserin is administered to post-treat at least 270 minutes after the psilocybin HCl cocrystal Form A. In some embodiments, the serotonin receptor modulator is volinanserin and the psychedelic is psilocybin HCl cocrystal Form A, wherein the volinanserin is administered to post-treat at least 300 minutes after the psilocybin HCl cocrystal Form A. In some embodiments, the serotonin receptor modulator is volinanserin and the psychedelic is psilocybin HCl cocrystal Form A, wherein the volinanserin is administered to post-treat at least 330 minutes after the psilocybin HCl cocrystal Form A. In some embodiments, the serotonin receptor modulator is volinanserin and the psychedelic is psilocybin HCl cocrystal Form A, wherein the volinanserin is administered to post-treat at least 360 minutes after the psilocybin HCl cocrystal Form A. In some preferred embodiments, the serotonin receptor modulator is volinanserin and the psychedelic is psilocybin HCl cocrystal Form A, wherein volinanserin is administered to post-treat between about 60 minutes and about 180 minutes after the administration of the ®-MDMA form.

In some embodiments, the serotonin receptor modulator is ketanserin and the psychedelic is psilocybin HCl cocrystal Form A, wherein the ketanserin is administered to post-treat at least 15 minutes after the administration of the psilocybin HCl cocrystal Form A. In some embodiments, the serotonin receptor modulator is ketanserin and the psychedelic is psilocybin HCl cocrystal Form A, wherein the ketanserin is administered to post-treat between at least 30 minutes and 360 minutes after the administration or release of the psilocybin HCl cocrystal Form A. In some embodiments, the serotonin receptor modulator is ketanserin and the psychedelic is psilocybin HCl cocrystal Form A, wherein the ketanserin is administered to post-treat between at least 60 minutes and 240 minutes after the administration or release of the psilocybin HCl cocrystal Form A. In some embodiments, the serotonin receptor modulator is ketanserin and the psychedelic is psilocybin HCl cocrystal Form A, wherein the ketanserin is administered to post-treat at least 90 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 120 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 150 minutes after the psilocybin HCl cocrystal Form A. In some embodiments, the serotonin receptor modulator is ketanserin and the psychedelic is psilocybin HCl cocrystal Form A, wherein the ketanserin is administered to post-treat between about 15 minutes and about 150 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 180 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 210 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 240 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 270 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 300 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 330 minutes after the psilocybin HCl cocrystal Form A. In some embodiments, the serotonin receptor modulator is ketanserin and the psychedelic is psilocybin HCl cocrystal Form A, wherein the ketanserin is administered to post-treat at least 360 minutes after the psilocybin HCl cocrystal Form A. In some preferred embodiments, the serotonin receptor modulator is ketanserin and the psychedelic is psilocybin HCl cocrystal Form A, wherein ketanserin is administered to post-treat between about 60 minutes and about 180 minutes after the administration of the psilocybin HCl cocrystal Form A.

In some embodiments, the serotonin receptor modulator is ritanserin and the psychedelic is psilocybin HCl cocrystal Form A, wherein the ritanserin is administered to post-treat at least 15 minutes after the administration of the psilocybin HCl cocrystal Form A. In some embodiments, the serotonin receptor modulator is ritanserin and the psychedelic is psilocybin HCl cocrystal Form A, wherein the ritanserin is administered to post-treat at least 30 minutes after the psilocybin HCl cocrystal Form A. In some embodiments, the serotonin receptor modulator is ritanserin and the psychedelic is psilocybin HCl cocrystal Form A, wherein the ritanserin is administered to post-treat between at least 60 minutes and 240 minutes after the administration or release of the psilocybin HCl cocrystal Form A. In some embodiments, the serotonin receptor modulator is ritanserin and the psychedelic is psilocybin HCl cocrystal Form A, wherein the ritanserin is administered to post-treat at least 90 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 120 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 150 minutes after the psilocybin HCl cocrystal Form A. In some embodiments, the serotonin receptor modulator is ritanserin and the psychedelic is psilocybin HCl cocrystal Form A, wherein the ritanserin is administered to post-treat between about 15 minutes and about 150 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 180 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 210 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 240 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 270 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 300 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 330 minutes after the psilocybin HCl cocrystal Form A. In some embodiments, the serotonin receptor modulator is ritanserin and the psychedelic is psilocybin HCl cocrystal Form A, wherein the ritanserin is administered to post-treat at least 360 minutes after the psilocybin HCl cocrystal Form A. In some preferred embodiments, the serotonin receptor modulator is ritanserin and the psychedelic is psilocybin HCl cocrystal Form A, wherein ritanserin is administered to post-treat between about 60 minutes and about 180 minutes after the administration of the psilocybin HCl cocrystal Form A.

In some embodiments, the serotonin receptor modulator is pimavanserin and the psychedelic is psilocybin HCl cocrystal Form A, wherein the pimavanserin is administered to post-treat at least 15 minutes after the administration of the psilocybin HCl cocrystal Form A. In some embodiments, the serotonin receptor modulator is pimavanserin and the psychedelic is psilocybin HCl cocrystal Form A, wherein the pimavanserin is administered to post-treat at least 30 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat between at least 60 minutes and 240 minutes after the administration or release of the psilocybin HCl cocrystal Form A. In some embodiments, the serotonin receptor modulator is pimavanserin and the psychedelic is psilocybin HCl cocrystal Form A, wherein the pimavanserin is administered to post-treat at least 90 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 120 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 150 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat between about 15 minutes and about 150 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 180 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 210 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 240 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 270 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 300 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 330 minutes after the psilocybin HCl cocrystal Form A. In some embodiments, the serotonin receptor modulator is pimavanserin and the psychedelic is psilocybin HCl cocrystal Form A, wherein the pimavanserin is administered to post-treat at least 360 minutes after the psilocybin HCl cocrystal Form A. In some preferred embodiments, the serotonin receptor modulator is pimavanserin and the psychedelic is psilocybin HCl cocrystal Form A, wherein pimavanserin is administered to post-treat between about 60 minutes and about 180 minutes after the administration of the psilocybin HCl cocrystal Form A.

In some embodiments, the serotonin receptor modulator is nelotanserin and the psychedelic is psilocybin HCl cocrystal Form A, wherein the nelotanserin is administered to post-treat at least 15 minutes after the administration of the psilocybin HCl cocrystal Form A. In some embodiments, the serotonin receptor modulator is nelotanserin and the psychedelic is psilocybin HCl cocrystal Form A, wherein the nelotanserin is administered to post-treat at least 30 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat between at least 60 minutes and 240 minutes after the administration or release of the psilocybin HCl cocrystal Form A. In some embodiments, the serotonin receptor modulator is nelotanserin and the psychedelic is psilocybin HCl cocrystal Form A, wherein the nelotanserin is administered to post-treat at least 90 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat at least 120 minutes after the psilocybin HCl cocrystal Form A.

In some embodiments, the serotonin receptor modulator is nelotanserin and the psychedelic is psilocybin HCl cocrystal Form A, wherein the nelotanserin is administered to post-treat at least 150 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat between about 15 minutes and about 150 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat at least 180 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat at least 210 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat at least 240 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat at least 270 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat at least 300 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat at least 330 minutes after the psilocybin HCl cocrystal Form A. In some embodiments, the serotonin receptor modulator is nelotanserin and the psychedelic is psilocybin HCl cocrystal Form A, wherein the nelotanserin is administered to post-treat at least 360 minutes after the psilocybin HCl cocrystal Form A. In some preferred embodiments, the serotonin receptor modulator is nelotanserin and the psychedelic is psilocybin HCl cocrystal Form A, wherein nelotanserin is administered to post-treat between about 60 minutes and about 180 minutes after the administration of the psilocybin HCl cocrystal Form A.

In some embodiments, the serotonin receptor modulator is pruvanserin and the psychedelic is psilocybin HCl cocrystal Form A, wherein the pruvanserin is administered to post-treat at least 15 minutes after the administration of the psilocybin HCl cocrystal Form A. In some embodiments, the serotonin receptor modulator is pruvanserin and the psychedelic is psilocybin HCl cocrystal Form A, wherein the pruvanserin is administered to post-treat at least 30 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat between at least 60 minutes and 240 minutes after the administration or release of the psilocybin HCl cocrystal Form A. In some embodiments, the serotonin receptor modulator is pruvanserin and the psychedelic is psilocybin HCl cocrystal Form A, wherein the pruvanserin is administered to post-treat at least 90 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat at least 120 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat at least 150 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat between about 15 minutes and about 150 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat at least 180 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat at least 210 minutes after the psilocybin HCl cocrystal Form A.

In some embodiments, the serotonin receptor modulator is pruvanserin and the psychedelic is psilocybin HCl cocrystal Form A, wherein the pruvanserin is administered to post-treat at least 240 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat at least 270 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat at least 300 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat at least 330 minutes after the psilocybin HCl cocrystal Form A. In some embodiments, the serotonin receptor modulator is pruvanserin and the psychedelic is psilocybin HCl cocrystal Form A, wherein the pruvanserin is administered to post-treat at least 360 minutes after the psilocybin HCl cocrystal Form A. In some preferred embodiments, the serotonin receptor modulator is pruvanserin and the psychedelic is psilocybin HCl cocrystal Form A, wherein pruvanserin is administered to post-treat between about 60 minutes and about 180 minutes after the administration of the psilocybin HCl cocrystal Form A.

In some embodiments, the serotonin receptor modulator is flibanserin, wherein the flibanserin is administered to post-treat at least 15 minutes post to the administration of the psilocybin HCl cocrystal Form A. In some embodiments, the serotonin receptor modulator is flibanserin, wherein the flibanserin is administered to post-treat at least 30 minutes post to the psilocybin HCl cocrystal Form A. In some embodiments, the serotonin receptor modulator is flibanserin, wherein the flibanserin is administered to post-treat between at least 60 minutes and 240 minutes post to the administration or release of the psilocybin HCl cocrystal Form A. In some embodiments, the serotonin receptor modulator is flibanserin, wherein the flibanserin is administered to post-treat at least 90 minutes post to the psilocybin HCl cocrystal Form A. In some embodiments, the serotonin receptor modulator is flibanserin, wherein the flibanserin is administered to post-treat at least 120 minutes post to the psilocybin HCl cocrystal Form A. In some embodiments, the serotonin receptor modulator is flibanserin, wherein the flibanserin is administered to post-treat at least 150 minutes post to the psilocybin HCl cocrystal Form A. In some embodiments, the serotonin receptor modulator is flibanserin, wherein the flibanserin is administered to post-treat between about 15 minutes and about 150 minutes post to the psilocybin HCl cocrystal Form A. In some embodiments, the serotonin receptor modulator is flibanserin, wherein the flibanserin is administered to post-treat at least 180 minutes post to the psilocybin HCl cocrystal Form A. In some embodiments, the serotonin receptor modulator is flibanserin, wherein the flibanserin is administered to post-treat at least 210 minutes post to the psilocybin HCl cocrystal Form A.

In some embodiments, the serotonin receptor modulator is flibanserin, wherein the flibanserin is administered to post-treat at least 240 minutes post to the psilocybin HCl cocrystal Form A. In some embodiments, the serotonin receptor modulator is flibanserin, wherein the flibanserin is administered to post-treat at least 270 minutes post to the psilocybin HCl cocrystal Form A. In some embodiments, the serotonin receptor modulator is flibanserin, wherein the flibanserin is administered to post-treat at least 300 minutes post to the psilocybin HCl cocrystal Form A. In some embodiments, the serotonin receptor modulator is flibanserin, wherein the flibanserin is administered to post-treat at least 330 minutes post to the psilocybin HCl cocrystal Form A. In some embodiments, the serotonin receptor modulator is flibanserin, wherein the flibanserin is administered to post-treat at least 360 minutes post to the psilocybin HCl cocrystal Form A. In some preferred embodiments, the serotonin receptor modulator is flibanserin, wherein flibanserin is administered to post-treat between about 60 minutes and about 180 minutes post to the administration of the psilocybin HCl cocrystal Form A.

In some embodiments, the serotonin receptor modulator is olanzapine, wherein the olanzapine is administered to post-treat at least 15 minutes post to the administration of the psilocybin HCl cocrystal Form A. In some embodiments, the serotonin receptor modulator is olanzapine, wherein the olanzapine is administered to post-treat at least 30 minutes post to the psilocybin HCl cocrystal Form A. In some embodiments, the serotonin receptor modulator is olanzapine, wherein the olanzapine is administered to post-treat between at least 60 minutes and 240 minutes post to the administration or release of the psilocybin HCl cocrystal Form A. In some embodiments, the serotonin receptor modulator is olanzapine, wherein the olanzapine is administered to post-treat at least 90 minutes post to the psilocybin HCl cocrystal Form A. In some embodiments, the serotonin receptor modulator is olanzapine, wherein the olanzapine is administered to post-treat at least 120 minutes post to the psilocybin HCl cocrystal Form A. In some embodiments, the serotonin receptor modulator is olanzapine, wherein the olanzapine is administered to post-treat at least 150 minutes post to the psilocybin HCl cocrystal Form A. In some embodiments, the serotonin receptor modulator is olanzapine, wherein the olanzapine is administered to post-treat between about 15 minutes and about 150 minutes post to the psilocybin HCl cocrystal Form A. In some embodiments, the serotonin receptor modulator is olanzapine, wherein the olanzapine is administered to post-treat at least 180 minutes post to the psilocybin HCl cocrystal Form A. In some embodiments, the serotonin receptor modulator is olanzapine, wherein the olanzapine is administered to post-treat at least 210 minutes post to the psilocybin HCl cocrystal Form A.

In some embodiments, the serotonin receptor modulator is olanzapine, wherein the olanzapine is administered to post-treat at least 240 minutes post to the psilocybin HCl cocrystal Form A. In some embodiments, the serotonin receptor modulator is olanzapine, wherein the olanzapine is administered to post-treat at least 270 minutes post to the psilocybin HCl cocrystal Form A. In some embodiments, the serotonin receptor modulator is olanzapine, wherein the olanzapine is administered to post-treat at least 300 minutes post to the psilocybin HCl cocrystal Form A. In some embodiments, the serotonin receptor modulator is olanzapine, wherein the olanzapine is administered to post-treat at least 330 minutes post to the psilocybin HCl cocrystal Form A. In some embodiments, the serotonin receptor modulator is olanzapine, wherein the olanzapine is administered to post-treat at least 360 minutes post to the psilocybin HCl cocrystal Form A. In some preferred embodiments, the serotonin receptor modulator is olanzapine, wherein olanzapine is administered to post-treat between about 60 minutes and about 180 minutes post to the administration of the psilocybin HCl cocrystal Form A.

In some embodiments, the serotonin receptor modulator is quetiapine, wherein the quetiapine is administered to post-treat at least 15 minutes post to the administration of the psilocybin HCl cocrystal Form A. In some embodiments, the serotonin receptor modulator is quetiapine, wherein the quetiapine is administered to post-treat at least 30 minutes post to the psilocybin HCl cocrystal Form A. In some embodiments, the serotonin receptor modulator is quetiapine, wherein the quetiapine is administered to post-treat between at least 60 minutes and 240 minutes post to the administration or release of the psilocybin HCl cocrystal Form A. In some embodiments, the serotonin receptor modulator is quetiapine, wherein the quetiapine is administered to post-treat at least 90 minutes post to the psilocybin HCl cocrystal Form A. In some embodiments, the serotonin receptor modulator is quetiapine, wherein the quetiapine is administered to post-treat at least 120 minutes post to the psilocybin HCl cocrystal Form A. In some embodiments, the serotonin receptor modulator is quetiapine, wherein the quetiapine is administered to post-treat at least 150 minutes post to the psilocybin HCl cocrystal Form A. In some embodiments, the serotonin receptor modulator is quetiapine, wherein the quetiapine is administered to post-treat between about 15 minutes and about 150 minutes post to the psilocybin HCl cocrystal Form A. In some embodiments, the serotonin receptor modulator is quetiapine, wherein the quetiapine is administered to post-treat at least 180 minutes post to the psilocybin HCl cocrystal Form A. In some embodiments, the serotonin receptor modulator is quetiapine, wherein the quetiapine is administered to post-treat at least 210 minutes post to the psilocybin HCl cocrystal Form A.

In some embodiments, the serotonin receptor modulator is quetiapine, wherein the quetiapine is administered to post-treat at least 240 minutes post to the psilocybin HCl cocrystal Form A. In some embodiments, the serotonin receptor modulator is quetiapine, wherein the quetiapine is administered to post-treat at least 270 minutes post to the psilocybin HCl cocrystal Form A. In some embodiments, the serotonin receptor modulator is quetiapine, wherein the quetiapine is administered to post-treat at least 300 minutes post to the psilocybin HCl cocrystal Form A. In some embodiments, the serotonin receptor modulator is quetiapine, wherein the quetiapine is administered to post-treat at least 330 minutes post to the psilocybin HCl cocrystal Form A. In some embodiments, the serotonin receptor modulator is quetiapine, wherein the quetiapine is administered to post-treat at least 360 minutes post to the psilocybin HCl cocrystal Form A. In some preferred embodiments, the serotonin receptor modulator is quetiapine, wherein quetiapine is administered to post-treat between about 60 minutes and about 180 minutes post to the administration of the psilocybin HCl cocrystal Form A.

In some embodiments, the serotonin receptor modulator is risperidone, wherein the risperidone is administered to post-treat at least 15 minutes post to the administration of the psilocybin HCl cocrystal Form A. In some embodiments, the serotonin receptor modulator is risperidone, wherein the risperidone is administered to post-treat at least 30 minutes post to the psilocybin HCl cocrystal Form A. In some embodiments, the serotonin receptor modulator is risperidone, wherein the risperidone is administered to post-treat between at least 60 minutes and 240 minutes post to the administration or release of the psilocybin HCl cocrystal Form A. In some embodiments, the serotonin receptor modulator is risperidone, wherein the risperidone is administered to post-treat at least 90 minutes post to the psilocybin HCl cocrystal Form A. In some embodiments, the serotonin receptor modulator is risperidone, wherein the risperidone is administered to post-treat at least 120 minutes post to the psilocybin HCl cocrystal Form A. In some embodiments, the serotonin receptor modulator is risperidone, wherein the risperidone is administered to post-treat at least 150 minutes post to the psilocybin HCl cocrystal Form A. In some embodiments, the serotonin receptor modulator is risperidone, wherein the risperidone is administered to post-treat between about 15 minutes and about 150 minutes post to the psilocybin HCl cocrystal Form A. In some embodiments, the serotonin receptor modulator is risperidone, wherein the risperidone is administered to post-treat at least 180 minutes post to the psilocybin HCl cocrystal Form A. In some embodiments, the serotonin receptor modulator is risperidone, wherein the risperidone is administered to post-treat at least 210 minutes post to the psilocybin HCl cocrystal Form A.

In some embodiments, the serotonin receptor modulator is risperidone, wherein the risperidone is administered to post-treat at least 240 minutes post to the psilocybin HCl cocrystal Form A. In some embodiments, the serotonin receptor modulator is risperidone, wherein the risperidone is administered to post-treat at least 270 minutes post to the psilocybin HCl cocrystal Form A. In some embodiments, the serotonin receptor modulator is risperidone, wherein the risperidone is administered to post-treat at least 300 minutes post to the psilocybin HCl cocrystal Form A. In some embodiments, the serotonin receptor modulator is risperidone, wherein the risperidone is administered to post-treat at least 330 minutes post to the psilocybin HCl cocrystal Form A. In some embodiments, the serotonin receptor modulator is risperidone, wherein the risperidone is administered to post-treat at least 360 minutes post to the psilocybin HCl cocrystal Form A. In some preferred embodiments, the serotonin receptor modulator is risperidone, wherein risperidone is administered to post-treat between about 60 minutes and about 180 minutes post to the administration of the psilocybin HCl cocrystal Form A.

In some embodiments, the serotonin receptor modulator is eplivanserin and the psychedelic is psilocybin HCl Form A, wherein the eplivanserin is administered to post-treat at least 15 minutes after the administration of the psilocybin HCl Form A. In some embodiments, the serotonin receptor modulator is eplivanserin and the psychedelic is psilocybin HCl Form A, wherein the eplivanserin is administered to post-treat between at least 30 minutes after and 360 minutes after the release or administration of the psilocybin HCl Form A. In some embodiments, the serotonin receptor modulator is eplivanserin and the psychedelic is psilocybin HCl Form A, wherein the eplivanserin is administered to post-treat between at least 60 minutes after and 360 minutes after the release or administration of the psilocybin HCl Form A. In some embodiments, the serotonin receptor modulator is eplivanserin and the psychedelic is psilocybin HCl Form A, wherein the eplivanserin is administered to post-treat between at least 90 minutes and 240 minutes after the psilocybin HCl Form A. In some embodiments, the serotonin receptor modulator is eplivanserin and the psychedelic is psilocybin HCl Form A, wherein the eplivanserin is administered to post-treat at least 120 minutes after the psilocybin HCl Form A.

In some embodiments, the serotonin receptor modulator is eplivanserin and the psychedelic is psilocybin HCl Form A, wherein the eplivanserin is administered to post-treat at least 150 minutes after the psilocybin HCl Form A. In some embodiments, the serotonin receptor modulator is eplivanserin and the psychedelic is psilocybin HCl Form A, wherein the eplivanserin is administered to post-treat between about 15 minutes and about 150 minutes after the psilocybin HCl Form A. In some embodiments, the serotonin receptor modulator is eplivanserin and the psychedelic is psilocybin HCl Form A, wherein the eplivanserin is administered to post-treat at least 180 minutes after the psilocybin HCl Form A. In some embodiments, the serotonin receptor modulator is eplivanserin and the psychedelic is psilocybin HCl Form A, wherein the eplivanserin is administered to post-treat at least 210 minutes after the psilocybin HCl Form A. In some embodiments, the serotonin receptor modulator is eplivanserin and the psychedelic is psilocybin HCl Form A, wherein the eplivanserin is administered to post-treat at least 240 minutes after the psilocybin HCl Form A.

In some embodiments, the serotonin receptor modulator is eplivanserin and the psychedelic is psilocybin HCl Form A, wherein the eplivanserin is administered to post-treat at least 270 minutes after the psilocybin HCl Form A. In some embodiments, the serotonin receptor modulator is eplivanserin and the psychedelic is psilocybin HCl Form A, wherein the eplivanserin is administered to post-treat at least 300 minutes after the psilocybin HCl Form A. In some embodiments, the serotonin receptor modulator is eplivanserin and the psychedelic is psilocybin HCl Form A, wherein the eplivanserin is administered to post-treat at least 330 minutes after the psilocybin HCl Form A. In some embodiments, the serotonin receptor modulator is eplivanserin and the psychedelic is psilocybin HCl Form A, wherein the eplivanserin is administered to post-treat at least 360 minutes after the psilocybin HCl Form A.

In some preferred embodiments, the serotonin receptor modulator is eplivanserin and the psychedelic is psilocybin HCl Form A, wherein eplivanserin is administered to post-treat between about 60 minutes and about 180 minutes after the administration of the psilocybin HCl Form A.

In some embodiments, the serotonin receptor modulator is volinanserin and the psychedelic is psilocybin HCl Form A, wherein the volinanserin is administered to post-treat a subject between at least 15 minutes and 360 minutes after the administration or release of the psilocybin HCl Form A. In some embodiments, the serotonin receptor modulator is volinanserin and the psychedelic is psilocybin HCl Form A, wherein the volinanserin is administered to post-treat between at least 30 minutes and 360 minutes after the administration or release of the psilocybin HCl Form A. In some embodiments, the serotonin receptor modulator is volinanserin and the psychedelic is psilocybin HCl Form A, wherein volinanserin is administered to post-treat between at least 60 minutes and 240 minutes after the administration or release of the psilocybin HCl Form A. In some embodiments, the serotonin receptor modulator is volinanserin and psychedelic is psilocybin HCl Form A, wherein volinanserin is administered to post-treat at least 90 minutes after psilocybin HCl. In some embodiments, the serotonin receptor modulator is volinanserin and psychedelic is psilocybin HCl Form A, wherein volinanserin is administered to post-treat at least 120 minutes after psilocybin HCl Form A.

In some embodiments, the serotonin receptor modulator is volinanserin and the psychedelic is psilocybin HCl Form A, wherein the volinanserin is administered to post-treat at least 150 minutes after the psilocybin HCl Form A. In some embodiments, the serotonin receptor modulator is volinanserin and the psychedelic is psilocybin HCl Form A, wherein the volinanserin is administered to post-treat between about 15 minutes and about 150 minutes after the psilocybin HCl Form A. In some embodiments, the serotonin receptor modulator is volinanserin and the psychedelic is psilocybin HCl Form A, wherein the volinanserin is administered to post-treat at least 180 minutes after the psilocybin HCl Form A. In some embodiments, the serotonin receptor modulator is volinanserin and the psychedelic is psilocybin HCl Form A, wherein the volinanserin is administered to post-treat at least 210 minutes after the psilocybin HCl Form A. In some embodiments, the serotonin receptor modulator is volinanserin and the psychedelic is psilocybin HCl Form A, wherein the volinanserin is administered to post-treat at least 240 minutes after the psilocybin HCl Form A. In some embodiments, the serotonin receptor modulator is volinanserin and the psychedelic is psilocybin HCl Form A, wherein the volinanserin is administered to post-treat at least 270 minutes after the psilocybin HCl Form A. In some embodiments, the serotonin receptor modulator is volinanserin and the psychedelic is psilocybin HCl Form A, wherein the volinanserin is administered to post-treat at least 300 minutes after the psilocybin HCl Form A. In some embodiments, the serotonin receptor modulator is volinanserin and the psychedelic is psilocybin HCl Form A, wherein the volinanserin is administered to post-treat at least 330 minutes after the psilocybin HCl Form A. In some embodiments, the serotonin receptor modulator is volinanserin and the psychedelic is psilocybin HCl Form A, wherein the volinanserin is administered to post-treat at least 360 minutes after the psilocybin HCl Form A. In some preferred embodiments, the serotonin receptor modulator is volinanserin and the psychedelic is psilocybin HCl Form A, wherein volinanserin is administered to post-treat between about 60 minutes and about 180 minutes after the administration of the ®-MDMA form.

In some embodiments, the serotonin receptor modulator is ketanserin and the psychedelic is psilocybin HCl Form A, wherein the ketanserin is administered to post-treat at least 15 minutes after the administration of the psilocybin HCl Form A. In some embodiments, the serotonin receptor modulator is ketanserin and the psychedelic is psilocybin HCl Form A, wherein the ketanserin is administered to post-treat between at least 30 minutes and 360 minutes after the administration or release of the psilocybin HCl Form A. In some embodiments, the serotonin receptor modulator is ketanserin and the psychedelic is psilocybin HCl Form A, wherein the ketanserin is administered to post-treat between at least 60 minutes and 240 minutes after the administration or release of the psilocybin HCl Form A. In some embodiments, the serotonin receptor modulator is ketanserin and the psychedelic is psilocybin HCl Form A, wherein the ketanserin is administered to post-treat at least 90 minutes after the psilocybin HCl Form A. In some embodiments, the serotonin receptor modulator is ketanserin and the psychedelic is psilocybin HCl Form A, wherein the ketanserin is administered to post-treat at least 120 minutes after the psilocybin HCl Form A. In some embodiments, the serotonin receptor modulator is ketanserin and the psychedelic is psilocybin HCl Form A, wherein the ketanserin is administered to post-treat at least 150 minutes after the psilocybin HCl Form A. In some embodiments, the serotonin receptor modulator is ketanserin and the psychedelic is psilocybin HCl Form A, wherein the ketanserin is administered to post-treat between about 15 minutes and about 150 minutes after the psilocybin HCl Form A. In some embodiments, the serotonin receptor modulator is ketanserin and the psychedelic is psilocybin HCl Form A, wherein the ketanserin is administered to post-treat at least 180 minutes after the psilocybin HCl Form A. In some embodiments, the serotonin receptor modulator is ketanserin and the psychedelic is psilocybin HCl Form A, wherein the ketanserin is administered to post-treat at least 210 minutes after the psilocybin HCl Form A. In some embodiments, the serotonin receptor modulator is ketanserin and the psychedelic is psilocybin HCl Form A, wherein the ketanserin is administered to post-treat at least 240 minutes after the psilocybin HCl Form A. In some embodiments, the serotonin receptor modulator is ketanserin and the psychedelic is psilocybin HCl Form A, wherein the ketanserin is administered to post-treat at least 270 minutes after the psilocybin HCl Form A. In some embodiments, the serotonin receptor modulator is ketanserin and the psychedelic is psilocybin HCl Form A, wherein the ketanserin is administered to post-treat at least 300 minutes after the psilocybin HCl Form A. In some embodiments, the serotonin receptor modulator is ketanserin and the psychedelic is psilocybin HCl Form A, wherein the ketanserin is administered to post-treat at least 330 minutes after the psilocybin HCl Form A. In some embodiments, the serotonin receptor modulator is ketanserin and the psychedelic is psilocybin HCl Form A, wherein the ketanserin is administered to post-treat at least 360 minutes after the psilocybin HCl Form A. In some preferred embodiments, the serotonin receptor modulator is ketanserin and the psychedelic is psilocybin HCl Form A, wherein ketanserin is administered to post-treat between about 60 minutes and about 180 minutes after the administration of the psilocybin HCl Form A.

In some embodiments, the serotonin receptor modulator is ritanserin and the psychedelic is psilocybin HCl Form A, wherein the ritanserin is administered to post-treat at least 15 minutes after the administration of the psilocybin HCl Form A. In some embodiments, the serotonin receptor modulator is ritanserin and the psychedelic is psilocybin HCl Form A, wherein the ritanserin is administered to post-treat at least 30 minutes after the psilocybin HCl Form A. In some embodiments, the serotonin receptor modulator is ritanserin and the psychedelic is psilocybin HCl Form A, wherein the ritanserin is administered to post-treat between at least 60 minutes and 240 minutes after the administration or release of the psilocybin HCl Form A. In some embodiments, the serotonin receptor modulator is ritanserin and the psychedelic is psilocybin HCl Form A, wherein the ritanserin is administered to post-treat at least 90 minutes after the psilocybin HCl Form A. In some embodiments, the serotonin receptor modulator is ritanserin and the psychedelic is psilocybin HCl Form A, wherein the ritanserin is administered to post-treat at least 120 minutes after the psilocybin HCl Form A. In some embodiments, the serotonin receptor modulator is ritanserin and the psychedelic is psilocybin HCl Form A, wherein the ritanserin is administered to post-treat at least 150 minutes after the psilocybin HCl Form A. In some embodiments, the serotonin receptor modulator is ritanserin and the psychedelic is psilocybin HCl Form A, wherein the ritanserin is administered to post-treat between about 15 minutes and about 150 minutes after the psilocybin HCl Form A. In some embodiments, the serotonin receptor modulator is ritanserin and the psychedelic is psilocybin HCl Form A, wherein the ritanserin is administered to post-treat at least 180 minutes after the psilocybin HCl Form A. In some embodiments, the serotonin receptor modulator is ritanserin and the psychedelic is psilocybin HCl Form A, wherein the ritanserin is administered to post-treat at least 210 minutes after the psilocybin HCl Form A. In some embodiments, the serotonin receptor modulator is ritanserin and the psychedelic is psilocybin HCl Form A, wherein the ritanserin is administered to post-treat at least 240 minutes after the psilocybin HCl Form A. In some embodiments, the serotonin receptor modulator is ritanserin and the psychedelic is psilocybin HCl Form A, wherein the ritanserin is administered to post-treat at least 270 minutes after the psilocybin HCl Form A. In some embodiments, the serotonin receptor modulator is ritanserin and the psychedelic is psilocybin HCl Form A, wherein the ritanserin is administered to post-treat at least 300 minutes after the psilocybin HCl Form A. In some embodiments, the serotonin receptor modulator is ritanserin and the psychedelic is psilocybin HCl Form A, wherein the ritanserin is administered to post-treat at least 330 minutes after the psilocybin HCl Form A. In some embodiments, the serotonin receptor modulator is ritanserin and the psychedelic is psilocybin HCl Form A, wherein the ritanserin is administered to post-treat at least 360 minutes after the psilocybin HCl Form A. In some preferred embodiments, the serotonin receptor modulator is ritanserin and the psychedelic is psilocybin HCl Form A, wherein ritanserin is administered to post-treat between about 60 minutes and about 180 minutes after the administration of the psilocybin HCl Form A.

In some embodiments, the serotonin receptor modulator is pimavanserin and the psychedelic is psilocybin HCl Form A, wherein the pimavanserin is administered to post-treat at least 15 minutes after the administration of the psilocybin HCl Form A. In some embodiments, the serotonin receptor modulator is pimavanserin and the psychedelic is psilocybin HCl Form A, wherein the pimavanserin is administered to post-treat at least 30 minutes after the psilocybin HCl Form A. In some embodiments, the serotonin receptor modulator is pimavanserin and the psychedelic is psilocybin HCl Form A, wherein the pimavanserin is administered to post-treat between at least 60 minutes and 240 minutes after the administration or release of the psilocybin HCl Form A. In some embodiments, the serotonin receptor modulator is pimavanserin and the psychedelic is psilocybin HCl Form A, wherein the pimavanserin is administered to post-treat at least 90 minutes after the psilocybin HCl Form A. In some embodiments, the serotonin receptor modulator is pimavanserin and the psychedelic is psilocybin HCl Form A, wherein the pimavanserin is administered to post-treat at least 120 minutes after the psilocybin HCl Form A. In some embodiments, the serotonin receptor modulator is pimavanserin and the psychedelic is psilocybin HCl Form A, wherein the pimavanserin is administered to post-treat at least 150 minutes after the psilocybin HCl Form A. In some embodiments, the serotonin receptor modulator is pimavanserin and the psychedelic is psilocybin HCl Form A, wherein the pimavanserin is administered to post-treat between about 15 minutes and about 150 minutes after the psilocybin HCl Form A. In some embodiments, the serotonin receptor modulator is pimavanserin and the psychedelic is psilocybin HCl Form A, wherein the pimavanserin is administered to post-treat at least 180 minutes after the psilocybin HCl Form A. In some embodiments, the serotonin receptor modulator is pimavanserin and the psychedelic is psilocybin HCl Form A, wherein the pimavanserin is administered to post-treat at least 210 minutes after the psilocybin HCl Form A. In some embodiments, the serotonin receptor modulator is pimavanserin and the psychedelic is psilocybin HCl Form A, wherein the pimavanserin is administered to post-treat at least 240 minutes after the psilocybin HCl Form A. In some embodiments, the serotonin receptor modulator is pimavanserin and the psychedelic is psilocybin HCl Form A, wherein the pimavanserin is administered to post-treat at least 270 minutes after the psilocybin HCl Form A. In some embodiments, the serotonin receptor modulator is pimavanserin and the psychedelic is psilocybin HCl Form A, wherein the pimavanserin is administered to post-treat at least 300 minutes after the psilocybin HCl Form A. In some embodiments, the serotonin receptor modulator is pimavanserin and the psychedelic is psilocybin HCl Form A, wherein the pimavanserin is administered to post-treat at least 330 minutes after the psilocybin HCl Form A. In some embodiments, the serotonin receptor modulator is pimavanserin and the psychedelic is psilocybin HCl Form A, wherein the pimavanserin is administered to post-treat at least 360 minutes after the psilocybin HCl Form A. In some preferred embodiments, the serotonin receptor modulator is pimavanserin and the psychedelic is psilocybin HCl Form A, wherein pimavanserin is administered to post-treat between about 60 minutes and about 180 minutes after the administration of the psilocybin HCl Form A.

In some embodiments, the serotonin receptor modulator is nelotanserin and the psychedelic is psilocybin HCl Form A, wherein the nelotanserin is administered to post-treat at least 15 minutes after the administration of the psilocybin HCl Form A. In some embodiments, the serotonin receptor modulator is nelotanserin and the psychedelic is psilocybin HCl Form A, wherein nelotanserin is administered to post-treat at least 30 minutes after the psilocybin HCl Form A. In some embodiments, the serotonin receptor modulator is nelotanserin and the psychedelic is psilocybin HCl Form A, wherein nelotanserin is administered to post-treat between at least 60 minutes and 240 minutes after the administration or release of the psilocybin HCl Form A. In some embodiments, the serotonin receptor modulator is nelotanserin and psychedelic is psilocybin HCl Form A, wherein nelotanserin is administered to post-treat at least 90 minutes after the psilocybin HCl Form A. In some embodiments, the serotonin receptor modulator is nelotanserin and the psychedelic is psilocybin HCl Form A, wherein nelotanserin is administered to post-treat at least 120 minutes after psilocybin HCl Form A.

In some embodiments, the serotonin receptor modulator is nelotanserin and the psychedelic is psilocybin HCl Form A, wherein the nelotanserin is administered to post-treat at least 150 minutes after the psilocybin HCl Form A. In some embodiments, the serotonin receptor modulator is nelotanserin and the psychedelic is psilocybin HCl Form A, wherein the nelotanserin is administered to post-treat between about 15 minutes and about 150 minutes after the psilocybin HCl Form A. In some embodiments, the serotonin receptor modulator is nelotanserin and the psychedelic is psilocybin HCl Form A, wherein the nelotanserin is administered to post-treat at least 180 minutes after the psilocybin HCl Form A. In some embodiments, the serotonin receptor modulator is nelotanserin and the psychedelic is psilocybin HCl Form A, wherein the nelotanserin is administered to post-treat at least 210 minutes after the psilocybin HCl Form A. In some embodiments, the serotonin receptor modulator is nelotanserin and the psychedelic is psilocybin HCl Form A, wherein the nelotanserin is administered to post-treat at least 240 minutes after the psilocybin HCl Form A. In some embodiments, the serotonin receptor modulator is nelotanserin and the psychedelic is psilocybin HCl Form A, wherein nelotanserin is administered to post-treat at least 270 minutes after psilocybin HCl Form A.

In some embodiments, the serotonin receptor modulator is nelotanserin and the psychedelic is psilocybin HCl Form A, wherein the nelotanserin is administered to post-treat at least 300 minutes after the psilocybin HCl Form A. In some embodiments, the serotonin receptor modulator is nelotanserin and the psychedelic is psilocybin HCl Form A, wherein the nelotanserin is administered to post-treat at least 330 minutes after the psilocybin HCl Form A. In some embodiments, the serotonin receptor modulator is nelotanserin and the psychedelic is psilocybin HCl Form A, wherein the nelotanserin is administered to post-treat at least 360 minutes after the psilocybin HCl Form A. In some preferred embodiments, the serotonin receptor modulator is nelotanserin and the psychedelic is psilocybin HCl Form A, wherein nelotanserin is administered to post-treat between about 60 minutes and about 180 minutes after the administration of the psilocybin HCl Form A.

In some embodiments, the serotonin receptor modulator is pruvanserin and the psychedelic is psilocybin HCl Form A, wherein the pruvanserin is administered to post-treat at least 15 minutes after the administration of the psilocybin HCl Form A. In some embodiments, the serotonin receptor modulator is pruvanserin and the psychedelic is psilocybin HCl Form A, wherein the pruvanserin is administered to post-treat at least 30 minutes after the psilocybin HCl Form A. In some embodiments, the serotonin receptor modulator is pruvanserin and the psychedelic is psilocybin HCl Form A, wherein the pruvanserin is administered to post-treat between at least 60 minutes and 240 minutes after the administration or release of the psilocybin HCl Form A. In some embodiments, the serotonin receptor modulator is pruvanserin and the psychedelic is psilocybin HCl Form A, wherein the pruvanserin is administered to post-treat at least 90 minutes after the psilocybin HCl Form A. In some embodiments, the serotonin receptor modulator is pruvanserin and the psychedelic is psilocybin HCl Form A, wherein the pruvanserin is administered to post-treat at least 120 minutes after the psilocybin HCl Form A. In some embodiments, the serotonin receptor modulator is pruvanserin and the psychedelic is psilocybin HCl Form A, wherein the pruvanserin is administered to post-treat at least 150 minutes after the psilocybin HCl Form A. In some embodiments, the serotonin receptor modulator is pruvanserin and the psychedelic is psilocybin HCl Form A, wherein the pruvanserin is administered to post-treat between about 15 minutes and about 150 minutes after the psilocybin HCl Form A. In some embodiments, the serotonin receptor modulator is pruvanserin and the psychedelic is psilocybin HCl Form A, wherein the pruvanserin is administered to post-treat at least 180 minutes after the psilocybin HCl Form A. In some embodiments, the serotonin receptor modulator is pruvanserin and the psychedelic is psilocybin HCl Form A, wherein the pruvanserin is administered to post-treat at least 210 minutes after the psilocybin HCl Form A.

In some embodiments, the serotonin receptor modulator is pruvanserin and the psychedelic is psilocybin HCl Form A, wherein the pruvanserin is administered to post-treat at least 240 minutes after the psilocybin HCl Form A. In some embodiments, the serotonin receptor modulator is pruvanserin and the psychedelic is psilocybin HCl Form A, wherein the pruvanserin is administered to post-treat at least 270 minutes after the psilocybin HCl Form A. In some embodiments, the serotonin receptor modulator is pruvanserin and the psychedelic is psilocybin HCl Form A, wherein the pruvanserin is administered to post-treat at least 300 minutes after the psilocybin HCl Form A. In some embodiments, the serotonin receptor modulator is pruvanserin and the psychedelic is psilocybin HCl Form A, wherein the pruvanserin is administered to post-treat at least 330 minutes after the psilocybin HCl Form A. In some embodiments, the serotonin receptor modulator is pruvanserin and the psychedelic is psilocybin HCl Form A, wherein the pruvanserin is administered to post-treat at least 360 minutes after the psilocybin HCl Form A. In some preferred embodiments, the serotonin receptor modulator is pruvanserin and the psychedelic is psilocybin HCl Form A, wherein pruvanserin is administered to post-treat between about 60 minutes and about 180 minutes after the administration of the psilocybin HCl Form A.

In some embodiments, the serotonin receptor modulator is flibanserin, wherein the flibanserin is administered to post-treat at least 15 minutes post to the administration of the psilocybin HCl Form A. In some embodiments, the serotonin receptor modulator is flibanserin, wherein the flibanserin is administered to post-treat at least 30 minutes post to the psilocybin HCl Form A. In some embodiments, the serotonin receptor modulator is flibanserin, wherein the flibanserin is administered to post-treat between at least 60 minutes and 240 minutes post to the administration or release of the psilocybin HCl Form A. In some embodiments, the serotonin receptor modulator is flibanserin, wherein the flibanserin is administered to post-treat at least 90 minutes post to the psilocybin HCl Form A. In some embodiments, the serotonin receptor modulator is flibanserin, wherein the flibanserin is administered to post-treat at least 120 minutes post to the psilocybin HCl Form A. In some embodiments, the serotonin receptor modulator is flibanserin, wherein the flibanserin is administered to post-treat at least 150 minutes post to the psilocybin HCl Form A. In some embodiments, the serotonin receptor modulator is flibanserin, wherein the flibanserin is administered to post-treat between about 15 minutes and about 150 minutes post to the psilocybin HCl Form A. In some embodiments, the serotonin receptor modulator is flibanserin, wherein the flibanserin is administered to post-treat at least 180 minutes post to the psilocybin HCl Form A. In some embodiments, the serotonin receptor modulator is flibanserin, wherein the flibanserin is administered to post-treat at least 210 minutes post to the psilocybin HCl Form A.

In some embodiments, the serotonin receptor modulator is flibanserin, wherein the flibanserin is administered to post-treat at least 240 minutes post to the psilocybin HCl Form A. In some embodiments, the serotonin receptor modulator is flibanserin, wherein the flibanserin is administered to post-treat at least 270 minutes post to the psilocybin HCl Form A. In some embodiments, the serotonin receptor modulator is flibanserin, wherein the flibanserin is administered to post-treat at least 300 minutes post to the psilocybin HCl Form A. In some embodiments, the serotonin receptor modulator is flibanserin, wherein the flibanserin is administered to post-treat at least 330 minutes post to the psilocybin HCl Form A. In some embodiments, the serotonin receptor modulator is flibanserin, wherein the flibanserin is administered to post-treat at least 360 minutes post to the psilocybin HCl Form A. In some preferred embodiments, the serotonin receptor modulator is flibanserin, wherein flibanserin is administered to post-treat between about 60 minutes and about 180 minutes post to the administration of the psilocybin HCl Form A.

In some embodiments, the serotonin receptor modulator is olanzapine, wherein the olanzapine is administered to post-treat at least 15 minutes post to the administration of the psilocybin HCl Form A. In some embodiments, the serotonin receptor modulator is olanzapine, wherein the olanzapine is administered to post-treat at least 30 minutes post to the psilocybin HCl Form A. In some embodiments, the serotonin receptor modulator is olanzapine, wherein the olanzapine is administered to post-treat between at least 60 minutes and 240 minutes post to the administration or release of the psilocybin HCl Form A. In some embodiments, the serotonin receptor modulator is olanzapine, wherein the olanzapine is administered to post-treat at least 90 minutes post to the psilocybin HCl Form A. In some embodiments, the serotonin receptor modulator is olanzapine, wherein the olanzapine is administered to post-treat at least 120 minutes post to the psilocybin HCl Form A. In some embodiments, the serotonin receptor modulator is olanzapine, wherein the olanzapine is administered to post-treat at least 150 minutes post to the psilocybin HCl Form A. In some embodiments, the serotonin receptor modulator is olanzapine, wherein the olanzapine is administered to post-treat between about 15 minutes and about 150 minutes post to the psilocybin HCl Form A. In some embodiments, the serotonin receptor modulator is olanzapine, wherein the olanzapine is administered to post-treat at least 180 minutes post to the psilocybin HCl Form A. In some embodiments, the serotonin receptor modulator is olanzapine, wherein the olanzapine is administered to post-treat at least 210 minutes post to the psilocybin HCl Form A.

In some embodiments, the serotonin receptor modulator is olanzapine, wherein the olanzapine is administered to post-treat at least 240 minutes post to the psilocybin HCl Form A. In some embodiments, the serotonin receptor modulator is olanzapine, wherein the olanzapine is administered to post-treat at least 270 minutes post to the psilocybin HCl Form A. In some embodiments, the serotonin receptor modulator is olanzapine, wherein the olanzapine is administered to post-treat at least 300 minutes post to the psilocybin HCl Form A. In some embodiments, the serotonin receptor modulator is olanzapine, wherein the olanzapine is administered to post-treat at least 330 minutes post to the psilocybin HCl Form A. In some embodiments, the serotonin receptor modulator is olanzapine, wherein the olanzapine is administered to post-treat at least 360 minutes post to the psilocybin HCl Form A. In some preferred embodiments, the serotonin receptor modulator is olanzapine, wherein olanzapine is administered to post-treat between about 60 minutes and about 180 minutes post to the administration of the psilocybin HCl Form A.

In some embodiments, the serotonin receptor modulator is quetiapine, wherein the quetiapine is administered to post-treat at least 15 minutes post to the administration of the psilocybin HCl Form A. In some embodiments, the serotonin receptor modulator is quetiapine, wherein the quetiapine is administered to post-treat at least 30 minutes post to the psilocybin HCl Form A. In some embodiments, the serotonin receptor modulator is quetiapine, wherein the quetiapine is administered to post-treat between at least 60 minutes and 240 minutes post to the administration or release of the psilocybin HCl Form A. In some embodiments, the serotonin receptor modulator is quetiapine, wherein the quetiapine is administered to post-treat at least 90 minutes post to the psilocybin HCl Form A. In some embodiments, the serotonin receptor modulator is quetiapine, wherein the quetiapine is administered to post-treat at least 120 minutes post to the psilocybin HCl Form A. In some embodiments, the serotonin receptor modulator is quetiapine, wherein the quetiapine is administered to post-treat at least 150 minutes post to the psilocybin HCl Form A. In some embodiments, the serotonin receptor modulator is quetiapine, wherein the quetiapine is administered to post-treat between about 15 minutes and about 150 minutes post to the psilocybin HCl Form A. In some embodiments, the serotonin receptor modulator is quetiapine, wherein the quetiapine is administered to post-treat at least 180 minutes post to the psilocybin HCl Form A. In some embodiments, the serotonin receptor modulator is quetiapine, wherein the quetiapine is administered to post-treat at least 210 minutes post to the psilocybin HCl Form A.

In some embodiments, the serotonin receptor modulator is quetiapine, wherein the quetiapine is administered to post-treat at least 240 minutes post to the psilocybin HCl Form A. In some embodiments, the serotonin receptor modulator is quetiapine, wherein the quetiapine is administered to post-treat at least 270 minutes post to the psilocybin HCl Form A. In some embodiments, the serotonin receptor modulator is quetiapine, wherein the quetiapine is administered to post-treat at least 300 minutes post to the psilocybin HCl Form A. In some embodiments, the serotonin receptor modulator is quetiapine, wherein the quetiapine is administered to post-treat at least 330 minutes post to the psilocybin HCl Form A. In some embodiments, the serotonin receptor modulator is quetiapine, wherein the quetiapine is administered to post-treat at least 360 minutes post to the psilocybin HCl Form A. In some preferred embodiments, the serotonin receptor modulator is quetiapine, wherein quetiapine is administered to post-treat between about 60 minutes and about 180 minutes post to the administration of the psilocybin HCl Form A.

In some embodiments, the serotonin receptor modulator is risperidone, wherein the risperidone is administered to post-treat at least 15 minutes post to the administration of the psilocybin HCl Form A. In some embodiments, the serotonin receptor modulator is risperidone, wherein the risperidone is administered to post-treat at least 30 minutes post to the psilocybin HCl Form A. In some embodiments, the serotonin receptor modulator is risperidone, wherein the risperidone is administered to post-treat between at least 60 minutes and 240 minutes post to the administration or release of the psilocybin HCl Form A. In some embodiments, the serotonin receptor modulator is risperidone, wherein the risperidone is administered to post-treat at least 90 minutes post to the psilocybin HCl Form A. In some embodiments, the serotonin receptor modulator is risperidone, wherein the risperidone is administered to post-treat at least 120 minutes post to the psilocybin HCl Form A. In some embodiments, the serotonin receptor modulator is risperidone, wherein the risperidone is administered to post-treat at least 150 minutes post to the psilocybin HCl Form A. In some embodiments, the serotonin receptor modulator is risperidone, wherein the risperidone is administered to post-treat between about 15 minutes and about 150 minutes post to the psilocybin HCl Form A. In some embodiments, the serotonin receptor modulator is risperidone, wherein the risperidone is administered to post-treat at least 180 minutes post to the psilocybin HCl Form A. In some embodiments, the serotonin receptor modulator is risperidone, wherein the risperidone is administered to post-treat at least 210 minutes post to the psilocybin HCl Form A.

In some embodiments, the serotonin receptor modulator is risperidone, wherein the risperidone is administered to post-treat at least 240 minutes post to the psilocybin HCl Form A. In some embodiments, the serotonin receptor modulator is risperidone, wherein the risperidone is administered to post-treat at least 270 minutes post to the psilocybin HCl Form A. In some embodiments, the serotonin receptor modulator is risperidone, wherein the risperidone is administered to post-treat at least 300 minutes post to the psilocybin HCl Form A. In some embodiments, the serotonin receptor modulator is risperidone, wherein the risperidone is administered to post-treat at least 330 minutes post to the psilocybin HCl Form A. In some embodiments, the serotonin receptor modulator is risperidone, wherein the risperidone is administered to post-treat at least 360 minutes post to the psilocybin HCl Form A. In some preferred embodiments, the serotonin receptor modulator is risperidone, wherein risperidone is administered to post-treat between about 60 minutes and about 180 minutes post to the administration of the psilocybin HCl Form A.

Combinations with Psilocybin Salts and Solid Forms

In another embodiment of such combination therapy, a form of psilocybin described herein is administered in combination with a serotonin receptor modulator. In certain embodiments the serotonin receptor modulator is selected from altanserin, blonanserin, eplivanserin, glemanserin, volinanserin, ketanserin, ritanserin, pimavanserin, nelotanserin, pruvanserin, and flibanserin. In one embodiment, the serotonin receptor modulator is selected from the group consisting of serotonin receptor modulator is selected from the group consisting of eplivanserin, volinanserin, ketanserin, ritanserin, pimavanserin, nelotanserin, pruvanserin, and flibanserin.

In some embodiments, the serotonin receptor modulator for use with the psychedelic salt or solid form of psilocybin, including those described in Table 13, is eplivanserin, wherein the eplivanserin is administered in about 1 mg to about 40 mg, or about 5 mg to about 10 mg, and the salt or solid form of psilocybin, including those described in Table 13, is administered between about 10 mg to about 50 mg, or about 25 mg to about 30 mg. In some embodiments, the amount of psilocybin salt is provided on a psilocybin basis.

In some embodiments, the serotonin receptor modulator is volinanserin and the psychedelic is a salt or solid form of psilocybin, wherein the volinanserin is administered in about 1 mg to about 60 mg, or about 5 mg to about 20 mg, and the salt or solid form of psilocybin, including those described in Table 13, is administered between about 10 mg to about 50 mg, or about 25 mg to about 30 mg. In some embodiments, the amount of psilocybin salt is provided on a psilocybin basis.

In some embodiments, the serotonin receptor modulator for use with the psychedelic salt or solid form of psilocybin, including those described in Table 13, is ketanserin, wherein the ketanserin is administered in about 10 mg to about 80 mg, about 30 mg to about 50 mg, or about 40 mg and the salt or solid form of psilocybin, including those described in Table 13, is administered between about 10 mg to about 50 mg, or about 25 mg to about 30 mg. In some embodiments, the amount of psilocybin salt is provided on a psilocybin basis.

In some embodiments, the serotonin receptor modulator for use with the psychedelic salt or solid form of psilocybin, including those described in Table 13, is ritanserin, wherein the ritanserin is administered in about 1 mg to about 40 mg, or about 2.5 mg to about 10 mg, and the salt or solid form of psilocybin, including those described in Table 13, is administered between about 10 mg to about 50 mg, or about 25 mg to about 30 mg. In some embodiments, the amount of psilocybin salt is provided on a psilocybin basis.

In some embodiments, the serotonin receptor modulator is pimavanserin and the psychedelic is a salt or solid form of psilocybin, wherein the pimavanserin is administered in about 1 mg to about 60 mg, or about 17 mg to about 34 mg, and the salt or solid form of psilocybin, including those described in Table 13, is administered between about 10 mg to about 50 mg, or about 25 mg to about 30 mg. In some embodiments, the amount of psilocybin salt is provided on a psilocybin basis.

In some embodiments, the serotonin receptor modulator for use with the psychedelic salt or solid form of psilocybin, including those described in Table 13, is nelotanserin, wherein the nelotanserin is administered in about 1 mg to about 80 mg, or about 40 mg to about 80 mg, and the salt or solid form of psilocybin, including those described in Table 13, is administered between about 10 mg to about 50 mg, or about 25 mg to about 30 mg. In some embodiments, the amount of psilocybin salt is provided on a psilocybin basis.

In some embodiments, the serotonin receptor modulator for use with the psychedelic salt or solid form of psilocybin, including those described in Table 13, is pruvanserin, wherein the pruvanserin is administered in about 1 mg to about 40 mg, or about 3 mg to about 10 mg, and the salt or solid form of psilocybin, including those described in Table 13, is administered between about 10 mg to about 50 mg, or about 25 mg to about 30 mg. In some embodiments, the amount of psilocybin salt is provided on a psilocybin basis.

In some embodiments, the serotonin receptor modulator for use with the psychedelic salt or solid form of psilocybin, including those described in Table 13, is flibanserin, wherein the flibanserin is administered in about 10 mg to about 200 mg, or about 80 mg to about 120 mg, or about 100 mg and the salt or solid form of psilocybin, including those described in Table 13, is administered between about 10 mg to about 50 mg, or about 25 mg to about 30 mg. In some embodiments, the amount of psilocybin salt is provided on a psilocybin basis.

In some embodiments, the salt or solid form of psilocybin is psilocybin mesylate Form A.

In some embodiments, the serotonin receptor modulator for use with the psilocybin mesylate Form A, is eplivanserin, wherein the eplivanserin is administered in about 1 mg to about 40 mg, or about 5 mg to about 10 mg, and the psilocybin mesylate Form A, is administered between about 10 mg to about 50 mg, or about 25 mg to about 30 mg.

In some embodiments, the serotonin receptor modulator for use with the psilocybin mesylate Form A, is volinanserin, wherein the volinanserin is administered in about 1 mg to about 60 mg, or about 5 mg to about 20 mg, and the psilocybin mesylate Form A, is administered between about 10 mg to about 50 mg, or about 25 mg to about 30 mg.

In some embodiments, the serotonin receptor modulator for use with the psilocybin mesylate Form A, is ketanserin, wherein the ketanserin is administered in about 10 mg to about 80 mg, about 30 mg to about 50 mg, or about 40 mg and the psilocybin mesylate Form A, is administered between about 10 mg to about 50 mg, or about 25 mg to about 30 mg.

In some embodiments, the serotonin receptor modulator for use with the psilocybin mesylate Form A, is ritanserin, wherein the ritanserin is administered in about 1 mg to about 40 mg, or about 2.5 mg to about 10 mg, and the psilocybin mesylate Form A, is administered between about 10 mg to about 50 mg, or about 25 mg to about 30 mg.

In some embodiments, the serotonin receptor modulator is pimavanserin and the psilocybin mesylate Form A, wherein the pimavanserin is administered in about 1 mg to about 60 mg, or about 17 mg to about 34 mg, and the psilocybin mesylate Form A, is administered between about 10 mg to about 50 mg, or about 25 mg to about 30 mg.

In some embodiments, the serotonin receptor modulator for use with the psilocybin mesylate Form A, is nelotanserin, wherein the nelotanserin is administered in about 1 mg to about 80 mg, or about 40 mg to about 80 mg, and the psilocybin mesylate Form A, is administered between about 10 mg to about 50 mg, or about 25 mg to about 30 mg.

In some embodiments, the serotonin receptor modulator for use with the psilocybin mesylate Form A, is pruvanserin, wherein the pruvanserin is administered in about 1 mg to about 40 mg, or about 3 mg to about 10 mg, and the psilocybin mesylate Form A, is administered between about 10 mg to about 50 mg, or about 25 mg to about 30 mg.

In some embodiments, the serotonin receptor modulator for use with the psilocybin mesylate Form A, is flibanserin, wherein the flibanserin is administered in about 10 mg to about 200 mg, or about 80 mg to about 120 mg, or about 100 mg and the psilocybin mesylate Form A, is administered between about 10 mg to about 50 mg, or about 25 mg to about 30 mg.

In some embodiments, the serotonin receptor modulator for use with the psilocybin mesylate Form A, is olanzapine, wherein the olanzapine is administered in about 2.5 mg to about 30 mg, or about 5 mg or about 10 mg, or about 20 mg or about 25 mg, and the psilocybin mesylate Form A, is administered between about 10 mg to about 50 mg, or about 25 mg to about 30 mg.

In some embodiments, the serotonin receptor modulator for use with the psilocybin mesylate Form A, is an extended-release of olanzapine such as ZYPREXA RELPREVV®, wherein the extended release olanzapine is administered in about 50 mg to about 450 mg, or about 150 mg or about 210 mg, or about 300 mg or about 405 mg, and the psilocybin mesylate Form A, is administered between about 10 mg to about 50 mg, or about 25 mg to about 30 mg.

In some embodiments, the serotonin receptor modulator for use with the psilocybin mesylate Form A, is quetiapine, wherein the quetiapine is administered in about 25 mg to about 800 mg, or about 50 mg to about 100 mg, or about 150 mg or about 200 mg or about 250 mg or about 300 mg, and the psilocybin mesylate Form A, is administered between about 10 mg to about 50 mg, or about 25 mg to about 30 mg.

In some embodiments, the serotonin receptor modulator for use with the psilocybin mesylate Form A, is an extended-release of quetiapine, wherein the extended-release of quetiapine is administered in about 50 mg to about 300 mg, or about 50 mg or about 100 mg or about 200 mg, or about 300 mg, and the psilocybin mesylate Form A, is administered between about 10 mg to about 50 mg, or about 25 mg to about 30 mg.

In some embodiments, the serotonin receptor modulator for use with the psilocybin mesylate Form A, is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the psilocybin mesylate Form A, is administered between about 10 mg to about 50 mg, or about 25 mg to about 30 mg.

In some embodiments, the serotonin receptor modulator for use with the psilocybin mesylate Form A, is an extended-release of risperidone including (RISPERDAL CONSTA®), wherein the extended-release of risperidone is administered in about 12.5 mg, or about 25 mg, or about 37.5 mg, or about 50 mg, and the psilocybin mesylate Form A, is administered between about 10 mg to about 50 mg, or about 25 mg to about 30 mg.

In certain embodiments, such as those described above a disclosed salt or solid form of psilocybin, including those described in Table 13, is co-administered with a serotonin receptor modulator in the same or in separate compositions. In one embodiment, the salt or solid form of psilocybin is administered in a modified release formulation such that the subject is effectively pretreated with serotonin receptor modulator prior to release of an effective amount of the psychedelic. Thus, in some embodiments, the serotonin receptor modulator is administered or released from a composition provided herein prior to the administration and/or release of the psychedelic. This allows pretreatment to attenuate activation of the serotonin receptor by the psychedelic. In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the psychedelic. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to release of the psychedelic.

In a preferred embodiment, the serotonin receptor modulator is administered at about 1 hour to about 3 hours prior to the administration of the psychedelic.

In some embodiments, the serotonin receptor modulator is eplivanserin and the psychedelic is a salt or solid form of psilocybin, wherein the eplivanserin is administered to pretreat at least 15 minutes prior to the administration of the salt or solid form of psilocybin, including those described in Table 13. In some embodiments, the serotonin receptor modulator is eplivanserin and the psychedelic is a salt or solid form of psilocybin, wherein the eplivanserin is administered to pretreat between at least 30 minutes prior and 360 minutes prior to the release or administration of the salt or solid form of psilocybin, including those described in Table 13. In some embodiments, the serotonin receptor modulator is eplivanserin and the psychedelic is a salt or solid form of psilocybin, wherein the eplivanserin is administered to pretreat between at least 60 minutes prior and 360 minutes prior to the release or administration the salt or solid form of psilocybin, including those described in Table 13. In some embodiments, the serotonin receptor modulator is eplivanserin and the psychedelic is a salt or solid form of psilocybin, wherein the eplivanserin is administered to pretreat between at least 90 minutes and 240 minutes prior to the salt or solid form of psilocybin, including those described in Table 13. In some embodiments, the serotonin receptor modulator is eplivanserin and the psychedelic is a salt or solid form of psilocybin, wherein the eplivanserin is administered to pretreat at least 120 minutes prior to the salt or solid form of psilocybin, including those described in Table 13.

In some embodiments, the serotonin receptor modulator is eplivanserin and the psychedelic is a salt or solid form of psilocybin, wherein the eplivanserin is administered to pretreat at least 150 minutes prior to the salt or solid form of psilocybin, including those described in Table 13. In some embodiments, the serotonin receptor modulator is eplivanserin and the psychedelic is a salt or solid form of psilocybin, wherein the eplivanserin is administered to pretreat between about 15 minutes and about 150 minutes prior to the salt or solid form of psilocybin, including those described in Table 13. In some embodiments, the serotonin receptor modulator is eplivanserin and the psychedelic is a salt or solid form of psilocybin, wherein the eplivanserin is administered to pretreat at least 180 minutes prior to the salt or solid form of psilocybin, including those described in Table 13. In some embodiments, the serotonin receptor modulator is eplivanserin and the psychedelic is a salt or solid form of psilocybin, wherein the eplivanserin is administered to pretreat at least 210 minutes prior to the salt or solid form of psilocybin, including those described in Table 13. In some embodiments, the serotonin receptor modulator is eplivanserin and the psychedelic is a salt or solid form of psilocybin, wherein the eplivanserin is administered to pretreat at least 240 minutes prior to the salt or solid form of psilocybin, including those described in Table 13.

In some embodiments, the serotonin receptor modulator is eplivanserin and the psychedelic is a salt or solid form of psilocybin, wherein the eplivanserin is administered to pretreat at least 270 minutes prior to salt or solid form of psilocybin, including those described in Table 13. In some embodiments, the serotonin receptor modulator is eplivanserin and the psychedelic is a salt or solid form of psilocybin, wherein the eplivanserin is administered to pretreat at least 300 minutes prior to the salt or solid form of psilocybin, including those described in Table 13. In some embodiments, the serotonin receptor modulator is eplivanserin and the psychedelic is a salt or solid form of psilocybin, wherein the eplivanserin is administered to pretreat at least 330 minutes prior to the salt or solid form of psilocybin, including those described in Table 13. In some embodiments, the serotonin receptor modulator is eplivanserin and the psychedelic is a salt or solid form of psilocybin, wherein the eplivanserin is administered to pretreat at least 360 minutes prior to the salt or solid form of psilocybin, including those described in Table 13.

In some preferred embodiments, the serotonin receptor modulator is eplivanserin and the psychedelic is a salt or solid form of psilocybin, wherein eplivanserin is administered to pretreat between about 60 minutes and about 180 minutes prior to the administration of salt or solid form of psilocybin, including those described in Table 13.

In some embodiments, the serotonin receptor modulator is volinanserin and the psychedelic is a salt or solid form of psilocybin, wherein the volinanserin is administered to pretreat a subject between at least 15 minutes and 360 minutes prior to the administration or release of salt or solid form of psilocybin, including those described in Table 13. In some embodiments, the serotonin receptor modulator is volinanserin and the psychedelic is a salt or solid form of psilocybin, wherein the volinanserin is administered to pretreat between at least 30 minutes and 360 minutes prior to the administration or release of salt or solid form of psilocybin, including those described in Table 13. In some embodiments, the serotonin receptor modulator is volinanserin and the psychedelic is a salt or solid form of psilocybin, wherein the volinanserin is administered to pretreat between at least 60 minutes and 240 minutes prior to the administration or release of salt or solid form of psilocybin, including those described in Table 13. In some embodiments, the serotonin receptor modulator is volinanserin and the psychedelic is a salt or solid form of psilocybin, wherein the volinanserin is administered to pretreat at least 90 minutes prior to salt or solid form of psilocybin, including those described in Table 13. In some embodiments, the serotonin receptor modulator is volinanserin and the psychedelic is a salt or solid form of psilocybin, wherein volinanserin is administered to pretreat at least 120 minutes prior to the salt or solid form of psilocybin, including those described in Table 13.

In some embodiments, the serotonin receptor modulator is volinanserin and the psychedelic is a salt or solid form of psilocybin, wherein the volinanserin is administered to pretreat at least 150 minutes prior to the salt or solid form of psilocybin, including those described in Table 13. In some embodiments, the serotonin receptor modulator is volinanserin and the psychedelic is a salt or solid form of psilocybin, wherein the volinanserin is administered to pretreat between about 15 minutes and about 150 minutes prior to the salt or solid form of psilocybin, including those described in Table 13. In some embodiments, the serotonin receptor modulator is volinanserin and the psychedelic is a salt or solid form of psilocybin, wherein the volinanserin is administered to pretreat at least 180 minutes prior to the salt or solid form of psilocybin, including those described in Table 13. In some embodiments, the serotonin receptor modulator is volinanserin and the psychedelic is a salt or solid form of psilocybin, wherein the volinanserin is administered to pretreat at least 210 minutes prior to the salt or solid form of psilocybin, including those described in Table 13. In some embodiments, the serotonin receptor modulator is volinanserin and the psychedelic is a salt or solid form of psilocybin, wherein the volinanserin is administered to pretreat at least 240 minutes prior to the salt or solid form of psilocybin, including those described in Table 13. In some embodiments, the serotonin receptor modulator is volinanserin and the psychedelic is a salt or solid form of psilocybin, wherein the volinanserin is administered to pretreat at least 270 minutes prior to the salt or solid form of psilocybin, including those described in Table 13. In some embodiments, the serotonin receptor modulator is volinanserin and the psychedelic is a salt or solid form of psilocybin, wherein the volinanserin is administered to pretreat at least 300 minutes prior to the salt or solid form of psilocybin, including those described in Table 13. In some embodiments, the serotonin receptor modulator is volinanserin and the psychedelic is a salt or solid form of psilocybin, wherein the volinanserin is administered to pretreat at least 330 minutes prior to the salt or solid form of psilocybin, including those described in Table 13. In some embodiments, the serotonin receptor modulator is volinanserin and the psychedelic is a salt or solid form of psilocybin, wherein the volinanserin is administered to pretreat at least 360 minutes prior to the salt or solid form of psilocybin, including those described in Table 13. In some preferred embodiments, the serotonin receptor modulator is volinanserin and the psychedelic is a salt or solid form of psilocybin, wherein volinanserin is administered to pretreat between about 60 minutes and about 180 minutes prior to the administration of salt or solid form of psilocybin, including those described in Table 13.

In some embodiments, the serotonin receptor modulator is ketanserin and the psychedelic is a salt or solid form of psilocybin, wherein the ketanserin is administered to pretreat at least 15 minutes prior to the administration of salt or solid form of psilocybin, including those described in Table 13. In some embodiments, the serotonin receptor modulator is ketanserin and the psychedelic is a salt or solid form of psilocybin, wherein the ketanserin is administered to pretreat between at least 30 minutes and 360 minutes prior to the administration or release salt or solid form of psilocybin, including those described in Table 13. In some embodiments, the serotonin receptor modulator is ketanserin and the psychedelic is a salt or solid form of psilocybin, wherein the ketanserin is administered to pretreat between at least 60 minutes and 240 minutes prior to the administration or release of salt or solid form of psilocybin, including those described in Table 13. In some embodiments, the serotonin receptor modulator is ketanserin and the psychedelic is a salt or solid form of psilocybin, wherein the ketanserin is administered to pretreat at least 90 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 120 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 150 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat between about 15 minutes and about 150 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 180 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 210 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 240 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 270 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 300 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 330 minutes prior to the salt or solid form of psilocybin, including those described in Table 13. In some embodiments, the serotonin receptor modulator is ketanserin and the psychedelic is a salt or solid form of psilocybin, wherein the ketanserin is administered to pretreat at least 360 minutes prior to the salt or solid form of psilocybin, including those described in Table 13. In some preferred embodiments, the serotonin receptor modulator is ketanserin and the psychedelic is a salt or solid form of psilocybin, wherein ketanserin is administered to pretreat between about 60 minutes and about 180 minutes prior to the administration of salt or solid form of psilocybin, including those described in Table 13.

In some embodiments, the serotonin receptor modulator is ritanserin and the psychedelic is a salt or solid form of psilocybin, wherein the ritanserin is administered to pretreat at least 15 minutes prior to the administration of salt or solid form of psilocybin, including those described in Table 13. In some embodiments, the serotonin receptor modulator is ritanserin and the psychedelic is a salt or solid form of psilocybin, wherein the ritanserin is administered to pretreat at least 30 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat between at least 60 minutes and 240 minutes prior to the administration or release of salt or solid form of psilocybin, including those described in Table 13. In some embodiments, the serotonin receptor modulator is ritanserin and the psychedelic is a salt or solid form of psilocybin, wherein the ritanserin is administered to pretreat at least 90 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 120 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 150 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat between about 15 minutes and about 150 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 180 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 210 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 240 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 270 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 300 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 330 minutes prior to the salt or solid form of psilocybin, including those described in Table 13. In some embodiments, the serotonin receptor modulator is ritanserin and the psychedelic is a salt or solid form of psilocybin, wherein the ritanserin is administered to pretreat at least 360 minutes prior to the salt or solid form of psilocybin, including those described in Table 13. In some preferred embodiments, the serotonin receptor modulator is ritanserin and the psychedelic is a salt or solid form of psilocybin, wherein ritanserin is administered to pretreat between about 60 minutes and about 180 minutes prior to the administration of salt or solid form of psilocybin, including those described in Table 13.

In some embodiments, the serotonin receptor modulator is pimavanserin and the psychedelic is a salt or solid form of psilocybin, wherein the pimavanserin is administered to pretreat at least 15 minutes prior to the administration of salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 30 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat between at least 60 minutes and 240 minutes prior to the administration or release of salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 90 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 120 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 150 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat between about 15 minutes and about 150 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 180 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 210 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 240 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 270 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 300 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 330 minutes prior to the salt or solid form of psilocybin, including those described in Table 13. In some embodiments, the serotonin receptor modulator is pimavanserin and the psychedelic is a salt or solid form of psilocybin, wherein the pimavanserin is administered to pretreat at least 360 minutes prior to the salt or solid form of psilocybin, including those described in Table 13. In some preferred embodiments, the serotonin receptor modulator is pimavanserin and the psychedelic is a salt or solid form of psilocybin, wherein pimavanserin is administered to pretreat between about 60 minutes and about 180 minutes prior to the administration of salt or solid form of psilocybin, including those described in Table 13.

In some embodiments, the serotonin receptor modulator is nelotanserin and the psychedelic is a salt or solid form of psilocybin, wherein the nelotanserin is administered to pretreat at least 15 minutes prior to the administration of salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 30 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat between at least 60 minutes and 240 minutes prior to the administration or release of salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 90 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 120 minutes prior to the salt or solid form of psilocybin, including those described in Table 13.

In some embodiments, the serotonin receptor modulator is nelotanserin and the psychedelic is a salt or solid form of psilocybin, wherein the nelotanserin is administered to pretreat at least 150 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat between about 15 minutes and about 150 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 180 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 210 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 240 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 270 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 300 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 330 minutes prior to the salt or solid form of psilocybin, including those described in Table 13. In some embodiments, the serotonin receptor modulator is nelotanserin and the psychedelic is a salt or solid form of psilocybin, wherein the nelotanserin is administered to pretreat at least 360 minutes prior to the salt or solid form of psilocybin, including those described in Table 13. In some preferred embodiments, the serotonin receptor modulator is nelotanserin and the psychedelic is a salt or solid form of psilocybin, wherein nelotanserin is administered to pretreat between about 60 minutes and about 180 minutes prior to the administration of salt or solid form of psilocybin, including those described in Table 13.

In some embodiments, the serotonin receptor modulator is pruvanserin and the psychedelic is a salt or solid form of psilocybin, wherein the pruvanserin is administered to pretreat at least 15 minutes prior to the administration of salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 30 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat between at least 60 minutes and 240 minutes prior to the administration or release of salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 90 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 120 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 150 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat between about 15 minutes and about 150 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 180 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 210 minutes prior to the salt or solid form of psilocybin, including those described in Table 13.

In some embodiments, the serotonin receptor modulator is pruvanserin and the psychedelic is a salt or solid form of psilocybin, wherein the pruvanserin is administered to pretreat at least 240 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 270 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 300 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 330 minutes prior to the salt or solid form of psilocybin, including those described in Table 13. In some embodiments, the serotonin receptor modulator is pruvanserin and the psychedelic is a salt or solid form of psilocybin, wherein the pruvanserin is administered to pretreat at least 360 minutes prior to the salt or solid form of psilocybin, including those described in Table 13. In some preferred embodiments, the serotonin receptor modulator is pruvanserin and the psychedelic is a salt or solid form of psilocybin, wherein pruvanserin is administered to pretreat between about 60 minutes and about 180 minutes prior to the administration of salt or solid form of psilocybin, including those described in Table 13.

In some embodiments, the serotonin receptor modulator is flibanserin and the psychedelic is a salt or solid form of psilocybin, wherein the flibanserin is administered to pretreat at least 15 minutes prior to the administration of salt or solid form of psilocybin, including those described in Table 13. In some embodiments, the serotonin receptor modulator is flibanserin and the psychedelic is a salt or solid form of psilocybin, wherein the flibanserin is administered to pretreat at least 30 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat between at least 60 minutes and 240 minutes prior to the administration or release of salt or solid form of psilocybin, including those described in Table 13. In some embodiments, the serotonin receptor modulator is flibanserin and the psychedelic is a salt or solid form of psilocybin, wherein the flibanserin is administered to pretreat at least 90 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat at least 120 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat at least 150 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat between about 15 minutes and about 150 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat at least 180 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat at least 210 minutes prior to the salt or solid form of psilocybin, including those described in Table 13.

In some embodiments, the serotonin receptor modulator is flibanserin and the psychedelic is a salt or solid form of psilocybin, wherein the flibanserin is administered to pretreat at least 240 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat at least 270 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat at least 300 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat at least 330 minutes prior to the salt or solid form of psilocybin, including those described in Table 13. In some embodiments, the serotonin receptor modulator is flibanserin and the psychedelic is a salt or solid form of psilocybin, wherein the flibanserin is administered to pretreat at least 360 minutes prior to the salt or solid form of psilocybin, including those described in Table 13. In some preferred embodiments, the serotonin receptor modulator is flibanserin and the psychedelic is a salt or solid form of psilocybin, wherein flibanserin is administered to pretreat between about 60 minutes and about 180 minutes prior to the administration of salt or solid form of psilocybin, including those described in Table 13.

In some embodiments, the serotonin receptor modulator is olanzapine and the psychedelic is a salt or solid form of psilocybin, wherein the olanzapine is administered to pretreat at least 15 minutes prior to the administration of salt or solid form of psilocybin, including those described in Table 13. In some embodiments, the serotonin receptor modulator is olanzapine and the psychedelic is a salt or solid form of psilocybin, wherein the olanzapine is administered to pretreat at least 30 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat between at least 60 minutes and 240 minutes prior to the administration or release of salt or solid form of psilocybin, including those described in Table 13. In some embodiments, the serotonin receptor modulator is olanzapine and the psychedelic is a salt or solid form of psilocybin, wherein the olanzapine is administered to pretreat at least 90 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat at least 120 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat at least 150 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat between about 15 minutes and about 150 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat at least 180 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat at least 210 minutes prior to the salt or solid form of psilocybin, including those described in Table 13.

In some embodiments, the serotonin receptor modulator is olanzapine and the psychedelic is a salt or solid form of psilocybin, wherein the olanzapine is administered to pretreat at least 240 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat at least 270 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat at least 300 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat at least 330 minutes prior to the salt or solid form of psilocybin, including those described in Table 13. In some embodiments, the serotonin receptor modulator is olanzapine and the psychedelic is a salt or solid form of psilocybin, wherein the olanzapine is administered to pretreat at least 360 minutes prior to the salt or solid form of psilocybin, including those described in Table 13. In some preferred embodiments, the serotonin receptor modulator is olanzapine and the psychedelic is a salt or solid form of psilocybin, wherein olanzapine is administered to pretreat between about 60 minutes and about 180 minutes prior to the administration of salt or solid form of psilocybin, including those described in Table 13.

In some embodiments, the serotonin receptor modulator is quetiapine and the psychedelic is a salt or solid form of psilocybin, wherein the quetiapine is administered to pretreat at least 15 minutes prior to the administration of salt or solid form of psilocybin, including those described in Table 13. In some embodiments, the serotonin receptor modulator is quetiapine and the psychedelic is a salt or solid form of psilocybin, wherein the quetiapine is administered to pretreat at least 30 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat between at least 60 minutes and 240 minutes prior to the administration or release of salt or solid form of psilocybin, including those described in Table 13. In some embodiments, the serotonin receptor modulator is quetiapine and the psychedelic is a salt or solid form of psilocybin, wherein the quetiapine is administered to pretreat at least 90 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat at least 120 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat at least 150 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat between about 15 minutes and about 150 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat at least 180 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat at least 210 minutes prior to the salt or solid form of psilocybin, including those described in Table 13.

In some embodiments, the serotonin receptor modulator is quetiapine and the psychedelic is a salt or solid form of psilocybin, wherein the quetiapine is administered to pretreat at least 240 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat at least 270 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat at least 300 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat at least 330 minutes prior to the salt or solid form of psilocybin, including those described in Table 13. In some embodiments, the serotonin receptor modulator is quetiapine and the psychedelic is a salt or solid form of psilocybin, wherein the quetiapine is administered to pretreat at least 360 minutes prior to the salt or solid form of psilocybin, including those described in Table 13. In some preferred embodiments, the serotonin receptor modulator is quetiapine and the psychedelic is a salt or solid form of psilocybin, wherein quetiapine is administered to pretreat between about 60 minutes and about 180 minutes prior to the administration of salt or solid form of psilocybin, including those described in Table 13.

In some embodiments, the serotonin receptor modulator is risperidone and the psychedelic is a salt or solid form of psilocybin, wherein the risperidone is administered to pretreat at least 15 minutes prior to the administration of salt or solid form of psilocybin, including those described in Table 13. In some embodiments, the serotonin receptor modulator is risperidone and the psychedelic is a salt or solid form of psilocybin, wherein the risperidone is administered to pretreat at least 30 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat between at least 60 minutes and 240 minutes prior to the administration or release of salt or solid form of psilocybin, including those described in Table 13. In some embodiments, the serotonin receptor modulator is risperidone and the psychedelic is a salt or solid form of psilocybin, wherein the risperidone is administered to pretreat at least 90 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat at least 120 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat at least 150 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat between about 15 minutes and about 150 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat at least 180 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat at least 210 minutes prior to the salt or solid form of psilocybin, including those described in Table 13.

In some embodiments, the serotonin receptor modulator is risperidone and the psychedelic is a salt or solid form of psilocybin, wherein the risperidone is administered to pretreat at least 240 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat at least 270 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat at least 300 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat at least 330 minutes prior to the salt or solid form of psilocybin, including those described in Table 13. In some embodiments, the serotonin receptor modulator is risperidone and the psychedelic is a salt or solid form of psilocybin, wherein the risperidone is administered to pretreat at least 360 minutes prior to the salt or solid form of psilocybin, including those described in Table 13. In some preferred embodiments, the serotonin receptor modulator is risperidone and the psychedelic is a salt or solid form of psilocybin, wherein risperidone is administered to pretreat between about 60 minutes and about 180 minutes prior to the administration of salt or solid form of psilocybin, including those described in Table 13.

In some embodiments, the serotonin receptor modulator is eplivanserin and the psychedelic is psilocybin mesylate Form A, wherein the eplivanserin is administered to pretreat at least 15 minutes prior to the administration of the psilocybin mesylate Form A. In some embodiments, the serotonin receptor modulator is eplivanserin and the psychedelic is psilocybin mesylate Form A, wherein the eplivanserin is administered to pretreat between at least 30 minutes prior and 360 minutes prior to the release or administration of the psilocybin mesylate Form A. In some embodiments, the serotonin receptor modulator is eplivanserin and the psychedelic is psilocybin mesylate Form A, wherein the eplivanserin is administered to pretreat between at least 60 minutes prior and 360 minutes prior to the release or administration of the psilocybin mesylate Form A. In some embodiments, the serotonin receptor modulator is eplivanserin and the psychedelic is psilocybin mesylate Form A, wherein the eplivanserin is administered to pretreat between at least 90 minutes and 240 minutes prior to the psilocybin mesylate Form A. In some embodiments, the serotonin receptor modulator is eplivanserin and the psychedelic is psilocybin mesylate Form A, wherein the eplivanserin is administered to pretreat at least 120 minutes prior to the psilocybin mesylate Form A.

In some embodiments, the serotonin receptor modulator is eplivanserin and the psychedelic is psilocybin mesylate Form A, wherein the eplivanserin is administered to pretreat at least 150 minutes prior to the psilocybin mesylate Form A In some embodiments, the serotonin receptor modulator is eplivanserin and the psychedelic is psilocybin mesylate Form A, wherein the eplivanserin is administered to pretreat between about 15 minutes and about 150 minutes prior to the psilocybin mesylate Form A. In some embodiments, the serotonin receptor modulator is eplivanserin and the psychedelic is psilocybin mesylate Form A, wherein the eplivanserin is administered to pretreat at least 180 minutes prior to the psilocybin mesylate Form A. In some embodiments, the serotonin receptor modulator is eplivanserin and the psychedelic is psilocybin mesylate Form A, wherein the eplivanserin is administered to pretreat at least 210 minutes prior to the psilocybin mesylate Form A. In some embodiments, the serotonin receptor modulator is eplivanserin and the psychedelic is psilocybin mesylate Form A, wherein the eplivanserin is administered to pretreat at least 240 minutes prior to the psilocybin mesylate Form A.

In some embodiments, the serotonin receptor modulator is eplivanserin and the psychedelic is psilocybin mesylate Form A, wherein the eplivanserin is administered to pretreat at least 270 minutes prior to psilocybin HCl. In some embodiments, the serotonin receptor modulator is eplivanserin and the psychedelic is psilocybin mesylate Form A, wherein the eplivanserin is administered to pretreat at least 300 minutes prior to the psilocybin mesylate Form A. In some embodiments, the serotonin receptor modulator is eplivanserin and the psychedelic is psilocybin mesylate Form A, wherein the eplivanserin is administered to pretreat at least 330 minutes prior to the psilocybin mesylate Form A. In some embodiments, the serotonin receptor modulator is eplivanserin and the psychedelic is psilocybin mesylate Form A, wherein the eplivanserin is administered to pretreat at least 360 minutes prior to the psilocybin mesylate Form A.

In some preferred embodiments, the serotonin receptor modulator is eplivanserin and the psychedelic is psilocybin mesylate Form A, wherein eplivanserin is administered to pretreat between about 60 minutes and about 180 minutes prior to administration of the psilocybin mesylate Form A.

In some embodiments, the serotonin receptor modulator is volinanserin and the psychedelic is psilocybin mesylate Form A, wherein the volinanserin is administered to pretreat a subject between at least 15 minutes and 360 minutes prior to the administration or release of the psilocybin mesylate Form A. In some embodiments, the serotonin receptor modulator is volinanserin and the psychedelic is psilocybin mesylate Form A, wherein the volinanserin is administered to pretreat between at least 30 minutes and 360 minutes prior to the administration or release of the psilocybin mesylate Form A. In some embodiments, the serotonin receptor modulator is volinanserin and the psychedelic is psilocybin mesylate Form A, wherein the volinanserin is administered to pretreat between at least 60 minutes and 240 minutes prior to the administration or release of the psilocybin mesylate Form A. In some embodiments, the serotonin receptor modulator is volinanserin and the psychedelic is psilocybin mesylate Form A, wherein the volinanserin is administered to pretreat at least 90 minutes prior to the psilocybin mesylate Form A. In some embodiments, the serotonin receptor modulator is volinanserin and the psychedelic is psilocybin mesylate Form A, wherein the volinanserin is administered to pretreat at least 120 minutes prior to the psilocybin mesylate Form A.

In some embodiments, the serotonin receptor modulator is volinanserin and the psychedelic is psilocybin mesylate Form A, wherein the volinanserin is administered to pretreat at least 150 minutes prior to the psilocybin mesylate Form A. In some embodiments, the serotonin receptor modulator is volinanserin and the psychedelic is psilocybin mesylate Form A, wherein the volinanserin is administered to pretreat between about 15 minutes and about 150 minutes prior to the psilocybin mesylate Form A. In some embodiments, the serotonin receptor modulator is volinanserin and the psychedelic is psilocybin mesylate Form A, wherein the volinanserin is administered to pretreat at least 180 minutes prior to the psilocybin mesylate Form A. In some embodiments, the serotonin receptor modulator is volinanserin and the psychedelic is psilocybin mesylate Form A, wherein the volinanserin is administered to pretreat at least 210 minutes prior to the psilocybin mesylate Form A. In some embodiments, the serotonin receptor modulator is volinanserin and the psychedelic is psilocybin mesylate Form A, wherein the volinanserin is administered to pretreat at least 240 minutes prior to the psilocybin mesylate Form A. In some embodiments, the serotonin receptor modulator is volinanserin and the psychedelic is psilocybin mesylate Form A, wherein the volinanserin is administered to pretreat at least 270 minutes prior to the psilocybin mesylate Form A. In some embodiments, the serotonin receptor modulator is volinanserin and the psychedelic is psilocybin mesylate Form A, wherein the volinanserin is administered to pretreat at least 300 minutes prior to the psilocybin mesylate Form A. In some embodiments, the serotonin receptor modulator is volinanserin and the psychedelic is psilocybin mesylate Form A, wherein volinanserin is administered to pretreat at least 330 minutes prior to the psilocybin mesylate Form A. In some embodiments, the serotonin receptor modulator is volinanserin and the psychedelic is psilocybin mesylate Form A, wherein the volinanserin is administered to pretreat at least 360 minutes prior to the psilocybin mesylate Form A. In some preferred embodiments, the serotonin receptor modulator is volinanserin and the psychedelic is psilocybin mesylate Form A, wherein volinanserin is administered to pretreat between about 60 minutes and about 180 minutes prior to administration of the psilocybin mesylate Form A.

In some embodiments, the serotonin receptor modulator is ketanserin and the psychedelic is psilocybin mesylate Form A, wherein the ketanserin is administered to pretreat at least 15 minutes prior to the administration of the psilocybin mesylate Form A. In some embodiments, the serotonin receptor modulator is ketanserin and the psychedelic is psilocybin mesylate Form A, wherein the ketanserin is administered to pretreat between at least 30 minutes and 360 minutes prior to the administration or release of the psilocybin mesylate Form A. In some embodiments, the serotonin receptor modulator is ketanserin and the psychedelic is psilocybin mesylate Form A, wherein the ketanserin is administered to pretreat between at least 60 minutes and 240 minutes prior to the administration or release of the psilocybin mesylate Form A. In some embodiments, the serotonin receptor modulator is ketanserin and the psychedelic is psilocybin mesylate Form A, wherein the ketanserin is administered to pretreat at least 90 minutes prior to the psilocybin mesylate Form A. In some embodiments, the serotonin receptor modulator is ketanserin and the psychedelic is psilocybin mesylate Form A, wherein the ketanserin is administered to pretreat at least 120 minutes prior to the psilocybin mesylate Form A. In some embodiments, the serotonin receptor modulator is ketanserin and the psychedelic is psilocybin mesylate Form A, wherein the ketanserin is administered to pretreat at least 150 minutes prior to the psilocybin mesylate Form A. In some embodiments, the serotonin receptor modulator is ketanserin and the psychedelic is psilocybin mesylate Form A, wherein the ketanserin is administered to pretreat between about 15 minutes and about 150 minutes prior to the psilocybin mesylate Form A. In some embodiments, the serotonin receptor modulator is ketanserin and the psychedelic is psilocybin mesylate Form A, wherein the ketanserin is administered to pretreat at least 180 minutes prior to the psilocybin mesylate Form A. In some embodiments, the serotonin receptor modulator is ketanserin and the psychedelic is psilocybin mesylate Form A, wherein the ketanserin is administered to pretreat at least 210 minutes prior to the psilocybin mesylate Form A. In some embodiments, the serotonin receptor modulator is ketanserin and the psychedelic is psilocybin mesylate Form A, wherein the ketanserin is administered to pretreat at least 240 minutes prior to the psilocybin mesylate Form A. In some embodiments, the serotonin receptor modulator is ketanserin and the psychedelic is psilocybin mesylate Form A, wherein the ketanserin is administered to pretreat at least 270 minutes prior to the psilocybin mesylate Form A. In some embodiments, the serotonin receptor modulator is ketanserin and the psychedelic is psilocybin mesylate Form A, wherein the ketanserin is administered to pretreat at least 300 minutes prior to the psilocybin mesylate Form A. In some embodiments, the serotonin receptor modulator is ketanserin and the psychedelic is psilocybin mesylate Form A, wherein the ketanserin is administered to pretreat at least 330 minutes prior to the psilocybin mesylate Form A. In some embodiments, the serotonin receptor modulator is ketanserin and the psychedelic is psilocybin mesylate Form A, wherein the ketanserin is administered to pretreat at least 360 minutes prior to the psilocybin mesylate Form A. In some preferred embodiments, the serotonin receptor modulator is ketanserin and the psychedelic is psilocybin mesylate Form A, wherein ketanserin is administered to pretreat between about 60 minutes and about 180 minutes prior to the administration of the psilocybin mesylate Form A.

In some embodiments, the serotonin receptor modulator is ritanserin and the psychedelic is psilocybin mesylate Form A, wherein the ritanserin is administered to pretreat at least 15 minutes prior to the administration of the psilocybin mesylate Form A. In some embodiments, the serotonin receptor modulator is ritanserin and the psychedelic is psilocybin mesylate Form A, wherein the ritanserin is administered to pretreat at least 30 minutes prior to the psilocybin mesylate Form A. In some embodiments, the serotonin receptor modulator is ritanserin and the psychedelic is psilocybin mesylate Form A, wherein the ritanserin is administered to pretreat between at least 60 minutes and 240 minutes prior to the administration or release of the psilocybin mesylate Form A. In some embodiments, the serotonin receptor modulator is ritanserin and the psychedelic is psilocybin mesylate Form A, wherein the ritanserin is administered to pretreat at least 90 minutes prior to the psilocybin mesylate Form A. In some embodiments, the serotonin receptor modulator is ritanserin and the psychedelic is psilocybin mesylate Form A, wherein the ritanserin is administered to pretreat at least 120 minutes prior to the psilocybin mesylate Form A. In some embodiments, the serotonin receptor modulator is ritanserin and the psychedelic is psilocybin mesylate Form A, wherein the ritanserin is administered to pretreat at least 150 minutes prior to the psilocybin mesylate Form A. In some embodiments, the serotonin receptor modulator is ritanserin and the psychedelic is psilocybin mesylate Form A, wherein the ritanserin is administered to pretreat between about 15 minutes and about 150 minutes prior to the psilocybin mesylate Form A. In some embodiments, the serotonin receptor modulator is ritanserin and the psychedelic is psilocybin mesylate Form A, wherein the ritanserin is administered to pretreat at least 180 minutes prior to the psilocybin mesylate Form A. In some embodiments, the serotonin receptor modulator is ritanserin and the psychedelic is psilocybin mesylate Form A, wherein the ritanserin is administered to pretreat at least 210 minutes prior to the psilocybin mesylate Form A. In some embodiments, the serotonin receptor modulator is ritanserin and the psychedelic is psilocybin mesylate Form A, wherein the ritanserin is administered to pretreat at least 240 minutes prior to the psilocybin mesylate Form A. In some embodiments, the serotonin receptor modulator is ritanserin and the psychedelic is psilocybin mesylate Form A, wherein the ritanserin is administered to pretreat at least 270 minutes prior to the psilocybin mesylate Form A. In some embodiments, the serotonin receptor modulator is ritanserin and the psychedelic is psilocybin mesylate Form A, wherein the ritanserin is administered to pretreat at least 300 minutes prior to the psilocybin mesylate Form A. In some embodiments, the serotonin receptor modulator is ritanserin and the psychedelic is psilocybin mesylate Form A, wherein the ritanserin is administered to pretreat at least 330 minutes prior to the psilocybin mesylate Form A. In some embodiments, the serotonin receptor modulator is ritanserin and the psychedelic is psilocybin mesylate Form A, wherein the ritanserin is administered to pretreat at least 360 minutes prior to the psilocybin mesylate Form A. In some preferred embodiments, the serotonin receptor modulator is ritanserin and the psychedelic is psilocybin mesylate Form A, wherein ritanserin is administered to pretreat between about 60 minutes and about 180 minutes prior to the administration of the psilocybin mesylate Form A.

In some embodiments, the serotonin receptor modulator is pimavanserin and the psychedelic is psilocybin mesylate Form A, wherein the pimavanserin is administered to pretreat at least 15 minutes prior to the administration of the psilocybin mesylate Form A. In some embodiments, the serotonin receptor modulator is pimavanserin and the psychedelic is psilocybin mesylate Form A, wherein the pimavanserin is administered to pretreat at least 30 minutes prior to the psilocybin mesylate Form A. In some embodiments, the serotonin receptor modulator is pimavanserin and the psychedelic is psilocybin mesylate Form A, wherein the pimavanserin is administered to pretreat between at least 60 minutes and 240 minutes prior to the administration or release of the psilocybin mesylate Form A. In some embodiments, the serotonin receptor modulator is pimavanserin and the psychedelic is psilocybin mesylate Form A, wherein the pimavanserin is administered to pretreat at least 90 minutes prior to the psilocybin mesylate Form A. In some embodiments, the serotonin receptor modulator is pimavanserin and the psychedelic is psilocybin mesylate Form A, wherein the pimavanserin is administered to pretreat at least 120 minutes prior to the psilocybin mesylate Form A. In some embodiments, the serotonin receptor modulator is pimavanserin and the psychedelic is psilocybin mesylate Form A, wherein the pimavanserin is administered to pretreat at least 150 minutes prior to the psilocybin mesylate Form A. In some embodiments, the serotonin receptor modulator is pimavanserin and the psychedelic is psilocybin mesylate Form A, wherein the pimavanserin is administered to pretreat between about 15 minutes and about 150 minutes prior to the psilocybin mesylate Form A. In some embodiments, the serotonin receptor modulator is pimavanserin and the psychedelic is psilocybin mesylate Form A, wherein the pimavanserin is administered to pretreat at least 180 minutes prior to the psilocybin mesylate Form A. In some embodiments, the serotonin receptor modulator is pimavanserin and the psychedelic is psilocybin mesylate Form A, wherein the pimavanserin is administered to pretreat at least 210 minutes prior to the psilocybin mesylate Form A. In some embodiments, the serotonin receptor modulator is pimavanserin and the psychedelic is psilocybin mesylate Form A, wherein the pimavanserin is administered to pretreat at least 240 minutes prior to the psilocybin mesylate Form A. In some embodiments, the serotonin receptor modulator is pimavanserin and the psychedelic is psilocybin mesylate Form A, wherein the pimavanserin is administered to pretreat at least 270 minutes prior to the psilocybin mesylate Form A. In some embodiments, the serotonin receptor modulator is pimavanserin and the psychedelic is psilocybin mesylate Form A, wherein the pimavanserin is administered to pretreat at least 300 minutes prior to the psilocybin mesylate Form A. In some embodiments, the serotonin receptor modulator is pimavanserin and the psychedelic is psilocybin mesylate Form A, wherein the pimavanserin is administered to pretreat at least 330 minutes prior to the psilocybin mesylate Form A. In some embodiments, the serotonin receptor modulator is pimavanserin and the psychedelic is psilocybin mesylate Form A, wherein the pimavanserin is administered to pretreat at least 360 minutes prior to the psilocybin mesylate Form A. In some preferred embodiments, the serotonin receptor modulator is pimavanserin and the psychedelic is psilocybin mesylate Form A, wherein pimavanserin is administered to pretreat between about 60 minutes and about 180 minutes prior to the administration of the psilocybin mesylate Form A.

In some embodiments, the serotonin receptor modulator is nelotanserin and the psychedelic is psilocybin mesylate Form A, wherein the nelotanserin is administered to pretreat at least 15 minutes prior to the administration of the psilocybin mesylate Form A. In some embodiments, the serotonin receptor modulator is nelotanserin and the psychedelic is psilocybin mesylate Form A, wherein the nelotanserin is administered to pretreat at least 30 minutes prior to the psilocybin mesylate Form A. In some embodiments, the serotonin receptor modulator is nelotanserin and the psychedelic is psilocybin mesylate Form A, wherein the nelotanserin is administered to pretreat between at least 60 minutes and 240 minutes prior to the administration or release of the psilocybin mesylate Form A. In some embodiments, the serotonin receptor modulator is nelotanserin and the psychedelic is psilocybin mesylate Form A, wherein the nelotanserin is administered to pretreat at least 90 minutes prior to the psilocybin mesylate Form A. In some embodiments, the serotonin receptor modulator is nelotanserin and the psychedelic is psilocybin mesylate Form A, wherein the nelotanserin is administered to pretreat at least 120 minutes prior to the psilocybin mesylate Form A.

In some embodiments, the serotonin receptor modulator is nelotanserin and the psychedelic is psilocybin mesylate Form A, wherein the nelotanserin is administered to pretreat at least 150 minutes prior to the psilocybin mesylate Form A. In some embodiments, the serotonin receptor modulator is nelotanserin and the psychedelic is psilocybin mesylate Form A, wherein the nelotanserin is administered to pretreat between about 15 minutes and about 150 minutes prior to the psilocybin mesylate Form A. In some embodiments, the serotonin receptor modulator is nelotanserin and the psychedelic is psilocybin mesylate Form A, wherein the nelotanserin is administered to pretreat at least 180 minutes prior to the psilocybin mesylate Form A. In some embodiments, the serotonin receptor modulator is nelotanserin and the psychedelic is psilocybin mesylate Form A, wherein the nelotanserin is administered to pretreat at least 210 minutes prior to the psilocybin mesylate Form A. In some embodiments, the serotonin receptor modulator is nelotanserin and the psychedelic is psilocybin mesylate Form A, wherein the nelotanserin is administered to pretreat at least 240 minutes prior to the psilocybin mesylate Form A. In some embodiments, the serotonin receptor modulator is nelotanserin and the psychedelic is psilocybin mesylate Form A, wherein the nelotanserin is administered to pretreat at least 270 minutes prior to the psilocybin mesylate Form A.

In some embodiments, the serotonin receptor modulator is nelotanserin and the psychedelic is psilocybin mesylate Form A, wherein the nelotanserin is administered to pretreat at least 300 minutes prior to the psilocybin mesylate Form A. In some embodiments, the serotonin receptor modulator is nelotanserin and the psychedelic is psilocybin mesylate Form A, wherein the nelotanserin is administered to pretreat at least 330 minutes prior to the psilocybin mesylate Form A. In some embodiments, the serotonin receptor modulator is nelotanserin and the psychedelic is psilocybin mesylate Form A, wherein the nelotanserin is administered to pretreat at least 360 minutes prior to the psilocybin mesylate Form A. In some preferred embodiments, the serotonin receptor modulator is nelotanserin and the psychedelic is psilocybin mesylate Form A, wherein nelotanserin is administered to pretreat between about 60 minutes and about 180 minutes prior to the administration of the psilocybin mesylate Form A.

In some embodiments, the serotonin receptor modulator is pruvanserin and the psychedelic is psilocybin mesylate Form A, wherein the pruvanserin is administered to pretreat at least 15 minutes prior to the administration of the psilocybin mesylate Form A. In some embodiments, the serotonin receptor modulator is pruvanserin and the psychedelic is psilocybin mesylate Form A, wherein the pruvanserin is administered to pretreat at least 30 minutes prior to the psilocybin mesylate Form A. In some embodiments, the serotonin receptor modulator is pruvanserin and the psychedelic is psilocybin mesylate Form A, wherein the pruvanserin is administered to pretreat between at least 60 minutes and 240 minutes prior to the administration or release of the psilocybin mesylate Form A. In some embodiments, the serotonin receptor modulator is pruvanserin and the psychedelic is psilocybin mesylate Form A, wherein the pruvanserin is administered to pretreat at least 90 minutes prior to the psilocybin mesylate Form A. In some embodiments, the serotonin receptor modulator is pruvanserin and the psychedelic is psilocybin mesylate Form A, wherein the pruvanserin is administered to pretreat at least 120 minutes prior to the psilocybin mesylate Form A. In some embodiments, the serotonin receptor modulator is pruvanserin and the psychedelic is psilocybin mesylate Form A, wherein the pruvanserin is administered to pretreat at least 150 minutes prior to the psilocybin mesylate Form A. In some embodiments, the serotonin receptor modulator is pruvanserin and the psychedelic is psilocybin mesylate Form A, wherein the pruvanserin is administered to pretreat between about 15 minutes and about 150 minutes prior to the psilocybin mesylate Form A. In some embodiments, the serotonin receptor modulator is pruvanserin and the psychedelic is psilocybin mesylate Form A, wherein the pruvanserin is administered to pretreat at least 180 minutes prior to the psilocybin mesylate Form A. In some embodiments, the serotonin receptor modulator is pruvanserin and the psychedelic is psilocybin mesylate Form A, wherein the pruvanserin is administered to pretreat at least 210 minutes prior to the psilocybin mesylate Form A.

In some embodiments, the serotonin receptor modulator is pruvanserin and the psychedelic is psilocybin mesylate Form A, wherein the pruvanserin is administered to pretreat at least 240 minutes prior to the psilocybin mesylate Form A. In some embodiments, the serotonin receptor modulator is pruvanserin and the psychedelic is psilocybin mesylate Form A, wherein the pruvanserin is administered to pretreat at least 270 minutes prior to the psilocybin mesylate Form A. In some embodiments, the serotonin receptor modulator is pruvanserin and the psychedelic is psilocybin mesylate Form A, wherein the pruvanserin is administered to pretreat at least 300 minutes prior to the psilocybin mesylate Form A. In some embodiments, the serotonin receptor modulator is pruvanserin and the psychedelic is psilocybin mesylate Form A, wherein the pruvanserin is administered to pretreat at least 330 minutes prior to the psilocybin mesylate Form A. In some embodiments, the serotonin receptor modulator is pruvanserin and the psychedelic is psilocybin mesylate Form A, wherein the pruvanserin is administered to pretreat at least 360 minutes prior to the psilocybin mesylate Form A. In some preferred embodiments, the serotonin receptor modulator is pruvanserin and the psychedelic is psilocybin mesylate Form A, wherein pruvanserin is administered to pretreat between about 60 minutes and about 180 minutes prior to the administration of the psilocybin mesylate Form A.

In some embodiments, the serotonin receptor modulator is flibanserin and the psychedelic is psilocybin mesylate Form A, wherein the flibanserin is administered to pretreat at least 15 minutes prior to the administration of the psilocybin mesylate Form A. In some embodiments, the serotonin receptor modulator is flibanserin and the psychedelic is psilocybin mesylate Form A, wherein the flibanserin is administered to pretreat at least 30 minutes prior to the psilocybin mesylate Form A. In some embodiments, the serotonin receptor modulator is flibanserin and the psychedelic is psilocybin mesylate Form A, wherein the flibanserin is administered to pretreat between at least 60 minutes and 240 minutes prior to the administration or release of the psilocybin mesylate Form A. In some embodiments, the serotonin receptor modulator is flibanserin and the psychedelic is psilocybin mesylate Form A, wherein the flibanserin is administered to pretreat at least 90 minutes prior to the psilocybin mesylate Form A. In some embodiments, the serotonin receptor modulator is flibanserin and the psychedelic is psilocybin mesylate Form A, wherein the flibanserin is administered to pretreat at least 120 minutes prior to the psilocybin mesylate Form A. In some embodiments, the serotonin receptor modulator is flibanserin and the psychedelic is psilocybin mesylate Form A, wherein the flibanserin is administered to pretreat at least 150 minutes prior to the psilocybin mesylate Form A. In some embodiments, the serotonin receptor modulator is flibanserin and the psychedelic is psilocybin mesylate Form A, wherein the flibanserin is administered to pretreat between about 15 minutes and about 150 minutes prior to the psilocybin mesylate Form A. In some embodiments, the serotonin receptor modulator is flibanserin and the psychedelic is psilocybin mesylate Form A, wherein the flibanserin is administered to pretreat at least 180 minutes prior to the psilocybin mesylate Form A. In some embodiments, the serotonin receptor modulator is flibanserin and the psychedelic is psilocybin mesylate Form A, wherein the flibanserin is administered to pretreat at least 210 minutes prior to the psilocybin mesylate Form A.

In some embodiments, the serotonin receptor modulator is flibanserin and the psychedelic is psilocybin mesylate Form A, wherein the flibanserin is administered to pretreat at least 240 minutes prior to the psilocybin mesylate Form A. In some embodiments, the serotonin receptor modulator is flibanserin and the psychedelic is psilocybin mesylate Form A, wherein the flibanserin is administered to pretreat at least 270 minutes prior to the psilocybin mesylate Form A. In some embodiments, the serotonin receptor modulator is flibanserin and the psychedelic is psilocybin mesylate Form A, wherein the flibanserin is administered to pretreat at least 300 minutes prior to the psilocybin mesylate Form A. In some embodiments, the serotonin receptor modulator is flibanserin and the psychedelic is psilocybin mesylate Form A, wherein the flibanserin is administered to pretreat at least 330 minutes prior to the psilocybin mesylate Form A. In some embodiments, the serotonin receptor modulator is flibanserin and the psychedelic is psilocybin mesylate Form A, wherein the flibanserin is administered to pretreat at least 360 minutes prior to the psilocybin mesylate Form A. In some preferred embodiments, the serotonin receptor modulator is flibanserin and the psychedelic is psilocybin mesylate Form A, wherein flibanserin is administered to pretreat between about 60 minutes and about 180 minutes prior to the administration of the psilocybin mesylate Form A.

In some embodiments, the serotonin receptor modulator is olanzapine and the psychedelic is psilocybin mesylate Form A, wherein the olanzapine is administered to pretreat at least 15 minutes prior to the administration of the psilocybin mesylate Form A. In some embodiments, the serotonin receptor modulator is olanzapine and the psychedelic is psilocybin mesylate Form A, wherein the olanzapine is administered to pretreat at least 30 minutes prior to the psilocybin mesylate Form A. In some embodiments, the serotonin receptor modulator is olanzapine and the psychedelic is psilocybin mesylate Form A, wherein the olanzapine is administered to pretreat between at least 60 minutes and 240 minutes prior to the administration or release of the psilocybin mesylate Form A. In some embodiments, the serotonin receptor modulator is olanzapine and the psychedelic is psilocybin mesylate Form A, wherein the olanzapine is administered to pretreat at least 90 minutes prior to the psilocybin mesylate Form A. In some embodiments, the serotonin receptor modulator is olanzapine and the psychedelic is psilocybin mesylate Form A, wherein the olanzapine is administered to pretreat at least 120 minutes prior to the psilocybin mesylate Form A. In some embodiments, the serotonin receptor modulator is olanzapine and the psychedelic is psilocybin mesylate Form A, wherein the olanzapine is administered to pretreat at least 150 minutes prior to the psilocybin mesylate Form A. In some embodiments, the serotonin receptor modulator is olanzapine and the psychedelic is psilocybin mesylate Form A, wherein the olanzapine is administered to pretreat between about 15 minutes and about 150 minutes prior to the psilocybin mesylate Form A. In some embodiments, the serotonin receptor modulator is olanzapine and the psychedelic is psilocybin mesylate Form A, wherein the olanzapine is administered to pretreat at least 180 minutes prior to the psilocybin mesylate Form A. In some embodiments, the serotonin receptor modulator is olanzapine and the psychedelic is psilocybin mesylate Form A, wherein the olanzapine is administered to pretreat at least 210 minutes prior to the psilocybin mesylate Form A.

In some embodiments, the serotonin receptor modulator is olanzapine and the psychedelic is psilocybin mesylate Form A, wherein the olanzapine is administered to pretreat at least 240 minutes prior to the psilocybin mesylate Form A. In some embodiments, the serotonin receptor modulator is olanzapine and the psychedelic is psilocybin mesylate Form A, wherein the olanzapine is administered to pretreat at least 270 minutes prior to the psilocybin mesylate Form A. In some embodiments, the serotonin receptor modulator is olanzapine and the psychedelic is psilocybin mesylate Form A, wherein the olanzapine is administered to pretreat at least 300 minutes prior to the psilocybin mesylate Form A. In some embodiments, the serotonin receptor modulator is olanzapine and the psychedelic is psilocybin mesylate Form A, wherein the olanzapine is administered to pretreat at least 330 minutes prior to the psilocybin mesylate Form A. In some embodiments, the serotonin receptor modulator is olanzapine and the psychedelic is psilocybin mesylate Form A, wherein the olanzapine is administered to pretreat at least 360 minutes prior to the psilocybin mesylate Form A. In some preferred embodiments, the serotonin receptor modulator is olanzapine and the psychedelic is psilocybin mesylate Form A, wherein olanzapine is administered to pretreat between about 60 minutes and about 180 minutes prior to the administration of the psilocybin mesylate Form A.

In some embodiments, the serotonin receptor modulator is risperidone and the psychedelic is psilocybin mesylate Form A, wherein the risperidone is administered to pretreat at least 15 minutes prior to the administration of the psilocybin mesylate Form A. In some embodiments, the serotonin receptor modulator is risperidone and the psychedelic is psilocybin mesylate Form A, wherein the risperidone is administered to pretreat at least 30 minutes prior to the psilocybin mesylate Form A. In some embodiments, the serotonin receptor modulator is risperidone and the psychedelic is psilocybin mesylate Form A, wherein the risperidone is administered to pretreat between at least 60 minutes and 240 minutes prior to the administration or release of the psilocybin mesylate Form A. In some embodiments, the serotonin receptor modulator is risperidone and the psychedelic is psilocybin mesylate Form A, wherein the risperidone is administered to pretreat at least 90 minutes prior to the psilocybin mesylate Form A. In some embodiments, the serotonin receptor modulator is risperidone and the psychedelic is psilocybin mesylate Form A, wherein the risperidone is administered to pretreat at least 120 minutes prior to the psilocybin mesylate Form A. In some embodiments, the serotonin receptor modulator is risperidone and the psychedelic is psilocybin mesylate Form A, wherein the risperidone is administered to pretreat at least 150 minutes prior to the psilocybin mesylate Form A.

In some embodiments, the serotonin receptor modulator is risperidone and the psychedelic is psilocybin mesylate Form A, wherein the risperidone is administered to pretreat between about 15 minutes and about 150 minutes prior to the psilocybin mesylate Form A. In some embodiments, the serotonin receptor modulator is risperidone and the psychedelic is psilocybin mesylate Form A, wherein the risperidone is administered to pretreat at least 180 minutes prior to the psilocybin mesylate Form A. In some embodiments, the serotonin receptor modulator is risperidone and the psychedelic is psilocybin mesylate Form A, wherein the risperidone is administered to pretreat at least 210 minutes prior to the psilocybin mesylate Form A.

In some embodiments, the serotonin receptor modulator is risperidone and the psychedelic is psilocybin mesylate Form A, wherein the risperidone is administered to pretreat at least 240 minutes prior to the psilocybin mesylate Form A. In some embodiments, the serotonin receptor modulator is risperidone and the psychedelic is psilocybin mesylate Form A, wherein the risperidone is administered to pretreat at least 270 minutes prior to the psilocybin mesylate Form A. In some embodiments, the serotonin receptor modulator is risperidone and the psychedelic is psilocybin mesylate Form A, wherein the risperidone is administered to pretreat at least 300 minutes prior to the psilocybin mesylate Form A. In some embodiments, the serotonin receptor modulator is risperidone and the psychedelic is psilocybin mesylate Form A, wherein the risperidone is administered to pretreat at least 330 minutes prior to the psilocybin mesylate Form A. In some embodiments, the serotonin receptor modulator is risperidone and the psychedelic is psilocybin mesylate Form A, wherein the risperidone is administered to pretreat at least 360 minutes prior to the psilocybin mesylate Form A. In some preferred embodiments, the serotonin receptor modulator is risperidone and the psychedelic is psilocybin mesylate Form A, wherein risperidone is administered to pretreat between about 60 minutes and about 180 minutes prior to the administration of the psilocybin mesylate Form A.

In some embodiments, the serotonin receptor modulator is quetiapine and the psychedelic is psilocybin mesylate Form A, wherein the quetiapine is administered to pretreat at least 15 minutes prior to the administration of the psilocybin mesylate Form A. In some embodiments, the serotonin receptor modulator is quetiapine and the psychedelic is psilocybin mesylate Form A, wherein the quetiapine is administered to pretreat at least 30 minutes prior to the psilocybin mesylate Form A. In some embodiments, the serotonin receptor modulator is quetiapine and the psychedelic is psilocybin mesylate Form A, wherein the quetiapine is administered to pretreat between at least 60 minutes and 240 minutes prior to the administration or release of the psilocybin mesylate Form A. In some embodiments, the serotonin receptor modulator is quetiapine and the psychedelic is psilocybin mesylate Form A, wherein the quetiapine is administered to pretreat at least 90 minutes prior to the psilocybin mesylate Form A. In some embodiments, the serotonin receptor modulator is quetiapine and the psychedelic is psilocybin mesylate Form A, wherein the quetiapine is administered to pretreat at least 120 minutes prior to the psilocybin mesylate Form A. In some embodiments, the serotonin receptor modulator is quetiapine and the psychedelic is psilocybin mesylate Form A, wherein the quetiapine is administered to pretreat at least 150 minutes prior to the psilocybin mesylate Form A. In some embodiments, the serotonin receptor modulator is quetiapine and the psychedelic is psilocybin mesylate Form A, wherein the quetiapine is administered to pretreat between about 15 minutes and about 150 minutes prior to the psilocybin mesylate Form A. In some embodiments, the serotonin receptor modulator is quetiapine and the psychedelic is psilocybin mesylate Form A, wherein the quetiapine is administered to pretreat at least 180 minutes prior to the psilocybin mesylate Form A. In some embodiments, the serotonin receptor modulator is quetiapine and the psychedelic is psilocybin mesylate Form A, wherein the quetiapine is administered to pretreat at least 210 minutes prior to the psilocybin mesylate Form A.

In some embodiments, the serotonin receptor modulator is quetiapine and the psychedelic is psilocybin mesylate Form A, wherein the quetiapine is administered to pretreat at least 240 minutes prior to the psilocybin mesylate Form A. In some embodiments, the serotonin receptor modulator is quetiapine and the psychedelic is psilocybin mesylate Form A, wherein the quetiapine is administered to pretreat at least 270 minutes prior to the psilocybin mesylate Form A. In some embodiments, the serotonin receptor modulator is quetiapine and the psychedelic is psilocybin mesylate Form A, wherein the quetiapine is administered to pretreat at least 300 minutes prior to the psilocybin mesylate Form A. In some embodiments, the serotonin receptor modulator is quetiapine and the psychedelic is psilocybin mesylate Form A, wherein the quetiapine is administered to pretreat at least 330 minutes prior to the psilocybin mesylate Form A. In some embodiments, the serotonin receptor modulator is quetiapine and the psychedelic is psilocybin mesylate Form A, wherein the quetiapine is administered to pretreat at least 360 minutes prior to the psilocybin mesylate Form A. In some preferred embodiments, the serotonin receptor modulator is quetiapine and the psychedelic is psilocybin mesylate Form A, wherein quetiapine is administered to pretreat between about 60 minutes and about 180 minutes prior to the administration of the psilocybin mesylate Form A.

In certain embodiments, such as those described above a psilocybin salt or solid form disclosed herein, including those described in Table 13, is co-administered with a serotonin receptor modulator in the same or in separate compositions. In one embodiment, the serotonin receptor modulator is administered after the psilocybin salt or solid form disclosed herein, including those described in Table 13. In one embodiment, the psilocybin salt or solid form disclosed herein, including those described in Table 13, is administered in a modified release formulation such that the subject is effectively post-treated with serotonin receptor modulator post to release of an effective amount of the psilocybin salt or solid. In some embodiments, the serotonin receptor modulator is part of a single fixed dose formulation that releases the psilocybin salt or solid first followed by serotonin receptor modulator on two different release profiles. In another embodiment, the psilocybin salt or solid form disclosed herein, including those described in Table 13, is administered first as a single dosage and, after a length of time, serotonin receptor modulator is administered as a second dosage separate from the first dosage. Thus, in some embodiments, the serotonin receptor modulator is administered or released from a composition provided herein post to the administration and/or release of the psychedelic. This allows post-treatment to attenuate activation of the serotonin receptor by the psychedelic. In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours post to the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post to the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post to the release of the psychedelic.

In a preferred embodiment, the serotonin receptor modulator is administered at about 1 hour to about 3 hours post to the administration of the psychedelic.

In some embodiments, the serotonin receptor modulator is eplivanserin and the psychedelic is psilocybin salt or solid, wherein the eplivanserin is administered to post-treat at least 15 minutes after the administration of the psilocybin salt or solid form disclosed herein, including those described in Table 13. In some embodiments, the serotonin receptor modulator is eplivanserin and the psychedelic is psilocybin salt or solid, wherein eplivanserin is administered to post-treat between at least 30 minutes after and 360 minutes after the release or administration of the psilocybin salt or solid form disclosed herein, including those described in Table 13. In some embodiments, the serotonin receptor modulator is eplivanserin and the psychedelic is psilocybin salt or solid, wherein eplivanserin is administered to post-treat between at least 60 minutes after and 360 minutes after the release or administration of the psilocybin salt or solid form disclosed herein, including those described in Table 13. In some embodiments, the serotonin receptor modulator is eplivanserin and the psychedelic is psilocybin salt or solid, wherein eplivanserin is administered to post-treat between at least 90 minutes and 240 minutes after the psilocybin salt or solid form disclosed herein, including those described in Table 13. In some embodiments, the serotonin receptor modulator is eplivanserin and the psychedelic is psilocybin salt or solid, wherein eplivanserin is administered to post-treat at least 120 minutes after the psilocybin salt or solid form disclosed herein, including those described in Table 13.

In some embodiments, the serotonin receptor modulator is eplivanserin and the psychedelic is psilocybin salt or solid, wherein the eplivanserin is administered to post-treat at least 150 minutes after the psilocybin salt or solid form disclosed herein, including those described in Table 13. In some embodiments, the serotonin receptor modulator is eplivanserin and the psychedelic is psilocybin salt or solid, wherein the eplivanserin is administered to post-treat between about 15 minutes and about 150 minutes after the psilocybin salt or solid form disclosed herein, including those described in Table 13. In some embodiments, the serotonin receptor modulator is eplivanserin and the psychedelic is psilocybin salt or solid, wherein the eplivanserin is administered to post-treat at least 180 minutes after the psilocybin salt or solid form disclosed herein, including those described in Table 13. In some embodiments, the serotonin receptor modulator is eplivanserin and the psychedelic is psilocybin salt or solid, wherein the eplivanserin is administered to post-treat at least 210 minutes after the psilocybin salt or solid form disclosed herein, including those described in Table 13. In some embodiments, the serotonin receptor modulator is eplivanserin and the psychedelic is psilocybin salt or solid, wherein the eplivanserin is administered to post-treat at least 240 minutes after the psilocybin salt or solid form disclosed herein, including those described in Table 13.

In some embodiments, the serotonin receptor modulator is eplivanserin and the psychedelic is psilocybin salt or solid, wherein the eplivanserin is administered to post-treat at least 270 minutes after the psilocybin salt or solid form disclosed herein, including those described in Table 13. In some embodiments, the serotonin receptor modulator is eplivanserin and the psychedelic is psilocybin salt or solid, wherein the eplivanserin is administered to post-treat at least 300 minutes after the psilocybin salt or solid form disclosed herein, including those described in Table 13. In some embodiments, the serotonin receptor modulator is eplivanserin and the psychedelic is psilocybin salt or solid, wherein the eplivanserin is administered to post-treat at least 330 minutes after the psilocybin salt or solid form disclosed herein, including those described in Table 13. In some embodiments, the serotonin receptor modulator is eplivanserin and the psychedelic is psilocybin salt or solid, wherein the eplivanserin is administered to post-treat at least 360 minutes after the psilocybin salt or solid form disclosed herein, including those described in Table 13.

In some preferred embodiments, the serotonin receptor modulator is eplivanserin and the psychedelic is psilocybin salt or solid, wherein eplivanserin is administered to post-treat between about 60 minutes and about 180 minutes after the administration of the psilocybin salt or solid form disclosed herein, including those described in Table 13.

In some embodiments, the serotonin receptor modulator is volinanserin and the psychedelic is psilocybin salt or solid, wherein the volinanserin is administered to post-treat a subject between at least 15 minutes and 360 minutes after the administration or release of the psilocybin salt or solid form disclosed herein, including those described in Table 13. In some embodiments, the serotonin receptor modulator is volinanserin and the psychedelic is psilocybin salt or solid, wherein the volinanserin is administered to post-treat between at least 30 minutes and 360 minutes after the administration or release of the psilocybin salt or solid form disclosed herein, including those described in Table 13. In some embodiments, the serotonin receptor modulator is volinanserin and the psychedelic is psilocybin salt or solid, wherein the volinanserin is administered to post-treat between at least 60 minutes and 240 minutes after the administration or release of the psilocybin salt or solid form disclosed herein, including those described in Table 13. In some embodiments, the serotonin receptor modulator is volinanserin and the psychedelic is psilocybin salt or solid, wherein the volinanserin is administered to post-treat at least 90 minutes after psilocybin salt or solid. In some embodiments, the serotonin receptor modulator is volinanserin and the psychedelic is psilocybin salt or solid, wherein the volinanserin is administered to post-treat at least 120 minutes after the psilocybin salt or solid form disclosed herein, including those described in Table 13.

In some embodiments, the serotonin receptor modulator is volinanserin and the psychedelic is psilocybin salt or solid, wherein the volinanserin is administered to post-treat at least 150 minutes after the psilocybin salt or solid form disclosed herein, including those described in Table 13. In some embodiments, the serotonin receptor modulator is volinanserin and the psychedelic is psilocybin salt or solid, wherein the volinanserin is administered to post-treat between about 15 minutes and about 150 minutes after the psilocybin salt or solid form disclosed herein, including those described in Table 13. In some embodiments, the serotonin receptor modulator is volinanserin and the psychedelic is psilocybin salt or solid, wherein the volinanserin is administered to post-treat at least 180 minutes after the psilocybin salt or solid form disclosed herein, including those described in Table 13. In some embodiments, the serotonin receptor modulator is volinanserin and the psychedelic is psilocybin salt or solid, wherein the volinanserin is administered to post-treat at least 210 minutes after the psilocybin salt or solid form disclosed herein, including those described in Table 13. In some embodiments, the serotonin receptor modulator is volinanserin and the psychedelic is psilocybin salt or solid, wherein the volinanserin is administered to post-treat at least 240 minutes after the psilocybin salt or solid form disclosed herein, including those described in Table 13. In some embodiments, the serotonin receptor modulator is volinanserin and the psychedelic is psilocybin salt or solid, wherein the volinanserin is administered to post-treat at least 270 minutes after the psilocybin salt or solid form disclosed herein, including those described in Table 13. In some embodiments, the serotonin receptor modulator is volinanserin and the psychedelic is psilocybin salt or solid, wherein the volinanserin is administered to post-treat at least 300 minutes after the psilocybin salt or solid form disclosed herein, including those described in Table 13. In some embodiments, the serotonin receptor modulator is volinanserin and the psychedelic is psilocybin salt or solid, wherein the volinanserin is administered to post-treat at least 330 minutes after the psilocybin salt or solid form disclosed herein, including those described in Table 13. In some embodiments, the serotonin receptor modulator is volinanserin and the psychedelic is psilocybin salt or solid, wherein the volinanserin is administered to post-treat at least 360 minutes after the psilocybin salt or solid form disclosed herein, including those described in Table 13. In some preferred embodiments, the serotonin receptor modulator is volinanserin and the psychedelic is psilocybin salt or solid, wherein volinanserin is administered to post-treat between about 60 minutes and about 180 minutes after the administration of the ®-MDMA form.

In some embodiments, the serotonin receptor modulator is ketanserin and the psychedelic is psilocybin salt or solid, wherein the ketanserin is administered to post-treat at least 15 minutes after the administration of the psilocybin salt or solid form disclosed herein, including those described in Table 13. In some embodiments, the serotonin receptor modulator is ketanserin and the psychedelic is psilocybin salt or solid, wherein the ketanserin is administered to post-treat between at least 30 minutes and 360 minutes after the administration or release of the psilocybin salt or solid form disclosed herein, including those described in Table 13. In some embodiments, the serotonin receptor modulator is ketanserin and the psychedelic is psilocybin salt or solid, wherein the ketanserin is administered to post-treat between at least 60 minutes and 240 minutes after the administration or release of the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 90 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 120 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 150 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat between about 15 minutes and about 150 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 180 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 210 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 240 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 270 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 300 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 330 minutes after the psilocybin salt or solid form disclosed herein, including those described in Table 13. In some embodiments, the serotonin receptor modulator is ketanserin and the psychedelic is psilocybin salt or solid, wherein the ketanserin is administered to post-treat at least 360 minutes after the psilocybin salt or solid form disclosed herein, including those described in Table 13. In some preferred embodiments, the serotonin receptor modulator is ketanserin and the psychedelic is psilocybin salt or solid, wherein ketanserin is administered to post-treat between about 60 minutes and about 180 minutes after the administration of the psilocybin salt or solid form disclosed herein, including those described in Table 13.

In some embodiments, the serotonin receptor modulator is ritanserin and the psychedelic is psilocybin salt or solid, wherein the ritanserin is administered to post-treat at least 15 minutes after the administration of the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 30 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat between at least 60 minutes and 240 minutes after the administration or release of the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 90 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 120 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 150 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat between about 15 minutes and about 150 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 180 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 210 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 240 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 270 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 300 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 330 minutes after the psilocybin salt or solid form disclosed herein, including those described in Table 13. In some embodiments, the serotonin receptor modulator is ritanserin and the psychedelic is psilocybin salt or solid, wherein the ritanserin is administered to post-treat at least 360 minutes after the psilocybin salt or solid form disclosed herein, including those described in Table 13. In some preferred embodiments, the serotonin receptor modulator is ritanserin and the psychedelic is psilocybin salt or solid, wherein ritanserin is administered to post-treat between about 60 minutes and about 180 minutes after the administration of the psilocybin salt or solid form disclosed herein, including those described in Table 13.

In some embodiments, the serotonin receptor modulator is pimavanserin and the psychedelic is psilocybin salt or solid, wherein the pimavanserin is administered to post-treat at least 15 minutes after the administration of the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 30 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat between at least 60 minutes and 240 minutes after the administration or release of the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 90 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 120 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 150 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat between about 15 minutes and about 150 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 180 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 210 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 240 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 270 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 300 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 330 minutes after the psilocybin salt or solid form disclosed herein, including those described in Table 13. In some embodiments, the serotonin receptor modulator is pimavanserin and the psychedelic is psilocybin salt or solid, wherein the pimavanserin is administered to post-treat at least 360 minutes after the psilocybin salt or solid form disclosed herein, including those described in Table 13. In some preferred embodiments, the serotonin receptor modulator is pimavanserin and the psychedelic is psilocybin salt or solid, wherein pimavanserin is administered to post-treat between about 60 minutes and about 180 minutes after the administration of the psilocybin salt or solid form disclosed herein, including those described in Table 13.

In some embodiments, the serotonin receptor modulator is nelotanserin and the psychedelic is psilocybin salt or solid, wherein the nelotanserin is administered to post-treat at least 15 minutes after the administration of the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 30 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat between at least 60 minutes and 240 minutes after the administration or release of the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 90 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 120 minutes after the psilocybin salt or solid form disclosed herein, including those described in Table 13.

In some embodiments, the serotonin receptor modulator is nelotanserin and the psychedelic is psilocybin salt or solid, wherein the nelotanserin is administered to post-treat at least 150 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat between about 15 minutes and about 150 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 180 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 210 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 240 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 270 minutes after the psilocybin salt or solid form disclosed herein, including those described in Table 13.

In some embodiments, the serotonin receptor modulator is nelotanserin and the psychedelic is psilocybin salt or solid, wherein the nelotanserin is administered to post-treat at least 300 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 330 minutes after the psilocybin salt or solid form disclosed herein, including those described in Table 13. In some embodiments, the serotonin receptor modulator is nelotanserin and the psychedelic is psilocybin salt or solid, wherein the nelotanserin is administered to post-treat at least 360 minutes after the psilocybin salt or solid form disclosed herein, including those described in Table 13. In some preferred embodiments, the serotonin receptor modulator is nelotanserin and the psychedelic is psilocybin salt or solid, wherein nelotanserin is administered to post-treat between about 60 minutes and about 180 minutes after the administration of the psilocybin salt or solid form disclosed herein, including those described in Table 13.

In some embodiments, the serotonin receptor modulator is pruvanserin and the psychedelic is psilocybin salt or solid, wherein the pruvanserin is administered to post-treat at least 15 minutes after the administration of the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 30 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat between at least 60 minutes and 240 minutes after the administration or release of the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 90 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 120 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 150 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat between about 15 minutes and about 150 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 180 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 210 minutes after the psilocybin salt or solid form disclosed herein, including those described in Table 13.

In some embodiments, the serotonin receptor modulator is pruvanserin and the psychedelic is psilocybin salt or solid, wherein the pruvanserin is administered to post-treat at least 240 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 270 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 300 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 330 minutes after the psilocybin salt or solid form disclosed herein, including those described in Table 13. In some embodiments, the serotonin receptor modulator is pruvanserin and the psychedelic is psilocybin salt or solid, wherein the pruvanserin is administered to post-treat at least 360 minutes after the psilocybin salt or solid form disclosed herein, including those described in Table 13. In some preferred embodiments, the serotonin receptor modulator is pruvanserin and the psychedelic is psilocybin salt or solid, wherein pruvanserin is administered to post-treat between about 60 minutes and about 180 minutes after the administration of the psilocybin salt or solid form disclosed herein, including those described in Table 13.

In some embodiments, the serotonin receptor modulator is flibanserin, wherein the flibanserin is administered to post-treat at least 15 minutes post to the administration of the psilocybin salt or solid form disclosed herein, including those described in Table 13. In some embodiments, the serotonin receptor modulator is flibanserin, wherein the flibanserin is administered to post-treat at least 30 minutes post to the psilocybin salt or solid form disclosed herein, including those described in Table 13. In some embodiments, the serotonin receptor modulator is flibanserin, wherein the flibanserin is administered to post-treat between at least 60 minutes and 240 minutes post to the administration or release of the psilocybin salt or solid form disclosed herein, including those described in Table 13. In some embodiments, the serotonin receptor modulator is flibanserin, wherein the flibanserin is administered to post-treat at least 90 minutes post to the psilocybin salt or solid form disclosed herein, including those described in Table 13. In some embodiments, the serotonin receptor modulator is flibanserin, wherein the flibanserin is administered to post-treat at least 120 minutes post to the psilocybin salt or solid form disclosed herein, including those described in Table 13. In some embodiments, the serotonin receptor modulator is flibanserin, wherein the flibanserin is administered to post-treat at least 150 minutes post to the psilocybin salt or solid form disclosed herein, including those described in Table 13. In some embodiments, the serotonin receptor modulator is flibanserin, wherein the flibanserin is administered to post-treat between about 15 minutes and about 150 minutes post to the psilocybin salt or solid form disclosed herein, including those described in Table 13. In some embodiments, the serotonin receptor modulator is flibanserin, wherein the flibanserin is administered to post-treat at least 180 minutes post to the psilocybin salt or solid form disclosed herein, including those described in Table 13. In some embodiments, the serotonin receptor modulator is flibanserin, wherein the flibanserin is administered to post-treat at least 210 minutes post to the psilocybin salt or solid form disclosed herein, including those described in Table 13.

In some embodiments, the serotonin receptor modulator is flibanserin, wherein the flibanserin is administered to post-treat at least 240 minutes post to the psilocybin salt or solid form disclosed herein, including those described in Table 13. In some embodiments, the serotonin receptor modulator is flibanserin, wherein the flibanserin is administered to post-treat at least 270 minutes post to the psilocybin salt or solid form disclosed herein, including those described in Table 13. In some embodiments, the serotonin receptor modulator is flibanserin, wherein the flibanserin is administered to post-treat at least 300 minutes post to the psilocybin salt or solid form disclosed herein, including those described in Table 13. In some embodiments, the serotonin receptor modulator is flibanserin, wherein the flibanserin is administered to post-treat at least 330 minutes post to the psilocybin salt or solid form disclosed herein, including those described in Table 13. In some embodiments, the serotonin receptor modulator is flibanserin, wherein the flibanserin is administered to post-treat at least 360 minutes post to the psilocybin salt or solid form disclosed herein, including those described in Table 13. In some preferred embodiments, the serotonin receptor modulator is flibanserin, wherein flibanserin is administered to post-treat between about 60 minutes and about 180 minutes post to the administration of psilocybin salt or solid form disclosed herein, including those described in Table 13.

In some embodiments, the serotonin receptor modulator is olanzapine, wherein the olanzapine is administered to post-treat at least 15 minutes post to the administration of the psilocybin salt or solid form disclosed herein, including those described in Table 13. In some embodiments, the serotonin receptor modulator is olanzapine, wherein the olanzapine is administered to post-treat at least 30 minutes post to the psilocybin salt or solid form disclosed herein, including those described in Table 13. In some embodiments, the serotonin receptor modulator is olanzapine, wherein the olanzapine is administered to post-treat between at least 60 minutes and 240 minutes post to the administration or release of the psilocybin salt or solid form disclosed herein, including those described in Table 13. In some embodiments, the serotonin receptor modulator is olanzapine, wherein the olanzapine is administered to post-treat at least 90 minutes post to the psilocybin salt or solid form disclosed herein, including those described in Table 13. In some embodiments, the serotonin receptor modulator is olanzapine, wherein the olanzapine is administered to post-treat at least 120 minutes post to the psilocybin salt or solid form disclosed herein, including those described in Table 13. In some embodiments, the serotonin receptor modulator is olanzapine, wherein the olanzapine is administered to post-treat at least 150 minutes post to the psilocybin salt or solid form disclosed herein, including those described in Table 13. In some embodiments, the serotonin receptor modulator is olanzapine, wherein the olanzapine is administered to post-treat between about 15 minutes and about 150 minutes post to the psilocybin salt or solid form disclosed herein, including those described in Table 13. In some embodiments, the serotonin receptor modulator is olanzapine, wherein the olanzapine is administered to post-treat at least 180 minutes post to the psilocybin salt or solid form disclosed herein, including those described in Table 13. In some embodiments, the serotonin receptor modulator is olanzapine, wherein the olanzapine is administered to post-treat at least 210 minutes post to the psilocybin salt or solid form disclosed herein, including those described in Table 13. In some embodiments, the serotonin receptor modulator is olanzapine, wherein the olanzapine is administered to post-treat at least 240 minutes post to the psilocybin salt or solid form disclosed herein, including those described in Table 13. In some embodiments, the serotonin receptor modulator is olanzapine, wherein the olanzapine is administered to post-treat at least 270 minutes post to the psilocybin salt or solid form disclosed herein, including those described in Table 13. In some embodiments, the serotonin receptor modulator is olanzapine, wherein the olanzapine is administered to post-treat at least 300 minutes post to the psilocybin salt or solid form disclosed herein, including those described in Table 13. In some embodiments, the serotonin receptor modulator is olanzapine, wherein the olanzapine is administered to post-treat at least 330 minutes post to the psilocybin salt or solid form disclosed herein, including those described in Table 13. In some embodiments, the serotonin receptor modulator is olanzapine, wherein the olanzapine is administered to post-treat at least 360 minutes post to the psilocybin salt or solid form disclosed herein, including those described in Table 13. In some preferred embodiments, the serotonin receptor modulator is olanzapine, wherein olanzapine is administered to post-treat between about 60 minutes and about 180 minutes post to the administration of psilocybin salt or solid form disclosed herein, including those described in Table 13.

In some embodiments, the serotonin receptor modulator is quetiapine, wherein the quetiapine is administered to post-treat at least 15 minutes post to the administration of the psilocybin salt or solid form disclosed herein, including those described in Table 13. In some embodiments, the serotonin receptor modulator is quetiapine, wherein the quetiapine is administered to post-treat at least 30 minutes post to the psilocybin salt or solid form disclosed herein, including those described in Table 13. In some embodiments, the serotonin receptor modulator is quetiapine, wherein the quetiapine is administered to post-treat between at least 60 minutes and 240 minutes post to the administration or release of the psilocybin salt or solid form disclosed herein, including those described in Table 13. In some embodiments, the serotonin receptor modulator is quetiapine, wherein the quetiapine is administered to post-treat at least 90 minutes post to the psilocybin salt or solid form disclosed herein, including those described in Table 13. In some embodiments, the serotonin receptor modulator is quetiapine, wherein the quetiapine is administered to post-treat at least 120 minutes post to the psilocybin salt or solid form disclosed herein, including those described in Table 13. In some embodiments, the serotonin receptor modulator is quetiapine, wherein the quetiapine is administered to post-treat at least 150 minutes post to the psilocybin salt or solid form disclosed herein, including those described in Table 13. In some embodiments, the serotonin receptor modulator is quetiapine, wherein the quetiapine is administered to post-treat between about 15 minutes and about 150 minutes post to the psilocybin salt or solid form disclosed herein, including those described in Table 13. In some embodiments, the serotonin receptor modulator is quetiapine, wherein the quetiapine is administered to post-treat at least 180 minutes post to the psilocybin salt or solid form disclosed herein, including those described in Table 13. In some embodiments, the serotonin receptor modulator is quetiapine, wherein the quetiapine is administered to post-treat at least 210 minutes post to the psilocybin salt or solid form disclosed herein, including those described in Table 13.

In some embodiments, the serotonin receptor modulator is quetiapine, wherein the quetiapine is administered to post-treat at least 240 minutes post to the psilocybin salt or solid form disclosed herein, including those described in Table 13. In some embodiments, the serotonin receptor modulator is quetiapine, wherein the quetiapine is administered to post-treat at least 270 minutes post to the psilocybin salt or solid form disclosed herein, including those described in Table 13. In some embodiments, the serotonin receptor modulator is quetiapine, wherein the quetiapine is administered to post-treat at least 300 minutes post to the psilocybin salt or solid form disclosed herein, including those described in Table 13. In some embodiments, the serotonin receptor modulator is quetiapine, wherein the quetiapine is administered to post-treat at least 330 minutes post to the psilocybin salt or solid form disclosed herein, including those described in Table 13. In some embodiments, the serotonin receptor modulator is quetiapine, wherein the quetiapine is administered to post-treat at least 360 minutes post to the psilocybin salt or solid form disclosed herein, including those described in Table 13. In some preferred embodiments, the serotonin receptor modulator is quetiapine, wherein quetiapine is administered to post-treat between about 60 minutes and about 180 minutes post to the administration of psilocybin salt or solid form disclosed herein, including those described in Table 13.

In some embodiments, the serotonin receptor modulator is risperidone, wherein the risperidone is administered to post-treat at least 15 minutes post to the administration of the psilocybin salt or solid form disclosed herein, including those described in Table 13. In some embodiments, the serotonin receptor modulator is risperidone, wherein the risperidone is administered to post-treat at least 30 minutes post to the psilocybin salt or solid form disclosed herein, including those described in Table 13. In some embodiments, the serotonin receptor modulator is risperidone, wherein the risperidone is administered to post-treat between at least 60 minutes and 240 minutes post to the administration or release of the psilocybin salt or solid form disclosed herein, including those described in Table 13. In some embodiments, the serotonin receptor modulator is risperidone, wherein the risperidone is administered to post-treat at least 90 minutes post to the psilocybin salt or solid form disclosed herein, including those described in Table 13. In some embodiments, the serotonin receptor modulator is risperidone, wherein the risperidone is administered to post-treat at least 120 minutes post to the psilocybin salt or solid form disclosed herein, including those described in Table 13. In some embodiments, the serotonin receptor modulator is risperidone, wherein the risperidone is administered to post-treat at least 150 minutes post to the psilocybin salt or solid form disclosed herein, including those described in Table 13. In some embodiments, the serotonin receptor modulator is risperidone, wherein the risperidone is administered to post-treat between about 15 minutes and about 150 minutes post to the psilocybin salt or solid form disclosed herein, including those described in Table 13. In some embodiments, the serotonin receptor modulator is risperidone, wherein the risperidone is administered to post-treat at least 180 minutes post to the psilocybin salt or solid form disclosed herein, including those described in Table 13. In some embodiments, the serotonin receptor modulator is risperidone, wherein the risperidone is administered to post-treat at least 210 minutes post to the psilocybin salt or solid form disclosed herein, including those described in Table 13.

In some embodiments, the serotonin receptor modulator is risperidone, wherein the risperidone is administered to post-treat at least 240 minutes post to the psilocybin salt or solid form disclosed herein, including those described in Table 13. In some embodiments, the serotonin receptor modulator is risperidone, wherein the risperidone is administered to post-treat at least 270 minutes post to the psilocybin salt or solid form disclosed herein, including those described in Table 13. In some embodiments, the serotonin receptor modulator is risperidone, wherein the risperidone is administered to post-treat at least 300 minutes post to the psilocybin salt or solid form disclosed herein, including those described in Table 13. In some embodiments, the serotonin receptor modulator is risperidone, wherein the risperidone is administered to post-treat at least 330 minutes post to the psilocybin salt or solid form disclosed herein, including those described in Table 13. In some embodiments, the serotonin receptor modulator is risperidone, wherein the risperidone is administered to post-treat at least 360 minutes post to the psilocybin salt or solid form disclosed herein, including those described in Table 13. In some preferred embodiments, the serotonin receptor modulator is risperidone, wherein risperidone is administered to post-treat between about 60 minutes and about 180 minutes post to the administration of the psilocybin salt or solid form disclosed herein, including those described in Table 13.

In some embodiments, the serotonin receptor modulator is eplivanserin and the psychedelic is psilocybin mesylate Form A, wherein the eplivanserin is administered to post-treat at least 15 minutes after the administration of the psilocybin mesylate Form A. In some embodiments, the serotonin receptor modulator is eplivanserin and the psychedelic is psilocybin mesylate Form A, wherein the eplivanserin is administered to post-treat between at least 30 minutes after and 360 minutes after the release or administration of the psilocybin mesylate Form A. In some embodiments, the serotonin receptor modulator is eplivanserin and the psychedelic is psilocybin mesylate Form A, wherein the eplivanserin is administered to post-treat between at least 60 minutes after and 360 minutes after the release or administration of the psilocybin mesylate Form A. In some embodiments, the serotonin receptor modulator is eplivanserin and the psychedelic is psilocybin mesylate Form A, wherein the eplivanserin is administered to post-treat between at least 90 minutes and 240 minutes after the psilocybin mesylate Form A. In some embodiments, the serotonin receptor modulator is eplivanserin and the psychedelic is psilocybin mesylate Form A, wherein the eplivanserin is administered to post-treat at least 120 minutes after the psilocybin mesylate Form A.

In some embodiments, the serotonin receptor modulator is eplivanserin and the psychedelic is psilocybin mesylate Form A, wherein the eplivanserin is administered to post-treat at least 150 minutes after the psilocybin mesylate Form A. In some embodiments, the serotonin receptor modulator is eplivanserin and the psychedelic is psilocybin mesylate Form A, wherein the eplivanserin is administered to post-treat between about 15 minutes and about 150 minutes after the psilocybin mesylate Form A. In some embodiments, the serotonin receptor modulator is eplivanserin and the psychedelic is psilocybin mesylate Form A, wherein the eplivanserin is administered to post-treat at least 180 minutes after the psilocybin mesylate Form A. In some embodiments, the serotonin receptor modulator is eplivanserin and the psychedelic is psilocybin mesylate Form A, wherein the eplivanserin is administered to post-treat at least 210 minutes after the psilocybin mesylate Form A. In some embodiments, the serotonin receptor modulator is eplivanserin and the psychedelic is psilocybin mesylate Form A, wherein the eplivanserin is administered to post-treat at least 240 minutes after the psilocybin mesylate Form A.

In some embodiments, the serotonin receptor modulator is eplivanserin and the psychedelic is psilocybin mesylate Form A, wherein the eplivanserin is administered to post-treat at least 270 minutes after the psilocybin mesylate Form A. In some embodiments, the serotonin receptor modulator is eplivanserin and the psychedelic is psilocybin mesylate Form A, wherein the eplivanserin is administered to post-treat at least 300 minutes after the psilocybin mesylate Form A. In some embodiments, the serotonin receptor modulator is eplivanserin and the psychedelic is psilocybin mesylate Form A, wherein the eplivanserin is administered to post-treat at least 330 minutes after the psilocybin mesylate Form A. In some embodiments, the serotonin receptor modulator is eplivanserin and the psychedelic is psilocybin mesylate Form A, wherein the eplivanserin is administered to post-treat at least 360 minutes after the psilocybin mesylate Form A.

In some preferred embodiments, the serotonin receptor modulator is eplivanserin and the psychedelic is psilocybin mesylate Form A, wherein eplivanserin is administered to post-treat between about 60 minutes and about 180 minutes after the administration of the psilocybin mesylate Form A.

In some embodiments, the serotonin receptor modulator is volinanserin and the psychedelic is psilocybin mesylate Form A, wherein the volinanserin is administered to post-treat a subject between at least 15 minutes and 360 minutes after the administration or release of the psilocybin mesylate Form A. In some embodiments, the serotonin receptor modulator is volinanserin and the psychedelic is psilocybin mesylate Form A, wherein the volinanserin is administered to post-treat between at least 30 minutes and 360 minutes after the administration or release of the psilocybin mesylate Form A. In some embodiments, the serotonin receptor modulator is volinanserin and the psychedelic is psilocybin mesylate Form A, wherein the volinanserin is administered to post-treat between at least 60 minutes and 240 minutes after the administration or release of the psilocybin mesylate Form A. In some embodiments, the serotonin receptor modulator is volinanserin and the psychedelic is psilocybin mesylate Form A, wherein the volinanserin is administered to post-treat at least 90 minutes after psilocybin HCl. In some embodiments, the serotonin receptor modulator is volinanserin and the psychedelic is psilocybin mesylate Form A, wherein the volinanserin is administered to post-treat at least 120 minutes after the psilocybin mesylate Form A.

In some embodiments, the serotonin receptor modulator is volinanserin and the psychedelic is psilocybin mesylate Form A, wherein the volinanserin is administered to post-treat at least 150 minutes after the psilocybin mesylate Form A. In some embodiments, the serotonin receptor modulator is volinanserin and the psychedelic is psilocybin mesylate Form A, wherein the volinanserin is administered to post-treat between about 15 minutes and about 150 minutes after the psilocybin mesylate Form A. In some embodiments, the serotonin receptor modulator is volinanserin and the psychedelic is psilocybin mesylate Form A, wherein the volinanserin is administered to post-treat at least 180 minutes after the psilocybin mesylate Form A. In some embodiments, the serotonin receptor modulator is volinanserin and the psychedelic is psilocybin mesylate Form A, wherein the volinanserin is administered to post-treat at least 210 minutes after the psilocybin mesylate Form A. In some embodiments, the serotonin receptor modulator is volinanserin and the psychedelic is psilocybin mesylate Form A, wherein the volinanserin is administered to post-treat at least 240 minutes after the psilocybin mesylate Form A. In some embodiments, the serotonin receptor modulator is volinanserin and the psychedelic is psilocybin mesylate Form A, wherein the volinanserin is administered to post-treat at least 270 minutes after the psilocybin mesylate Form A. In some embodiments, the serotonin receptor modulator is volinanserin and the psychedelic is psilocybin mesylate Form A, wherein the volinanserin is administered to post-treat at least 300 minutes after the psilocybin mesylate Form A. In some embodiments, the serotonin receptor modulator is volinanserin and the psychedelic is psilocybin mesylate Form A, wherein the volinanserin is administered to post-treat at least 330 minutes after the psilocybin mesylate Form A. In some embodiments, the serotonin receptor modulator is volinanserin and the psychedelic is psilocybin mesylate Form A, wherein the volinanserin is administered to post-treat at least 360 minutes after the psilocybin mesylate Form A. In some preferred embodiments, the serotonin receptor modulator is volinanserin and the psychedelic is psilocybin mesylate Form A, wherein volinanserin is administered to post-treat between about 60 minutes and about 180 minutes after the administration of the ®-MDMA form.

In some embodiments, the serotonin receptor modulator is ketanserin and the psychedelic is psilocybin mesylate Form A, wherein the ketanserin is administered to post-treat at least 15 minutes after the administration of the psilocybin mesylate Form A. In some embodiments, the serotonin receptor modulator is ketanserin and the psychedelic is psilocybin mesylate Form A, wherein the ketanserin is administered to post-treat between at least 30 minutes and 360 minutes after the administration or release of the psilocybin mesylate Form A. In some embodiments, the serotonin receptor modulator is ketanserin and the psychedelic is psilocybin mesylate Form A, wherein the ketanserin is administered to post-treat between at least 60 minutes and 240 minutes after the administration or release of the psilocybin mesylate Form A. In some embodiments, the serotonin receptor modulator is ketanserin and the psychedelic is psilocybin mesylate Form A, wherein the ketanserin is administered to post-treat at least 90 minutes after the psilocybin mesylate Form A. In some embodiments, the serotonin receptor modulator is ketanserin and the psychedelic is psilocybin mesylate Form A, wherein the ketanserin is administered to post-treat at least 120 minutes after the psilocybin mesylate Form A. In some embodiments, the serotonin receptor modulator is ketanserin and the psychedelic is psilocybin mesylate Form A, wherein the ketanserin is administered to post-treat at least 150 minutes after the psilocybin mesylate Form A. In some embodiments, the serotonin receptor modulator is ketanserin and the psychedelic is psilocybin mesylate Form A, wherein the ketanserin is administered to post-treat between about 15 minutes and about 150 minutes after the psilocybin mesylate Form A. In some embodiments, the serotonin receptor modulator is ketanserin and the psychedelic is psilocybin mesylate Form A, wherein the ketanserin is administered to post-treat at least 180 minutes after the psilocybin mesylate Form A. In some embodiments, the serotonin receptor modulator is ketanserin and the psychedelic is psilocybin mesylate Form A, wherein the ketanserin is administered to post-treat at least 210 minutes after the psilocybin mesylate Form A. In some embodiments, the serotonin receptor modulator is ketanserin and the psychedelic is psilocybin mesylate Form A, wherein the ketanserin is administered to post-treat at least 240 minutes after the psilocybin mesylate Form A. In some embodiments, the serotonin receptor modulator is ketanserin and the psychedelic is psilocybin mesylate Form A, wherein the ketanserin is administered to post-treat at least 270 minutes after the psilocybin mesylate Form A. In some embodiments, the serotonin receptor modulator is ketanserin and the psychedelic is psilocybin mesylate Form A, wherein the ketanserin is administered to post-treat at least 300 minutes after the psilocybin mesylate Form A. In some embodiments, the serotonin receptor modulator is ketanserin and the psychedelic is psilocybin mesylate Form A, wherein the ketanserin is administered to post-treat at least 330 minutes after the psilocybin mesylate Form A. In some embodiments, the serotonin receptor modulator is ketanserin and the psychedelic is psilocybin mesylate Form A, wherein the ketanserin is administered to post-treat at least 360 minutes after the psilocybin mesylate Form A. In some preferred embodiments, the serotonin receptor modulator is ketanserin and the psychedelic is psilocybin mesylate Form A, wherein ketanserin is administered to post-treat between about 60 minutes and about 180 minutes after the administration of the psilocybin mesylate Form A.

In some embodiments, the serotonin receptor modulator is ritanserin and the psychedelic is psilocybin mesylate Form A, wherein the ritanserin is administered to post-treat at least 15 minutes after the administration of the psilocybin mesylate Form A. In some embodiments, the serotonin receptor modulator is ritanserin and the psychedelic is psilocybin mesylate Form A, wherein the ritanserin is administered to post-treat at least 30 minutes after the psilocybin mesylate Form A. In some embodiments, the serotonin receptor modulator is ritanserin and the psychedelic is psilocybin mesylate Form A, wherein the ritanserin is administered to post-treat between at least 60 minutes and 240 minutes after the administration or release of the psilocybin mesylate Form A. In some embodiments, the serotonin receptor modulator is ritanserin and the psychedelic is psilocybin mesylate Form A, wherein the ritanserin is administered to post-treat at least 90 minutes after the psilocybin mesylate Form A. In some embodiments, the serotonin receptor modulator is ritanserin and the psychedelic is psilocybin mesylate Form A, wherein the ritanserin is administered to post-treat at least 120 minutes after the psilocybin mesylate Form A. In some embodiments, the serotonin receptor modulator is ritanserin and the psychedelic is psilocybin mesylate Form A, wherein the ritanserin is administered to post-treat at least 150 minutes after the psilocybin mesylate Form A. In some embodiments, the serotonin receptor modulator is ritanserin and the psychedelic is psilocybin mesylate Form A, wherein the ritanserin is administered to post-treat between about 15 minutes and about 150 minutes after the psilocybin mesylate Form A. In some embodiments, the serotonin receptor modulator is ritanserin and the psychedelic is psilocybin mesylate Form A, wherein the ritanserin is administered to post-treat at least 180 minutes after the psilocybin mesylate Form A. In some embodiments, the serotonin receptor modulator is ritanserin and the psychedelic is psilocybin mesylate Form A, wherein the ritanserin is administered to post-treat at least 210 minutes after the psilocybin mesylate Form A. In some embodiments, the serotonin receptor modulator is ritanserin and the psychedelic is psilocybin mesylate Form A, wherein the ritanserin is administered to post-treat at least 240 minutes after the psilocybin mesylate Form A. In some embodiments, the serotonin receptor modulator is ritanserin and the psychedelic is psilocybin mesylate Form A, wherein the ritanserin is administered to post-treat at least 270 minutes after the psilocybin mesylate Form A. In some embodiments, the serotonin receptor modulator is ritanserin and the psychedelic is psilocybin mesylate Form A, wherein the ritanserin is administered to post-treat at least 300 minutes after the psilocybin mesylate Form A. In some embodiments, the serotonin receptor modulator is ritanserin and the psychedelic is psilocybin mesylate Form A, wherein the ritanserin is administered to post-treat at least 330 minutes after the psilocybin mesylate Form A. In some embodiments, the serotonin receptor modulator is ritanserin and the psychedelic is psilocybin mesylate Form A, wherein the ritanserin is administered to post-treat at least 360 minutes after the psilocybin mesylate Form A. In some preferred embodiments, the serotonin receptor modulator is ritanserin and the psychedelic is psilocybin mesylate Form A, wherein ritanserin is administered to post-treat between about 60 minutes and about 180 minutes after the administration of the psilocybin mesylate Form A.

In some embodiments, the serotonin receptor modulator is pimavanserin and the psychedelic is psilocybin mesylate Form A, wherein the pimavanserin is administered to post-treat at least 15 minutes after the administration of the psilocybin mesylate Form A. In some embodiments, the serotonin receptor modulator is pimavanserin and the psychedelic is psilocybin mesylate Form A, wherein the pimavanserin is administered to post-treat at least 30 minutes after the psilocybin mesylate Form A. In some embodiments, the serotonin receptor modulator is pimavanserin and the psychedelic is psilocybin mesylate Form A, wherein the pimavanserin is administered to post-treat between at least 60 minutes and 240 minutes after the administration or release of the psilocybin mesylate Form A. In some embodiments, the serotonin receptor modulator is pimavanserin and the psychedelic is psilocybin mesylate Form A, wherein the pimavanserin is administered to post-treat at least 90 minutes after the psilocybin mesylate Form A. In some embodiments, the serotonin receptor modulator is pimavanserin and the psychedelic is psilocybin mesylate Form A, wherein the pimavanserin is administered to post-treat at least 120 minutes after the psilocybin mesylate Form A. In some embodiments, the serotonin receptor modulator is pimavanserin and the psychedelic is psilocybin mesylate Form A, wherein the pimavanserin is administered to post-treat at least 150 minutes after the psilocybin mesylate Form A. In some embodiments, the serotonin receptor modulator is pimavanserin and the psychedelic is psilocybin mesylate Form A, wherein the pimavanserin is administered to post-treat between about 15 minutes and about 150 minutes after the psilocybin mesylate Form A. In some embodiments, the serotonin receptor modulator is pimavanserin and the psychedelic is psilocybin mesylate Form A, wherein the pimavanserin is administered to post-treat at least 180 minutes after the psilocybin mesylate Form A. In some embodiments, the serotonin receptor modulator is pimavanserin and the psychedelic is psilocybin mesylate Form A, wherein the pimavanserin is administered to post-treat at least 210 minutes after the psilocybin mesylate Form A. In some embodiments, the serotonin receptor modulator is pimavanserin and the psychedelic is psilocybin mesylate Form A, wherein the pimavanserin is administered to post-treat at least 240 minutes after the psilocybin mesylate Form A. In some embodiments, the serotonin receptor modulator is pimavanserin and the psychedelic is psilocybin mesylate Form A, wherein the pimavanserin is administered to post-treat at least 270 minutes after the psilocybin mesylate Form A. In some embodiments, the serotonin receptor modulator is pimavanserin and the psychedelic is psilocybin mesylate Form A, wherein the pimavanserin is administered to post-treat at least 300 minutes after the psilocybin mesylate Form A. In some embodiments, the serotonin receptor modulator is pimavanserin and the psychedelic is psilocybin mesylate Form A, wherein the pimavanserin is administered to post-treat at least 330 minutes after the psilocybin mesylate Form A. In some embodiments, the serotonin receptor modulator is pimavanserin and the psychedelic is psilocybin mesylate Form A, wherein the pimavanserin is administered to post-treat at least 360 minutes after the psilocybin mesylate Form A. In some preferred embodiments, the serotonin receptor modulator is pimavanserin and the psychedelic is psilocybin mesylate Form A, wherein pimavanserin is administered to post-treat between about 60 minutes and about 180 minutes after the administration of the psilocybin mesylate Form A.

In some embodiments, the serotonin receptor modulator is nelotanserin and the psychedelic is psilocybin mesylate Form A, wherein the nelotanserin is administered to post-treat at least 15 minutes after the administration of the psilocybin mesylate Form A. In some embodiments, the serotonin receptor modulator is nelotanserin and the psychedelic is psilocybin mesylate Form A, wherein the nelotanserin is administered to post-treat at least 30 minutes after the psilocybin mesylate Form A. In some embodiments, the serotonin receptor modulator is nelotanserin and the psychedelic is psilocybin mesylate Form A, wherein the nelotanserin is administered to post-treat between at least 60 minutes and 240 minutes after the administration or release of the psilocybin mesylate Form A. In some embodiments, the serotonin receptor modulator is nelotanserin and the psychedelic is psilocybin mesylate Form A, wherein the nelotanserin is administered to post-treat at least 90 minutes after the psilocybin mesylate Form A. In some embodiments, the serotonin receptor modulator is nelotanserin and the psychedelic is psilocybin mesylate Form A, wherein the nelotanserin is administered to post-treat at least 120 minutes after the psilocybin mesylate Form A.

In some embodiments, the serotonin receptor modulator is nelotanserin and the psychedelic is psilocybin mesylate Form A, wherein the nelotanserin is administered to post-treat at least 150 minutes after the psilocybin mesylate Form A. In some embodiments, the serotonin receptor modulator is nelotanserin and the psychedelic is psilocybin mesylate Form A, wherein the nelotanserin is administered to post-treat between about 15 minutes and about 150 minutes after the psilocybin mesylate Form A. In some embodiments, the serotonin receptor modulator is nelotanserin and the psychedelic is psilocybin mesylate Form A, wherein the nelotanserin is administered to post-treat at least 180 minutes after the psilocybin mesylate Form A. In some embodiments, the serotonin receptor modulator is nelotanserin and the psychedelic is psilocybin mesylate Form A, wherein the nelotanserin is administered to post-treat at least 210 minutes after the psilocybin mesylate Form A. In some embodiments, the serotonin receptor modulator is nelotanserin and the psychedelic is psilocybin mesylate Form A, wherein the nelotanserin is administered to post-treat at least 240 minutes after the psilocybin mesylate Form A. In some embodiments, the serotonin receptor modulator is nelotanserin and the psychedelic is psilocybin mesylate Form A, wherein the nelotanserin is administered to post-treat at least 270 minutes after the psilocybin mesylate Form A.

In some embodiments, the serotonin receptor modulator is nelotanserin and the psychedelic is psilocybin mesylate Form A, wherein the nelotanserin is administered to post-treat at least 300 minutes after the psilocybin mesylate Form A. In some embodiments, the serotonin receptor modulator is nelotanserin and the psychedelic is psilocybin mesylate Form A, wherein the nelotanserin is administered to post-treat at least 330 minutes after the psilocybin mesylate Form A. In some embodiments, the serotonin receptor modulator is nelotanserin and the psychedelic is psilocybin mesylate Form A, wherein the nelotanserin is administered to post-treat at least 360 minutes after the psilocybin mesylate Form A. In some preferred embodiments, the serotonin receptor modulator is nelotanserin and the psychedelic is psilocybin mesylate Form A, wherein nelotanserin is administered to post-treat between about 60 minutes and about 180 minutes after the administration of the psilocybin mesylate Form A.

In some embodiments, the serotonin receptor modulator is pruvanserin and the psychedelic is psilocybin mesylate Form A, wherein the pruvanserin is administered to post-treat at least 15 minutes after the administration of the psilocybin mesylate Form A. In some embodiments, the serotonin receptor modulator is pruvanserin and the psychedelic is psilocybin mesylate Form A, wherein the pruvanserin is administered to post-treat at least 30 minutes after the psilocybin mesylate Form A. In some embodiments, the serotonin receptor modulator is pruvanserin and the psychedelic is psilocybin mesylate Form A, wherein the pruvanserin is administered to post-treat between at least 60 minutes and 240 minutes after the administration or release of the psilocybin mesylate Form A. In some embodiments, the serotonin receptor modulator is pruvanserin and the psychedelic is psilocybin mesylate Form A, wherein the pruvanserin is administered to post-treat at least 90 minutes after the psilocybin mesylate Form A. In some embodiments, the serotonin receptor modulator is pruvanserin and the psychedelic is psilocybin mesylate Form A, wherein the pruvanserin is administered to post-treat at least 120 minutes after the psilocybin mesylate Form A. In some embodiments, the serotonin receptor modulator is pruvanserin and the psychedelic is psilocybin mesylate Form A, wherein the pruvanserin is administered to post-treat at least 150 minutes after the psilocybin mesylate Form A. In some embodiments, the serotonin receptor modulator is pruvanserin and the psychedelic is psilocybin mesylate Form A, wherein the pruvanserin is administered to post-treat between about 15 minutes and about 150 minutes after the psilocybin mesylate Form A. In some embodiments, the serotonin receptor modulator is pruvanserin and the psychedelic is psilocybin mesylate Form A, wherein the pruvanserin is administered to post-treat at least 180 minutes after the psilocybin mesylate Form A. In some embodiments, the serotonin receptor modulator is pruvanserin and the psychedelic is psilocybin mesylate Form A, wherein the pruvanserin is administered to post-treat at least 210 minutes after the psilocybin mesylate Form A.

In some embodiments, the serotonin receptor modulator is pruvanserin and the psychedelic is psilocybin mesylate Form A, wherein the pruvanserin is administered to post-treat at least 240 minutes after the psilocybin mesylate Form A. In some embodiments, the serotonin receptor modulator is pruvanserin and the psychedelic is psilocybin mesylate Form A, wherein the pruvanserin is administered to post-treat at least 270 minutes after the psilocybin mesylate Form A. In some embodiments, the serotonin receptor modulator is pruvanserin and the psychedelic is psilocybin mesylate Form A, wherein the pruvanserin is administered to post-treat at least 300 minutes after the psilocybin mesylate Form A. In some embodiments, the serotonin receptor modulator is pruvanserin and the psychedelic is psilocybin mesylate Form A, wherein the pruvanserin is administered to post-treat at least 330 minutes after the psilocybin mesylate Form A. In some embodiments, the serotonin receptor modulator is pruvanserin and the psychedelic is psilocybin mesylate Form A, wherein the pruvanserin is administered to post-treat at least 360 minutes after the psilocybin mesylate Form A. In some preferred embodiments, the serotonin receptor modulator is pruvanserin and the psychedelic is psilocybin mesylate Form A, wherein pruvanserin is administered to post-treat between about 60 minutes and about 180 minutes after the administration of the psilocybin mesylate Form A.

In some embodiments, the serotonin receptor modulator is flibanserin, wherein the flibanserin is administered to post-treat at least 15 minutes post to the administration of the psilocybin mesylate Form A. In some embodiments, the serotonin receptor modulator is flibanserin, wherein the flibanserin is administered to post-treat at least 30 minutes post to the psilocybin mesylate Form A. In some embodiments, the serotonin receptor modulator is flibanserin, wherein the flibanserin is administered to post-treat between at least 60 minutes and 240 minutes post to the administration or release of the psilocybin mesylate Form A. In some embodiments, the serotonin receptor modulator is flibanserin, wherein the flibanserin is administered to post-treat at least 90 minutes post to the psilocybin mesylate Form A. In some embodiments, the serotonin receptor modulator is flibanserin, wherein the flibanserin is administered to post-treat at least 120 minutes post to the psilocybin mesylate Form A. In some embodiments, the serotonin receptor modulator is flibanserin, wherein the flibanserin is administered to post-treat at least 150 minutes post to the psilocybin mesylate Form A. In some embodiments, the serotonin receptor modulator is flibanserin, wherein the flibanserin is administered to post-treat between about 15 minutes and about 150 minutes post to the psilocybin mesylate Form A. In some embodiments, the serotonin receptor modulator is flibanserin, wherein the flibanserin is administered to post-treat at least 180 minutes post to the psilocybin mesylate Form A. In some embodiments, the serotonin receptor modulator is flibanserin, wherein the flibanserin is administered to post-treat at least 210 minutes post to the psilocybin mesylate Form A.

In some embodiments, the serotonin receptor modulator is flibanserin, wherein the flibanserin is administered to post-treat at least 240 minutes post to the psilocybin mesylate Form A. In some embodiments, the serotonin receptor modulator is flibanserin, wherein the flibanserin is administered to post-treat at least 270 minutes post to the psilocybin mesylate Form A. In some embodiments, the serotonin receptor modulator is flibanserin, wherein the flibanserin is administered to post-treat at least 300 minutes post to the psilocybin mesylate Form A. In some embodiments, the serotonin receptor modulator is flibanserin, wherein the flibanserin is administered to post-treat at least 330 minutes post to the psilocybin mesylate Form A. In some embodiments, the serotonin receptor modulator is flibanserin, wherein the flibanserin is administered to post-treat at least 360 minutes post to the psilocybin mesylate Form A. In some preferred embodiments, the serotonin receptor modulator is flibanserin, wherein flibanserin is administered to post-treat between about 60 minutes and about 180 minutes post to the administration of the psilocybin mesylate Form A.

In some embodiments, the serotonin receptor modulator is olanzapine, wherein the olanzapine is administered to post-treat at least 15 minutes post to the administration of the psilocybin mesylate Form A. In some embodiments, the serotonin receptor modulator is olanzapine, wherein the olanzapine is administered to post-treat at least 30 minutes post to the psilocybin mesylate Form A. In some embodiments, the serotonin receptor modulator is olanzapine, wherein the olanzapine is administered to post-treat between at least 60 minutes and 240 minutes post to the administration or release of the psilocybin mesylate Form A. In some embodiments, the serotonin receptor modulator is olanzapine, wherein the olanzapine is administered to post-treat at least 90 minutes post to the psilocybin mesylate Form A. In some embodiments, the serotonin receptor modulator is olanzapine, wherein the olanzapine is administered to post-treat at least 120 minutes post to the psilocybin mesylate Form A. In some embodiments, the serotonin receptor modulator is olanzapine, wherein the olanzapine is administered to post-treat at least 150 minutes post to the psilocybin mesylate Form A. In some embodiments, the serotonin receptor modulator is olanzapine, wherein the olanzapine is administered to post-treat between about 15 minutes and about 150 minutes post to the psilocybin mesylate Form A. In some embodiments, the serotonin receptor modulator is olanzapine, wherein the olanzapine is administered to post-treat at least 180 minutes post to the psilocybin mesylate Form A. In some embodiments, the serotonin receptor modulator is olanzapine, wherein the olanzapine is administered to post-treat at least 210 minutes post to the psilocybin mesylate Form A.

In some embodiments, the serotonin receptor modulator is olanzapine, wherein the olanzapine is administered to post-treat at least 240 minutes post to the psilocybin mesylate Form A. In some embodiments, the serotonin receptor modulator is olanzapine, wherein the olanzapine is administered to post-treat at least 270 minutes post to the psilocybin mesylate Form A. In some embodiments, the serotonin receptor modulator is olanzapine, wherein the olanzapine is administered to post-treat at least 300 minutes post to the psilocybin mesylate Form A. In some embodiments, the serotonin receptor modulator is olanzapine, wherein the olanzapine is administered to post-treat at least 330 minutes post to the psilocybin mesylate Form A. In some embodiments, the serotonin receptor modulator is olanzapine, wherein the olanzapine is administered to post-treat at least 360 minutes post to the psilocybin mesylate Form A. In some preferred embodiments, the serotonin receptor modulator is olanzapine, wherein olanzapine is administered to post-treat between about 60 minutes and about 180 minutes post to the administration of the psilocybin mesylate Form A.

In some embodiments, the serotonin receptor modulator is quetiapine, wherein the quetiapine is administered to post-treat at least 15 minutes post to the administration of the psilocybin mesylate Form A. In some embodiments, the serotonin receptor modulator is quetiapine, wherein the quetiapine is administered to post-treat at least 30 minutes post to the psilocybin mesylate Form A. In some embodiments, the serotonin receptor modulator is quetiapine, wherein the quetiapine is administered to post-treat between at least 60 minutes and 240 minutes post to the administration or release of the psilocybin mesylate Form A. In some embodiments, the serotonin receptor modulator is quetiapine, wherein the quetiapine is administered to post-treat at least 90 minutes post to the psilocybin mesylate Form A. In some embodiments, the serotonin receptor modulator is quetiapine, wherein the quetiapine is administered to post-treat at least 120 minutes post to the psilocybin mesylate Form A. In some embodiments, the serotonin receptor modulator is quetiapine, wherein the quetiapine is administered to post-treat at least 150 minutes post to the psilocybin mesylate Form A. In some embodiments, the serotonin receptor modulator is quetiapine, wherein the quetiapine is administered to post-treat between about 15 minutes and about 150 minutes post to the psilocybin mesylate Form A. In some embodiments, the serotonin receptor modulator is quetiapine, wherein the quetiapine is administered to post-treat at least 180 minutes post to the psilocybin mesylate Form A. In some embodiments, the serotonin receptor modulator is quetiapine, wherein the quetiapine is administered to post-treat at least 210 minutes post to the psilocybin mesylate Form A.

In some embodiments, the serotonin receptor modulator is quetiapine, wherein the quetiapine is administered to post-treat at least 240 minutes post to the psilocybin mesylate Form A. In some embodiments, the serotonin receptor modulator is quetiapine, wherein the quetiapine is administered to post-treat at least 270 minutes post to the psilocybin mesylate Form A. In some embodiments, the serotonin receptor modulator is quetiapine, wherein the quetiapine is administered to post-treat at least 300 minutes post to the psilocybin mesylate Form A. In some embodiments, the serotonin receptor modulator is quetiapine, wherein the quetiapine is administered to post-treat at least 330 minutes post to the psilocybin mesylate Form A. In some embodiments, the serotonin receptor modulator is quetiapine, wherein the quetiapine is administered to post-treat at least 360 minutes post to the psilocybin mesylate Form A. In some preferred embodiments, the serotonin receptor modulator is quetiapine, wherein quetiapine is administered to post-treat between about 60 minutes and about 180 minutes post to the administration of the psilocybin mesylate Form A.

In some embodiments, the serotonin receptor modulator is risperidone, wherein the risperidone is administered to post-treat at least 15 minutes post to the administration of the psilocybin mesylate Form A. In some embodiments, the serotonin receptor modulator is risperidone, wherein the risperidone is administered to post-treat at least 30 minutes post to the psilocybin mesylate Form A. In some embodiments, the serotonin receptor modulator is risperidone, wherein the risperidone is administered to post-treat between at least 60 minutes and 240 minutes post to the administration or release of the psilocybin mesylate Form A. In some embodiments, the serotonin receptor modulator is risperidone, wherein the risperidone is administered to post-treat at least 90 minutes post to the psilocybin mesylate Form A. In some embodiments, the serotonin receptor modulator is risperidone, wherein the risperidone is administered to post-treat at least 120 minutes post to the psilocybin mesylate Form A. In some embodiments, the serotonin receptor modulator is risperidone, wherein the risperidone is administered to post-treat at least 150 minutes post to the psilocybin mesylate Form A. In some embodiments, the serotonin receptor modulator is risperidone, wherein the risperidone is administered to post-treat between about 15 minutes and about 150 minutes post to the psilocybin mesylate Form A. In some embodiments, the serotonin receptor modulator is risperidone, wherein the risperidone is administered to post-treat at least 180 minutes post to the psilocybin mesylate Form A. In some embodiments, the serotonin receptor modulator is risperidone, wherein the risperidone is administered to post-treat at least 210 minutes post to the psilocybin mesylate Form A.

In some embodiments, the serotonin receptor modulator is risperidone, wherein the risperidone is administered to post-treat at least 240 minutes post to the psilocybin mesylate Form A. In some embodiments, the serotonin receptor modulator is risperidone, wherein the risperidone is administered to post-treat at least 270 minutes post to the psilocybin mesylate Form A. In some embodiments, the serotonin receptor modulator is risperidone, wherein the risperidone is administered to post-treat at least 300 minutes post to the psilocybin mesylate Form A. In some embodiments, the serotonin receptor modulator is risperidone, wherein the risperidone is administered to post-treat at least 330 minutes post to the psilocybin mesylate Form A. In some embodiments, the serotonin receptor modulator is risperidone, wherein the risperidone is administered to post-treat at least 360 minutes post to the psilocybin mesylate Form A. In some preferred embodiments, the serotonin receptor modulator is risperidone, wherein risperidone is administered to post-treat between about 60 minutes and about 180 minutes post to the administration of the psilocybin mesylate Form A.

Combinations with O-Acetylpsilocin Salt and Solid Forms

In another embodiment of such combination therapy, a form of O-acetylpsilocin salt described herein is administered in combination with a serotonin receptor modulator.

In some embodiments, the serotonin receptor modulator for use with the O-acetylpsilocin form disclosed herein, including those described in Table 19, is eplivanserin, wherein the eplivanserin is administered in about 1 mg to about 40 mg, or about 5 mg to about 10 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is volinanserin, wherein the volinanserin is administered in about 1 mg to about 60 mg, or about 5 mg to about 20 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is ketanserin, wherein the ketanserin is administered in about 10 mg to about 80 mg, about 30 mg to about 50 mg, or about 40 mg and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is ritanserin, wherein the ritanserin is administered in about 1 mg to about 40 mg, or about 2.5 mg to about 10 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is pimavanserin, wherein the pimavanserin is administered in about 1 mg to about 60 mg, or about 17 mg to about 34 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is nelotanserin, wherein the nelotanserin is administered in about 1 mg to about 80 mg, or about 40 mg to about 80 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is pruvanserin, wherein the pruvanserin is administered in about 1 mg to about 40 mg, or about 3 mg to about 10 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is flibanserin, wherein the flibanserin is administered in about 10 mg to about 200 mg, or about 80 mg to about 120 mg, or about 100 mg and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is olanzapine, wherein the olanzapine is administered in about 2.5 mg to about 30 mg, or about 5 mg or about 10 mg, or about 20 mg or about 25 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is an extended-release of olanzapine such as ZYPREXA RELPREVV®, wherein the extended release olanzapine is administered in about 50 mg to about 450 mg, or about 150 mg or about 210 mg, or about 300 mg or about 405 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is quetiapine, wherein the quetiapine is administered in about 25 mg to about 800 mg, or about 50 mg to about 100 mg, or about 150 mg or about 200 mg or about 250 mg or about 300 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is an extended-release of quetiapine, wherein the extended-release of quetiapine is administered in about 50 mg to about 300 mg, or about 50 mg or about 100 mg or about 200 mg or about 300 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the O-acetylpsilocin form disclosed herein, including those described in Table 19, is an extended-release of risperidone including (RISPERDAL CONSTA®), wherein the extended-release of risperidone is administered in about 12.5 mg, or about 25 mg, or about 37.5 mg, or about 50 mg, and the O-acetylpsilocin form disclosed herein, including those described in Table 19, is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the psychedelic O-acetylpsilocin salt is eplivanserin and, wherein the eplivanserin is administered in about 1 mg to about 40 mg, or about 5 mg to about 10 mg, and the O-acetylpsilocin salt is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator is volinanserin and the psychedelic is O-acetylpsilocin salt, wherein the volinanserin is administered in about 1 mg to about 60 mg, or about 5 mg to about 20 mg, and the O-acetylpsilocin salt is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the psychedelic O-acetylpsilocin salt is ketanserin, wherein the ketanserin is administered in about 10 mg to about 80 mg, about 30 mg to about 50 mg, or about 40 mg and the O-acetylpsilocin salt is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the psychedelic O-acetylpsilocin salt is ritanserin, wherein the ritanserin is administered in about 1 mg to about 40 mg, or about 2.5 mg to about 10 mg, and the O-acetylpsilocin salt is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator is pimavanserin and the psychedelic is O-acetylpsilocin salt, wherein the pimavanserin is administered in about 1 mg to about 60 mg, or about 17 mg to about 34 mg, and the O-acetylpsilocin salt is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the psychedelic O-acetylpsilocin salt is nelotanserin, wherein the nelotanserin is administered in about 1 mg to about 80 mg, or about 40 mg to about 80 mg, and the O-acetylpsilocin salt is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the psychedelic O-acetylpsilocin salt is pruvanserin, wherein the pruvanserin is administered in about 1 mg to about 40 mg, or about 3 mg to about 10 mg, and the O-acetylpsilocin salt is administered between about 5 mg to about 50 mg, or about 10 mg to about 25 mg. In some embodiments, the amount of the O-acetylpsilocin form disclosed herein is provided on an O-acetylpsilocin basis.

In some embodiments, the serotonin receptor modulator for use with the psychedelic O-acetylpsilocin salt is flibanserin, wherein the flibanserin is administered in about 10 mg to about 200 mg, or about 80 mg to about 120 mg, or about 100 mg and the O-acetylpsilocin salt is administered between about 5 mg to about 50 mg, or about 10 mg to about 25 mg. In some embodiments, the amount of the O-acetylpsilocin form disclosed herein is provided on an O-acetylpsilocin basis.

In some embodiments, the O-acetylpsilocin form disclosed herein is O-acetylpsilocin maleate Form A.

In some embodiments, the serotonin receptor modulator for use with the O-acetylpsilocin maleate Form A is eplivanserin, wherein the eplivanserin is administered in about 1 mg to about 40 mg, or about 5 mg to about 10 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is volinanserin, wherein the volinanserin is administered in about 1 mg to about 60 mg, or about 5 mg to about 20 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is ketanserin, wherein the ketanserin is administered in about 10 mg to about 80 mg, about 30 mg to about 50 mg, or about 40 mg and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is ritanserin, wherein the ritanserin is administered in about 1 mg to about 40 mg, or about 2.5 mg to about 10 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is pimavanserin, wherein the pimavanserin is administered in about 1 mg to about 60 mg, or about 17 mg to about 34 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is nelotanserin, wherein the nelotanserin is administered in about 1 mg to about 80 mg, or about 40 mg to about 80 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is pruvanserin, wherein the pruvanserin is administered in about 1 mg to about 40 mg, or about 3 mg to about 10 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is flibanserin, wherein the flibanserin is administered in about 10 mg to about 200 mg, or about 80 mg to about 120 mg, or about 100 mg and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is olanzapine, wherein the olanzapine is administered in about 2.5 mg to about 30 mg, or about 5 mg or about 10 mg, or about 20 mg or about 25 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is an extended-release of olanzapine such as ZYPREXA RELPREVV®, wherein the extended release olanzapine is administered in about 50 mg to about 450 mg, or about 150 mg or about 210 mg, or about 300 mg or about 405 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is quetiapine, wherein the quetiapine is administered in about 25 mg to about 800 mg, or about 50 mg to about 100 mg, or about 150 mg or about 200 mg or about 250 mg or about 300 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is an extended-release of quetiapine, wherein the extended-release of quetiapine is administered in about 50 mg to about 300 mg, or about 50 mg or about 100 mg or about 200 mg, or about 300 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the O-acetylpsilocin maleate Form A is administered between about 5 mg to about 50 mg, or about 10 mg to about 25 mg.

In some embodiments, the serotonin receptor modulator for use with the O-acetylpsilocin maleate Form A is an extended-release of risperidone including (RISPERDAL CONSTA®), wherein the extended-release of risperidone is administered in about 12.5 mg, or about 25 mg, or about 37.5 mg, or about 50 mg, and the O-acetylpsilocin maleate Form A is administered between about 5 mg to about 50 mg, or about 10 mg to about 25 mg.

In certain embodiments, such as those described above a O-acetylpsilocin form disclosed herein, including those described in Table 19, is co-administered with a serotonin receptor modulator in the same or in separate compositions. In one embodiment, the serotonin receptor modulator is administered prior to the O-acetylpsilocin form disclosed herein, including those described in Table 19. In one embodiment, the O-acetylpsilocin form disclosed herein, including those described in Table 19, is administered in a modified release formulation such that the subject is effectively pretreated with serotonin receptor modulator prior to release of an effective amount of O-acetylpsilocin. In some embodiments the serotonin receptor modulator is part of a single fixed dose formulation that releases serotonin receptor modulator first followed by O-acetylpsilocin on two different release profiles. In another embodiment the serotonin receptor modulator is administered first as a single dosage and after a length of time, the O-acetylpsilocin form disclosed herein, including those described in Table 19, is administered as a second dosage separate from the first dosage. Thus, in some embodiments, the serotonin receptor modulator is administered or released from a composition provided herein prior to the administration and/or release of the psychedelic. This allows pretreatment to attenuate activation of the serotonin receptor by the psychedelic. In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the psychedelic. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the psychedelic.

In a preferred embodiment, the serotonin receptor modulator is administered at about 1 hour to about 3 hours prior to the administration of the psychedelic.

In some embodiments, the serotonin receptor modulator is eplivanserin and the psychedelic is O-acetylpsilocin, wherein the eplivanserin is administered to pretreat at least 15 minutes prior to the administration of the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat between at least 30 minutes prior and 360 minutes prior to the release or administration of the O-acetylpsilocin form disclosed herein, including those described in Table 19 form. In some embodiments, the serotonin receptor modulator is eplivanserin and the psychedelic is O-acetylpsilocin, wherein the eplivanserin is administered to pretreat between at least 60 minutes prior and 360 minutes prior to the release or administration the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat between at least 90 minutes and 240 minutes prior to the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat at least 120 minutes prior to the O-acetylpsilocin form disclosed herein, including those described in Table 19.

In some embodiments, the serotonin receptor modulator is eplivanserin and the psychedelic is O-acetylpsilocin, wherein the eplivanserin is administered to pretreat at least 150 minutes prior to the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat between about 15 minutes and about 150 minutes prior to the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat at least 180 minutes prior to the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat at least 210 minutes prior to the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat at least 240 minutes prior to the O-acetylpsilocin form disclosed herein, including those described in Table 19.

In some embodiments, the serotonin receptor modulator is eplivanserin and the psychedelic is O-acetylpsilocin, wherein the eplivanserin is administered to pretreat at least 270 minutes prior to the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat at least 300 minutes prior to the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat at least 330 minutes prior to the O-acetylpsilocin form disclosed herein, including those described in Table 19. In some embodiments, the serotonin receptor modulator is eplivanserin and the psychedelic is O-acetylpsilocin, wherein the eplivanserin is administered to pretreat at least 360 minutes prior to the O-acetylpsilocin form disclosed herein, including those described in Table 19.

In some preferred embodiments, the serotonin receptor modulator is eplivanserin and the psychedelic is O-acetylpsilocin, wherein eplivanserin is administered to pretreat between about 60 minutes and about 180 minutes prior to the administration of the O-acetylpsilocin form disclosed herein, including those described in Table 19.

In some embodiments, the serotonin receptor modulator is volinanserin and the psychedelic is O-acetylpsilocin, wherein the volinanserin is administered to pretreat a subject between at least 15 minutes and 360 minutes prior to the administration or release of the O-acetylpsilocin form disclosed herein, including those described in Table 19. In some embodiments, the serotonin receptor modulator is volinanserin and the psychedelic is O-acetylpsilocin, wherein the volinanserin is administered to pretreat between at least 30 minutes and 360 minutes prior to the administration or release of the O-acetylpsilocin form disclosed herein, including those described in Table 19. In some embodiments, the serotonin receptor modulator is volinanserin and the psychedelic is O-acetylpsilocin, wherein the volinanserin is administered to pretreat between at least 60 minutes and 240 minutes prior to the administration or release of the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 90 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 120 minutes prior to the O-acetylpsilocin form disclosed herein, including those described in Table 19.

In some embodiments, the serotonin receptor modulator is volinanserin and the psychedelic is O-acetylpsilocin, wherein the volinanserin is administered to pretreat at least 150 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat between about 15 minutes and about 150 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 180 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 210 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 240 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 270 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 300 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 330 minutes prior to the O-acetylpsilocin form disclosed herein, including those described in Table 19. In some embodiments, the serotonin receptor modulator is volinanserin and the psychedelic is O-acetylpsilocin, wherein the volinanserin is administered to pretreat at least 360 minutes prior to the O-acetylpsilocin form disclosed herein, including those described in Table 19. In some preferred embodiments, the serotonin receptor modulator is volinanserin and the psychedelic is O-acetylpsilocin, wherein volinanserin is administered to pretreat between about 60 minutes and about 180 minutes prior to the administration of O-acetylpsilocin.

In some embodiments, the serotonin receptor modulator is ketanserin and the psychedelic is O-acetylpsilocin, wherein the ketanserin is administered to pretreat at least 15 minutes prior to the administration of the O-acetylpsilocin form disclosed herein, including those described in Table 19. In some embodiments, the serotonin receptor modulator is ketanserin and the psychedelic is O-acetylpsilocin, wherein the ketanserin is administered to pretreat between at least 30 minutes and 360 minutes prior to the administration or release of the O-acetylpsilocin form disclosed herein, including those described in Table 19. In some embodiments, the serotonin receptor modulator is ketanserin and the psychedelic is O-acetylpsilocin, wherein the ketanserin is administered to pretreat between at least 60 minutes and 240 minutes prior to the administration or release of O-acetylpsilocin. In some embodiments, the serotonin receptor modulator is ketanserin and the psychedelic is O-acetylpsilocin, wherein the ketanserin is administered to pretreat at least 90 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 120 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 150 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat between about 15 minutes and about 150 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 180 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 210 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 240 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 270 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 300 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 330 minutes prior to the O-acetylpsilocin form disclosed herein, including those described in Table 19. In some embodiments, the serotonin receptor modulator is ketanserin and the psychedelic is O-acetylpsilocin, wherein the ketanserin is administered to pretreat at least 360 minutes prior to the O-acetylpsilocin form disclosed herein, including those described in Table 19.

In some preferred embodiments, the serotonin receptor modulator is ketanserin and the psychedelic is O-acetylpsilocin, wherein ketanserin is administered to pretreat between about 60 minutes and about 180 minutes prior to administration of O-acetylpsilocin form disclosed herein, including those described in Table 19.

In some embodiments, the serotonin receptor modulator is ritanserin and the psychedelic is O-acetylpsilocin, wherein the ritanserin is administered to pretreat at least 15 minutes prior to the administration of the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 30 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat between at least 60 minutes and 240 minutes prior to the administration or release of the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 90 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 120 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 150 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat between about 15 minutes and about 150 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 180 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 210 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 240 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 270 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 300 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 330 minutes prior to the O-acetylpsilocin form disclosed herein, including those described in Table 19. In some embodiments, the serotonin receptor modulator is ritanserin and the psychedelic is O-acetylpsilocin, wherein the ritanserin is administered to pretreat at least 360 minutes prior to the O-acetylpsilocin form disclosed herein, including those described in Table 19. In some preferred embodiments, the serotonin receptor modulator is ritanserin and the psychedelic is O-acetylpsilocin, wherein ritanserin is administered to pretreat between about 60 minutes and about 180 minutes prior to administration of O-acetylpsilocin form disclosed herein, including those described in Table 19.

In some embodiments, the serotonin receptor modulator is pimavanserin and the psychedelic is O-acetylpsilocin, wherein the pimavanserin is administered to pretreat at least 15 minutes prior to the administration of the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 30 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat between at least 60 minutes and 240 minutes prior to the administration or release of the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 90 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 120 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 150 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat between about 15 minutes and about 150 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 180 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 210 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 240 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 270 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 300 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 330 minutes prior to the O-acetylpsilocin form disclosed herein, including those described in Table 19. In some embodiments, the serotonin receptor modulator is pimavanserin and the psychedelic is O-acetylpsilocin, wherein the pimavanserin is administered to pretreat at least 360 minutes prior to the O-acetylpsilocin form disclosed herein, including those described in Table 19. In some preferred embodiments, the serotonin receptor modulator is pimavanserin and the psychedelic is O-acetylpsilocin, wherein pimavanserin is administered to pretreat between about 60 minutes and about 180 minutes prior to the administration of the O-acetylpsilocin form disclosed herein, including those described in Table 19.

In some embodiments, the serotonin receptor modulator is nelotanserin and the psychedelic is O-acetylpsilocin, wherein the nelotanserin is administered to pretreat at least 15 minutes prior to the administration of the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 30 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat between at least 60 minutes and 240 minutes prior to the administration or release of the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 90 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 120 minutes prior to the O-acetylpsilocin form disclosed herein, including those described in Table 19.

In some embodiments, the serotonin receptor modulator is nelotanserin and the psychedelic is O-acetylpsilocin, wherein the nelotanserin is administered to pretreat at least 150 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat between about 15 minutes and about 150 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 180 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 210 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 240 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 270 minutes prior to the O-acetylpsilocin form disclosed herein, including those described in Table 19.

In some embodiments, the serotonin receptor modulator is nelotanserin and the psychedelic is O-acetylpsilocin, wherein the nelotanserin is administered to pretreat at least 300 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 330 minutes prior to the O-acetylpsilocin form disclosed herein, including those described in Table 19. In some embodiments, the serotonin receptor modulator is nelotanserin and the psychedelic is O-acetylpsilocin, wherein the nelotanserin is administered to pretreat at least 360 minutes prior to the O-acetylpsilocin form disclosed herein, including those described in Table 19. In some preferred embodiments, the serotonin receptor modulator is nelotanserin and the psychedelic is O-acetylpsilocin, wherein nelotanserin is administered to pretreat between about 60 minutes and about 180 minutes prior to the administration of the O-acetylpsilocin form disclosed herein, including those described in Table 19.

In some embodiments, the serotonin receptor modulator is pruvanserin and the psychedelic is O-acetylpsilocin, wherein the pruvanserin is administered to pretreat at least 15 minutes prior to the administration of the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 30 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat between at least 60 minutes and 240 minutes prior to the administration or release of the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 90 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 120 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 150 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat between about 15 minutes and about 150 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 180 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 210 minutes prior to the O-acetylpsilocin form disclosed herein, including those described in Table 19.

In some embodiments, the serotonin receptor modulator is pruvanserin and the psychedelic is O-acetylpsilocin, wherein the pruvanserin is administered to pretreat at least 240 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 270 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 300 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 330 minutes prior to the O-acetylpsilocin form disclosed herein, including those described in Table 19. In some embodiments, the serotonin receptor modulator is pruvanserin and the psychedelic is O-acetylpsilocin, wherein the pruvanserin is administered to pretreat at least 360 minutes prior to the O-acetylpsilocin form disclosed herein, including those described in Table 19. In some preferred embodiments, the serotonin receptor modulator is pruvanserin and the psychedelic is O-acetylpsilocin, wherein pruvanserin is administered to pretreat between about 60 minutes and about 180 minutes prior to the administration of O-acetylpsilocin.

In some embodiments, the serotonin receptor modulator is flibanserin and the psychedelic is O-acetylpsilocin, wherein the flibanserin is administered to pretreat at least 15 minutes prior to the administration of the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 30 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat between at least 60 minutes and 240 minutes prior to the administration or release of the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 90 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 120 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 150 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat between about 15 minutes and about 150 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 180 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 210 minutes prior to the O-acetylpsilocin form disclosed herein, including those described in Table 19.

In some embodiments, the serotonin receptor modulator is flibanserin and the psychedelic is O-acetylpsilocin, wherein the flibanserin is administered to pretreat at least 240 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 270 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 300 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 330 minutes prior to the O-acetylpsilocin form disclosed herein, including those described in Table 19. In some embodiments, the serotonin receptor modulator is flibanserin and the psychedelic is O-acetylpsilocin, wherein the flibanserin is administered to pretreat at least 360 minutes prior to the O-acetylpsilocin form disclosed herein, including those described in Table 19. In some preferred embodiments, the serotonin receptor modulator is flibanserin and the psychedelic is O-acetylpsilocin, wherein flibanserin is administered to pretreat between about 60 minutes and about 180 minutes prior to the administration of the O-acetylpsilocin form disclosed herein, including those described in Table 19.

In some embodiments, the serotonin receptor modulator is olanzapine and the psychedelic is O-acetylpsilocin, wherein the olanzapine is administered to pretreat at least 15 minutes prior to the administration of the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 30 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat between at least 60 minutes and 240 minutes prior to the administration or release of the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 90 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 120 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 150 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat between about 15 minutes and about 150 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 180 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 210 minutes prior to the O-acetylpsilocin form disclosed herein, including those described in Table 19.

In some embodiments, the serotonin receptor modulator is olanzapine and the psychedelic is O-acetylpsilocin, wherein the olanzapine is administered to pretreat at least 240 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 270 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 300 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 330 minutes prior to the O-acetylpsilocin form disclosed herein, including those described in Table 19. In some embodiments, the serotonin receptor modulator is olanzapine and the psychedelic is O-acetylpsilocin, wherein the olanzapine is administered to pretreat at least 360 minutes prior to the O-acetylpsilocin form disclosed herein, including those described in Table 19. In some preferred embodiments, the serotonin receptor modulator is olanzapine and the psychedelic is O-acetylpsilocin, wherein olanzapine is administered to pretreat between about 60 minutes and about 180 minutes prior to the administration of the O-acetylpsilocin form disclosed herein, including those described in Table 19.

In some embodiments, the serotonin receptor modulator is quetiapine and the psychedelic is O-acetylpsilocin, wherein the quetiapine is administered to pretreat at least 15 minutes prior to the administration of the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 30 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat between at least 60 minutes and 240 minutes prior to the administration or release of the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 90 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 120 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 150 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat between about 15 minutes and about 150 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 180 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 210 minutes prior to the O-acetylpsilocin form disclosed herein, including those described in Table 19.

In some embodiments, the serotonin receptor modulator is quetiapine and the psychedelic is O-acetylpsilocin, wherein the quetiapine is administered to pretreat at least 240 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 270 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 300 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 330 minutes prior to the O-acetylpsilocin form disclosed herein, including those described in Table 19. In some embodiments, the serotonin receptor modulator is quetiapine and the psychedelic is O-acetylpsilocin, wherein the quetiapine is administered to pretreat at least 360 minutes prior to the O-acetylpsilocin form disclosed herein, including those described in Table 19. In some preferred embodiments, the serotonin receptor modulator is quetiapine and the psychedelic is O-acetylpsilocin, wherein quetiapine is administered to pretreat between about 60 minutes and about 180 minutes prior to the administration of the O-acetylpsilocin form disclosed herein, including those described in Table 19.

In some embodiments, the serotonin receptor modulator is risperidone and the psychedelic is O-acetylpsilocin, wherein the risperidone is administered to pretreat at least 15 minutes prior to the administration of the O-acetylpsilocin form disclosed herein, including those described in Table 19. In some embodiments, the serotonin receptor modulator is risperidone and the psychedelic is O-acetylpsilocin, wherein the risperidone is administered to pretreat at least 30 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat between at least 60 minutes and 240 minutes prior to the administration or release of the O-acetylpsilocin form disclosed herein, including those described in Table 19. In some embodiments, the serotonin receptor modulator is risperidone and the psychedelic is O-acetylpsilocin, wherein the risperidone is administered to pretreat at least 90 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat at least 120 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat at least 150 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat between about 15 minutes and about 150 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat at least 180 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat at least 210 minutes prior to the O-acetylpsilocin form disclosed herein, including those described in Table 19.

In some embodiments, the serotonin receptor modulator is risperidone and the psychedelic is O-acetylpsilocin, wherein the risperidone is administered to pretreat at least 240 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat at least 270 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat at least 300 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat at least 330 minutes prior to the O-acetylpsilocin form disclosed herein, including those described in Table 19. In some embodiments, the serotonin receptor modulator is risperidone and the psychedelic is O-acetylpsilocin, wherein the risperidone is administered to pretreat at least 360 minutes prior to the O-acetylpsilocin form disclosed herein, including those described in Table 19. In some preferred embodiments, the serotonin receptor modulator is risperidone and the psychedelic is O-acetylpsilocin, wherein risperidone is administered to pretreat between about 60 minutes and about 180 minutes prior to administration of the O-acetylpsilocin form disclosed herein, including those described in Table 19.

In some embodiments, the serotonin receptor modulator is eplivanserin and the psychedelic is O-acetylpsilocin salt, wherein the eplivanserin is administered to pretreat at least 15 minutes prior to the administration of O-acetylpsilocin salt. In some embodiments, the serotonin receptor modulator is eplivanserin and the psychedelic is O-acetylpsilocin salt, wherein the eplivanserin is administered to pretreat between at least 30 minutes prior and 360 minutes prior to the release or administration of the O-acetylpsilocin salt. In some embodiments, the serotonin receptor modulator is eplivanserin and the psychedelic is O-acetylpsilocin salt, wherein the eplivanserin is administered to pretreat between at least 60 minutes prior and 360 minutes prior to the release or administration the O-acetylpsilocin salt. In some embodiments, the serotonin receptor modulator is eplivanserin and the psychedelic is O-acetylpsilocin salt, wherein the eplivanserin is administered to pretreat at between least 90 minutes and 240 minutes prior to the O-acetylpsilocin salt. In some embodiments, the serotonin receptor modulator is eplivanserin and the psychedelic is O-acetylpsilocin salt, wherein the eplivanserin is administered to pretreat at least 120 minutes prior to the O-acetylpsilocin salt.

In some embodiments, the serotonin receptor modulator is eplivanserin and the psychedelic is O-acetylpsilocin salt, wherein the eplivanserin is administered to pretreat at least 150 minutes prior to the O-acetylpsilocin salt. In some embodiments, the serotonin receptor modulator is eplivanserin and the psychedelic is O-acetylpsilocin salt, wherein the eplivanserin is administered to pretreat at least 180 minutes prior to the O-acetylpsilocin salt. In some embodiments, the serotonin receptor modulator is eplivanserin and the psychedelic is O-acetylpsilocin salt, wherein the eplivanserin is administered to pretreat at least 210 minutes prior to the O-acetylpsilocin salt. In some embodiments, the serotonin receptor modulator is eplivanserin and the psychedelic is O-acetylpsilocin salt, wherein the eplivanserin is administered to pretreat at least 240 minutes prior to the O-acetylpsilocin salt.

In some embodiments, the serotonin receptor modulator is eplivanserin and the psychedelic is O-acetylpsilocin salt, wherein the eplivanserin is administered to pretreat at least 270 minutes prior to O-acetylpsilocin salt. In some embodiments, the serotonin receptor modulator is eplivanserin and the psychedelic is O-acetylpsilocin salt, wherein the eplivanserin is administered to pretreat at least 300 minutes prior to the O-acetylpsilocin salt. In some embodiments, the serotonin receptor modulator is eplivanserin and the psychedelic is O-acetylpsilocin salt, wherein the eplivanserin is administered to pretreat at least 330 minutes prior to the O-acetylpsilocin salt. In some embodiments, the serotonin receptor modulator is eplivanserin and the psychedelic is O-acetylpsilocin salt, wherein the eplivanserin is administered to pretreat at least 360 minutes prior to the O-acetylpsilocin salt.

In some preferred embodiments, the serotonin receptor modulator is eplivanserin and the psychedelic is O-acetylpsilocin salt, wherein eplivanserin is administered to pretreat between about 60 minutes and about 180 minutes prior to the administration of O-acetylpsilocin salt.

In some embodiments, the serotonin receptor modulator is volinanserin and the psychedelic is O-acetylpsilocin salt, wherein the volinanserin is administered to pretreat a subject between at least 15 minutes and 360 minutes prior to the administration or release of O-acetylpsilocin salt. In some embodiments, the serotonin receptor modulator is volinanserin and the psychedelic is O-acetylpsilocin salt, wherein the volinanserin is administered to pretreat between at least 30 minutes and 360 minutes prior to the administration or release of O-acetylpsilocin salt. In some embodiments, the serotonin receptor modulator is volinanserin and the psychedelic is O-acetylpsilocin salt, wherein the volinanserin is administered to pretreat between at least 60 minutes and 240 minutes prior to the administration or release of O-acetylpsilocin salt. In some embodiments, the serotonin receptor modulator is volinanserin and the psychedelic is O-acetylpsilocin salt, wherein the volinanserin is administered to pretreat at least 90 minutes prior to O-acetylpsilocin salt. In some embodiments, the serotonin receptor modulator is volinanserin and the psychedelic is O-acetylpsilocin salt, wherein the volinanserin is administered to pretreat at least 120 minutes prior to the O-acetylpsilocin salt.

In some embodiments, the serotonin receptor modulator is volinanserin and the psychedelic is O-acetylpsilocin salt, wherein the volinanserin is administered to pretreat at least 150 minutes prior to the O-acetylpsilocin salt. In some embodiments, the serotonin receptor modulator is volinanserin and the psychedelic is O-acetylpsilocin salt, wherein the volinanserin is administered to pretreat between about 15 minutes and about 150 minutes prior to the O-acetylpsilocin salt. In some embodiments, the serotonin receptor modulator is volinanserin and the psychedelic is O-acetylpsilocin salt, wherein the volinanserin is administered to pretreat at least 180 minutes prior to the O-acetylpsilocin salt. In some embodiments, the serotonin receptor modulator is volinanserin and the psychedelic is O-acetylpsilocin salt, wherein the volinanserin is administered to pretreat at least 210 minutes prior to the O-acetylpsilocin salt. In some embodiments, the serotonin receptor modulator is volinanserin and the psychedelic is O-acetylpsilocin salt, wherein the volinanserin is administered to pretreat at least 240 minutes prior to the O-acetylpsilocin salt. In some embodiments, the serotonin receptor modulator is volinanserin and the psychedelic is O-acetylpsilocin salt, wherein the volinanserin is administered to pretreat at least 270 minutes prior to the O-acetylpsilocin salt. In some embodiments, the serotonin receptor modulator is volinanserin and the psychedelic is O-acetylpsilocin salt, wherein the volinanserin is administered to pretreat at least 300 minutes prior to the O-acetylpsilocin salt. In some embodiments, the serotonin receptor modulator is volinanserin and the psychedelic is O-acetylpsilocin salt, wherein the volinanserin is administered to pretreat at least 330 minutes prior to the O-acetylpsilocin salt. In some embodiments, the serotonin receptor modulator is volinanserin and the psychedelic is O-acetylpsilocin salt, wherein the volinanserin is administered to pretreat at least 360 minutes prior to the O-acetylpsilocin salt. In some preferred embodiments, the serotonin receptor modulator is volinanserin and the psychedelic is O-acetylpsilocin salt, wherein volinanserin is administered to pretreat between about 60 minutes and about 180 minutes prior to the administration of O-acetylpsilocin salt.

In some embodiments, the serotonin receptor modulator is ketanserin and the psychedelic is O-acetylpsilocin salt, wherein the ketanserin is administered to pretreat at least 15 minutes prior to the administration of O-acetylpsilocin salt. In some embodiments, the serotonin receptor modulator is ketanserin and the psychedelic is O-acetylpsilocin salt, wherein the ketanserin is administered to pretreat between at least 30 minutes and 360 minutes prior to the administration or release O-acetylpsilocin salt. In some embodiments, the serotonin receptor modulator is ketanserin and the psychedelic is O-acetylpsilocin salt, wherein the ketanserin is administered to pretreat between at least 60 minutes and 240 minutes prior to the administration or release of O-acetylpsilocin salt. In some embodiments, the serotonin receptor modulator is ketanserin and the psychedelic is O-acetylpsilocin salt, wherein the ketanserin is administered to pretreat at least 90 minutes prior to the O-acetylpsilocin salt. In some embodiments, the serotonin receptor modulator is ketanserin and the psychedelic is O-acetylpsilocin salt, wherein the ketanserin is administered to pretreat at least 120 minutes prior to the O-acetylpsilocin salt. In some embodiments, the serotonin receptor modulator is ketanserin and the psychedelic is O-acetylpsilocin salt, wherein the ketanserin is administered to pretreat at least 150 minutes prior to the O-acetylpsilocin salt. In some embodiments, the serotonin receptor modulator is ketanserin and the psychedelic is O-acetylpsilocin salt, wherein the ketanserin is administered to pretreat between about 15 minutes and about 150 minutes prior to the O-acetylpsilocin salt. In some embodiments, the serotonin receptor modulator is ketanserin and the psychedelic is O-acetylpsilocin salt, wherein the ketanserin is administered to pretreat at least 180 minutes prior to the O-acetylpsilocin salt. In some embodiments, the serotonin receptor modulator is ketanserin and the psychedelic is O-acetylpsilocin salt, wherein the ketanserin is administered to pretreat at least 210 minutes prior to the O-acetylpsilocin salt. In some embodiments, the serotonin receptor modulator is ketanserin and the psychedelic is O-acetylpsilocin salt, wherein the ketanserin is administered to pretreat at least 240 minutes prior to the O-acetylpsilocin salt. In some embodiments, the serotonin receptor modulator is ketanserin and the psychedelic is O-acetylpsilocin salt, wherein the ketanserin is administered to pretreat at least 270 minutes prior to the O-acetylpsilocin salt. In some embodiments, the serotonin receptor modulator is ketanserin and the psychedelic is O-acetylpsilocin salt, wherein the ketanserin is administered to pretreat at least 300 minutes prior to the O-acetylpsilocin salt. In some embodiments, the serotonin receptor modulator is ketanserin and the psychedelic is O-acetylpsilocin salt, wherein the ketanserin is administered to pretreat at least 330 minutes prior to the O-acetylpsilocin salt. In some embodiments, the serotonin receptor modulator is ketanserin and the psychedelic is O-acetylpsilocin salt, wherein the ketanserin is administered to pretreat at least 360 minutes prior to the O-acetylpsilocin salt. In some preferred embodiments, the serotonin receptor modulator is ketanserin and the psychedelic is O-acetylpsilocin salt, wherein ketanserin is administered to pretreat between about 60 minutes and about 180 minutes prior to the administration of O-acetylpsilocin salt.

In some embodiments, the serotonin receptor modulator is ritanserin and the psychedelic is O-acetylpsilocin salt, wherein the ritanserin is administered to pretreat at least 15 minutes prior to the administration of O-acetylpsilocin salt. In some embodiments, the serotonin receptor modulator is ritanserin and the psychedelic is O-acetylpsilocin salt, wherein the ritanserin is administered to pretreat at least 30 minutes prior to the O-acetylpsilocin salt. In some embodiments, the serotonin receptor modulator is ritanserin and the psychedelic is O-acetylpsilocin salt, wherein the ritanserin is administered to pretreat between at least 60 minutes and 240 minutes prior to the administration or release of O-acetylpsilocin salt. In some embodiments, the serotonin receptor modulator is ritanserin and the psychedelic is O-acetylpsilocin salt, wherein the ritanserin is administered to pretreat at least 90 minutes prior to the O-acetylpsilocin salt. In some embodiments, the serotonin receptor modulator is ritanserin and the psychedelic is O-acetylpsilocin salt, wherein the ritanserin is administered to pretreat at least 120 minutes prior to the O-acetylpsilocin salt. In some embodiments, the serotonin receptor modulator is ritanserin and the psychedelic is O-acetylpsilocin salt, wherein the ritanserin is administered to pretreat at least 150 minutes prior to the O-acetylpsilocin salt. In some embodiments, the serotonin receptor modulator is ritanserin and the psychedelic is O-acetylpsilocin salt, wherein the ritanserin is administered to pretreat between about 15 minutes and about 150 minutes prior to the O-acetylpsilocin salt. In some embodiments, the serotonin receptor modulator is ritanserin and the psychedelic is O-acetylpsilocin salt, wherein the ritanserin is administered to pretreat at least 180 minutes prior to the O-acetylpsilocin salt. In some embodiments, the serotonin receptor modulator is ritanserin and the psychedelic is O-acetylpsilocin salt, wherein the ritanserin is administered to pretreat at least 210 minutes prior to the O-acetylpsilocin salt. In some embodiments, the serotonin receptor modulator is ritanserin and the psychedelic is O-acetylpsilocin salt, wherein the ritanserin is administered to pretreat at least 240 minutes prior to the O-acetylpsilocin salt. In some embodiments, the serotonin receptor modulator is ritanserin and the psychedelic is O-acetylpsilocin salt, wherein the ritanserin is administered to pretreat at least 270 minutes prior to the O-acetylpsilocin salt. In some embodiments, the serotonin receptor modulator is ritanserin and the psychedelic is O-acetylpsilocin salt, wherein the ritanserin is administered to pretreat at least 300 minutes prior to the O-acetylpsilocin salt. In some embodiments, the serotonin receptor modulator is ritanserin and the psychedelic is O-acetylpsilocin salt, wherein the ritanserin is administered to pretreat at least 330 minutes prior to the O-acetylpsilocin salt. In some embodiments, the serotonin receptor modulator is ritanserin and the psychedelic is O-acetylpsilocin salt, wherein the ritanserin is administered to pretreat at least 360 minutes prior to the O-acetylpsilocin salt. In some preferred embodiments, the serotonin receptor modulator is ritanserin and the psychedelic is O-acetylpsilocin salt, wherein ritanserin is administered to pretreat between about 60 minutes and about 180 minutes prior to the administration of O-acetylpsilocin salt.

In some embodiments, the serotonin receptor modulator is pimavanserin and the psychedelic is O-acetylpsilocin salt, wherein the pimavanserin is administered to pretreat at least 15 minutes prior to the administration of O-acetylpsilocin salt. In some embodiments, the serotonin receptor modulator is pimavanserin and the psychedelic is O-acetylpsilocin salt, wherein the pimavanserin is administered to pretreat at least 30 minutes prior to the O-acetylpsilocin salt. In some embodiments, the serotonin receptor modulator is pimavanserin and the psychedelic is O-acetylpsilocin salt, wherein the pimavanserin is administered to pretreat between at least 60 minutes and 240 minutes prior to the administration or release of O-acetylpsilocin salt. In some embodiments, the serotonin receptor modulator is pimavanserin and the psychedelic is O-acetylpsilocin salt, wherein the pimavanserin is administered to pretreat at least 90 minutes prior to the O-acetylpsilocin salt. In some embodiments, the serotonin receptor modulator is pimavanserin and the psychedelic is O-acetylpsilocin salt, wherein the pimavanserin is administered to pretreat at least 120 minutes prior to the O-acetylpsilocin salt. In some embodiments, the serotonin receptor modulator is pimavanserin and the psychedelic is O-acetylpsilocin salt, wherein the pimavanserin is administered to pretreat at least 150 minutes prior to the O-acetylpsilocin salt. In some embodiments, the serotonin receptor modulator is pimavanserin and the psychedelic is O-acetylpsilocin salt, wherein the pimavanserin is administered to pretreat between about 15 minutes and about 150 minutes prior to the O-acetylpsilocin salt. In some embodiments, the serotonin receptor modulator is pimavanserin and the psychedelic is O-acetylpsilocin salt, wherein the pimavanserin is administered to pretreat at least 180 minutes prior to the O-acetylpsilocin salt. In some embodiments, the serotonin receptor modulator is pimavanserin and the psychedelic is O-acetylpsilocin salt, wherein the pimavanserin is administered to pretreat at least 210 minutes prior to the O-acetylpsilocin salt. In some embodiments, the serotonin receptor modulator is pimavanserin and the psychedelic is O-acetylpsilocin salt, wherein the pimavanserin is administered to pretreat at least 240 minutes prior to the O-acetylpsilocin salt. In some embodiments, the serotonin receptor modulator is pimavanserin and the psychedelic is O-acetylpsilocin salt, wherein the pimavanserin is administered to pretreat at least 270 minutes prior to the O-acetylpsilocin salt. In some embodiments, the serotonin receptor modulator is pimavanserin and the psychedelic is O-acetylpsilocin salt, wherein the pimavanserin is administered to pretreat at least 300 minutes prior to the O-acetylpsilocin salt. In some embodiments, the serotonin receptor modulator is pimavanserin and the psychedelic is O-acetylpsilocin salt, wherein the pimavanserin is administered to pretreat at least 330 minutes prior to the O-acetylpsilocin salt. In some embodiments, the serotonin receptor modulator is pimavanserin and the psychedelic is O-acetylpsilocin salt, wherein the pimavanserin is administered to pretreat at least 360 minutes prior to the O-acetylpsilocin salt. In some preferred embodiments, the serotonin receptor modulator is pimavanserin and the psychedelic is O-acetylpsilocin salt, wherein pimavanserin is administered to pretreat between about 60 minutes and about 180 minutes prior to the administration of O-acetylpsilocin salt.

In some embodiments, the serotonin receptor modulator is nelotanserin and the psychedelic is O-acetylpsilocin salt, wherein the nelotanserin is administered to pretreat at least 15 minutes prior to the administration of O-acetylpsilocin salt. In some embodiments, the serotonin receptor modulator is nelotanserin and the psychedelic is O-acetylpsilocin salt, wherein the nelotanserin is administered to pretreat at least 30 minutes prior to the O-acetylpsilocin salt. In some embodiments, the serotonin receptor modulator is nelotanserin and the psychedelic is O-acetylpsilocin salt, wherein the nelotanserin is administered to pretreat between at least 60 minutes and 240 minutes prior to the administration or release of O-acetylpsilocin salt. In some embodiments, the serotonin receptor modulator is nelotanserin and the psychedelic is O-acetylpsilocin salt, wherein the nelotanserin is administered to pretreat at least 90 minutes prior to the O-acetylpsilocin salt. In some embodiments, the serotonin receptor modulator is nelotanserin and the psychedelic is O-acetylpsilocin salt, wherein the nelotanserin is administered to pretreat at least 120 minutes prior to the O-acetylpsilocin salt.

In some embodiments, the serotonin receptor modulator is nelotanserin and the psychedelic is O-acetylpsilocin salt, wherein the nelotanserin is administered to pretreat at least 150 minutes prior to the O-acetylpsilocin salt. In some embodiments, the serotonin receptor modulator is nelotanserin and the psychedelic is O-acetylpsilocin salt, wherein the nelotanserin is administered to pretreat between about 15 minutes and about 150 minutes prior to the O-acetylpsilocin salt. In some embodiments, the serotonin receptor modulator is nelotanserin and the psychedelic is O-acetylpsilocin salt, wherein the nelotanserin is administered to pretreat at least 180 minutes prior to the O-acetylpsilocin salt. In some embodiments, the serotonin receptor modulator is nelotanserin and the psychedelic is O-acetylpsilocin salt, wherein the nelotanserin is administered to pretreat at least 210 minutes prior to the O-acetylpsilocin salt. In some embodiments, the serotonin receptor modulator is nelotanserin and the psychedelic is O-acetylpsilocin salt, wherein the nelotanserin is administered to pretreat at least 240 minutes prior to the O-acetylpsilocin salt. In some embodiments, the serotonin receptor modulator is nelotanserin and the psychedelic is O-acetylpsilocin salt, wherein the nelotanserin is administered to pretreat at least 270 minutes prior to the O-acetylpsilocin salt.

In some embodiments, the serotonin receptor modulator is nelotanserin and the psychedelic is O-acetylpsilocin salt, wherein the nelotanserin is administered to pretreat at least 300 minutes prior to the O-acetylpsilocin salt. In some embodiments, the serotonin receptor modulator is nelotanserin and the psychedelic is O-acetylpsilocin salt, wherein the nelotanserin is administered to pretreat at least 330 minutes prior to the O-acetylpsilocin salt. In some embodiments, the serotonin receptor modulator is nelotanserin and the psychedelic is O-acetylpsilocin salt, wherein the nelotanserin is administered to pretreat at least 360 minutes prior to the O-acetylpsilocin salt. In some preferred embodiments, the serotonin receptor modulator is nelotanserin and the psychedelic is O-acetylpsilocin salt, wherein nelotanserin is administered to pretreat between about 60 minutes and about 180 minutes prior to the administration of O-acetylpsilocin salt.

In some embodiments, the serotonin receptor modulator is pruvanserin and the psychedelic is O-acetylpsilocin salt, wherein the pruvanserin is administered to pretreat at least 15 minutes prior to the administration of O-acetylpsilocin salt. In some embodiments, the serotonin receptor modulator is pruvanserin and the psychedelic is O-acetylpsilocin salt, wherein the pruvanserin is administered to pretreat at least 30 minutes prior to the O-acetylpsilocin salt. In some embodiments, the serotonin receptor modulator is pruvanserin and the psychedelic is O-acetylpsilocin salt, wherein the pruvanserin is administered to pretreat between at least 60 minutes and 240 minutes prior to the administration or release of O-acetylpsilocin salt. In some embodiments, the serotonin receptor modulator is pruvanserin and the psychedelic is O-acetylpsilocin salt, wherein the pruvanserin is administered to pretreat at least 90 minutes prior to the O-acetylpsilocin salt. In some embodiments, the serotonin receptor modulator is pruvanserin and the psychedelic is O-acetylpsilocin salt, wherein the pruvanserin is administered to pretreat at least 120 minutes prior to the O-acetylpsilocin salt. In some embodiments, the serotonin receptor modulator is pruvanserin and the psychedelic is O-acetylpsilocin salt, wherein the pruvanserin is administered to pretreat at least 150 minutes prior to the O-acetylpsilocin salt. In some embodiments, the serotonin receptor modulator is pruvanserin and the psychedelic is O-acetylpsilocin salt, wherein the pruvanserin is administered to pretreat between about 15 minutes and about 150 minutes prior to the O-acetylpsilocin salt. In some embodiments, the serotonin receptor modulator is pruvanserin and the psychedelic is O-acetylpsilocin salt, wherein the pruvanserin is administered to pretreat at least 180 minutes prior to the O-acetylpsilocin salt. In some embodiments, the serotonin receptor modulator is pruvanserin and the psychedelic is O-acetylpsilocin salt, wherein pruvanserin is administered to pretreat at least 210 minutes prior to O-acetylpsilocin salt.

In some embodiments, the serotonin receptor modulator is pruvanserin and the psychedelic is O-acetylpsilocin salt, wherein the pruvanserin is administered to pretreat at least 240 minutes prior to the O-acetylpsilocin salt. In some embodiments, the serotonin receptor modulator is pruvanserin and the psychedelic is O-acetylpsilocin salt, wherein the pruvanserin is administered to pretreat at least 270 minutes prior to the O-acetylpsilocin salt. In some embodiments, the serotonin receptor modulator is pruvanserin and the psychedelic is O-acetylpsilocin salt, wherein the pruvanserin is administered to pretreat at least 300 minutes prior to the O-acetylpsilocin salt. In some embodiments, the serotonin receptor modulator is pruvanserin and the psychedelic is O-acetylpsilocin salt, wherein the pruvanserin is administered to pretreat at least 330 minutes prior to the O-acetylpsilocin salt. In some embodiments, the serotonin receptor modulator is pruvanserin and the psychedelic is O-acetylpsilocin salt, wherein the pruvanserin is administered to pretreat at least 360 minutes prior to the O-acetylpsilocin salt. In some preferred embodiments, the serotonin receptor modulator is pruvanserin and the psychedelic is O-acetylpsilocin salt, wherein pruvanserin is administered to pretreat between about 60 minutes and about 180 minutes prior to the administration of O-acetylpsilocin salt.

In some embodiments, the serotonin receptor modulator is eplivanserin and the psychedelic is O-acetylpsilocin maleate Form A, wherein the eplivanserin is administered to pretreat at least 15 minutes prior to the administration of the O-acetylpsilocin maleate Form A. In some embodiments, the serotonin receptor modulator is eplivanserin and the psychedelic is O-acetylpsilocin maleate Form A, wherein the eplivanserin is administered to pretreat between at least 30 minutes prior and 360 minutes prior to the release or administration of the O-acetylpsilocin maleate Form A. In some embodiments, the serotonin receptor modulator is eplivanserin and the psychedelic is O-acetylpsilocin maleate Form A, wherein the eplivanserin is administered to pretreat between at least 60 minutes prior and 360 minutes prior to the release or administration of the O-acetylpsilocin maleate Form A. In some embodiments, the serotonin receptor modulator is eplivanserin and the psychedelic is O-acetylpsilocin maleate Form A, wherein the eplivanserin is administered to pretreat between at least 90 minutes and 240 minutes prior to the O-acetylpsilocin maleate Form A. In some embodiments, the serotonin receptor modulator is eplivanserin and the psychedelic is O-acetylpsilocin maleate Form A, wherein eplivanserin is administered to pretreat at least 120 minutes prior to O-acetylpsilocin maleate Form A.

In some embodiments, the serotonin receptor modulator is eplivanserin and the psychedelic is O-acetylpsilocin maleate Form A, wherein the eplivanserin is administered to pretreat at least 150 minutes prior to the O-acetylpsilocin maleate Form A In some embodiments, the serotonin receptor modulator is eplivanserin and the psychedelic is O-acetylpsilocin maleate Form A, wherein the eplivanserin is administered to pretreat between about 15 minutes and about 150 minutes prior to the O-acetylpsilocin maleate Form A. In some embodiments, the serotonin receptor modulator is eplivanserin and the psychedelic is O-acetylpsilocin maleate Form A, wherein the eplivanserin is administered to pretreat at least 180 minutes prior to the O-acetylpsilocin maleate Form A. In some embodiments, the serotonin receptor modulator is eplivanserin and the psychedelic is O-acetylpsilocin maleate Form A, wherein the eplivanserin is administered to pretreat at least 210 minutes prior to the O-acetylpsilocin maleate Form A. In some embodiments, the serotonin receptor modulator is eplivanserin and the psychedelic is O-acetylpsilocin maleate Form A, wherein the eplivanserin is administered to pretreat at least 240 minutes prior to the O-acetylpsilocin maleate Form A.

In some embodiments, the serotonin receptor modulator is eplivanserin and the psychedelic is O-acetylpsilocin maleate Form A, wherein the eplivanserin is administered to pretreat at least 270 minutes prior to psilocybin HCl. In some embodiments, the serotonin receptor modulator is eplivanserin and the psychedelic is O-acetylpsilocin maleate Form A, wherein the eplivanserin is administered to pretreat at least 300 minutes prior to the O-acetylpsilocin maleate Form A. In some embodiments, the serotonin receptor modulator is eplivanserin and the psychedelic is O-acetylpsilocin maleate Form A, wherein the eplivanserin is administered to pretreat at least 330 minutes prior to the O-acetylpsilocin maleate Form A. In some embodiments, the serotonin receptor modulator is eplivanserin and the psychedelic is O-acetylpsilocin maleate Form A, wherein the eplivanserin is administered to pretreat at least 360 minutes prior to the O-acetylpsilocin maleate Form A.

In some preferred embodiments, the serotonin receptor modulator is eplivanserin and the psychedelic is O-acetylpsilocin maleate Form A, wherein eplivanserin is administered to pretreat between about 60 minutes and about 180 minutes prior to the administration of the O-acetylpsilocin maleate Form A.

In some embodiments, the serotonin receptor modulator is volinanserin and the psychedelic is O-acetylpsilocin maleate Form A, wherein the volinanserin is administered to pretreat a subject between at least 15 minutes and 360 minutes prior to the administration or release of the O-acetylpsilocin maleate Form A. In some embodiments, the serotonin receptor modulator is volinanserin and the psychedelic is O-acetylpsilocin maleate Form A, wherein the volinanserin is administered to pretreat between at least 30 minutes and 360 minutes prior to the administration or release of the O-acetylpsilocin maleate Form A. In some embodiments, the serotonin receptor modulator is volinanserin and the psychedelic is O-acetylpsilocin maleate Form A, wherein the volinanserin is administered to pretreat between at least 60 minutes and 240 minutes prior to the administration or release of the O-acetylpsilocin maleate Form A. In some embodiments, the serotonin receptor modulator is volinanserin and the psychedelic is O-acetylpsilocin maleate Form A, wherein the volinanserin is administered to pretreat at least 90 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat at least 120 minutes prior to the O-acetylpsilocin maleate Form A.

In some embodiments, the serotonin receptor modulator is volinanserin and the psychedelic is O-acetylpsilocin maleate Form A, wherein the volinanserin is administered to pretreat at least 150 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat between about 15 minutes and about 150 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat at least 180 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat at least 210 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat at least 240 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat at least 270 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat at least 300 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat at least 330 minutes prior to the O-acetylpsilocin maleate Form A. In some embodiments, the serotonin receptor modulator is volinanserin and the psychedelic is O-acetylpsilocin maleate Form A, wherein the volinanserin is administered to pretreat at least 360 minutes prior to the O-acetylpsilocin maleate Form A. In some preferred embodiments, the serotonin receptor modulator is volinanserin and the psychedelic is O-acetylpsilocin maleate Form A, wherein volinanserin is administered to pretreat between about 60 minutes and about 180 minutes prior to the administration of the O-acetylpsilocin maleate Form A.

In some embodiments, the serotonin receptor modulator is ketanserin and the psychedelic is O-acetylpsilocin maleate Form A, wherein the ketanserin is administered to pretreat at least 15 minutes prior to the administration of the O-acetylpsilocin maleate Form A. In some embodiments, the serotonin receptor modulator is ketanserin and the psychedelic is O-acetylpsilocin maleate Form A, wherein the ketanserin is administered to pretreat between at least 30 minutes and 360 minutes prior to the administration or release of the O-acetylpsilocin maleate Form A. In some embodiments, the serotonin receptor modulator is ketanserin and the psychedelic is O-acetylpsilocin maleate Form A, wherein the ketanserin is administered to pretreat between at least 60 minutes and 240 minutes prior to the administration or release of the O-acetylpsilocin maleate Form A. In some embodiments, the serotonin receptor modulator is ketanserin and the psychedelic is O-acetylpsilocin maleate Form A, wherein the ketanserin is administered to pretreat at least 90 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 120 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 150 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat between about 15 minutes and about 150 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 180 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 210 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 240 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 270 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 300 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 330 minutes prior to the O-acetylpsilocin maleate Form A. In some embodiments, the serotonin receptor modulator is ketanserin and the psychedelic is O-acetylpsilocin maleate Form A, wherein the ketanserin is administered to pretreat at least 360 minutes prior to the O-acetylpsilocin maleate Form A. In some preferred embodiments, the serotonin receptor modulator is ketanserin and the psychedelic is O-acetylpsilocin maleate Form A, wherein ketanserin is administered to pretreat between about 60 minutes and about 180 minutes prior to the administration of the O-acetylpsilocin maleate Form A.

In some embodiments, the serotonin receptor modulator is ritanserin and the psychedelic is O-acetylpsilocin maleate Form A, wherein the ritanserin is administered to pretreat at least 15 minutes prior to the administration of the O-acetylpsilocin maleate Form A. In some embodiments, the serotonin receptor modulator is ritanserin and the psychedelic is O-acetylpsilocin maleate Form A, wherein the ritanserin is administered to pretreat at least 30 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat between at least 60 minutes and 240 minutes prior to the administration or release of the O-acetylpsilocin maleate Form A. In some embodiments, the serotonin receptor modulator is ritanserin and the psychedelic is O-acetylpsilocin maleate Form A, wherein the ritanserin is administered to pretreat at least 90 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 120 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 150 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat between about 15 minutes and about 150 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 180 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 210 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 240 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 270 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 300 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 330 minutes prior to the O-acetylpsilocin maleate Form A. In some embodiments, the serotonin receptor modulator is ritanserin and the psychedelic is O-acetylpsilocin maleate Form A, wherein the ritanserin is administered to pretreat at least 360 minutes prior to the O-acetylpsilocin maleate Form A. In some preferred embodiments, the serotonin receptor modulator is ritanserin and the psychedelic is O-acetylpsilocin maleate Form A, wherein ritanserin is administered to pretreat between about 60 minutes and about 180 minutes prior to the administration of the O-acetylpsilocin maleate Form A.

In some embodiments, the serotonin receptor modulator is pimavanserin and the psychedelic is O-acetylpsilocin maleate Form A, wherein the pimavanserin is administered to pretreat at least 15 minutes prior to the administration of the O-acetylpsilocin maleate Form A. In some embodiments, the serotonin receptor modulator is pimavanserin and the psychedelic is O-acetylpsilocin maleate Form A, wherein the pimavanserin is administered to pretreat at least 30 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat between at least 60 minutes and 240 minutes prior to the administration or release of the O-acetylpsilocin maleate Form A. In some embodiments, the serotonin receptor modulator is pimavanserin and the psychedelic is O-acetylpsilocin maleate Form A, wherein the pimavanserin is administered to pretreat at least 90 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 120 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 150 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat between about 15 minutes and about 150 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 180 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 210 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 240 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 270 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 300 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 330 minutes prior to the O-acetylpsilocin maleate Form A. In some embodiments, the serotonin receptor modulator is pimavanserin and the psychedelic is O-acetylpsilocin maleate Form A, wherein the pimavanserin is administered to pretreat at least 360 minutes prior to the O-acetylpsilocin maleate Form A. In some preferred embodiments, the serotonin receptor modulator is pimavanserin and the psychedelic is O-acetylpsilocin maleate Form A, wherein pimavanserin is administered to pretreat between about 60 minutes and about 180 minutes prior to the administration of the O-acetylpsilocin maleate Form A.

In some embodiments, the serotonin receptor modulator is nelotanserin and the psychedelic is O-acetylpsilocin maleate Form A, wherein the nelotanserin is administered to pretreat at least 15 minutes prior to the administration of the O-acetylpsilocin maleate Form A. In some embodiments, the serotonin receptor modulator is nelotanserin and the psychedelic is O-acetylpsilocin maleate Form A, wherein the nelotanserin is administered to pretreat at least 30 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat between at least 60 minutes and 240 minutes prior to the administration or release of the O-acetylpsilocin maleate Form A. In some embodiments, the serotonin receptor modulator is nelotanserin and the psychedelic is O-acetylpsilocin maleate Form A, wherein the nelotanserin is administered to pretreat at least 90 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat at least 120 minutes prior to the O-acetylpsilocin maleate Form A.

In some embodiments, the serotonin receptor modulator is nelotanserin and the psychedelic is O-acetylpsilocin maleate Form A, wherein the nelotanserin is administered to pretreat at least 150 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat between about 15 minutes and about 150 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat at least 180 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat at least 210 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat at least 240 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat at least 270 minutes prior to the O-acetylpsilocin maleate Form A.

In some embodiments, the serotonin receptor modulator is nelotanserin and the psychedelic is O-acetylpsilocin maleate Form A, wherein the nelotanserin is administered to pretreat at least 300 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat at least 330 minutes prior to the O-acetylpsilocin maleate Form A. In some embodiments, the serotonin receptor modulator is nelotanserin and the psychedelic is O-acetylpsilocin maleate Form A, wherein the nelotanserin is administered to pretreat at least 360 minutes prior to the O-acetylpsilocin maleate Form A. In some preferred embodiments, the serotonin receptor modulator is nelotanserin and the psychedelic is O-acetylpsilocin maleate Form A, wherein nelotanserin is administered to pretreat between about 60 minutes and about 180 minutes prior to the administration of the O-acetylpsilocin maleate Form A.

In some embodiments, the serotonin receptor modulator is pruvanserin and the psychedelic is O-acetylpsilocin maleate Form A, wherein the pruvanserin is administered to pretreat at least 15 minutes prior to the administration of the O-acetylpsilocin maleate Form A. In some embodiments, the serotonin receptor modulator is pruvanserin and the psychedelic is O-acetylpsilocin maleate Form A, wherein the pruvanserin is administered to pretreat at least 30 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat between at least 60 minutes and 240 minutes prior to the administration or release of the O-acetylpsilocin maleate Form A. In some embodiments, the serotonin receptor modulator is pruvanserin and the psychedelic is O-acetylpsilocin maleate Form A, wherein the pruvanserin is administered to pretreat at least 90 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat at least 120 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat at least 150 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat between about 15 minutes and about 150 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat at least 180 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat at least 210 minutes prior to the O-acetylpsilocin maleate Form A.

In some embodiments, the serotonin receptor modulator is pruvanserin and the psychedelic is O-acetylpsilocin maleate Form A, wherein the pruvanserin is administered to pretreat at least 240 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat at least 270 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat at least 300 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat at least 330 minutes prior to the O-acetylpsilocin maleate Form A. In some embodiments, the serotonin receptor modulator is pruvanserin and the psychedelic is O-acetylpsilocin maleate Form A, wherein the pruvanserin is administered to pretreat at least 360 minutes prior to the O-acetylpsilocin maleate Form A. In some preferred embodiments, the serotonin receptor modulator is pruvanserin and the psychedelic is O-acetylpsilocin maleate Form A, wherein pruvanserin is administered to pretreat between about 60 minutes and about 180 minutes prior to the administration of the O-acetylpsilocin maleate Form A.

In some embodiments, the serotonin receptor modulator is flibanserin and the psychedelic is O-acetylpsilocin maleate Form A, wherein the flibanserin is administered to pretreat at least 15 minutes prior to the administration of the O-acetylpsilocin maleate Form A. In some embodiments, the serotonin receptor modulator is flibanserin and the psychedelic is O-acetylpsilocin maleate Form A, wherein the flibanserin is administered to pretreat at least 30 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat between at least 60 minutes and 240 minutes prior to the administration or release of the O-acetylpsilocin maleate Form A. In some embodiments, the serotonin receptor modulator is flibanserin and the psychedelic is O-acetylpsilocin maleate Form A, wherein the flibanserin is administered to pretreat at least 90 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat at least 120 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat at least 150 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat between about 15 minutes and about 150 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat at least 180 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat at least 210 minutes prior to the O-acetylpsilocin maleate Form A.

In some embodiments, the serotonin receptor modulator is flibanserin and the psychedelic is O-acetylpsilocin maleate Form A, wherein the flibanserin is administered to pretreat at least 240 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat at least 270 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat at least 300 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat at least 330 minutes prior to the O-acetylpsilocin maleate Form A. In some embodiments, the serotonin receptor modulator is flibanserin and the psychedelic is O-acetylpsilocin maleate Form A, wherein the flibanserin is administered to pretreat at least 360 minutes prior to the O-acetylpsilocin maleate Form A. In some preferred embodiments, the serotonin receptor modulator is flibanserin and the psychedelic is O-acetylpsilocin maleate Form A, wherein flibanserin is administered to pretreat between about 60 minutes and about 180 minutes prior to the administration of the O-acetylpsilocin maleate Form A.

In some embodiments, the serotonin receptor modulator is olanzapine and the psychedelic is O-acetylpsilocin maleate Form A, wherein the olanzapine is administered to pretreat at least 15 minutes prior to the administration of the O-acetylpsilocin maleate Form A. In some embodiments, the serotonin receptor modulator is olanzapine and the psychedelic is O-acetylpsilocin maleate Form A, wherein the olanzapine is administered to pretreat at least 30 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat between at least 60 minutes and 240 minutes prior to the administration or release of the O-acetylpsilocin maleate Form A. In some embodiments, the serotonin receptor modulator is olanzapine and the psychedelic is O-acetylpsilocin maleate Form A, wherein the olanzapine is administered to pretreat at least 90 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat at least 120 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat at least 150 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat between about 15 minutes and about 150 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat at least 180 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat at least 210 minutes prior to the O-acetylpsilocin maleate Form A.

In some embodiments, the serotonin receptor modulator is olanzapine and the psychedelic is O-acetylpsilocin maleate Form A, wherein the olanzapine is administered to pretreat at least 240 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat at least 270 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat at least 300 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat at least 330 minutes prior to the O-acetylpsilocin maleate Form A. In some embodiments, the serotonin receptor modulator is olanzapine and the psychedelic is O-acetylpsilocin maleate Form A, wherein the olanzapine is administered to pretreat at least 360 minutes prior to the O-acetylpsilocin maleate Form A. In some preferred embodiments, the serotonin receptor modulator is olanzapine and the psychedelic is O-acetylpsilocin maleate Form A, wherein olanzapine is administered to pretreat between about 60 minutes and about 180 minutes prior to the administration of the O-acetylpsilocin maleate Form A.

In some embodiments, the serotonin receptor modulator is risperidone and the psychedelic is O-acetylpsilocin maleate Form A, wherein the risperidone is administered to pretreat at least 15 minutes prior to the administration of the O-acetylpsilocin maleate Form A. In some embodiments, the serotonin receptor modulator is risperidone and the psychedelic is O-acetylpsilocin maleate Form A, wherein the risperidone is administered to pretreat at least 30 minutes prior to the O-acetylpsilocin maleate Form A. In some embodiments, the serotonin receptor modulator is risperidone and the psychedelic is O-acetylpsilocin maleate Form A, wherein the risperidone is administered to pretreat between at least 60 minutes and 240 minutes prior to the administration or release of the O-acetylpsilocin maleate Form A. In some embodiments, the serotonin receptor modulator is risperidone and the psychedelic is O-acetylpsilocin maleate Form A, wherein the risperidone is administered to pretreat at least 90 minutes prior to the O-acetylpsilocin maleate Form A. In some embodiments, the serotonin receptor modulator is risperidone and the psychedelic is O-acetylpsilocin maleate Form A, wherein the risperidone is administered to pretreat at least 120 minutes prior to the O-acetylpsilocin maleate Form A. In some embodiments, the serotonin receptor modulator is risperidone and the psychedelic is O-acetylpsilocin maleate Form A, wherein the risperidone is administered to pretreat at least 150 minutes prior to the O-acetylpsilocin maleate Form A. In some embodiments, the serotonin receptor modulator is risperidone and the psychedelic is O-acetylpsilocin maleate Form A, wherein the risperidone is administered to pretreat between about 15 minutes and about 150 minutes prior to the O-acetylpsilocin maleate Form A. In some embodiments, the serotonin receptor modulator is risperidone and the psychedelic is O-acetylpsilocin maleate Form A, wherein the risperidone is administered to pretreat at least 180 minutes prior to the O-acetylpsilocin maleate Form A. In some embodiments, the serotonin receptor modulator is risperidone and the psychedelic is O-acetylpsilocin maleate Form A, wherein the risperidone is administered to pretreat at least 210 minutes prior to the O-acetylpsilocin maleate Form A.

In some embodiments, the serotonin receptor modulator is risperidone and the psychedelic is O-acetylpsilocin maleate Form A, wherein the risperidone is administered to pretreat at least 240 minutes prior to the O-acetylpsilocin maleate Form A. In some embodiments, the serotonin receptor modulator is risperidone and the psychedelic is O-acetylpsilocin maleate Form A, wherein the risperidone is administered to pretreat at least 270 minutes prior to the O-acetylpsilocin maleate Form A. In some embodiments, the serotonin receptor modulator is risperidone and the psychedelic is 0-acetylpsilocin maleate Form A, wherein the risperidone is administered to pretreat at least 300 minutes prior to the O-acetylpsilocin maleate Form A. In some embodiments, the serotonin receptor modulator is risperidone and the psychedelic is O-acetylpsilocin maleate Form A, wherein the risperidone is administered to pretreat at least 330 minutes prior to the O-acetylpsilocin maleate Form A. In some embodiments, the serotonin receptor modulator is risperidone and the psychedelic is O-acetylpsilocin maleate Form A, wherein the risperidone is administered to pretreat at least 360 minutes prior to the O-acetylpsilocin maleate Form A. In some preferred embodiments, the serotonin receptor modulator is risperidone and the psychedelic is O-acetylpsilocin maleate Form A, wherein risperidone is administered to pretreat between about 60 minutes and about 180 minutes prior to the administration of the O-acetylpsilocin maleate Form A.

In some embodiments, the serotonin receptor modulator is quetiapine and the psychedelic is O-acetylpsilocin maleate Form A, wherein the quetiapine is administered to pretreat at least 15 minutes prior to the administration of the O-acetylpsilocin maleate Form A. In some embodiments, the serotonin receptor modulator is quetiapine and the psychedelic is O-acetylpsilocin maleate Form A, wherein the quetiapine is administered to pretreat at least 30 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat between at least 60 minutes and 240 minutes prior to the administration or release of the O-acetylpsilocin maleate Form A. In some embodiments, the serotonin receptor modulator is quetiapine and the psychedelic is O-acetylpsilocin maleate Form A, wherein the quetiapine is administered to pretreat at least 90 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat at least 120 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat at least 150 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat between about 15 minutes and about 150 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat at least 180 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat at least 210 minutes prior to the O-acetylpsilocin maleate Form A.

In some embodiments, the serotonin receptor modulator is quetiapine and the psychedelic is O-acetylpsilocin maleate Form A, wherein the quetiapine is administered to pretreat at least 240 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat at least 270 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat at least 300 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat at least 330 minutes prior to the O-acetylpsilocin maleate Form A. In some embodiments, the serotonin receptor modulator is quetiapine and the psychedelic is O-acetylpsilocin maleate Form A, wherein the quetiapine is administered to pretreat at least 360 minutes prior to the O-acetylpsilocin maleate Form A. In some preferred embodiments, the serotonin receptor modulator is quetiapine and the psychedelic is O-acetylpsilocin maleate Form A, wherein quetiapine is administered to pretreat between about 60 minutes and about 180 minutes prior to the administration of the O-acetylpsilocin maleate Form A.

In certain embodiments, such as those described above a O-acetylpsilocin form disclosed herein, including those described in Table 19, is co-administered with a serotonin receptor modulator in the same or in separate compositions. In one embodiment, the serotonin receptor modulator is administered after the O-acetylpsilocin form disclosed herein, including those described in Table 19. In one embodiment, the O-acetylpsilocin form disclosed herein, including those described in Table 19, is administered in a modified release formulation such that the subject is effectively post-treated with serotonin receptor modulator prior to release of an effective amount of O-acetylpsilocin. In some embodiments, the serotonin receptor modulator is part of a single fixed dose formulation that releases O-acetylpsilocin first followed by serotonin receptor modulator on two different release profiles. In another embodiment, the O-acetylpsilocin form disclosed herein, including those described in Table 19, is administered first as a single dosage and, after a length of time, serotonin receptor modulator is administered as a second dosage separate from the first dosage. Thus, in some embodiments, the serotonin receptor modulator is administered or released from a composition provided herein after the administration and/or release of the psychedelic. This allows post-treatment to attenuate activation of the serotonin receptor by the psychedelic. In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours after the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours after the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour after the release of the psychedelic.

In a preferred embodiment, the serotonin receptor modulator is administered at about 1 hour to about 3 hours after the administration of the psychedelic.

In some embodiments, the serotonin receptor modulator is eplivanserin and the psychedelic is O-acetylpsilocin, wherein the eplivanserin is administered to post-treat at least 15 minutes after the administration of the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat between at least 30 minutes after and 360 minutes after the release or administration of the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat between at least 60 minutes after and 360 minutes after the release or administration the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat between at least 90 minutes and 240 minutes after the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat at least 120 minutes after the O-acetylpsilocin form disclosed herein, including those described in Table 19.

In some embodiments, the serotonin receptor modulator is eplivanserin and the psychedelic is O-acetylpsilocin, wherein the eplivanserin is administered to post-treat at least 150 minutes after the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat between about 15 minutes and about 150 minutes after the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat at least 180 minutes after the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat at least 210 minutes after the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat at least 240 minutes after the O-acetylpsilocin form disclosed herein, including those described in Table 19.

In some embodiments, the serotonin receptor modulator is eplivanserin and the psychedelic is O-acetylpsilocin, wherein the eplivanserin is administered to post-treat at least 270 minutes after the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat at least 300 minutes after the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat at least 330 minutes after the O-acetylpsilocin form disclosed herein, including those described in Table 19. In some embodiments, the serotonin receptor modulator is eplivanserin and the psychedelic is O-acetylpsilocin, wherein the eplivanserin is administered to post-treat at least 360 minutes after the O-acetylpsilocin form disclosed herein, including those described in Table 19.

In some preferred embodiments, the serotonin receptor modulator is eplivanserin and the psychedelic is O-acetylpsilocin, wherein eplivanserin is administered to post-treat between about 60 minutes and about 180 minutes after the administration of the O-acetylpsilocin form disclosed herein, including those described in Table 19.

In some embodiments, the serotonin receptor modulator is volinanserin and the psychedelic is O-acetylpsilocin, wherein the volinanserin is administered to post-treat a subject between at least 15 minutes and 360 minutes after the administration or release of the O-acetylpsilocin form disclosed herein, including those described in Table 19. In some embodiments, the serotonin receptor modulator is volinanserin and the psychedelic is O-acetylpsilocin, wherein the volinanserin is administered to post-treat between at least 30 minutes and 360 minutes after the administration or release of the O-acetylpsilocin form disclosed herein, including those described in Table 19. In some embodiments, the serotonin receptor modulator is volinanserin and the psychedelic is O-acetylpsilocin, wherein the volinanserin is administered to post-treat between at least 60 minutes and 240 minutes after the administration or release of the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 90 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 120 minutes after the O-acetylpsilocin form disclosed herein, including those described in Table 19.

In some embodiments, the serotonin receptor modulator is volinanserin and the psychedelic is O-acetylpsilocin, wherein the volinanserin is administered to post-treat at least 150 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat between about 15 minutes and about 150 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 180 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 210 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 240 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 270 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 300 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 330 minutes after the O-acetylpsilocin form disclosed herein, including those described in Table 19. In some embodiments, the serotonin receptor modulator is volinanserin and the psychedelic is O-acetylpsilocin, wherein the volinanserin is administered to post-treat at least 360 minutes after the O-acetylpsilocin form disclosed herein, including those described in Table 19. In some preferred embodiments, the serotonin receptor modulator is volinanserin and the psychedelic is O-acetylpsilocin, wherein volinanserin is administered to post-treat between about 60 minutes and about 180 minutes after the administration of O-acetylpsilocin.

In some embodiments, the serotonin receptor modulator is ketanserin and the psychedelic is O-acetylpsilocin, wherein the ketanserin is administered to post-treat at least 15 minutes after the administration of the O-acetylpsilocin form disclosed herein, including those described in Table 19. In some embodiments, the serotonin receptor modulator is ketanserin and the psychedelic is O-acetylpsilocin, wherein the ketanserin is administered to post-treat between at least 30 minutes and 360 minutes after the administration or release of the O-acetylpsilocin form disclosed herein, including those described in Table 19. In some embodiments, the serotonin receptor modulator is ketanserin and the psychedelic is O-acetylpsilocin, wherein the ketanserin is administered to post-treat between at least 60 minutes and 240 minutes after the administration or release of the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 90 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 120 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 150 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat between about 15 minutes and about 150 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 180 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 210 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 240 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 270 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 300 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 330 minutes after the O-acetylpsilocin form disclosed herein, including those described in Table 19. In some embodiments, the serotonin receptor modulator is ketanserin and the psychedelic is O-acetylpsilocin, wherein the ketanserin is administered to post-treat at least 360 minutes after the O-acetylpsilocin form disclosed herein, including those described in Table 19. In some preferred embodiments, the serotonin receptor modulator is ketanserin and the psychedelic is O-acetylpsilocin, wherein ketanserin is administered to post-treat between about 60 minutes and about 180 minutes after the administration of the O-acetylpsilocin form disclosed herein, including those described in Table 19.

In some embodiments, the serotonin receptor modulator is ritanserin and the psychedelic is O-acetylpsilocin, wherein the ritanserin is administered to post-treat at least 15 minutes after the administration of the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 30 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat between at least 60 minutes and 240 minutes after the administration or release of the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 90 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 120 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 150 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat between about 15 minutes and about 150 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 180 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 210 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 240 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 270 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 300 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 330 minutes after the O-acetylpsilocin form disclosed herein, including those described in Table 19. In some embodiments, the serotonin receptor modulator is ritanserin and the psychedelic is O-acetylpsilocin, wherein the ritanserin is administered to post-treat at least 360 minutes after the O-acetylpsilocin form disclosed herein, including those described in Table 19. In some preferred embodiments, the serotonin receptor modulator is ritanserin and the psychedelic is O-acetylpsilocin, wherein ritanserin is administered to post-treat between about 60 minutes and about 180 minutes after administration of the O-acetylpsilocin form disclosed herein, including those described in Table 19.

In some embodiments, the serotonin receptor modulator is pimavanserin and the psychedelic is O-acetylpsilocin, wherein the pimavanserin is administered to post-treat at least 15 minutes after the administration of the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 30 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat between at least 60 minutes and 240 minutes after the administration or release of the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 90 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 120 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 150 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat between about 15 minutes and about 150 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 180 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 210 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 240 minutes after the O-acetylpsilocin form disclosed herein, including those described in Table 19. In some embodiments, the serotonin receptor modulator is pimavanserin and the psychedelic is 0-acetylpsilocin, wherein the pimavanserin is administered to post-treat at least 270 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 300 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 330 minutes after the O-acetylpsilocin form disclosed herein, including those described in Table 19. In some embodiments, the serotonin receptor modulator is pimavanserin and the psychedelic is O-acetylpsilocin, wherein the pimavanserin is administered to post-treat at least 360 minutes after the O-acetylpsilocin form disclosed herein, including those described in Table 19. In some preferred embodiments, the serotonin receptor modulator is pimavanserin and the psychedelic is O-acetylpsilocin, wherein pimavanserin is administered to post-treat between about 60 minutes and about 180 minutes after the administration of the O-acetylpsilocin form disclosed herein, including those described in Table 19.

In some embodiments, the serotonin receptor modulator is nelotanserin and the psychedelic is O-acetylpsilocin, wherein the nelotanserin is administered to post-treat at least 15 minutes after the administration of the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 30 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat between at least 60 minutes and 240 minutes after the administration or release of the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 90 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 120 minutes after the O-acetylpsilocin form disclosed herein, including those described in Table 19.

In some embodiments, the serotonin receptor modulator is nelotanserin and the psychedelic is O-acetylpsilocin, wherein the nelotanserin is administered to post-treat at least 150 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat between about 15 minutes and about 150 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 180 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 210 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 240 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 270 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 300 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 330 minutes after the O-acetylpsilocin form disclosed herein, including those described in Table 19. In some embodiments, the serotonin receptor modulator is nelotanserin and the psychedelic is O-acetylpsilocin, wherein the nelotanserin is administered to post-treat at least 360 minutes after the O-acetylpsilocin form disclosed herein, including those described in Table 19. In some preferred embodiments, the serotonin receptor modulator is nelotanserin and the psychedelic is O-acetylpsilocin, wherein nelotanserin is administered to post-treat between about 60 minutes and about 180 minutes after the administration of the O-acetylpsilocin form disclosed herein, including those described in Table 19.

In some embodiments, the serotonin receptor modulator is pruvanserin and the psychedelic is O-acetylpsilocin, wherein the pruvanserin is administered to post-treat at least 15 minutes after the administration of the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 30 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat between at least 60 minutes and 240 minutes after the administration or release of the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 90 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 120 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 150 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat between about 15 minutes and about 150 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 180 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 210 minutes after the O-acetylpsilocin form disclosed herein, including those described in Table 19.

In some embodiments, the serotonin receptor modulator is pruvanserin and the psychedelic is O-acetylpsilocin, wherein the pruvanserin is administered to post-treat at least 240 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 270 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 300 minutes after the O-acetylpsilocin form disclosed herein, including those described in Table 19. In some embodiments, the serotonin receptor modulator is pruvanserin and psychedelic is O-acetylpsilocin, wherein pruvanserin is administered to post-treat at least 330 minutes after the O-acetylpsilocin form disclosed herein, including those described in Table 19. In some embodiments, the serotonin receptor modulator is pruvanserin and the psychedelic is O-acetylpsilocin, wherein the pruvanserin is administered to post-treat at least 360 minutes after the O-acetylpsilocin form disclosed herein, including those described in Table 19. In some preferred embodiments, the serotonin receptor modulator is pruvanserin and psychedelic is O-acetylpsilocin, wherein pruvanserin is administered to post-treat between about 60 minutes and about 180 minutes after administration of the O-acetylpsilocin form disclosed herein, including those described in Table 19.

In some embodiments, the serotonin receptor modulator is flibanserin, wherein the flibanserin is administered to post-treat at least 15 minutes post to the administration of the O-acetylpsilocin form disclosed herein, including those described in Table 19. In some embodiments, the serotonin receptor modulator is flibanserin, wherein the flibanserin is administered to post-treat at least 30 minutes post to the O-acetylpsilocin form disclosed herein, including those described in Table 19. In some embodiments, the serotonin receptor modulator is flibanserin, wherein the flibanserin is administered to post-treat between at least 60 minutes and 240 minutes post to the administration or release of the O-acetylpsilocin form disclosed herein, including those described in Table 19. In some embodiments, the serotonin receptor modulator is flibanserin, wherein the flibanserin is administered to post-treat at least 90 minutes post to the O-acetylpsilocin form disclosed herein, including those described in Table 19. In some embodiments, the serotonin receptor modulator is flibanserin, wherein the flibanserin is administered to post-treat at least 120 minutes post to the O-acetylpsilocin form disclosed herein, including those described in Table 19. In some embodiments, the serotonin receptor modulator is flibanserin, wherein the flibanserin is administered to post-treat at least 150 minutes post to the O-acetylpsilocin form disclosed herein, including those described in Table 19. In some embodiments, the serotonin receptor modulator is flibanserin, wherein the flibanserin is administered to post-treat between about 15 minutes and about 150 minutes post to the O-acetylpsilocin form disclosed herein, including those described in Table 19. In some embodiments, the serotonin receptor modulator is flibanserin, wherein flibanserin is administered to post-treat at least 180 minutes post to the O-acetylpsilocin form disclosed herein, including those described in Table 19. In some embodiments, the serotonin receptor modulator is flibanserin, wherein flibanserin is administered to post-treat at least 210 minutes post to the O-acetylpsilocin form disclosed herein, including those described in Table 19.

In some embodiments, the serotonin receptor modulator is flibanserin, wherein the flibanserin is administered to post-treat at least 240 minutes post to the O-acetylpsilocin form disclosed herein, including those described in Table 19. In some embodiments, the serotonin receptor modulator is flibanserin, wherein the flibanserin is administered to post-treat at least 270 minutes post to the O-acetylpsilocin form disclosed herein, including those described in Table 19. In some embodiments, the serotonin receptor modulator is flibanserin, wherein the flibanserin is administered to post-treat at least 300 minutes post to the O-acetylpsilocin form disclosed herein, including those described in Table 19. In some embodiments, the serotonin receptor modulator is flibanserin, wherein the flibanserin is administered to post-treat at least 330 minutes post to the O-acetylpsilocin form disclosed herein, including those described in Table 19. In some embodiments, the serotonin receptor modulator is flibanserin, wherein the flibanserin is administered to post-treat at least 360 minutes post to the O-acetylpsilocin form disclosed herein, including those described in Table 19. In some preferred embodiments, the serotonin receptor modulator is flibanserin, wherein flibanserin is administered to post-treat between about 60 minutes and about 180 minutes post to the administration of the O-acetylpsilocin form disclosed herein, including those described in Table 19.

In some embodiments, the serotonin receptor modulator is olanzapine, wherein the olanzapine is administered to post-treat at least 15 minutes post to the administration of the O-acetylpsilocin form disclosed herein, including those described in Table 19. In some embodiments, the serotonin receptor modulator is olanzapine, wherein the olanzapine is administered to post-treat at least 30 minutes post to the O-acetylpsilocin form disclosed herein, including those described in Table 19. In some embodiments, the serotonin receptor modulator is olanzapine, wherein the olanzapine is administered to post-treat between at least 60 minutes and 240 minutes post to the administration or release of the O-acetylpsilocin form disclosed herein, including those described in Table 19. In some embodiments, the serotonin receptor modulator is olanzapine, wherein the olanzapine is administered to post-treat at least 90 minutes post to the O-acetylpsilocin form disclosed herein, including those described in Table 19. In some embodiments, the serotonin receptor modulator is olanzapine, wherein the olanzapine is administered to post-treat at least 120 minutes post to the O-acetylpsilocin form disclosed herein, including those described in Table 19. In some embodiments, the serotonin receptor modulator is olanzapine, wherein the olanzapine is administered to post-treat at least 150 minutes post to the O-acetylpsilocin form disclosed herein, including those described in Table 19. In some embodiments, the serotonin receptor modulator is olanzapine, wherein the olanzapine is administered to post-treat between about 15 minutes and about 150 minutes post to the O-acetylpsilocin form disclosed herein, including those described in Table 19. In some embodiments, the serotonin receptor modulator is olanzapine, wherein the olanzapine is administered to post-treat at least 180 minutes post to the O-acetylpsilocin form disclosed herein, including those described in Table 19. In some embodiments, the serotonin receptor modulator is olanzapine, wherein the olanzapine is administered to post-treat at least 210 minutes post to the O-acetylpsilocin form disclosed herein, including those described in Table 19.

In some embodiments, the serotonin receptor modulator is olanzapine, wherein the olanzapine is administered to post-treat at least 240 minutes post to the O-acetylpsilocin form disclosed herein, including those described in Table 19. In some embodiments, the serotonin receptor modulator is olanzapine, wherein the olanzapine is administered to post-treat at least 270 minutes post to the O-acetylpsilocin form disclosed herein, including those described in Table 19. In some embodiments, the serotonin receptor modulator is olanzapine, wherein the olanzapine is administered to post-treat at least 300 minutes post to the O-acetylpsilocin form disclosed herein, including those described in Table 19. In some embodiments, the serotonin receptor modulator is olanzapine, wherein the olanzapine is administered to post-treat at least 330 minutes post to the O-acetylpsilocin form disclosed herein, including those described in Table 19. In some embodiments, the serotonin receptor modulator is olanzapine, wherein the olanzapine is administered to post-treat at least 360 minutes post to the O-acetylpsilocin form disclosed herein, including those described in Table 19. In some preferred embodiments, the serotonin receptor modulator is olanzapine, wherein olanzapine is administered to post-treat between about 60 minutes and about 180 minutes post to the administration of the O-acetylpsilocin form disclosed herein, including those described in Table 19.

In some embodiments, the serotonin receptor modulator is quetiapine, wherein the quetiapine is administered to post-treat at least 15 minutes post to the administration of the O-acetylpsilocin form disclosed herein, including those described in Table 19. In some embodiments, the serotonin receptor modulator is quetiapine, wherein the quetiapine is administered to post-treat at least 30 minutes post to the O-acetylpsilocin form disclosed herein, including those described in Table 19. In some embodiments, the serotonin receptor modulator is quetiapine, wherein the quetiapine is administered to post-treat between at least 60 minutes and 240 minutes post to the administration or release of the O-acetylpsilocin form disclosed herein, including those described in Table 19. In some embodiments, the serotonin receptor modulator is quetiapine, wherein the quetiapine is administered to post-treat at least 90 minutes post to the O-acetylpsilocin form disclosed herein, including those described in Table 19. In some embodiments, the serotonin receptor modulator is quetiapine, wherein the quetiapine is administered to post-treat at least 120 minutes post to the O-acetylpsilocin form disclosed herein, including those described in Table 19. In some embodiments, the serotonin receptor modulator is quetiapine, wherein the quetiapine is administered to post-treat at least 150 minutes post to the O-acetylpsilocin form disclosed herein, including those described in Table 19. In some embodiments, the serotonin receptor modulator is quetiapine, wherein the quetiapine is administered to post-treat between about 15 minutes and about 150 minutes post to the O-acetylpsilocin form disclosed herein, including those described in Table 19. In some embodiments, the serotonin receptor modulator is quetiapine, wherein the quetiapine is administered to post-treat at least 180 minutes post to the O-acetylpsilocin form disclosed herein, including those described in Table 19. In some embodiments, the serotonin receptor modulator is quetiapine, wherein quetiapine is administered to post-treat at least 210 minutes post to the O-acetylpsilocin form disclosed herein, including those described in Table 19.

In some embodiments, the serotonin receptor modulator is quetiapine, wherein the quetiapine is administered to post-treat at least 240 minutes post to the O-acetylpsilocin form disclosed herein, including those described in Table 19. In some embodiments, the serotonin receptor modulator is quetiapine, wherein the quetiapine is administered to post-treat at least 270 minutes post to the O-acetylpsilocin form disclosed herein, including those described in Table 19. In some embodiments, the serotonin receptor modulator is quetiapine, wherein the quetiapine is administered to post-treat at least 300 minutes post to the O-acetylpsilocin form disclosed herein, including those described in Table 19. In some embodiments, the serotonin receptor modulator is quetiapine, wherein the quetiapine is administered to post-treat at least 330 minutes post to the O-acetylpsilocin form disclosed herein, including those described in Table 19. In some embodiments, the serotonin receptor modulator is quetiapine, wherein the quetiapine is administered to post-treat at least 360 minutes post to the O-acetylpsilocin form disclosed herein, including those described in Table 19. In some preferred embodiments, the serotonin receptor modulator is quetiapine, wherein quetiapine is administered to post-treat between about 60 minutes and about 180 minutes post to the administration of the O-acetylpsilocin form disclosed herein, including those described in Table 19.

In some embodiments, the serotonin receptor modulator is risperidone, wherein the risperidone is administered to post-treat at least 15 minutes post to the administration of the O-acetylpsilocin form disclosed herein, including those described in Table 19. In some embodiments, the serotonin receptor modulator is risperidone, wherein the risperidone is administered to post-treat at least 30 minutes post to the O-acetylpsilocin form disclosed herein, including those described in Table 19. In some embodiments, the serotonin receptor modulator is risperidone, wherein the risperidone is administered to post-treat between at least 60 minutes and 240 minutes post to the administration or release of the O-acetylpsilocin form disclosed herein, including those described in Table 19. In some embodiments, the serotonin receptor modulator is risperidone, wherein the risperidone is administered to post-treat at least 90 minutes post to the O-acetylpsilocin form disclosed herein, including those described in Table 19. In some embodiments, the serotonin receptor modulator is risperidone, wherein the risperidone is administered to post-treat at least 120 minutes post to the O-acetylpsilocin form disclosed herein, including those described in Table 19. In some embodiments, the serotonin receptor modulator is risperidone, wherein the risperidone is administered to post-treat at least 150 minutes post to the O-acetylpsilocin form disclosed herein, including those described in Table 19. In some embodiments, the serotonin receptor modulator is risperidone, wherein the risperidone is administered to post-treat between about 15 minutes and about 150 minutes post to the O-acetylpsilocin form disclosed herein, including those described in Table 19. In some embodiments, the serotonin receptor modulator is risperidone, wherein the risperidone is administered to post-treat at least 180 minutes post to the O-acetylpsilocin form disclosed herein, including those described in Table 19. In some embodiments, the serotonin receptor modulator is risperidone, wherein the risperidone is administered to post-treat at least 210 minutes post to the O-acetylpsilocin form disclosed herein, including those described in Table 19.

In some embodiments, the serotonin receptor modulator is risperidone, wherein the risperidone is administered to post-treat at least 240 minutes post to the O-acetylpsilocin form disclosed herein, including those described in Table 19. In some embodiments, the serotonin receptor modulator is risperidone, wherein the risperidone is administered to post-treat at least 270 minutes post to the O-acetylpsilocin form disclosed herein, including those described in Table 19. In some embodiments, the serotonin receptor modulator is risperidone, wherein the risperidone is administered to post-treat at least 300 minutes post to the O-acetylpsilocin form disclosed herein, including those described in Table 19. In some embodiments, the serotonin receptor modulator is risperidone, wherein the risperidone is administered to post-treat at least 330 minutes post to the O-acetylpsilocin form disclosed herein, including those described in Table 19. In some embodiments, the serotonin receptor modulator is risperidone, wherein the risperidone is administered to post-treat at least 360 minutes post to the O-acetylpsilocin form disclosed herein, including those described in Table 19. In some preferred embodiments, the serotonin receptor modulator is risperidone, wherein risperidone is administered to post-treat between about 60 minutes and about 180 minutes post to the administration of the O-acetylpsilocin form disclosed herein, including those described in Table 19.

In some embodiments, the serotonin receptor modulator is eplivanserin and the psychedelic is O-acetylpsilocin maleate Form A, wherein the eplivanserin is administered to post-treat at least 15 minutes after the administration of the O-acetylpsilocin maleate Form A. In some embodiments, the serotonin receptor modulator is eplivanserin and the psychedelic is O-acetylpsilocin maleate Form A, wherein the eplivanserin is administered to post-treat between at least 30 minutes after and 360 minutes after the release or administration of O-acetylpsilocin maleate Form A. In some embodiments, the serotonin receptor modulator is eplivanserin and the psychedelic is O-acetylpsilocin maleate Form A, wherein the eplivanserin is administered to post-treat between at least 60 minutes after and 360 minutes after the release or administration of the O-acetylpsilocin maleate Form A. In some embodiments, the serotonin receptor modulator is eplivanserin and the psychedelic is O-acetylpsilocin maleate Form A, wherein the eplivanserin is administered to post-treat between at least 90 minutes and 240 minutes after the O-acetylpsilocin maleate Form A. In some embodiments, the serotonin receptor modulator is eplivanserin and psychedelic is O-acetylpsilocin maleate Form A, wherein eplivanserin is administered to post-treat at least 120 minutes after O-acetylpsilocin maleate Form A.

In some embodiments, the serotonin receptor modulator is eplivanserin and the psychedelic is O-acetylpsilocin maleate Form A, wherein the eplivanserin is administered to post-treat at least 150 minutes after the O-acetylpsilocin maleate Form A. In some embodiments, the serotonin receptor modulator is eplivanserin and the psychedelic is O-acetylpsilocin maleate Form A, wherein the eplivanserin is administered to post-treat between about 15 minutes and about 150 minutes after the O-acetylpsilocin maleate Form A. In some embodiments, the serotonin receptor modulator is eplivanserin and the psychedelic is O-acetylpsilocin maleate Form A, wherein the eplivanserin is administered to post-treat at least 180 minutes after the O-acetylpsilocin maleate Form A. In some embodiments, the serotonin receptor modulator is eplivanserin and the psychedelic is O-acetylpsilocin maleate Form A, wherein the eplivanserin is administered to post-treat at least 210 minutes after the O-acetylpsilocin maleate Form A. In some embodiments, the serotonin receptor modulator is eplivanserin and the psychedelic is O-acetylpsilocin maleate Form A, wherein the eplivanserin is administered to post-treat at least 240 minutes after the O-acetylpsilocin maleate Form A.

In some embodiments, the serotonin receptor modulator is eplivanserin and the psychedelic is O-acetylpsilocin maleate Form A, wherein the eplivanserin is administered to post-treat at least 270 minutes after the O-acetylpsilocin maleate Form A. In some embodiments, the serotonin receptor modulator is eplivanserin and the psychedelic is O-acetylpsilocin maleate Form A, wherein the eplivanserin is administered to post-treat at least 300 minutes after the O-acetylpsilocin maleate Form A. In some embodiments, the serotonin receptor modulator is eplivanserin and the psychedelic is O-acetylpsilocin maleate Form A, wherein the eplivanserin is administered to post-treat at least 330 minutes after the O-acetylpsilocin maleate Form A. In some embodiments, the serotonin receptor modulator is eplivanserin and psychedelic is O-acetylpsilocin maleate Form A, wherein eplivanserin is administered to post-treat at least 360 minutes after the O-acetylpsilocin maleate Form A.

In some preferred embodiments, the serotonin receptor modulator is eplivanserin and the psychedelic is O-acetylpsilocin maleate Form A, wherein eplivanserin is administered to post-treat between about 60 minutes and about 180 minutes after the administration of the O-acetylpsilocin maleate Form A.

In some embodiments, the serotonin receptor modulator is volinanserin and the psychedelic is O-acetylpsilocin maleate Form A, wherein the volinanserin is administered to post-treat a subject between at least 15 minutes and 360 minutes after the administration or release of the O-acetylpsilocin maleate Form A. In some embodiments, the serotonin receptor modulator is volinanserin and the psychedelic is O-acetylpsilocin maleate Form A, wherein the volinanserin is administered to post-treat between at least 30 minutes and 360 minutes after the administration or release of the O-acetylpsilocin maleate Form A. In some embodiments, the serotonin receptor modulator is volinanserin and the psychedelic is O-acetylpsilocin maleate Form A, wherein the volinanserin is administered to post-treat between at least 60 minutes and 240 minutes after the administration or release of the O-acetylpsilocin maleate Form A. In some embodiments, the serotonin receptor modulator is volinanserin and the psychedelic is O-acetylpsilocin maleate Form A, wherein the volinanserin is administered to post-treat at least 90 minutes after psilocybin HCl. In some embodiments, the serotonin receptor modulator is volinanserin and the psychedelic is O-acetylpsilocin maleate Form A, wherein the volinanserin is administered to post-treat at least 120 minutes after the O-acetylpsilocin maleate Form A.

In some embodiments, the serotonin receptor modulator is volinanserin and the psychedelic is O-acetylpsilocin maleate Form A, wherein the volinanserin is administered to post-treat at least 150 minutes after the O-acetylpsilocin maleate Form A. In some embodiments, the serotonin receptor modulator is volinanserin and the psychedelic is O-acetylpsilocin maleate Form A, wherein the volinanserin is administered to post-treat between about 15 minutes and about 150 minutes after the O-acetylpsilocin maleate Form A. In some embodiments, the serotonin receptor modulator is volinanserin and the psychedelic is O-acetylpsilocin maleate Form A, wherein the volinanserin is administered to post-treat at least 180 minutes after the O-acetylpsilocin maleate Form A. In some embodiments, the serotonin receptor modulator is volinanserin and the psychedelic is O-acetylpsilocin maleate Form A, wherein the volinanserin is administered to post-treat at least 210 minutes after the O-acetylpsilocin maleate Form A. In some embodiments, the serotonin receptor modulator is volinanserin and the psychedelic is O-acetylpsilocin maleate Form A, wherein the volinanserin is administered to post-treat at least 240 minutes after the O-acetylpsilocin maleate Form A. In some embodiments, the serotonin receptor modulator is volinanserin and the psychedelic is O-acetylpsilocin maleate Form A, wherein the volinanserin is administered to post-treat at least 270 minutes after the O-acetylpsilocin maleate Form A. In some embodiments, the serotonin receptor modulator is volinanserin and the psychedelic is O-acetylpsilocin maleate Form A, wherein the volinanserin is administered to post-treat at least 300 minutes after the O-acetylpsilocin maleate Form A. In some embodiments, the serotonin receptor modulator is volinanserin and the psychedelic is O-acetylpsilocin maleate Form A, wherein the volinanserin is administered to post-treat at least 330 minutes after the O-acetylpsilocin maleate Form A. In some embodiments, the serotonin receptor modulator is volinanserin and the psychedelic is O-acetylpsilocin maleate Form A, wherein the volinanserin is administered to post-treat at least 360 minutes after the O-acetylpsilocin maleate Form A. In some preferred embodiments, the serotonin receptor modulator is volinanserin and the psychedelic is O-acetylpsilocin maleate Form A, wherein volinanserin is administered to post-treat between about 60 minutes and about 180 minutes after the administration of the ®-MDMA form.

In some embodiments, the serotonin receptor modulator is ketanserin and the psychedelic is O-acetylpsilocin maleate Form A, wherein the ketanserin is administered to post-treat at least 15 minutes after the administration of the O-acetylpsilocin maleate Form A. In some embodiments, the serotonin receptor modulator is ketanserin and the psychedelic is O-acetylpsilocin maleate Form A, wherein the ketanserin is administered to post-treat between at least 30 minutes and 360 minutes after the administration or release of the O-acetylpsilocin maleate Form A. In some embodiments, the serotonin receptor modulator is ketanserin and the psychedelic is O-acetylpsilocin maleate Form A, wherein the ketanserin is administered to post-treat between at least 60 minutes and 240 minutes after the administration or release of the O-acetylpsilocin maleate Form A. In some embodiments, the serotonin receptor modulator is ketanserin and the psychedelic is O-acetylpsilocin maleate Form A, wherein the ketanserin is administered to post-treat at least 90 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 120 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 150 minutes after the O-acetylpsilocin maleate Form A. In some embodiments, the serotonin receptor modulator is ketanserin and the psychedelic is O-acetylpsilocin maleate Form A, wherein the ketanserin is administered to post-treat between about 15 minutes and about 150 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 180 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 210 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 240 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 270 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 300 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 330 minutes after the O-acetylpsilocin maleate Form A. In some embodiments, the serotonin receptor modulator is ketanserin and the psychedelic is O-acetylpsilocin maleate Form A, wherein the ketanserin is administered to post-treat at least 360 minutes after the O-acetylpsilocin maleate Form A. In some preferred embodiments, the serotonin receptor modulator is ketanserin and the psychedelic is O-acetylpsilocin maleate Form A, wherein ketanserin is administered to post-treat between about 60 minutes and about 180 minutes after the administration of the O-acetylpsilocin maleate Form A.

In some embodiments, the serotonin receptor modulator is ritanserin and the psychedelic is O-acetylpsilocin maleate Form A, wherein the ritanserin is administered to post-treat at least 15 minutes after the administration of the O-acetylpsilocin maleate Form A. In some embodiments, the serotonin receptor modulator is ritanserin and the psychedelic is O-acetylpsilocin maleate Form A, wherein the ritanserin is administered to post-treat at least 30 minutes after the O-acetylpsilocin maleate Form A. In some embodiments, the serotonin receptor modulator is ritanserin and the psychedelic is O-acetylpsilocin maleate Form A, wherein the ritanserin is administered to post-treat between at least 60 minutes and 240 minutes after the administration or release of the O-acetylpsilocin maleate Form A. In some embodiments, the serotonin receptor modulator is ritanserin and the psychedelic is O-acetylpsilocin maleate Form A, wherein the ritanserin is administered to post-treat at least 90 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 120 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 150 minutes after the O-acetylpsilocin maleate Form A. In some embodiments, the serotonin receptor modulator is ritanserin and the psychedelic is O-acetylpsilocin maleate Form A, wherein the ritanserin is administered to post-treat between about 15 minutes and about 150 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 180 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 210 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 240 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 270 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 300 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 330 minutes after the O-acetylpsilocin maleate Form A. In some embodiments, the serotonin receptor modulator is ritanserin and the psychedelic is O-acetylpsilocin maleate Form A, wherein the ritanserin is administered to post-treat at least 360 minutes after the O-acetylpsilocin maleate Form A. In some preferred embodiments, the serotonin receptor modulator is ritanserin and the psychedelic is O-acetylpsilocin maleate Form A, wherein ritanserin is administered to post-treat between about 60 minutes and about 180 minutes after the administration of the O-acetylpsilocin maleate Form A.

In some embodiments, the serotonin receptor modulator is pimavanserin and the psychedelic is O-acetylpsilocin maleate Form A, wherein the pimavanserin is administered to post-treat at least 15 minutes after the administration of the O-acetylpsilocin maleate Form A. In some embodiments, the serotonin receptor modulator is pimavanserin and the psychedelic is O-acetylpsilocin maleate Form A, wherein the pimavanserin is administered to post-treat at least 30 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat between at least 60 minutes and 240 minutes after the administration or release of the O-acetylpsilocin maleate Form A. In some embodiments, the serotonin receptor modulator is pimavanserin and the psychedelic is O-acetylpsilocin maleate Form A, wherein the pimavanserin is administered to post-treat at least 90 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 120 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 150 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat between about 15 minutes and about 150 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 180 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 210 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 240 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 270 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 300 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 330 minutes after the O-acetylpsilocin maleate Form A. In some embodiments, the serotonin receptor modulator is pimavanserin and the psychedelic is O-acetylpsilocin maleate Form A, wherein the pimavanserin is administered to post-treat at least 360 minutes after the O-acetylpsilocin maleate Form A. In some preferred embodiments, the serotonin receptor modulator is pimavanserin and the psychedelic is O-acetylpsilocin maleate Form A, wherein pimavanserin is administered to post-treat between about 60 minutes and about 180 minutes after the administration of the O-acetylpsilocin maleate Form A.

In some embodiments, the serotonin receptor modulator is nelotanserin and the psychedelic is O-acetylpsilocin maleate Form A, wherein the nelotanserin is administered to post-treat at least 15 minutes after the administration of the O-acetylpsilocin maleate Form A. In some embodiments, the serotonin receptor modulator is nelotanserin and the psychedelic is O-acetylpsilocin maleate Form A, wherein the nelotanserin is administered to post-treat at least 30 minutes after the O-acetylpsilocin maleate Form A. In some embodiments, the serotonin receptor modulator is nelotanserin and the psychedelic is O-acetylpsilocin maleate Form A, wherein the nelotanserin is administered to post-treat between at least 60 minutes and 240 minutes after the administration or release of the O-acetylpsilocin maleate Form A. In some embodiments, the serotonin receptor modulator is nelotanserin and the psychedelic is O-acetylpsilocin maleate Form A, wherein the nelotanserin is administered to post-treat at least 90 minutes after the O-acetylpsilocin maleate Form A. In some embodiments, the serotonin receptor modulator is nelotanserin and the psychedelic is O-acetylpsilocin maleate Form A, wherein nelotanserin is administered to post-treat at least 120 minutes after O-acetylpsilocin maleate Form A.

In some embodiments, the serotonin receptor modulator is nelotanserin and the psychedelic is O-acetylpsilocin maleate Form A, wherein the nelotanserin is administered to post-treat at least 150 minutes after the O-acetylpsilocin maleate Form A. In some embodiments, the serotonin receptor modulator is nelotanserin and the psychedelic is O-acetylpsilocin maleate Form A, wherein the nelotanserin is administered to post-treat between about 15 minutes and about 150 minutes after the O-acetylpsilocin maleate Form A. In some embodiments, the serotonin receptor modulator is nelotanserin and the psychedelic is O-acetylpsilocin maleate Form A, wherein the nelotanserin is administered to post-treat at least 180 minutes after the O-acetylpsilocin maleate Form A. In some embodiments, the serotonin receptor modulator is nelotanserin and the psychedelic is O-acetylpsilocin maleate Form A, wherein the nelotanserin is administered to post-treat at least 210 minutes after the O-acetylpsilocin maleate Form A. In some embodiments, the serotonin receptor modulator is nelotanserin and the psychedelic is O-acetylpsilocin maleate Form A, wherein the nelotanserin is administered to post-treat at least 240 minutes after the O-acetylpsilocin maleate Form A. In some embodiments, the serotonin receptor modulator is nelotanserin and the psychedelic is O-acetylpsilocin maleate Form A, wherein the nelotanserin is administered to post-treat at least 270 minutes after the O-acetylpsilocin maleate Form A.

In some embodiments, the serotonin receptor modulator is nelotanserin and the psychedelic is O-acetylpsilocin maleate Form A, wherein the nelotanserin is administered to post-treat at least 300 minutes after the O-acetylpsilocin maleate Form A. In some embodiments, the serotonin receptor modulator is nelotanserin and the psychedelic is O-acetylpsilocin maleate Form A, wherein the nelotanserin is administered to post-treat at least 330 minutes after the O-acetylpsilocin maleate Form A. In some embodiments, the serotonin receptor modulator is nelotanserin and the psychedelic is O-acetylpsilocin maleate Form A, wherein the nelotanserin is administered to post-treat at least 360 minutes after the O-acetylpsilocin maleate Form A. In some preferred embodiments, the serotonin receptor modulator is nelotanserin and the psychedelic is O-acetylpsilocin maleate Form A, wherein nelotanserin is administered to post-treat between about 60 minutes and about 180 minutes after the administration of the O-acetylpsilocin maleate Form A.

In some embodiments, the serotonin receptor modulator is pruvanserin and the psychedelic is O-acetylpsilocin maleate Form A, wherein the pruvanserin is administered to post-treat at least 15 minutes after the administration of the O-acetylpsilocin maleate Form A. In some embodiments, the serotonin receptor modulator is pruvanserin and the psychedelic is O-acetylpsilocin maleate Form A, wherein the pruvanserin is administered to post-treat at least 30 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat between at least 60 minutes and 240 minutes after the administration or release of the O-acetylpsilocin maleate Form A. In some embodiments, the serotonin receptor modulator is pruvanserin and the psychedelic is O-acetylpsilocin maleate Form A, wherein the pruvanserin is administered to post-treat at least 90 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat at least 120 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat at least 150 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat between about 15 minutes and about 150 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat at least 180 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat at least 210 minutes after the O-acetylpsilocin maleate Form A.

In some embodiments, the serotonin receptor modulator is pruvanserin and the psychedelic is O-acetylpsilocin maleate Form A, wherein the pruvanserin is administered to post-treat at least 240 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat at least 270 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat at least 300 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat at least 330 minutes after the O-acetylpsilocin maleate Form A. In some embodiments, the serotonin receptor modulator is pruvanserin and the psychedelic is O-acetylpsilocin maleate Form A, wherein the pruvanserin is administered to post-treat at least 360 minutes after the O-acetylpsilocin maleate Form A. In some preferred embodiments, the serotonin receptor modulator is pruvanserin and the psychedelic is O-acetylpsilocin maleate Form A, wherein pruvanserin is administered to post-treat between about 60 minutes and about 180 minutes after the administration of the O-acetylpsilocin maleate Form A.

In some embodiments, the serotonin receptor modulator is flibanserin, wherein the flibanserin is administered to post-treat at least 15 minutes post to the administration of the O-acetylpsilocin maleate Form A. In some embodiments, the serotonin receptor modulator is flibanserin, wherein the flibanserin is administered to post-treat at least 30 minutes post to the O-acetylpsilocin maleate Form A. In some embodiments, the serotonin receptor modulator is flibanserin, wherein the flibanserin is administered to post-treat between at least 60 minutes and 240 minutes post to the administration or release of the O-acetylpsilocin maleate Form A. In some embodiments, the serotonin receptor modulator is flibanserin, wherein the flibanserin is administered to post-treat at least 90 minutes post to the O-acetylpsilocin maleate Form A. In some embodiments, the serotonin receptor modulator is flibanserin, wherein the flibanserin is administered to post-treat at least 120 minutes post to the O-acetylpsilocin maleate Form A. In some embodiments, the serotonin receptor modulator is flibanserin, wherein the flibanserin is administered to post-treat at least 150 minutes post to the O-acetylpsilocin maleate Form A. In some embodiments, the serotonin receptor modulator is flibanserin, wherein the flibanserin is administered to post-treat between about 15 minutes and about 150 minutes post to the O-acetylpsilocin maleate Form A. In some embodiments, the serotonin receptor modulator is flibanserin, wherein the flibanserin is administered to post-treat at least 180 minutes post to the O-acetylpsilocin maleate Form A. In some embodiments, the serotonin receptor modulator is flibanserin, wherein the flibanserin is administered to post-treat at least 210 minutes post to the O-acetylpsilocin maleate Form A.

In some embodiments, the serotonin receptor modulator is flibanserin, wherein the flibanserin is administered to post-treat at least 240 minutes post to the O-acetylpsilocin maleate Form A. In some embodiments, the serotonin receptor modulator is flibanserin, wherein the flibanserin is administered to post-treat at least 270 minutes post to the O-acetylpsilocin maleate Form A. In some embodiments, the serotonin receptor modulator is flibanserin, wherein the flibanserin is administered to post-treat at least 300 minutes post to the O-acetylpsilocin maleate Form A. In some embodiments, the serotonin receptor modulator is flibanserin, wherein the flibanserin is administered to post-treat at least 330 minutes post to the O-acetylpsilocin maleate Form A. In some embodiments, the serotonin receptor modulator is flibanserin, wherein the flibanserin is administered to post-treat at least 360 minutes post to the O-acetylpsilocin maleate Form A. In some preferred embodiments, the serotonin receptor modulator is flibanserin, wherein flibanserin is administered to post-treat between about 60 minutes and about 180 minutes post to the administration of the O-acetylpsilocin maleate Form A.

In some embodiments, the serotonin receptor modulator is olanzapine, wherein the olanzapine is administered to post-treat at least 15 minutes post to the administration of the O-acetylpsilocin maleate Form A. In some embodiments, the serotonin receptor modulator is olanzapine, wherein the olanzapine is administered to post-treat at least 30 minutes post to the O-acetylpsilocin maleate Form A. In some embodiments, the serotonin receptor modulator is olanzapine, wherein the olanzapine is administered to post-treat between at least 60 minutes and 240 minutes post to the administration or release of the O-acetylpsilocin maleate Form A. In some embodiments, the serotonin receptor modulator is olanzapine, wherein the olanzapine is administered to post-treat at least 90 minutes post to the O-acetylpsilocin maleate Form A. In some embodiments, the serotonin receptor modulator is olanzapine, wherein the olanzapine is administered to post-treat at least 120 minutes post to the O-acetylpsilocin maleate Form A. In some embodiments, the serotonin receptor modulator is olanzapine, wherein the olanzapine is administered to post-treat at least 150 minutes post to the O-acetylpsilocin maleate Form A. In some embodiments, the serotonin receptor modulator is olanzapine, wherein the olanzapine is administered to post-treat between about 15 minutes and about 150 minutes post to the O-acetylpsilocin maleate Form A. In some embodiments, the serotonin receptor modulator is olanzapine, wherein the olanzapine is administered to post-treat at least 180 minutes post to the O-acetylpsilocin maleate Form A. In some embodiments, the serotonin receptor modulator is olanzapine, wherein the olanzapine is administered to post-treat at least 210 minutes post to the O-acetylpsilocin maleate Form A.

In some embodiments, the serotonin receptor modulator is olanzapine, wherein the olanzapine is administered to post-treat at least 240 minutes post to the O-acetylpsilocin maleate Form A. In some embodiments, the serotonin receptor modulator is olanzapine, wherein the olanzapine is administered to post-treat at least 270 minutes post to the O-acetylpsilocin maleate Form A. In some embodiments, the serotonin receptor modulator is olanzapine, wherein the olanzapine is administered to post-treat at least 300 minutes post to the O-acetylpsilocin maleate Form A. In some embodiments, the serotonin receptor modulator is olanzapine, wherein the olanzapine is administered to post-treat at least 330 minutes post to the O-acetylpsilocin maleate Form A. In some embodiments, the serotonin receptor modulator is olanzapine, wherein the olanzapine is administered to post-treat at least 360 minutes post to the O-acetylpsilocin maleate Form A. In some preferred embodiments, the serotonin receptor modulator is olanzapine, wherein olanzapine is administered to post-treat between about 60 minutes and about 180 minutes post to the administration of the O-acetylpsilocin maleate Form A.

In some embodiments, the serotonin receptor modulator is quetiapine, wherein the quetiapine is administered to post-treat at least 15 minutes post to the administration of the O-acetylpsilocin maleate Form A. In some embodiments, the serotonin receptor modulator is quetiapine, wherein the quetiapine is administered to post-treat at least 30 minutes post to the O-acetylpsilocin maleate Form A. In some embodiments, the serotonin receptor modulator is quetiapine, wherein the quetiapine is administered to post-treat between at least 60 minutes and 240 minutes post to the administration or release of the O-acetylpsilocin maleate Form A. In some embodiments, the serotonin receptor modulator is quetiapine, wherein the quetiapine is administered to post-treat at least 90 minutes post to the O-acetylpsilocin maleate Form A. In some embodiments, the serotonin receptor modulator is quetiapine, wherein the quetiapine is administered to post-treat at least 120 minutes post to the O-acetylpsilocin maleate Form A. In some embodiments, the serotonin receptor modulator is quetiapine, wherein the quetiapine is administered to post-treat at least 150 minutes post to the O-acetylpsilocin maleate Form A. In some embodiments, the serotonin receptor modulator is quetiapine, wherein the quetiapine is administered to post-treat between about 15 minutes and about 150 minutes post to the O-acetylpsilocin maleate Form A. In some embodiments, the serotonin receptor modulator is quetiapine, wherein the quetiapine is administered to post-treat at least 180 minutes post to the O-acetylpsilocin maleate Form A. In some embodiments, the serotonin receptor modulator is quetiapine, wherein the quetiapine is administered to post-treat at least 210 minutes post to the O-acetylpsilocin maleate Form A.

In some embodiments, the serotonin receptor modulator is quetiapine, wherein the quetiapine is administered to post-treat at least 240 minutes post to the O-acetylpsilocin maleate Form A. In some embodiments, the serotonin receptor modulator is quetiapine, wherein the quetiapine is administered to post-treat at least 270 minutes post to the O-acetylpsilocin maleate Form A. In some embodiments, the serotonin receptor modulator is quetiapine, wherein the quetiapine is administered to post-treat at least 300 minutes post to the O-acetylpsilocin maleate Form A. In some embodiments, the serotonin receptor modulator is quetiapine, wherein the quetiapine is administered to post-treat at least 330 minutes post to the O-acetylpsilocin maleate Form A. In some embodiments, the serotonin receptor modulator is quetiapine, wherein the quetiapine is administered to post-treat at least 360 minutes post to the O-acetylpsilocin maleate Form A. In some preferred embodiments, the serotonin receptor modulator is quetiapine, wherein quetiapine is administered to post-treat between about 60 minutes and about 180 minutes post to the administration of the O-acetylpsilocin maleate Form A.

In some embodiments, the serotonin receptor modulator is risperidone, wherein the risperidone is administered to post-treat at least 15 minutes post to the administration of the O-acetylpsilocin maleate Form A. In some embodiments, the serotonin receptor modulator is risperidone, wherein the risperidone is administered to post-treat at least 30 minutes post to the O-acetylpsilocin maleate Form A. In some embodiments, the serotonin receptor modulator is risperidone, wherein the risperidone is administered to post-treat between at least 60 minutes and 240 minutes post to the administration or release of the O-acetylpsilocin maleate Form A. In some embodiments, the serotonin receptor modulator is risperidone, wherein the risperidone is administered to post-treat at least 90 minutes post to the O-acetylpsilocin maleate Form A. In some embodiments, the serotonin receptor modulator is risperidone, wherein the risperidone is administered to post-treat at least 120 minutes post to the O-acetylpsilocin maleate Form A. In some embodiments, the serotonin receptor modulator is risperidone, wherein the risperidone is administered to post-treat at least 150 minutes post to the O-acetylpsilocin maleate Form A. In some embodiments, the serotonin receptor modulator is risperidone, wherein the risperidone is administered to post-treat between about 15 minutes and about 150 minutes post to the O-acetylpsilocin maleate Form A. In some embodiments, the serotonin receptor modulator is risperidone, wherein the risperidone is administered to post-treat at least 180 minutes post to the O-acetylpsilocin maleate Form A. In some embodiments, the serotonin receptor modulator is risperidone, wherein the risperidone is administered to post-treat at least 210 minutes post to the O-acetylpsilocin maleate Form A.

In some embodiments, the serotonin receptor modulator is risperidone, wherein the risperidone is administered to post-treat at least 240 minutes post to the O-acetylpsilocin maleate Form A. In some embodiments, the serotonin receptor modulator is risperidone, wherein the risperidone is administered to post-treat at least 270 minutes post to the O-acetylpsilocin maleate Form A. In some embodiments, the serotonin receptor modulator is risperidone, wherein the risperidone is administered to post-treat at least 300 minutes post to the O-acetylpsilocin maleate Form A. In some embodiments, the serotonin receptor modulator is risperidone, wherein the risperidone is administered to post-treat at least 330 minutes post to the O-acetylpsilocin maleate Form A. In some embodiments, the serotonin receptor modulator is risperidone, wherein the risperidone is administered to post-treat at least 360 minutes post to the O-acetylpsilocin maleate Form A. In some preferred embodiments, the serotonin receptor modulator is risperidone, wherein risperidone is administered to post-treat between about 60 minutes and about 180 minutes post to the administration of the O-acetylpsilocin maleate Form A.

Combinations with O-Acetylpsilocin Fumarate

In another embodiment of such combination therapy, a form of O-acetylpsilocin-fumarate described herein is administered in combination with a serotonin receptor modulator. In certain embodiments the serotonin receptor modulator is selected from the group consisting of altanserin, blonanserin, eplivanserin, glemanserin, volinanserin, ketanserin, ritanserin, pimavanserin, nelotanserin, pruvanserin, and flibanserin. In one embodiment, the serotonin receptor modulator is selected from the group consisting of serotonin receptor modulator is selected from the group consisting of eplivanserin, volinanserin, ketanserin, ritanserin, pimavanserin, nelotanserin, pruvanserin, and flibanserin.

In some embodiments, the serotonin receptor modulator for use with the O-acetylpsilocin fumarate form disclosed herein, including those described in Table 32, is eplivanserin, wherein the eplivanserin is administered in about 1 mg to about 40 mg, or about 5 mg to about 10 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is volinanserin, wherein the volinanserin is administered in about 1 mg to about 60 mg, or about 5 mg to about 20 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is ketanserin, wherein the ketanserin is administered in about 10 mg to about 80 mg, about 30 mg to about 50 mg, or about 40 mg and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is ritanserin, wherein the ritanserin is administered in about 1 mg to about 40 mg, or about 2.5 mg to about 10 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is pimavanserin, wherein the pimavanserin is administered in about 1 mg to about 60 mg, or about 17 mg to about 34 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is nelotanserin, wherein the nelotanserin is administered in about 1 mg to about 80 mg, or about 40 mg to about 80 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is pruvanserin, wherein the pruvanserin is administered in about 1 mg to about 40 mg, or about 3 mg to about 10 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is flibanserin, wherein the flibanserin is administered in about 10 mg to about 200 mg, or about 80 mg to about 120 mg, or about 100 mg and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is olanzapine, wherein the olanzapine is administered in about 2.5 mg to about 30 mg, or about 5 mg or about 10 mg, or about 20 mg or about 25 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is an extended-release of olanzapine such as ZYPREXA RELPREVV®, wherein the extended release olanzapine is administered in about 50 mg to about 450 mg, or about 150 mg or about 210 mg, or about 300 mg or about 405 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is quetiapine, wherein the quetiapine is administered in about 25 mg to about 800 mg, or about 50 mg to about 100 mg, or about 150 mg or about 200 mg or about 250 mg or about 300 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is an extended-release of quetiapine, wherein the extended-release of quetiapine is administered in about 50 mg to about 300 mg, or about 50 mg or about 100 mg or about 200 mg, or about 300 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the O-acetylpsilocin fumarate form disclosed herein, including those described in Table 32, is an extended-release of risperidone including (RISPERDAL CONSTA®), wherein the extended-release of risperidone is administered in about 12.5 mg, or about 25 mg, or about 37.5 mg, or about 50 mg, and the O-acetylpsilocin fumarate form disclosed herein, including those described in Table 32, is administered between about 5 mg to about 50 mg, or about 10 mg to about 25 mg.

In some embodiments, the serotonin receptor modulator for use with the psychedelic O-acetylpsilocin fumarate is eplivanserin, wherein the eplivanserin is administered in about 1 mg to about 40 mg, or about 5 mg to about 10 mg, and the O-acetylpsilocin fumarate is administered between about 5 mg to about 50 mg, or about 10 mg to about 25 mg. In some embodiments, the amount of the O-acetylpsilocin fumarate is provided on an O-acetylpsilocin basis.

In some embodiments, the serotonin receptor modulator is volinanserin and the psychedelic is O-acetylpsilocin fumarate, wherein the volinanserin is administered in about 1 mg to about 60 mg, or about 5 mg to about 20 mg, and the O-acetylpsilocin fumarate is administered between about 5 mg to about 50 mg, or about 10 mg to about 25 mg. In some embodiments, the amount of the O-acetylpsilocin fumarate is provided on an O-acetylpsilocin basis.

In some embodiments, the serotonin receptor modulator for use with the psychedelic O-acetylpsilocin fumarate is ketanserin, wherein the ketanserin is administered in about 10 mg to about 80 mg, about 30 mg to about 50 mg, or about 40 mg and the O-acetylpsilocin fumarate is administered between about 5 mg to about 50 mg, or about 10 mg to about 25 mg. In some embodiments, the amount of the O-acetylpsilocin fumarate is provided on an O-acetylpsilocin basis.

In some embodiments, the serotonin receptor modulator for use with the psychedelic O-acetylpsilocin fumarate is ritanserin, wherein the ritanserin is administered in about 1 mg to about 40 mg, or about 2.5 mg to about 10 mg, and the O-acetylpsilocin fumarate is administered between about 5 mg to about 50 mg, or about 10 mg to about 25 mg. In some embodiments, the amount of the O-acetylpsilocin fumarate is provided on an O-acetylpsilocin basis.

In some embodiments, the serotonin receptor modulator is pimavanserin and the psychedelic is O-acetylpsilocin fumarate, wherein the pimavanserin is administered in about 1 mg to about 60 mg, or about 17 mg to about 34 mg, and the O-acetylpsilocin fumarate is administered between about 5 mg to about 50 mg, or about 10 mg to about 25 mg. In some embodiments, the amount of the O-acetylpsilocin fumarate is provided on an O-acetylpsilocin basis.

In some embodiments, the serotonin receptor modulator for use with the psychedelic O-acetylpsilocin fumarate is nelotanserin, wherein the nelotanserin is administered in about 1 mg to about 80 mg, or about 40 mg to about 80 mg, and the O-acetylpsilocin fumarate is administered between about 5 mg to about 50 mg, or about 10 mg to about 25 mg. In some embodiments, the amount of the O-acetylpsilocin fumarate is provided on an O-acetylpsilocin basis.

In some embodiments, the serotonin receptor modulator for use with the psychedelic O-acetylpsilocin fumarate is pruvanserin, wherein the pruvanserin is administered in about 1 mg to about 40 mg, or about 3 mg to about 10 mg, and the O-acetylpsilocin fumarate is administered between about 5 mg to about 50 mg, or about 10 mg to about 25 mg. In some embodiments, the amount of the O-acetylpsilocin fumarate is provided on an O-acetylpsilocin basis.

In some embodiments, the serotonin receptor modulator for use with the psychedelic O-acetylpsilocin fumarate is flibanserin, wherein the flibanserin is administered in about 10 mg to about 200 mg, or about 80 mg to about 120 mg, or about 100 mg and the O-acetylpsilocin fumarate is administered between about 5 mg to about 50 mg, or about 10 mg to about 25 mg. In some embodiments, the amount of the O-acetylpsilocin fumarate is provided on an O-acetylpsilocin basis.

In certain embodiments, such as those described above a disclosed O-acetylpsilocin fumarate form, including those described in Table 32, is co-administered with a serotonin receptor modulator in the same or in separate compositions. In one embodiment, the O-acetylpsilocin fumarate is administered in a modified release formulation such that the subject is effectively pretreated with serotonin receptor modulator prior to release of an effective amount of the psychedelic. Thus, in some embodiments, the serotonin receptor modulator is administered or released from a composition provided herein prior to the administration and/or release of the psychedelic. This allows pretreatment to attenuate activation of the serotonin receptor by the psychedelic. In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the psychedelic. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the psychedelic.

In a preferred embodiment, the serotonin receptor modulator is administered at about 1 hour to about 3 hours prior to the administration of the psychedelic.

In some embodiments, the serotonin receptor modulator is eplivanserin and the psychedelic is O-acetylpsilocin fumarate, wherein the eplivanserin is administered to pretreat at least 15 minutes prior to the administration of the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat between at least 30 minutes prior and 360 minutes prior to the release or administration of the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat between at least 60 minutes prior and 360 minutes prior to the release or administration of the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat between at least 90 minutes and 240 minutes prior to the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat at least 120 minutes prior to the O-acetylpsilocin fumarate form disclosed herein, including those described in Table 32.

In some embodiments, the serotonin receptor modulator is eplivanserin and the psychedelic is O-acetylpsilocin fumarate, wherein the eplivanserin is administered to pretreat at least 150 minutes prior to the O-acetylpsilocin fumarate form disclosed herein, including those described in Table 32 In some embodiments, the serotonin receptor modulator is eplivanserin and the psychedelic is O-acetylpsilocin fumarate, wherein the eplivanserin is administered to pretreat between about 15 minutes and about 150 minutes prior to the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat at least 180 minutes prior to the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat at least 210 minutes prior to the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat at least 240 minutes prior to the O-acetylpsilocin fumarate form disclosed herein, including those described in Table 32.

In some embodiments, the serotonin receptor modulator is eplivanserin and the psychedelic is O-acetylpsilocin fumarate, wherein the eplivanserin is administered to pretreat at least 270 minutes prior to O-acetylpsilocin fumarate. In some embodiments, the serotonin receptor modulator is eplivanserin and the psychedelic is O-acetylpsilocin fumarate, wherein the eplivanserin is administered to pretreat at least 300 minutes prior to the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat at least 330 minutes prior to the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to pretreat at least 360 minutes prior to the O-acetylpsilocin fumarate form disclosed herein, including those described in Table 32.

In some preferred embodiments, the serotonin receptor modulator is eplivanserin and the psychedelic is O-acetylpsilocin fumarate, wherein eplivanserin is administered to pretreat between about 60 minutes and about 180 minutes prior to the administration of the O-acetylpsilocin fumarate form disclosed herein, including those described in Table 32.

In some embodiments, the serotonin receptor modulator is volinanserin and the psychedelic is O-acetylpsilocin fumarate, wherein the volinanserin is administered to pretreat a subject between at least 15 minutes and 360 minutes prior to the administration or release of the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat between at least 30 minutes and 360 minutes prior to the administration or release of the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat between at least 60 minutes and 240 minutes prior to the administration or release of the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 90 minutes prior to the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 120 minutes prior to the O-acetylpsilocin fumarate form disclosed herein, including those described in Table 32.

In some embodiments, the serotonin receptor modulator is volinanserin and the psychedelic is O-acetylpsilocin fumarate, wherein the volinanserin is administered to pretreat at least 150 minutes prior to the O-acetylpsilocin fumarate form disclosed herein, including those described in Table 32.

In some embodiments, the serotonin receptor modulator is volinanserin and the psychedelic is O-acetylpsilocin fumarate, wherein the volinanserin is administered to pretreat between about 15 minutes and about 150 minutes prior to the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 180 minutes prior to the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 210 minutes prior to the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 240 minutes prior to the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 270 minutes prior to the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 300 minutes prior to the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 330 minutes prior to the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to pretreat at least 360 minutes prior to the O-acetylpsilocin fumarate form disclosed herein, including those described in Table 32. In some preferred embodiments, the serotonin receptor modulator is volinanserin and the psychedelic is O-acetylpsilocin fumarate, wherein volinanserin is administered to pretreat between about 60 minutes and about 180 minutes prior to the administration of the O-acetylpsilocin fumarate form disclosed herein, including those described in Table 32.

In some embodiments, the serotonin receptor modulator is ketanserin and the psychedelic is O-acetylpsilocin fumarate, wherein the ketanserin is administered to pretreat at least 15 minutes prior to the administration of the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat between at least 30 minutes and 360 minutes prior to the administration or release of the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat between at least 60 minutes and 240 minutes prior to the administration or release of the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 90 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 120 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 150 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat between about 15 minutes and about 150 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 180 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 210 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 240 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 270 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 300 minutes prior to the 0-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 330 minutes prior to the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to pretreat at least 360 minutes prior to the O-acetylpsilocin fumarate form disclosed herein, including those described in Table 32. In some preferred embodiments, the serotonin receptor modulator is ketanserin and the psychedelic is O-acetylpsilocin fumarate, wherein ketanserin is administered to pretreat between about 60 minutes and about 180 minutes prior to the administration of the O-acetylpsilocin fumarate form disclosed herein, including those described in Table 32.

In some embodiments, the serotonin receptor modulator is ritanserin and the psychedelic is O-acetylpsilocin fumarate, wherein the ritanserin is administered to pretreat at least 15 minutes prior to the administration of the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 30 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat between at least 60 minutes and 240 minutes prior to the administration or release of the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 90 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 120 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 150 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat between about 15 minutes and about 150 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 180 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 210 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 240 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 270 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 300 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 330 minutes prior to the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to pretreat at least 360 minutes prior to the O-acetylpsilocin fumarate form disclosed herein, including those described in Table 32. In some preferred embodiments, the serotonin receptor modulator is ritanserin and the psychedelic is O-acetylpsilocin fumarate, wherein ritanserin is administered to pretreat between about 60 minutes and about 180 minutes prior to the administration of the O-acetylpsilocin fumarate form disclosed herein, including those described in Table 32.

In some embodiments, the serotonin receptor modulator is pimavanserin and the psychedelic is O-acetylpsilocin fumarate, wherein the pimavanserin is administered to pretreat at least 15 minutes prior to the administration of the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 30 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat between at least 60 minutes and 240 minutes prior to the administration or release of the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 90 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 120 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 150 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat between about 15 minutes and about 150 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 180 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 210 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 240 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 270 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 300 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 330 minutes prior to the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to pretreat at least 360 minutes prior to the O-acetylpsilocin fumarate form disclosed herein, including those described in Table 32. In some preferred embodiments, the serotonin receptor modulator is pimavanserin and the psychedelic is O-acetylpsilocin fumarate, wherein pimavanserin is administered to pretreat between about 60 minutes and about 180 minutes prior to the administration of the O-acetylpsilocin fumarate form disclosed herein, including those described in Table 32.

In some embodiments, the serotonin receptor modulator is nelotanserin and the psychedelic is O-acetylpsilocin fumarate, wherein the nelotanserin is administered to pretreat at least 15 minutes prior to the administration of the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat at least 30 minutes prior to the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat between at least 60 minutes and 240 minutes prior to the administration or release of the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat at least 90 minutes prior to the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat at least 120 minutes prior to the O-acetylpsilocin fumarate form disclosed herein, including those described in Table 32.

In some embodiments, the serotonin receptor modulator is nelotanserin and the psychedelic is O-acetylpsilocin fumarate, wherein the nelotanserin is administered to pretreat at least 150 minutes prior to the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat between about 15 minutes and about 150 minutes prior to the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat at least 180 minutes prior to the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat at least 210 minutes prior to the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat at least 240 minutes prior to the O-acetylpsilocin fumarate form disclosed herein, including those described in Table 32. In some embodiments, the serotonin receptor modulator is nelotanserin and psychedelic is O-acetylpsilocin fumarate, wherein the nelotanserin is administered to pretreat at least 270 minutes prior to O-acetylpsilocin fumarate form disclosed herein, including those described in Table 32.

In some embodiments, the serotonin receptor modulator is nelotanserin and the psychedelic is O-acetylpsilocin fumarate, wherein the nelotanserin is administered to pretreat at least 300 minutes prior to the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat at least 330 minutes prior to the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to pretreat at least 360 minutes prior to the O-acetylpsilocin fumarate form disclosed herein, including those described in Table 32. In some preferred embodiments, the serotonin receptor modulator is nelotanserin and the psychedelic is O-acetylpsilocin fumarate, wherein nelotanserin is administered to pretreat between about 60 minutes and about 180 minutes prior to the administration of the O-acetylpsilocin fumarate form disclosed herein, including those described in Table 32.

In some embodiments, the serotonin receptor modulator is pruvanserin and the psychedelic is O-acetylpsilocin fumarate, wherein the pruvanserin is administered to pretreat at least 15 minutes prior to the administration of the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 30 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat between at least 60 minutes and 240 minutes prior to the administration or release of the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 90 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 120 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 150 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat between about 15 minutes and about 150 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 180 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 210 minutes prior to the O-acetylpsilocin fumarate form disclosed herein, including those described in Table 32.

In some embodiments, the serotonin receptor modulator is pruvanserin and the psychedelic is O-acetylpsilocin fumarate, wherein the pruvanserin is administered to pretreat at least 240 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 270 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 300 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 330 minutes prior to the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to pretreat at least 360 minutes prior to the O-acetylpsilocin fumarate form disclosed herein, including those described in Table 32. In some preferred embodiments, the serotonin receptor modulator is pruvanserin and the psychedelic is O-acetylpsilocin fumarate, wherein pruvanserin is administered to pretreat between about 60 minutes and about 180 minutes prior to the administration of the O-acetylpsilocin fumarate form disclosed herein, including those described in Table 32.

In some embodiments, the serotonin receptor modulator is flibanserin and the psychedelic is O-acetylpsilocin fumarate, wherein the flibanserin is administered to pretreat at least 15 minutes prior to the administration of the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 30 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat between at least 60 minutes and 240 minutes prior to the administration or release of the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 90 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 120 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 150 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat between about 15 minutes and about 150 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 180 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 210 minutes prior to the O-acetylpsilocin fumarate form disclosed herein, including those described in Table 32.

In some embodiments, the serotonin receptor modulator is flibanserin and the psychedelic is O-acetylpsilocin fumarate, wherein the flibanserin is administered to pretreat at least 240 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 270 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 300 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 330 minutes prior to the O-acetylpsilocin fumarate form disclosed herein, including those described in Table 32. In some embodiments, the serotonin receptor modulator is flibanserin and the psychedelic is O-acetylpsilocin fumarate, wherein the flibanserin is administered to pretreat at least 360 minutes prior to the O-acetylpsilocin fumarate form disclosed herein, including those described in Table 32. In some preferred embodiments, the serotonin receptor modulator is flibanserin and the psychedelic is O-acetylpsilocin fumarate, wherein flibanserin is administered to pretreat between about 60 minutes and about 180 minutes prior to the administration of the O-acetylpsilocin fumarate form disclosed herein, including those described in Table 32.

In some embodiments, the serotonin receptor modulator is olanzapine and the psychedelic is O-acetylpsilocin fumarate, wherein the olanzapine is administered to pretreat at least 15 minutes prior to the administration of the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat at least 30 minutes prior to the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat between at least 60 minutes and 240 minutes prior to the administration or release of the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat at least 90 minutes prior to the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat at least 120 minutes prior to the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat at least 150 minutes prior to the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat between about 15 minutes and about 150 minutes prior to the O-acetylpsilocin fumarate form disclosed herein, including those described in Table 32. In some embodiments, the serotonin receptor modulator is olanzapine and psychedelic is O-acetylpsilocin fumarate, wherein olanzapine is administered to pretreat at least 180 minutes prior to the O-acetylpsilocin fumarate form disclosed in Table 32. In some embodiments, the serotonin receptor modulator is olanzapine and the psychedelic is O-acetylpsilocin fumarate, wherein the olanzapine is administered to pretreat at least 210 minutes prior to O-acetylpsilocin fumarate form disclosed herein, including those described in Table 32.

In some embodiments, the serotonin receptor modulator is olanzapine and the psychedelic is O-acetylpsilocin fumarate, wherein the olanzapine is administered to pretreat at least 240 minutes prior to the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat at least 270 minutes prior to the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat at least 300 minutes prior to the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat at least 330 minutes prior to the O-acetylpsilocin fumarate form disclosed herein, including those described in Table 32. In some embodiments, the serotonin receptor modulator is olanzapine and the psychedelic is O-acetylpsilocin fumarate, wherein the olanzapine is administered to pretreat at least 360 minutes prior to the O-acetylpsilocin fumarate form disclosed herein, including those described in Table 32. In some preferred embodiments, the serotonin receptor modulator is olanzapine and the psychedelic is O-acetylpsilocin fumarate, wherein olanzapine is administered to pretreat between about 60 minutes and about 180 minutes prior to the administration of the O-acetylpsilocin fumarate form disclosed herein, including those described in Table 32.

In some embodiments, the serotonin receptor modulator is risperidone and the psychedelic is O-acetylpsilocin fumarate, wherein the risperidone is administered to pretreat at least 15 minutes prior to the administration of the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 30 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat between at least 60 minutes and 240 minutes prior to the administration or release of the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 90 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 120 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 150 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat between about 15 minutes and about 150 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 180 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 210 minutes prior to the O-acetylpsilocin fumarate form disclosed herein, including those described in Table 32.

In some embodiments, the serotonin receptor modulator is risperidone and the psychedelic is O-acetylpsilocin fumarate, wherein the risperidone is administered to pretreat at least 240 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 270 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 300 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 330 minutes prior to the O-acetylpsilocin fumarate form disclosed herein, including those described in Table 32. In some embodiments, the serotonin receptor modulator is risperidone and the psychedelic is O-acetylpsilocin fumarate, wherein the risperidone is administered to pretreat at least 360 minutes prior to the O-acetylpsilocin fumarate form disclosed herein, including those described in Table 32. In some preferred embodiments, the serotonin receptor modulator is risperidone and the psychedelic is O-acetylpsilocin fumarate, wherein risperidone is administered to pretreat between about 60 minutes and about 180 minutes prior to the administration of the O-acetylpsilocin fumarate form disclosed herein, including those described in Table 32.

In some embodiments, the serotonin receptor modulator is quetiapine and the psychedelic is O-acetylpsilocin fumarate, wherein the quetiapine is administered to pretreat at least 15 minutes prior to the administration of the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 30 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat between at least 60 minutes and 240 minutes prior to the administration or release of the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 90 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 120 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 150 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat between about 15 minutes and about 150 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 180 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 210 minutes prior to the O-acetylpsilocin fumarate form disclosed herein, including those described in Table 32.

In some embodiments, the serotonin receptor modulator is quetiapine and the psychedelic is O-acetylpsilocin fumarate, wherein the quetiapine is administered to pretreat at least 240 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 270 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 300 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 330 minutes prior to the O-acetylpsilocin fumarate form disclosed herein, including those described in Table 32. In some embodiments, the serotonin receptor modulator is quetiapine and the psychedelic is O-acetylpsilocin fumarate, wherein the quetiapine is administered to pretreat at least 360 minutes prior to the O-acetylpsilocin fumarate form disclosed herein, including those described in Table 32. In some preferred embodiments, the serotonin receptor modulator is quetiapine and the psychedelic is O-acetylpsilocin fumarate, wherein quetiapine is administered to pretreat between about 60 minutes and about 180 minutes prior to the administration of the O-acetylpsilocin fumarate form disclosed herein, including those described in Table 32.

In some embodiments, the serotonin receptor modulator is eplivanserin and the psychedelic is O-acetylpsilocin fumarate, wherein the eplivanserin is administered to pretreat at least 15 minutes prior to the administration of O-acetylpsilocin fumarate. In some embodiments, the serotonin receptor modulator is eplivanserin and the psychedelic is O-acetylpsilocin fumarate, wherein the eplivanserin is administered to pretreat between at least 30 minutes prior and 360 minutes prior to the release or administration of the O-acetylpsilocin fumarate. In some embodiments, the serotonin receptor modulator is eplivanserin and the psychedelic is O-acetylpsilocin fumarate, wherein the eplivanserin is administered to pretreat between at least 60 minutes prior and 360 minutes prior to the release or administration the O-acetylpsilocin fumarate. In some embodiments, the serotonin receptor modulator is eplivanserin and the psychedelic is O-acetylpsilocin fumarate, wherein the eplivanserin is administered to pretreat between at least 90 minutes and 240 minutes prior to the O-acetylpsilocin fumarate. In some embodiments, the serotonin receptor modulator is eplivanserin and the psychedelic is O-acetylpsilocin fumarate, wherein the eplivanserin is administered to pretreat at least 120 minutes prior to the O-acetylpsilocin fumarate.

In some embodiments, the serotonin receptor modulator is eplivanserin and the psychedelic is O-acetylpsilocin fumarate, wherein the eplivanserin is administered to pretreat at least 150 minutes prior to the O-acetylpsilocin fumarate. In some embodiments, the serotonin receptor modulator is eplivanserin and the psychedelic is O-acetylpsilocin fumarate, wherein the eplivanserin is administered to pretreat between about 15 minutes and about 150 minutes prior to the O-acetylpsilocin fumarate. In some embodiments, the serotonin receptor modulator is eplivanserin and the psychedelic is O-acetylpsilocin fumarate, wherein the eplivanserin is administered to pretreat at least 180 minutes prior to the O-acetylpsilocin fumarate. In some embodiments, the serotonin receptor modulator is eplivanserin and the psychedelic is O-acetylpsilocin fumarate, wherein the eplivanserin is administered to pretreat at least 210 minutes prior to the O-acetylpsilocin fumarate. In some embodiments, the serotonin receptor modulator is eplivanserin and the psychedelic is O-acetylpsilocin fumarate, wherein the eplivanserin is administered to pretreat at least 240 minutes prior to the O-acetylpsilocin fumarate.

In some embodiments, the serotonin receptor modulator is eplivanserin and the psychedelic is O-acetylpsilocin fumarate, wherein the eplivanserin is administered to pretreat at least 270 minutes prior to O-acetylpsilocin fumarate. In some embodiments, the serotonin receptor modulator is eplivanserin and the psychedelic is O-acetylpsilocin fumarate, wherein the eplivanserin is administered to pretreat at least 300 minutes prior to the O-acetylpsilocin fumarate. In some embodiments, the serotonin receptor modulator is eplivanserin and the psychedelic is O-acetylpsilocin fumarate, wherein the eplivanserin is administered to pretreat at least 330 minutes prior to the O-acetylpsilocin fumarate. In some embodiments, the serotonin receptor modulator is eplivanserin and the psychedelic is O-acetylpsilocin fumarate, wherein the eplivanserin is administered to pretreat at least 360 minutes prior to the O-acetylpsilocin fumarate.

In some preferred embodiments, the serotonin receptor modulator is eplivanserin and the psychedelic is O-acetylpsilocin fumarate, wherein eplivanserin is administered to pretreat between about 60 minutes and about 180 minutes prior to the administration of O-acetylpsilocin fumarate.

In some embodiments, the serotonin receptor modulator is volinanserin and the psychedelic is O-acetylpsilocin fumarate, wherein the volinanserin is administered to pretreat a subject between at least 15 minutes and 360 minutes prior to the administration or release of O-acetylpsilocin fumarate. In some embodiments, the serotonin receptor modulator is volinanserin and the psychedelic is O-acetylpsilocin fumarate, wherein the volinanserin is administered to pretreat between at least 30 minutes and 360 minutes prior to the administration or release of O-acetylpsilocin fumarate. In some embodiments, the serotonin receptor modulator is volinanserin and the psychedelic is O-acetylpsilocin fumarate, wherein the volinanserin is administered to pretreat between at least 60 minutes and 240 minutes prior to the administration or release of O-acetylpsilocin fumarate. In some embodiments, the serotonin receptor modulator is volinanserin and the psychedelic is O-acetylpsilocin fumarate, wherein the volinanserin is administered to pretreat at least 90 minutes prior to O-acetylpsilocin fumarate. In some embodiments, the serotonin receptor modulator is volinanserin and the psychedelic is O-acetylpsilocin fumarate, wherein the volinanserin is administered to pretreat at least 120 minutes prior to the O-acetylpsilocin fumarate.

In some embodiments, the serotonin receptor modulator is volinanserin and the psychedelic is O-acetylpsilocin fumarate, wherein the volinanserin is administered to pretreat at least 150 minutes prior to the O-acetylpsilocin fumarate. In some embodiments, the serotonin receptor modulator is volinanserin and the psychedelic is O-acetylpsilocin fumarate, wherein the volinanserin is administered to pretreat between about 15 minutes and about 150 minutes prior to the O-acetylpsilocin fumarate. In some embodiments, the serotonin receptor modulator is volinanserin and the psychedelic is O-acetylpsilocin fumarate, wherein the volinanserin is administered to pretreat at least 180 minutes prior to the O-acetylpsilocin fumarate. In some embodiments, the serotonin receptor modulator is volinanserin and the psychedelic is O-acetylpsilocin fumarate, wherein the volinanserin is administered to pretreat at least 210 minutes prior to the O-acetylpsilocin fumarate. In some embodiments, the serotonin receptor modulator is volinanserin and the psychedelic is O-acetylpsilocin fumarate, wherein the volinanserin is administered to pretreat at least 240 minutes prior to the O-acetylpsilocin fumarate. In some embodiments, the serotonin receptor modulator is volinanserin and the psychedelic is O-acetylpsilocin fumarate, wherein the volinanserin is administered to pretreat at least 270 minutes prior to the O-acetylpsilocin fumarate. In some embodiments, the serotonin receptor modulator is volinanserin and the psychedelic is O-acetylpsilocin fumarate, wherein the volinanserin is administered to pretreat at least 300 minutes prior to the O-acetylpsilocin fumarate. In some embodiments, the serotonin receptor modulator is volinanserin and the psychedelic is O-acetylpsilocin fumarate, wherein the volinanserin is administered to pretreat at least 330 minutes prior to the O-acetylpsilocin fumarate. In some embodiments, the serotonin receptor modulator is volinanserin and the psychedelic is O-acetylpsilocin fumarate, wherein the volinanserin is administered to pretreat at least 360 minutes prior to the O-acetylpsilocin fumarate. In some preferred embodiments, the serotonin receptor modulator is volinanserin and the psychedelic is O-acetylpsilocin fumarate, wherein volinanserin is administered to pretreat between about 60 minutes and about 180 minutes prior to the administration of O-acetylpsilocin fumarate.

In some embodiments, the serotonin receptor modulator is ketanserin and the psychedelic is O-acetylpsilocin fumarate, wherein the ketanserin is administered to pretreat at least 15 minutes prior to the administration of O-acetylpsilocin fumarate. In some embodiments, the serotonin receptor modulator is ketanserin and the psychedelic is O-acetylpsilocin fumarate, wherein the ketanserin is administered to pretreat between at least 30 minutes and 360 minutes prior to the administration or release O-acetylpsilocin fumarate. In some embodiments, the serotonin receptor modulator is ketanserin and the psychedelic is O-acetylpsilocin fumarate, wherein the ketanserin is administered to pretreat between at least 60 minutes and 240 minutes prior to the administration or release of O-acetylpsilocin fumarate. In some embodiments, the serotonin receptor modulator is ketanserin and the psychedelic is O-acetylpsilocin fumarate, wherein the ketanserin is administered to pretreat at least 90 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 120 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 150 minutes prior to the O-acetylpsilocin fumarate. In some embodiments, the serotonin receptor modulator is ketanserin and the psychedelic is O-acetylpsilocin fumarate, wherein the ketanserin is administered to pretreat between about 15 minutes and about 150 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 180 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 210 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 240 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 270 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 300 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 330 minutes prior to the O-acetylpsilocin fumarate. In some embodiments, the serotonin receptor modulator is ketanserin and the psychedelic is O-acetylpsilocin fumarate, wherein the ketanserin is administered to pretreat at least 360 minutes prior to the O-acetylpsilocin fumarate. In some preferred embodiments, the serotonin receptor modulator is ketanserin and the psychedelic is O-acetylpsilocin fumarate, wherein ketanserin is administered to pretreat between about 60 minutes and about 180 minutes prior to the administration of O-acetylpsilocin fumarate.

In some embodiments, the serotonin receptor modulator is ritanserin and the psychedelic is O-acetylpsilocin fumarate, wherein the ritanserin is administered to pretreat at least 15 minutes prior to the administration of O-acetylpsilocin fumarate. In some embodiments, the serotonin receptor modulator is ritanserin and the psychedelic is O-acetylpsilocin fumarate, wherein the ritanserin is administered to pretreat at least 30 minutes prior to the O-acetylpsilocin fumarate. In some embodiments, the serotonin receptor modulator is ritanserin and the psychedelic is O-acetylpsilocin fumarate, wherein the ritanserin is administered to pretreat between at least 60 minutes and 240 minutes prior to the administration or release of O-acetylpsilocin fumarate. In some embodiments, the serotonin receptor modulator is ritanserin and the psychedelic is O-acetylpsilocin fumarate, wherein the ritanserin is administered to pretreat at least 90 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 120 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 150 minutes prior to the O-acetylpsilocin fumarate. In some embodiments, the serotonin receptor modulator is ritanserin and the psychedelic is O-acetylpsilocin fumarate, wherein the ritanserin is administered to pretreat between about 15 minutes and about 150 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 180 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 210 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 240 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 270 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 300 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 330 minutes prior to the O-acetylpsilocin fumarate. In some embodiments, the serotonin receptor modulator is ritanserin and the psychedelic is O-acetylpsilocin fumarate, wherein the ritanserin is administered to pretreat at least 360 minutes prior to the O-acetylpsilocin fumarate. In some preferred embodiments, the serotonin receptor modulator is ritanserin and the psychedelic is O-acetylpsilocin fumarate, wherein ritanserin is administered to pretreat between about 60 minutes and about 180 minutes prior to administration of O-acetylpsilocin fumarate.

In some embodiments, the serotonin receptor modulator is pimavanserin and the psychedelic is O-acetylpsilocin fumarate, wherein the pimavanserin is administered to pretreat at least 15 minutes prior to the administration of O-acetylpsilocin fumarate. In some embodiments, the serotonin receptor modulator is pimavanserin and the psychedelic is O-acetylpsilocin fumarate, wherein the pimavanserin is administered to pretreat at least 30 minutes prior to the O-acetylpsilocin fumarate. In some embodiments, the serotonin receptor modulator is pimavanserin and the psychedelic is O-acetylpsilocin fumarate, wherein the pimavanserin is administered to pretreat between at least 60 minutes and 240 minutes prior to the administration or release of O-acetylpsilocin fumarate. In some embodiments, the serotonin receptor modulator is pimavanserin and the psychedelic is O-acetylpsilocin fumarate, wherein the pimavanserin is administered to pretreat at least 90 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 120 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 150 minutes prior to the O-acetylpsilocin fumarate. In some embodiments, the serotonin receptor modulator is pimavanserin and the psychedelic is O-acetylpsilocin fumarate, wherein the pimavanserin is administered to pretreat between about 15 minutes and about 150 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 180 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 210 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 240 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 270 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 300 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 330 minutes prior to the O-acetylpsilocin fumarate. In some embodiments, the serotonin receptor modulator is pimavanserin and the psychedelic is O-acetylpsilocin fumarate, wherein the pimavanserin is administered to pretreat at least 360 minutes prior to the O-acetylpsilocin fumarate. In some preferred embodiments, the serotonin receptor modulator is pimavanserin and the psychedelic is O-acetylpsilocin fumarate, wherein pimavanserin is administered to pretreat between about 60 minutes and about 180 minutes prior to the administration of O-acetylpsilocin fumarate.

In some embodiments, the serotonin receptor modulator is nelotanserin and the psychedelic is O-acetylpsilocin fumarate, wherein the nelotanserin is administered to pretreat at least 15 minutes prior to the administration of O-acetylpsilocin fumarate. In some embodiments, the serotonin receptor modulator is nelotanserin and the psychedelic is O-acetylpsilocin fumarate, wherein the nelotanserin is administered to pretreat at least 30 minutes prior to the O-acetylpsilocin fumarate. In some embodiments, the serotonin receptor modulator is nelotanserin and the psychedelic is O-acetylpsilocin fumarate, wherein the nelotanserin is administered to pretreat between at least 60 minutes and 240 minutes prior to the administration or release of O-acetylpsilocin fumarate. In some embodiments, the serotonin receptor modulator is nelotanserin and the psychedelic is O-acetylpsilocin fumarate, wherein the nelotanserin is administered to pretreat at least 90 minutes prior to the O-acetylpsilocin fumarate. In some embodiments, the serotonin receptor modulator is nelotanserin and the psychedelic is O-acetylpsilocin fumarate, wherein the nelotanserin is administered to pretreat at least 120 minutes prior to the O-acetylpsilocin fumarate.

In some embodiments, the serotonin receptor modulator is nelotanserin and the psychedelic is O-acetylpsilocin fumarate, wherein the nelotanserin is administered to pretreat at least 150 minutes prior to the O-acetylpsilocin fumarate. In some embodiments, the serotonin receptor modulator is nelotanserin and the psychedelic is O-acetylpsilocin fumarate, wherein the nelotanserin is administered to pretreat between about 15 minutes and about 150 minutes prior to the O-acetylpsilocin fumarate. In some embodiments, the serotonin receptor modulator is nelotanserin and the psychedelic is O-acetylpsilocin fumarate, wherein the nelotanserin is administered to pretreat at least 180 minutes prior to the O-acetylpsilocin fumarate. In some embodiments, the serotonin receptor modulator is nelotanserin and the psychedelic is O-acetylpsilocin fumarate, wherein the nelotanserin is administered to pretreat at least 210 minutes prior to the O-acetylpsilocin fumarate. In some embodiments, the serotonin receptor modulator is nelotanserin and the psychedelic is O-acetylpsilocin fumarate, wherein the nelotanserin is administered to pretreat at least 240 minutes prior to the O-acetylpsilocin fumarate. In some embodiments, the serotonin receptor modulator is nelotanserin and the psychedelic is O-acetylpsilocin fumarate, wherein the nelotanserin is administered to pretreat at least 270 minutes prior to the O-acetylpsilocin fumarate. In some embodiments, the serotonin receptor modulator is nelotanserin and the psychedelic is O-acetylpsilocin fumarate, wherein the nelotanserin is administered to pretreat at least 300 minutes prior to the O-acetylpsilocin fumarate. In some embodiments, the serotonin receptor modulator is nelotanserin and the psychedelic is O-acetylpsilocin fumarate, wherein the nelotanserin is administered to pretreat at least 330 minutes prior to the O-acetylpsilocin fumarate. In some embodiments, the serotonin receptor modulator is nelotanserin and the psychedelic is O-acetylpsilocin fumarate, wherein the nelotanserin is administered to pretreat at least 360 minutes prior to the O-acetylpsilocin fumarate. In some preferred embodiments, the serotonin receptor modulator is nelotanserin and the psychedelic is O-acetylpsilocin fumarate, wherein nelotanserin is administered to pretreat between about 60 minutes and about 180 minutes prior to the administration of O-acetylpsilocin fumarate.

In some embodiments, the serotonin receptor modulator is pruvanserin and the psychedelic is O-acetylpsilocin fumarate, wherein the pruvanserin is administered to pretreat at least 15 minutes prior to the administration of O-acetylpsilocin fumarate. In some embodiments, the serotonin receptor modulator is pruvanserin and the psychedelic is O-acetylpsilocin fumarate, wherein the pruvanserin is administered to pretreat at least 30 minutes prior to the O-acetylpsilocin fumarate. In some embodiments, the serotonin receptor modulator is pruvanserin and the psychedelic is O-acetylpsilocin fumarate, wherein the pruvanserin is administered to pretreat between at least 60 minutes and 240 minutes prior to the administration or release of O-acetylpsilocin fumarate. In some embodiments, the serotonin receptor modulator is pruvanserin and the psychedelic is O-acetylpsilocin fumarate, wherein the pruvanserin is administered to pretreat at least 90 minutes prior to the O-acetylpsilocin fumarate. In some embodiments, the serotonin receptor modulator is pruvanserin and the psychedelic is O-acetylpsilocin fumarate, wherein the pruvanserin is administered to pretreat at least 120 minutes prior to the O-acetylpsilocin fumarate. In some embodiments, the serotonin receptor modulator is pruvanserin and the psychedelic is O-acetylpsilocin fumarate, wherein the pruvanserin is administered to pretreat at least 150 minutes prior to the O-acetylpsilocin fumarate. In some embodiments, the serotonin receptor modulator is pruvanserin and the psychedelic is O-acetylpsilocin fumarate, wherein the pruvanserin is administered to pretreat between about 15 minutes and about 150 minutes prior to the O-acetylpsilocin fumarate. In some embodiments, the serotonin receptor modulator is pruvanserin and the psychedelic is O-acetylpsilocin fumarate, wherein the pruvanserin is administered to pretreat at least 180 minutes prior to the O-acetylpsilocin fumarate. In some embodiments, the serotonin receptor modulator is pruvanserin and the psychedelic is O-acetylpsilocin fumarate, wherein the pruvanserin is administered to pretreat at least 210 minutes prior to the O-acetylpsilocin fumarate.

In some embodiments, the serotonin receptor modulator is pruvanserin and the psychedelic is O-acetylpsilocin fumarate, wherein the pruvanserin is administered to pretreat at least 240 minutes prior to the O-acetylpsilocin fumarate. In some embodiments, the serotonin receptor modulator is pruvanserin and the psychedelic is O-acetylpsilocin fumarate, wherein the pruvanserin is administered to pretreat at least 270 minutes prior to the O-acetylpsilocin fumarate. In some embodiments, the serotonin receptor modulator is pruvanserin and the psychedelic is O-acetylpsilocin fumarate, wherein the pruvanserin is administered to pretreat at least 300 minutes prior to the O-acetylpsilocin fumarate. In some embodiments, the serotonin receptor modulator is pruvanserin and the psychedelic is O-acetylpsilocin fumarate, wherein the pruvanserin is administered to pretreat at least 330 minutes prior to the O-acetylpsilocin fumarate. In some embodiments, the serotonin receptor modulator is pruvanserin and the psychedelic is O-acetylpsilocin fumarate, wherein the pruvanserin is administered to pretreat at least 360 minutes prior to the O-acetylpsilocin fumarate. In some preferred embodiments, the serotonin receptor modulator is pruvanserin and the psychedelic is O-acetylpsilocin fumarate, wherein pruvanserin is administered to pretreat between about 60 minutes and about 180 minutes prior to the administration of O-acetylpsilocin fumarate.

In certain embodiments, such as those described above a 0-acetylpsilocin fumarate form disclosed herein, including those described in Table 32, is co-administered with a serotonin receptor modulator in the same or in separate compositions. In one embodiment, the serotonin receptor modulator is administered after the O-acetylpsilocin fumarate form disclosed herein, including those described in Table 32. In one embodiment, the O-acetylpsilocin fumarate form disclosed herein, including those described in Table 32, is administered in a modified release formulation such that the subject is effectively post-treated with serotonin receptor modulator post to release of an effective amount of the O-acetylpsilocin fumarate. In some embodiments, the serotonin receptor modulator is part of a single fixed dose formulation that releases the O-acetylpsilocin fumarate first followed by serotonin receptor modulator on two different release profiles. In another embodiment, the O-acetylpsilocin fumarate form disclosed herein, including those described in Table 32, is administered first as a single dosage and, after a length of time, serotonin receptor modulator is administered as a second dosage separate from the first dosage. Thus, in some embodiments, the serotonin receptor modulator is administered or released from a composition provided herein post to the administration and/or release of the psychedelic. This allows post-treatment to attenuate activation of the serotonin receptor by the psychedelic. In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours post to the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post to the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post to the release of the psychedelic.

In a preferred embodiment, the serotonin receptor modulator is administered at about 1 hour to about 3 hours post to the administration of the psychedelic.

In some embodiments, the serotonin receptor modulator is eplivanserin and the psychedelic is O-acetylpsilocin fumarate, wherein the eplivanserin is administered to post-treat at least 15 minutes after the administration of the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat between at least 30 minutes after and 360 minutes after the release or administration of the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat between at least 60 minutes after and 360 minutes after the release or administration of the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat between at least 90 minutes and 240 minutes after the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat at least 120 minutes after the O-acetylpsilocin fumarate form disclosed herein, including those described in Table 32.

In some embodiments, the serotonin receptor modulator is eplivanserin and the psychedelic is O-acetylpsilocin fumarate, wherein the eplivanserin is administered to post-treat at least 150 minutes after the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat between about 15 minutes and about 150 minutes after the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat at least 180 minutes after the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat at least 210 minutes after the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat at least 240 minutes after the O-acetylpsilocin fumarate form disclosed herein, including those described in Table 32.

In some embodiments, the serotonin receptor modulator is eplivanserin and the psychedelic is O-acetylpsilocin fumarate, wherein the eplivanserin is administered to post-treat at least 270 minutes after the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat at least 300 minutes after the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat at least 330 minutes after the O-acetylpsilocin fumarate form disclosed herein, including those described in Table 32. In some embodiments, the serotonin receptor modulator is eplivanserin and the psychedelic is O-acetylpsilocin fumarate, wherein the eplivanserin is administered to post-treat at least 360 minutes after the O-acetylpsilocin fumarate form disclosed herein, including those described in Table 32.

In some preferred embodiments, the serotonin receptor modulator is eplivanserin and the psychedelic is O-acetylpsilocin fumarate, wherein eplivanserin is administered to post-treat between about 60 minutes and about 180 minutes after the administration of the O-acetylpsilocin fumarate form disclosed herein, including those described in Table 32.

In some embodiments, the serotonin receptor modulator is volinanserin and the psychedelic is O-acetylpsilocin fumarate, wherein the volinanserin is administered to post-treat a subject between at least 15 minutes and 360 minutes after the administration or release of the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat between at least 30 minutes and 360 minutes after the administration or release of the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat between at least 60 minutes and 240 minutes after the administration or release of the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat at least 90 minutes after O-acetylpsilocin fumarate. In some embodiments, the serotonin receptor modulator is volinanserin and the psychedelic is O-acetylpsilocin fumarate, wherein the volinanserin is administered to post-treat at least 120 minutes after the O-acetylpsilocin fumarate form disclosed herein, including those described in Table 32.

In some embodiments, the serotonin receptor modulator is volinanserin and the psychedelic is O-acetylpsilocin fumarate, wherein the volinanserin is administered to post-treat at least 150 minutes after the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat between about 15 minutes and about 150 minutes after the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat at least 180 minutes after the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat at least 210 minutes after the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat at least 240 minutes after the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat at least 270 minutes after the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat at least 300 minutes after the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat at least 330 minutes after the O-acetylpsilocin fumarate form disclosed herein, including those described in Table 32. In some embodiments, the serotonin receptor modulator is volinanserin and the psychedelic is O-acetylpsilocin fumarate, wherein the volinanserin is administered to post-treat at least 360 minutes after the O-acetylpsilocin fumarate form disclosed herein, including those described in Table 32. In some preferred embodiments, the serotonin receptor modulator is volinanserin and the psychedelic is O-acetylpsilocin fumarate, wherein volinanserin is administered to post-treat between about 60 minutes and about 180 minutes after the administration of the ®-MDMA form.

In some embodiments, the serotonin receptor modulator is ketanserin and the psychedelic is O-acetylpsilocin fumarate, wherein the ketanserin is administered to post-treat at least 15 minutes after the administration of the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat between at least 30 minutes and 360 minutes after the administration or release of the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat between at least 60 minutes and 240 minutes after the administration or release of the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 90 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 120 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 150 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat between about 15 minutes and about 150 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 180 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 210 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 240 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 270 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 300 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 330 minutes after the O-acetylpsilocin fumarate form disclosed herein, including those described in Table 32. In some embodiments, the serotonin receptor modulator is ketanserin and the psychedelic is O-acetylpsilocin fumarate, wherein the ketanserin is administered to post-treat at least 360 minutes after the O-acetylpsilocin fumarate form disclosed herein, including those described in Table 32. In some preferred embodiments, the serotonin receptor modulator is ketanserin and the psychedelic is O-acetylpsilocin fumarate, wherein ketanserin is administered to post-treat between about 60 minutes and about 180 minutes after the administration of the O-acetylpsilocin fumarate form disclosed herein, including those described in Table 32.

In some embodiments, the serotonin receptor modulator is ritanserin and the psychedelic is O-acetylpsilocin fumarate, wherein the ritanserin is administered to post-treat at least 15 minutes after the administration of the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 30 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat between at least 60 minutes and 240 minutes after the administration or release of the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 90 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 120 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 150 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat between about 15 minutes and about 150 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 180 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 210 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 240 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 270 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 300 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 330 minutes after the O-acetylpsilocin fumarate form disclosed herein, including those described in Table 32. In some embodiments, the serotonin receptor modulator is ritanserin and the psychedelic is O-acetylpsilocin fumarate, wherein the ritanserin is administered to post-treat at least 360 minutes after the 0-acetylpsilocin fumarate form disclosed herein, including those described in Table 32. In some preferred embodiments, the serotonin receptor modulator is ritanserin and the psychedelic is O-acetylpsilocin fumarate, wherein ritanserin is administered to post-treat between about 60 minutes and about 180 minutes after the administration of the O-acetylpsilocin fumarate form disclosed herein, including those described in Table 32.

In some embodiments, the serotonin receptor modulator is pimavanserin and the psychedelic is O-acetylpsilocin fumarate, wherein the pimavanserin is administered to post-treat at least 15 minutes after the administration of the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 30 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat between at least 60 minutes and 240 minutes after the administration or release of the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 90 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 120 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 150 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat between about 15 minutes and about 150 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 180 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 210 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 240 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 270 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 300 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 330 minutes after the O-acetylpsilocin fumarate form disclosed herein, including those described in Table 32. In some embodiments, the serotonin receptor modulator is pimavanserin and the psychedelic is O-acetylpsilocin fumarate, wherein the pimavanserin is administered to post-treat at least 360 minutes after the O-acetylpsilocin fumarate form disclosed herein, including those described in Table 32. In some preferred embodiments, the serotonin receptor modulator is pimavanserin and the psychedelic is O-acetylpsilocin fumarate, wherein pimavanserin is administered to post-treat between about 60 minutes and about 180 minutes after the administration of the O-acetylpsilocin fumarate form disclosed herein, including those described in Table 32.

In some embodiments, the serotonin receptor modulator is nelotanserin and the psychedelic is O-acetylpsilocin fumarate, wherein the nelotanserin is administered to post-treat at least 15 minutes after the administration of the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 30 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat between at least 60 minutes and 240 minutes after the administration or release of the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 90 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 120 minutes after the O-acetylpsilocin fumarate form disclosed herein, including those described in Table 32.

In some embodiments, the serotonin receptor modulator is nelotanserin and the psychedelic is O-acetylpsilocin fumarate, wherein the nelotanserin is administered to post-treat at least 150 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat between about 15 minutes and about 150 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 180 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 210 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 240 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 270 minutes after the O-acetylpsilocin fumarate form disclosed herein, including those described in Table 32.

In some embodiments, the serotonin receptor modulator is nelotanserin and the psychedelic is O-acetylpsilocin fumarate, wherein the nelotanserin is administered to post-treat at least 300 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 330 minutes after the O-acetylpsilocin fumarate form disclosed herein, including those described in Table 32. In some embodiments, the serotonin receptor modulator is nelotanserin and the psychedelic is O-acetylpsilocin fumarate, wherein the nelotanserin is administered to post-treat at least 360 minutes after the O-acetylpsilocin fumarate form disclosed herein, including those described in Table 32.

In some preferred embodiments, the serotonin receptor modulator is nelotanserin and the psychedelic is O-acetylpsilocin fumarate, wherein nelotanserin is administered to post-treat between about 60 minutes and about 180 minutes after the administration of the O-acetylpsilocin fumarate form disclosed herein, including those described in Table 32.

In some embodiments, the serotonin receptor modulator is pruvanserin and the psychedelic is O-acetylpsilocin fumarate, wherein the pruvanserin is administered to post-treat at least 15 minutes after the administration of the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 30 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat between at least 60 minutes and 240 minutes after the administration or release of the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 90 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 120 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 150 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat between about 15 minutes and about 150 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 180 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 210 minutes after the O-acetylpsilocin fumarate form disclosed herein, including those described in Table 32.

In some embodiments, the serotonin receptor modulator is pruvanserin and the psychedelic is O-acetylpsilocin fumarate, wherein the pruvanserin is administered to post-treat at least 240 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 270 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 300 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 330 minutes after the O-acetylpsilocin fumarate form disclosed herein, including those described in Table 32. In some embodiments, the serotonin receptor modulator is pruvanserin and the psychedelic is O-acetylpsilocin fumarate, wherein the pruvanserin is administered to post-treat at least 360 minutes after the O-acetylpsilocin fumarate form disclosed herein, including those described in Table 32. In some preferred embodiments, the serotonin receptor modulator is pruvanserin and the psychedelic is O-acetylpsilocin fumarate, wherein pruvanserin is administered to post-treat between about 60 minutes and about 180 minutes after the administration of the O-acetylpsilocin fumarate form disclosed herein, including those described in Table 32.

In some embodiments, the serotonin receptor modulator is flibanserin, wherein the flibanserin is administered to post-treat at least 15 minutes post to the administration of the O-acetylpsilocin fumarate form disclosed herein, including those described in Table 32. In some embodiments, the serotonin receptor modulator is flibanserin, wherein the flibanserin is administered to post-treat at least 30 minutes post to the O-acetylpsilocin fumarate form disclosed herein, including those described in Table 32. In some embodiments, the serotonin receptor modulator is flibanserin, wherein the flibanserin is administered to post-treat between at least 60 minutes and 240 minutes post to the administration or release of the O-acetylpsilocin fumarate form disclosed herein, including those described in Table 32. In some embodiments, the serotonin receptor modulator is flibanserin, wherein the flibanserin is administered to post-treat at least 90 minutes post to the O-acetylpsilocin fumarate form disclosed herein, including those described in Table 32. In some embodiments, the serotonin receptor modulator is flibanserin, wherein the flibanserin is administered to post-treat at least 120 minutes post to the O-acetylpsilocin fumarate form disclosed herein, including those described in Table 32. In some embodiments, the serotonin receptor modulator is flibanserin, wherein the flibanserin is administered to post-treat at least 150 minutes post to the O-acetylpsilocin fumarate form disclosed herein, including those described in Table 32. In some embodiments, the serotonin receptor modulator is flibanserin, wherein the flibanserin is administered to post-treat between about 15 minutes and about 150 minutes post to O-acetylpsilocin fumarate form disclosed herein, including those described in Table 32. In some embodiments, the serotonin receptor modulator is flibanserin, wherein flibanserin is administered to post-treat at least 180 minutes post to O-acetylpsilocin fumarate form disclosed herein, including those described in Table 32. In some embodiments, the serotonin receptor modulator is flibanserin, wherein flibanserin is administered to post-treat at least 210 minutes post to O-acetylpsilocin fumarate form disclosed herein, including those described in Table 32.

In some embodiments, the serotonin receptor modulator is flibanserin, wherein the flibanserin is administered to post-treat at least 240 minutes post to the O-acetylpsilocin fumarate form disclosed herein, including those described in Table 32. In some embodiments, the serotonin receptor modulator is flibanserin, wherein the flibanserin is administered to post-treat at least 270 minutes post to the O-acetylpsilocin fumarate form disclosed herein, including those described in Table 32. In some embodiments, the serotonin receptor modulator is flibanserin, wherein the flibanserin is administered to post-treat at least 300 minutes post to the O-acetylpsilocin fumarate form disclosed herein, including those described in Table 32. In some embodiments, the serotonin receptor modulator is flibanserin, wherein the flibanserin is administered to post-treat at least 330 minutes post to the O-acetylpsilocin fumarate form disclosed herein, including those described in Table 32. In some embodiments, the serotonin receptor modulator is flibanserin, wherein the flibanserin is administered to post-treat at least 360 minutes post to the O-acetylpsilocin fumarate form disclosed herein, including those described in Table 32. In some preferred embodiments, the serotonin receptor modulator is flibanserin, wherein flibanserin is administered to post-treat between about 60 minutes and about 180 minutes post to the administration of the O-acetylpsilocin fumarate form disclosed herein, including those described in Table 32.

In some embodiments, the serotonin receptor modulator is olanzapine, wherein the olanzapine is administered to post-treat at least 15 minutes post to the administration of the O-acetylpsilocin fumarate form disclosed herein, including those described in Table 32. In some embodiments, the serotonin receptor modulator is olanzapine, wherein the olanzapine is administered to post-treat at least 30 minutes post to the O-acetylpsilocin fumarate form disclosed herein, including those described in Table 32. In some embodiments, the serotonin receptor modulator is olanzapine, wherein the olanzapine is administered to post-treat between at least 60 minutes and 240 minutes post to the administration or release of the O-acetylpsilocin fumarate form disclosed herein, including those described in Table 32. In some embodiments, the serotonin receptor modulator is olanzapine, wherein the olanzapine is administered to post-treat at least 90 minutes post to the O-acetylpsilocin fumarate form disclosed herein, including those described in Table 32. In some embodiments, the serotonin receptor modulator is olanzapine, wherein the olanzapine is administered to post-treat at least 120 minutes post to the O-acetylpsilocin fumarate form disclosed herein, including those described in Table 32. In some embodiments, the serotonin receptor modulator is olanzapine, wherein the olanzapine is administered to post-treat at least 150 minutes post to the O-acetylpsilocin fumarate form disclosed herein, including those described in Table 32. In some embodiments, the serotonin receptor modulator is olanzapine, wherein the olanzapine is administered to post-treat between about 15 minutes and about 150 minutes post to the O-acetylpsilocin fumarate form disclosed herein, including those described in Table 32. In some embodiments, the serotonin receptor modulator is olanzapine, wherein the olanzapine is administered to post-treat at least 180 minutes post to the O-acetylpsilocin fumarate form disclosed herein, including those described in Table 32. In some embodiments, the serotonin receptor modulator is olanzapine, wherein the olanzapine is administered to post-treat at least 210 minutes post to the O-acetylpsilocin fumarate form disclosed herein, including those described in Table 32.

In some embodiments, the serotonin receptor modulator is olanzapine, wherein the olanzapine is administered to post-treat at least 240 minutes post to the O-acetylpsilocin fumarate form disclosed herein, including those described in Table 32. In some embodiments, the serotonin receptor modulator is olanzapine, wherein the olanzapine is administered to post-treat at least 270 minutes post to the O-acetylpsilocin fumarate form disclosed herein, including those described in Table 32. In some embodiments, the serotonin receptor modulator is olanzapine, wherein the olanzapine is administered to post-treat at least 300 minutes post to the O-acetylpsilocin fumarate form disclosed herein, including those described in Table 32. In some embodiments, the serotonin receptor modulator is olanzapine, wherein the olanzapine is administered to post-treat at least 330 minutes post to the O-acetylpsilocin fumarate form disclosed herein, including those described in Table 32. In some embodiments, the serotonin receptor modulator is olanzapine, wherein the olanzapine is administered to post-treat at least 360 minutes post to the O-acetylpsilocin fumarate form disclosed herein, including those described in Table 32. In some preferred embodiments, the serotonin receptor modulator is olanzapine, wherein olanzapine is administered to post-treat between about 60 minutes and about 180 minutes post to the administration of the O-acetylpsilocin fumarate form disclosed herein, including those described in Table 32.

In some embodiments, the serotonin receptor modulator is quetiapine, wherein the quetiapine is administered to post-treat at least 15 minutes post to the administration of the O-acetylpsilocin fumarate form disclosed herein, including those described in Table 32. In some embodiments, the serotonin receptor modulator is quetiapine, wherein the quetiapine is administered to post-treat at least 30 minutes post to the O-acetylpsilocin fumarate form disclosed herein, including those described in Table 32. In some embodiments, the serotonin receptor modulator is quetiapine, wherein the quetiapine is administered to post-treat between at least 60 minutes and 240 minutes post to the administration or release of the O-acetylpsilocin fumarate form disclosed herein, including those described in Table 32. In some embodiments, the serotonin receptor modulator is quetiapine, wherein the quetiapine is administered to post-treat at least 90 minutes post to the O-acetylpsilocin fumarate form disclosed herein, including those described in Table 32. In some embodiments, the serotonin receptor modulator is quetiapine, wherein the quetiapine is administered to post-treat at least 120 minutes post to the O-acetylpsilocin fumarate form disclosed herein, including those described in Table 32. In some embodiments, the serotonin receptor modulator is quetiapine, wherein the quetiapine is administered to post-treat at least 150 minutes post to the O-acetylpsilocin fumarate form disclosed herein, including those described in Table 32. In some embodiments, the serotonin receptor modulator is quetiapine, wherein the quetiapine is administered to post-treat between about 15 minutes and about 150 minutes post to the O-acetylpsilocin fumarate form disclosed herein, including those described in Table 32. In some embodiments, the serotonin receptor modulator is quetiapine, wherein the quetiapine is administered to post-treat at least 180 minutes post to the O-acetylpsilocin fumarate form disclosed herein, including those described in Table 32. In some embodiments, the serotonin receptor modulator is quetiapine, wherein the quetiapine is administered to post-treat at least 210 minutes post to the O-acetylpsilocin fumarate form disclosed herein, including those described in Table 32.

In some embodiments, the serotonin receptor modulator is quetiapine, wherein the quetiapine is administered to post-treat at least 240 minutes post to the O-acetylpsilocin fumarate form disclosed herein, including those described in Table 32. In some embodiments, the serotonin receptor modulator is quetiapine, wherein the quetiapine is administered to post-treat at least 270 minutes post to the O-acetylpsilocin fumarate form disclosed herein, including those described in Table 32. In some embodiments, the serotonin receptor modulator is quetiapine, wherein the quetiapine is administered to post-treat at least 300 minutes post to the O-acetylpsilocin fumarate form disclosed herein, including those described in Table 32. In some embodiments, the serotonin receptor modulator is quetiapine, wherein the quetiapine is administered to post-treat at least 330 minutes post to the O-acetylpsilocin fumarate form disclosed herein, including those described in Table 32. In some embodiments, the serotonin receptor modulator is quetiapine, wherein the quetiapine is administered to post-treat at least 360 minutes post to the O-acetylpsilocin fumarate form disclosed herein, including those described in Table 32. In some preferred embodiments, the serotonin receptor modulator is quetiapine, wherein quetiapine is administered to post-treat between about 60 minutes and about 180 minutes post to the administration of the O-acetylpsilocin fumarate form disclosed herein, including those described in Table 32.

In some embodiments, the serotonin receptor modulator is risperidone, wherein the risperidone is administered to post-treat at least 15 minutes post to the administration of the O-acetylpsilocin fumarate form disclosed herein, including those described in Table 32. In some embodiments, the serotonin receptor modulator is risperidone, wherein the risperidone is administered to post-treat at least 30 minutes post to the O-acetylpsilocin fumarate form disclosed herein, including those described in Table 32. In some embodiments, the serotonin receptor modulator is risperidone, wherein the risperidone is administered to post-treat between at least 60 minutes and 240 minutes post to the administration or release of the O-acetylpsilocin fumarate form disclosed herein, including those described in Table 32. In some embodiments, the serotonin receptor modulator is risperidone, wherein the risperidone is administered to post-treat at least 90 minutes post to the O-acetylpsilocin fumarate form disclosed herein, including those described in Table 32. In some embodiments, the serotonin receptor modulator is risperidone, wherein the risperidone is administered to post-treat at least 120 minutes post to the O-acetylpsilocin fumarate form disclosed herein, including those described in Table 32. In some embodiments, the serotonin receptor modulator is risperidone, wherein the risperidone is administered to post-treat at least 150 minutes post to the O-acetylpsilocin fumarate form disclosed herein, including those described in Table 32. In some embodiments, the serotonin receptor modulator is risperidone, wherein the risperidone is administered to post-treat between about 15 minutes and about 150 minutes post to the O-acetylpsilocin fumarate form disclosed herein, including those described in Table 32. In some embodiments, the serotonin receptor modulator is risperidone, wherein the risperidone is administered to post-treat at least 180 minutes post to the O-acetylpsilocin fumarate form disclosed herein, including those described in Table 32. In some embodiments, the serotonin receptor modulator is risperidone, wherein the risperidone is administered to post-treat at least 210 minutes post to the O-acetylpsilocin fumarate form disclosed herein, including those described in Table 32.

In some embodiments, the serotonin receptor modulator is risperidone, wherein the risperidone is administered to post-treat at least 240 minutes post to the O-acetylpsilocin fumarate form disclosed herein, including those described in Table 32. In some embodiments, the serotonin receptor modulator is risperidone, wherein the risperidone is administered to post-treat at least 270 minutes post to the O-acetylpsilocin fumarate form disclosed herein, including those described in Table 32. In some embodiments, the serotonin receptor modulator is risperidone, wherein the risperidone is administered to post-treat at least 300 minutes post to the O-acetylpsilocin fumarate form disclosed herein, including those described in Table 32. In some embodiments, the serotonin receptor modulator is risperidone, wherein the risperidone is administered to post-treat at least 330 minutes post to the O-acetylpsilocin fumarate form disclosed herein, including those described in Table 32. In some embodiments, the serotonin receptor modulator is risperidone, wherein the risperidone is administered to post-treat at least 360 minutes post to the O-acetylpsilocin fumarate form disclosed herein, including those described in Table 32. In some preferred embodiments, the serotonin receptor modulator is risperidone, wherein risperidone is administered to post-treat between about 60 minutes and about 180 minutes post to the administration of the O-acetylpsilocin fumarate form disclosed herein, including those described in Table 32.

EXAMPLES

Example 1: Psilocybin·HCl Polymorph Screen

The active pharmaceutical ingredient (API), psilocybin·HCl, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity. PLM data is used to evaluate crystallinity and particle size/morphology. DSC data is used to evaluate melting point, thermal stability, and crystalline form conversion. TG data is used to evaluate if the API is a solvate or hydrate, and to evaluate thermal stability. DVS data is used to evaluate hygroscopicity of the API and if hydrates can be formed at high relative humidity. About 10 to 15 solvents may be selected from the list below, based on their properties (polarity, dielectric constant and dipole moment).

TABLE 3

| Solvents | |
| --- | --- |
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |
| 2-ethoxyethanol (Cellusolve) | 1,1,1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

- API is dissolved in a solvent or mixture of solvents, and the solvents are evaporated at different rates (slow evaporation or fast evaporation) and at different temperatures (ambient or elevated).
- API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).
- API is dissolved in a solvent or mixture of solvents, and an antisolvent is added to precipitate the salt. The solids formed will be recovered by filtration and dried (air dried or vacuum dried).
- API is added to a solvent or mixture of solvents, where the API is not fully dissolved. The slurry will be agitated at different temperatures for a number of days. The solids formed will be recovered by filtration and (air dried or vacuum dried).
- API is milled (by mechanical milling or by mortar and pestle), with a drop of solvent, or without any solvent.
- API is melted and cooled (at different cooling rates, fast and slow, and cooled to different temperatures) to obtain solids.
- API is suspended in a solvent or mixture of solvents, and the slurry is placed in a heating/cooling cycle for multiple cycles. The remaining solids after the final cooling cycle will be filtered and (air dried or vacuum dried).
- API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.
- API is exposed to elevated humidity (or elevated temperature, or combination thereof), or to solvent vapors for extended period of days.
- Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).
- API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50(TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45° 2θ with steps of 0.1°, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered CuKα1 radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005° 2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 2: Polymorph Screening of Psilocybin·HCl

Non-crystalline psilocybin·HCl was used as starting material to conduct polymorph screen experiments. A stock solution in methanol was prepared as the source of non-crystalline psilocybin·HCl; the stock solution was dispensed into vials and solvent was evaporated to leave psilocybin·HCl as a non-crystalline solid. A $^1$H NMR spectrum of this material is provided as FIG. 1.

Samples were generated from different solvents via evaporation and antisolvent precipitation via techniques known to those of skill in the art. Fast evaporation from MeOH/water (4:1) led to psilocybin Form B as characterized in the XRPD diffractogram of FIG. 18. Form B was characterized as the psilocybin trihydrate using thermogravimetry. Form B also was observed following water uptake by psilocybin Form A between 75 and 95% relative humidity.

Figure 9:
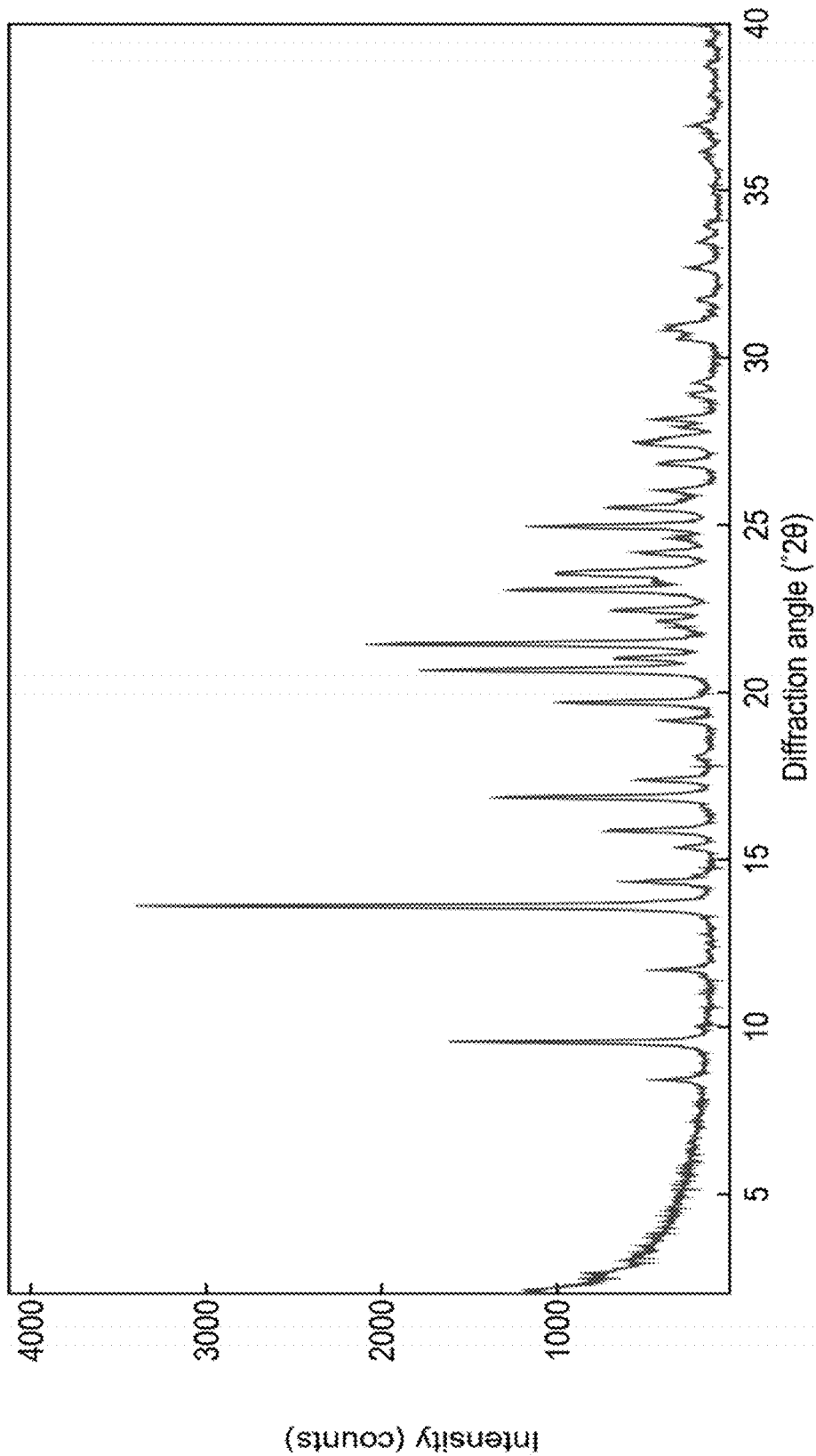
FIG. 9 provides an XRPD diffractogram of psilocybin hydrochloride Form C ethanoate.

Antisolvent precipitation from ethanol using toluene as the antisolvent, followed by fast evaporation yielded psilocybin·HCl Form C as characterized in the XRPD diffractogram of FIG. 9. Form C was characterized as an ethanol solvate of psilocybin via NMR and thermogravimetry (0.6% wt loss from ambient to 125° C., 12.4% wt loss from 125 to 185° C.).

Non-crystalline psilocybin·HCl was subjected to crystallization conditions using cooling in various solvents according to Example 1, including ethanol, methanol, a methanol MTBE (1:1) mixture and a methyl ethyl ketone:methanol (1:1) mixture. Cooling of an ethanol solution from 40 degrees Celsius to room temperature yielded crystalline psilocybin·HCl as illustrated by the XRPD diffractogram of this material provided in FIG. 2. This crystalline material was designated psilocybin·HCl Form A.

Slurry equilibration of non-crystalline psilocybin·HCl in a solution of ethanol and ethyl acetate (1:1) at 50 degrees Celsius also yielded crystalline psilocybin·HCl of Form. An XRPD diffractogram generated using this sample is provided in FIG. 3 as an overlay plot with the XRPD patterns of psilocybin zwitterion. Note that the three forms of psilocybin zwitterion are Form A (unsolvated), Form B (trihydate), and Form C (mono-ethanolate). Slurry equilibration of non-crystalline psilocybin·HCl in a solution of 2-MeTHF/methanol (9:1) yielded crystalline psilocybin·HCl having the XRPD diffractogram of FIG. 4.

Solid and crystalline forms thereof obtained from the polymorph screening experiments of psilocybin HCl are summarized in Table 4.

TABLE 4

Figure 2:
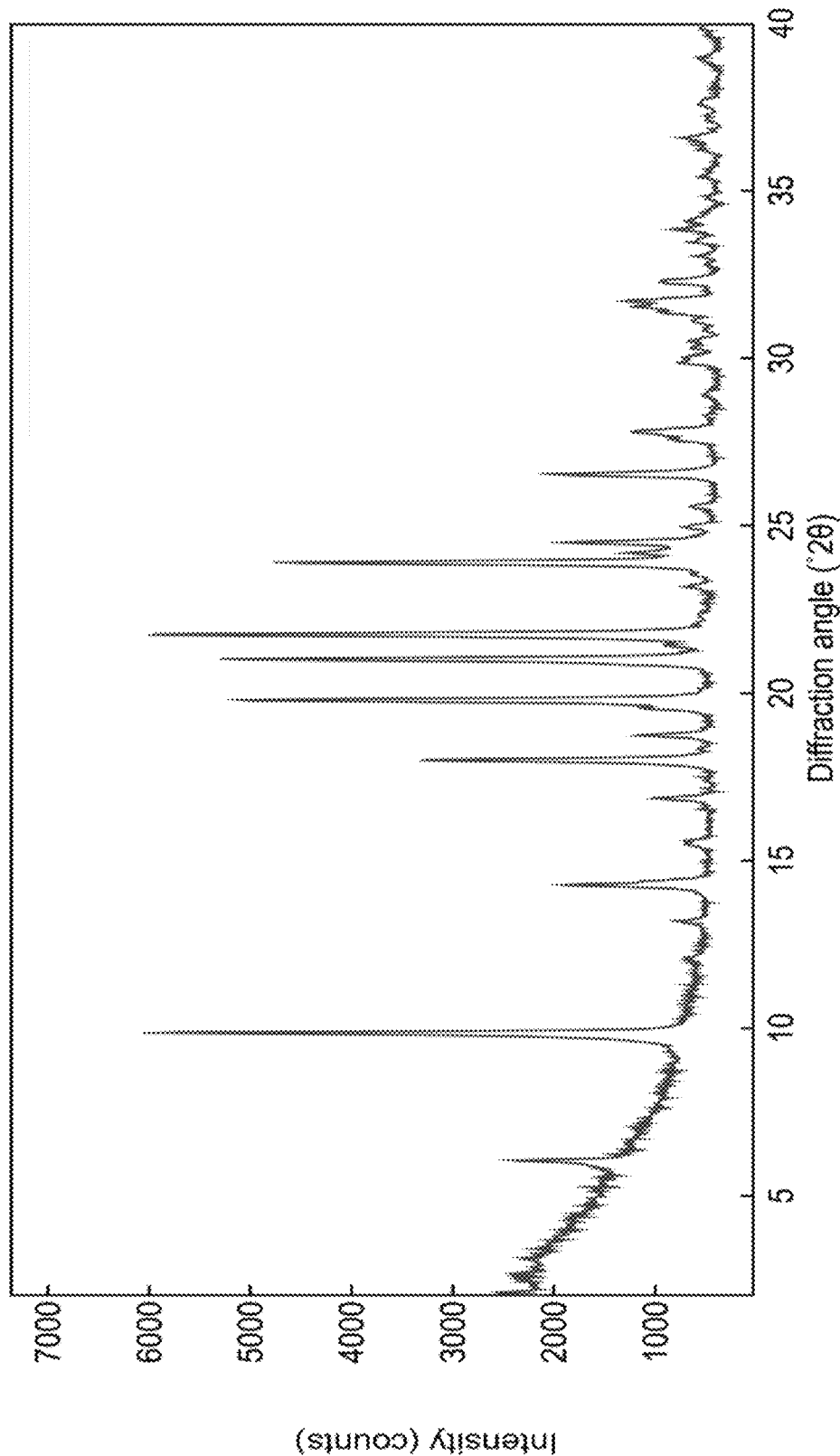
FIG. 2 provides an XRPD diffractogram of psilocybin·HCl Form A.
Figure 3:
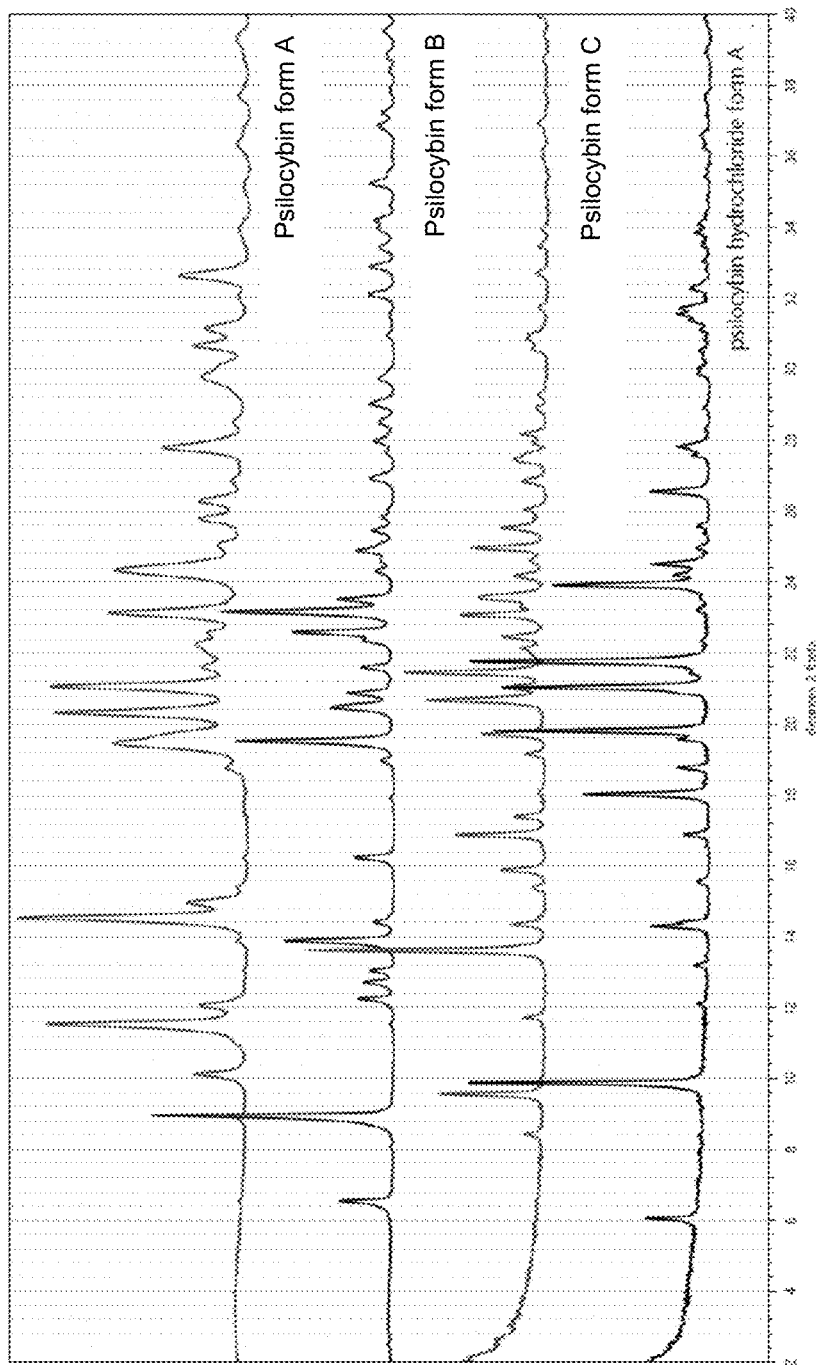
FIG. 3 is an overlay plot of an XRPD diffractogram of psilocybin·HCl Form A with XRPD diffractograms of different forms of psilocybin in a zwitterion form.
Figure 4:
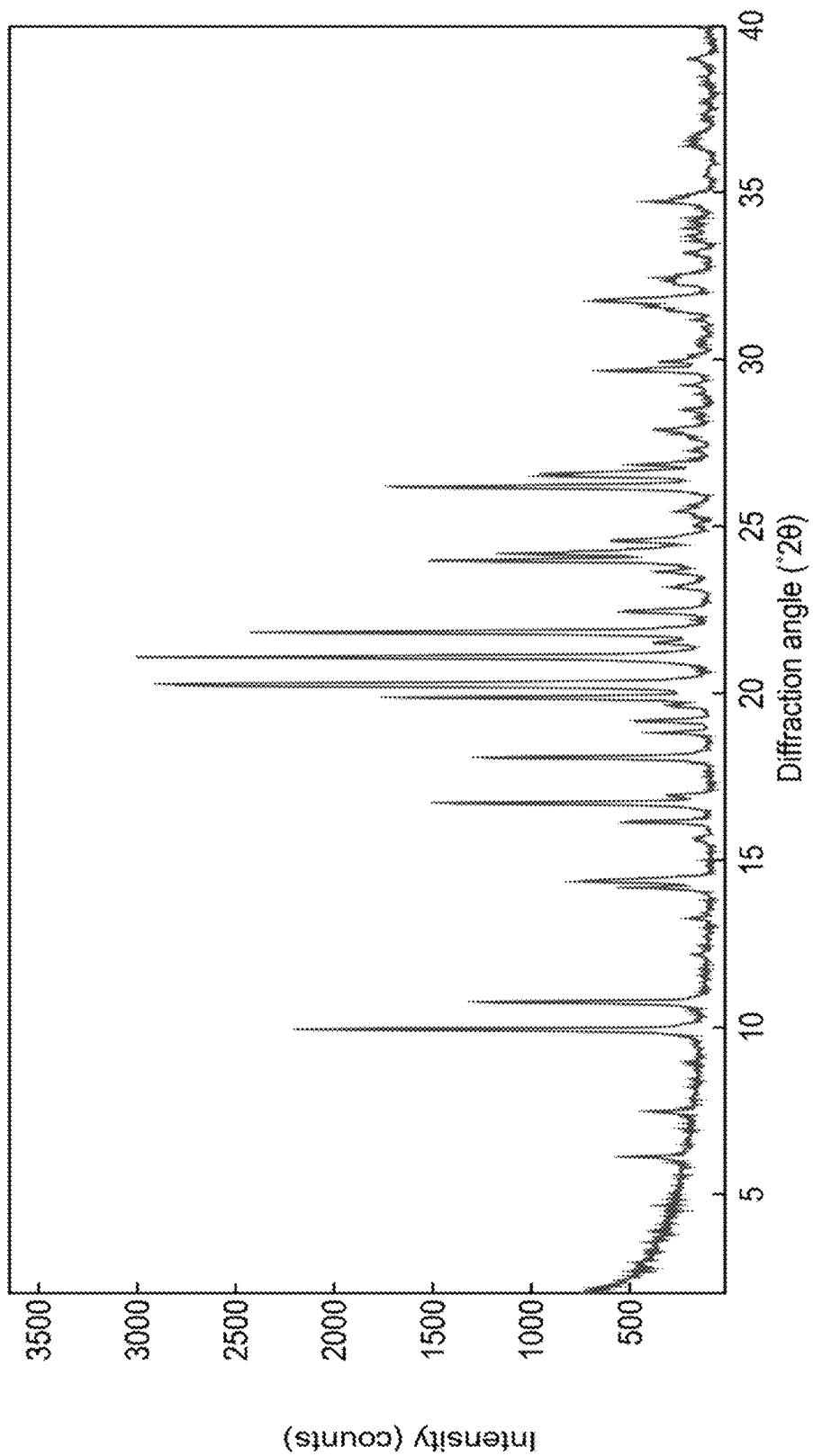
FIG. 4 provides an XRPD diffractogram of crystalline psilocybin·HCl Form A with additional peaks.
Figure 5:
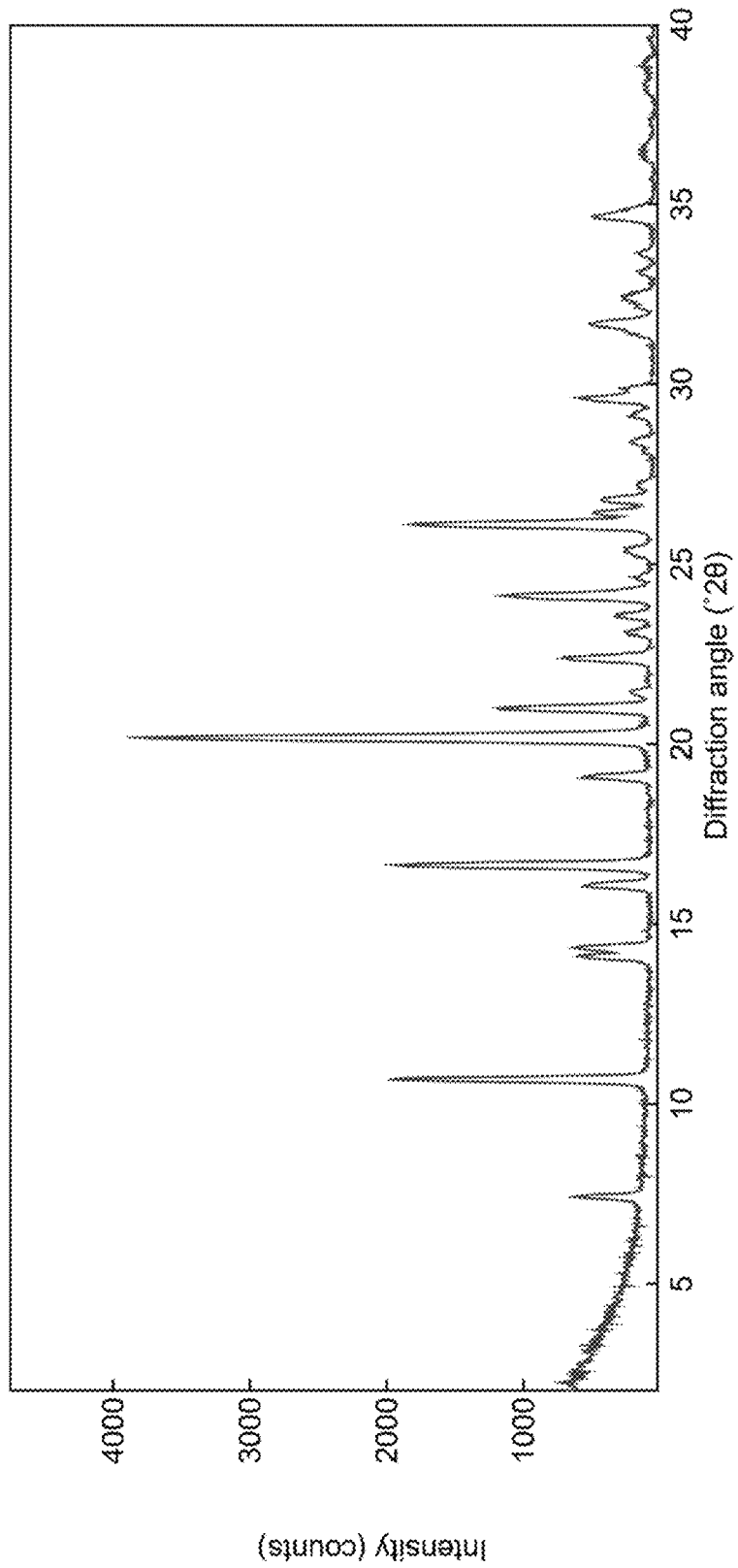
FIG. 5 provides an XRPD diffractogram of crystalline psilocybin·HCl Form B.
Figure 6:
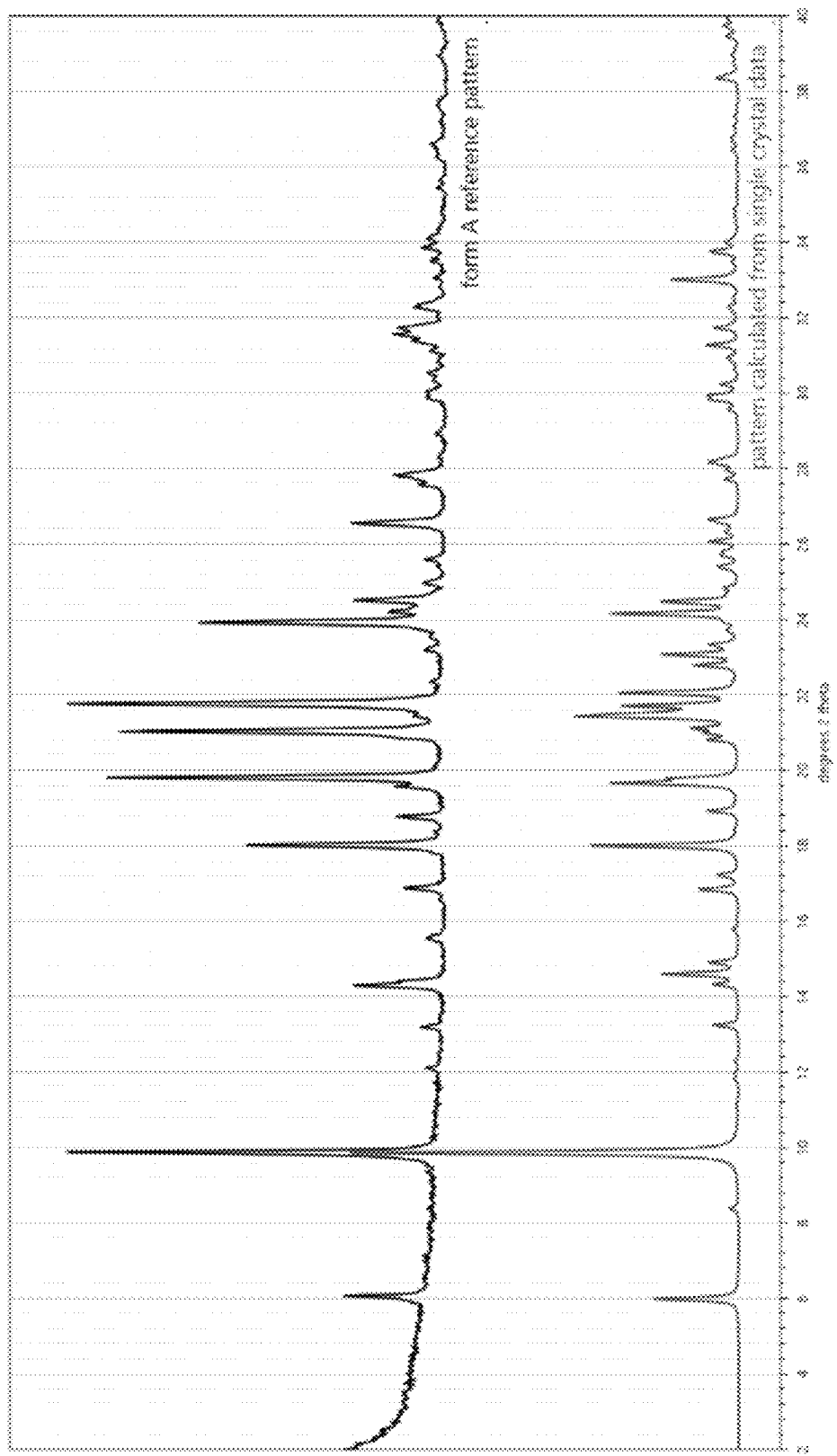
FIG. 6 is an overlay plot of an XRPD diffractogram of psilocybin·HCl Form A with an XRPD diffractogram calculated from single-crystal data.

| | |
|---|---|
| Psilocybin HCl Form A | FIG. 2 |
| Psilocybin HCl Form A overlaid with different forms of psilocybin in a zwitterion form | FIG. 3 |
| Psilocybin HCl Form A with additional peaks | FIG. 4 |
| Psilocybin HCl Form B | FIG. 5 |
| Psilocybin HCl Form A co-crystal form | FIG. 6 |
| Psilocybin HCl Form C ethanoate | FIG. 9 |

XRPD analysis of Psilocybin HCl Form A (FIG. 2) showed it to be crystalline with characteristic peaks at 6.1±0.2° 2-Theta, 9.9±0.2° 2-Theta, and 14.3±0.2° 2-Theta; optionally with further characteristic peaks at 18.0±0.2° 2-Theta and 19.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) |
|---|---|
| 6.1 | 40.2 |
| 9.9 | 99.3 |
| 12.1 | 11.9 |
| 13.2 | 13.4 |
| 14.3 | 31.8 |
| 15.5 | 11.9 |
| 16.9 | 17.0 |
| 18.0 | 55.1 |
| 18.7 | 19.4 |
| 19.8 | 85.1 |
| 21.0 | 86.6 |
| 21.7 | 100.0 |
| 23.2 | 11.9 |
| 23.9 | 77.7 |
| 24.2 | 21.5 |
| 24.5 | 31.9 |
| 25.0 | 12.1 |
| 25.6 | 10.9 |
| 26.5 | 33.7 |
| 27.8 | 20.6 |
| 28.9 | 8.8 |
| 29.9 | 13.0 |
| 30.3 | 10.8 |
| 30.8 | 8.7 |
| 31.1 | 10.6 |
| 31.5 | 20.5 |
| 31.7 | 21.9 |
| 32.3 | 15.7 |
| 32.8 | 8.5 |
| 33.0 | 10.2 |
| 33.5 | 11.0 |
| 33.8 | 14.2 |
| 34.1 | 11.8 |
| 34.8 | 8.6 |
| 35.4 | 9.2 |
| 36.4 | 9.8 |
| 36.6 | 12.5 |
| 37.1 | 8.4 |
| 37.6 | 9.7 |
| 38.9 | 9.5 |
| 39.8 | 9.4 |

XRPD analysis of Psilocybin HCl Form A with additional peaks (FIG. 4) showed it to be crystalline with characteristic peaks at 6.1±0.2° 2-Theta, 9.9±0.2° 2-Theta, and 10.8±0.2° 2-Theta; optionally with further characteristic peaks at 16.7±0.2° 2-Theta and 18.1±0.2° 2-Theta, as measured with Cu Kα radiation. A full list of peaks is found in the following table. The 2-Theta peak values that are provided for the XRPD are within ±0.2° 0.2-Theta.

| Angle 2-Theta (°) | Rel. Intensity (%) |
|---|---|
| 6.1 | 17.4 |
| 7.5 | 13.8 |
| 9.9 | 72.7 |
| 10.8 | 42.5 |
| 12.2 | 6.1 |
| 13.3 | 6.8 |
| 14.2 | 17.0 |
| 14.4 | 26.0 |
| 15.6 | 5.6 |
| 16.1 | 17.8 |
| 16.7 | 49.2 |
| 16.9 | 10.6 |
| 18.1 | 42.1 |
| 18.8 | 12.6 |
| 19.2 | 16.2 |
| 19.6 | 10.3 |
| 19.9 | 57.7 |
| 20.3 | 96.8 |
| 21.1 | 100.0 |
| 21.5 | 12.9 |
| 21.8 | 80.4 |
| 22.4 | 18.3 |
| 23.2 | 10.1 |

| Angle 2-Theta (°) | Rel. Intensity (%) |
| --- | --- |
| 23.6 | 12.5 |
| 24.0 | 51.4 |
| 24.2 | 37.8 |
| 24.6 | 20.2 |
| 25.0 | 5.9 |
| 25.4 | 9.0 |
| 25.6 | 6.2 |
| 26.2 | 57.4 |
| 26.5 | 32.0 |
| 26.6 | 30.3 |
| 26.8 | 16.2 |
| 27.3 | 6.7 |
| 27.9 | 12.9 |
| 27.9 | 12.9 |
| 28.5 | 7.7 |
| 29.0 | 5.4 |
| 29.2 | 7.2 |
| 29.7 | 21.4 |
| 29.7 | 14.4 |
| 29.9 | 11.9 |
| 30.4 | 5.2 |
| 31.2 | 6.1 |
| 31.5 | 10.7 |
| 31.6 | 13.6 |
| 31.7 | 23.0 |
| 32.3 | 9.6 |
| 32.4 | 11.9 |
| 33.2 | 7.5 |
| 33.7 | 6.9 |
| 33.9 | 7.5 |
| 34.1 | 6.6 |
| 34.7 | 13.8 |

XRPD analysis of Psilocybin HCl Form B (FIG. 5) showed it to be crystalline with characteristic peaks at 10.7±0.2° 2-Theta, 14.1±0.2° 2-Theta, and 16.6±0.2° 2-Theta; optionally with further characteristic peaks at 16.0±0.2° 2-Theta and 20.2±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) |
| --- | --- |
| 7.4 | 16.6 |
| 10.7 | 51.1 |
| 14.1 | 15.8 |
| 14.3 | 16.4 |
| 16.0 | 14.4 |
| 16.6 | 50.8 |
| 19.1 | 15.0 |
| 20.2 | 100.0 |
| 21.0 | 31.3 |
| 21.5 | 5.7 |
| 22.4 | 18.8 |
| 23.1 | 6.7 |
| 23.5 | 8.4 |
| 24.1 | 30.0 |
| 24.6 | 5.2 |
| 25.3 | 6.9 |
| 26.1 | 47.9 |
| 26.4 | 12.9 |
| 26.8 | 11.4 |
| 27.2 | 4.4 |
| 28.1 | 3.4 |
| 28.4 | 5.8 |
| 29.1 | 6.0 |
| 29.6 | 15.8 |
| 31.7 | 13.5 |
| 32.4 | 7.2 |
| 33.1 | 4.1 |
| 33.6 | 4.4 |
| 34.7 | 12.8 |
| 36.4 | 4.0 |
| 37.4 | 2.2 |
| 38.3 | 3.2 |
| 38.8 | 3.7 |
| 39.6 | 2.3 |

Psilocybin hydrochloride crystalline Form A also was isolated after slurry in acetone at room temperature—this material was characterized by NMR, DSC, and TGA. The data are summarized in Table 5. The NMR spectrum is consistent with a hydrochloride salt, and no organic solvents were observed. It appeared to be unsolvated, with a melting point around 189° C. The weight loss of around 1.300 observed through the melt may correspond to the loss of a small amount of water in the crystal and/or degradation of the molecule (for example, loss of hydrogen chloride).

TABLE 5

| Sample | Test | Results |
| --- | --- | --- |
| Psilocybin HCl Form A | NMR | Consistent with structure (data not shown) |
|  | DSC | Endo 189.3° C. |
|  | TGA | 0.2% loss up to 130° C. |
|  |  | 1.3% loss from 130° C. to 195° C. |

Additional Preparation of Psilocybin Hydrochloride Form A

Psilocybin hydrochloride crystalline Form A also was isolated after slurrying psilocybin in 1:1 EtOH:EtOAc and adding ½ equivalent of HCl at room temperature and allowing the resulting slurry to stir overnight.

Figure 7:
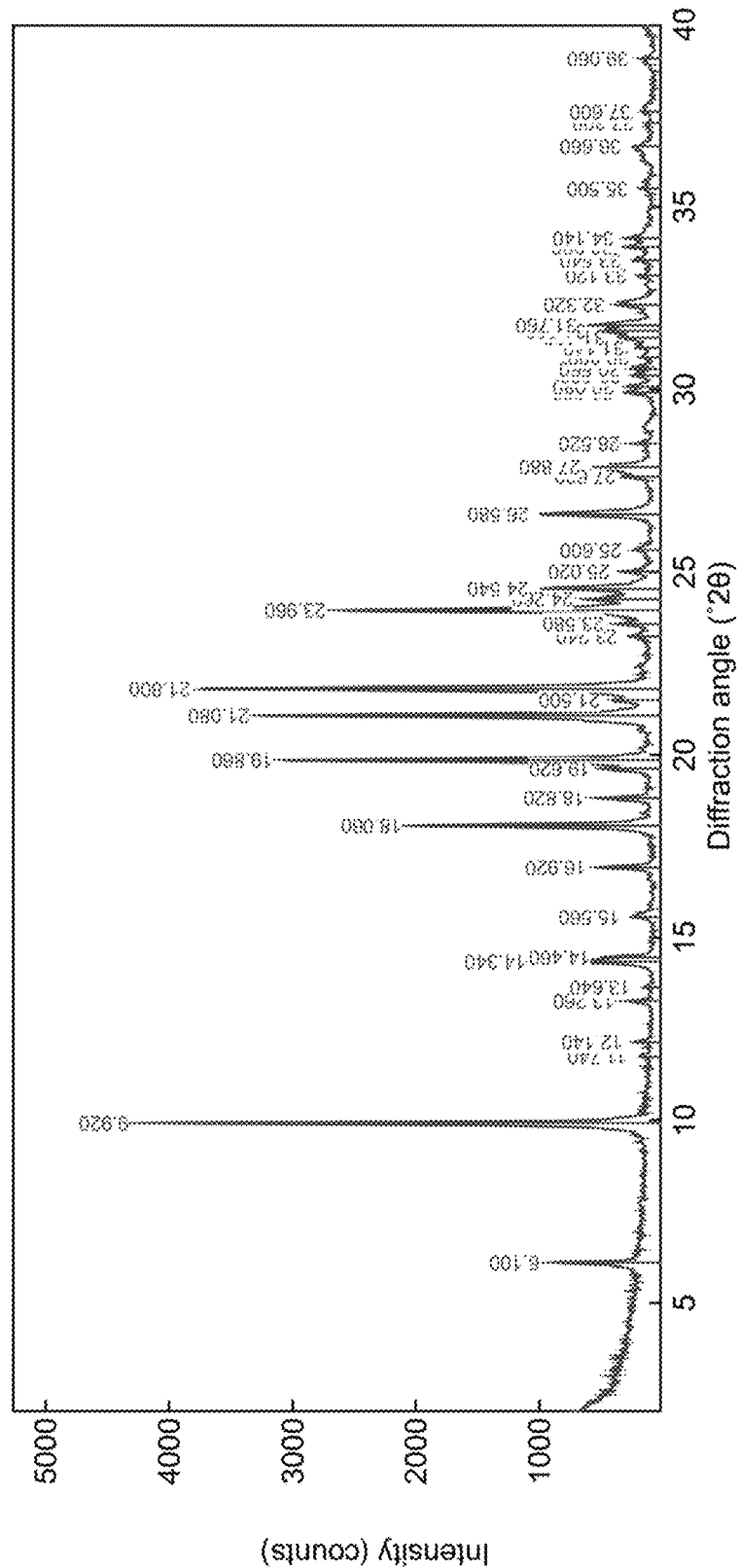
FIG. 7 provides an XRPD diffractogram of psilocybin hydrochloride Form A.

XRPD analysis (FIG. 7) showed it to be crystalline with characteristic peaks at 6.1±0.2° 2-Theta, 9.9±0.2° 2-Theta, and 14.3±0.2° 2-Theta; optionally with further characteristic peaks at 16.9±0.2° 2-Theta and 18.1±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) |
| --- | --- |
| 6.1 | 21.4 |
| 9.9 | 100.0 |
| 11.7 | 4.6 |
| 12.1 | 5.5 |
| 13.3 | 7.1 |
| 13.6 | 3.9 |
| 14.3 | 24.0 |
| 14.5 | 11.7 |
| 15.6 | 6.0 |
| 16.9 | 12.4 |
| 18.1 | 47.7 |
| 18.8 | 12.7 |
| 19.6 | 11.7 |
| 19.9 | 72.5 |
| 21.1 | 77.0 |
| 21.5 | 9.8 |
| 21.8 | 88.3 |
| 23.2 | 6.5 |
| 23.6 | 9.1 |
| 24.0 | 62.4 |
| 24.3 | 15.0 |
| 24.5 | 23.5 |
| 25.0 | 8.0 |
| 25.6 | 5.8 |
| 26.6 | 23.4 |
| 27.6 | 6.8 |
| 27.9 | 13.6 |
| 28.5 | 6.0 |

-continued

| Angle 2-Theta (°) | Rel. Intensity (%) |
|---|---|
| 29.9 | 7.4 |
| 30.1 | 7.2 |
| 30.4 | 5.9 |
| 30.6 | 5.9 |
| 30.9 | 4.3 |
| 31.1 | 5.2 |
| 31.4 | 8.8 |
| 31.6 | 12.4 |
| 31.8 | 14.2 |
| 32.3 | 8.9 |
| 33.1 | 4.7 |
| 33.5 | 5.8 |
| 33.9 | 7.4 |
| 34.1 | 7.2 |
| 35.5 | 4.5 |
| 36.7 | 5.8 |
| 37.3 | 3.4 |
| 37.6 | 3.9 |
| 39.1 | 4.4 |

Additional Preparation of Psilocybin Hydrochloride Form B

Psilocybin hydrochloride crystalline Form B also was isolated after slurrying psilocybin in 1:1 EtOH:EtOAc and adding ½ equivalent of HCl at room temperature. The slurry was seeded with form B and allowed to stir overnight.

Figure 8:
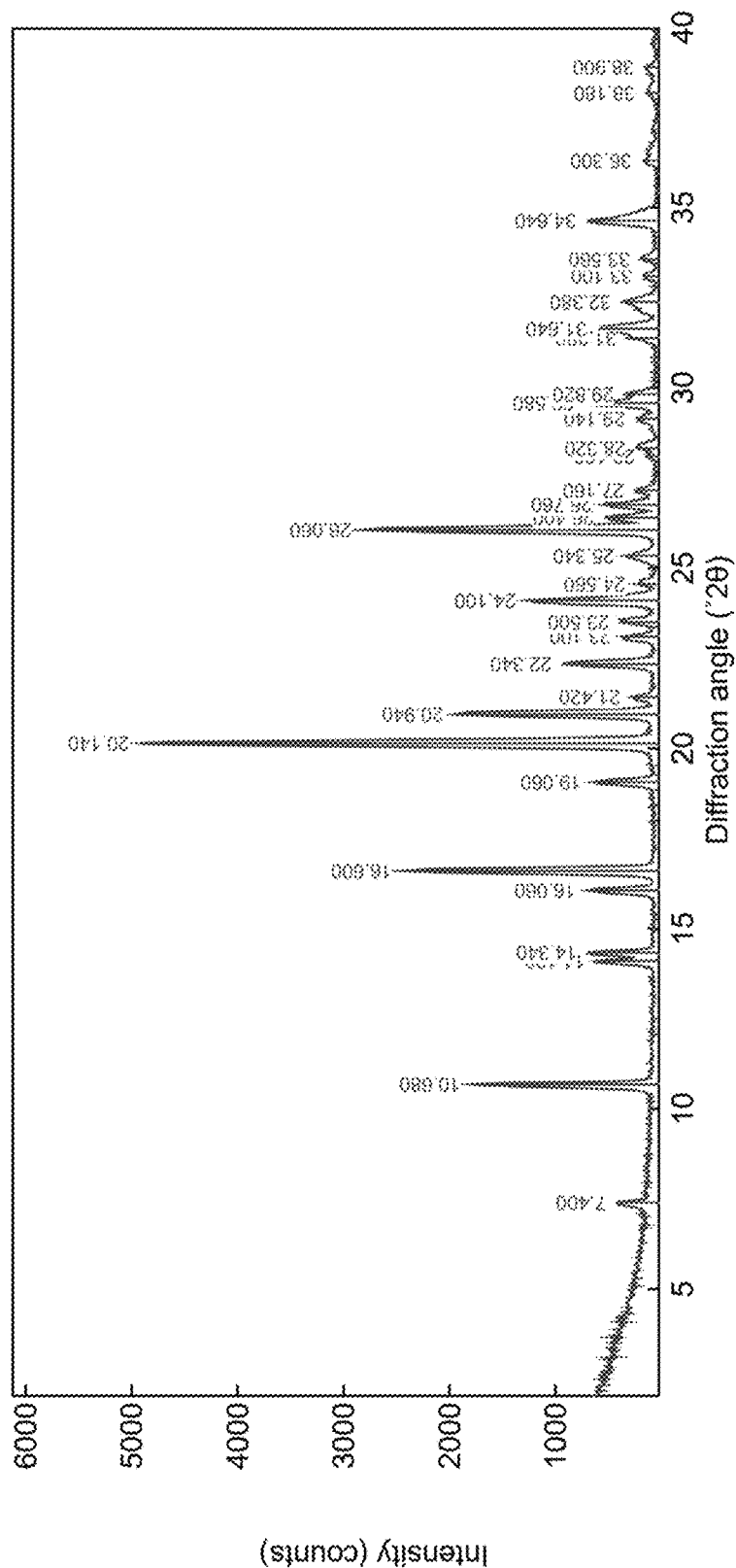
FIG. 8 provides an XRPD diffractogram of psilocybin hydrochloride Form B.

XRPD analysis (FIG. 8) showed it to be crystalline with characteristic peaks at 10.7±0.2° 2-Theta, 14.1±0.2° 2-Theta, and 16.6±0.2° 2-Theta; optionally with further characteristic peaks at 16.1±0.2° 2-Theta and 20.1±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) |
|---|---|
| 7.4 | 8.4 |
| 10.7 | 36.4 |
| 14.1 | 12.3 |
| 14.3 | 13.9 |
| 16.1 | 14.3 |
| 16.6 | 49.5 |
| 19.1 | 13.1 |
| 20.1 | 100.0 |
| 20.9 | 39.7 |
| 21.4 | 5.7 |
| 22.3 | 18.9 |
| 23.1 | 7.5 |
| 23.5 | 7.8 |
| 24.1 | 25.8 |
| 24.6 | 4.8 |
| 25.3 | 6.9 |
| 26.1 | 57.4 |
| 26.4 | 10.7 |
| 26.8 | 11.1 |
| 27.2 | 5.0 |
| 28.1 | 2.9 |
| 28.3 | 4.7 |
| 29.1 | 4.8 |
| 29.6 | 14.6 |
| 29.8 | 6.9 |
| 31.4 | 6.4 |
| 31.6 | 12.1 |
| 32.4 | 7.4 |
| 33.1 | 3.4 |
| 33.6 | 3.8 |
| 34.6 | 14.2 |
| 36.3 | 3.5 |
| 38.2 | 2.9 |
| 38.9 | 3.0 |

Preparation of Psilocybin Hydrochloride Form C Ethanoate

A Tempts to crystallize psilocybin hydrochloride crystalline Form A from ethanol using toluene as an antisolvent resulted in the preparation of psilocybin hydrochloride Form C ethanoate.

XRPD analysis (FIG. 9) showed it to be crystalline with characteristic peaks at 9.6±0.20 2-Theta, 13.6±0.2° 2-Theta, and 16.9±0.2° 2-Theta; optionally with further characteristic peaks at 15.9±0.2° 2-Theta and 20.7±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 8.4 | 12.5 | 20.7 | 51.6 |
| 9.6 | 46.3 | 21.0 | 20.2 |
| 11.7 | 12.6 | 21.4 | 60.6 |
| 13.6 | 100.0 | 22.1 | 13.0 |
| 14.3 | 17.6 | 22.4 | 20.7 |
| 15.4 | 9.5 | 23.1 | 37.8 |
| 15.9 | 21.5 | 23.6 | 30.3 |
| 16.9 | 39.7 | 24.2 | 16.3 |
| 17.4 | 16.2 | 24.6 | 10.2 |
| 18.1 | 6.3 | 25.0 | 33.4 |
| 19.2 | 12.1 | 25.5 | 21.3 |
| 19.7 | 29.3 | 26.0 | 12.6 |
| 26.8 | 12.7 | 32.7 | 7.4 |
| 27.5 | 16.7 | 33.4 | 6.1 |
| 27.9 | 9.2 | 33.9 | 4.8 |
| 28.2 | 13.5 | 36.1 | 5.2 |
| 28.9 | 7.1 | 36.9 | 6.9 |
| 29.2 | 6.5 | 37.8 | 4.0 |
| 30.6 | 9.4 | 38.7 | 4.6 |
| 30.8 | 11.4 | 39.4 | 4.1 |
| 31.8 | 5.9 | | |

Nuclear Magnetic Resonance (NMR) Spectroscopy

The $^1$H NMR spectra were acquired on a Bruker Avance II 400 spectrometer. Samples were prepared by dissolving material in DMSO-$d_6$. The solutions were filtered and placed into individual 5-mm NMR tubes for subsequent spectral acquisition. The temperature controlled (295K) $^1$H NMR spectra acquired on the Avance II 400 utilized a 5-mm cryoprobe operating at an observing frequency of 400.18 MHz.

FIG. 1 provides an NMR spectrum of the non-crystalline solid. The peaks in the NMR spectrum are consistent with the API with some peak shifting likely due to the HCl salt.

The XRPD diffractograms provided as FIGS. 2-9 were produced using the Rigaku Smart-Lab X-ray diffraction system was configured for reflection Bragg-Brentano geometry using a line source X-ray beam. The X-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40° 2θ using a continuous scan of 6° 2θ per minute with an effective step size of 0.02° 2θ.

The TG analysis described in this Example was carried out using a TA Instruments Q5500 Discovery Series instrument. The instrument balance was calibrated using class M weights and the temperature calibration was performed using alumel. The nitrogen purge was ~40 mL per minute at the balance and ~60 mL per minute at the furnace. Each sample was placed into a pre-tared platinum pan and heated from approximately 25° C. to 350° C. at a rate of 10° C. per minute.

DSC analyses were carried out using a TA Instruments Q2500 Discovery Series instrument consistent with Example 1.

Example 3: Single Crystal X-Ray Structure of Crystalline Psilocybin·HCl

The single crystal structure of Form A was solved. The structure was determined to be a cocrystal comprised of one mole of psilocybin hydrochloride salt and one mole of psilocybin. The overall stoichiometry of the cocrystal is 2:1 (two moles of psilocybin per one mole of hydrochloric acid). The unit cell parameters for the solved structure are shown in Table 6.

TABLE 6

Unit cell parameters of Psilocybin Hydrochloride Cocrystal Form A

| | |
|---|---|
| crystal system, space group | Monoclinic, P21/n |
| data collection temperature (K) | 150 |
| a (Å) | 8.4691 (4) |
| b (Å) | 29.5481 (14) |
| c (Å) | 11.5761 (5) |
| β (°) | 102.6579 (14) |
| volume (Å$^3$) | 2826.5 (2) |
| Z | 4 |

Single Crystal Growth

Non-crystalline psilocybin hydrochloride (5.1 mg) was mixed with 8 mL of acetone. The sample was left at room temperature and was found to contain an oily material with plate-shaped single crystals after 2 days. A single crystal was selected and mounted diffraction data were collected and solved.

Single Crystal X-ray Structure Determination

A colorless plate-shaped crystal of psilocybin hydrochloride with formula $C_{12}H_{17}N_2O_4P·C_{12}H_{18}N_2O_4P·Cl$ having approximate dimensions of 0.31×0.28×0.17 mm was mounted on a Mitegen micromesh mount in a random orientation. Preliminary examination and data collection were performed using Cu Kα radiation (λ=1.54178 Å) on Bruker AXS D8 Quest diffractometer equipped with a four-axis kappa stage, an I-μ-S microsource X-ray tube laterally graded multilayer optics, a PhotonIII_C14 area detector and an Oxford Cryosystems low temperature device. The initial unit cell was determined and data were collected using Apex4 v2021.10-RC10 [Bruker (2021). Apex4 v2021.10-RC6, Saint V8.40B, Bruker Nano Inc., Madison (WI), USA] at a temperature of 150 K. Frames were integrated using SAINT V8.40B. A total of 90,775 reflections were collected, of which 6,136 were unique. Cell constants for data collection were obtained from least-squares refinement using 9,378 reflections between 4.1904 and 79.3031°.

The monoclinic cell parameters and calculated volume are:

a=8.4691(4) Å, b=29.5481(14) Å, c=11.5761(5) Å, β=102.6579(14)° and V=2826.5(2) Å3.

For Z=4 and a formula weight of 604.95 the calculated density is 1.422 g/cm3. The linear absorption coefficient is 2.732/mm for Cu Kα radiation. Scaling and a multi-scan absorption correction using SADABS was applied [Krause, L., Herbst-Irmer, R., Sheldrick G. M. & Stalke D. (2015). J. Appl. Cryst. 48, 3-10.]. Transmission coefficients ranged from 0.6327 to 0.7543. Intensities of equivalent reflections were not averaged during data processing.

The space group was determined by the program XPREP as embedded in SHELXTL. [Bruker AXS (2003). SHELXTL (Version 6.14), Bruker AXS Inc., Madison (WI), USA.]. Systematic absences and intensity statistics indicated space group P21/n (#14). The structure was solved by dual methods using SHELXT [Sheldrick G. M. (2015). "SHELXT—Integrated space-group and crystal-structure determination", Acta Cryst. A71, 3-8.] and refined by full matrix least squares against F2 with all reflections using SHELXL-2019 [Sheldrick G. M. (2015). "Crystal structure refinement with SHELXL", Acta Cryst., C71, 3-8; Sheldrick, G. M. (2018). SHELXL2018. University of Gottingen, Germany] and the graphical user interface SheIXle [Hibschle, C. B., Sheldrick, G. M. and Dittrich, B. (2011). J. Appl. Cryst., 44, 1281-1284.]. Additional atoms were located in succeeding difference Fourier syntheses.

The diffraction pattern shows some minor non-Bragg diffraction intensity, recognizable as diffuse scattering between diffraction spots along the longest reciprocal axis. The non-Bragg behaviour originates from the presence of a minor fraction of the structure being replaced by a chemically identical component that is shifted along the a-axis direction by ca. 2.55 Å. The shift is incommensurate with the symmetry elements of the monoclinic unit cell (glide planes, screw axes and inversion centers), thus leading to the translated subunits having different relative orientations towards their symmetry related counterparts along b or c than the main fraction of the structure. This is most obvious for hydrogen bonding interactions between subunits parallel to each other along b or c, which differ for the main and the minor translated structural components.

Constructive interference of scattering from atoms of the main and minor components along (predominantly) the reciprocal b-axis are responsible for the non-Bragg intensity observed along this direction. For the purpose of data processing and structure refinement, the non-Bragg intensity was ignored and data reflect the "average disordered" structure as obtained from only the Bragg intensities of the unit cell in P21/n.

Two organic psilocybin moieties as well as one chloride anion are present in both the major and minor structural component. Thus there are formally each one cationic and one neutral psilocybin moiety. For both, the two nitrogen atoms are protonated (an uncharged indole N—H and a cationic RN(H)Me2 fragment). Both phosphonate units are protonated at least once with a well-defined H atom at O3 that is hydrogen bonded to an oxygen atom of another psilocybin moiety (along the a-axis direction). A third proton is present at the phosphonate units and is shared between the two psilocybin moieties, via close to symmetric hydrogen bonds. For the major component, this proton is located on two inversion centers, halfway between two symmetry equivalent oxygen atoms O2 (two half occupied protons, for one proton for the entire component). The very short O . . . O distances (2.409(3) and 2.402(3) Å, respectively) indicate these H-bonds to very strong interactions. All phosphonate oxygen atoms in this main component (other than the carbon bound O atom O1) are involved in O—H . . . O or O . . . H . . . O hydrogen bonds as either donors or acceptors.

In the minor component, the symmetric strong hydrogen bonds are not between symmetry equivalent oxygen atoms. Instead there is one fully occupied proton in a general position, between atoms O2B of the two minor psilocybin moieties. The distance between O2B_1 and O2B_2 (at 1-x, 1-y, 1-z) is substantially larger than in the main component (2.87(3) Å), indicating a weaker O . . . H . . . O interaction. Oxygen atoms O4B in both moieties are not involved in any hydrogen bonding interactions in the minor component. The occupancy of the minor component, while well resolved in difference density maps, is less than 6%, and thus some restraints and constraints were applied for refinement. Major and minor disordered moieties were restrained to have similar geometries (SAME commands of Shelxl). Major and minor moieties are related by close to perfect translations (along a) and ADPs of translated atoms were thus set to be pairwise identical (EADP commands of Shelxl). H atoms attached to carbon and nitrogen atoms were positioned geometrically and constrained to ride on their parent atoms. C—H bond distances were constrained to 0.95 Å for aromatic and alkene C—H moieties, and to 0.99 and 0.98 Å for aliphatic CH2 and CH3 moieties, respectively. N—H bond distances were constrained to 0.88 Å for planar (sp2 hybridized)N—H groups. N—H bond distances were constrained to 1.00 Å for pyramidal (sp3 hybridized) ammonium R3NH+ groups. Methyl CH3 were allowed to rotate but not to tip to best fit the experimental electron density. OH distances of hydroxyl H atoms attached to O3 or O3B were constrained to 0.84 Å and were allowed to rotate but not to tip to best fit the experimental electron density. One hydroxyl H atom position was further restrained based on hydrogen bonding considerations (H3B_1, to be H-bonded to O4B_2 at −1+x, +y, +z with a distance of 1.73(2) Å. H atoms involved in strong O . . . H . . . O hydrogen bonds were placed from difference density maps (on inversion centers for the main component and in a general position for the minor component) and were not refined.

Subject to these conditions the occupancy ratio refined to 0.9472(6) to 0.0528(6). The structure was refined using full-matrix least-squares where the function minimized was:

$\Sigma w(|Fo|2-|Fc|2)2$ and the weight $w$ is defined as $w=1/\sigma2(Fo2)+(0.0311P)2+3.1421P]$ where $P=(Fo2+2Fc2)/3$.

Scattering factors were taken from the International Tables for Crystallography[International Tables of Crystallography, Vol C Tables 4.2.6.8 and 6.1.1.4]. A total of 6,136 independent reflections were used in the refinements. 5,770 reflections with $F2>2\sigma(F2)$ were used in the calculation of R1.

The final cycle of refinement included 484 variable parameters and 99 restraints and converged (the largest parameter shift was 0.001 times its standard uncertainty) with unweighted and weighted agreement factors of:

$R1=\Sigma|Fo|-|Fc|/\Sigma|Fo|=0.0444$ $wR2=\{\Sigma[w(Fo2-Fc2)2]/\Sigma[w(Fo2)2]\}0.5=0.1138$ The goodness-of-fit parameter was 1.080. The highest peak in the final difference Fourier had a height of 0.362 e/Å3. The minimum negative peak had a height of −0.434 e/Å3.

Crystal data and data collection parameters are given in Table 7.

TABLE 7

| Crystal data | |
|---|---|
| Chemical formula | $C_{12}H_{17}N_2O_4P \cdot C_{12}H_{18}N_2O_4P \cdot Cl$ |
| Mr | 604.95 |
| Crystal system, space group | Monoclinic, P21/n |
| Temperature (K) | 150 |
| a, b, c (Å) | 8.4691 (4), 29.5481 (14), 11.5761 (5) |
| β (°) | 102.6579 (14) |
| V (Å$^3$) | 2826.5 (2) |
| Z | 4 |
| F(000) | 1272 |
| Dx (Mg m$^{-3}$) | 1.422 |
| Radiation type | Cu Kα |
| No. of reflections for cell measurement | 19378 |
| θ range (°) for cell measurement | 4.2-79.3 |
| μ (mm$^{-1}$) | 2.73 |
| Crystal shape | Plate |
| Colour | Colourless |
| Crystal size (mm) | 0.31 × 0.28 × 0.17 |
| Data collection | |
| Diffractometer | Bruker AXS D8 Quest diffractometer with PhotonIII_C14 charge-integrating and photon counting pixel array detector |
| Radiation source | I-mu-S microsource X-ray tube |
| Monochromator | Laterally graded multilayer (Goebel) mirror |
| Detector resolution (pixels mm$^{-1}$) | 7.4074 |
| Scan method | ω and phi scans |
| Absorption correction | Multi-scan (SADABS 2016/2, Krause et al. 2015) |
| $T_{min}$, $T_{max}$ | 0.633, 0.754 |
| No. of measured, independent and observed [I > 2σ(I)] reflections | 90775, 6136, 5770 |
| $R_{int}$ | 0.071 |
| θ values (°) | $\theta_{max}$ = 79.8, $\theta_{min}$ = 4.2 |
| (sin θ/λ)max (Å$^{-1}$) | 0.638 |
| Range of h, k, l | h = −10→10, k = −37→36, l = −14→14 |

TABLE 7-continued

| Crystal data | |
|---|---|
| Refinement | |
| Refinement on | $F^2$ |
| $R[F^2 > 2\sigma(F^2)]$, $wR(F^2)$, S | 0.044, 0.114, 1.09 |
| No. of reflections | 6136 |
| No. of parameters | 484 |
| No. of restraints | 99 |
| H-atom treatment | H atoms treated by a mixture of independent and constrained refinement |
| Weighting scheme | $w = 1/[\sigma^2(F_{o2}) + (0.0311P)_2 + 3.1421P]$ where $P = (F_{o2} + 2F_c)_2/3$ |
| $(\Delta/\sigma)$max | 0.001 |
| $\Delta\rho_{max}$, $\Delta\rho_{min}$ (e Å$^{-3}$) | 0.36, −0.43 |
| Extinction method | SHELXL2019/2 (Sheldrick 2019), $Fc^* = kFc[1 + 0.001 \times Fc^2\lambda^3/\sin(2\theta)]^{-1/4}$ |
| Extinction coefficient | 0.0017 (2) |

FIG. 6 provides an XRPD pattern calculated from the single-crystal data that is overlayed with an XRPD diffractogram of psilocybin·HCl cocrystal Form A. The calculated pattern matches the experimental XPRD obtained for the cocrystal Form A. Peak shifting observed between the two patterns was due to the temperature difference at which the single-crystal and X-ray powder diffraction data were collected.

XRPD analysis of calculated pattern of psilocybin·HCl cocrystal Form A (FIG. 6) shows characteristic peaks at 6.0° 2-Theta, 9.9° 2-Theta, and 14.6° 2-Theta; optionally with further characteristic peaks at 18.0° 2-Theta and 19.7° 2-Theta. A full list of calculated peaks is found in the following table:

| Angle 2-Theta (°) | Rel. Intensity (%) | Angle 2-Theta (°) | Rel. Intensity (%) |
|---|---|---|---|
| 6.0 | 21.9 | 17.2 | 6.0 |
| 8.4 | 2.6 | 18.0 | 38.1 |
| 9.9 | 100.0 | 18.4 | 1.2 |
| 11.1 | 0.6 | 18.9 | 8.2 |
| 11.8 | 1.3 | 19.7 | 33.2 |
| 12.0 | 1.1 | 20.8 | 8.3 |
| 12.3 | 1.1 | 21.0 | 9.4 |
| 13.2 | 6.5 | 21.1 | 12.4 |
| 14.3 | 6.8 | 21.4 | 42.3 |
| 14.6 | 20.0 | 21.7 | 30.5 |
| 14.9 | 7.9 | 22.0 | 30.8 |
| 15.8 | 1.6 | 22.8 | 11.8 |
| 16.1 | 0.7 | 23.1 | 20.0 |
| 16.8 | 10.3 | 23.3 | 7.8 |
| 23.7 | 3.2 | 31.3 | 8.6 |
| 24.1 | 33.2 | 31.7 | 6.5 |
| 24.5 | 20.1 | 32.3 | 2.8 |
| 24.8 | 4.2 | 32.5 | 1.4 |
| 25.4 | 5.5 | 33.0 | 17.4 |
| 25.7 | 5.1 | 33.5 | 1.9 |
| 26.1 | 7.8 | 33.7 | 7.6 |
| 26.3 | 3.8 | 34.0 | 3.9 |
| 26.6 | 8.0 | 34.7 | 1.2 |
| 27.7 | 3.6 | 34.9 | 1.4 |
| 27.9 | 3.3 | 36.5 | 2.0 |
| 28.2 | 7.9 | 36.8 | 2.0 |
| 29.2 | 0.7 | 37.1 | 1.4 |
| 29.6 | 2.8 | 37.3 | 1.1 |
| 29.8 | 7.8 | 38.3 | 5.9 |
| 29.9 | 8.3 | 38.7 | 1.4 |
| 30.2 | 4.8 | 38.9 | 2.0 |
| 30.6 | 1.3 | 39.5 | 3.5 |
| 30.9 | 2.9 | 39.7 | 4.0 |

Example 4: Salt Screen of Psilocybin

Psilocybin is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the free base is a solvate or hydrate, and to evaluate thermal stability. DVS data are used to evaluate hygroscopicity of the free base and if hydrates can be formed at high relative humidity. About 10 to 15 solvents are selected from the list below, based on their properties (polarity, dielectric constant and dipole moment).

TABLE 8

| Solvents | |
|---|---|
| acetic acid | n-heptane |
| Acetone | n-hexane |
| Acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | Methanol |
| Chlorobenzene | methoxybenzene (anisole) |
| Chloroform | methyl acetate |
| di(ethylene glycol) | methyl ethyl ketone (2-butanone) |
| Dichloromethane | methyl isobutyl ketone |
| diethyl ether | Nitromethane |
| Diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | Perfluorohexane |
| 1,4-dioxane | propyl acetate |
| 1,2-ethanediol (ethylene glycol) | 1,1,2,2-tetrachloroethane |
| Ethanol | Tetrahydrofuran |
| Ethanolamine | Toluene |
| 2-ethoxyethanol (Cellusolve) | 1,1,1-trichloroethane |
| ethyl acetate | 2,2,2-trifluoroethanol |
| ethyl formate | Water |
| formic acid | o-xylene (1,2-dimethylbenzene) |
| Glycerol | p-xylene (1,4-dimethylbenzene) |

The information obtained is used for designing the subsequent salt screen. The salt screen is performed by reacting the free base with pharmaceutically acceptable acids under various conditions in attempts to generate crystalline salts. Pharmaceutically acceptable acids that may be used are listed below. Specific acids are selected based on the pKa of the free base, and typically 15 to 20 acids are selected. Experiments are performed using 0.5 molar equivalent, 1 molar equivalent and/or 2 molar equivalents of the acid.

TABLE 9

Exemplary Acids

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| fumaric acid | carbonic acid |
| galactaric (mucic) acid | |

Solvent systems for the salt crystallization experiments are selected based on the solubility of the free base and the selected acid. Solvents are used as a single solvent or as solvent mixtures, some containing water. The techniques that are used for salt crystallization are chosen based on the solvent selected and properties of the free base. The following techniques (or combination of techniques) may be used for salt crystallization:

Free base and acid are dissolved in a solvent or mixture of solvents, and the solvents are evaporated at different rates (slow evaporation or fast evaporation) and at different temperatures (ambient or elevated).

Free base and acid are dissolved in a solvent or mixture of solvents (at ambient temperature or an elevated temperature), and the final solution is cooled to a sub-ambient temperature (between −78° C. to 15° C.). The cooling method can be a fast cooling (by plunging the sample into an ice bath or a dry ice/acetone bath), or slow cooling. The solids formed will be recovered by filtration and dried (air dried or vacuum dried).

Free base and acid are dissolved in a solvent or mixture of solvents, and an antisolvent is added to precipitate the salt. The solids formed will be recovered by filtration and dried (air dried or vacuum dried).

Free base and acid are added to a solvent or mixture of solvents, where one or both components are not fully dissolved. The slurry is agitated at different temperatures for a number of days. The solids formed will be recovered by filtration and dried (air dried or vacuum dried). The same experiment can be also performed in solvent systems where the solvents are not miscible.

Free base and acid are milled together (by mechanical milling or by mortar and pestle), with a drop of solvent, or without any solvent.

Free base and acid are melted together, and cooled to various temperatures using various cooling rates.

If an amorphous form of a salt is obtained, the amorphous salt will be exposed to elevated humidity, or elevated temperature (or combination of both), or solvent vapors at various temperatures to form crystalline salts.

The stoichiometric ratio of acid to psilocybin is confirmed by $^1$H NMR, HPLC, or both as is known to those of ordinary skill in the art.

The salts obtained are analyzed by XRPD to determine if they are crystalline and, if so, by DSC to see the melting point and by TG to see if they are hydrated/solvated, and by 1H NMR spectroscopy to ensure chemical integrity. KF water titration is performed on salts that are hydrated. DVS analysis is performed to evaluate hygroscopicity of the salt and if hydrated form is present.

Example 5: Polymorph Screen of Psilocybin

The active pharmaceutical ingredient (API), psilocybin, which may be a free base (zwitterionic) or a salt form, such as an acid addition salt form, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the API is a solvate or hydrate, and to evaluate thermal stability. DVS data are used to evaluate hygroscopicity of the API and if hydrates can be formed at high relative humidity. About 10 to 15 solvents may be selected from the list below, based on their properties (polarity, dielectric constant and dipole moment).

TABLE 10

Solvents

| | |
|---|---|
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |
| 2-ethoxyethanol (Cellusolve) | 1,1,1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

- API is dissolved in a solvent or mixture of solvents, and the solvents are evaporated at different rates (slow evaporation or fast evaporation) and at different temperatures (ambient or elevated).
- API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).
- API is dissolved in a solvent or mixture of solvents, and an antisolvent is added to precipitate the salt. The solids formed will be recovered by filtration and dried (air dried or vacuum dried).
- API is added to a solvent or mixture of solvents, where the API is not fully dissolved. The slurry will be agitated at different temperatures for a number of days. The solids formed will be recovered by filtration and (air dried or vacuum dried).
- API is milled (by mechanical milling or by mortar and pestle), with a drop of solvent, or without any solvent.
- API is melted and cooled (at different cooling rates, fast and slow, and cooled to different temperatures) to obtain solids.
- API is suspended in a solvent or mixture of solvents, and the slurry is placed in a heating/cooling cycle for multiple cycles. The remaining solids after the final cooling cycle will be filtered and (air dried or vacuum dried).
- API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.
- API is exposed to elevated humidity (or elevated temperature, or combination thereof), or to solvent vapors for extended period of days.
- Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).
- API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50(TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45° 2θ with steps of 0.1°, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered CuK$_{α1}$ radiation (λ=1.5405981 Å) produced at 40 kV and 20 mA by a Philips PW 1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005° 2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Characterization of Psilocybin

One sample of psilocybin was characterized by X-ray powder diffraction (XRPD), nuclear magnetic resonance (NMR) spectroscopy, differential scanning calorimetry (DSC), thermogravimetry (TG), polarized light microscopy (PLM), infrared (IR) spectroscopy, and dynamic vapor sorption (DVS). The remaining material after DVS analysis was analyzed by XRPD to determine if a solid form change occurred during the DVS experiment.

Figure 11:
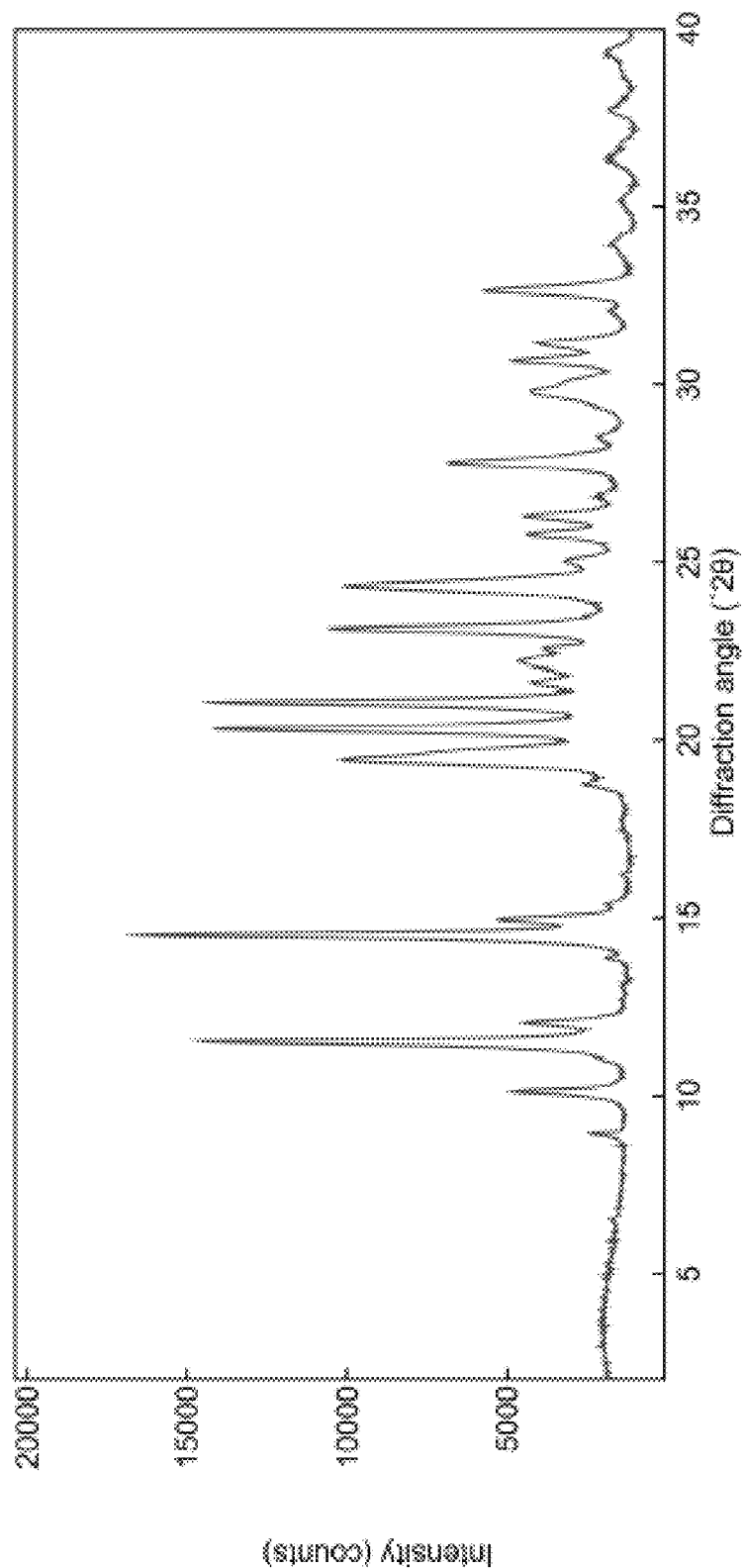
FIG. 11 provides an XRPD diffractogram of psilocybin Form A plus Form B.
Figure 24:
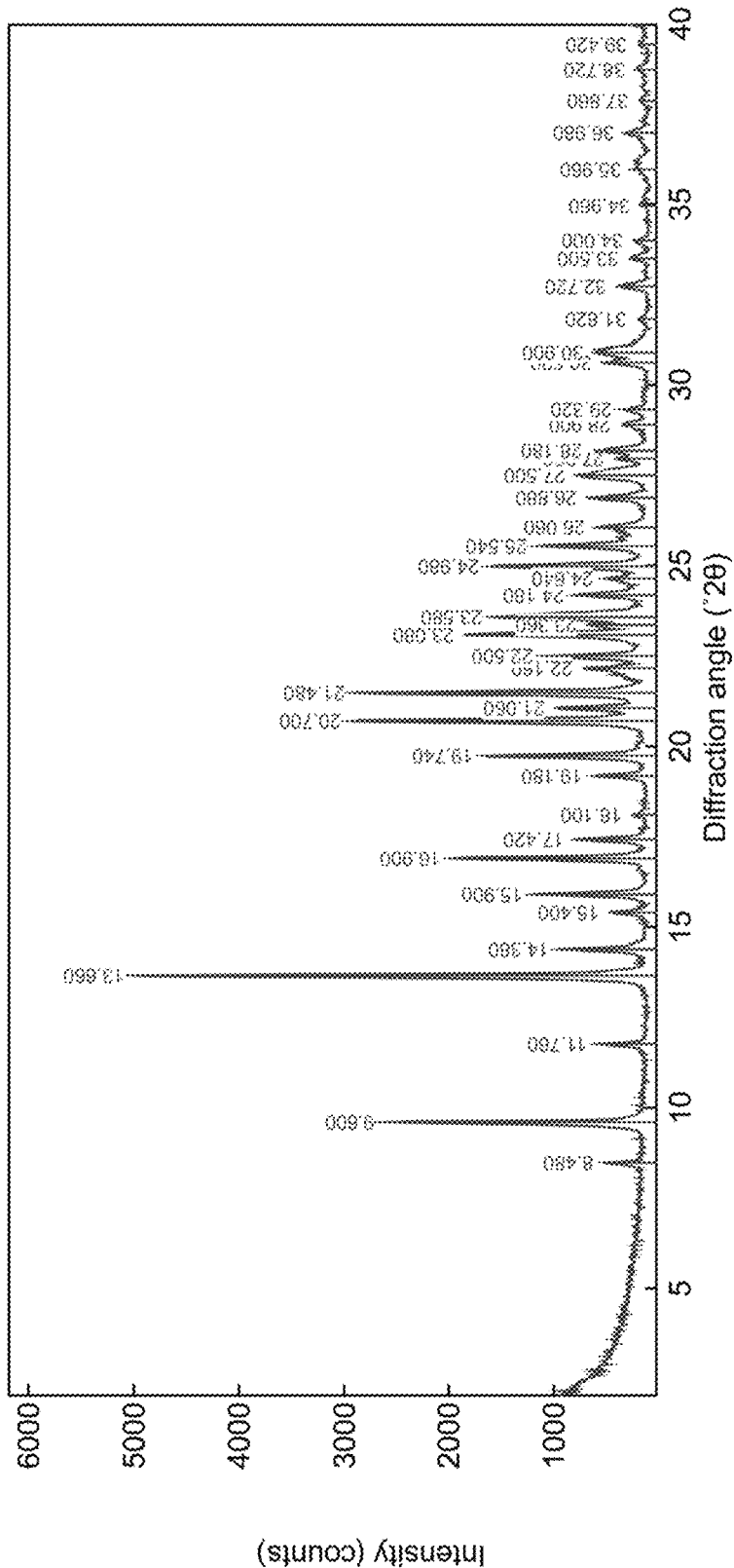
FIG. 24 provides an XRPD diffractogram of psilocybin Form C.

This sample of psilocybin was crystalline by XRPD analysis and designated as Form A (FIG. 11). However, XRPD analysis also showed weak diffraction peaks of another form present in the material. Based on DVS data and XRPD analysis of the post-DVS specimen, this form was identified as a hydrate of psilocybin and designated as Form B (FIG. 24). Thus, the XRPD pattern of this sample was characterized as a mixture of Forms A and B.

Figure 12:
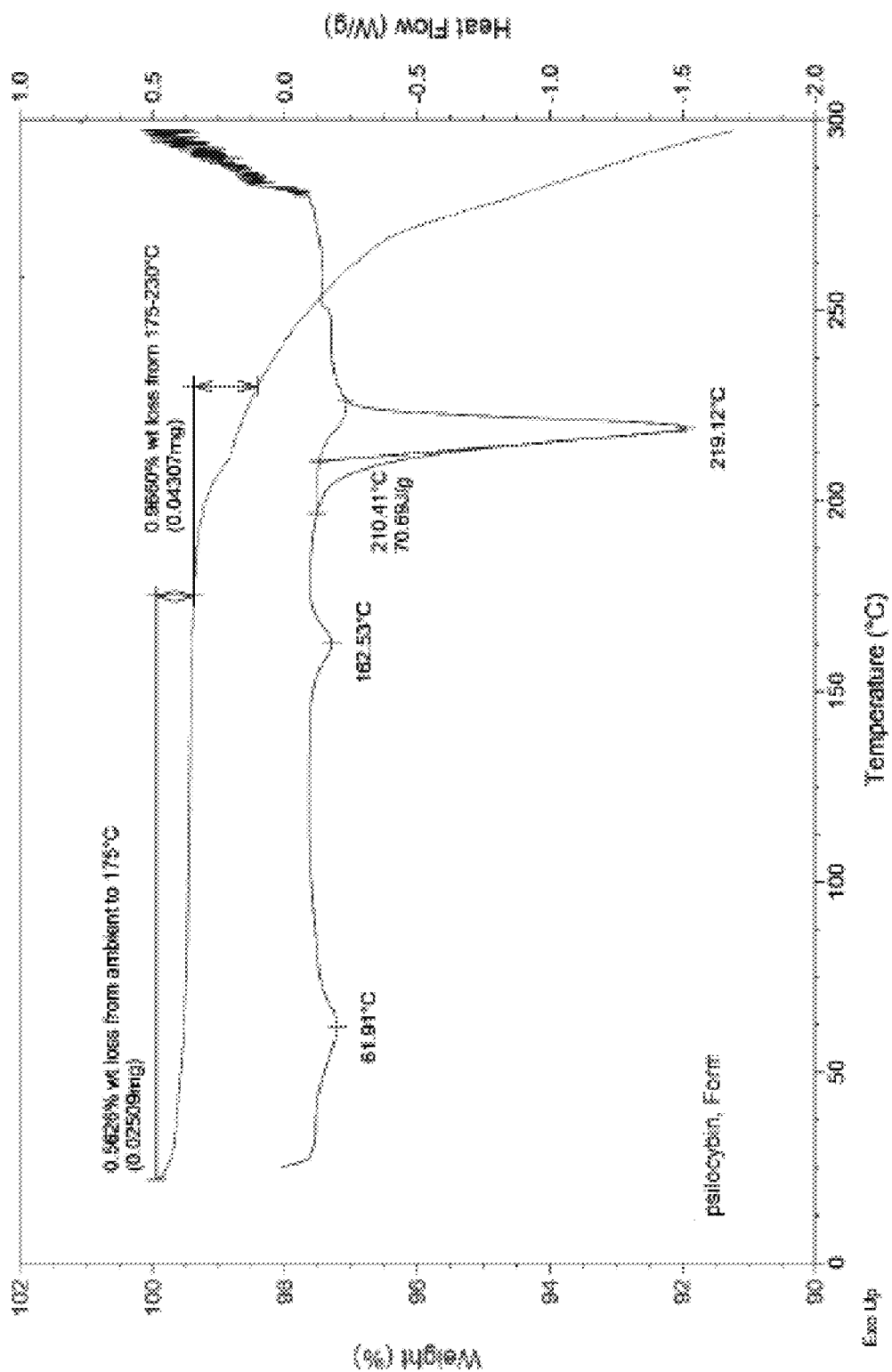
FIG. 12 provides a graph of weight and heat flow versus temperature, illustrating the results from the Thermogravimetric Analysis (TG) and Differential Scanning Calorimetry (DSC) of the psilocybin sample analyzed to produce FIG. 11.

By DSC analysis, this sample exhibited a probable melting point at approx. 219° C. (intense endotherm), likely attributed to unsolvated Form A. Weak endothermic transitions observed at approx. 62 and 163° C. may be attributed to small amounts of Form B (FIG. 12). By TGA, the sample exhibited approx. 0.6% weight loss between ambient temperature and 175° C., which may be due to presence of small amounts of Form B (FIG. 12).

This sample of psilocybin appeared hygroscopic between 75-95% RH, exhibiting approx. 18% water uptake in that RH range; the material converted to a hydrate Form B, as a result of the DVS experiment.

TABLE 11

Characterization of psilocybin

Figure 13:
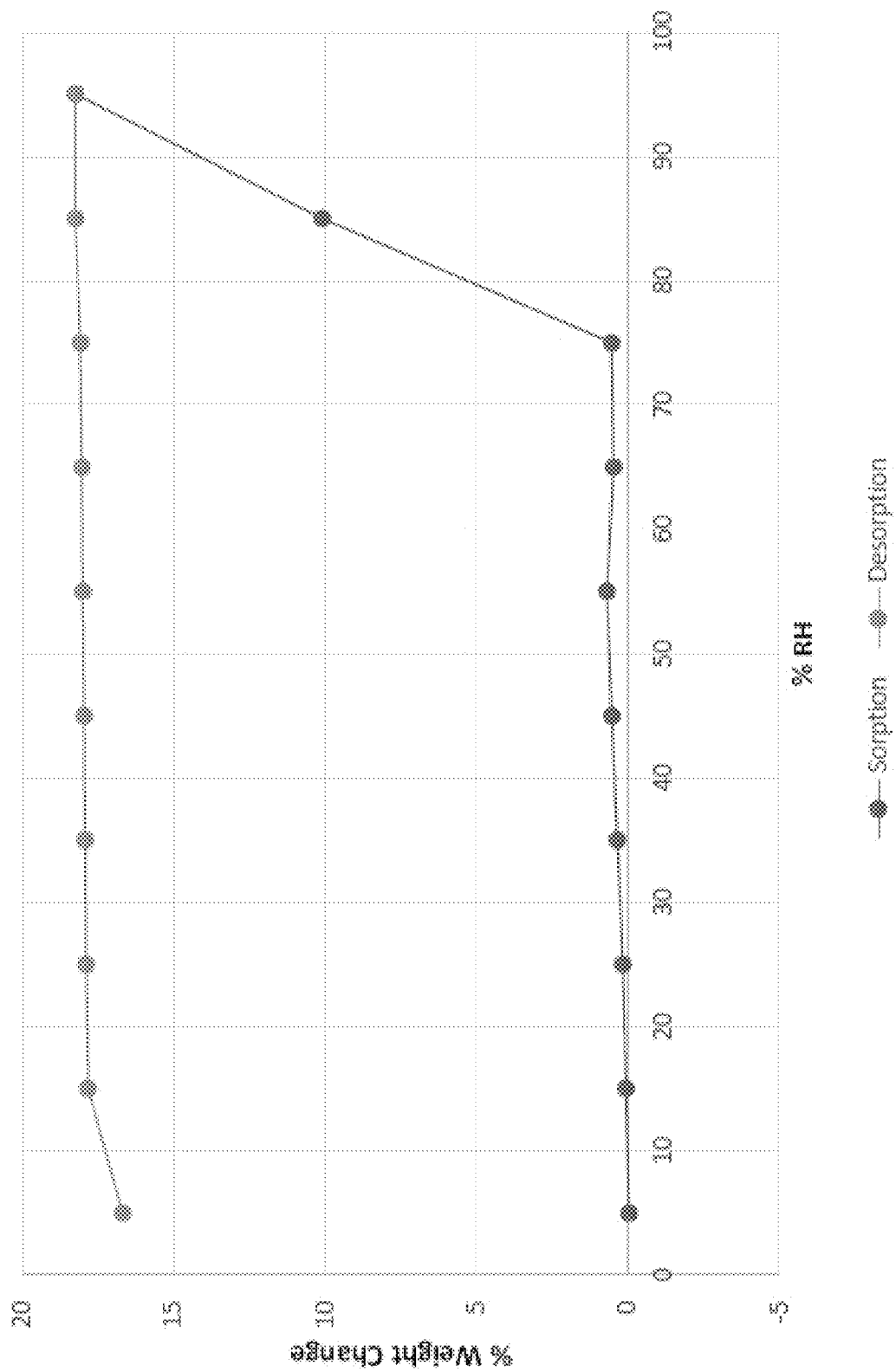
FIG. 13 provides a graph of weight change versus relative humidity (RH), illustrating the water sorption and desorption of psilocybin Form A.
Figure 14:
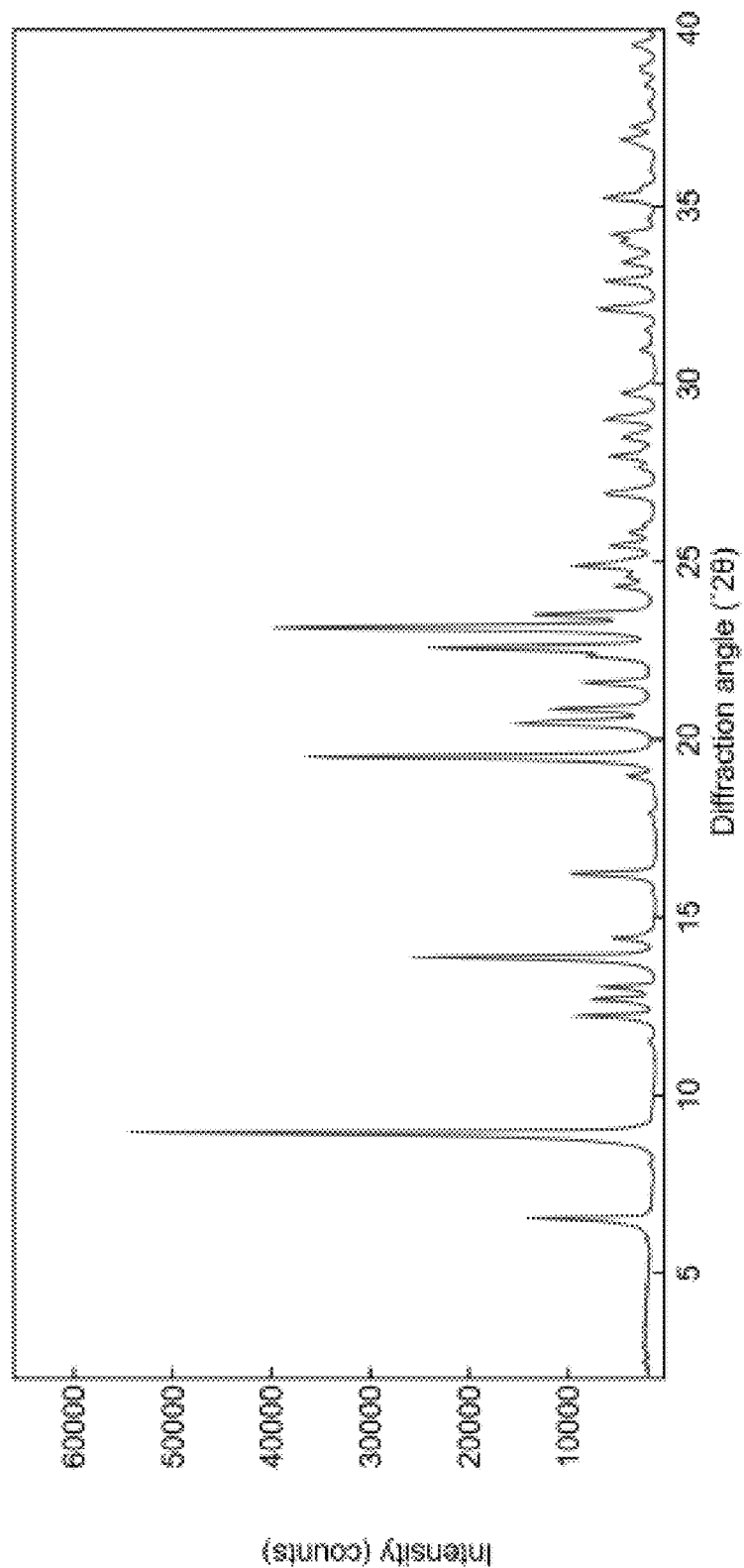
FIG. 14 provides an XRPD diffractogram of the psilocybin Form B identified after dynamic vapor sorption (DVS).
Figure 15:
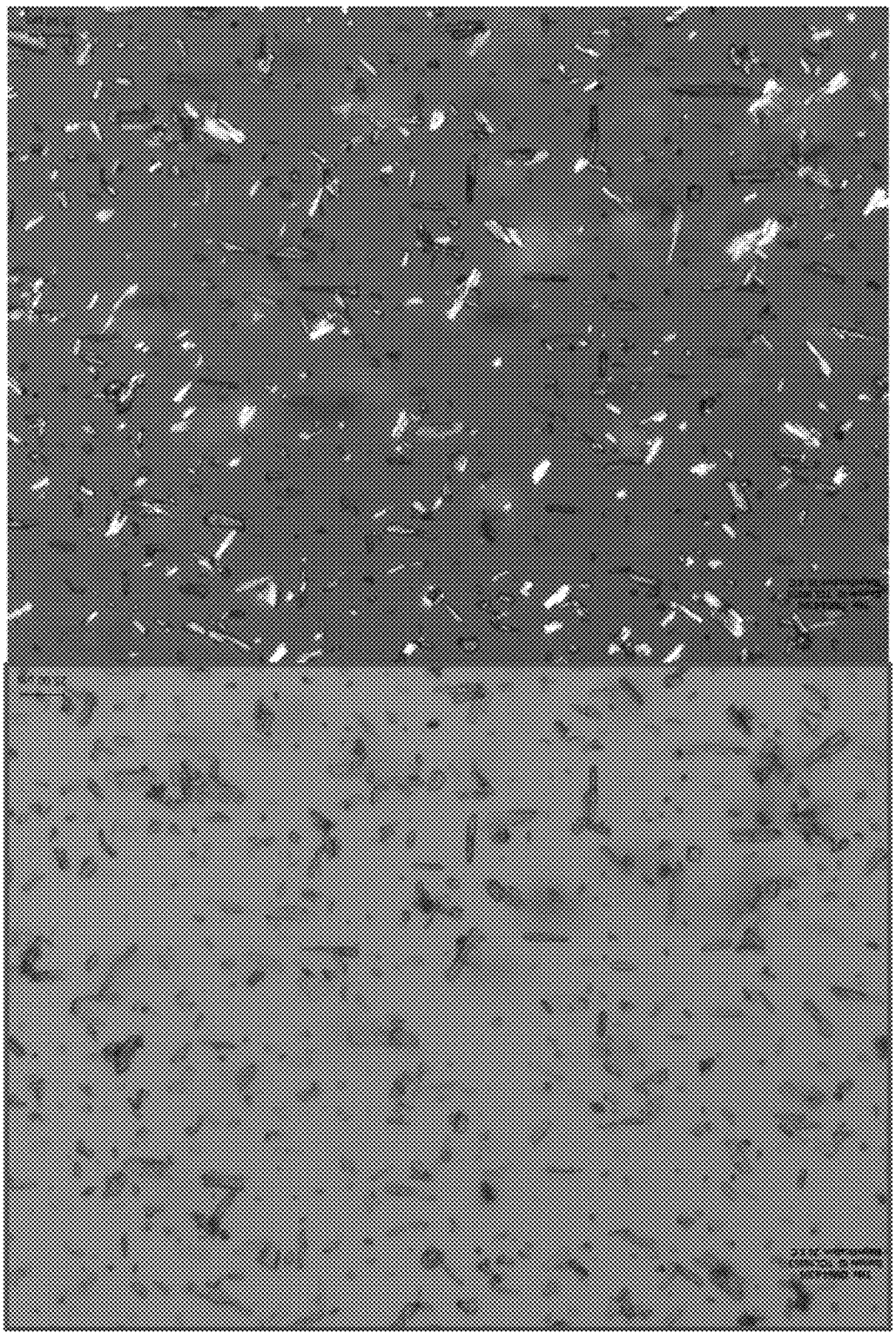
FIG. 15 provides a digital image illustrating the polarized microscopy data psilocybin sample of Form A.
Figure 16:
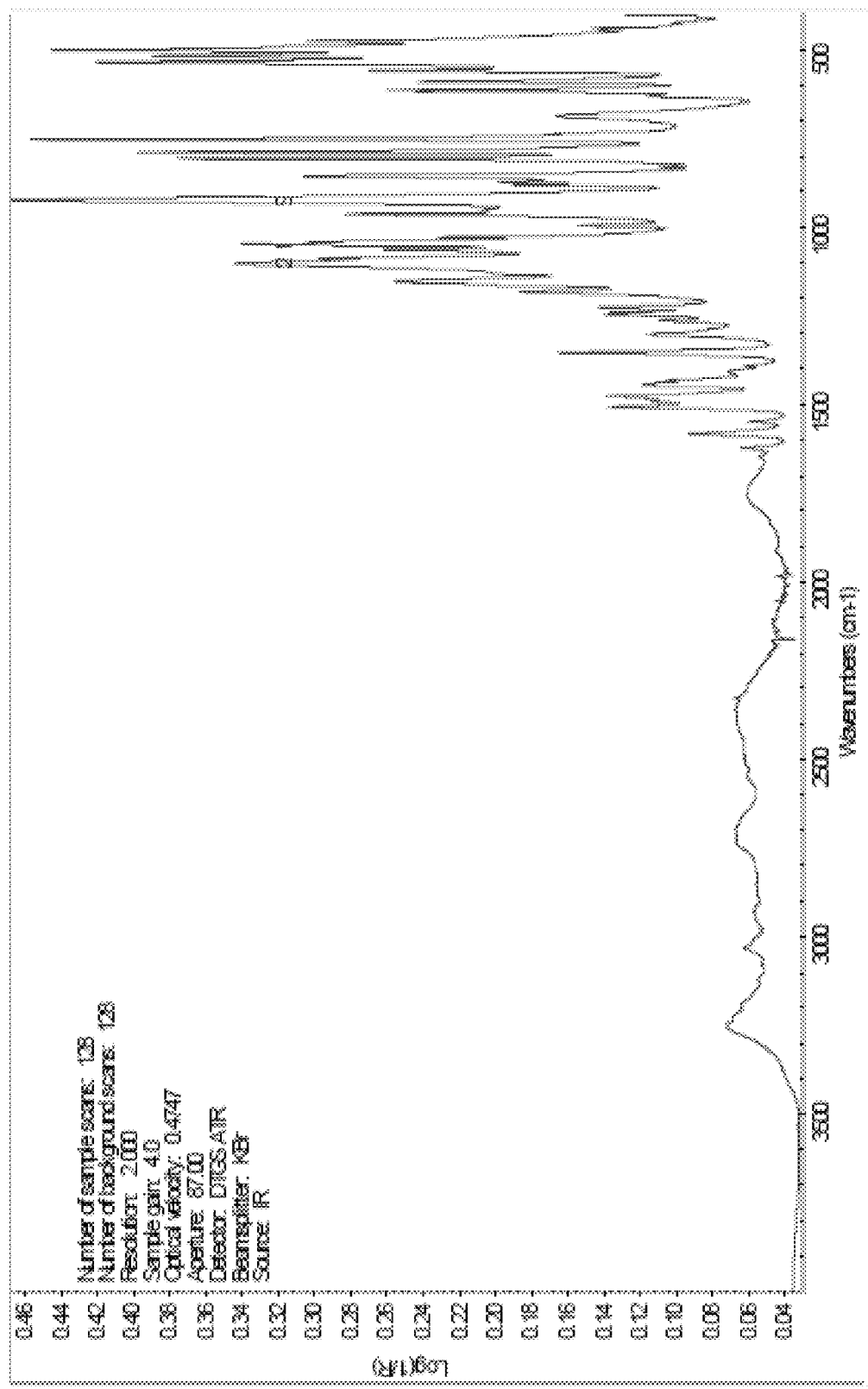
FIG. 16 provides the IR spectrum of the psilocybin sample Form A.
Figure 17:
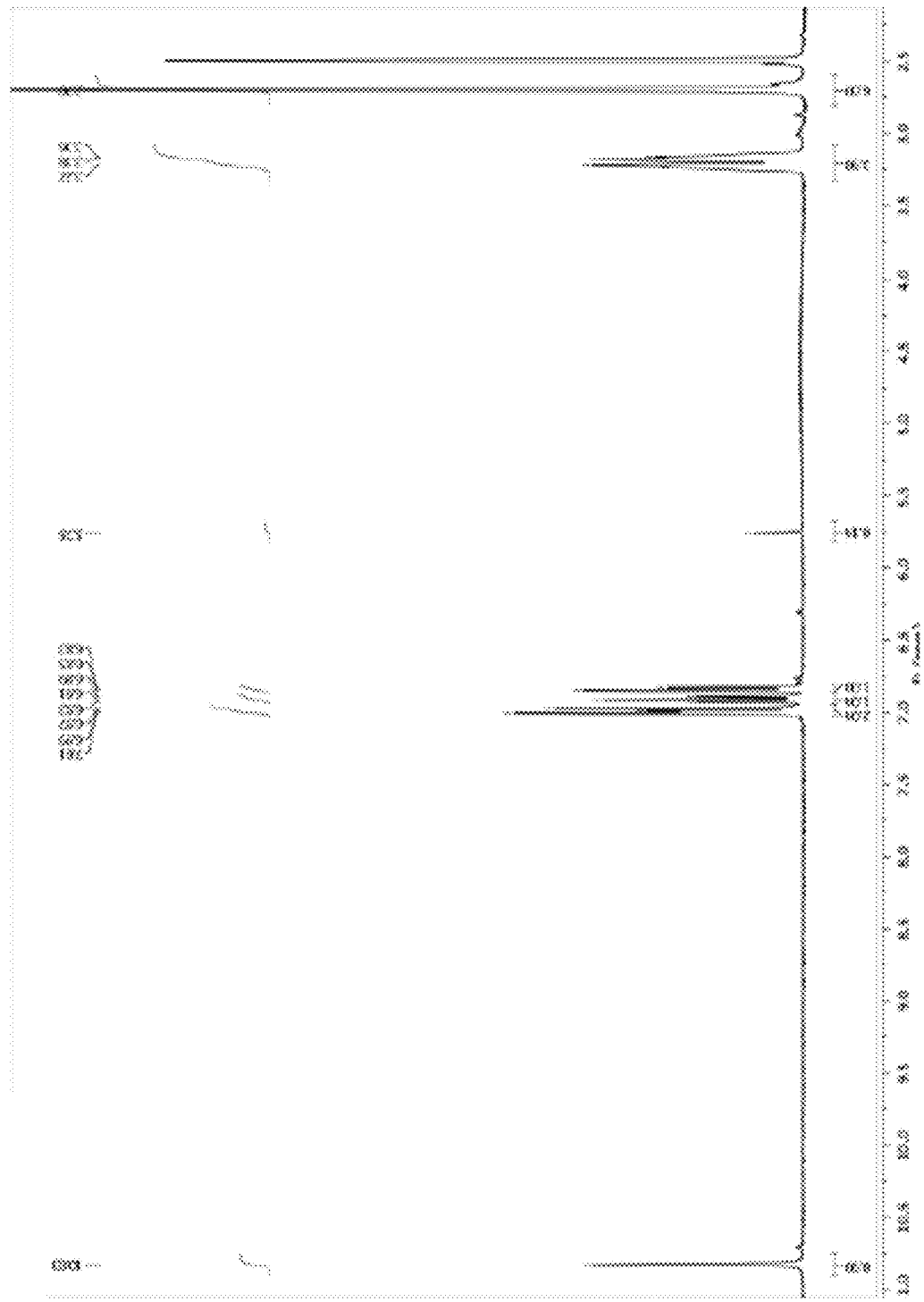
FIG. 17 provides an NMR spectrum of psilocybin sample analyzed to produce FIG. 11.

| Analytical Technique | Results | Figure |
|---|---|---|
| XRPD | Crystalline Form A + weak Form B peaks (hydrate) | FIG. 11 |
| DSC | Endo 62 (weak), 163 (weak), 219° C. (ΔH: 71 J/g) | FIG. 12 |
| TGA[a] | 0.6% wt loss from ambient to 175° C.; 1.0% wt loss from 175 to 230° C. | FIG. 12 |
| DVS[a] | Hygroscopic above 75% RH: approx.18% water uptake from 75-95% RH | FIG. 13 |
| Post-DVS XRPD | Crystalline Form B (hydrate) | FIG. 14 |
| PLM | Birefringence, possible single crystals present | FIG. 15 |
| IR | | FIG. 16 |
| $^1$H NMR | Consistent with structure | FIG. 17 |

[a]Reported weight change values are approximate.

XRPD analysis of Psilocybin Crystalline Form A (+weak B) (FIG. 11) showed it to be crystalline. A full list of peaks, as measured with Cu Kα radiation, is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 8.9 | 14.5 | 24.3 | 61.0 |
| 10.1 | 29.0 | 25.0 | 19.4 |
| 11.5 | 88.1 | 25.8 | 26.5 |
| 12.1 | 26.9 | 26.3 | 27.0 |
| 13.9 | 11.7 | 26.9 | 13.5 |
| 14.5 | 100.0 | 27.8 | 41.4 |
| 15.0 | 31.9 | 28.5 | 13.0 |
| 15.4 | 11.7 | 29.8 | 25.8 |
| 16.2 | 8.6 | 30.7 | 29.1 |
| 18.7 | 16.0 | 31.2 | 24.5 |
| 19.5 | 61.3 | 32.0 | 10.9 |
| 20.3 | 85.3 | 32.6 | 34.7 |
| 21.1 | 86.6 | 33.9 | 10.9 |
| 21.6 | 25.7 | 35.2 | 8.9 |
| 22.2 | 28.0 | 36.3 | 11.3 |
| 22.6 | 23.3 | 37.7 | 10.9 |
| 23.1 | 63.5 | 39.3 | 11.6 |

XRPD analysis of Psilocybin Crystalline Form B (FIG. 14) showed it to be crystalline with characteristic peaks at 6.5±0.2° 2-Theta and 9.0±0.2° 2-Theta; optionally with further characteristic peaks at 12.2±0.2° 2-Theta, 13.9±0.2° 2-Theta, and 16.2±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 6.5 | 24.4 | 17.6 | 2.7 |
| 8.1 | 3.4 | 17.9 | 3.5 |
| 9.0 | 100.0 | 19.0 | 7.6 |
| 11.5 | 3.3 | 19.5 | 66.3 |
| 12.2 | 16.4 | 20.5 | 28.1 |
| 12.7 | 14.1 | 20.9 | 21.1 |
| 13.0 | 11.9 | 21.6 | 15.5 |
| 13.9 | 46.3 | 22.3 | 14.9 |
| 14.4 | 10.3 | 22.6 | 43.4 |
| 15.7 | 2.8 | 23.2 | 72.6 |
| 16.2 | 18.1 | 23.5 | 25.0 |
| 24.3 | 9.9 | 32.9 | 11.6 |
| 24.6 | 7.8 | 33.4 | 8.3 |
| 24.9 | 17.1 | 34.0 | 8.6 |
| 25.4 | 10.8 | 34.2 | 10.4 |
| 25.8 | 7.2 | 34.6 | 3.5 |
| 26.0 | 4.5 | 35.2 | 12.0 |
| 26.9 | 11.6 | 35.5 | 5.1 |
| 27.6 | 5.6 | 36.0 | 3.2 |
| 28.0 | 10.7 | 36.9 | 8.7 |
| 28.5 | 8.3 | 37.2 | 6.8 |
| 29.0 | 11.8 | 37.9 | 3.5 |
| 29.8 | 8.3 | 38.4 | 4.0 |
| 31.0 | 5.1 | 38.9 | 5.0 |
| 31.5 | 3.8 | 39.5 | 6.5 |
| 32.1 | 12.7 | | |

Solubilities of psilocybin in a few solvents were estimated. The experiments were carried out by adding the test solvent in aliquots to weighed portions of solid. Whether dissolution had occurred was judged by visual inspection after addition of each solvent aliquot. The results are shown in Table 12. Solubility numbers were calculated by dividing the weight of the sample by the total amount of solvent used to dissolve the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than or equal to" if dissolution occurred on addition of the first solvent aliquot. All solubility measurements were carried out at room temperature unless noted otherwise.

TABLE 12

Estimated Solubilities of Psilocybin

| Solvent | Solubility (mg/mL) |
|---|---|
| Acetone | <1 |
| Acetonitrile (ACN) | <1 |
| Dichloromethane (DCM) | <1 |
| 1,4-dioxane | <1 |
| Ethanol (EtOH) | <1 |
| Ethyl acetate (EtOAc) | <1 |
| Methanol (MeOH) | 11 |
| 2-propanol (2-PrOH) | <1 |
| Tetrahydrofuran (THF) | <1 |
| Water | 4 |

Salt Screening of Psilocybin

Psilocybin was mixed with various acids under various conditions in attempts to generate crystalline salts. Samples generated and analyzed are listed in Table 13. All experiments were carried out using 1 molar equivalent of acid.

TABLE 13

Salt Screen Samples Generated and Analyzed

Figure 18:
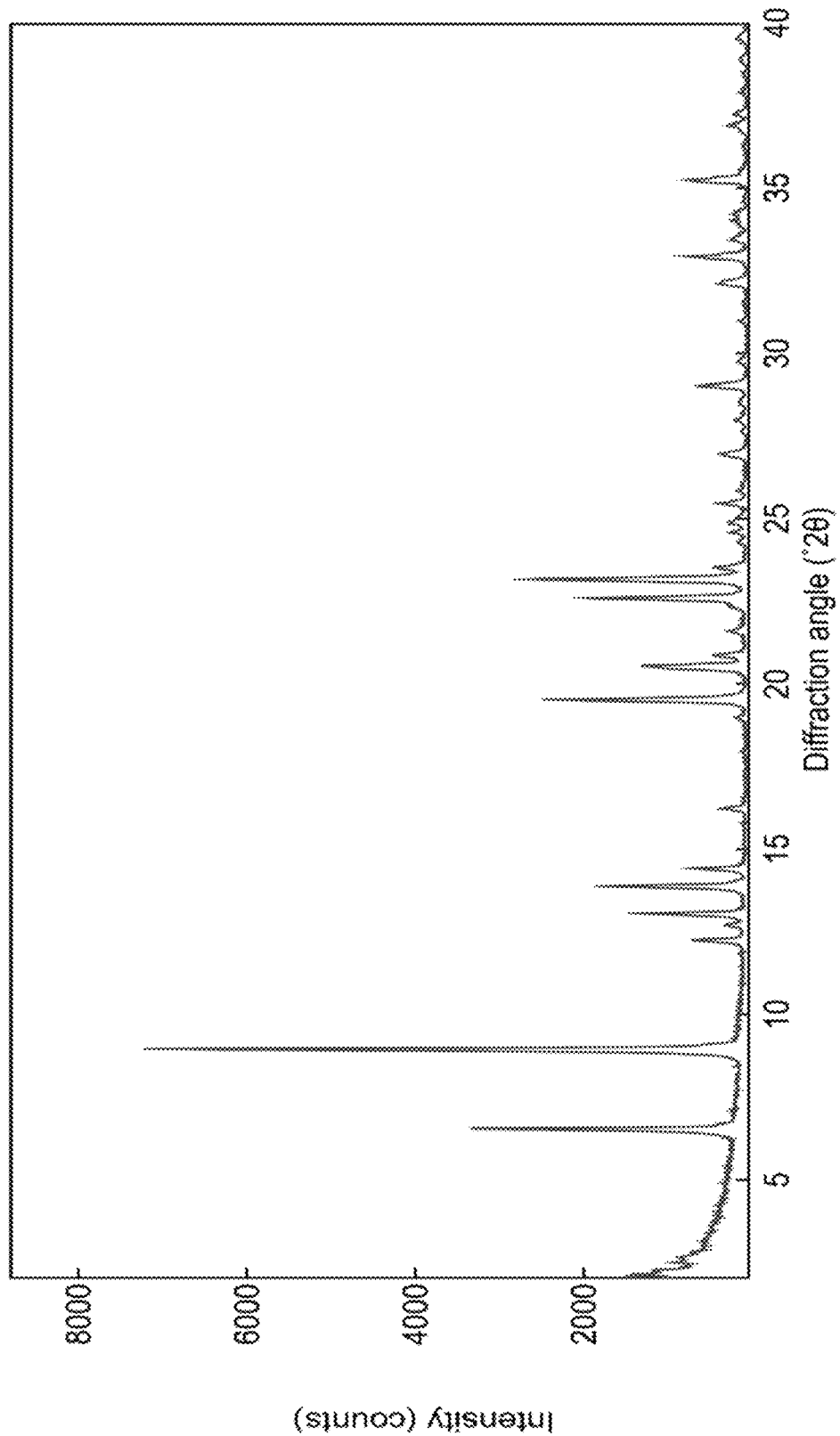
FIG. 18 provides an XRPD diffractogram of psilocybin Form B.
Figure 19:
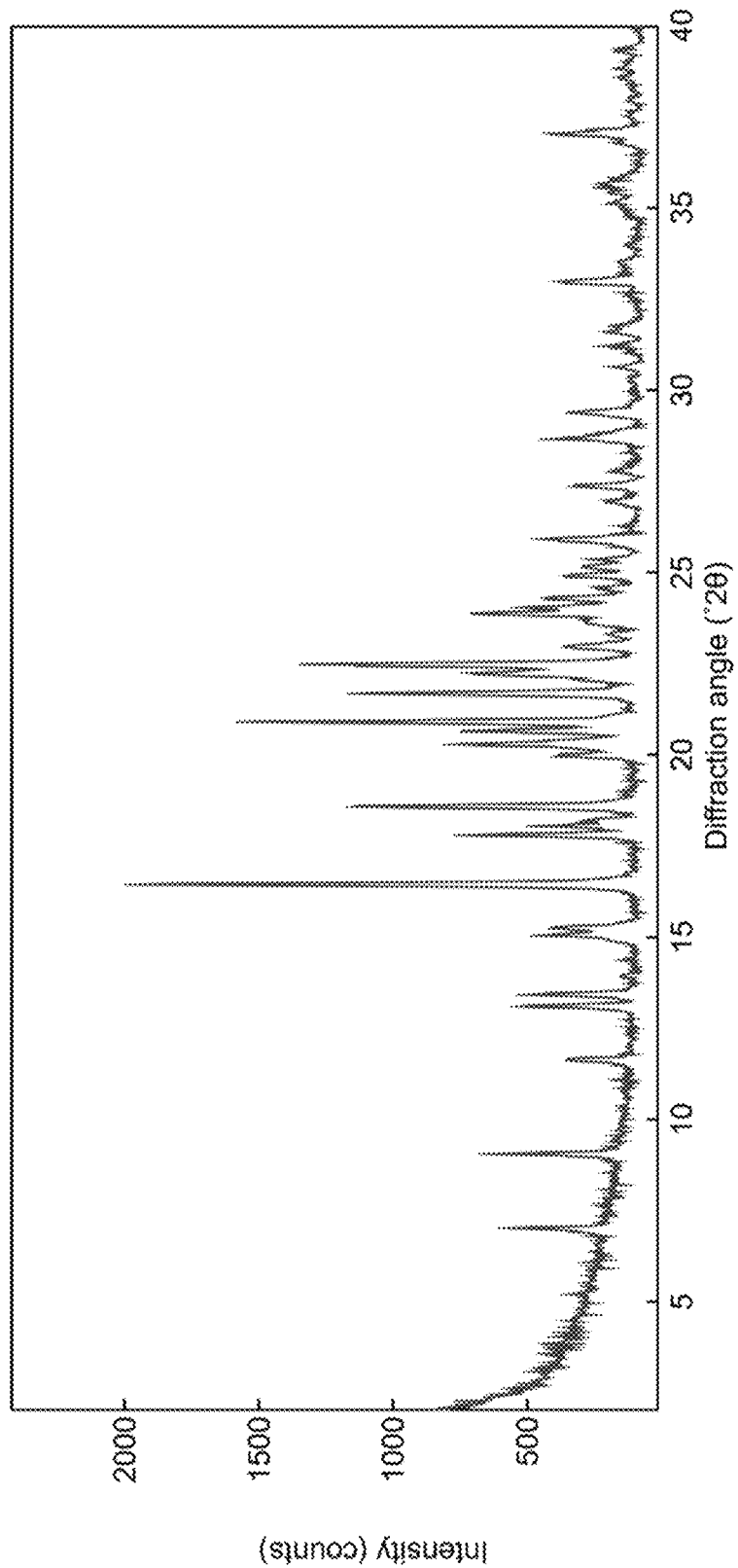
FIG. 19 provides an XRPD diffractogram of a psilocybin edisylate salt (Form A).
Figure 20:
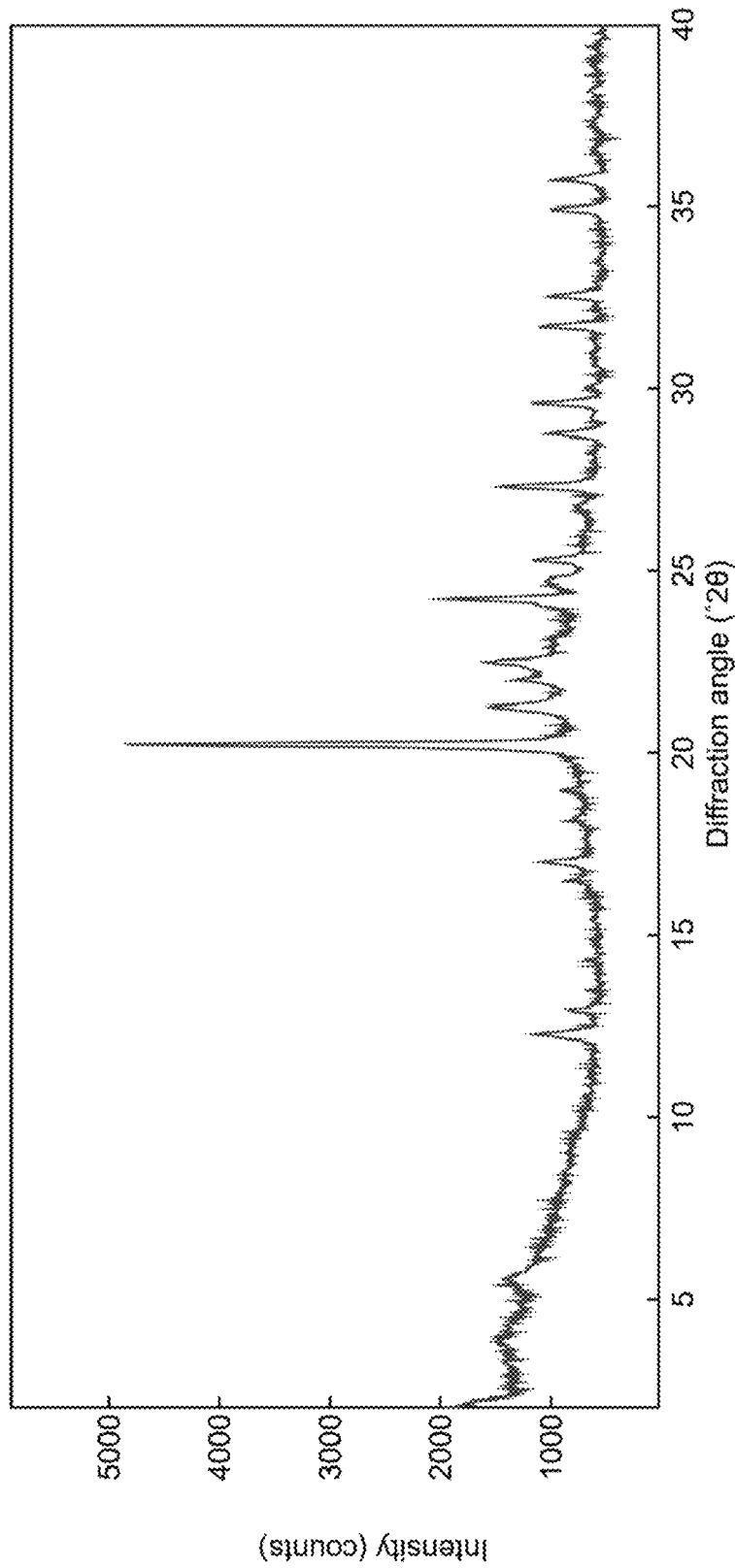
FIG. 20 provides an XRPD diffractogram of a psilocybin edisylate salt (Form B).
Figure 21:
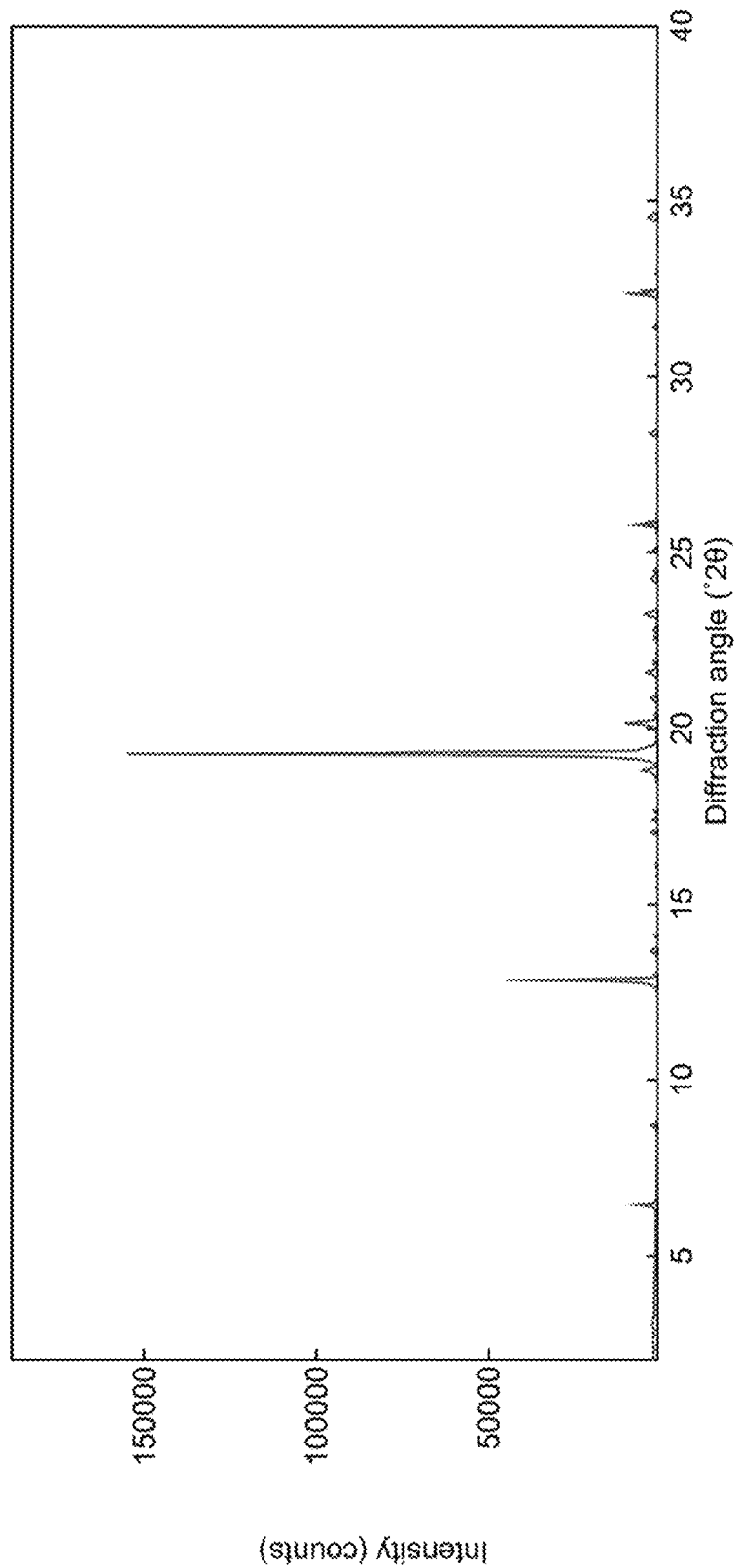
FIG. 21 provides an XRPD diffractogram of a psilocybin mesylate salt (Form A).
Figure 22:
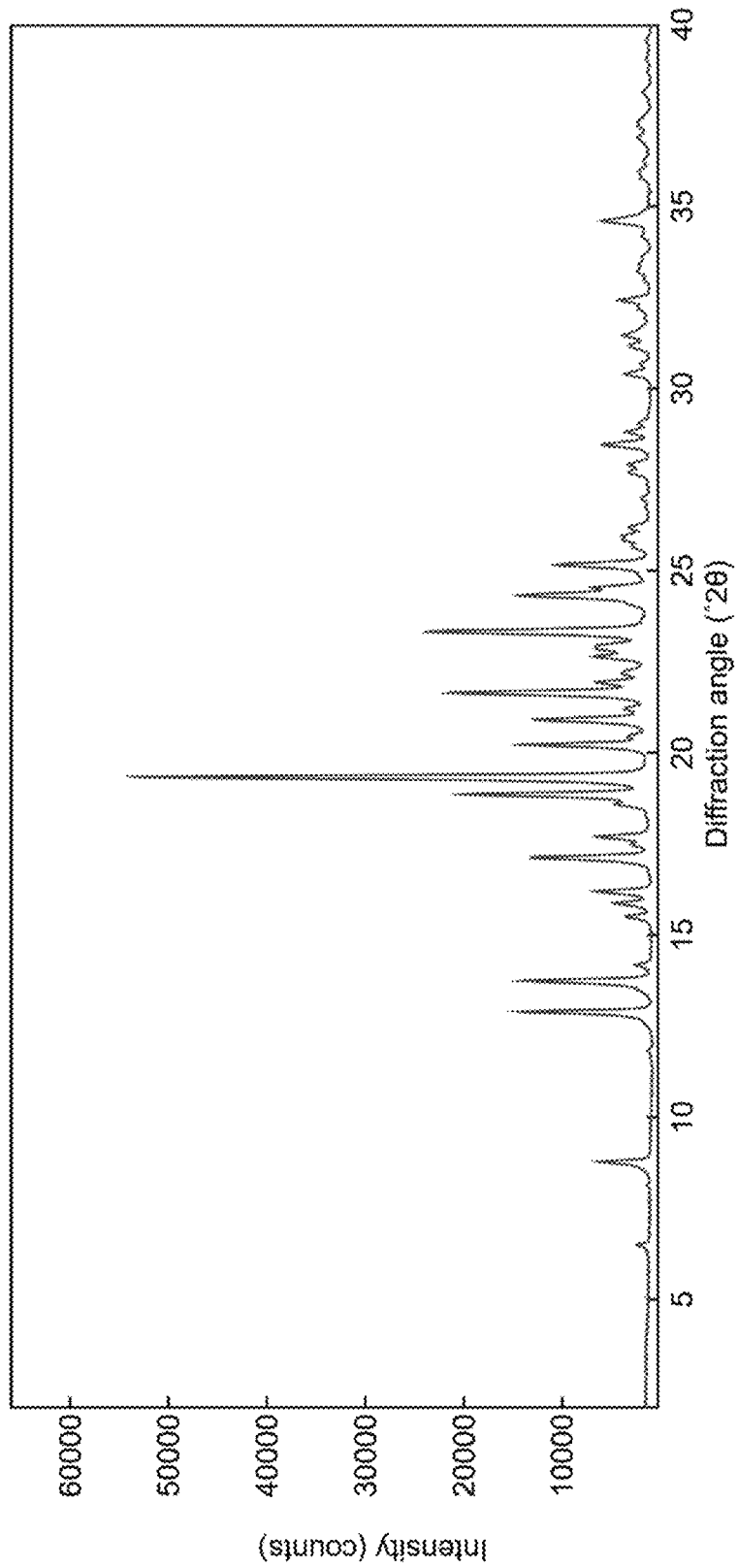
FIG. 22 provides an XRPD diffractogram of a psilocybin mesylate salt (Form A).
Figure 23:
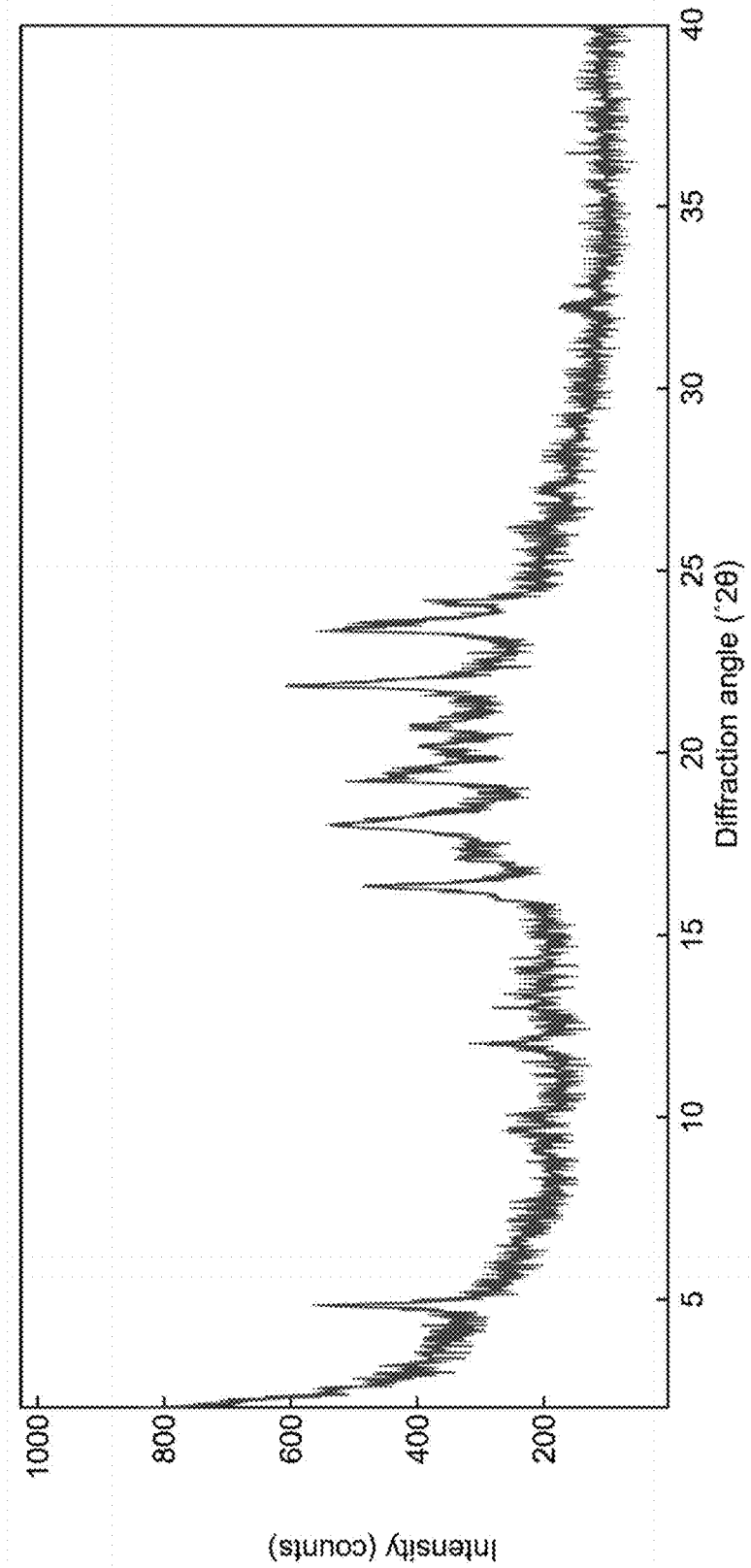
FIG. 23 provides an XRPD diffractogram of a naphthalene-2-sulfonic acid salt of psilocybin.

| Acid | Conditions[a] | XRPD Pattern[b] |
|---|---|---|
| Control (no acid) | E, MeOH/water (4:1):needles | FIG. 18 API B |
| Benzenesulfonic | SL, EtOH, 7 days | API C |
| Ethane-1,2-disulfonic | SL, EtOH, 7 days-no solids, FE: oil SL, hexanes RT to −15° C. | FIG. 19 (Edisylate Form A) |
| Ethane-1,2-disulfonic | 2:1 API:acid SL, EtOH; dissolved, FE, vac dried; oiled out when removed vac dried | FIG. 20 (Edisylate Form B) |
| HCl | EtOH, added 88 µL HCl in ether, slurry, RT | API C |
| methanesulfonic | SL, EtOH, 7 days-IS, added 500 µL hexanes, SL @ −15° C. | Low signal (18°pk) |
| methanesulfonic | SL, EtOH; FE | FIG. 21 (Mesylate Form A) |
| methanesulfonic | SL, EtOH; FE. Oil; added 1 mL Et₂O | FIG. 22 (Mesylate Form A) |
| Naphthalene-1,5-disulfonic | SL, EtOH, 7 days | API C pks + 18°pk |
| Naphthalene-2-sulfonic | SL, EtOH, 7 days | API C |
| Naphthalene-2-sulfonic | SL, MeOH/acetone (1:1); dissolved, SE: oil, added Et₂O, SL −15° C. | FIG. 23 (Napsylate) |
| p-toluenesulfonic | SL, EtOH, 7 days | API C |
| sulfuric | SL, EtOH, 7 days | NC + 18°pk |
| thiocyanic | SL, EtOH, 7 days | FIG. 24 API C | a. C = cool; EtOH = absolute ethanol; IS = insufficient solids; SE = slow evaporation; FE = full evaporation; RT = room temperature; SL = slurry.
b. NC = non-crystalline; pks = peaks.

XRPD analysis of Psilocybin Crystalline Form B (FIG. 18) showed it to be crystalline with characteristic peaks at 6.6±0.2° 2-Theta, 9.0±0.2° 2-Theta, and 13.9±0.2° 2-Theta; optionally with further characteristic peaks at 13.1±0.2° 2-Theta and 19.5±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 6.6 | 47.0 | 21.6 | 4.1 |
| 9.0 | 100.0 | 22.6 | 27.7 |
| 12.3 | 10.1 | 23.2 | 37.9 |
| 12.7 | 4.5 | 23.5 | 6.4 |
| 13.1 | 18.5 | 24.3 | 2.3 |
| 13.9 | 24.3 | 24.6 | 3.7 |
| 14.4 | 9.9 | 24.8 | 3.8 |
| 16.2 | 5.1 | 25.5 | 5.7 |
| 19.0 | 2.8 | 25.8 | 2.4 |
| 19.5 | 33.0 | 27.0 | 5.4 |
| 20.5 | 18.6 | 27.6 | 1.7 |
| 20.9 | 6.5 | 28.0 | 2.8 |
| 28.5 | 2.2 | 35.2 | 11.1 |
| 29.0 | 9.3 | 36.9 | 4.1 |
| 29.7 | 2.4 | 37.2 | 3.2 |
| 31.0 | 2.3 | 37.9 | 2.0 |
| 32.1 | 5.5 | 38.5 | 1.6 |
| 32.9 | 11.1 | 38.9 | 2.0 |
| 33.5 | 3.3 | 39.5 | 2.7 |
| 34.0 | 3.1 | | |

XRPD analysis of Psilocybin Crystalline Form C (FIG. 24) showed it to be crystalline with characteristic peaks at 9.6±0.2° 2-Theta, 11.8±0.2° 2-Theta, and 13.7±0.2° 2-Theta; optionally with further characteristic peaks at 16.9±0.2° 2-Theta and 19.7±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 8.5 | 10.3 | 25.0 | 32.2 |
| 9.6 | 52.2 | 25.5 | 23.0 |
| 11.8 | 11.5 | 26.1 | 11.9 |
| 13.7 | 100.0 | 26.9 | 13.5 |
| 14.4 | 18.7 | 27.5 | 15.7 |
| 15.4 | 9.2 | 28.0 | 8.2 |
| 15.9 | 23.8 | 28.2 | 12.5 |
| 16.9 | 39.4 | 28.9 | 7.1 |
| 17.4 | 15.9 | 29.3 | 6.8 |
| 18.1 | 4.9 | 30.6 | 10.6 |
| 19.2 | 12.4 | 30.9 | 12.2 |
| 19.7 | 33.3 | 31.8 | 4.1 |
| 20.7 | 58.7 | 32.7 | 7.9 |
| 21.1 | 19.6 | 33.5 | 5.5 |
| 21.5 | 57.9 | 34.0 | 4.7 |
| 22.2 | 14.3 | 35.0 | 3.3 |
| 22.5 | 21.9 | 36.0 | 5.0 |
| 23.1 | 37.0 | 37.0 | 6.4 |
| 23.4 | 13.5 | 37.9 | 3.7 |
| 23.6 | 31.6 | 38.7 | 4.3 |
| 24.2 | 15.9 | 39.4 | 3.9 |
| 24.6 | 10.4 | | |

XRPD analysis of Psilocybin Edisylate Form A (FIG. 19) showed it to be crystalline with characteristic peaks at 7.0±0.2° 2-Theta, 9.1±0.2° 2-Theta, and 11.6±0.2° 2-Theta; optionally with further characteristic peaks at 13.1±0.2° 2-Theta and 13.4±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.0 | 28.8 | 24.0 | 26.5 |
| 9.1 | 32.4 | 24.3 | 22.1 |
| 11.6 | 18.2 | 24.6 | 12.1 |
| 13.1 | 26.9 | 24.9 | 18.5 |
| 13.4 | 25.5 | 25.2 | 14.9 |
| 13.9 | 7.8 | 25.4 | 12.9 |
| 15.0 | 23.0 | 25.9 | 22.6 |
| 15.2 | 20.9 | 26.3 | 7.6 |
| 16.4 | 100.0 | 26.9 | 10.4 |
| 17.8 | 37.2 | 27.4 | 16.6 |
| 18.0 | 23.3 | 27.8 | 9.3 |
| 18.2 | 14.5 | 28.7 | 21.2 |
| 18.6 | 58.7 | 29.4 | 17.7 |
| 20.0 | 20.1 | 30.6 | 9.2 |
| 20.3 | 39.4 | 31.2 | 11.0 |
| 20.6 | 38.2 | 31.6 | 10.7 |
| 20.9 | 79.0 | 33.0 | 19.7 |
| 21.7 | 57.5 | 33.5 | 8.3 |
| 22.2 | 36.4 | 34.0 | 6.7 |
| 22.5 | 66.7 | 35.1 | 9.3 |
| 23.0 | 18.5 | 35.4 | 10.1 |
| 23.3 | 10.1 | 35.7 | 11.6 |
| 23.7 | 15.1 | 37.0 | 20.7 |
| 23.9 | 36.2 | 39.3 | 8.8 |

XRPD analysis of Psilocybin Edisylate Form B (FIG. 20) showed it to be crystalline with characteristic peaks at 12.3±0.2° 2-Theta, 20.2±0.2° 2-Theta, and 24.2±0.2° 2-Theta; optionally with further characteristic peaks at 17.0±0.2° 2-Theta and 21.2±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 3.8 | 31.3 | 24.2 | 41.3 |
| 5.6 | 29.8 | 24.7 | 21.9 |
| 12.3 | 24.0 | 25.3 | 24.0 |
| 13.0 | 17.3 | 26.7 | 16.1 |
| 16.5 | 17.4 | 27.3 | 30.5 |
| 17.0 | 22.6 | 28.8 | 21.2 |
| 18.1 | 17.3 | 29.6 | 24.2 |
| 19.0 | 18.9 | 30.0 | 13.8 |
| 20.2 | 100.0 | 31.7 | 22.9 |
| 21.2 | 32.3 | 32.5 | 21.3 |
| 22.0 | 27.9 | 34.9 | 20.6 |
| 22.5 | 32.8 | 35.7 | 19.8 |
| 23.1 | 21.2 | | |

XRPD analysis of Psilocybin Mesylate Form A (FIG. 21) showed it to be crystalline with characteristic peaks at 6.4±0.2° 2-Theta, 12.8±0.2° 2-Theta, and 19.3±0.2° 2-Theta; optionally with further characteristic peaks at 18.8±0.2° 2-Theta and 20.2±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 6.4 | 4.3 | 25.1 | 1.4 |
| 8.7 | 1.9 | 25.8 | 4.6 |
| 11.6 | 0.6 | 26.1 | 0.6 |
| 11.8 | 0.5 | 26.9 | 0.5 |
| 12.8 | 27.3 | 27.6 | 0.7 |
| 13.7 | 1.8 | 27.8 | 0.6 |
| 14.1 | 1.0 | 28.4 | 2.2 |
| 15.4 | 0.7 | 28.7 | 0.7 |
| 15.8 | 0.8 | 29.0 | 0.5 |
| 16.1 | 0.9 | 30.3 | 0.9 |
| 17.1 | 1.7 | 30.6 | 0.5 |
| 17.4 | 1.7 | 31.1 | 0.7 |
| 17.6 | 1.3 | 31.4 | 1.4 |
| 18.8 | 3.5 | 32.4 | 6.1 |
| 19.3 | 100.0 | 32.9 | 0.9 |
| 20.2 | 6.6 | 33.4 | 0.6 |
| 20.4 | 1.0 | 33.6 | 0.5 |
| 20.8 | 1.8 | 34.1 | 0.5 |
| 21.1 | 0.8 | 34.5 | 2.5 |
| 21.6 | 2.7 | 35.9 | 0.5 |
| 21.9 | 1.4 | 36.2 | 0.6 |
| 22.1 | 0.7 | 36.8 | 0.6 |
| 22.6 | 1.3 | 37.2 | 0.6 |
| 22.8 | 1.3 | 38.1 | 0.5 |
| 23.3 | 3.1 | 38.6 | 0.4 |
| 24.2 | 1.7 | 39.1 | 0.4 |
| 24.5 | 1.1 | 39.5 | 0.4 |

XRPD analysis of Psilocybin Mesylate Form A (FIG. 22) showed it to be crystalline with characteristic peaks at 8.8±0.2° 2-Theta, 12.9±0.2° 2-Theta, and 13.7±0.2° 2-Theta; optionally with further characteristic peaks at 17.1±0.2° 2-Theta and 18.9±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 6.5 | 4.7 | 8.8 | 11.9 |
| 8.1 | 2.7 | 11.8 | 2.5 |
| 12.9 | 26.9 | 26.2 | 6.2 |
| 13.7 | 26.4 | 27.0 | 3.7 |
| 14.2 | 4.9 | 27.7 | 6.3 |
| 15.5 | 6.8 | 27.9 | 6.1 |
| 15.9 | 9.0 | 28.5 | 11.2 |
| 16.2 | 12.5 | 28.8 | 6.8 |
| 17.1 | 25.0 | 29.0 | 4.4 |
| 17.7 | 12.3 | 30.4 | 7.0 |
| 18.6 | 8.7 | 30.7 | 4.0 |
| 18.9 | 37.7 | 31.2 | 5.8 |
| 19.3 | 100.0 | 31.5 | 7.2 |
| 20.2 | 26.2 | 32.2 | 4.3 |
| 20.5 | 6.4 | 32.4 | 8.1 |
| 20.9 | 24.2 | 33.0 | 3.3 |
| 21.2 | 7.0 | 33.2 | 4.4 |
| 21.6 | 40.6 | 33.4 | 4.3 |
| 21.9 | 12.4 | 33.7 | 3.2 |
| 22.2 | 7.5 | 34.2 | 3.6 |
| 22.6 | 12.8 | 34.6 | 11.4 |
| 22.9 | 12.3 | 35.8 | 3.9 |
| 23.3 | 44.8 | 36.0 | 4.2 |
| 24.3 | 27.2 | 36.3 | 3.4 |
| 24.5 | 13.1 | 36.9 | 4.4 |
| 25.2 | 20.0 | 37.2 | 4.5 |
| 25.7 | 5.3 | 38.1 | 3.5 |
| 26.0 | 7.5 | | |

XRPD analysis of Psilocybin Napsylate (FIG. 23) showed it to be crystalline with characteristic peaks at 4.8±0.2° 2-Theta, 16.3±0.2° 2-Theta, and 18.0±0.2° 2-Theta; optionally with further characteristic peaks at 12.0±0.2° 2-Theta and 21.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 4.8 | 93.1 | 18.0 | 89.5 |
| 9.6 | 43.3 | 19.2 | 84.0 |
| 10.1 | 41.3 | 20.2 | 67.5 |
| 12.0 | 51.0 | 20.8 | 69.8 |
| 13.0 | 44.7 | 21.8 | 100.0 |
| 13.4 | 42.1 | 23.3 | 91.7 |
| 14.0 | 41.2 | 24.2 | 63.2 |
| 16.3 | 79.5 | 27.2 | 34.9 |
| 17.1 | 57.0 | 32.2 | 27.1 |

New crystalline materials exhibiting unique XRPD patterns have been identified. A new crystalline material resulted from the dynamic vapor sorption experiment, specifically, based on DVS data and XRPD analysis of the post-DVS specimen, a hydrated form of psilocybin resulted from water sorption between 75-95% RH, and was designated as Form B. Note that a weak endothermic transition observed in the DSC of Form A at approx. 163° C. may be due to small amounts of the hydrated form (Form B).

Figure 25:
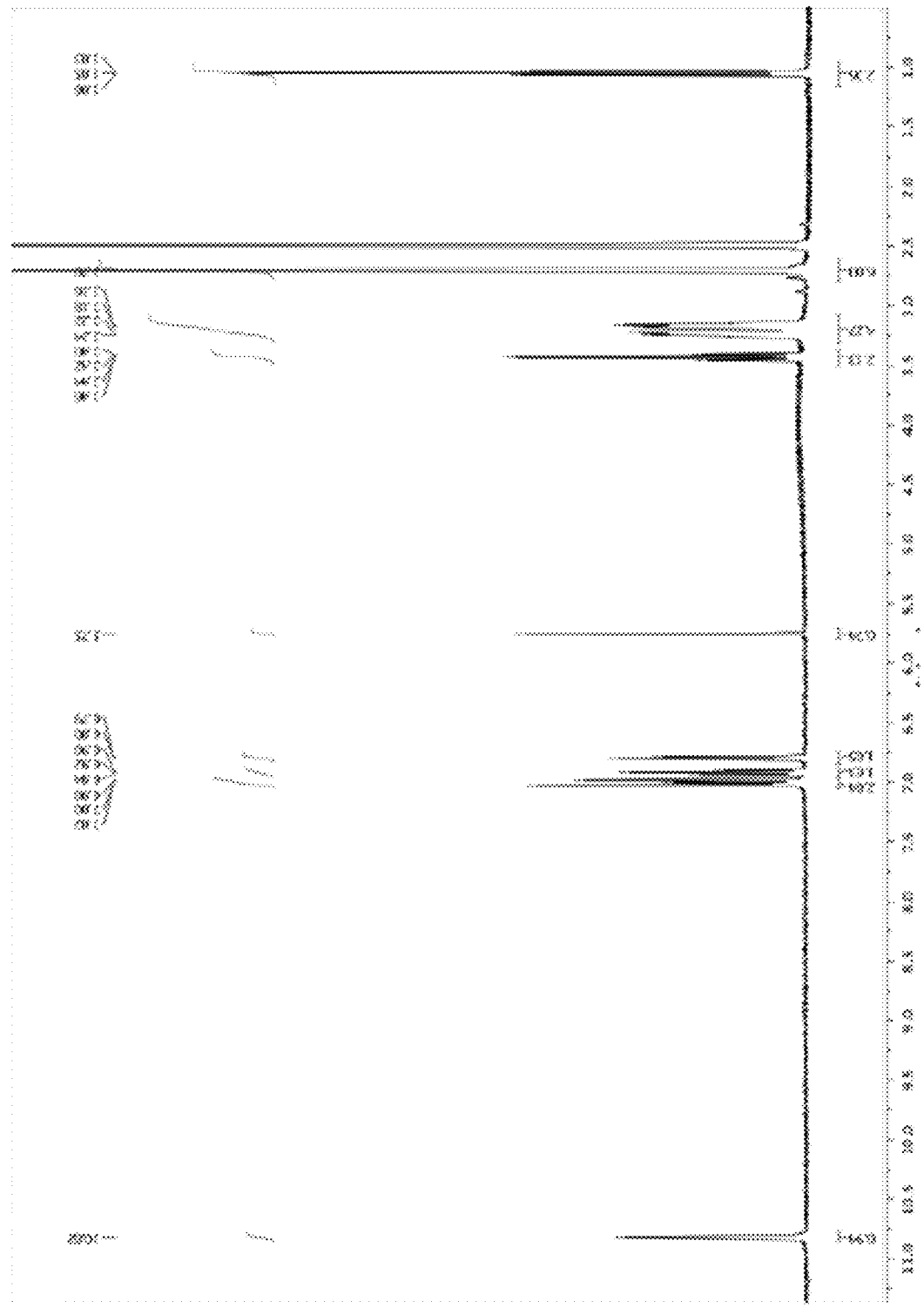
FIG. 25 provides an NMR spectrum of psilocybin Form C.
Figure 26:
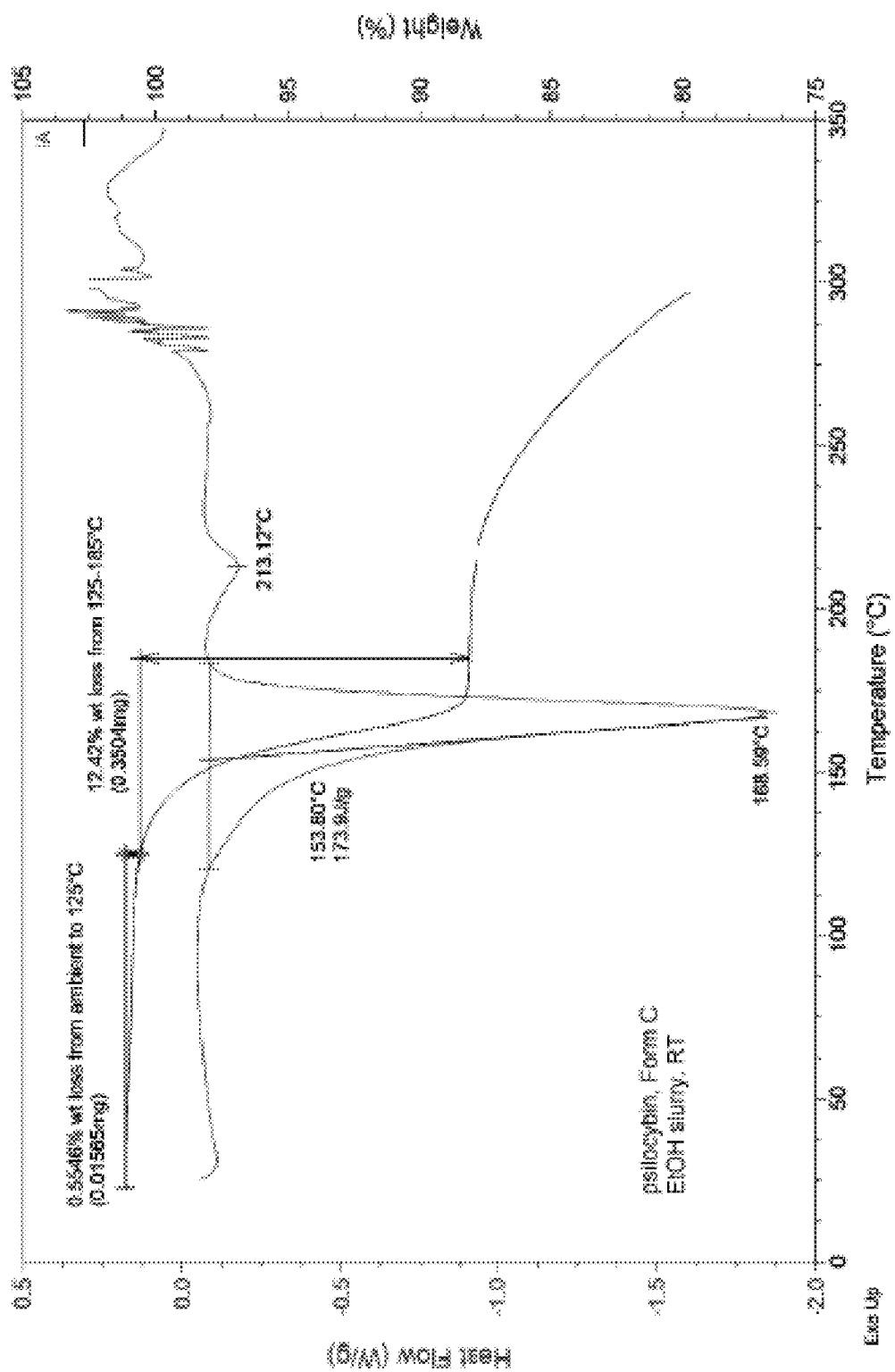
FIG. 26 provides a graph of weight and heat flow versus temperature, illustrating the results from the TG and DSC of psilocybin Form C.

Another new material was observed from several salt formation attempts involving various acids, and designated as Form C. Note that all these experiments were conducted by slurry in ethanol. By proton NMR analysis, Form C was found to contain approx. 1 mole of ethanol is a solvate (FIG. 25). Form C was also characterized by DSC and TG analysis (FIG. 26).

Figure 27:
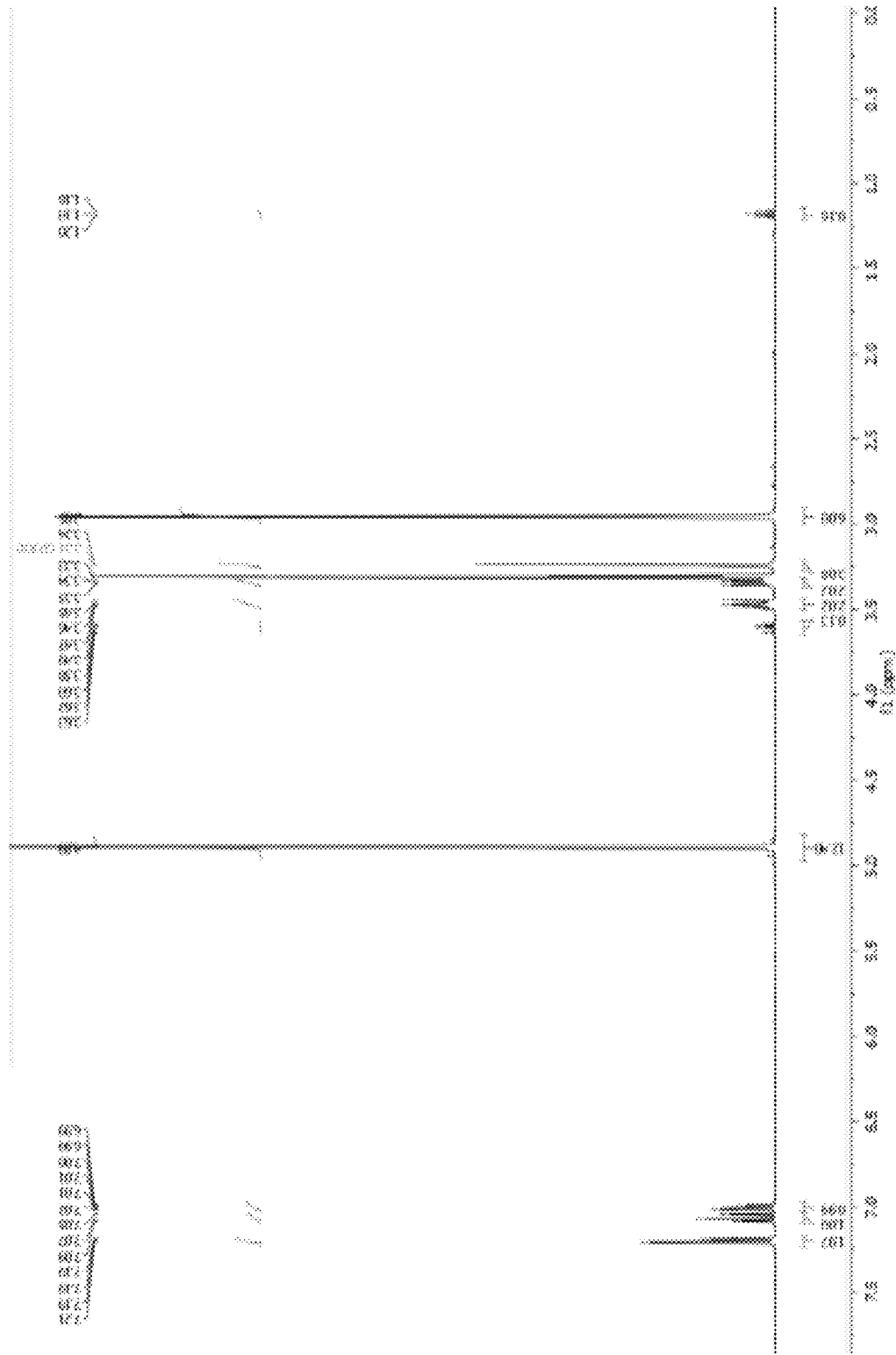
FIG. 27 provides an NMR spectrum of a psilocybin edisylate salt (Form A).
Figure 28:
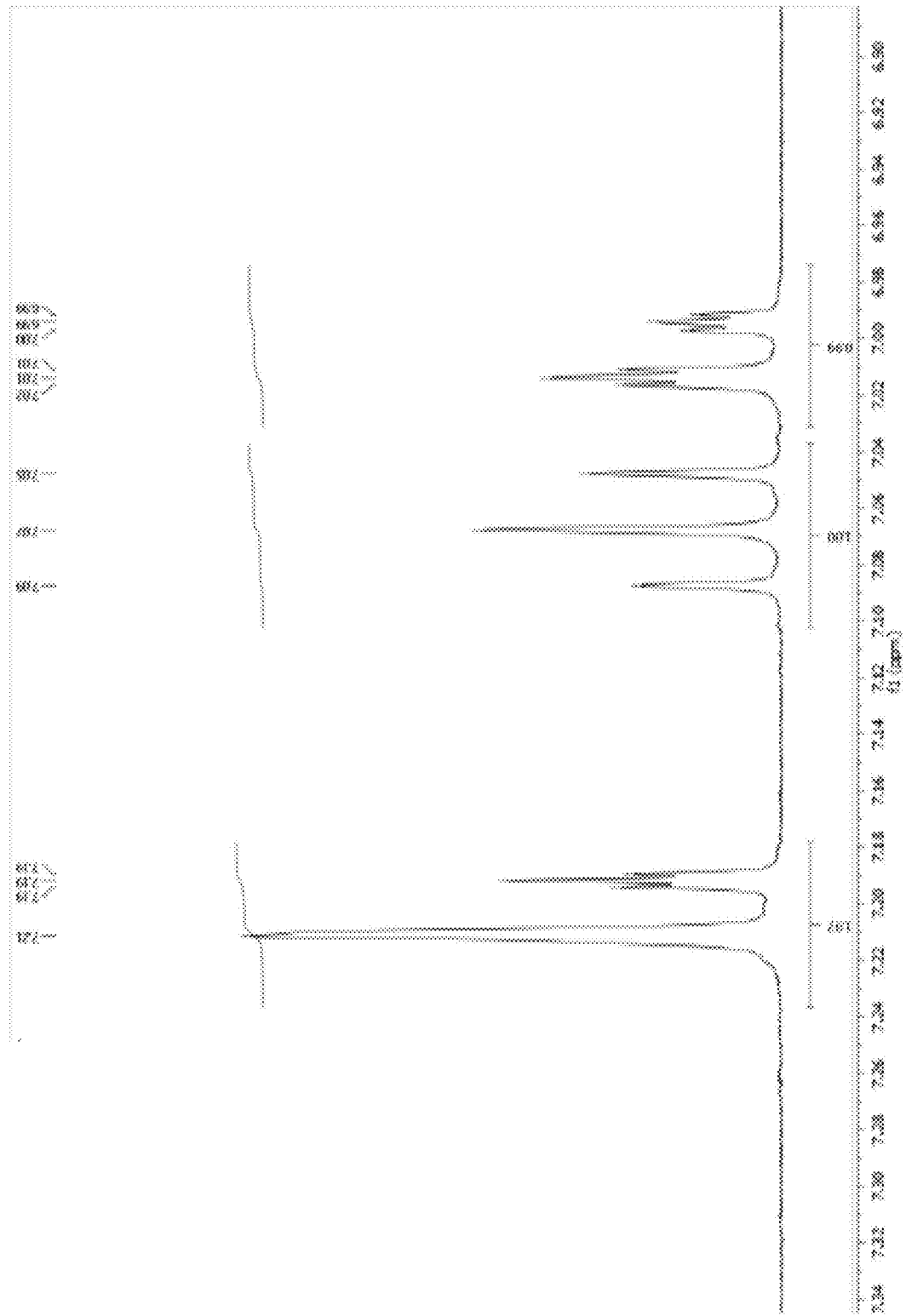
FIG. 28 provides an expanded section of the NMR spectrum of FIG. 27.
Figure 29:
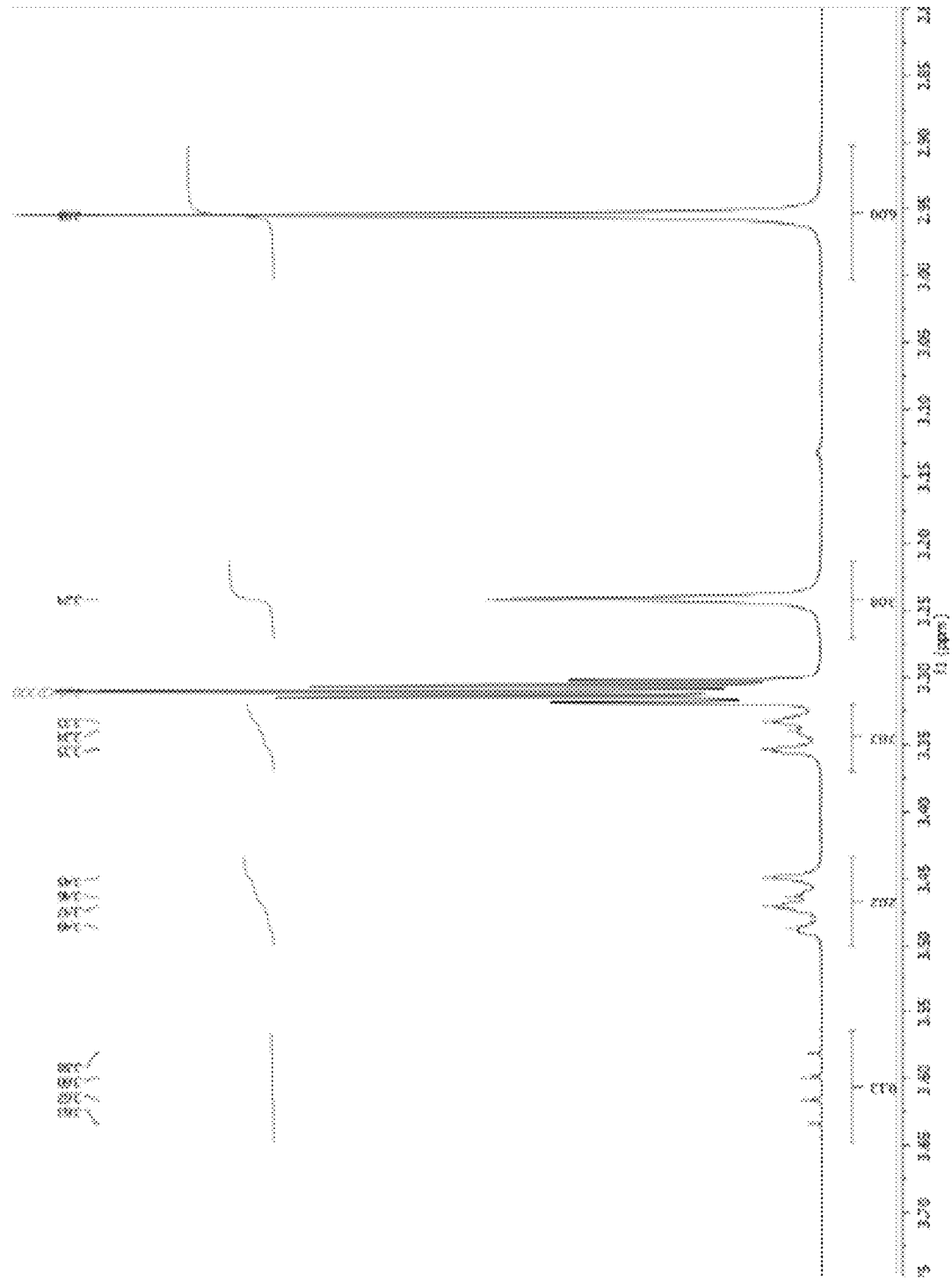
FIG. 29 provides an expanded section of the NMR spectrum of FIG. 27.

In addition, salt screening experiments involving ethane-1,2-disulfonic acid afforded a new crystalline material by XRPD analysis. Briefly and with reference to Table 13, the edisylate salt was produced by slurrying zwitterionic psilocybin in ethanol with ethane-1,2-disulfonic acid for seven days, followed by fast evaporation, addition of hexanes and slurrying at −15 degrees Celsius. The crystalline edisylate salt of psilocybin yielded the XRPD of FIG. 19, referred to herein as psilocybin edisylate Form A; the proton NMR of this material dissolved in deuterated methanol is provided in FIGS. 27-29. Edisylate salt having Form B was produced as described in Table 13.

The mesylate salt was produced by slurrying of zwitterionic psilocybin in ethanol in the presence of methanesulfonic acid followed by fast evaporation. The crystalline mesylate salt of psilocybin yielded the XRPD of FIG. 21.

Figure 10:
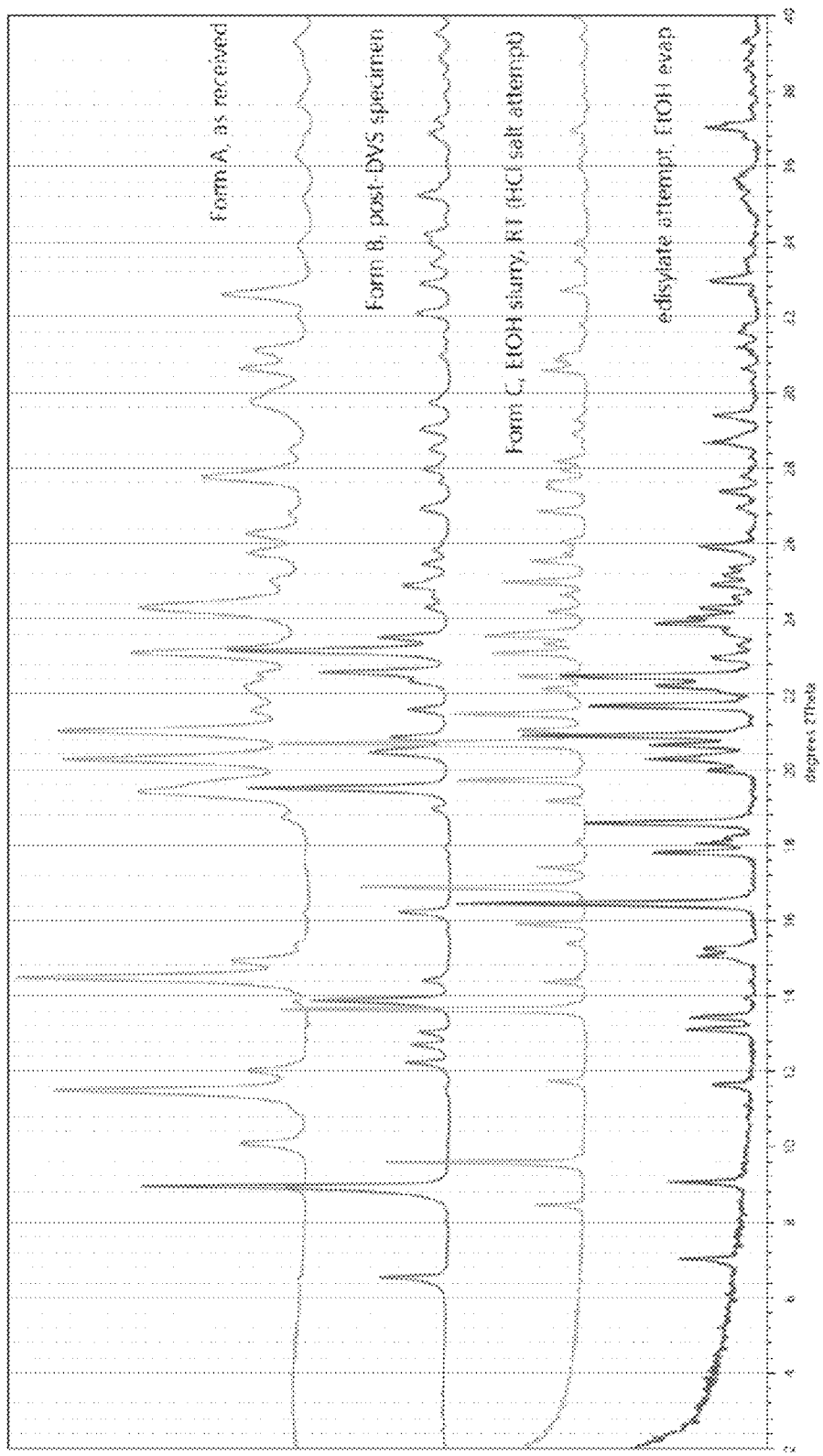
FIG. 10 is a graph providing overlaid XRPD spectra, illustrating the different XRPD spectra of Form A, Form B, Form C and an edisylate (ethane 1,2-disulfonic acid) salt of psilocybin.

An overlay plot of XRPD patterns is shown in FIG. 10. And characterization of new materials using thermal techniques and proton NMR analysis is summarized in Table 14.

TABLE 14

Characterization Data

Figure 30:
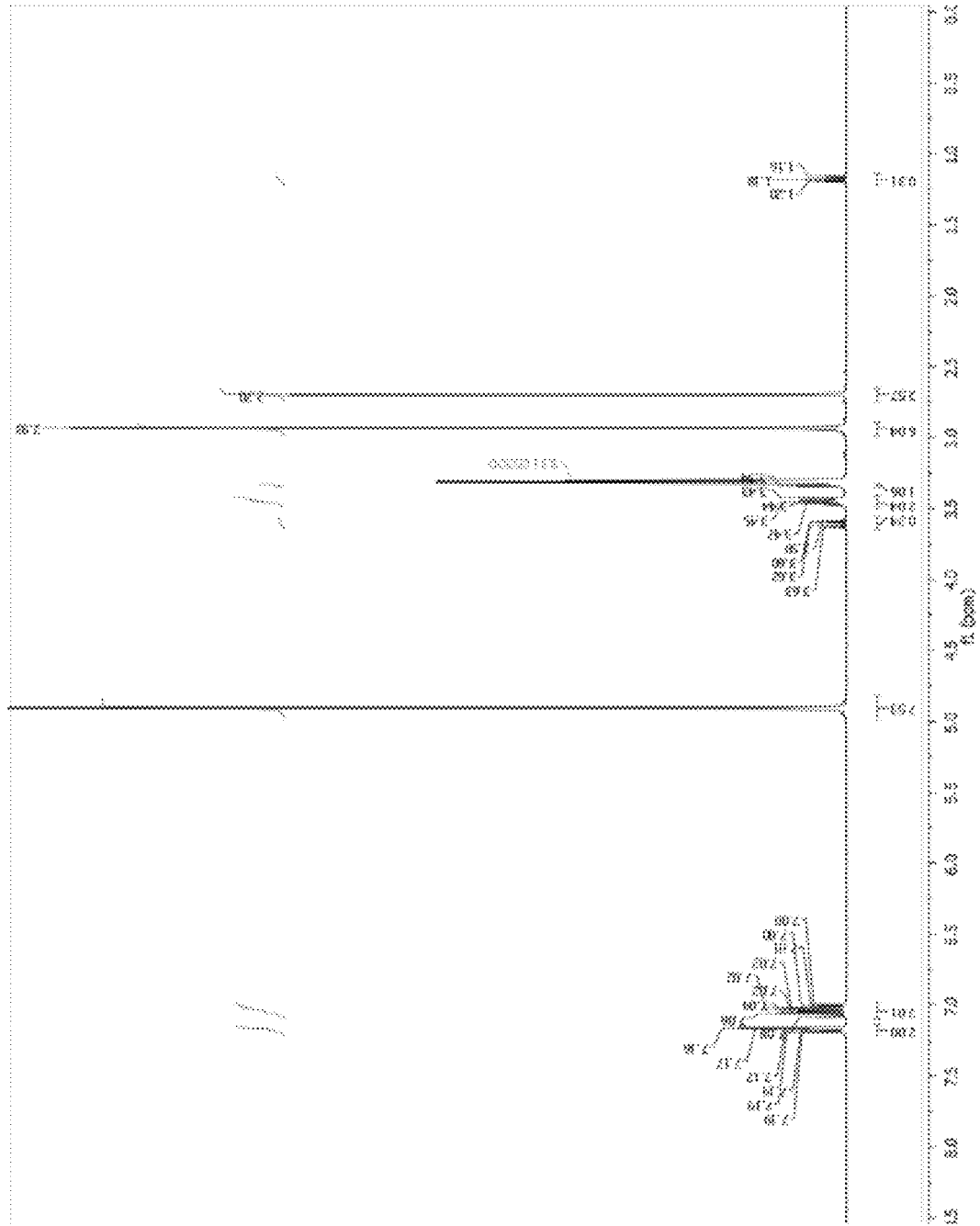
FIG. 30 provides an NMR spectrum of the sample used to produce FIG. 21, dissolved in deuterated methanol.

| New Material | Test (FIG.) | Results |
|---|---|---|
| Psilocybin, Form C | DSC (FIG. 26) | Endo 169° C. (broad, ΔH: 174 J/g); 213° C. (weak) |
| | TGA (FIG. 26) | 0.6% wt loss from ambient to 125° C. 12.4% wt loss from 125 to 185° C. |
| | $^1$H NMR (FIG. 25) | Consistent with API structure, approx. 1 mole EtOH present |
| Edisylate (Form A in solid state) | $^1$H NMR (FIGS. 27-29) | Consistent with salt formation (likely 2:1 API:acid), excess acid present |
| Mesylate | $^1$H NMR (FIG. 30) | Consistent with salt formation (likely 1:1 API:acid), slight excess of API present |
| | XRPD (FIG. 21) | |
| | DSC | Endo 158.8° C. (ΔH:74 J/g) |
| | TGA | 0.1% start to 160° C. |

Scale Up of Psilocybin Mesylate

A second preparation of the mesylate salt resulted in material having a stoichiometry of 1:1 by $^1$H-NMR spectroscopy and no impurities were noted. The thermal data suggests it is unsolvated and melts around 159° C. This sample was prepared similar to the original sample mesylate salt, but instead of evaporating all of the solvent, the solid was recovered from a slurry.

The scaled up psilocybin mesylate sample was further characterized (Table 15). It is unsolvated and melts around 160° C. The TG curve exhibits a 0.4% loss through the melt which corresponds to a negligible amount of water (0.08 moles water). No organic solvents or impurities were observed in the $^1$H NMR spectrum. It should be noted that the material became tacky and deliquesced when handled at ambient humidity (~50-60%).

TABLE 15

Characterization of Psilocybin Mesylate Form A

Figure 31:
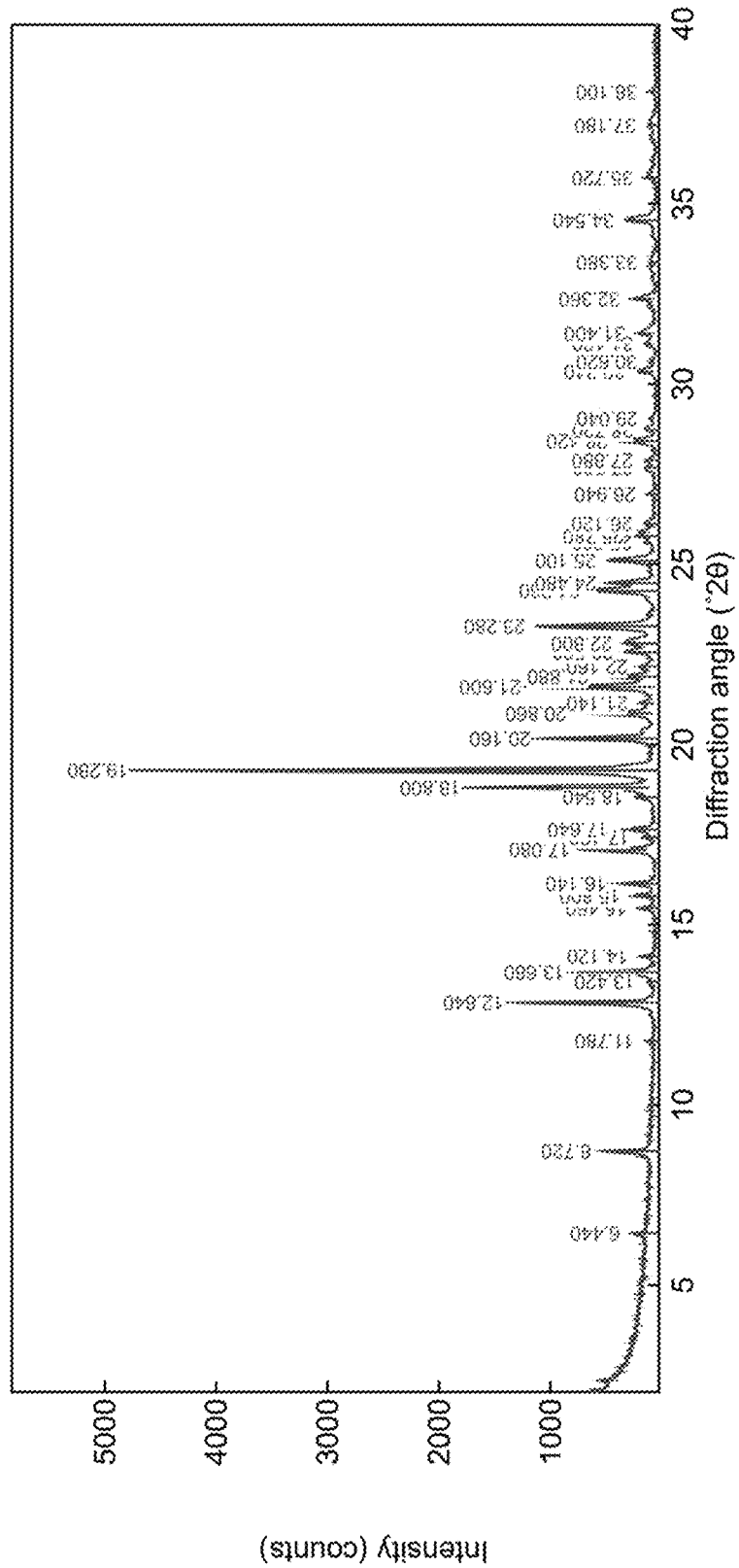
FIG. 31 provides an XRPD diffractogram of psilocybin mesylate Form A.

| Test (FIG.) | Results |
|---|---|
| DSC | Endo 159.0° C. |
| TGA | 0.4% start to 160° C. |
| $^1$H NMR | Consistent with 1:1 salt |
| XRPD (FIG. 31) | |

XRPD analysis of Psilocybin Mesylate Form A (FIG. 31) showed it to be crystalline with characteristic peaks at 8.7±0.2° 2-Theta, 12.8±0.2° 2-Theta, and 13.7±0.2° 2-Theta; optionally with further characteristic peaks at 17.1±0.2° 2-Theta and 18.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 6.4 | 5.8 | 22.8 | 7.2 |
| 8.7 | 11.3 | 23.3 | 23.9 |
| 11.8 | 3.0 | 24.3 | 13.4 |
| 12.8 | 28.0 | 24.5 | 10.3 |
| 13.4 | 2.8 | 25.1 | 10.3 |
| 13.7 | 16.3 | 25.6 | 3.4 |
| 14.1 | 4.2 | 25.8 | 5.0 |
| 15.5 | 4.4 | 26.1 | 3.3 |
| 15.8 | 5.6 | 26.9 | 2.8 |
| 16.1 | 8.3 | 27.7 | 3.1 |
| 17.1 | 15.3 | 27.9 | 3.3 |
| 17.4 | 3.8 | 28.4 | 8.1 |
| 17.6 | 7.9 | 28.7 | 3.2 |
| 18.5 | 5.0 | 29.0 | 2.3 |
| 18.8 | 36.2 | 30.3 | 4.8 |
| 19.3 | 100.0 | 30.6 | 2.4 |
| 20.2 | 22.9 | 31.1 | 3.2 |
| 20.9 | 16.0 | 31.4 | 4.7 |
| 21.1 | 4.2 | 32.4 | 5.8 |
| 21.6 | 24.8 | 33.4 | 2.4 |
| 21.9 | 11.8 | 34.5 | 6.9 |
| 22.2 | 4.3 | 35.7 | 3.3 |
| 22.6 | 7.0 | 37.2 | 2.7 |
| 38.1 | 2.4 | | |

Polymorph Screen of Psilocybin Mesylate

Samples of psilocybin mesylate were mixed with various solvents under various conditions to generate crystalline forms. The goal was to find the most stable form of the mesylate salt. The form previously identified during the salt screening study, was the only crystalline form identified in the screen. It is unsolvated, melts around 159° C., and was successfully made at a scale of 1.2 grams. It should be noted that the material became tacky and deliquesced when handled at ambient humidity (~50-60%).

Scale Up of Psilocybin Edisylate Form A

Edisylate salt form A has a stoichiometry of 2:1.5 API: acid by NMR. It is possible that it is a 2:1 API:acid salt with some excess acid present. Slurry experiments were carried out using solvents which were not used in prior edisylate salt attempts. One half molar equivalent of acid was used in each experiment because it was believed that the stoichiometry of the salt is 2:1 API:acid. One of the three experiments, a slurry involving acetonitrile, produced edisylate salt form A.

Figure 32:
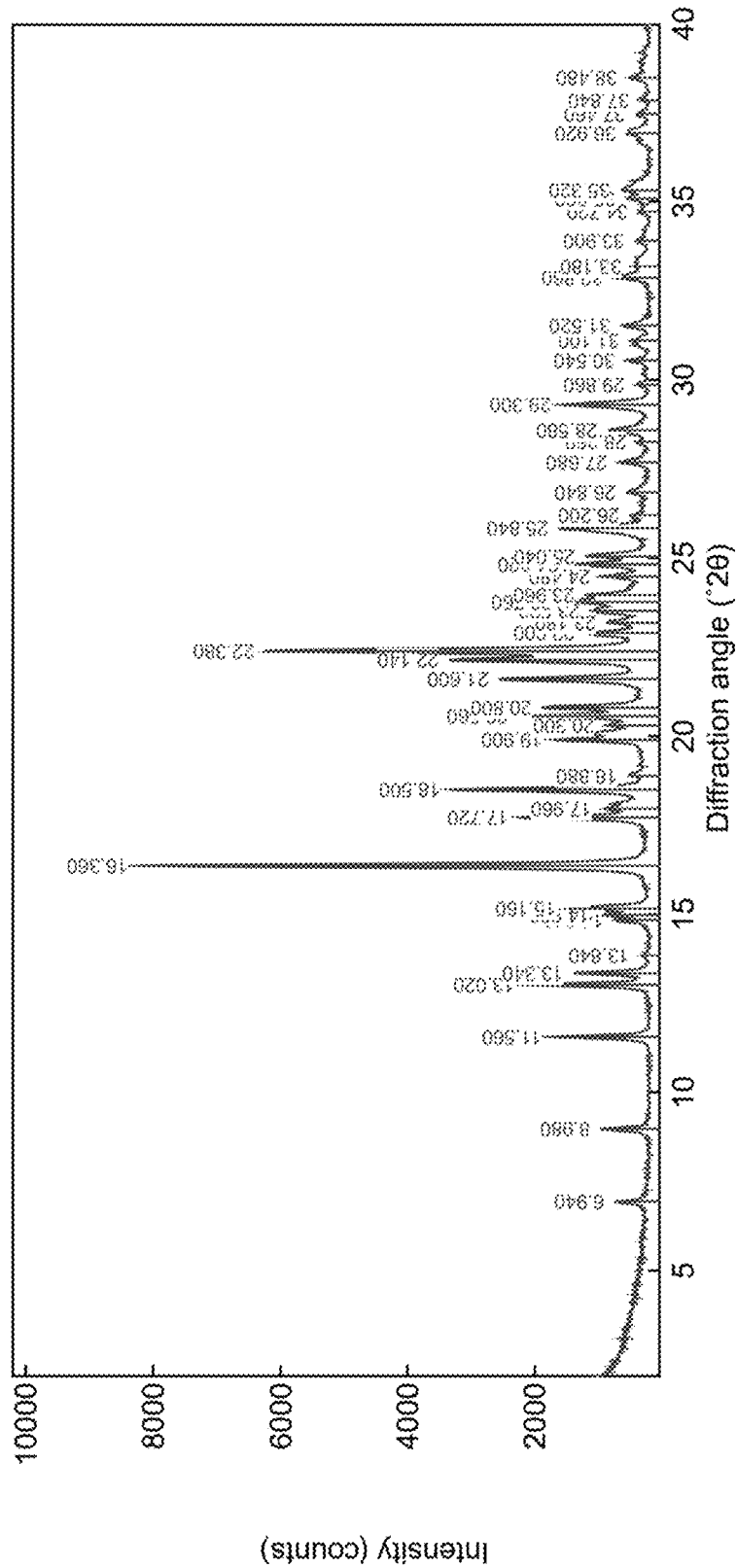
FIG. 32 provides an XRPD diffractogram of psilocybin edisylate Form A.

XRPD analysis of Edisylate Form A (FIG. 32) showed it to be crystalline with characteristic peaks at 9.0±0.2° 2-Theta, 11.6±0.2° 2-Theta, and 13.0±0.2° 2-Theta; optionally with further characteristic peaks at 16.4±0.2° 2-Theta and 18.5±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 6.9 | 8.8 | 20.8 | 22.7 |
| 9.0 | 11.5 | 21.6 | 31.0 |
| 11.6 | 20.8 | 22.1 | 40.5 |
| 13.0 | 26.0 | 22.4 | 75.9 |
| 13.3 | 16.6 | 22.9 | 14.5 |
| 13.8 | 4.0 | 23.2 | 10.4 |
| 14.8 | 8.9 | 23.5 | 13.5 |
| 15.0 | 11.6 | 23.8 | 18.7 |
| 15.2 | 18.0 | 24.0 | 14.5 |
| 16.4 | 100.0 | 24.5 | 11.6 |
| 17.7 | 27.1 | 24.8 | 17.5 |
| 18.0 | 11.2 | 25.0 | 14.4 |
| 18.5 | 40.2 | 25.8 | 19.6 |
| 18.9 | 6.3 | 26.2 | 6.0 |
| 19.9 | 20.7 | 26.8 | 6.7 |
| 20.3 | 10.7 | 27.7 | 8.3 |
| 20.6 | 27.3 | 28.3 | 4.6 |
| 28.6 | 10.2 | 33.9 | 5.0 |
| 29.3 | 19.0 | 34.7 | 4.3 |
| 29.9 | 5.0 | 35.1 | 6.6 |
| 30.5 | 6.8 | 35.3 | 7.7 |
| 31.1 | 5.9 | 36.9 | 6.6 |
| 31.5 | 7.7 | 37.5 | 4.8 |
| 32.9 | 9.1 | 37.8 | 4.1 |
| 33.2 | 5.6 | 38.5 | 6.4 |

Synthesis of Psilocybin

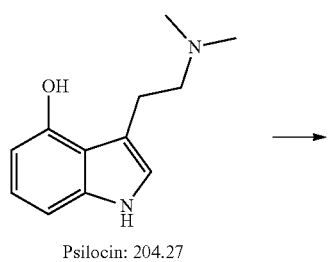

Psilocin: 204.27

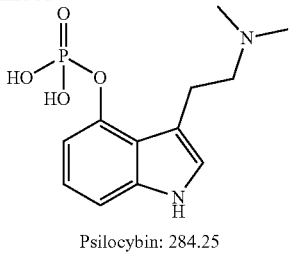

Psilocybin: 284.25

With reference to the scheme above, POCl$_3$ (2.70 g, 1.64 mL, 17.6 mmol, 1.2 equiv.) was added to a slurry of (NH$_4$)$_2$CO$_3$ (0.71 g, 7.34 mmol) in THF (30.0 mL) at −15° C., followed by a thin slurry of psilocin (3.00 g, 14.7 mmol) in THF (48.0 mL) over 15 min, during which time the (NH$_4$)2CO$_3$ started to coagulate. The reaction was stirred with the temperature being maintained between −15° C. and −5° C., and after ~ 15 min HPLC analysis showed 96.5% psilocybin and 2.6% psilocin.

After 1 h, reaction quenched by addition of 1.0 M (NH$_4$)2CO$_3$(aq) (19.1 mL, 19.1 mmol) over 40 min. Addition started at −5° C. and the mixture was allowed to warm to room temperature. During the addition a solid initially formed before dissolving and two immiscible layers were observed.

The reaction stirred and after 40 min solid started to appear. The flask was cooled in an ice-bath and stirred for a further 30 min at 0-5° C. Filtered product washed with THF (3×3 mL) and air-dried to give 4.94 g of a white solid. Further drying in vacuo, at room temperature, yielded 3.35 g (81%)

97.0% psilocybin and 2.1% psilocin by HPLC (detection at 267 nm)
$^1$H NMR consistent with psilocybin
$^{31}$P NMR showed a single peak consistent with psilocybin (~4.02 ppm)
The concentrated aqueous layer (5.11 g) showed by HPLC 52.4% psilocybin and 38.1% psilocin.
The primary material (3.35 g) was slurried in MeOH (34.0 mL) for 2 h before being filtered and washed with MeOH (2×3 mL) to give 2.99 g of psilocybin as a white solid (89% recovery; 72% for the two steps).
99.4% psilocybin with no detectable psilocin by HPLC (detection at 267 nm)
$^1$H NMR consistent with psilocybin with a trace of MeOH
$^{31}$P NMR showed a single peak consistent with psilocybin (~3.93 ppm)
The filtrate was concentrated to give a white semi-solid (~0.4 g) which by HPLC showed 83.3% psilocybin and 12.0% psilocin.

Figure 33:
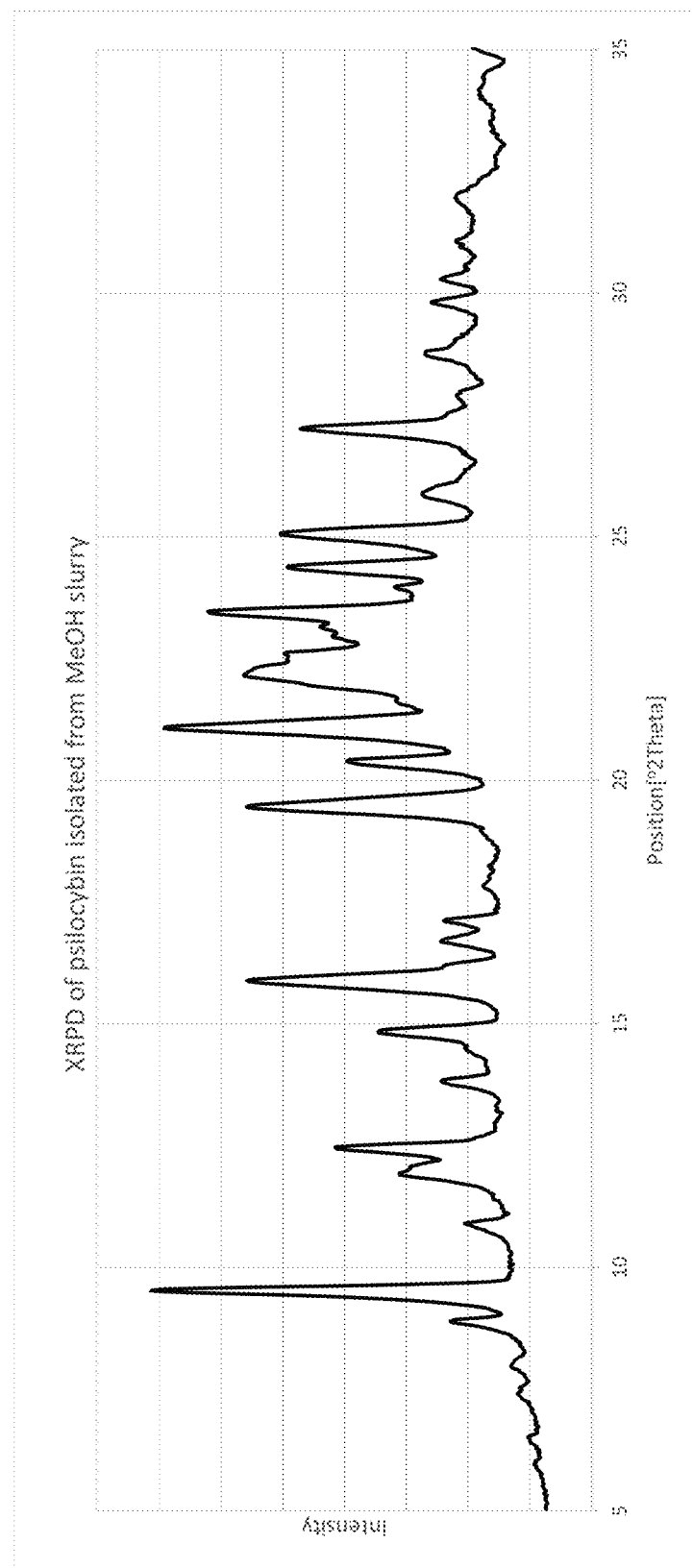
FIG. 33 provides an XRPD diffractogram of crystalline psilocybin prepared as described herein in Example 5.

The solid crystalline psilocybin produced was analyzed by XRPD yielding the diffractogram provided in FIG. 33. After drying this sample at 50° C. under high vacuum for 17 hours, XRPD the material yielded the diffractogram provided in FIG. 34.

Figure 34:
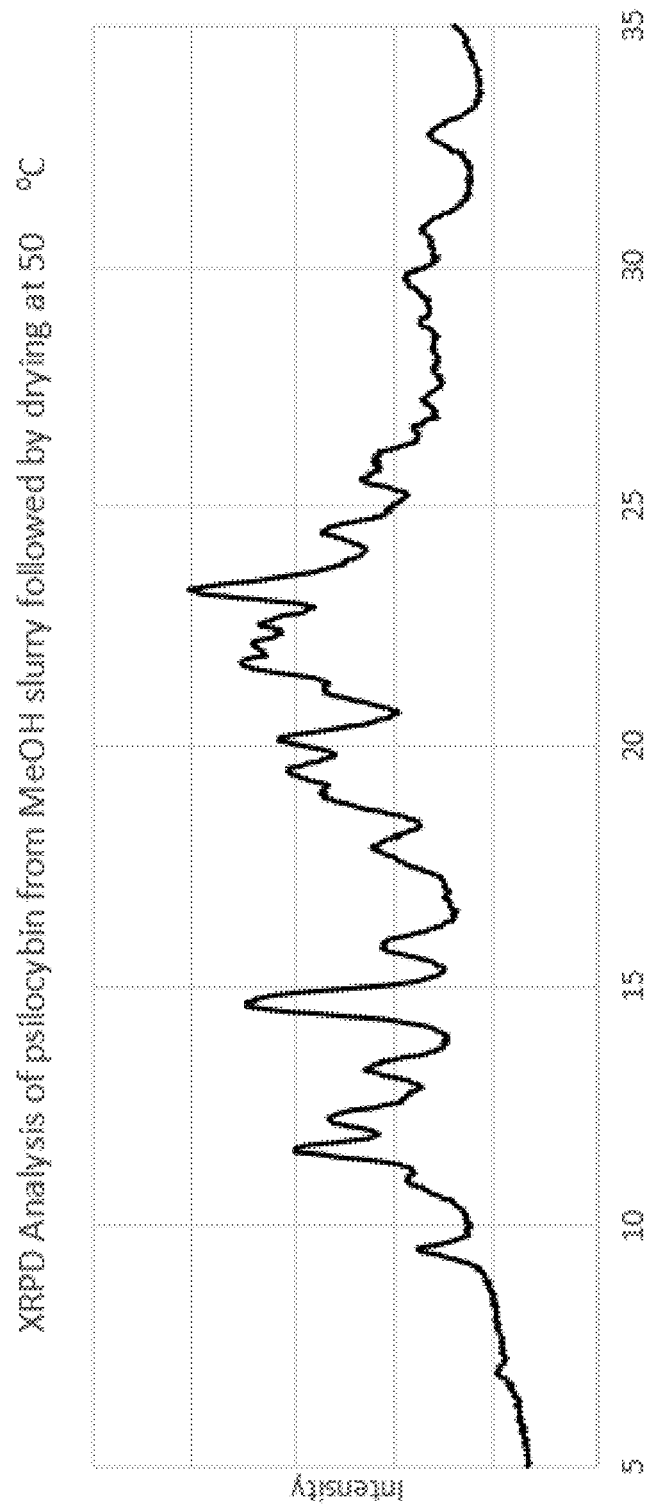
FIG. 34 provides an XRPD diffractogram of crystalline psilocybin prepared as described herein in Example 5.
Figure 35:
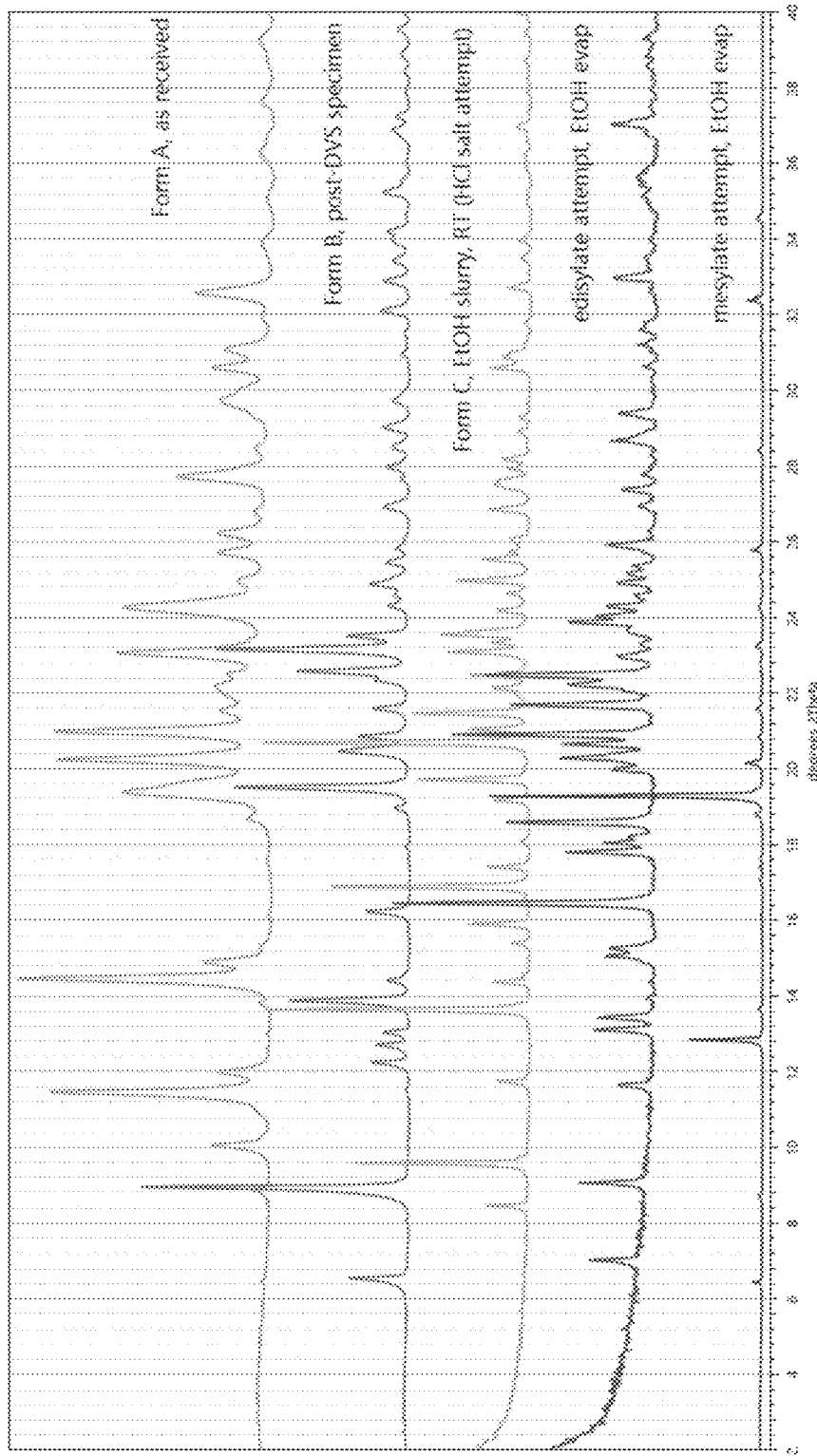
FIG. 35 overlays the XRPD diffractogram of FIG. 21 to the overlaid XRPD spectra provided in FIG. 10, illustrating the different XRPD spectra of Form A, Form B, Form C, edisylate Form A and the mesylate salt forms of psilocybin.

A PANalytical X'Pert Pro MPD with an XCelerator system using Detector Cu Kα radiation was used for the generation of FIG. 33 and FIG. 34, and the corresponding peak lists below.

XRPD analysis of crystalline psilocybin (FIG. 33) showed it to be crystalline with characteristic peaks at 8.9±0.2° 2-Theta, 9.5±0.2° 2-Theta, and 10.8±0.2° 2-Theta; optionally with further characteristic peaks at 11.9±0.2° 2-Theta and 12.4±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 8.9 | 21.8 | 23.4 | 72.9 |
| 9.5 | 100.0 | 24.0 | 10.3 |
| 10.8 | 16.0 | 24.3 | 53.9 |
| 11.9 | 31.9 | 25.0 | 55.8 |
| 12.4 | 49.0 | 25.9 | 23.5 |
| 13.8 | 21.8 | 27.2 | 55.2 |
| 14.8 | 38.2 | 27.8 | 9.9 |
| 15.9 | 73.2 | 28.7 | 23.1 |
| 16.7 | 19.7 | 29.8 | 14.8 |
| 17.1 | 16.6 | 30.3 | 11.9 |
| 19.4 | 74.5 | 31.0 | 11.5 |
| 20.3 | 40.4 | 31.9 | 13.9 |
| 21.0 | 88.7 | 35.0 | 10.8 |
| 22.1 | 59.9 | 36.7 | 16.0 |
| 22.5 | 35.2 | 39.4 | 13.4 |

XRPD analysis of crystalline psilocybin after drying (FIG. 34) showed it to be crystalline with characteristic peaks at 9.5±0.2° 2-Theta, 10.9±0.2° 2-Theta, and 11.6±±0.2° 2-Theta; optionally with further characteristic peaks at 12.3±0.2° 2-Theta and 13.3±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 9.5 | 21.0 | 14.7 | 86.8 |
| 10.9 | 18.0 | 15.8 | 31.2 |
| 11.6 | 64.7 | 17.9 | 31.7 |
| 12.3 | 47.8 | 18.9 | 37.2 |
| 13.3 | 35.8 | 19.5 | 61.8 |
| 20.1 | 56.2 | 25.6 | 26.7 |
| 21.1 | 37.6 | 26.0 | 20.3 |
| 21.7 | 66.0 | 27.2 | 10.2 |
| 22.1 | 46.7 | 28.8 | 11.3 |
| 22.5 | 40.9 | 29.7 | 23.1 |
| 23.2 | 100.0 | 30.7 | 16.8 |
| 24.5 | 40.4 | 32.7 | 18.4 |

Experimental

X-ray Powder Diffraction (XRPD)

The Rigaku Smart-Lab X-ray diffraction system was configured for reflection Bragg-Brentano geometry using a line source X-ray beam. The X-ray source was a Cu Long Fine Focus tube that was operated at 40 kV and 44 ma. That source provided an incident beam profile at the sample that changed from a narrow line at high angles to a broad rectangle at low angles. Beam conditioning slits were used on the line X-ray source to ensure that the maximum beam size was less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab was operated to give peak widths of 0.1° 2θ or less. The axial divergence of the X-ray beam was controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40° 2θ using a continuous scan of 6° 2θ per minute with an effective step size of 0.02° 2θ.

"Characteristic peaks", to the extent they exist, are a subset of observed peaks and are used to differentiate one crystalline polymorph from another crystalline polymorph (polymorphs being crystalline forms having the same chemical composition). Characteristic peaks are determined by evaluating which observed peaks, if any, are present in one crystalline polymorph of a compound against all other known crystalline polymorphs of that compound to within ±0.2° 2-Theta.

Differential Scanning Calorimetry (DSC)

DSC analyses were carried out using a TA Instruments Q2500 Discovery Series instrument. The instrument temperature calibration was performed using indium. The DSC cell was kept under a nitrogen purge of about 50 mL per minute during each analysis. The sample was placed in a standard, crimped, aluminum pan and was heated from approximately 25° C. to 350° C. at a rate of 10° C. per minute.

Thermogravimetric (TG) Analysis

The TG analysis was carried out using a TA Instruments Q5500 Discovery Series instrument. The instrument balance was calibrated using class M weights and the temperature calibration was performed using alumel. The nitrogen purge was about 40 mL per minute at the balance and about 60 mL per minute at the furnace. Each sample was placed into a pre-tared platinum pan and heated from approximately 25° C. to 350° C. at a rate of 10° C. per minute.

Dynamic Vapor Sorption (DVS) Analysis

DVS analysis was carried out using a TA Instruments Q5000 Dynamic Vapor Sorption analyzer. The instrument was calibrated with standard weights and a sodium bromide standard for humidity. Approximately 10-25 mg of sample was loaded into a metal-coated quartz pan for analysis. The sample was analyzed at 25° C. with a maximum equilibration time of one hour in 10% relative humidity (RH) steps from 5 to 95% RH (adsorption cycle) and from 95 to 5% RH (desorption cycle). The movement from one step to the next occurred either after satisfying the equilibrium criterion of 0.01% weight change or, if the equilibrium criterion was not met, after one hour. The percent weight change values were calculated using Microsoft Excel®.

Optical Microscopy

Optical microscopy experiments were carried out on a Leica DM 2500 P compound microscope. Images were captured using a QImaging MicroPublisher 3.3 RTV camera. Images were collected at 10x magnification.

Nuclear Magnetic Resonance (NMR) Spectroscopy

The $^1$H NMR spectra were acquired on a Bruker Avance II 400 spectrometer. Samples were prepared by dissolving material in DMSO-$d_6$. The solutions were filtered and placed into individual 5-mm NMR tubes for subsequent spectral acquisition. The temperature controlled (295K) $^1$H NMR spectra acquired on the Avance II 400 utilized a 5-mm cryoprobe operating at an observing frequency of 400.18 MHz.

Example 6: Salt Screen of O-Acetylpsilocin

O-acetylpsilocin is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the free base is a solvate or hydrate, and to evaluate thermal stability. DVS data are used to evaluate hygroscopicity of the free base and if hydrates can be formed at high relative humidity. About 10 to 15 solvents are selected from the list below, based on their properties (polarity, dielectric constant and dipole moment).

TABLE 16

Solvents

| | |
|---|---|
| acetic acid | n-heptane |
| Acetone | n-hexane |
| Acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | Methanol |
| Chlorobenzene | methoxybenzene (anisole) |
| Chloroform | methyl acetate |
| di(ethylene glycol) | methyl ethyl ketone (2-butanone) |
| Dichloromethane | methyl isobutyl ketone |
| diethyl ether | Nitromethane |
| Diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | Perfluorohexane |
| 1,4-dioxane | propyl acetate |
| 1,2-ethanediol (ethylene glycol) | 1,1,2,2-tetrachloroethane |
| Ethanol | Tetrahydrofuran |
| Ethanolamine | Toluene |
| 2-ethoxyethanol (Cellusolve) | 1,1,1-trichloroethane |
| ethyl acetate | 2,2,2-trifluoroethanol |
| ethyl formate | Water |
| formic acid | o-xylene (1,2-dimethylbenzene) |
| Glycerol | p-xylene (1,4-dimethylbenzene) |

The information obtained is used for designing the subsequent salt screen. The salt screen is performed by reacting the free base with pharmaceutically acceptable acids under various conditions in attempts to generate crystalline salts. Pharmaceutically acceptable acids that may be used are listed below. Specific acids are selected based on the pKa of the free base, and typically 15 to 20 acids are selected. Experiments are performed using 0.5 molar equivalent, 1 molar equivalent and/or 2 molar equivalents of the acid.

TABLE 17

Exemplary Acids

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |

TABLE 17-continued

Exemplary Acids

| | |
|---|---|
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| Hydrochloric acid | carbonic acid |
| galactaric (mucic) acid | |

Solvent systems for the salt crystallization experiments are selected based on the solubility of the free base and the selected acid. Solvents are used as a single solvent or as solvent mixtures, some containing water. The techniques that are used for salt crystallization are chosen based on the solvent selected and properties of the free base. The following techniques (or combination of techniques) may be used for salt crystallization:

Free base and acid are dissolved in a solvent or mixture of solvents, and the solvents are evaporated at different rates (slow evaporation or fast evaporation) and at different temperatures (ambient or elevated).

Free base and acid are dissolved in a solvent or mixture of solvents (at ambient temperature or an elevated temperature), and the final solution is cooled to a sub-ambient temperature (between −78° C. to 15° C.). The cooling method can be a fast cooling (by plunging the sample into an ice bath or a dry ice/acetone bath), or slow cooling. The solids formed will be recovered by filtration and dried (air dried or vacuum dried).

Free base and acid are dissolved in a solvent or mixture of solvents, and an antisolvent is added to precipitate the salt. The solids formed will be recovered by filtration and dried (air dried or vacuum dried).

Free base and acid are added to a solvent or mixture of solvents, where one or both components are not fully dissolved. The slurry is agitated at different temperatures for a number of days. The solids formed will be recovered by filtration and dried (air dried or vacuum dried). The same experiment can be also performed in solvent systems where the solvents are not miscible.

Free base and acid are milled together (by mechanical milling or by mortar and pestle), with a drop of solvent, or without any solvent.

Free base and acid are melted together, and cooled to various temperatures using various cooling rates.

If an amorphous form of a salt is obtained, the amorphous salt will be exposed to elevated humidity, or elevated temperature (or combination of both), or solvent vapors at various temperatures to form crystalline salts.

The stoichiometric ratio of acid to O-acetylpsilocin is confirmed by $^1$H NMR, HPLC, or both as is known to those of ordinary skill in the art.

The salts obtained are analyzed by XRPD to determine if they are crystalline and, if so, by DSC to see the melting point and by TG to see if they are hydrated/solvated, and by 1H NMR spectroscopy to ensure chemical integrity. KF water titration is performed on salts that are hydrated. DVS analysis is performed to evaluate hygroscopicity of the salt and if hydrated form is present.

Figure 36:
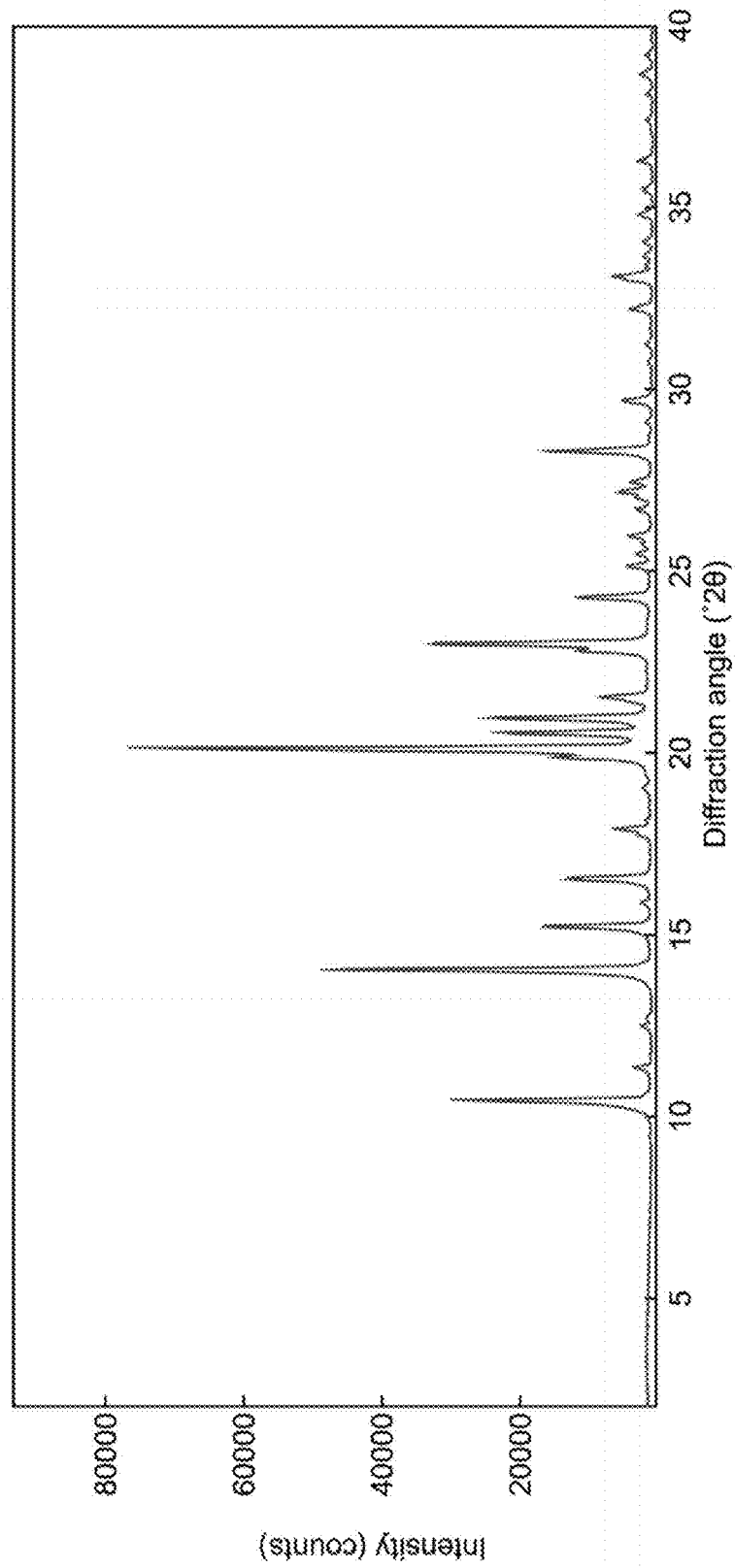
FIG. 36 provides an XRPD diffractogram of crystalline O-acetylpsilocin free base.
Figure 37:
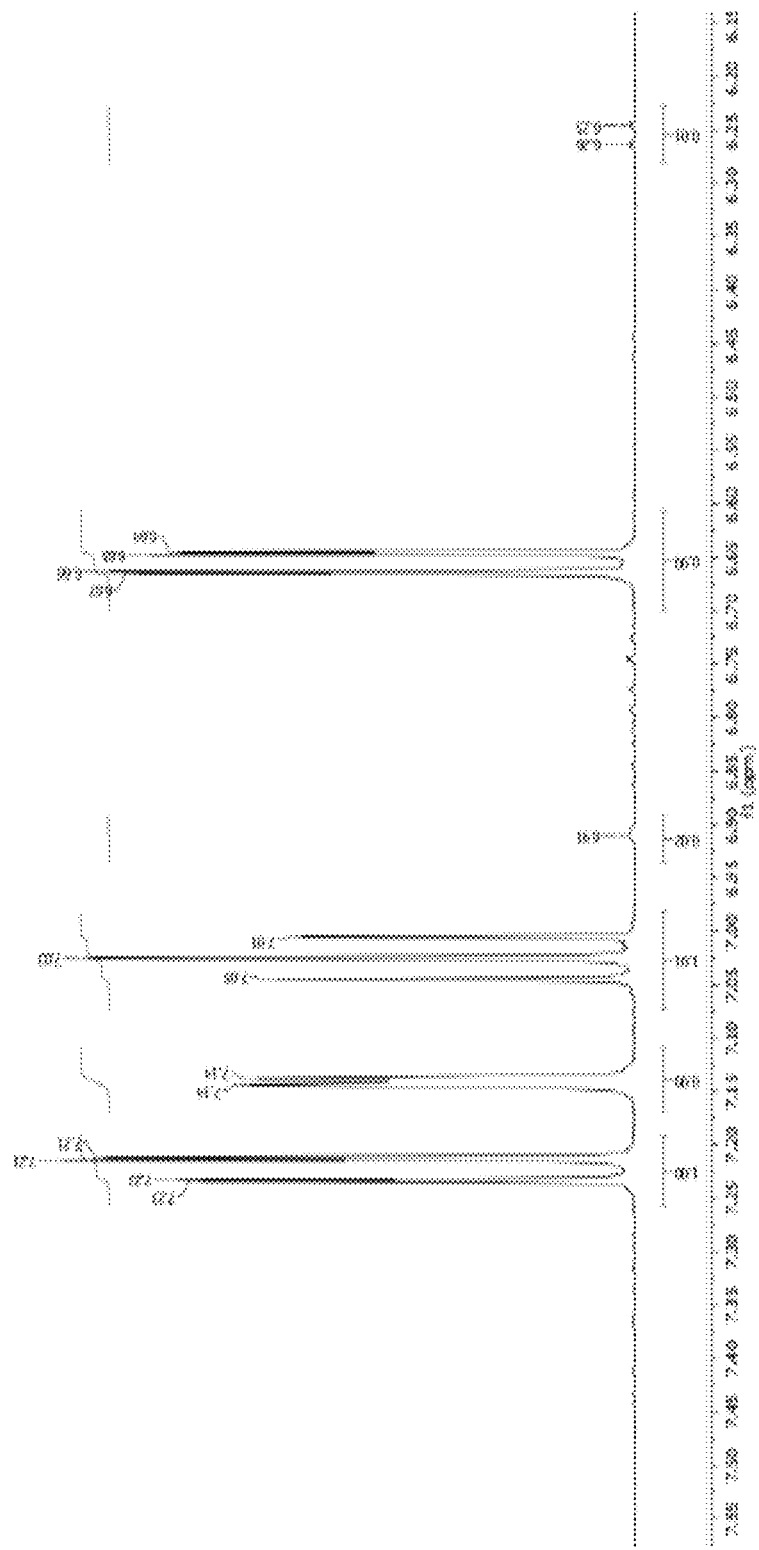
FIG. 37 provides a partial $^1$H NMR spectrum of O-acetylpsilocin free base.
Figure 38:
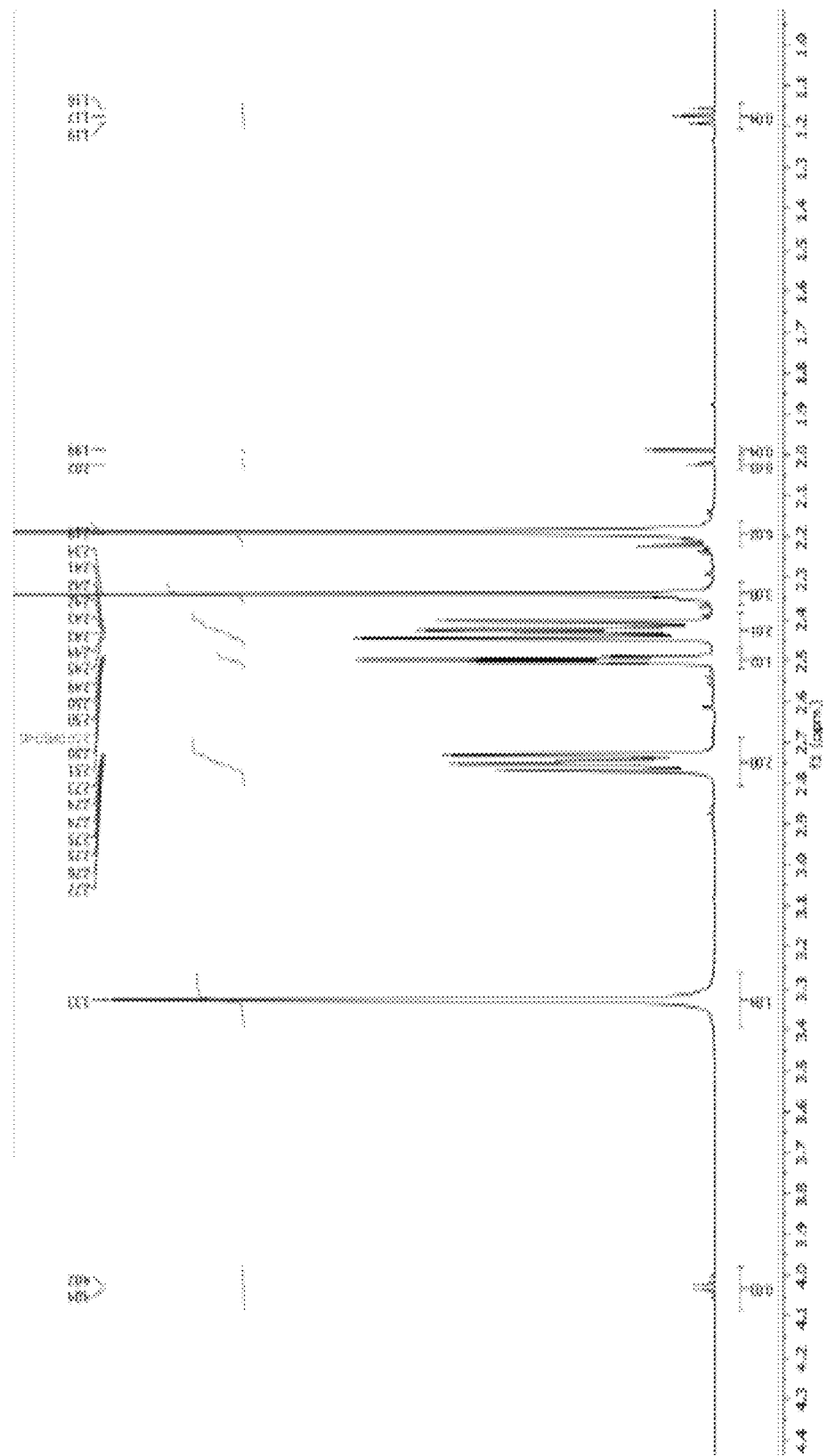
FIG. 38 provides a partial $^1$H NMR spectrum of O-acetylpsilocin free base.

To prepare O-acetyl psilocin freebase, a suspension of O-acetyl psilocin fumarate was treated with aqueous sodium carbonate in ethyl acetate with aqueous sodium carbonate. It was initially obtained as an oil, which began to crystallize upon vacuum drying to remove residual solvent. The XRPD diffractogram for the crystalline O-acetyl psilocin freebase is provided as FIG. 36 and the proton NMR in FIGS. 37 and 38.

XRPD analysis of O-Acetyl Psilocin free base (FIG. 36) showed it to be crystalline with characteristic peaks at 10.5±0.2° 2-Theta, 14.0±0.2° 2-Theta, and 15.2±0.2° 2-Theta; optionally with further characteristic peaks at 16.5±0.2° 2-Theta and 20.1±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 10.5 | 37.9 | 24.3 | 15.4 |
| 11.4 | 4.8 | 25.1 | 6.0 |
| 12.5 | 3.5 | 25.5 | 4.4 |
| 12.7 | 2.3 | 25.8 | 3.3 |
| 14.0 | 63.0 | 26.0 | 5.8 |
| 15.2 | 22.3 | 26.7 | 4.4 |
| 15.9 | 3.5 | 27.2 | 7.8 |
| 16.5 | 17.6 | 27.4 | 5.4 |
| 17.9 | 8.6 | 28.3 | 21.2 |
| 18.2 | 2.5 | 29.1 | 2.4 |
| 19.1 | 3.1 | 29.7 | 6.9 |
| 19.9 | 19.9 | 30.7 | 2.0 |
| 20.1 | 100.0 | 31.2 | 2.6 |
| 20.6 | 30.2 | 32.2 | 5.6 |
| 21.0 | 32.5 | 33.1 | 8.8 |
| 21.5 | 11.2 | 33.4 | 2.6 |
| 22.8 | 15.4 | 33.6 | 2.9 |
| 23.0 | 43.7 | 34.1 | 2.9 |
| 34.8 | 4.0 | 38.1 | 2.3 |
| 35.5 | 3.1 | 38.7 | 3.7 |
| 36.3 | 4.0 | 39.2 | 2.5 |
| 37.4 | 2.4 | | |

Solubility of O-acetyl psilocin freebase in a few solvents was estimated by adding the test solvent in aliquots to weighed portions of solid. Whether dissolution had occurred was judged by visual inspection after addition of each solvent aliquot. The results are recorded in Table 18. Solubility numbers were calculated by dividing the weight of the sample by the total amount of solvent used to dissolve the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than or equal to" if dissolution occurred on addition of the first solvent aliquot. All solubility measurements were carried out at room temperature unless noted otherwise.

TABLE 18

Estimated Solubilities of O-Acetyl Psilocin Freebase

| | |
|---|---|
| acetone | >59 |
| acetonitrile (ACN) | >67 |
| 1,4-dioxane | >62 |
| ethanol (EtOH) | >62 |
| ethyl acetate (EtOAc) | >49 |
| hexanes | <1 |
| Methyl tert-butyl ether (MTBE) | >23 |
| Methyl ethyl ketone (MEK) | >51 |
| methanol (MeOH) | >62 |
| 2-propanol (2-PrOH) | >32 |
| 2-methyltetrahydrofuran 2-Me(THF) | >50 |

TABLE 18-continued

Estimated Solubilities of O-Acetyl Psilocin Freebase

| | |
|---|---|
| toluene | >59 |
| water | <1 |

The free base form prepared as described above was mixed with various acids under various conditions in attempts to generate crystalline salts. Exemplary acids used included L-aspartic, benzenesulfonic, citric, ethanesulfonic, gentisic, D-gluconic, L-glutamic, glycolic, hydrochloric, xinafoic, DL-lactic, maleic, L-malic, malonic, methanesulfonic, mucic (galactaric), phosphoric, succinic, sulfuric, L-tartaric, and p-toluenesulfonic.

Samples generated and analyzed are listed in Table 19. All experiments were carried out using 1 molar equivalent of acid.

TABLE 19

Figure 39:
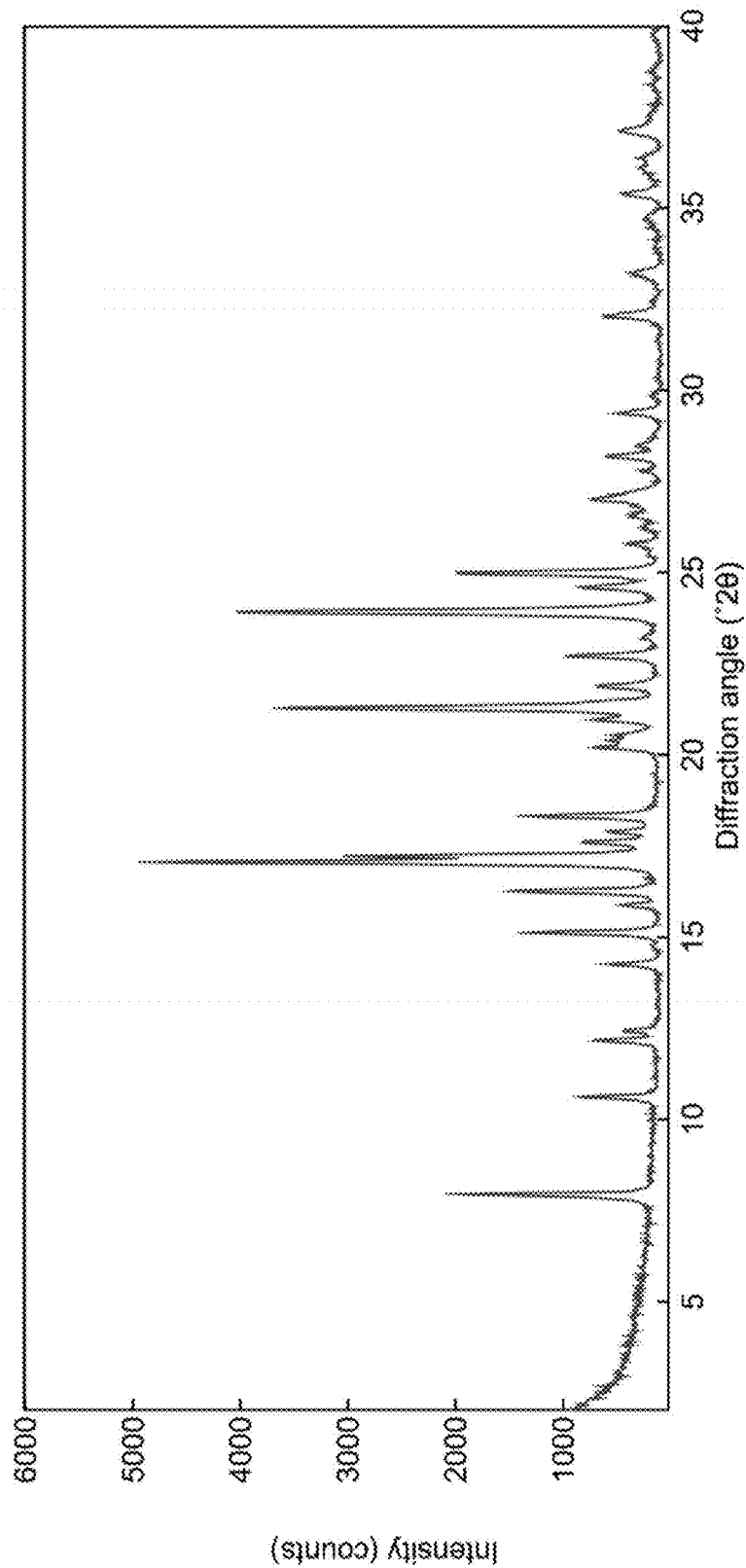
FIG. 39 provides an XRPD diffractogram of O-acetyl psilocin·glycolate.
Figure 40:
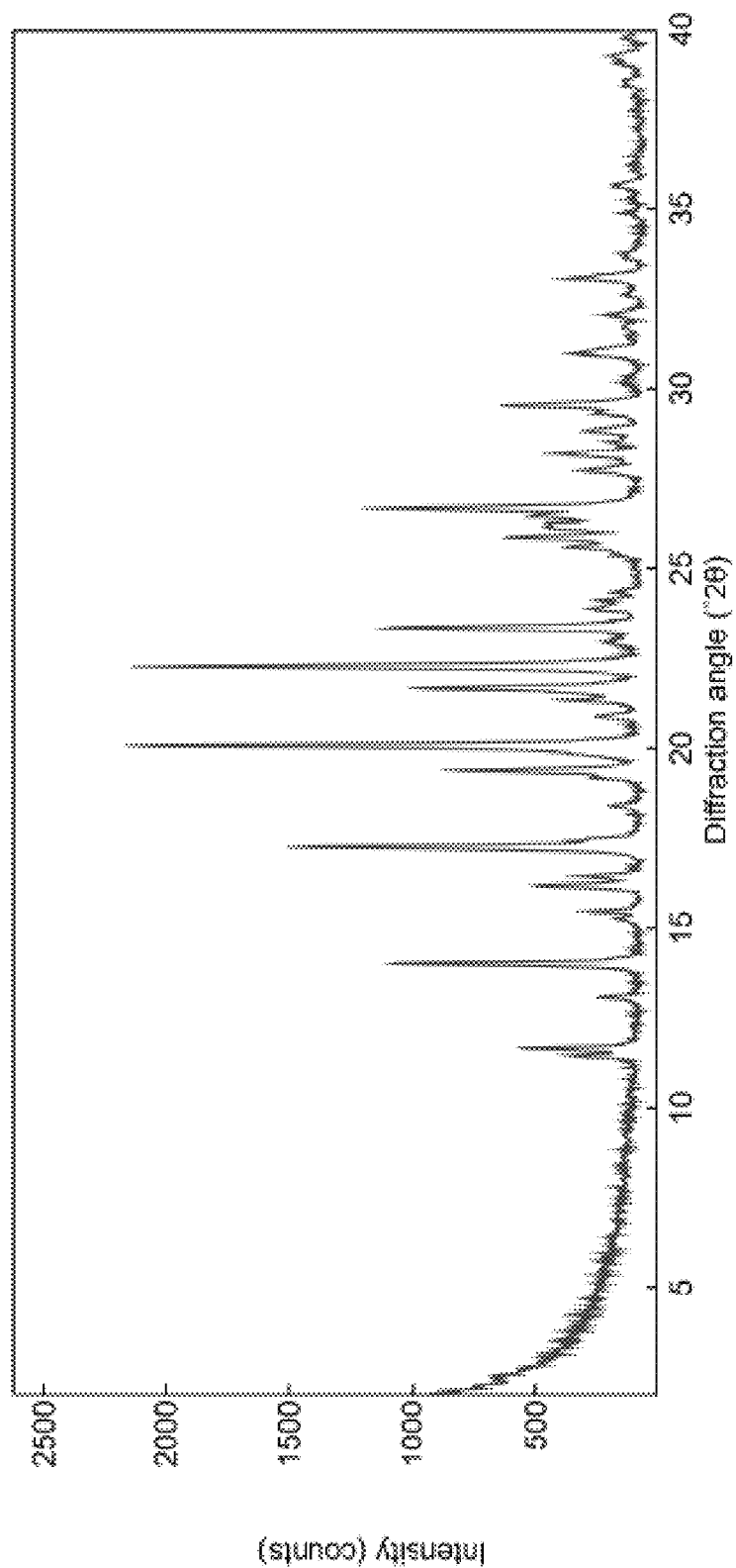
FIG. 40 provides an XRPD diffractogram of O-acetyl psilocin·hydrochloride
Figure 41:
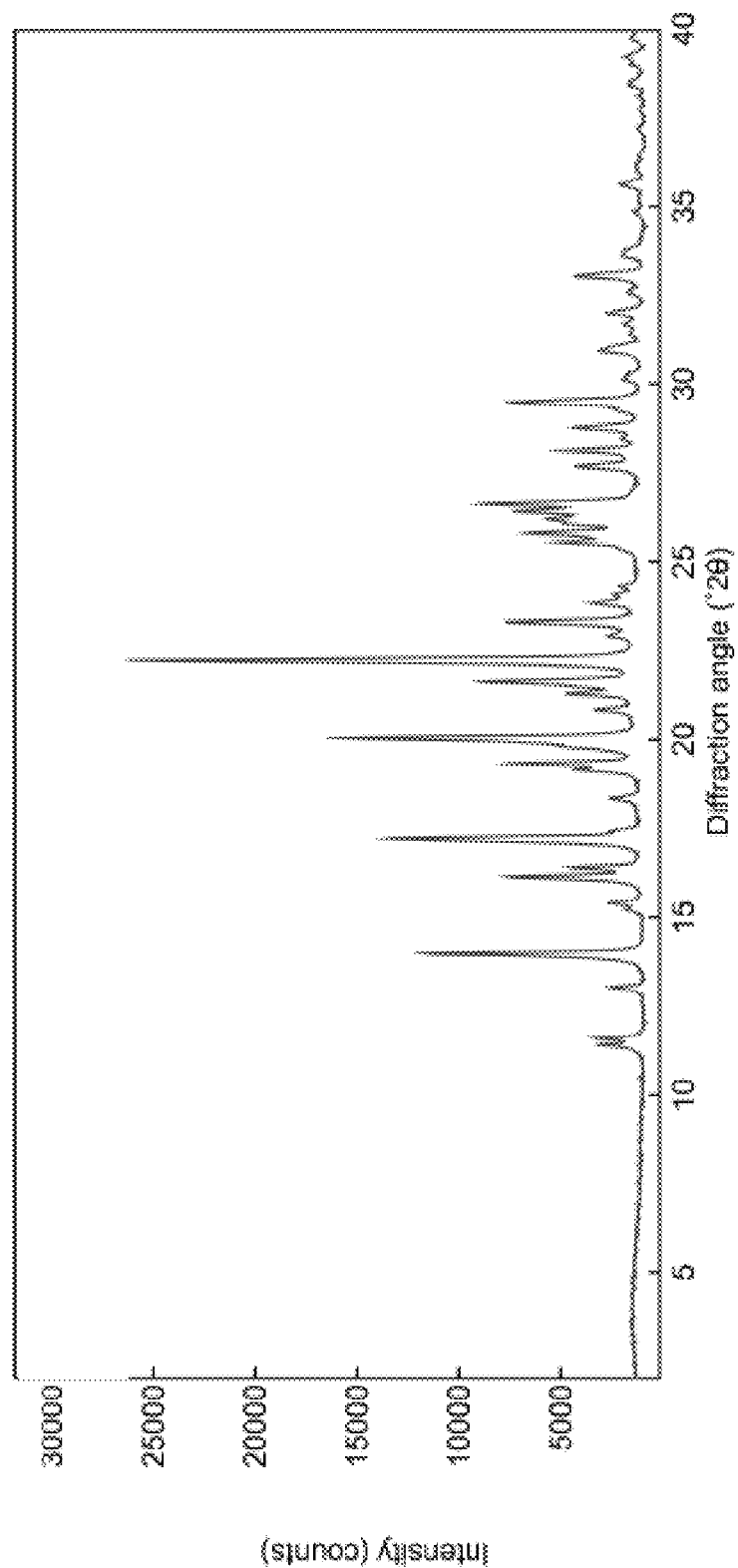
FIG. 41 provides an XRPD diffractogram of O-acetyl psilocin·hydrochloride made by an alternative method.
Figure 42:
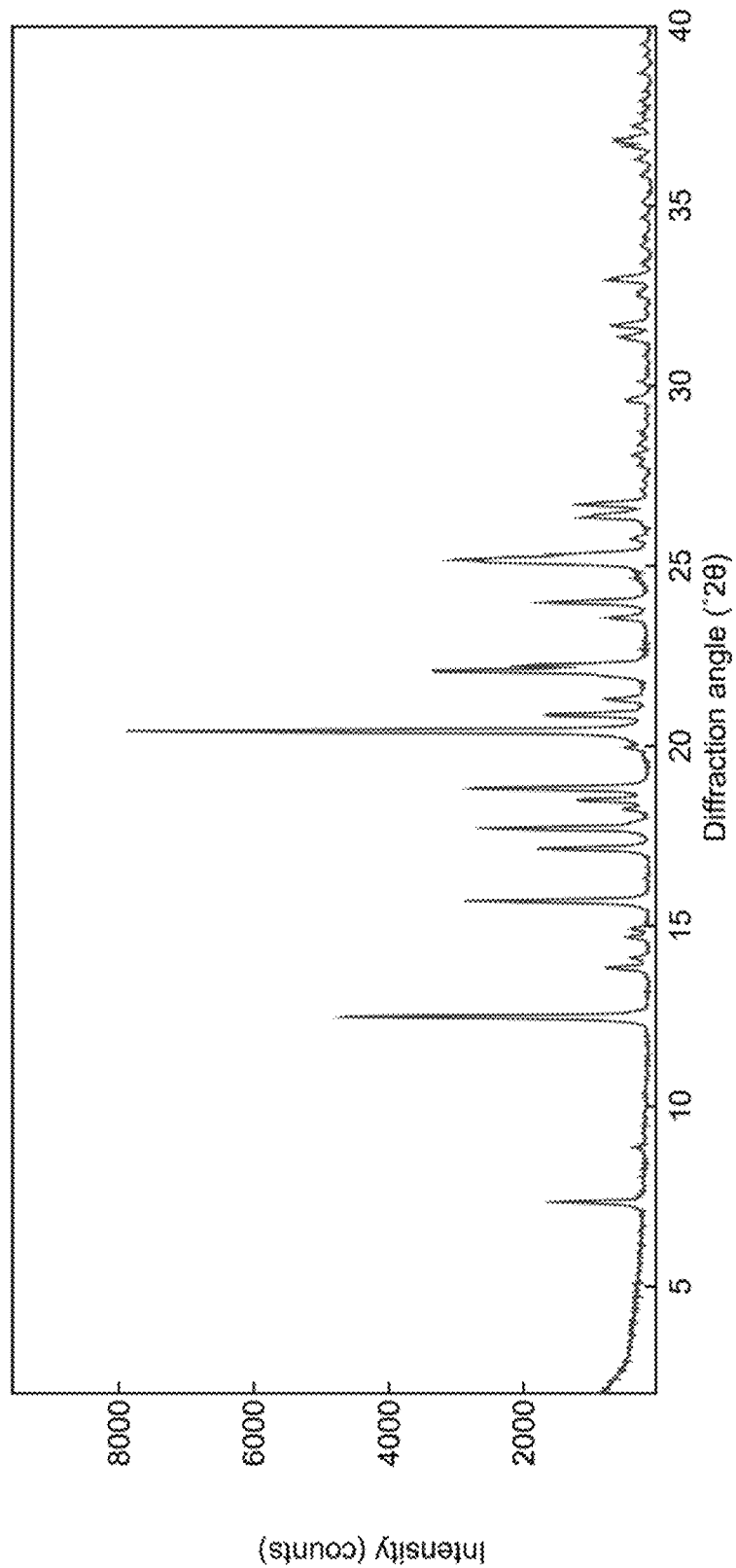
FIG. 42 provides an XRPD diffractogram of O-acetyl psilocin malate Form A.
Figure 43:
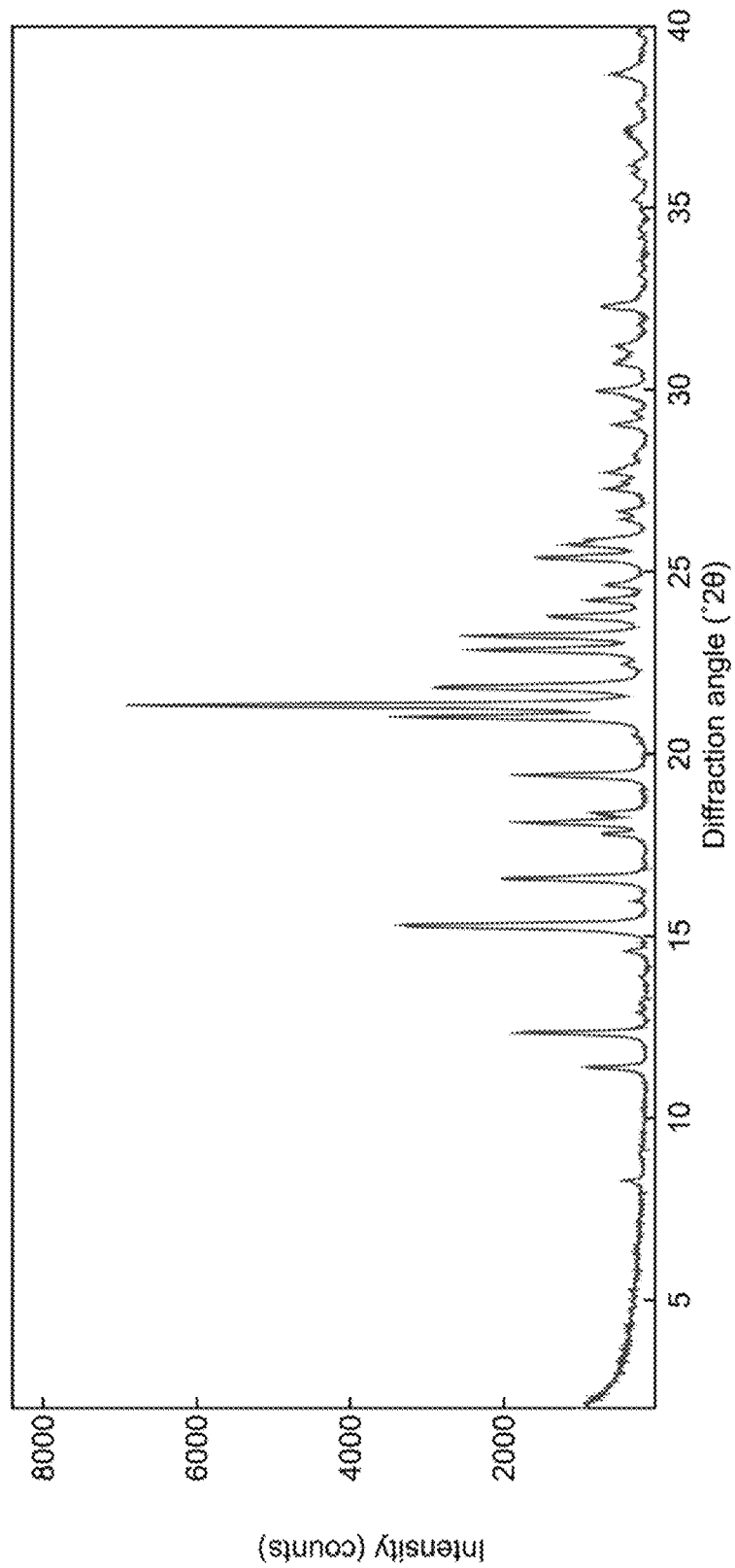
FIG. 43 provides an XRPD diffractogram of O-acetyl psilocin malate Form B.
Figure 44:
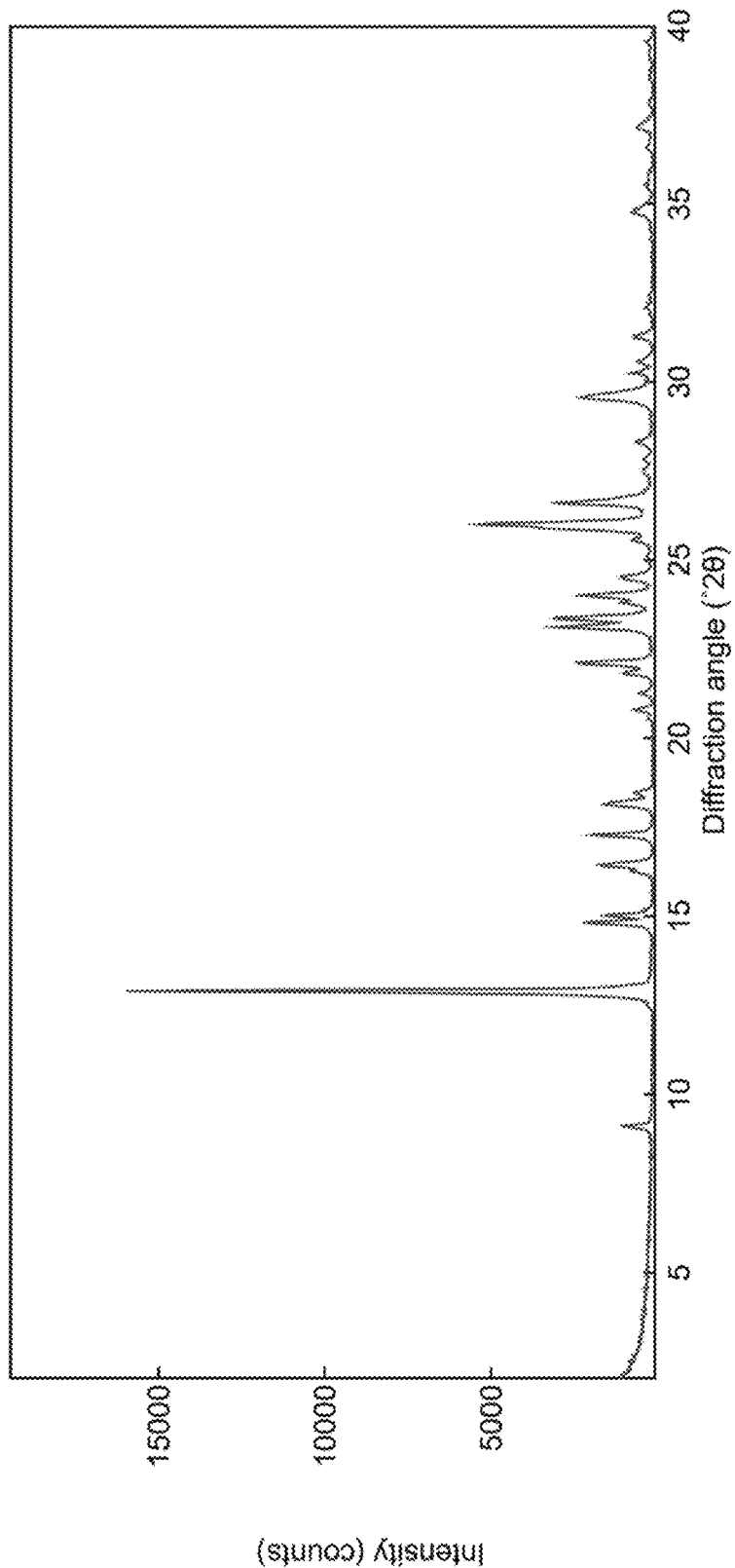
FIG. 44 provides an XRPD diffractogram of O-acetyl psilocin maleate Form A.
Figure 45:
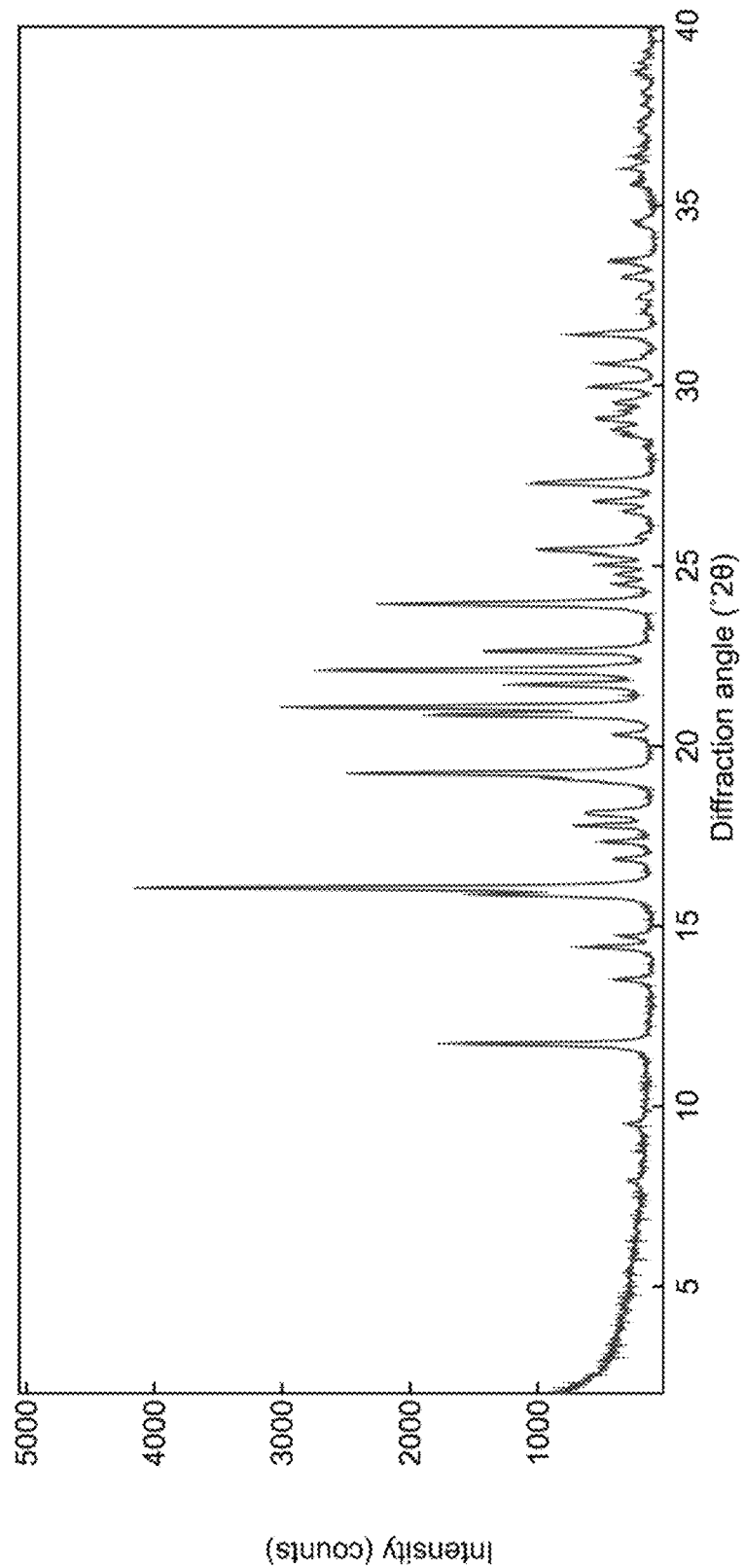
FIG. 45 provides an XRPD diffractogram of O-acetyl psilocin malonate.
Figure 46:
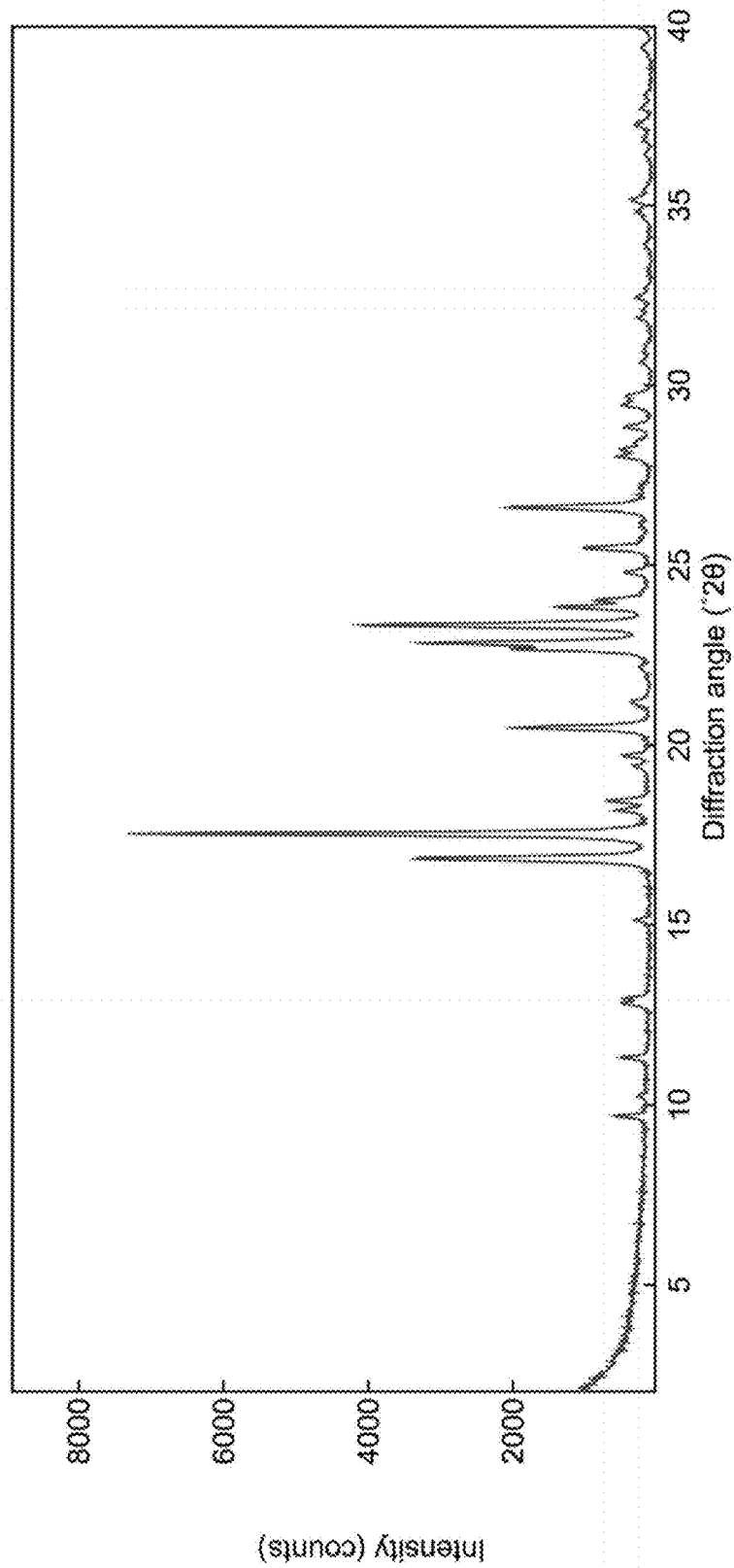
FIG. 46 provides an XRPD diffractogram of O-acetyl psilocin mesylate.
Figure 47:
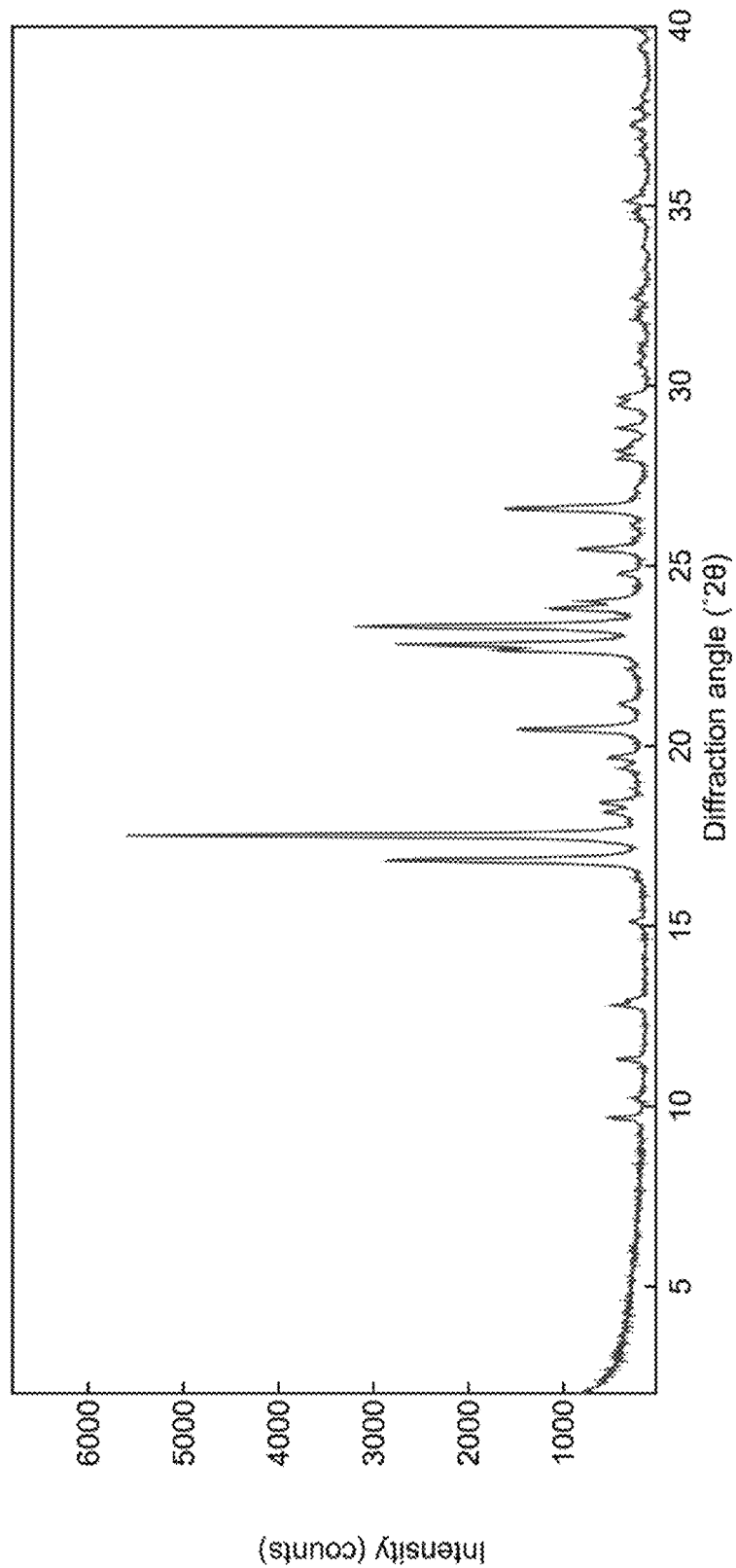
FIG. 47 provides an XRPD diffractogram of O-acetyl psilocin·mesylate.
Figure 48:
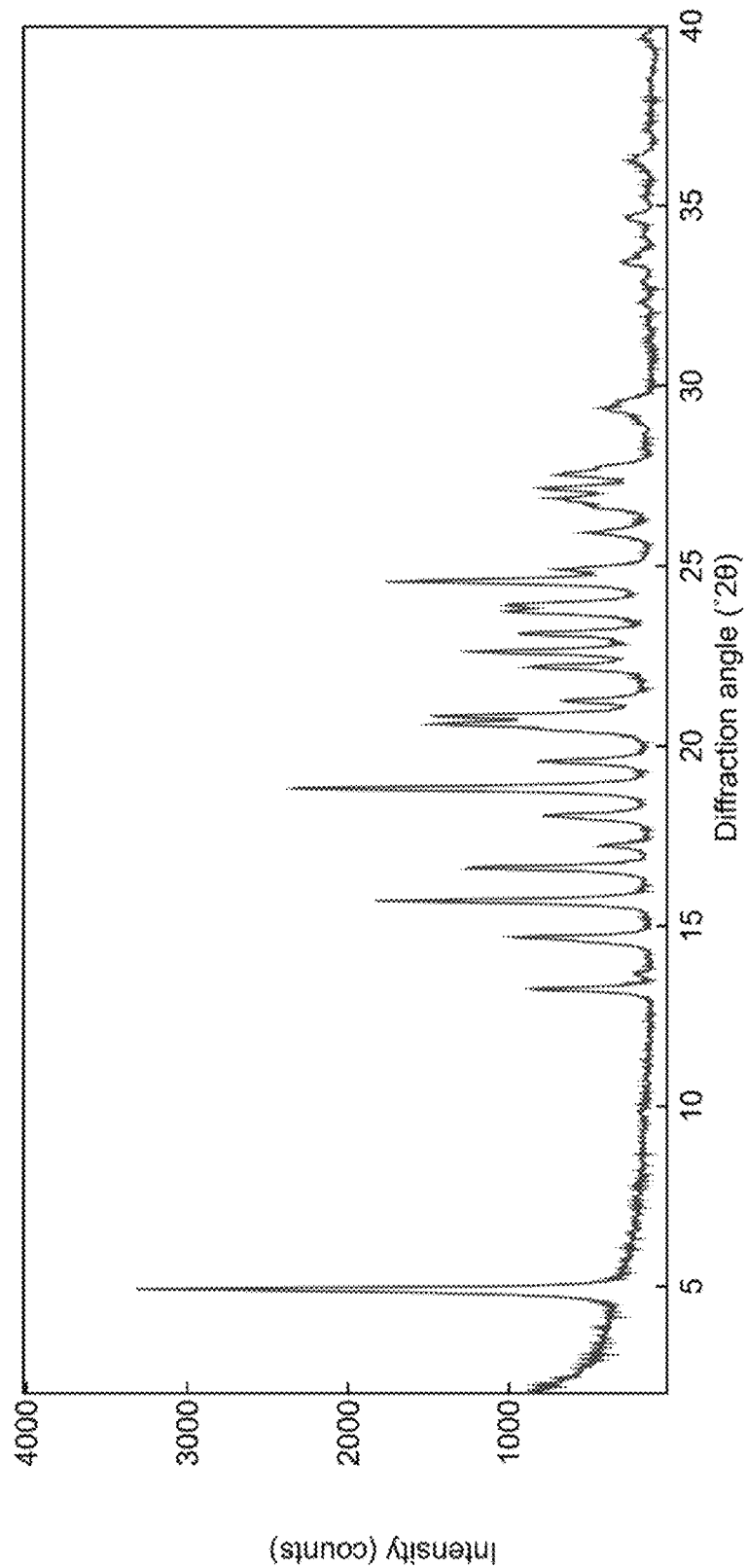
FIG. 48 provides an XRPD diffractogram of O-acetyl psilocin·phosphate Form A.
Figure 49:
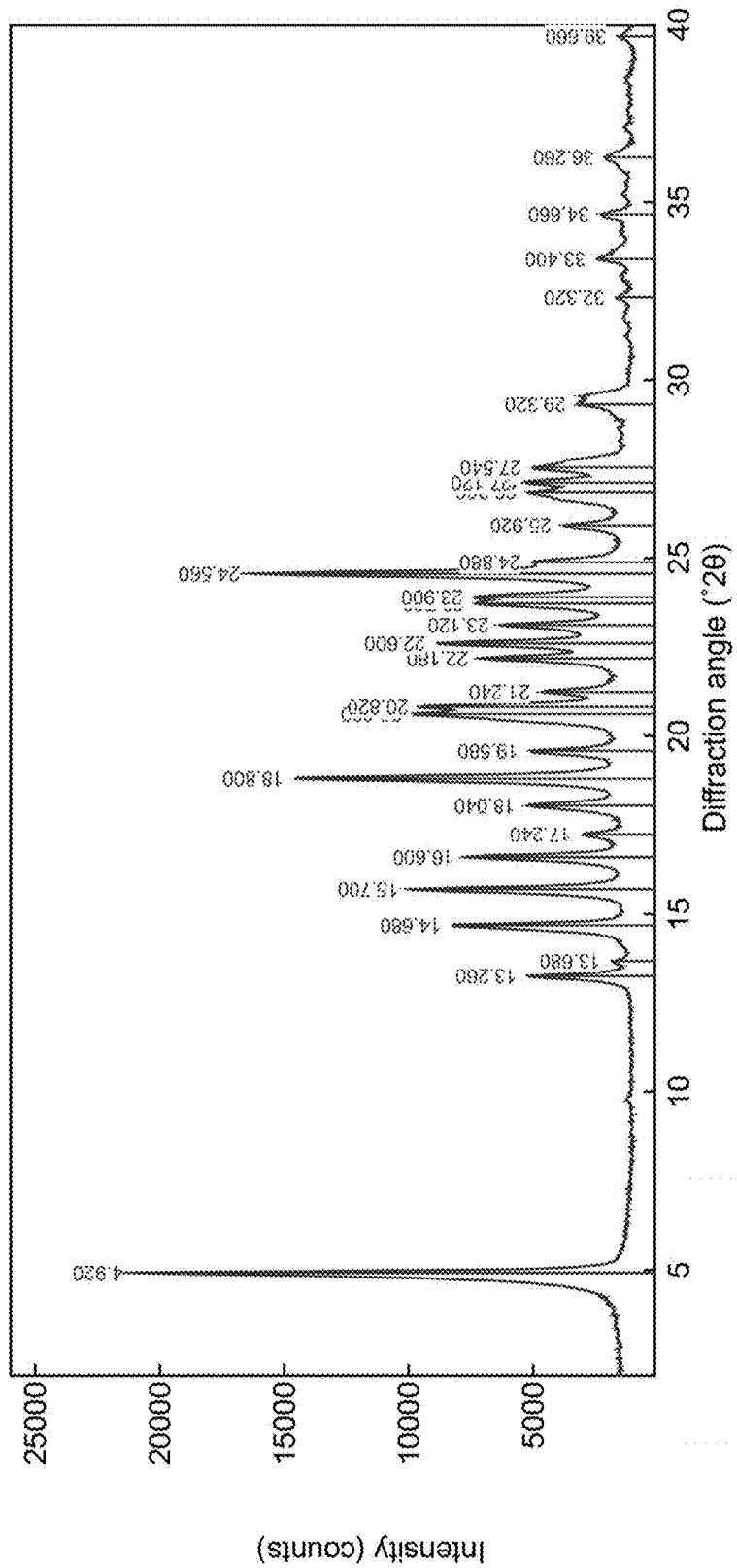
FIG. 49 provides an XRPD diffractogram of O-acetyl psilocin·phosphate Form A.
Figure 50:
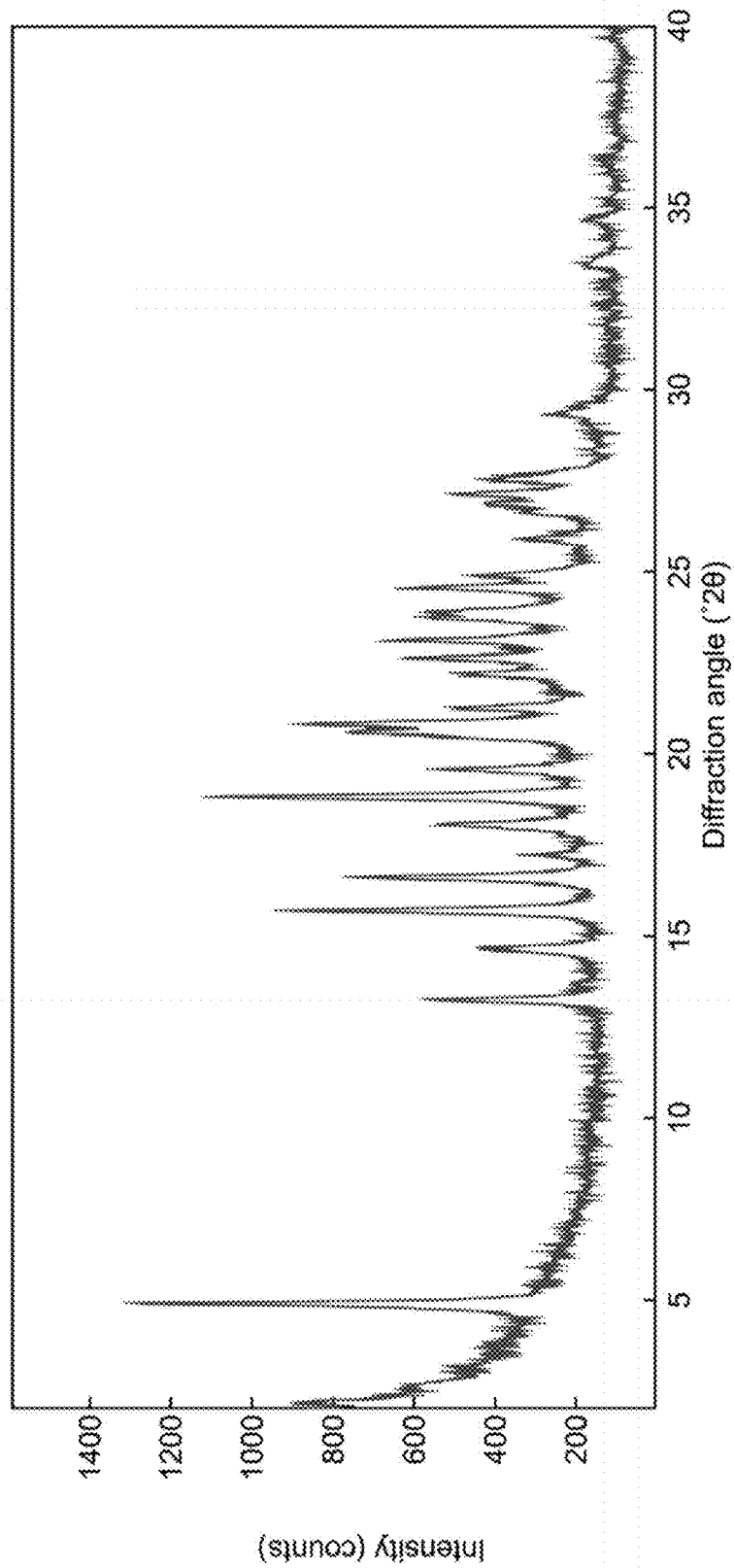
FIG. 50 provides an XRPD diffractogram of O-acetyl psilocin·phosphate Form A.
Figure 51:
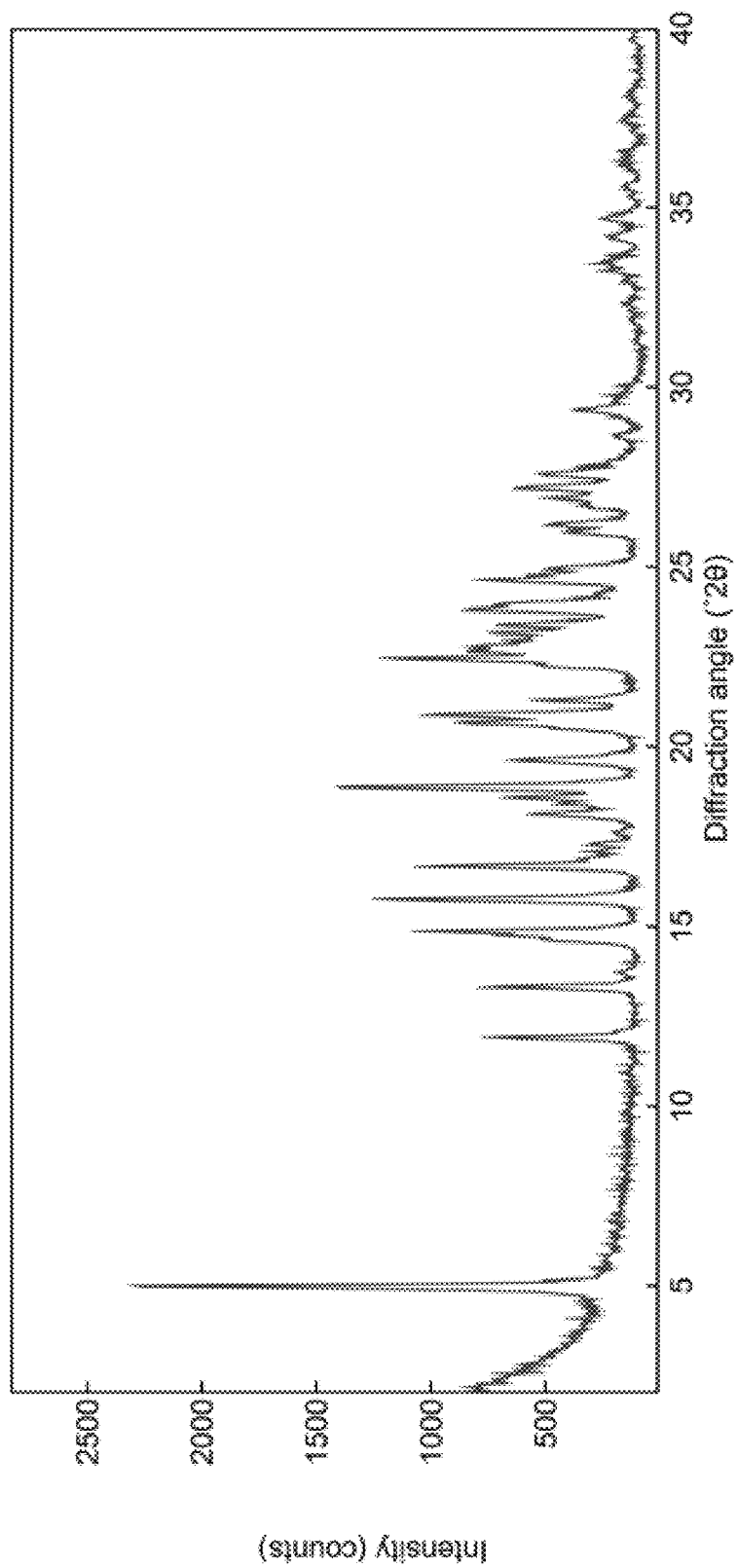
FIG. 51 provides an XRPD diffractogram of a mixture of O-acetyl psilocin·phosphate Forms A and B.
Figure 52:
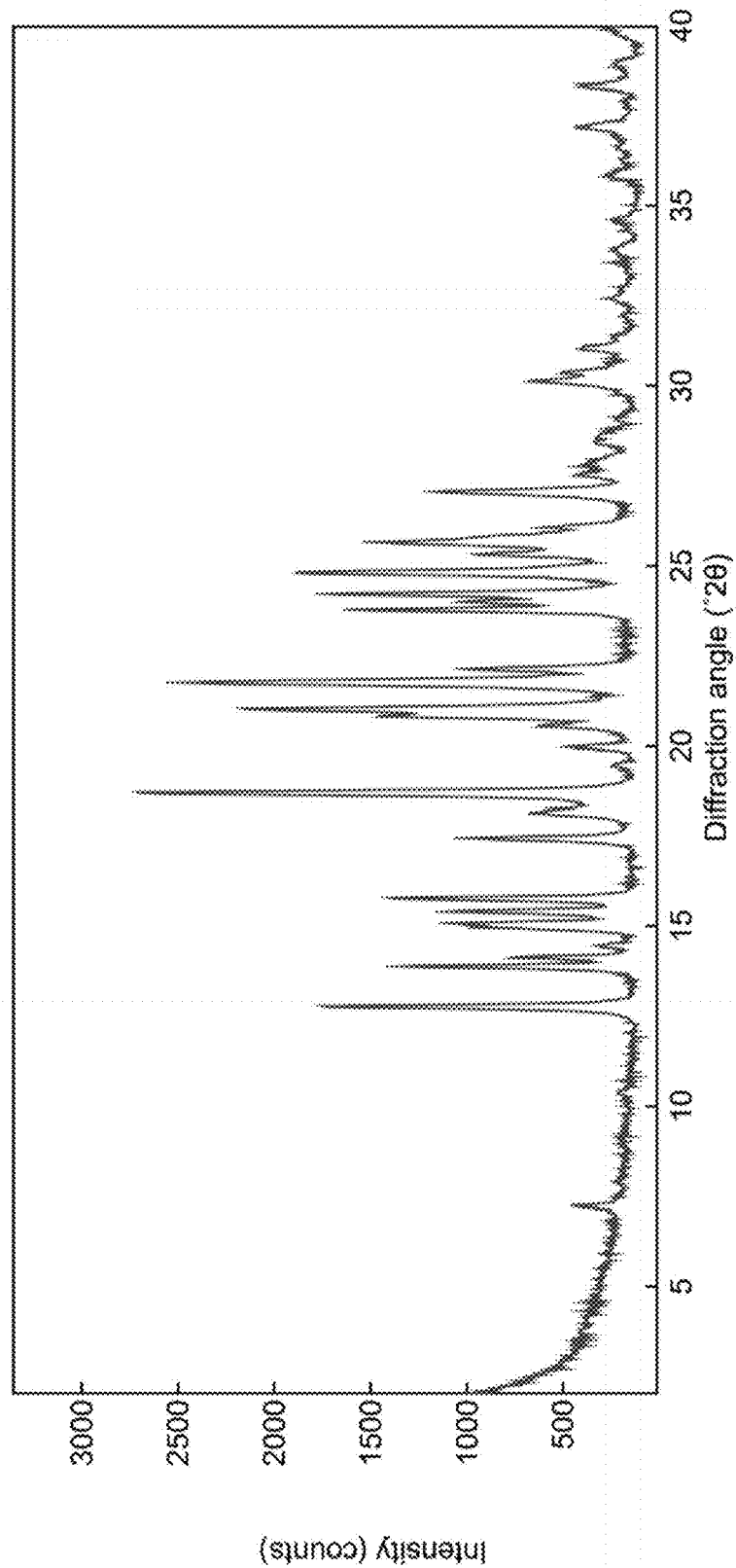
FIG. 52 provides an XRPD diffractogram of O-acetyl psilocin·succinate.
Figure 53:
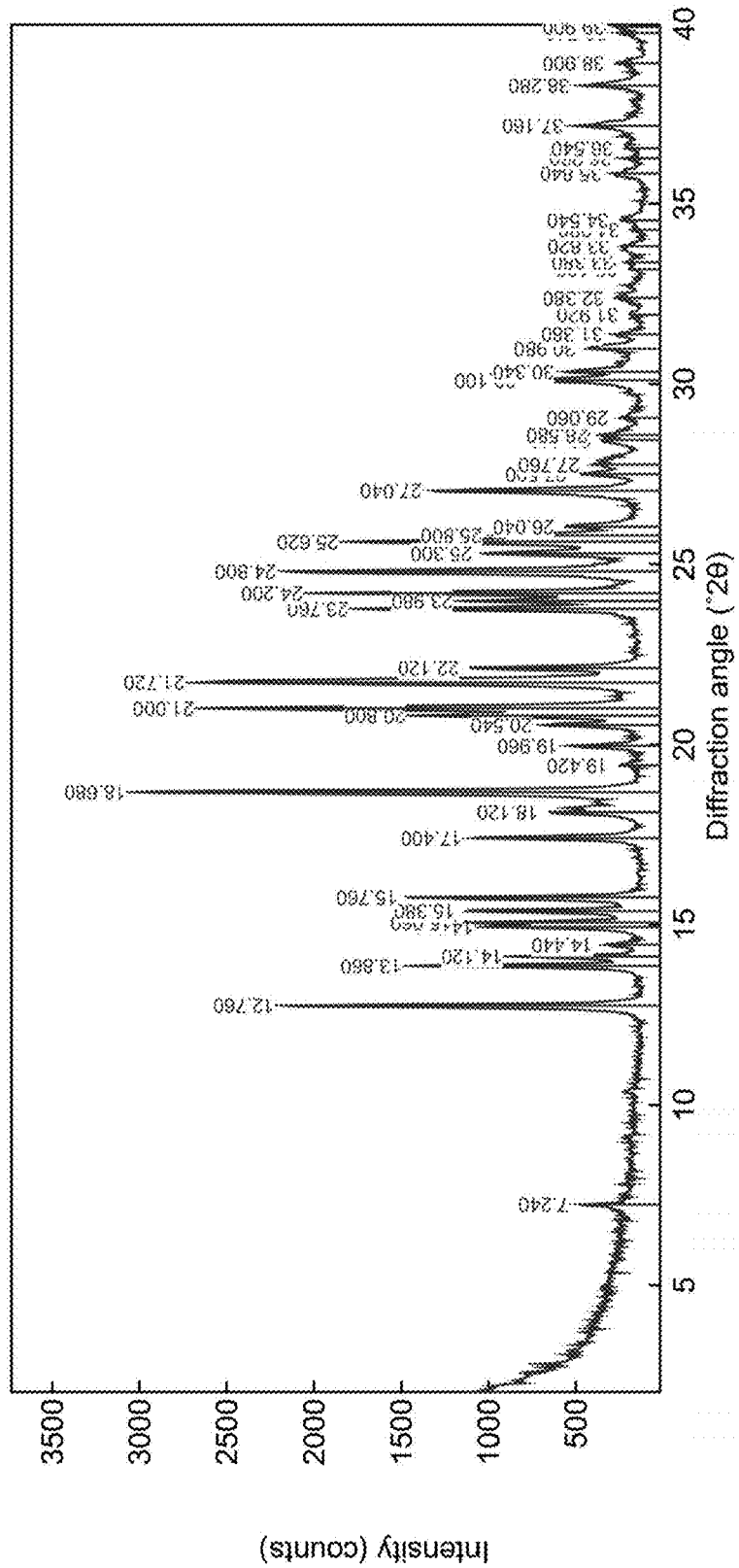
FIG. 53 provides an XRPD diffractogram of O-acetyl psilocin·succinate.
Figure 54:
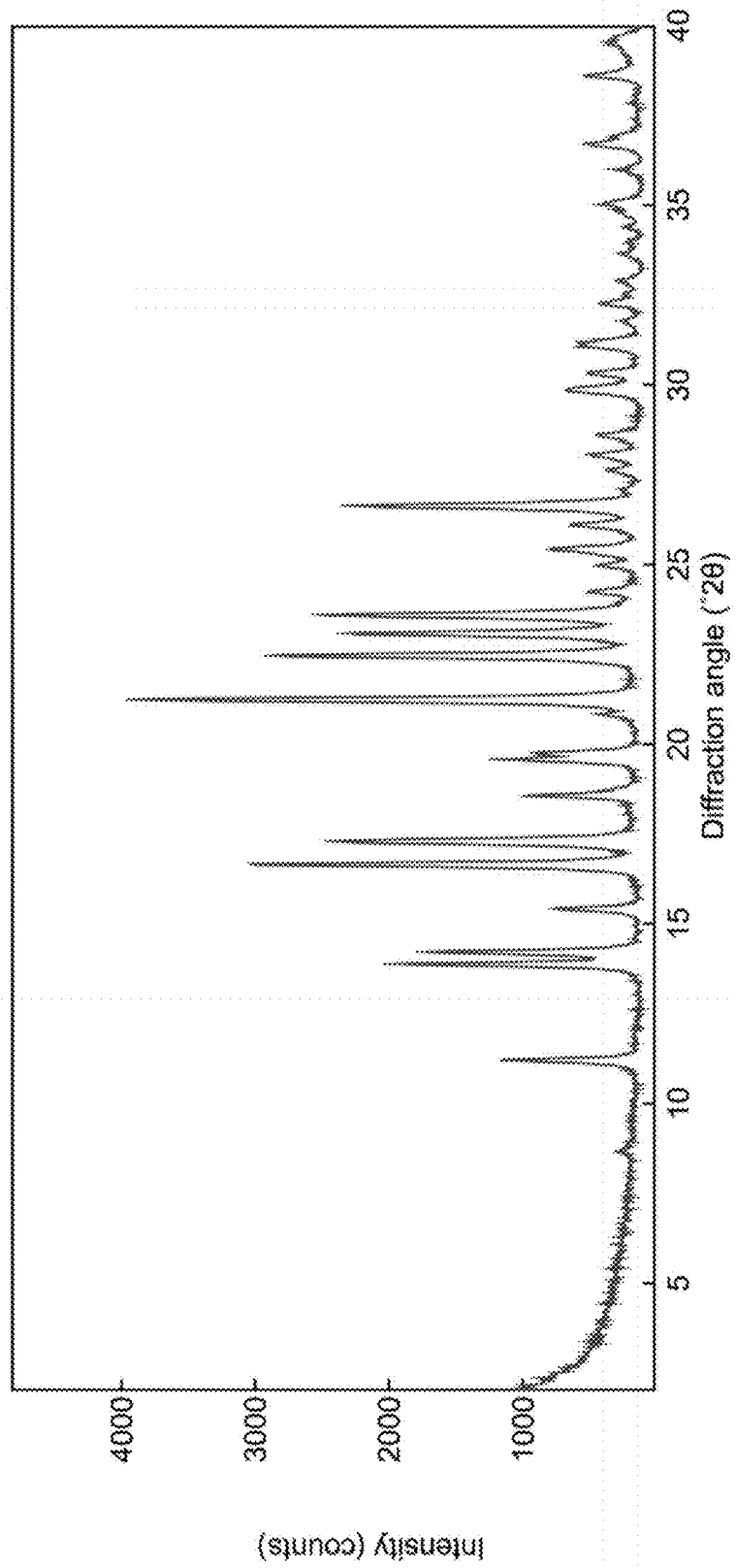
FIG. 54 provides an XRPD diffractogram of O-acetyl psilocin·tartrate Form A.
Figure 55:
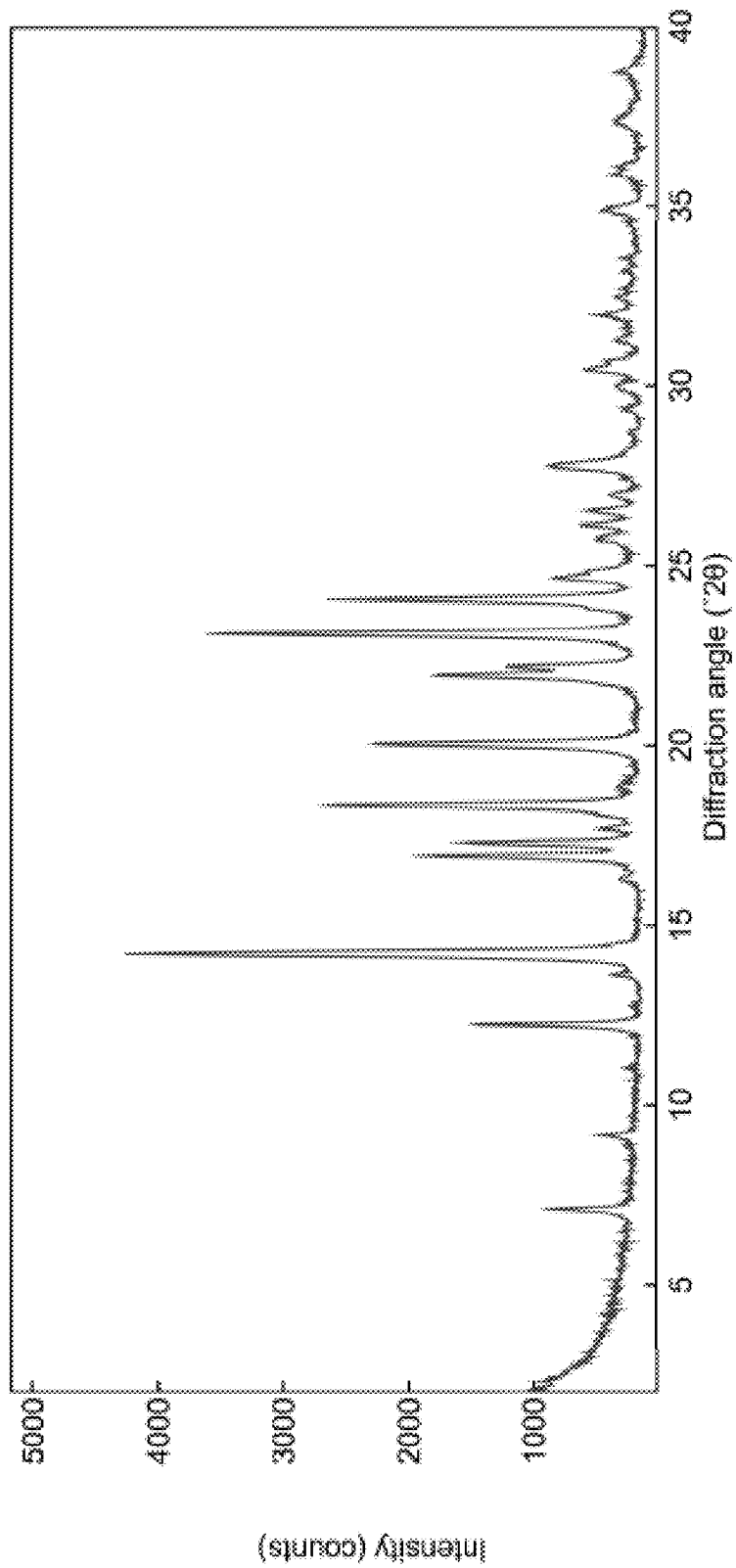
FIG. 55 provides an XRPD diffractogram of O-acetyl psilocin·tartrate Form B.
Figure 56:
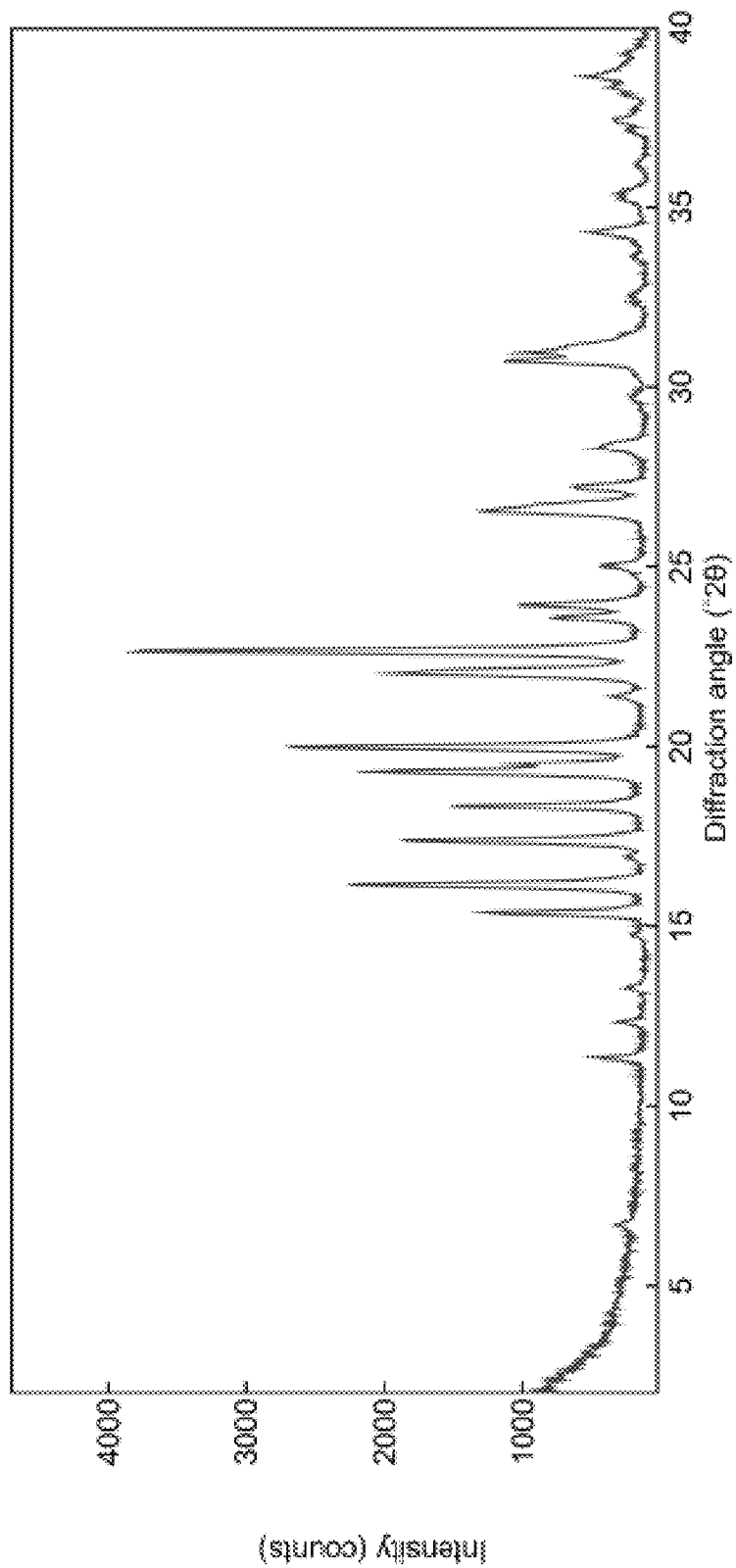
FIG. 56 provides an XRPD diffractogram of O-acetyl psilocin·tartrate Form C.
Figure 57:
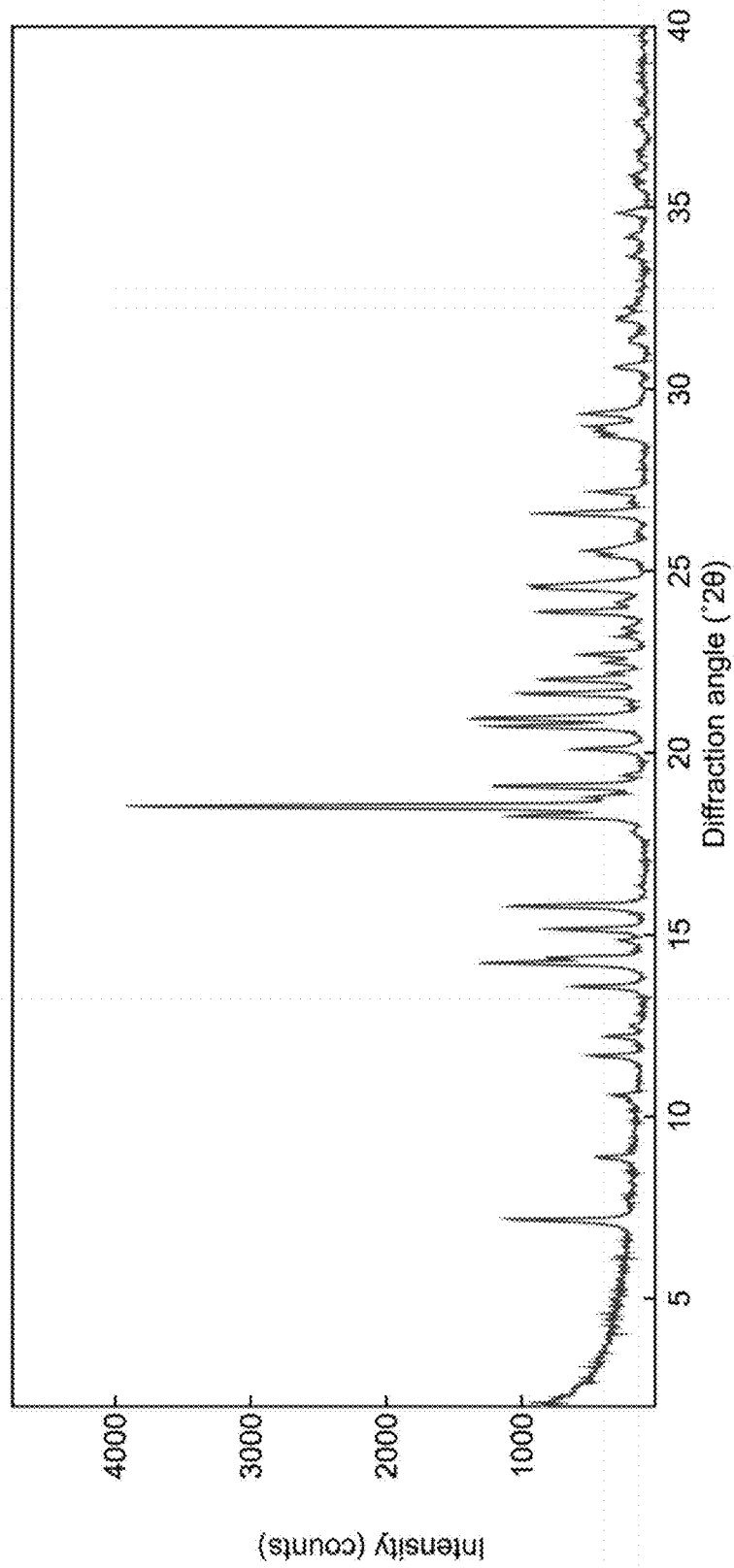
FIG. 57 provides an XRPD diffractogram of O-acetyl psilocin·tosylate.
Figure 58:
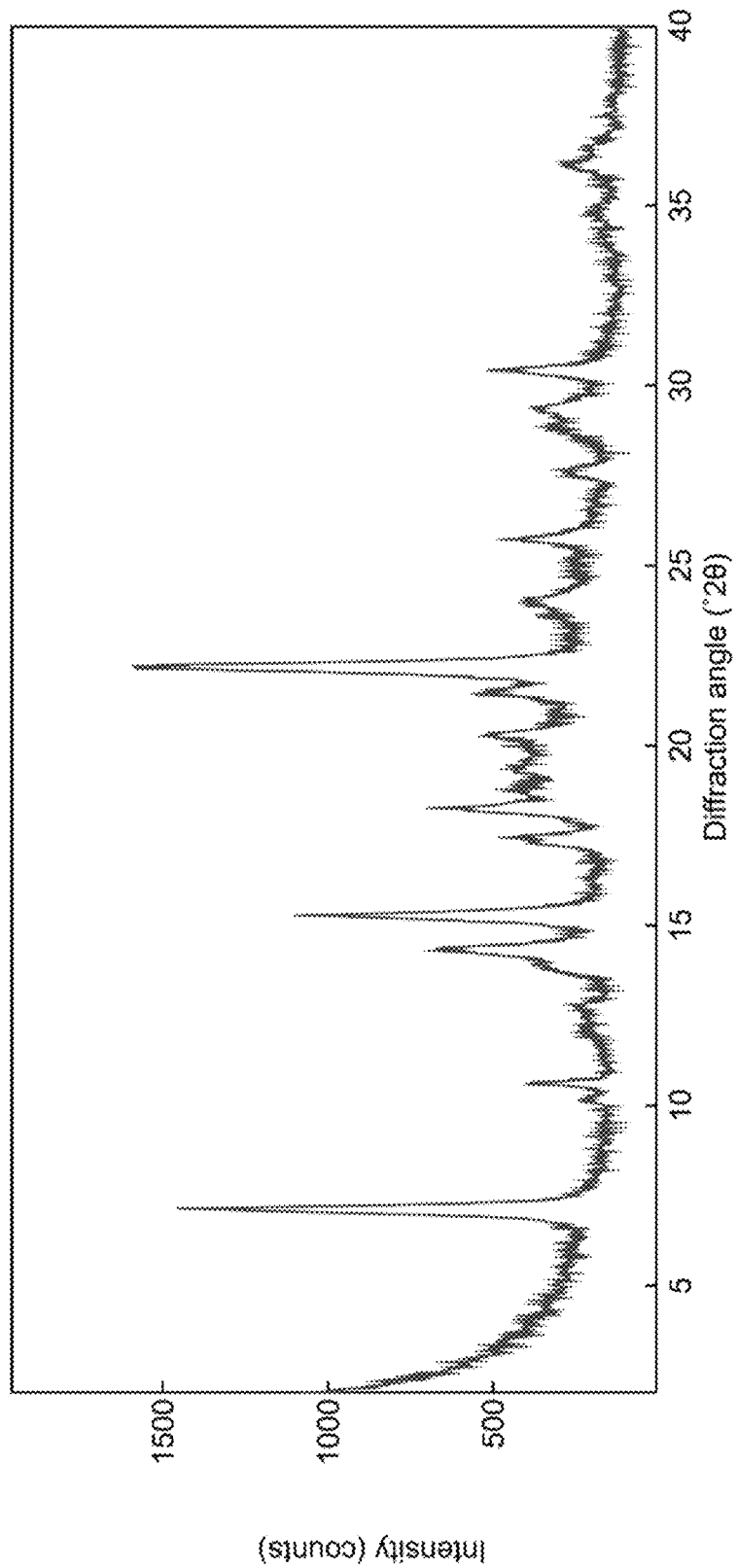
FIG. 58 provides an XRPD diffractogram of O-acetyl psilocin·citrate.
Figure 59:
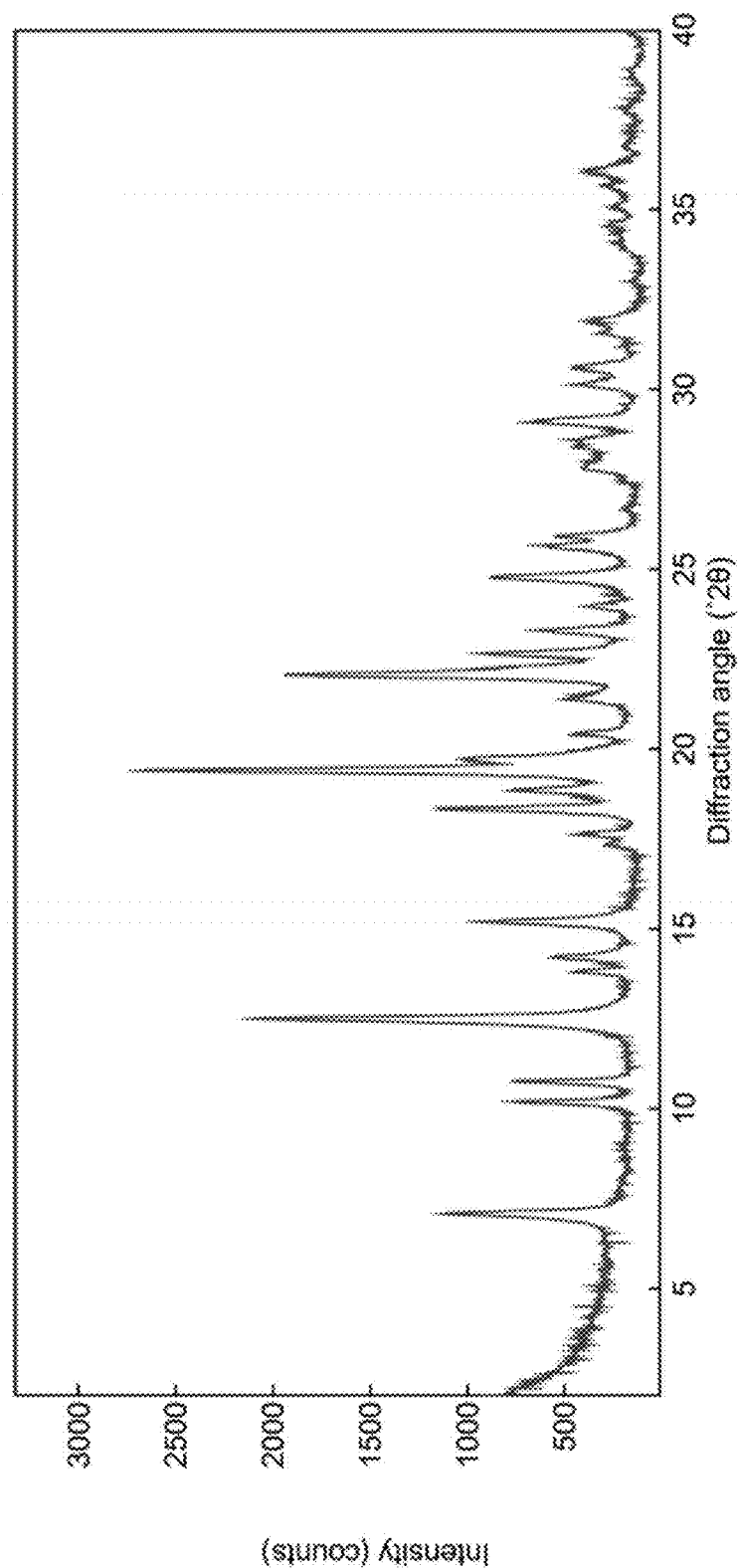
FIG. 59 provides an XRPD diffractogram of O-acetyl psilocin·citrate.
Figure 60:
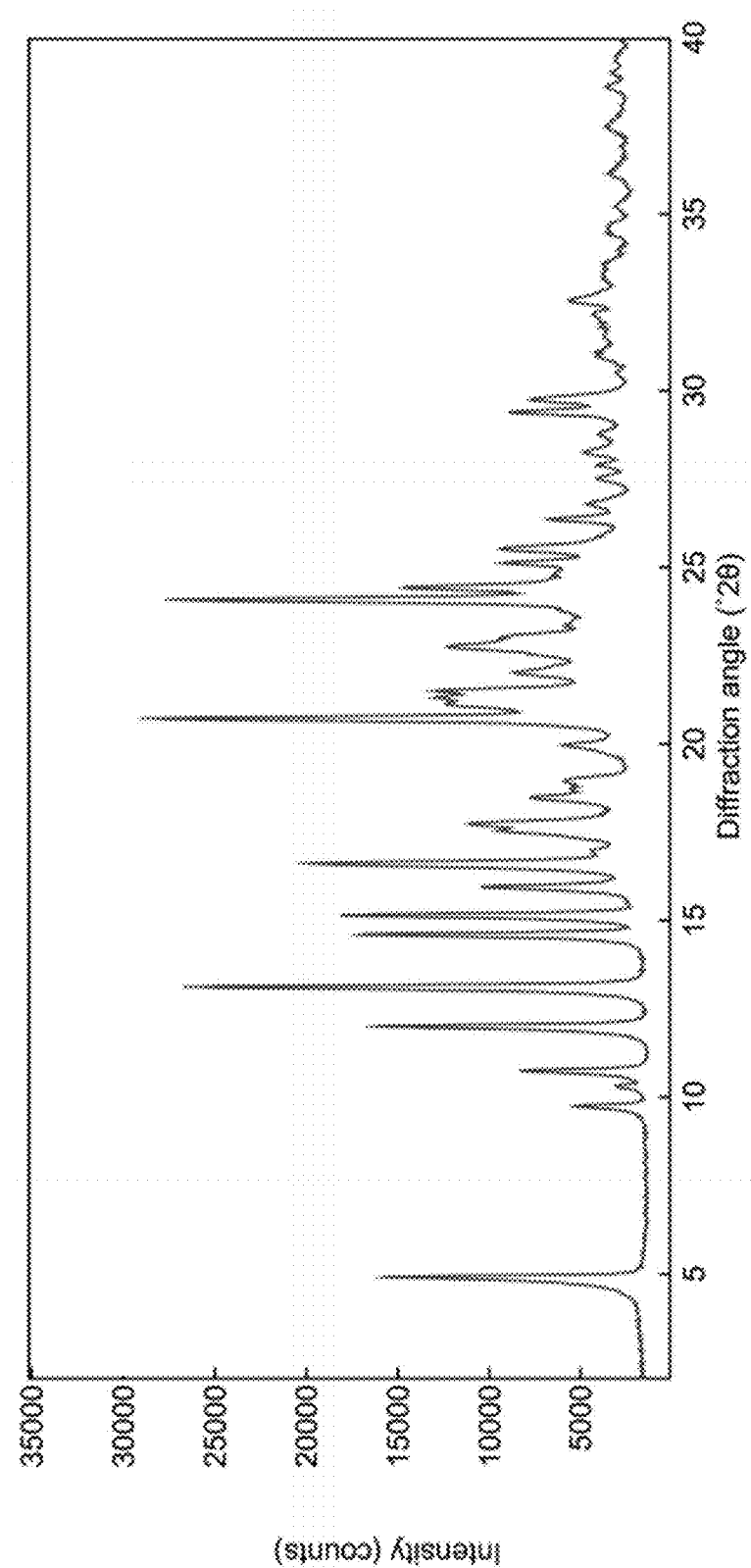
FIG. 60 provides an XRPD diffractogram of O-acetyl psilocin·mucate.

| Salt formed | Conditions | $^1$H NMR consistent with salt form | XRPD |
|---|---|---|---|
| Glycolate | SL, EtOAc, RT | Yes | FIG. 39 |
| Hydrochloride | P, acetone, RT to 15° C. | | FIG. 40 |
| Hydrochloride | ½ eq HCl, acetone, stir RT to 15° C.; clear solution; added ½ eq HCl; cloudy soln, stir −15° C./3 d | Yes | FIG. 41 |
| L-malate (Form A) | FE, ACN: single crystals present | Yes | FIG. 42 |
| L-malate B (Form B) | P, acetone, RT | Yes | FIG. 43 |
| Maleate (Form A) | FE, acetone; oil. Added IPA | Yes | FIG. 44 |
| Malonate | P, acetone, RT to 15° C. | Yes | FIG. 45 |
| Mesylate | SL, EtOAc, RT | Yes | FIG. 46 |
| Mesylate | P, MtBE, RT: tacky solids | Yes | FIG. 47 |
| Phosphate (Form A) | SL, EtOAc, RT | Yes | FIG. 48 |
| Phosphate (Form A) | SL, 2-Me-THF, RT (½ eq acid) | Yes | FIG. 49 |
| Phosphate (Form A) | P, MtBE, RT: tacky solids | Yes | FIG. 50 |
| Phosphate (Forms A and B) | P, 2-MeTHF, RT: some tacky residue present; stir −15° C./2 hours to RT/ON, vac dried RT/2 days | | FIG. 51 |
| Succinate | SL, 2-MeTHF, RT | Yes | FIG. 52 |
| Succinate | P, acetone, RT | Yes | FIG. 53 |
| L-tartrate (Form A) | SL, IPA, RT | Yes | FIG. 54 |
| L-tartrate (Form B) | P, acetone, RT to 2° C. | Yes | FIG. 55 |
| L-tartrate (Form C) | P, acetone, RT to 2° C./ON | | FIG. 56 |
| p-tosylate | P, acetone, RT to 2° C. | Yes | FIG. 57 |
| Citrate | P, acetone, RT to 2° C. | — | FIG. 58 |
| Citrate | SL, EtOAc, RT → −15° C. | Yes | FIG. 59 |
| Mucate | Grind, water, 30 min (½ eq acid) | Yes (2:1 O-Acetyl Psilocin:acid) | FIG. 60 |

Table 19 Abbreviations: ACN = acetonitrile; MEK = methyl ethyl ketone; MtBE = methyl t-butyl ether; FE = fast evaporation; P = precipitation; RT = room temperature; SL = slurry XRPD analysis of O-Acetyl Psilocin Glycolate (FIG. 39) showed it to be crystalline with characteristic peaks at 8.0±0.2° 2-Theta, 10.6±0.2° 2-Theta, and 12.2±0.2° 2-Theta; optionally with further characteristic peaks at 17.1±0.2° 2-Theta and 21.3±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 8.0 | 41.0 | 17.1 | 100.0 |
| 10.6 | 17.2 | 17.2 | 60.7 |
| 12.2 | 14.8 | 17.6 | 17.0 |
| 12.4 | 9.1 | 17.9 | 12.1 |
| 14.3 | 12.3 | 18.3 | 27.3 |
| 15.1 | 27.3 | 20.2 | 14.7 |
| 15.9 | 9.5 | 20.4 | 12.1 |
| 16.3 | 30.6 | 20.5 | 11.1 |
| 21.0 | 15.1 | 27.8 | 5.7 |
| 21.3 | 74.6 | 28.2 | 12.3 |
| 21.9 | 13.8 | 28.5 | 6.6 |
| 22.7 | 20.0 | 29.4 | 10.3 |
| 23.2 | 5.5 | 29.8 | 4.2 |
| 23.9 | 83.4 | 32.0 | 13.0 |
| 24.6 | 17.5 | 33.2 | 7.8 |
| 25.0 | 41.3 | 34.7 | 5.2 |
| 25.8 | 8.0 | 35.4 | 9.0 |
| 26.2 | 5.5 | 36.1 | 6.2 |
| 26.5 | 7.7 | 36.4 | 6.2 |
| 27.0 | 15.2 | 37.1 | 9.8 |

XRPD analysis of O-Acetyl Psilocin Hydrochloride (FIG. 40) showed it to be crystalline with characteristic peaks at 11.5±0.2° 2-Theta, 11.7±0.2° 2-Theta, and 14.0±0.2° 2-Theta; optionally with further characteristic peaks at 16.2±0.2° 2-Theta and 17.3±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 11.5 | 17.4 | 25.9 | 29.3 |
| 11.7 | 26.5 | 26.1 | 21.6 |
| 13.1 | 11.4 | 26.3 | 21.0 |
| 14.0 | 51.3 | 26.4 | 24.8 |
| 15.3 | 8.4 | 26.7 | 54.4 |
| 15.5 | 13.7 | 27.7 | 15.5 |
| 16.2 | 23.6 | 28.2 | 20.2 |
| 16.4 | 15.7 | 28.5 | 9.9 |
| 17.3 | 69.1 | 28.8 | 14.5 |
| 17.5 | 13.9 | 29.3 | 12.4 |
| 18.4 | 9.4 | 29.5 | 30.0 |
| 19.2 | 11.6 | 30.2 | 7.3 |
| 19.4 | 39.3 | 31.0 | 16.6 |
| 20.1 | 100.0 | 31.5 | 6.3 |
| 20.9 | 12.2 | 31.7 | 7.2 |
| 21.3 | 18.1 | 32.1 | 11.0 |
| 21.6 | 21.0 | 32.6 | 7.0 |
| 21.7 | 46.0 | 33.0 | 18.4 |
| 22.3 | 98.7 | 33.7 | 7.0 |
| 23.0 | 10.3 | 33.8 | 7.6 |
| 23.3 | 52.3 | 34.9 | 7.0 |
| 23.9 | 13.5 | 35.7 | 9.1 |
| 24.1 | 11.3 | 38.4 | 6.8 |
| 24.3 | 8.7 | 38.6 | 6.9 |
| 25.6 | 17.7 | 39.1 | 8.9 |
| 39.2 | 9.7 | 39.7 | 7.0 |

XRPD analysis of O-Acetyl Psilocin Hydrochloride (FIG. 41) showed it to be crystalline with characteristic peaks at 11.4±0.2° 2-Theta, 11.6±0.2° 2-Theta, and 14.0±0.2° 2-Theta; optionally with further characteristic peaks at 16.1±0.2° 2-Theta and 17.2±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 11.4 | 12.4 | 26.4 | 28.1 |
| 11.6 | 13.3 | 26.6 | 34.5 |
| 13.0 | 10.1 | 27.7 | 16.3 |
| 14.0 | 45.1 | 28.1 | 20.7 |
| 15.4 | 10.2 | 28.5 | 8.0 |
| 16.1 | 29.7 | 28.8 | 16.8 |
| 16.4 | 17.6 | 29.5 | 29.2 |
| 17.2 | 52.3 | 30.1 | 7.5 |
| 18.4 | 10.1 | 30.9 | 11.9 |
| 19.1 | 16.2 | 31.4 | 6.3 |
| 19.3 | 29.8 | 31.7 | 7.3 |
| 20.0 | 61.6 | 32.0 | 10.7 |
| 20.8 | 12.9 | 32.6 | 6.5 |
| 21.3 | 18.4 | 32.6 | 6.5 |
| 21.6 | 34.3 | 33.0 | 16.8 |
| 22.2 | 100.0 | 33.6 | 7.8 |
| 22.9 | 10.5 | 33.8 | 7.3 |
| 23.3 | 29.8 | 34.9 | 5.4 |
| 23.8 | 13.3 | 35.6 | 8.2 |
| 24.1 | 9.4 | 36.2 | 5.0 |
| 24.3 | 8.4 | 38.4 | 6.4 |
| 25.5 | 20.4 | 39.2 | 7.1 |
| 25.8 | 26.0 | 39.8 | 6.0 |
| 26.2 | 22.0 | | |

XRPD analysis of O-Acetyl Psilocin Malate Form A (FIG. 42) showed it to be crystalline with characteristic peaks at 7.3±0.2° 2-Theta, 12.5±0.2° 2-Theta, and 15.7±±0.2° 2-Theta; optionally with further characteristic peaks at 17.1±0.2° 2-Theta and 17.7±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.3 | 19.5 | 14.1 | 5.3 |
| 12.5 | 60.4 | 14.7 | 6.0 |
| 13.8 | 9.9 | 14.9 | 5.4 |
| 15.7 | 35.1 | 31.4 | 7.5 |
| 17.1 | 22.9 | 31.7 | 9.0 |
| 17.7 | 32.7 | 32.5 | 4.1 |
| 18.2 | 6.6 | 32.9 | 9.3 |
| 18.5 | 15.4 | 33.4 | 3.2 |
| 18.8 | 35.7 | 33.9 | 3.3 |
| 20.0 | 6.3 | 34.7 | 3.3 |
| 20.4 | 100.0 | 35.1 | 3.2 |
| 20.9 | 21.7 | 35.8 | 3.3 |
| 21.3 | 10.0 | 36.3 | 4.4 |
| 22.1 | 43.3 | 36.8 | 8.5 |
| 23.6 | 9.7 | 37.2 | 4.9 |
| 24.0 | 22.1 | 37.9 | 3.5 |
| 25.2 | 39.3 | 38.2 | 2.8 |
| 26.3 | 14.3 | 38.7 | 3.7 |
| 26.7 | 15.4 | 39.1 | 2.7 |
| 28.1 | 5.2 | 39.5 | 3.2 |
| 29.6 | 6.2 | | |

XRPD analysis of O-Acetyl Psilocin Malate Form B (FIG. 43) showed it to be crystalline with characteristic peaks at 11.4±0.2° 2-Theta, 12.3±0.2° 2-Theta, and 15.3±0.2° 2-Theta; optionally with further characteristic peaks at 16.6±0.2° 2-Theta and 19.4±0.2° 2-Theta, as measured with Cu Kα radiation. A full list of peaks is found in the following table. The 2-Theta peak values that are provided for the XRPD are within ±0.2° 0.2-Theta.

| Angle 2-Theta (°) | Rel. Intensity (%) | Angle 2-Theta (°) | Rel. Intensity (%) |
|---|---|---|---|
| 8.3 | 6.3 | 24.2 | 13.5 |
| 11.4 | 13.6 | 24.6 | 10.1 |
| 12.3 | 26.8 | 25.4 | 23.3 |
| 14.6 | 6.3 | 25.7 | 17.6 |
| 15.3 | 49.0 | 26.4 | 6.9 |
| 16.0 | 4.7 | 26.7 | 7.4 |
| 16.6 | 30.0 | 27.3 | 9.9 |
| 17.8 | 10.5 | 27.5 | 6.8 |
| 18.1 | 26.1 | 27.7 | 9.9 |
| 18.4 | 12.3 | 28.2 | 4.5 |
| 19.4 | 26.1 | 29.0 | 8.6 |
| 21.0 | 49.8 | 29.4 | 4.7 |
| 21.3 | 100.0 | 30.0 | 11.6 |
| 21.8 | 42.8 | 30.7 | 8.5 |
| 22.5 | 6.6 | 31.2 | 8.2 |
| 22.9 | 35.2 | 32.3 | 10.8 |
| 23.2 | 36.0 | 33.1 | 3.6 |
| 23.8 | 21.0 | 35.2 | 4.8 |
| 36.2 | 5.3 | 37.9 | 4.0 |
| 37.2 | 6.1 | 38.6 | 8.4 |

XRPD analysis of O-Acetyl Psilocin Maleate Form A (FIG. 44) showed it to be crystalline with characteristic peaks at 12.9±0.2° 2-Theta, 14.8±0.2° 2-Theta, and 17.3±0.2° 2-Theta; optionally with further characteristic peaks at 9.1±0.2° 2-Theta and 26.0±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 9.1 | 6.7 | 23.8 | 6.7 |
| 12.9 | 100.0 | 24.0 | 14.7 |
| 14.8 | 13.7 | 24.5 | 6.7 |
| 15.0 | 10.2 | 25.6 | 4.9 |
| 16.3 | 5.1 | 26.0 | 34.5 |
| 16.4 | 11.0 | 26.6 | 19.3 |
| 17.3 | 12.5 | 27.6 | 2.8 |
| 18.1 | 10.2 | 27.8 | 2.8 |
| 18.5 | 4.5 | 28.3 | 4.2 |
| 20.5 | 2.0 | 29.6 | 14.6 |
| 20.8 | 4.5 | 30.2 | 5.0 |
| 21.3 | 3.5 | 30.6 | 3.8 |
| 21.8 | 6.6 | 31.2 | 4.6 |
| 22.1 | 15.5 | 32.1 | 2.4 |
| 23.1 | 19.6 | 34.8 | 4.9 |
| 23.4 | 19.9 | 37.1 | 3.8 |

XRPD analysis of O-Acetyl Psilocin Malonate (FIG. 45) showed it to be crystalline with characteristic peaks at 11.7±0.2° 2-Theta, 14.4±0.2° 2-Theta, and 16.1±0.2° 2-Theta; optionally with further characteristic peaks at 19.2±0.2° 2-Theta and 22.1±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.9 | 7.2 | 17.8 | 17.5 |
| 9.5 | 7.5 | 18.1 | 15.3 |
| 11.7 | 41.6 | 19.2 | 59.1 |
| 13.5 | 9.7 | 20.3 | 10.0 |
| 14.4 | 15.9 | 20.9 | 44.7 |
| 14.7 | 8.9 | 21.1 | 72.0 |
| 15.9 | 36.4 | 21.7 | 29.2 |
| 16.1 | 100.0 | 22.1 | 65.2 |
| 16.9 | 10.0 | 22.6 | 34.9 |
| 17.3 | 12.3 | 23.9 | 53.3 |
| 24.5 | 10.0 | 32.0 | 4.5 |
| 24.8 | 9.5 | 32.4 | 5.3 |
| 25.0 | 13.1 | 33.0 | 8.5 |
| 25.5 | 24.4 | 33.4 | 10.8 |
| 25.8 | 5.6 | 34.6 | 5.9 |
| 26.5 | 8.3 | 35.6 | 6.7 |
| 26.8 | 13.7 | 36.0 | 8.0 |
| 27.3 | 25.7 | 36.4 | 6.3 |
| 28.6 | 8.1 | 37.2 | 5.3 |
| 28.8 | 10.3 | 37.3 | 5.5 |
| 29.1 | 13.3 | 37.8 | 4.7 |
| 29.3 | 8.6 | 38.1 | 4.6 |
| 29.5 | 10.1 | 38.7 | 5.9 |
| 30.0 | 14.6 | 39.0 | 5.3 |
| 30.6 | 12.9 | 39.3 | 4.2 |
| 31.4 | 17.9 | | |

XRPD analysis of O-Acetyl Psilocin Mesylate (FIG. 46) showed it to be crystalline with characteristic peaks at 16.8±0.2° 2-Theta, 17.5±0.2° 2-Theta, and 20.5±0.2° 2-Theta; optionally with further characteristic peaks at 22.8±0.2° 2-Theta and 23.3±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 9.7 | 8.3 | 24.8 | 6.3 |
| 10.2 | 3.9 | 25.5 | 14.2 |
| 11.3 | 7.2 | 26.6 | 29.0 |
| 12.8 | 7.0 | 28.0 | 7.9 |
| 13.0 | 6.5 | 28.2 | 7.2 |
| 15.1 | 4.4 | 28.8 | 6.5 |
| 16.8 | 46.8 | 29.4 | 6.7 |
| 17.5 | 100.0 | 29.7 | 6.1 |
| 18.2 | 8.2 | 30.6 | 3.3 |
| 18.4 | 9.8 | 30.9 | 2.7 |
| 19.4 | 4.6 | 31.9 | 4.0 |
| 19.7 | 6.7 | 32.1 | 3.0 |
| 20.5 | 27.2 | 32.4 | 4.1 |
| 21.2 | 5.1 | 33.9 | 2.6 |
| 22.2 | 3.6 | 34.8 | 4.0 |
| 22.7 | 28.3 | 35.2 | 5.0 |
| 22.8 | 45.7 | 36.4 | 2.6 |
| 23.3 | 57.0 | 36.9 | 2.7 |
| 23.8 | 19.4 | 37.2 | 4.3 |
| 24.0 | 11.9 | 37.7 | 3.3 |
| 38.1 | 2.5 | 39.9 | 3.5 |
| 39.4 | 3.2 | | |

XRPD analysis of O-Acetyl Psilocin Mesylate (FIG. 47) showed it to be crystalline with characteristic peaks at 16.8±0.2° 2-Theta, 17.5±0.2° 2-Theta, and 20.5±0.2° 2-Theta; optionally with further characteristic peaks at 22.8±0.2° 2-Theta and 23.3±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 9.7 | 9.5 | 25.5 | 15.2 |
| 10.2 | 5.0 | 26.1 | 5.1 |

-continued

| Angle 2-Theta (°) | Rel. Intensity (%) | Angle 2-Theta (°) | Rel. Intensity (%) |
|---|---|---|---|
| 11.3 | 8.0 | 26.6 | 29.3 |
| 12.8 | 8.6 | 27.1 | 4.7 |
| 12.9 | 6.4 | 28.0 | 7.9 |
| 15.1 | 5.6 | 28.2 | 8.2 |
| 16.8 | 51.5 | 28.8 | 7.8 |
| 17.5 | 100.0 | 29.4 | 7.5 |
| 18.2 | 10.6 | 29.7 | 7.4 |
| 18.4 | 11.1 | 30.6 | 4.2 |
| 19.4 | 7.3 | 30.9 | 3.8 |
| 19.7 | 9.6 | 31.8 | 5.1 |
| 20.5 | 26.9 | 32.4 | 5.1 |
| 21.2 | 7.5 | 34.8 | 4.9 |
| 22.7 | 31.2 | 35.1 | 6.3 |
| 22.8 | 48.4 | 36.4 | 3.8 |
| 23.3 | 56.3 | 36.8 | 3.8 |
| 23.8 | 20.8 | 37.2 | 5.3 |
| 24.0 | 14.2 | 37.7 | 4.4 |
| 24.8 | 7.7 | 39.4 | 3.7 |

XRPD analysis of O-Acetyl Psilocin Phosphate Form A (FIG. 48) showed it to be crystalline with characteristic peaks at 4.9±0.2° 2-Theta, 13.3±0.2° 2-Theta, and 14.7±0.2° 2-Theta; optionally with further characteristic peaks at 15.7±0.2° 2-Theta and 16.6±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 4.9 | 100.0 | 17.2 | 13.0 |
| 13.3 | 26.6 | 18.1 | 24.2 |
| 13.7 | 6.8 | 18.8 | 72.0 |
| 14.7 | 30.0 | 19.6 | 25.1 |
| 15.7 | 54.3 | 20.6 | 45.3 |
| 16.6 | 38.7 | 20.8 | 45.2 |
| 21.3 | 20.5 | 27.5 | 21.4 |
| 22.2 | 26.9 | 29.4 | 12.8 |
| 22.6 | 37.9 | 32.3 | 5.8 |
| 23.1 | 28.8 | 32.9 | 5.4 |
| 23.7 | 31.4 | 33.4 | 9.1 |
| 23.9 | 31.2 | 34.7 | 8.4 |
| 24.6 | 52.2 | 35.3 | 5.4 |
| 24.9 | 21.3 | 36.3 | 8.1 |
| 25.9 | 16.1 | 37.1 | 4.8 |
| 26.9 | 22.7 | 39.6 | 5.5 |
| 27.2 | 25.0 | | |

XRPD analysis of O-Acetyl Psilocin Phosphate Form A (FIG. 49) showed it to be crystalline with characteristic peaks at 4.9±0.2° 2-Theta and 13.3±0.2° 2-Theta; optionally with further characteristic peaks at 14.7±0.2° 2-Theta and 16.6±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 4.9 | 100.0 | 23.1 | 30.1 |
| 13.3 | 24.7 | 23.7 | 34.8 |
| 13.7 | 8.7 | 23.9 | 35.0 |
| 14.7 | 39.2 | 24.6 | 77.7 |
| 15.7 | 47.3 | 24.9 | 24.0 |
| 16.6 | 36.7 | 25.9 | 18.2 |
| 17.2 | 14.3 | 26.9 | 24.7 |
| 18.0 | 25.0 | 27.1 | 25.6 |
| 18.8 | 69.2 | 27.5 | 23.8 |
| 19.6 | 24.3 | 29.3 | 15.3 |
| 20.6 | 46.7 | 32.3 | 7.8 |
| 20.8 | 45.4 | 33.4 | 11.5 |
| 21.2 | 22.2 | 34.7 | 10.9 |
| 22.2 | 34.0 | 36.3 | 9.9 |
| 22.6 | 42.1 | 39.7 | 7.6 |

XRPD analysis of O-Acetyl Psilocin Phosphate Form A (FIG. 50) showed it to be crystalline with characteristic peaks at 4.9±0.2° 2-Theta, 13.3±0.2° 2-Theta, and 14.7±0.2° 2-Theta; optionally with further characteristic peaks at 15.7±0.2° 2-Theta and 16.6±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 4.9 | 100.0 | 23.1 | 51.5 |
| 13.3 | 43.8 | 23.8 | 44.7 |
| 13.7 | 16.6 | 23.9 | 43.4 |
| 14.7 | 34.2 | 24.5 | 48.1 |
| 15.7 | 71.3 | 24.9 | 35.4 |
| 16.6 | 57.9 | 25.9 | 26.6 |
| 17.2 | 24.7 | 26.9 | 32.9 |
| 18.0 | 41.3 | 27.1 | 39.4 |
| 18.8 | 84.8 | 27.5 | 32.8 |
| 19.6 | 42.3 | 29.3 | 20.4 |
| 20.6 | 59.1 | 33.5 | 14.5 |
| 20.8 | 68.1 | 34.6 | 13.9 |
| 21.3 | 38.7 | 36.3 | 10.9 |
| 22.2 | 37.7 | 39.7 | 10.1 |
| 22.6 | 48.3 | | |

XRPD analysis of a mixture of O-acetyl psilocin phosphate Forms A and B (FIG. 51) showed it to be crystalline with characteristic peaks at 5.0±0.2° 2-Theta, 11.9±0.2° 2-Theta, and 13.3±0.2° 2-Theta; optionally with further characteristic peaks at 14.9±0.2° 2-Theta and 15.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 5.0 | 100.0 | 22.3 | 23.3 |
| 11.9 | 31.8 | 22.5 | 51.5 |
| 13.3 | 32.9 | 22.7 | 36.8 |
| 13.7 | 8.2 | 22.8 | 34.1 |
| 14.6 | 22.5 | 23.2 | 32.3 |
| 14.9 | 45.2 | 23.4 | 31.0 |
| 15.8 | 52.7 | 23.8 | 36.6 |
| 16.7 | 44.7 | 24.0 | 30.8 |
| 16.9 | 14.6 | 24.6 | 33.8 |
| 17.1 | 11.7 | 24.9 | 21.6 |
| 17.3 | 10.6 | 26.0 | 17.5 |
| 17.6 | 8.5 | 26.2 | 21.4 |
| 18.1 | 24.7 | 26.7 | 14.1 |
| 18.4 | 19.8 | 26.9 | 21.5 |
| 18.6 | 28.9 | 27.2 | 27.7 |
| 18.9 | 61.4 | 27.6 | 22.8 |
| 19.6 | 27.8 | 28.6 | 8.8 |
| 20.5 | 20.6 | 29.4 | 16.0 |

| Angle 2-Theta (°) | Rel. Intensity (%) | Angle 2-Theta (°) | Rel. Intensity (%) |
|---|---|---|---|
| 20.7 | 38.2 | 29.8 | 7.5 |
| 20.9 | 43.9 | 30.0 | 6.3 |
| 21.3 | 22.8 | 32.4 | 7.3 |
| 33.2 | 10.7 | 36.3 | 8.0 |
| 33.4 | 12.3 | 37.4 | 7.5 |
| 34.2 | 10.1 | 38.1 | 6.4 |
| 34.7 | 11.3 | 39.7 | 5.9 |
| 35.6 | 7.0 | | |

XRPD analysis of O-Acetyl Psilocin Succinate (FIG. 52) showed it to be crystalline with characteristic peaks at 7.3±0.2° 2-Theta, 12.8±0.2° 2-Theta, and 13.9±0.2° 2-Theta; optionally with further characteristic peaks at 15.4±0.2° 2-Theta and 15.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.3 | 16.6 | 25.7 | 54.6 |
| 12.8 | 64.3 | 25.8 | 35.1 |
| 13.9 | 49.9 | 26.1 | 22.2 |
| 14.1 | 28.0 | 27.1 | 42.9 |
| 14.5 | 11.8 | 27.5 | 16.2 |
| 15.0 | 32.9 | 27.8 | 15.2 |
| 15.1 | 40.0 | 28.4 | 12.4 |
| 15.4 | 40.8 | 29.1 | 8.4 |
| 15.8 | 51.5 | 30.1 | 25.1 |
| 17.4 | 37.0 | 30.3 | 18.8 |
| 18.1 | 24.9 | 31.0 | 15.3 |
| 18.7 | 100.0 | 31.9 | 7.3 |
| 19.4 | 9.1 | 32.4 | 10.1 |
| 20.0 | 17.7 | 33.4 | 8.9 |
| 20.5 | 22.8 | 33.7 | 8.9 |
| 20.8 | 53.8 | 34.3 | 7.3 |
| 21.0 | 79.6 | 34.6 | 8.9 |
| 21.8 | 92.2 | 35.8 | 10.3 |
| 22.1 | 37.3 | 36.3 | 7.5 |
| 23.8 | 58.3 | 36.6 | 7.5 |
| 24.0 | 37.8 | 37.2 | 16.0 |
| 24.2 | 63.7 | 38.3 | 15.1 |
| 24.8 | 69.7 | 38.9 | 8.8 |
| 25.3 | 35.2 | | |

XRPD analysis of O-Acetyl Psilocin Succinate (FIG. 53) showed it to be crystalline with characteristic peaks at 7.2±0.2° 2-Theta, 12.8±0.2° 2-Theta, and 13.9±0.2° 2-Theta; optionally with further characteristic peaks at 15.4±0.2° 2-Theta and 15.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.2 | 15.7 | 26.0 | 18.4 |
| 12.8 | 71.7 | 27.0 | 43.7 |
| 13.9 | 47.4 | 27.5 | 16.1 |
| 14.1 | 28.2 | 27.8 | 13.6 |
| 14.4 | 11.1 | 28.4 | 11.5 |
| 14.9 | 33.7 | 28.6 | 12.1 |
| 15.1 | 37.9 | 29.1 | 8.2 |
| 15.4 | 37.3 | 30.1 | 25.7 |
| 15.8 | 48.3 | 30.3 | 18.5 |
| 17.4 | 36.0 | 31.0 | 14.4 |
| 18.1 | 21.5 | 31.4 | 9.2 |
| 18.7 | 100.0 | 31.9 | 6.3 |
| 19.4 | 8.2 | 32.4 | 8.9 |
| 20.0 | 17.6 | 33.2 | 6.5 |
| 20.5 | 22.7 | 33.4 | 7.2 |
| 20.8 | 46.7 | 33.8 | 8.0 |
| 21.0 | 87.0 | 34.3 | 6.0 |
| 21.7 | 88.7 | 34.5 | 8.1 |
| 22.1 | 36.5 | 35.8 | 9.4 |
| 23.8 | 57.6 | 36.3 | 7.6 |
| 24.0 | 37.8 | 36.5 | 7.3 |
| 24.2 | 66.4 | 37.2 | 16.7 |
| 24.8 | 71.4 | 38.3 | 15.5 |
| 25.3 | 34.1 | 38.9 | 8.9 |
| 25.6 | 59.5 | 39.7 | 8.4 |
| 25.8 | 32.1 | 39.9 | 9.0 |

XRPD analysis of O-Acetyl Psilocin Tartrate Form A (FIG. 54) showed it to be crystalline with characteristic peaks at 11.2±0.2° 2-Theta, 13.9±0.2° 2-Theta, and 14.2±0.2° 2-Theta; optionally with further characteristic peaks at 15.4±0.2° 2-Theta and 16.7±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 8.7 | 7.5 | 21.2 | 100.0 |
| 11.2 | 29.8 | 22.5 | 73.6 |
| 13.9 | 50.4 | 23.1 | 59.5 |
| 14.2 | 44.2 | 23.6 | 64.4 |
| 15.4 | 19.6 | 24.2 | 13.2 |
| 16.7 | 77.8 | 25.0 | 11.3 |
| 17.3 | 61.9 | 25.4 | 20.7 |
| 18.6 | 25.0 | 26.1 | 16.4 |
| 19.6 | 29.9 | 26.6 | 58.6 |
| 19.8 | 23.3 | 27.1 | 7.1 |
| 20.8 | 11.1 | 27.6 | 9.0 |
| 28.1 | 13.0 | 34.0 | 5.7 |
| 28.6 | 11.3 | 34.4 | 6.5 |
| 29.9 | 17.4 | 34.8 | 7.5 |
| 30.3 | 13.5 | 35.0 | 11.0 |
| 31.2 | 15.0 | 36.0 | 7.6 |
| 31.8 | 6.9 | 36.7 | 13.8 |
| 32.3 | 10.9 | 36.9 | 9.0 |
| 32.9 | 7.7 | 38.6 | 13.8 |
| 33.7 | 7.1 | 39.5 | 9.4 |

XRPD analysis of O-Acetyl Psilocin Tartrate Form B (FIG. 55) showed it to be crystalline with characteristic peaks at 7.1±0.2° 2-Theta, 9.2±0.2° 2-Theta, and 12.3±0.2° 2-Theta; optionally with further characteristic peaks at 14.2±0.2° 2-Theta and 18.3±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.1 | 20.9 | 26.5 | 13.5 |
| 9.2 | 11.0 | 27.0 | 9.7 |
| 12.3 | 35.0 | 27.8 | 21.4 |
| 13.6 | 9.2 | 28.7 | 5.9 |
| 14.2 | 100.0 | 29.3 | 6.8 |
| 16.3 | 7.8 | 30.0 | 8.5 |

| Angle 2-Theta (°) | Rel. Intensity (%) | Angle 2-Theta (°) | Rel. Intensity (%) |
|---|---|---|---|
| 16.9 | 44.9 | 30.4 | 14.2 |
| 17.3 | 38.0 | 30.7 | 10.5 |
| 17.7 | 11.5 | 31.3 | 8.6 |
| 18.3 | 63.0 | 32.0 | 11.5 |
| 18.8 | 8.3 | 32.5 | 8.6 |
| 20.0 | 54.6 | 32.7 | 7.4 |
| 21.9 | 41.4 | 33.1 | 6.6 |
| 22.2 | 29.2 | 33.5 | 6.8 |
| 23.1 | 84.5 | 34.9 | 10.8 |
| 24.1 | 61.0 | 35.9 | 9.0 |
| 24.7 | 20.2 | 36.1 | 8.3 |
| 25.7 | 11.9 | 37.4 | 8.8 |
| 26.1 | 14.8 | 38.7 | 8.0 |

XRPD analysis of O-Acetyl Psilocin Tartrate Form C (FIG. 56) showed it to be crystalline with characteristic peaks at 11.4±0.2° 2-Theta, 15.4±0.2° 2-Theta, and 16.2±0.2° 2-Theta; optionally with further characteristic peaks at 17.4±0.2° 2-Theta and 18.3±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 6.7 | 8.5 | 25.0 | 11.4 |
| 11.4 | 12.1 | 26.5 | 34.2 |
| 12.3 | 8.3 | 27.2 | 16.4 |
| 13.3 | 6.6 | 28.3 | 12.7 |
| 14.8 | 5.4 | 29.8 | 5.6 |
| 15.4 | 33.6 | 30.7 | 29.1 |
| 16.2 | 58.9 | 31.0 | 26.9 |
| 16.9 | 6.5 | 32.5 | 5.9 |
| 17.4 | 48.9 | 33.6 | 5.4 |
| 18.3 | 38.9 | 34.3 | 13.8 |
| 19.3 | 55.6 | 35.4 | 8.2 |
| 19.5 | 28.5 | 36.2 | 4.7 |
| 20.0 | 70.7 | 37.1 | 6.3 |
| 21.4 | 9.3 | 37.4 | 8.7 |
| 22.0 | 52.2 | 38.3 | 10.2 |
| 22.6 | 100.0 | 38.6 | 14.3 |
| 23.6 | 20.6 | 39.2 | 7.1 |
| 23.9 | 27.0 | | |

XRPD analysis of O-Acetyl Psilocin Tosylate (FIG. 57) showed it to be crystalline with characteristic peaks at 7.2±0.2° 2-Theta, 8.9±0.2° 2-Theta, and 11.7±0.2° 2-Theta; optionally with further characteristic peaks at 14.2±0.2° 2-Theta and 15.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.2 | 28.4 | 20.9 | 35.6 |
| 8.9 | 11.8 | 21.6 | 26.4 |
| 10.6 | 8.2 | 22.0 | 22.4 |
| 11.7 | 12.6 | 22.5 | 10.1 |
| 12.2 | 10.1 | 22.7 | 14.4 |
| 12.5 | 5.3 | 23.2 | 7.6 |
| 13.6 | 15.9 | 23.4 | 6.5 |
| 14.2 | 33.3 | 23.9 | 22.7 |
| 14.9 | 7.5 | 24.1 | 7.8 |
| 15.2 | 20.6 | 24.6 | 24.4 |
| 15.8 | 28.1 | 25.6 | 13.8 |
| 17.8 | 4.9 | 26.6 | 22.3 |
| 18.3 | 27.8 | 27.2 | 12.0 |
| 18.5 | 100.0 | 28.7 | 10.4 |
| 18.8 | 13.1 | 28.8 | 11.4 |
| 19.1 | 31.6 | 29.0 | 13.2 |
| 20.1 | 15.5 | 29.3 | 14.2 |
| 20.7 | 31.8 | 30.6 | 8.3 |
| 31.3 | 5.4 | 35.9 | 5.1 |
| 31.9 | 7.9 | 36.3 | 3.8 |
| 32.2 | 6.2 | 36.5 | 4.1 |
| 33.7 | 5.4 | 37.4 | 4.3 |
| 34.2 | 5.9 | 37.8 | 3.6 |
| 34.8 | 7.5 | 38.0 | 3.7 |
| 35.6 | 4.4 | | |

XRPD analysis of O-Acetyl Psilocin Citrate (FIG. 58) showed it to be crystalline with characteristic peaks at 7.1±0.2° 2-Theta, 10.2±0.2° 2-Theta, and 10.6±0.2° 2-Theta; optionally with further characteristic peaks at 14.3±0.2° 2-Theta and 15.3±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.1 | 89.5 | 21.4 | 33.5 |
| 10.2 | 14.6 | 22.2 | 100.0 |
| 10.6 | 24.7 | 24.0 | 25.7 |
| 12.0 | 14.9 | 25.7 | 28.6 |
| 12.8 | 16.0 | 27.7 | 18.2 |
| 13.9 | 24.0 | 28.9 | 21.6 |
| 14.3 | 42.3 | 29.4 | 23.5 |
| 15.3 | 67.1 | 30.4 | 30.3 |
| 17.4 | 28.2 | 33.1 | 9.5 |
| 18.3 | 42.1 | 34.0 | 11.8 |
| 18.8 | 28.8 | 34.8 | 13.3 |
| 19.3 | 28.3 | 36.1 | 18.1 |
| 20.3 | 32.9 | 37.9 | 9.6 |

XRPD analysis of O-Acetyl Psilocin Citrate (FIG. 59) showed it to be crystalline with characteristic peaks at 7.1±0.2° 2-Theta, 10.2±0.2° 2-Theta, and 10.8±0.2° 2-Theta; optionally with further characteristic peaks at 12.5±0.2° 2-Theta and 15.2±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 7.1 | 41.9 | 17.6 | 16.1 |
| 10.2 | 28.7 | 18.3 | 42.1 |
| 10.8 | 28.5 | 18.8 | 29.3 |
| 12.5 | 78.2 | 19.4 | 100.0 |
| 13.8 | 16.9 | 19.7 | 38.5 |
| 14.2 | 21.1 | 20.4 | 16.9 |
| 15.2 | 35.2 | 21.4 | 18.8 |
| 17.3 | 10.9 | 22.1 | 72.2 |
| 22.7 | 34.9 | 30.6 | 17.2 |
| 23.3 | 23.9 | 31.5 | 11.9 |
| 24.0 | 14.7 | 31.9 | 14.2 |
| 24.8 | 32.9 | 33.0 | 6.7 |
| 25.7 | 23.5 | 34.5 | 10.5 |
| 25.9 | 20.4 | 35.1 | 9.8 |
| 27.8 | 15.4 | 35.6 | 11.2 |

| Angle 2-Theta (°) | Rel. Intensity (%) | Angle 2-Theta (°) | Rel. Intensity (%) |
|---|---|---|---|
| 28.4 | 16.5 | 36.0 | 15.2 |
| 28.6 | 17.6 | 36.8 | 7.7 |
| 29.1 | 25.7 | 37.8 | 8.0 |
| 30.1 | 17.0 | 38.9 | 6.9 |

XRPD analysis of O-Acetyl Psilocin Mucate (FIG. 60) showed it to be crystalline with characteristic peaks at 4.9±0.2° 2-Theta, 10.8±0.2° 2-Theta, and 12.0±0.2° 2-Theta; optionally with further characteristic peaks at 9.7±0.2° 2-Theta and 13.1±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) | Angle 2-Theta (°) | Rel. Intensity (%) |
|---|---|---|---|
| 4.9 | 55.0 | 25.1 | 32.7 |
| 9.7 | 18.8 | 25.5 | 33.1 |
| 10.3 | 10.9 | 26.4 | 23.9 |
| 10.8 | 29.0 | 26.8 | 16.4 |
| 12.0 | 56.5 | 27.5 | 14.5 |
| 13.1 | 91.7 | 27.9 | 14.6 |
| 14.6 | 59.8 | 28.3 | 17.1 |
| 15.2 | 63.6 | 28.8 | 14.2 |
| 16.0 | 36.6 | 29.4 | 31.3 |
| 16.6 | 69.8 | 29.7 | 27.4 |
| 17.5 | 33.4 | 30.5 | 10.9 |
| 17.7 | 39.1 | 31.0 | 14.5 |
| 18.5 | 27.3 | 32.1 | 15.2 |
| 18.9 | 20.7 | 32.6 | 19.7 |
| 20.0 | 21.1 | 33.3 | 13.4 |
| 20.7 | 100.0 | 34.0 | 10.5 |
| 21.1 | 43.5 | 34.5 | 12.5 |
| 21.3 | 45.6 | 35.2 | 11.1 |
| 21.5 | 45.7 | 36.1 | 12.4 |
| 22.0 | 30.6 | 37.5 | 12.8 |
| 22.7 | 43.3 | 38.6 | 12.8 |
| 24.1 | 95.1 | 39.0 | 11.7 |
| 24.4 | 51.6 | 39.3 | 11.1 |

Characterization of Salt Forms of O-Acetyl Psilocin

Characterization of the Salt Forms of O-Acetyl Psilocin using proton NMR spectroscopy is summarized in the following Table. Organic solvents were detected in trace amounts, thus none of the new crystalline salts appeared to be solvated.

| Salt Form | Results[a] |
|---|---|
| Citrate, Form A | Consistent with salt formation (1:1 stoichiometry); trace EtOAc present |
| Glycolate, Form A | Consistent with salt formation |
| HCl salt, Form A | Consistent with salt formation, trace acetone present |
| L-malate, Form A | Consistent with salt formation (1:1 stoichiometry), trace acetonitrile present |
| L-malate, Form B | Consistent with salt formation (1:1 stoichiometry), trace acetone present |
| Maleate, Form A | Consistent with salt formation (1:1 stoichiometry), trace isopropanol present |
| Malonate, Form A | Consistent with salt formation (1:1 stoichiometry), trace acetone present |
| Mesylate, Form A | Consistent with salt formation, trace ethyl acetate present |
| Mucate, Form A | Consistent with salt/cocrystal formation (2:1 API:acid stoichiometry) |
| Phosphate, Form A[a] | Consistent with salt formation |
| Succinate, Form A | Consistent with salt formation (1:1 stoichiometry) |
| L-tartrate, Form A | Consistent with salt formation (1:1 stoichiometry), trace isopropanol present |
| L-tartrate, Form B | Consistent with salt formation, trace acetone present |
| L-tartrate, Form C | Consistent with salt formation, trace acetone present |
| p-Tosylate, Form A | Consistent with salt formation |

Characterization of the Salt Forms of O-Acetyl Psilocin using thermal data (DSC and TGA) is summarized in the following Table.

| New Material | Test | Results[a] |
|---|---|---|
| Citrate A | DSC | Endo 101 (ΔH: 76 J/g), 117° C. (into decomp) |
| | TGA | 0.5% wt loss from ambient to 130° C. 154° C. onset decomposition |
| Glycolate A | DSC | Endo 83 (ΔH: 95 J/g), 245° C. (decomp) |
| | TGA | 0.3% wt loss from ambient to 140° C. 193° C. onset decomposition |
| HCl salt A | DSC | Endo 55 (weak, broad), 79 (weak, broad), 138 (ΔH: 56 J/g), 261° C. (decomp); exo 198 (weak)[b] |
| | TGA | 1.0% wt loss from ambient to 150° C. 236° C. onset decomposition |
| HCl salt A, vac dried/40° C. | DSC | Endo 147 (ΔH: 84 J/g) |
| | TGA | 0.2% wt loss from ambient to 190° C. 252° C. onset decomposition |

-continued

| New Material | Test | Results[a] |
|---|---|---|
| L-malate A | DSC | Endo 103 (ΔH: 82 J/g), 127 (weak), 179° C. (decomp) |
|  | TGA | 0.3% wt loss from ambient to 140° C. |
|  |  | 182° C. onset decomposition |
| L-malate B | DSC | Endo 128 (ΔH: 94 J/g) |
|  | TGA | 0.2% wt loss from ambient to 140° C. |
|  |  | 175° C. onset decomposition |
| Maleate A | DSC | Endo 129 (ΔH: 116 J/g) |
|  | TGA | 0.3% wt loss from ambient to 140° C. |
|  |  | 179° C. onset decomposition |
| Malonate A | DSC | Endo 120 (ΔH: 123 J/g), 207° C. (decomp) |
|  | TGA | 0.1% wt loss from ambient to 110° C. |
|  |  | 131° C. onset decomposition |
| Mesylate A | DSC | Endo 158 (ΔH: 84 J/g) |
|  | TGA | 0.1% wt loss from ambient to 140° C. |
|  |  | 0.3% wt loss from 140 to 180° C. |
|  |  | 175° C. onset decomposition |
| Mucate A | DSC | Endo 101 (broad, shoulder at 94° C.), |
| (2:1 API:acid, |  | 169° C. (ΔH: 134 J/g, into decomp) |
| possible cocrystal) | TGA | 4.8% wt loss from ambient to 130° C. |
|  |  | 167° C. onset decomposition |
| Phosphate A | DSC | Endo 193 (ΔH: 97 J/g) |
|  | TGA | 0.2% wt loss from ambient to 160° C. |
|  |  | 193° C. onset decomposition |
| Succinate A | DSC | Endo 121 (ΔH: 94 J/g) |
|  | TGA | 0.2% wt loss from ambient to 140° C. |
|  |  | 168° C. onset decomposition |
| L-tartrate A | DSC | Endo 166° C. (ΔH: 110 J/g) |
|  | TGA | 0.1% wt loss from ambient to 160° C. |
|  |  | 184° C. onset decomposition |
| L-tartrate B | DSC | Endo 144, exo 146, endo 168° C. (ΔH: 87 J/g) |
|  | TGA | 0.3% wt loss from ambient to 160° C. |
|  |  | 184° C. onset decomposition |
| L-tartrate C | DSC | Endo 143° C. (ΔH: 99 J/g) |
|  | TGA | 0.4% wt loss from ambient to 150° C. |
|  |  | 180° C. onset decomposition |
| p-tosylate A | DSC | Endo 116 (ΔH: 75 J/g) |
|  | TGA | 0.1% wt loss from ambient to 200° C. |
|  |  | 263° C. onset decomposition |

Based on negligible weight loss by TGA, the majority of salts were determined to be non-solvated. By DSC analysis, a single sharp endotherm characteristic of a melting event was observed for the majority of salts. However, some of the salts exhibited a more complex thermal behavior, as detailed below:

Citrate salt, Form A: exhibited two probable melting events—endothermic transitions at approx. 101 and 117° C.—with the latter occurring immediately prior to decomposition; a negligible weight loss was observed concurrently by TGA.

Hydrochloride salt, Form A: showed weak broad endotherms at approx. 55 and 79° C., corresponding to a total weight loss of less than 1% by TGA (trace amounts of acetone were detected by proton NMR spectroscopy). A probable meting endotherm was observed at approx. 138° C. Another HCl salt was additionally dried in vacuum at 40° C. to remove residual solvent. The resulting material was consistent with Form A by XRPD analysis and exhibited a probable melting endotherm at approx. 147° C. by DSC, with a negligible weight loss observed by TGA.

L-malate salt, Form A: exhibited a probable melting endotherm at approx. 103° C., followed by a weak sharp endothermic transition at approx. 127° C., both corresponding to a negligible weight loss by TGA. Note that the temperature of the second endothermic transition was similar to the melting point observed for Form B. This suggests small amounts of Form B could be present in the Form A sample, or a possible minor conversion of A to B upon heating.

Mucate salt (cocrystal), Form A: showed closely overlapping endotherms (broad event) around 100° C., corresponding to approx. 4.8% weight loss by TGA, which could be associated with the loss of water that was used to generate the material by grinding. An intense endotherm at approx. 168° C. is likely due to the melting of the dehydrated material. Note that the crystallization method (grinding) resulting in a 2:1 API: acid stoichiometry, as well as the acid pKa values, all suggest Form A could be a cocrystal. The original experiment using a 1:1 molar ratio of the components resulted in a mixture of Form A and mucic acid by XRPD analysis. Grinding with one-half equivalent of the acid yielded Form A.

L-tartrate salt, Form B: exhibited a probable melt/recrystallization (overlapping intense endotherm (144° C.)/exotherm (146° C.), which suggests a form change. A second melting event occurred at approx. 168° C., which is similar to the probable melting point of Form A (166° C.), thus suggesting possible conversion of Form B to A upon heating. It should also be noted that Forms B and C exhibited very similar probable melting points: 144° C. for Form B vs. 143° C. for Form C. Relative thermodynamic stabilities of Forms A, B, and C were not investigated in this study.

Salt Selection and Scale-Up

Thirteen crystalline materials exhibiting unique XRPD patterns were identified from the salt screen experiments. Several salts were scaled-up for further investigation (maleate, L-malate B, mesylate, L-tartrate, phosphate). The phosphate scale-up resulted in mixtures and was removed from consideration. The phosphate salt was found to deliquesce at 65% RH, and Malate B and Tartrate A exhibited possible hydrate formation above 85% RH and issues with the solubility measurement, therefore, these salts were not moved forward. The maleate salt was chosen based in its anhydrate designation, minimal water sorption over the RH range, lack of other forms, and acceptable solubility. Key properties of the salts are tabulated below:

|  | Maleate | Malate Form B | Tartrate Form A | Mesylate |
|---|---|---|---|---|
| XRPD | crystalline | crystalline | crystalline | crystalline |
| TGA volatile content % | 0.4 (at 140° C.) | 0.4 (at 140° C.) | 0.3 (at 150° C.) | 0.3 (at 140° C.) |
| Designation | anhydrate | anhydrate | anhydrate | anhydrate |
| Stoichiometry | 1:1 | 1:1 | 1:1 |  |
| NMR-salt formation | consistent with salt | consistent with salt | consistent with salt | consistent with salt |
| NMR solvent | trace IPA | trace acetone | trace IPA | trace EtOAc, small impurities present |
| DSC transition maximum temp (° C.) | 129 | 128 | 166 | 158 |
| Water uptake (25-65% RH) % | ~0.3 | ~0.3 | 0.1 | ~3 |
| Water uptake | ~0.8, 5-95% RH | 0.8%, 5-85% RH; 4.5% above 85% RH | 5-6% 85-95% RH | ~40 |
| Water solubility (mg/mL) | >50 mg/mL | Small particles present at ≤ 50 mg/mL | Small particles present at ≤ 26 mg/mL | Small particles present at ≤ 55 mg/mL |
| Other forms | no other forms reported; possible minor peak upon scale-up | Malate A and B found in salt screen | Tartrate A, B, and C found in salt screen; Tartrate A shows likely hydrate formation at 95% RH | appears to deliquesce above 65% RH in DVS |
| Particle size (optical microscopy) μm | ~10 or less | ~10-70 | ~10 or less | ~10 or less |
| Morphology optical microscopy | irregular chunks | irregular particles | irregular chunks | irregular chunks |
| Morphology SEM | fused particles | fused particles | fused particles | fused particles |

Five selected salt candidates were prepared in larger quantities for additional evaluation. Characterization results for the selected materials are summarized in the table below.

| Salt candidate | Characterization results |
|---|---|
| L-malate, Forms A and B | Two crystalline, non-solvated Forms A and B were identified<br>Form A: $M_p$~103° C. (DSC); single crystal structure was solved<br>Form B: $M_p$~128° C. (DSC); non-hygroscopic at 5-85% RH, hygroscopic above 85% RH (approx. 4.5% water uptake. DVS)<br>aqueous solubility < 50 mg/mL<br>not pursued further |
| Maleate, Form A | One crystalline Form A was identified<br>single crystal structure was solved<br>Form A: $M_p$~129° C. (DSC); non-hygroscopic to slightly hygroscopic over the range of 5-95% RH (approx. 0.8% water uptake, DVS)<br>aqueous solubility 49 < S < 114 mg/mL<br>selected for stable from screening; prepared at 1.5-g scale |
| Mesylate, Form A | One crystalline Form A was identified<br>Form A: $M_p$~155° C. (DSC); non-hygroscopic at 5-55% RH, highly hygroscopic above 55% RH (approx. 40% water uptake, DVS), no hydrate formation<br>aqueous solubility < 50 mg/mL<br>not pursued further |
| L-tartrate, Forms A, B, C and D | Three crystalline, non-solvated Forms A, B and C, and a hydrate Form D were identified; limited characterization was obtained for Forms B and C, Form D was not characterized.<br>Form A: $M_p$~166° C. (DSC); non-hygroscopic at 5-85% RH, hygroscopic above 85% RH (approx. 6% water uptake, DVS), resulting in hydrate formation (Form D)<br>aqueous solubility < 26 mg/mL<br>not pursued further |

-continued

| Salt candidate | Characterization results |
| --- | --- |
| Phosphate, Form A | Two crystalline, non-solvated Forms A and B were identified<br>Form A: $M_p$ 193-196° C. (DSC); salt stoichiometry was not confirmed<br>Form B: obtained as a mixture with Form A only; possible $M_p$~158° C.<br>(DSC of A + B mixture); single crystal structure was solved<br>Forms A + B mixture: non-hygroscopic at 75% RH (RH jar)<br>aqueous solubility < 40 mg/mL<br>not pursued further |

Results of Scale-up Experiments
L-Malate Salt, Form B

The L-malate salt, Form B was characterized as a crystalline, non-solvated material with a probable melting point of approx. 128° C. (DSC). Form B was found to be non-hygroscopic in the range between 5-85% RH, and hygroscopic above 85% RH, based on approx. 4.500 water uptake. The DVS curve did not show a notable hysteresis, indicating no hydrate formation occurred. The post-DVS specimen was consistent with Form B by XRPD analysis.

The aqueous solubility of the L-malate salt, Form B was estimated to be below 50 mg/mL (aliquot addition method). Additional studies would be needed to obtain a more accurate solubility value.

Maleate Salt, Form A

The maleate salt, Form A was characterized as a crystalline, non-solvated, and non-hygroscopic material with a probable melting point of approx. 129° C. (DSC). The overall water uptake in the range between 5-95% RH was approx. 0.8%; the post-DVS specimen was consistent with Form A by XRPD analysis. Single crystals of sufficient size and quality resulted from recrystallization in water (experiment to estimate aqueous solubility). The single crystal structure of O-acetyl psilocin maleate Form A was solved (see below).

The aqueous solubility of the maleate salt, Form A was estimated to be above in the range from 49<S<114 mg/mL (aliquot addition method). Additional studies would be needed to obtain a more accurate solubility value.

Mesylate Salt, Form A

The mesylate salt, Form A was characterized as a crystalline, non-solvated material with a probable melting point of approx. 155° C. (DSC). While the mesylate salt was found to be non-hygroscopic in the range from 5-55% RH, it behaved as a highly hygroscopic material above 55% RH, based on 40% water uptake. The post-DVS specimen was a liquid; however, after drying in the open air the mesylate salt crystalized and was consistent with Form A by XRPD analysis. Note that the proton NMR spectrum for the scale-up salt showed some impurities which could be caused by a 5% excess of methanesulfonic acid used in the experiment.

The aqueous solubility of the mesylate salt, Form A was estimated to be below 55 mg/mL (aliquot addition method). Due to high hygroscopicity, the mesylate salt was not pursued further.

Phosphate Salt, Forms A and B

A new crystalline form of the phosphate salt was identified from the scale-up experiments and designated as Form B. Two scale-up experiments were conducted following a procedure from the salt screen. While both experiments produced Form A, the material exhibited additional peaks by XRPD analysis, indicating a mixture of phases. Single crystals of Form B were grown from the filtrate and the crystal structure was solved (see below). Therefore, a calculated XRPD pattern for Form B was obtained and a 1:1 salt stoichiometry confirmed. Form B was not characterized by thermal analysis, due to insufficient sample quantity.

A competitive slurry experiment on a mixture of Forms A and B suspended in ethyl acetate to attempt conversion to one of the forms was not successful. No additional work was conducted to evaluate the relative thermodynamic stability of Forms A and B. Note that the salt stoichiometry for Form A was not determined in this study.

Similar to proton NMR analysis of the mesylate salt, the phosphate salt showed small impurities, which were likely caused by a 5% acid excess used in the scale-up experiment. When repeated with 1 molar equivalent of phosphoric acid, the NMR spectrum of the scale-up material did not show impurities.

The phosphate salt, as a mixture of Forms A and B, was analyzed by DSC and TGA. The material exhibited a weak broad endotherm at approx. 158° C., possibly due to the melting of Form B, which was followed by a sharp intense endotherm at approx. 196° C., previously attributed to the probable melt of Form A. By TGA, a negligible weight loss (approx. 0.1%) was observed upon heating to 170° C. The phosphate salt was not characterized by DVS analysis; however, based on evaluation using RH jars, hygroscopicity of the material as a mixture of Forms A and B appeared to be low.

The aqueous solubility of the phosphate salt (Forms A+B) was estimated to be below 40 mg/mL (aliquot addition method). Since the scale-up experiments resulted in a mixture of two forms, the phosphate salt was not pursued further.

L-Tartrate Salt, Form A

The L-tartrate salt, Form A was characterized as a crystalline, non-solvated material with a probable melting point of approx. 166° C. (DSC). Form A was found to be non-hygroscopic in the range from 5-85% RH, and hygroscopic above 85% RH, based on approx. 6% water uptake. The post-DVS specimen was consistent with Form A by XRPD analysis and exhibited additional diffraction peaks, which were identified as a probable hydrate and designated as Form D. The DVS curve showed a large hysteresis consistent with hydrate formation.

The aqueous solubility of L-tartrate salt, Form A was estimated to be below 26 mg/mL (aliquot addition method). As the L-tartrate salt showed a complex polymorphic nature compared to the other salt candidates, it was not pursued further.

Example 7: Polymorph Screen

The active pharmaceutical ingredient (API), which may be a free base or a salt, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the API is a solvate or hydrate, and to evaluate thermal stability. DVS data are used to evaluate hygroscopicity of the API and if hydrates can be formed at high relative humidity. About 10 to 15 solvents may be selected from the list below, based on their properties (polarity, dielectric constant and dipole moment).

TABLE 20

Solvents

| | |
|---|---|
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |
| 2-ethoxyethanol (Cellusolve) | 1,1,1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

API is dissolved in a solvent or mixture of solvents, and the solvents are evaporated at different rates (slow evaporation or fast evaporation) and at different temperatures (ambient or elevated).

API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling.

The solids formed will be recovered by filtration and dried (air dried or vacuum dried).

API is dissolved in a solvent or mixture of solvents, and an antisolvent is added to precipitate the salt. The solids formed will be recovered by filtration and dried (air dried or vacuum dried).

API is added to a solvent or mixture of solvents, where the API is not fully dissolved. The slurry will be agitated at different temperatures for a number of days. The solids formed will be recovered by filtration and (air dried or vacuum dried).

API is milled (by mechanical milling or by mortar and pestle), with a drop of solvent, or without any solvent.

API is melted and cooled (at different cooling rates, fast and slow, and cooled to different temperatures) to obtain solids.

API is suspended in a solvent or mixture of solvents, and the slurry is placed in a heating/cooling cycle for multiple cycles. The remaining solids after the final cooling cycle will be filtered and (air dried or vacuum dried).

API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.

API is exposed to elevated humidity (or elevated temperature, or combination thereof), or to solvent vapors for extended period of days.

Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).

API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50(TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45° 2θ with steps of 0.1°, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered CuK$_{α1}$ radiation (λ=1.5405981 Å) produced at 40 kV and 20 mA by a Philips PW 1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005° 2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

O-Acetyl Psilocin Maleate

A stable form screen of O-acetyl psilocin maleate salt, Form A was conducted. Non-crystalline O-acetyl psilocin maleate was generated by lyophilization and melt-quench and appeared to be a tacky solid/frozen glass. The non-crystalline maleate salt was unstable at ambient relative humidity (50% RH in summertime) and crystallized yielding Form A. The non-crystalline material also crystallized when brought in contact with various solvents (liquid or vapor). Form A was the only crystalline form found in approximately 50 experiments conducted in the course of stable form screening.

Example 8: Single Crystal Structure of O-Acetyl Psilocin L-Malate (Form A)

The crystal structure of O-acetyl psilocin L-malate (Form A) was solved. The structure was determined to be anhydrous and unsolvated, 1:1 O-acetyl psilocin:L-malic acid salt with formula $C_{14}H_{19}N_2O_2$—$C_4H_5O_5$. Unit cell parameters are shown in Table 21.

TABLE 21

| Unit cell parameters of O-acetyl psilocin L-malate Form A | |
|---|---|
| Crystal system, space group | Monoclinic |
| Space group (number) | P2$_1$ (4) |
| Data collection temperature (K) | 150 |
| a (Å) | 12.176(5) |
| b (Å) | 7.5241(11) |
| c (Å) | 20.274(7) |

TABLE 21-continued

| Unit cell parameters of O-acetyl psilocin L-malate Form A | |
|---|---|
| Crystal system, space group | Monoclinic |
| α [°] | 90 |
| β [°] | 100.67(3) |
| γ [°] | 90 |
| volume (Å$^3$) | 1825.3(11) |
| Z | 4 |

Figure 61:
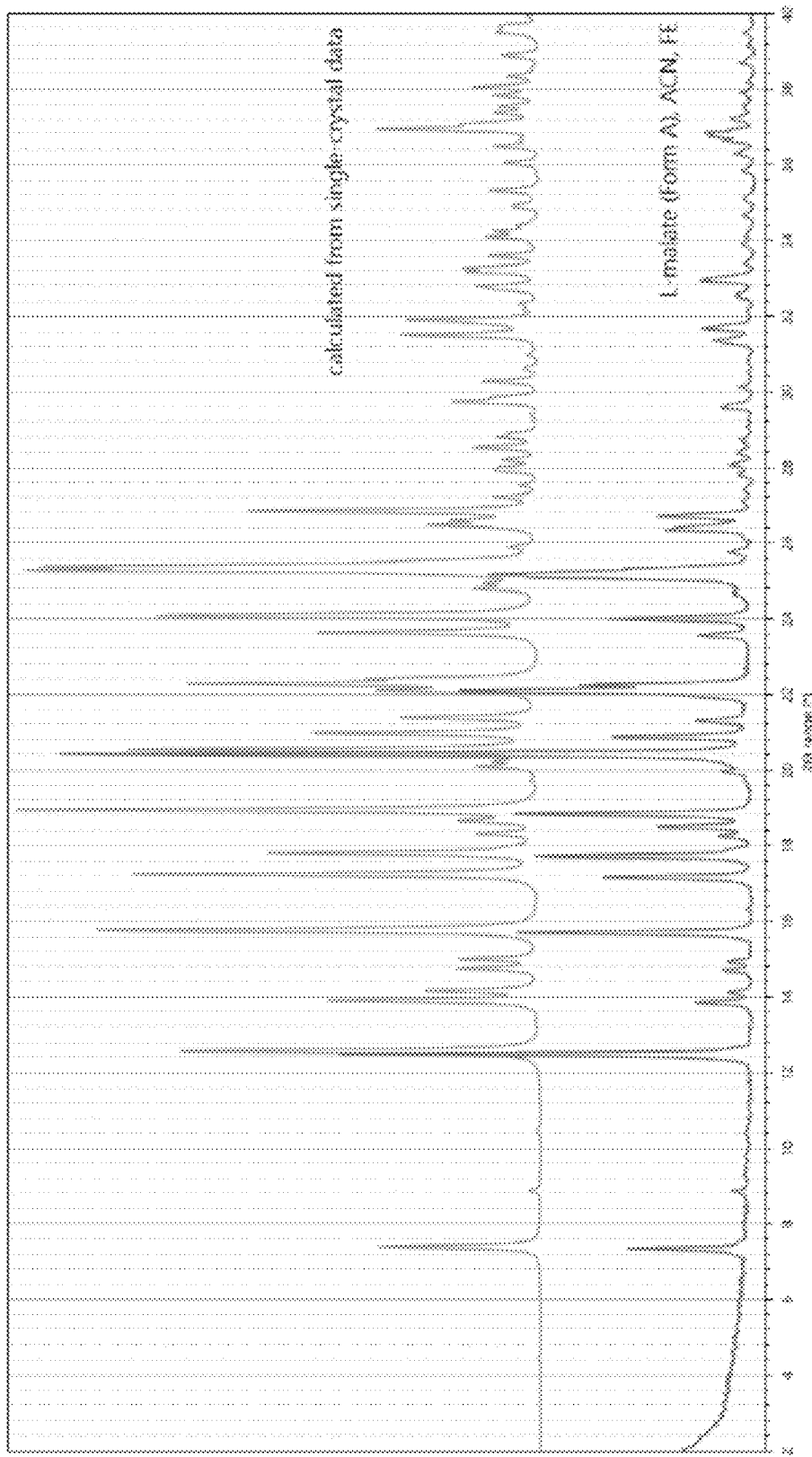
FIG. 61 provides an overlay plot of an XRPD diffractogram of O-acetyl psilocin L-malate Form A with an XRPD diffractogram calculated from single-crystal data.

An XRPD pattern calculated from the single-crystal data was overlaid with a pattern obtained for O-acetyl psilocin L-malate (Form A) (FIG. 61). The calculated XRPD pattern overall matched the XRPD pattern of the bulk material. The observed peak shifting was due to the temperature difference at which the single crystal and X-ray powder diffraction data were collected.

XRPD analysis of calculated pattern of O-acetyl psilocin L-malate (Form A) (FIG. 61) shows characteristic peaks at 7.4° 2-Theta, 12.6° 2-Theta, and 15.8° 2-Theta; optionally with further characteristic peaks at 17.2° 2-Theta and 17.8° 2-Theta. A full list of calculated peaks is found in the following table:

| Angle 2-Theta (°) | Rel. Intensity (%) | Angle 2-Theta (°) | Rel. Intensity (%) |
|---|---|---|---|
| 7.4 | 30.8 | 21.0 | 43.4 |
| 8.9 | 2.1 | 21.4 | 26.6 |
| 10.4 | 0.7 | 22.1 | 31.3 |
| 12.6 | 68.5 | 22.3 | 67.2 |
| 13.3 | 1.1 | 23.6 | 42.5 |
| 13.9 | 40.5 | 24.1 | 72.9 |
| 14.2 | 21.9 | 24.8 | 13.0 |
| 14.7 | 16.0 | 24.9 | 10.7 |
| 15.0 | 15.5 | 25.3 | 98.2 |
| 15.8 | 84.5 | 25.9 | 6.1 |
| 16.4 | 1.3 | 26.5 | 21.7 |
| 17.2 | 77.7 | 26.8 | 55.5 |
| 17.8 | 52.0 | 27.2 | 8.9 |
| 18.3 | 12.4 | 27.5 | 4.0 |
| 18.6 | 15.8 | 27.9 | 8.8 |
| 18.9 | 100.0 | 28.2 | 7.3 |
| 19.7 | 2.1 | 28.5 | 12.9 |
| 20.1 | 12.4 | 28.8 | 8.5 |
| 20.2 | 9.2 | 29.2 | 1.5 |
| 20.5 | 78.6 | 29.4 | 2.1 |
| 29.7 | 17.1 | 34.9 | 5.3 |
| 30.3 | 11.1 | 35.3 | 9.6 |
| 30.6 | 3.1 | 35.8 | 0.9 |
| 31.0 | 2.6 | 36.0 | 7.0 |
| 31.2 | 1.7 | 36.5 | 8.8 |
| 31.5 | 26.6 | 36.7 | 4.2 |
| 31.9 | 25.4 | 36.9 | 31.3 |
| 32.2 | 3.3 | 37.4 | 8.9 |
| 32.3 | 4.1 | 37.6 | 8.0 |
| 32.8 | 12.3 | 37.8 | 9.0 |
| 33.2 | 14.3 | 38.1 | 12.8 |
| 33.3 | 14.7 | 38.3 | 6.4 |
| 33.6 | 9.9 | 38.9 | 7.5 |
| 33.9 | 2.2 | 39.5 | 8.6 |
| 34.1 | 10.7 | 39.7 | 8.0 |
| 34.2 | 9.0 | 39.9 | 2.7 |

Single Crystal Growth

O-acetyl psilocin (25.3 mg) and L-malic acid (13.6 mg, 1:1 molar ratio) were combined in a vial and acetonitrile (1 mL) was added. A clear solution resulted and the solvent was allowed to evaporate (open vial). Crystalline solids formed after 4 days and were found to contain single crystals of sufficient size and quality for structural determination.

Single Crystal X-Ray Structure Determination

A colourless rod-shaped crystal from sample prepared above, with a formula $C_{14}H_{19}N_2O_2C_4H_5O_5$ having approximate dimensions of 0.31×0.11×0.10 mm was mounted on a Mitegen micromesh mount in a random orientation. The crystal was flash cooled to 150(2) K and data for the crystal were collected on a Bruker AXS D8 Quest three-circle diffractometer with a fine focus sealed tube X-ray source using a Triumph curved graphite crystal as the monochromator and a PhotonII charge-integrating pixel array (CPAD) detector. The diffractometer was equipped with an Oxford Cryosystems low temperature device and used MoKα radiation ($\lambda$=0.71073 Å). Data were collected using Apex4 v2022. 10-RC10 and all data were integrated with SAINT and a multi-scan absorption correction using SADABS was applied. The structure was solved by dual methods using SHELXT and refined by full-matrix least-squares methods against F2 by SHELXL-2018/3 using ShelXle. All non-hydrogen atoms were refined with anisotropic displacement parameters. The hydrogen atoms were refined isotropically on calculated positions using a riding model with their $U_{iso}$ values constrained to 1.5 times the $U_{eq}$ of their pivot atoms for terminal sp$^3$ carbon atoms and 1.2 times for all other carbon atoms.

The structure emulated a centrosymmetric setting in space group P21/c with an 81% fit for an inversion center. Exact centrosymmetry was broken by the chiral center of hydromalic acid at carbon atoms C16 (enantiopure L-malic acid was used in the synthesis).

The Flack parameter was determined using 4,083 quotients [(I+)−(I−)]/[(I+)+(I−)] using Parsons method and refined to −0.3(2). Chiral centers at C16_1 and C16_2 had the S configuration. Table 22 provides the crystal data and data collection parameters.

TABLE 22

| Crystal data and structure refinement | |
|---|---|
| Empirical formula | $C_{18}H_{24}N_2O_7$ |
| Moiety formula | $C_{14}H_{19}N_2O_2$, $C_4H_5O_5$ |
| Formula weight | 380.39 |
| Temperature [K] | 150(2) |
| Crystal system | monoclinic |
| Space group (number) | $P2_1$ (4) |
| a [Å] | 12.176(5) |
| b [Å] | 7.5241(11) |
| c [Å] | 20.274(7) |
| α [°] | 90 |
| β [°] | 100.67(3) |
| γ [°] | 90 |
| Volume [Å$^3$] | 1825.3(11) |
| Z | 4 |
| $\rho_{calc}$ [gcm$^{-3}$] | 1.384 |
| μ [mm$^{-1}$] | 0.107 |
| F(000) | 808 |
| Crystal size [mm$^3$] | 0.310 × 0.110 × 0.100 |
| Crystal colour | colourless |
| Crystal shape | rod |
| Radiation | MoK$_\alpha$ ($\lambda$ = 0.71073 Å) |
| 2θ range [°] | 4.28 to 61.05 (0.70 Å) |
| Index ranges | −17 ≤ h ≤ 17 |
| | −10 ≤ k ≤ 10 |
| | −28 ≤ l ≤ 28 |
| Reflections collected | 51759 |
| Independent reflections | 11116 |
| | $R_{int}$ = 0.0492 |
| | $R_{sigma}$ = 0.0343 |
| Completeness to θ = 25.242° | 99.1% |
| Data/Restraints/Parameters | 11116/1/497 |
| Goodness-of-fit on F$^2$ | 1.011 |
| Final R indexes [I ≥ 2σ(I)] | R1 = 0.0381 wR2 = 0.0971 |
| Final R indexes [all data] | R1 = 0.0479 wR2 = 0.1037 |

TABLE 22-continued

| Crystal data and structure refinement | |
|---|---|
| Largest peak/hole [eÅ$^{-3}$] | 0.33/−0.28 |
| Flack x parameter | −0.3(2) |

X-ray Powder Diffraction (XRPD)

The Rigaku SmartLab X-ray diffractometer was configured in Bragg-Brentano reflection geometry equipped with a beam stop and knife edge to reduce incident beam and air scatter. Data collection parameters are shown in the Table 23.

TABLE 23

| Data Collection Parameters | | | |
|---|---|---|---|
| Parameter | Value | Parameter | Value |
| Geometry | Bragg-Brentano | Receiving Slit 1 (mm) | 18 |
| Tube Anode | Cu | Receiving Slit 2 (mm) | open |
| Tube Type | Long Fine Focus | Start Angle 2θ (°) | 2 |
| Tube Voltage (kV) | 40 | End Angle 2θ (°) | 40 |
| Tube Current (mA) | 44 | Step Size (°) | 0.02 |
| Detector | HyPix-3000 | Scan Speed (°/min) | 6 |
| Monochromator | Ni foil Cu Kβ Filter | Spinning (rpm) | 11 |
| Incident Slit (°) | ⅓ | Sample Holder | Low-background Si |

Example 9: Single Crystal Structure of O-Acetyl Psilocin Maleate (Form A)

The crystal structure of O-acetyl psilocin maleate (Form A) was solved. The structure was determined to be anhydrous and unsolvated, 1:1 O-acetyl psilocin:maleic acid salt with formula $C_{14}H_{19}N_2O_2 \cdot C_4H_3O_4$. Unit cell parameters are shown in Table 24.

TABLE 24

| Unit cell parameters of O-acetyl psilocin maleate Form A | |
|---|---|
| Crystal system, space group | Triclinic |
| Space group (number) | P$\bar{1}$ (2) |
| Data collection temperature (K) | 150(2) |
| a (Å) | 7.5153(11) |
| b (Å) | 11.2098(18) |
| c (Å) | 12.201(2) |
| α [°] | 110.707(6) |
| β [°] | 100.626(6) |
| γ [°] | 106.088(6) |
| volume (Å$^3$) | 877.0(2) |
| Z | 2 |

Figure 62:
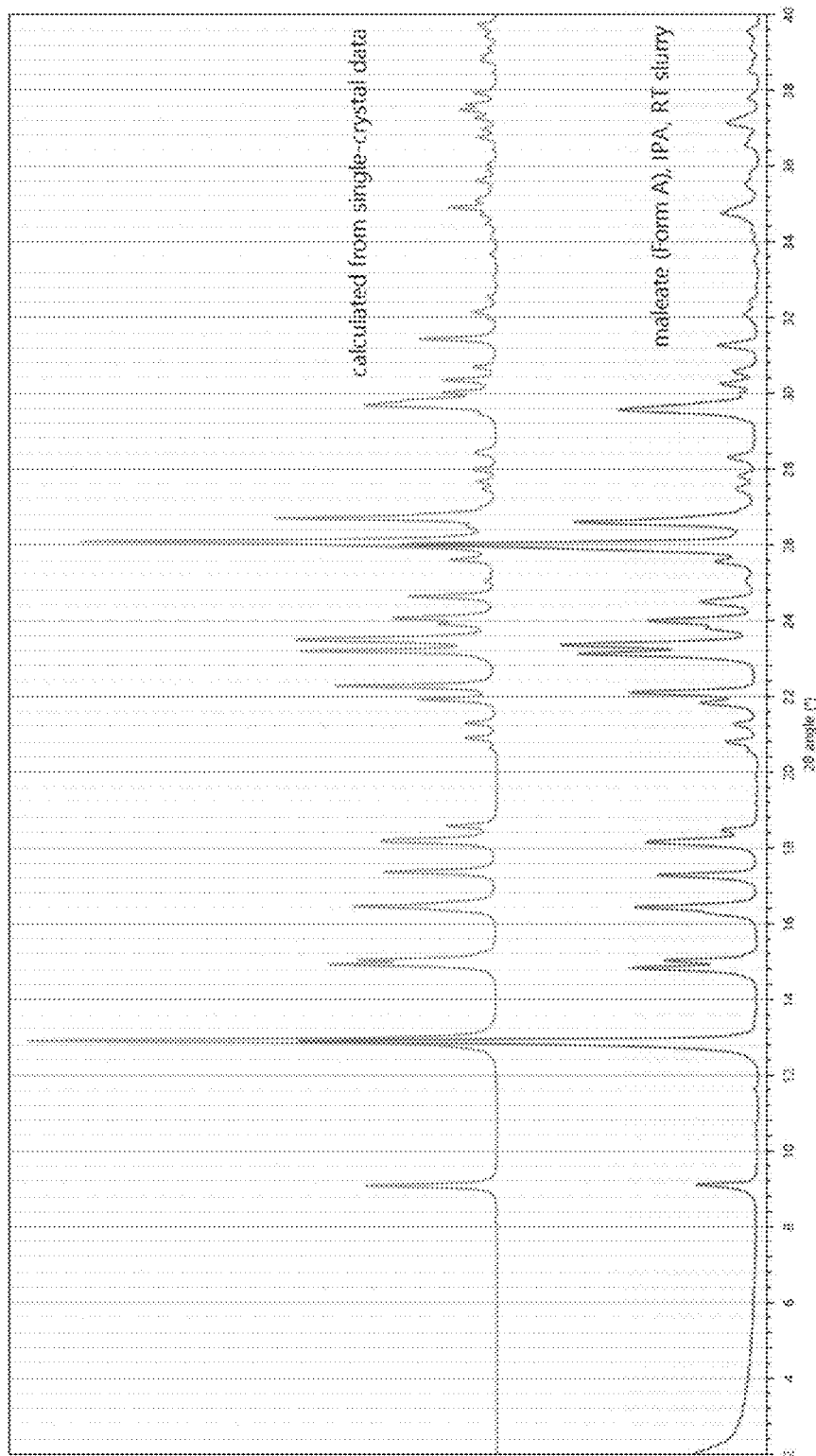
FIG. 62 provides an overlay plot of an XRPD diffractogram of O-acetyl psilocin maleate Form A with an XRPD diffractogram calculated from single-crystal data.

An XRPD pattern calculated from the single-crystal data was overlaid with a pattern obtained for O-acetyl psilocin maleate (Form A) (FIG. 62). The calculated XRPD pattern overall matched the XRPD pattern of the bulk material. The observed peak shifting was due to the temperature difference at which the single crystal and X-ray powder diffraction data were collected.

XRPD analysis of calculated pattern of O-acetyl psilocin maleate (Form A) (FIG. 62) shows characteristic peaks at 9.1° 2-Theta, 12.9° 2-Theta, and 14.9° 2-Theta; optionally with further characteristic peaks at 16.5° 2-Theta and 17.4° 2-Theta. A full list of calculated peaks is found in the following table:

| Angle 2-Theta (°) | Rel. Intensity (%) | Angle 2-Theta (°) | Rel. Intensity (%) |
|---|---|---|---|
| 8.2 | 0.5 | 18.6 | 10.8 |
| 9.1 | 28.4 | 20.6 | 2.0 |
| 12.9 | 100.0 | 20.9 | 7.1 |
| 14.9 | 36.0 | 21.3 | 7.0 |
| 16.5 | 30.8 | 21.9 | 17.0 |
| 17.4 | 24.5 | 22.3 | 34.8 |
| 18.2 | 24.6 | 23.2 | 42.4 |
| 23.5 | 43.1 | 33.0 | 1.0 |
| 23.9 | 12.7 | 33.7 | 1.6 |
| 24.1 | 22.2 | 34.1 | 1.6 |
| 24.6 | 19.0 | 34.5 | 2.8 |
| 25.0 | 2.9 | 34.7 | 3.9 |
| 25.2 | 1.6 | 34.9 | 10.7 |
| 25.6 | 10.2 | 35.1 | 4.8 |
| 26.1 | 88.7 | 35.4 | 1.7 |
| 26.5 | 7.1 | 35.6 | 4.8 |
| 26.7 | 47.3 | 35.9 | 2.2 |
| 27.5 | 3.2 | 36.0 | 2.2 |
| 27.7 | 4.3 | 36.4 | 1.0 |
| 28.0 | 5.4 | 36.7 | 4.3 |
| 28.4 | 5.0 | 37.0 | 3.2 |
| 29.4 | 4.0 | 37.3 | 5.1 |
| 29.7 | 28.3 | 37.5 | 8.1 |
| 30.0 | 11.7 | 37.6 | 6.6 |
| 30.3 | 11.7 | 37.9 | 5.1 |
| 30.7 | 5.3 | 38.8 | 3.6 |
| 31.4 | 16.8 | 38.9 | 3.1 |
| 32.0 | 2.1 | 39.1 | 2.1 |
| 32.1 | 5.4 | 39.4 | 2.9 |
| 32.5 | 2.3 | 39.7 | 4.2 |

Single Crystal Growth

O-acetyl psilocin maleate (5.7 mg) was mixed with 50 μL of water in a vial. Some solids remained undissolved in solution and were stored in a capped vial at ambient temperature. In a few days, the sample was found to contain single crystals of sufficient size and quality.

Single Crystal X-ray Structure Determination

A colourless prism-shaped crystal of sample prepared above with formula $C_{14}H_{19}N_2O_2 \times C_4H_3O_4$ having approximate dimensions of 0.32×0.22×0.18 mm was mounted on a Mitegen micromesh mount in a random orientation. The crystal was flash cooled to 150(2) K and data were collected on a Bruker AXS D8 Quest three circle diffractometer with a fine focus sealed tube X-ray source using a Triumph curved graphite crystal as monochromator and a PhotonII charge-integrating pixel array (CPAD) detector. The diffractometer was equipped with an Oxford Cryosystems low temperature device and used $MoK_\alpha$ radiation Q, =0.71073 Å). All data were integrated with SAINT and a multi-scan absorption correction using SADABS was applied. The structure was solved by dual methods using SHELXT and refined by full-matrix least-squares methods against $F^2$ by SHELXL-2018/3 using ShelXle.

All non-hydrogen atoms were refined with anisotropic displacement parameters. Carbon bound hydrogen atoms were refined isotropically on calculated positions using a riding model with their $U_{iso}$ values constrained to 1.5 times the $U_{eq}$ of their pivot atoms for terminal sp³ carbon atoms and 1.2 times for all other carbon atoms. Nitrogen bound H atoms were refined isotropically with their $U_{iso}$ values constrained to 1.2 times the $U_{eq}$ of their pivot atoms. Position and isotropic displacement parameter of the hydromaleate hydroxyl H atom were freely refined.

This report and the CIF file were generated using FinalCif.

Crystal data and data collection parameters are given in Table 25.

TABLE 25

Crystal data and structure refinement

| | |
|---|---|
| Empirical formula | $C_{18}H_{22}N_2O_6$ |
| Moiety formula | $C_{14}H_{19}N_2O_2 \times C_4H_3O_4$ |
| Formula weight | 362.37 |
| Temperature [K] | 150(2) |
| Crystal system | triclinic |
| Space group (number) | $P\bar{1}$ (2) |
| a [Å] | 7.5153(11) |
| b [Å] | 11.2098(18) |
| c [Å] | 12.201(2) |
| α [°] | 110.707(6) |
| β [°] | 100.626(6) |
| γ [°] | 106.088(6) |
| Volume [Å³] | 877.0(2) |
| Z | 2 |
| $\rho_{calc}$ [gcm⁻³] | 1.372 |
| μ [mm⁻¹] | 0.104 |
| F(000) | 384 |
| Crystal size [mm³] | 0.320 × 0.220 × 0.180 |
| Crystal colour | colourless |
| Crystal shape | prism |
| Radiation | $MoK_\alpha$ (2 = 0.71073 Å) |
| 2θ range [°] | 3.76 to 66.57 (0.65 Å) |
| Index ranges | −11 ≤ h ≤ 11 |
| | −17 ≤ k ≤ 17 |
| | −18 ≤ l ≤ 18 |
| Reflections collected | 19168 |
| Independent reflections | 6629 |
| | $R_{int}$ = 0.0428 |
| | $R_{sigma}$ = 0.0492 |
| Completeness to θ = 25.242° | 99.8 % |
| Data/Restraints/Parameters | 6629/0/248 |
| Goodness-of-fit on $F^2$ | 1.039 |
| Final R indexes [I ≥ 2σ(I)] | $R_1$ = 0.0449 |
| | $wR_2$ = 0.1156 |
| Final R indexes [all data] | $R_1$ = 0.0674 |
| | $wR_2$ = 0.1298 |
| Largest peak/hole [eÅ⁻³] | 0.41/−0.25 |

X-Ray Powder Diffraction (XRPD)

The Rigaku SmartLab X-ray diffractometer was configured in Bragg-Brentano reflection geometry equipped with a beam stop and knife edge to reduce incident beam and air scatter. Data collection parameters are shown in the following table:

| Parameter | Value | Parameter | Value |
|---|---|---|---|
| Geometry | Bragg-Brentano | Receiving Slit 1 (mm) | 18 |
| Tube Anode | Cu | Receiving Slit 2 (mm) | open |
| Tube Type | Long Fine Focus | Start Angle 2θ (°) | 2 |
| Tube Voltage (kV) | 40 | End Angle 2θ (°) | 40 |
| Tube Current (mA) | 44 | Step Size (°) | 0.02 |
| Detector | D/teX Ultra 250 | Scan Speed (°/min) | 6 |
| Monochromator | Ni foil Cu Kβ Filter | Spinning (rpm) | 11 |
| Incident Slit (°) | ⅓ | Sample Holder | Low-background Si |

Example 10: Single Crystal Structure of O-Acetyl Psilocin Phosphate (Form B)

The crystal structure of O-acetyl psilocin phosphate salt (Form B) was solved. The structure was determined to be anhydrous and unsolvated, 1:1 O-acetyl psilocin:phosphoric acid salt with formula $C_{14}H_{19}N_2O_2 \times H_2O_4P$. The calculated powder pattern from the single crystal data matched the peaks identified as Form B in the X-ray powder diffraction (XRPD) pattern of a mixture of Forms A and B, which was obtained during the phosphate salt scale-up. Unit cell parameters are in Table 26.

TABLE 26

Unit cell parameters of O-acetyl psilocin phosphate Form B

| | |
|---|---|
| Crystal system, space group | Monoclinic |
| Space group (number) | C2/c (15) |
| Data collection temperature (K) | 150(2) |
| a [Å] | 16.2887(3) |
| b [Å] | 5.51730(10) |
| c [Å] | 35.7125(7) |
| α [°] | 90 |
| β [°] | 91.0140(8) |
| γ [°] | 90 |
| volume (Å$^3$) | 3208.97(10) |
| Z | 8 |

Figure 63:
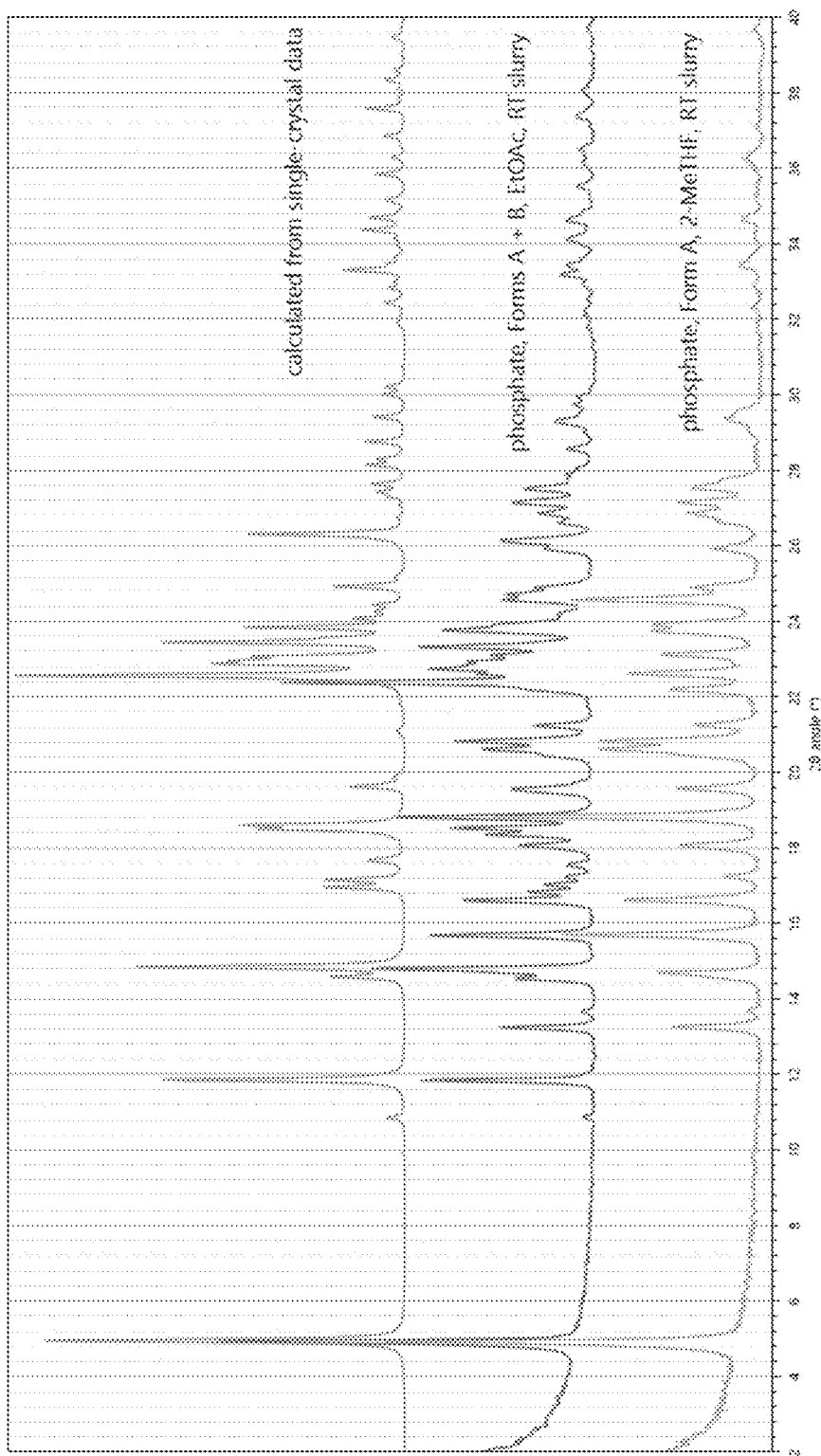
FIG. 63 provides an overlay plot of an XRPD diffractogram of O-acetyl psilocin phosphate Form A, and Forms A and B, with an XRPD diffractogram calculated from single-crystal data of O-acetyl psilocin phosphate Form A.

Form B of O-acetyl psilocin phosphate salt was not observed during the salt screen as a single crystalline phase. Thus, an XRPD pattern calculated from the single-crystal data was compared with patterns obtained for O-acetyl psilocin phosphate salt Form A, as well as a mixture of Forms A and B (FIG. 63). By visual comparison, the calculated pattern matches the peaks identified as Form B in the mixture of A+B. The observed peak shifting is due to the temperature difference at which the single crystal and X-ray powder diffraction data were collected.

XRPD analysis of calculated pattern of O-acetyl psilocin phosphate (Form B) (FIG. 63) shows characteristic peaks at 4.9° 2-Theta, 11.9° 2-Theta, and 14.6° 2-Theta; optionally with further characteristic peaks at 18.6° 2-Theta and 22.6° 2-Theta. A full list of calculated peaks is found in the following table:

| Angle 2-Theta (°) | Rel. Intensity (%) | Angle 2-Theta (°) | Rel. Intensity (%) |
|---|---|---|---|
| 4.9 | 92.3 | 11.9 | 62.3 |
| 10.9 | 4.7 | 14.6 | 19.2 |
| 14.8 | 68.8 | 29.4 | 8.3 |
| 17.0 | 20.8 | 30.0 | 5.7 |
| 17.1 | 20.5 | 30.2 | 5.0 |
| 17.7 | 9.3 | 30.7 | 0.7 |
| 18.6 | 42.3 | 31.8 | 1.6 |
| 19.6 | 14.1 | 31.9 | 2.1 |
| 19.9 | 3.3 | 32.4 | 5.3 |
| 21.1 | 1.8 | 32.8 | 4.0 |
| 21.8 | 1.4 | 33.0 | 2.9 |
| 22.6 | 100.0 | 33.3s | 15.7 |
| 22.9 | 49.8 | 33.6 | 3.0 |
| 23.4 | 62.3 | 34.0 | 2.1 |
| 23.8 | 41.2 | 34.1 | 2.9 |
| 24.1 | 13.4 | 34.4 | 10.8 |
| 24.3 | 7.8 | 34.7 | 9.3 |
| 24.4 | 8.2 | 35.2 | 5.1 |
| 24.9 | 18.4 | 35.8 | 7.4 |
| 25.2 | 2.8 | 36.3 | 3.3 |
| 26.3 | 40.3 | 36.9 | 5.5 |
| 26.7 | 1.9 | 37.6 | 10.3 |
| 27.1 | 1.4 | 37.9 | 1.9 |
| 27.4 | 7.3 | 38.1 | 2.0 |
| 27.6 | 8.5 | 38.3 | 5.4 |
| 28.1 | 9.9 | 38.6 | 2.9 |
| 28.3 | 7.5 | 39.0 | 0.8 |
| 28.8 | 10.2 | 39.5 | 3.1 |

Single Crystal Growth

Single crystals were grown from a filtrate (mother liquor) of a sample generated during a scale-up experiment. The original screen sample was prepared as follows:

To a solution of O-acetyl psilocin (270.7 mg) in 8 mL of 2-MeTHF was added phosphoric acid (125.1 mg, approx. 1 molar eq, diluted in 1 mL of 2-MeTHF) upon stirring. A white precipitate formed immediately with some tacky solids observed on the bottom of the flask, and the sample was transferred to stir in a freezer overnight. The solid was isolated by vacuum filtration, washed with 2-MeTHF (2 mL) and air-dried on filter. The mother liquor was transferred to a clean vial and allowed to evaporate slowly. After a few days, the sample was found to contain a few single crystals of sufficient size and quality.

Single Crystal X-ray Structure Determination

A colourless plate-shaped crystal of sample prepared above with formula $C_{14}H_{19}N_2O_2 \times H_2O_4P$ having approximate dimensions of 0.21×0.10×0.03 mm was mounted on a Mitegen micromesh mount in a random orientation. The crystal was flash cooled to 150(2) K and data were collected on a Bruker AXS D8 Quest four circle diffractometer with an I-mu-S microsource X-ray tube using a laterally graded multilayer (Goebel) mirror as monochromator and a PhotonIII_C14 charge-integrating and photon counting pixel array detector. The diffractometer was equipped with a low temperature device and used CuK$_\alpha$ radiation, (λ=1.54178 Å). All data were integrated with SAINT and a multi-scan absorption correction using SADABS was applied. The structure was solved by dual methods using SHELXT and refined by full-matrix least-squares methods against by SHELXL-2018/3 using ShelXle.

Carbon bound hydrogen atoms were refined isotropically on calculated positions using a riding model with their $U_{iso}$ values constrained to 1.5 times the $U_{eq}$ of their pivot atoms for terminal sp$^3$ carbon atoms and 1.2 times for all other carbon atoms. Positions of nitrogen and oxygen bound H atoms were refined isotropically with their $U_{iso}$ values constrained to 1.5 times the $U_{eq}$ of their pivot atoms.

This report and the CIF file were generated using FinalCif.

Crystal data and data collection parameters are given in Table 27.

TABLE 27

Crystal data and structure refinement

| | |
|---|---|
| Empirical formula | $C_{14}H_{21}N_2O_6P$ |
| Moiety formula | $C_{14}H_{19}N_2O_2 \times H_2O_4P$ |
| Formula weight | 344.30 |
| Temperature [K] | 150(2) |
| Crystal system | monoclinic |
| Space group (number) | C2/c (15) |
| a [Å] | 16.2887(3) |
| b [Å] | 5.51730(10) |
| c [Å] | 35.7125(7) |
| α [°] | 90 |
| β [°] | 91.0140(8) |
| γ [°] | 90 |
| Volume [Å$^3$] | 3208.97(10) |
| Z | 8 |
| $\rho_{calc}$ [gcm$^{-3}$] | 1.425 |
| μ [mm$^{-1}$] | 1.825 |
| F(000) | 1456 |
| Crystal size [mm$^3$] | 0.210 × 0.100 × 0.030 |
| Crystal colour | colourless |
| Crystal shape | plate |
| Radiation | CuK$_\alpha$ (λ = 1.54178 Å) |
| 2θ range [°] | 4.95 to 158.99 (0.78 Å) |
| Index ranges | −15 ≤ h ≤ 20 |
| | −6 ≤ k ≤ 6 |
| | −44 ≤ l ≤ 45 |
| Reflections collected | 16031 |
| Independent reflections | 3363 |
| | $R_{int}$ = 0.0374 |
| | $R_{sigma}$ = 0.0262 |

TABLE 27-continued

| Crystal data and structure refinement | |
|---|---|
| Completeness to θ = 25.242° | 99.4% |
| Data/Restraints/Parameters | 3363/0/223 |
| Goodness-of-fit on $F^2$ | 1.051 |
| Final R indexes [I ≥ 2σ(I)] | $R_1$ = 0.0308 |
| | $wR_2$ = 0.0770 |
| Final R indexes [all data] | $R_1$ = 0.0361 |
| | $wR_2$ = 0.0803 |
| Largest peak/hole [eÅ$^{-3}$] | 0.25/−0.38 |

X-Ray Powder Diffraction (XRPD)

The Rigaku SmartLab X-ray diffractometer was configured in Bragg-Brentano reflection geometry equipped with a beam stop and knife edge to reduce incident beam and air scatter. Data collection parameters are shown in the following table:

| Parameter | Value | Parameter | Value |
|---|---|---|---|
| Geometry | Bragg-Brentano | Receiving Slit 1 (mm) | 18 |
| Tube Anode | Cu | Receiving Slit 2 (mm) | open |
| Tube Type | Long Fine Focus | Start Angle 2θ (°) | 2 |
| Tube Voltage (kV) | 40 | End Angle 2θ (°) | 40 |
| Tube Current (mA) | 44 | Step Size (°) | 0.02 |
| Detector | HyPix-3000 | Scan Speed (°/min) | 6 |
| Monochromator | Ni foil Cu Kβ Filter | Spinning (rpm) | 11 |
| Incident Slit (°) | ⅓ | Sample Holder | Low-background Si |

Example 11: Single Crystal Structure of O-Acetyl Psilocin Hydrochloride (Form A)

The crystal structure of O-acetyl psilocin hydrochloride salt (Form A) was solved. The structure was determined to be anhydrous and unsolvated, 1:1 O-acetyl psilocin:HCl salt with formula $C_{14}H_{19}N_2O_2 \cdot Cl$. The calculated powder pattern from the single crystal data matched the X-ray powder diffraction (XRPD) pattern of the bulk sample. Unit cell parameters are shown in Table 28.

TABLE 28

| Unit cell parameters of O-acetyl psilocin hydrochloride Form A | |
|---|---|
| Crystal system, space group | Orthorhombic |
| Space group (number) | Pbca (61) |
| Data collection temperature (K) | 150(2) |
| a (Å) | 8.9824(3) |
| b (Å) | 10.8111(3) |
| c (Å) | 30.3980(9) |
| α [°] | 90 |
| β [°] | 90 |
| γ [°] | 90 |
| volume (Å$^3$) | 2951.94(16) |
| Z | 8 |

Figure 64:
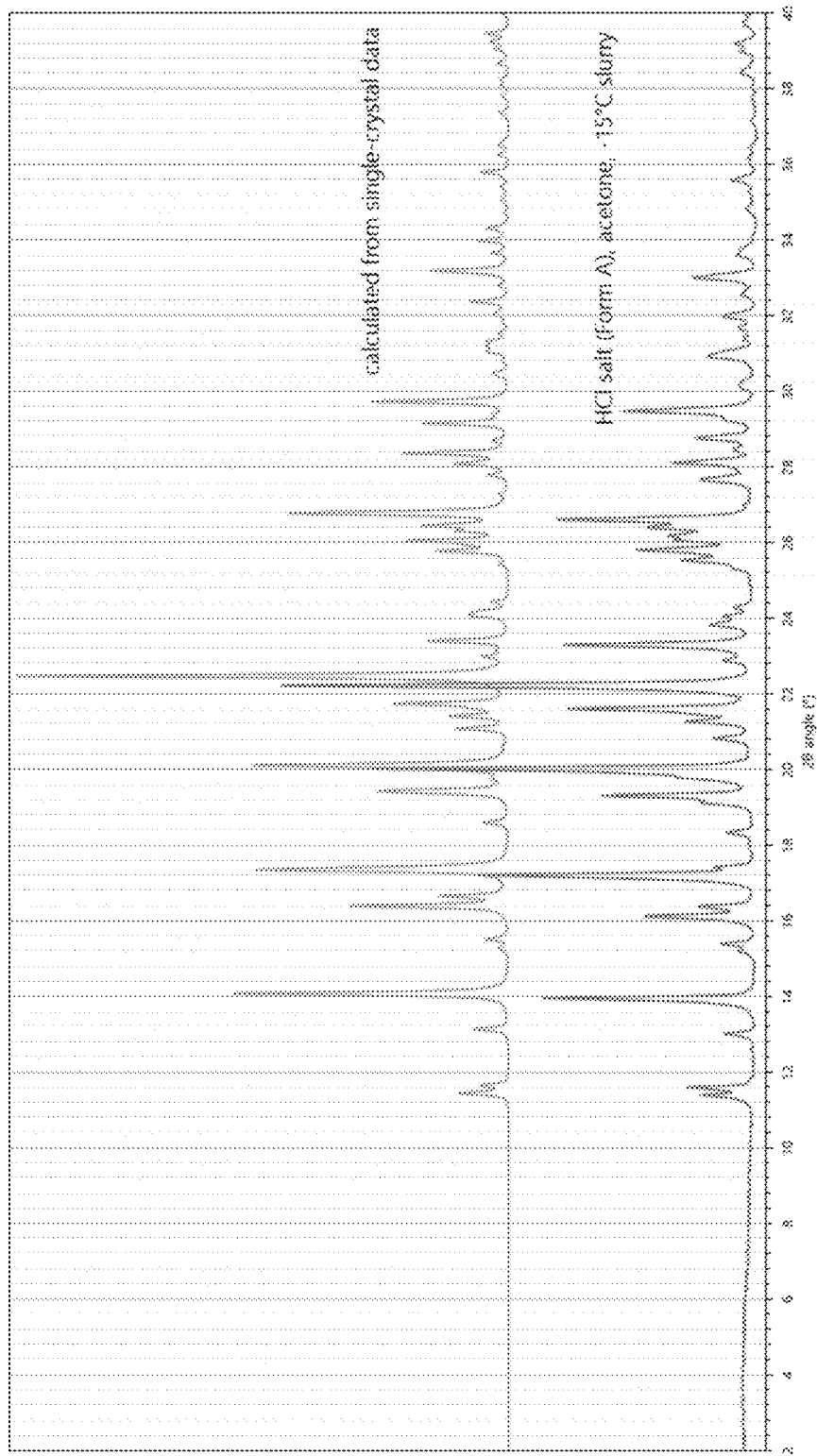
FIG. 64 provides an overlay plot of an XRPD diffractogram of O-acetyl psilocin hydrochloride Form A with an XRPD diffractogram calculated from single-crystal data.

The XRPD pattern calculated from the single-crystal data is overlaid with a pattern obtained for O-acetyl psilocin hydrochloride (Form A) in (FIG. 64), and overall matches the XRPD pattern of the bulk material. The observed peak shifting is due to the temperature difference at which the single crystal and X-ray powder diffraction data were collected.

XRPD analysis of calculated pattern of O-acetyl psilocin hydrochloride (Form A) (FIG. 64) shows characteristic peaks at 11.4° 2-Theta, 11.6° 2-Theta, and 14.1° 2-Theta; optionally with further characteristic peaks at 16.4° 2-Theta and 17.3° 2-Theta. A full list of calculated peaks is found in the following table:

| Angle 2-Theta (°) | Rel. Intensity (%) | Angle 2-Theta (°) | Rel. Intensity (%) |
|---|---|---|---|
| 11.4 | 10.3 | 28.7 | 3.6 |
| 11.6 | 6.0 | 29.1 | 17.6 |
| 13.1 | 7.3 | 29.4 | 3.3 |
| 14.1 | 56.3 | 29.7 | 28.3 |
| 15.3 | 2.3 | 30.5 | 3.4 |
| 15.5 | 4.8 | 30.8 | 1.3 |
| 16.4 | 32.6 | 31.0 | 4.7 |
| 16.6 | 14.3 | 31.2 | 5.2 |
| 17.3 | 51.5 | 31.3 | 4.6 |
| 18.6 | 5.4 | 31.5 | 2.1 |
| 19.4 | 26.9 | 31.8 | 1.2 |
| 19.8 | 3.8 | 32.0 | 3.5 |
| 20.1 | 52.2 | 32.2 | 2.1 |
| 20.6 | 1.3 | 32.4 | 8.1 |
| 21.1 | 11.0 | 32.8 | 2.2 |
| 21.4 | 12.2 | 33.2 | 16.0 |
| 21.6 | 8.6 | 33.7 | 3.5 |
| 21.7 | 23.9 | 34.0 | 6.3 |
| 22.5 | 100.0 | 34.3 | 4.6 |
| 23.0 | 5.6 | 34.7 | 0.9 |
| 23.2 | 2.8 | 35.1 | 1.8 |
| 23.4 | 16.4 | 35.4 | 1.8 |
| 24.1 | 8.3 | 35.6 | 1.5 |
| 24.1 | 7.4 | 35.8 | 5.7 |
| 24.4 | 3.4 | 36.2 | 2.2 |
| 25.4 | 2.2 | 36.5 | 2.0 |
| 25.8 | 14.6 | 36.6 | 1.5 |
| 25.9 | 9.6 | 37.2 | 0.5 |
| 26.0 | 21.0 | 37.4 | 2.0 |
| 26.3 | 10.7 | 37.8 | 1.5 |
| 26.4 | 18.1 | 38.1 | 1.8 |
| 26.8 | 44.9 | 38.2 | 2.1 |
| 27.3 | 2.0 | 38.7 | 2.6 |
| 27.8 | 4.4 | 39.0 | 2.8 |
| 28.1 | 11.4 | 39.2 | 4.2 |
| 28.4 | 21.6 | 39.5 | 4.9 |

Single Crystal Growth

O-acetyl psilocin hydrochloride (1-2 mg) in an open vial was placed inside a 75% RH jar (hygroscopicity test). Solids deliquesced within approx. 1 hour of exposure to elevated relative humidity. The sample was capped and placed in a freezer for storage. In about 4 months, the sample was found to contain a small agglomerate with single crystals of sufficient size and quality.

Single Crystal X-ray Structure Determination

A colourless needle-shaped crystal of sample prepared above with formula $C_{14}H_{19}N_2O_2$—Cl having approximate dimensions of 0.040×0.060×0.330 mm was mounted on a Mitegen micromesh mount in a random orientation. Data were collected from a shock-cooled single crystal at 150(2) K on a Bruker AXS D8 Quest four circle diffractometer with an I-mu-S microsource X-ray tube using a laterally graded multilayer (Goebel) mirror as monochromator and a PhotonIII_C14 charge-integrating and photon counting pixel array detector. The diffractometer used CuK$_\alpha$ radiation (λ=1.54178 Å). All data were integrated with SAINT V8.40B and a multi-scan absorption correction using SADABS 2016/2 was applied. The structure was solved by dual methods with SHELXT and refined by full-matrix least-squares methods against F using SHELXL-2018/3. All non-hydrogen atoms were refined with anisotropic displacement parameters. Hydrogen atoms were refined isotropically on calculated positions using a riding model. Methyl H atoms were allowed to rotate but not to tip to best fit the experimental electron density. $U_{iso}$ values were constrained to 1.5 times the $U_{eq}$ of their pivot atoms methyl carbon atoms and to 1.2 times for all other hydrogen atoms.

This report and the CIF file were generated using FinalCif.

Crystal data and data collection parameters are given in Table 29.

TABLE 29

| Crystal data and structure refinement | |
|---|---|
| Empirical formula | $C_{14}H_{19}ClN_2O_2$ |
| Moiety formula | $C_{14}H_{19}N_2O_2 \cdot Cl$ |
| Formula weight | 282.76 |
| Temperature [K] | 150(2) |
| Crystal system | orthorhombic |
| Space group (number) | Pbca (61) |
| a [Å] | 8.9824(3) |
| b [Å] | 10.8111(3) |
| c [Å] | 30.3980(9) |
| α [°] | 90 |
| β [°] | 90 |
| γ [°] | 90 |
| Volume [Å$^3$] | 2951.94(16) |
| Z | 8 |
| $\rho_{calc}$ [gcm$^{-3}$] | 1.272 |
| μ [mm$^{-1}$] | 2.294 |
| F(000) | 1200 |
| Crystal size [mm$^3$] | 0.040 × 0.060 × 0.330 |
| Crystal colour | colourless |
| Crystal shape | needle |
| Radiation | CuK$_\alpha$ (λ = 1.54178 Å) |
| 2θ range [°] | 5.81 to 158.88 (0.78 Å) |
| Index ranges | −11 ≤ h ≤ 11 |
| | −13 ≤ k ≤ 7 |
| | −30 ≤ l ≤ 38 |
| Reflections collected | 14771 |
| Independent reflections | 3048 |
| | $R_{int}$ = 0.0461 |
| | $R_{sigma}$ = 0.0347 |
| Completeness to θ = 25.242° | 98.2% |
| Data/Restraints/Parameters | 3048/0/175 |
| Goodness-of-fit on $F_2$ | 1.018 |
| Final R indexes [I ≥ 2σ(I)] | $R_1$ = 0.0360 |
| | $wR_2$ = 0.0884 |
| Final R indexes [all data] | $R_1$ = 0.0476 |
| | $wR_2$ = 0.0963 |
| Largest peak/hole [eÅ$^{-3}$] | 0.19/−0.22 |

X-ray Powder Diffraction (XRPD)

The Rigaku SmartLab X-ray diffractometer was configured in Bragg-Brentano reflection geometry equipped with a beam stop and knife edge to reduce incident beam and air scatter. Data collection parameters are shown in the following table:

| Parameter | Value | Parameter | Value |
|---|---|---|---|
| Geometry | Bragg-Brentano | Receiving Slit 1 (mm) | 18 |
| Tube Anode | Cu | Receiving Slit 2 (mm) | open |
| Tube Type | Long Fine Focus | Start Angle 2θ (°) | 2 |
| Tube Voltage (kV) | 40 | End Angle 2θ (°) | 40 |
| Tube Current (mA) | 44 | Step Size (°) | 0.02 |
| Detector | D/teX Ultra 250 | Scan Speed (°/min) | 6 |
| Monochromator | Ni foil Cu Kβ Filter | Spinning (rpm) | 11 |
| Incident Slit (°) | ⅓ | Sample Holder | Low-background Si |

Example 12: Polymorph Production of O-Acetylpsilocin-Fumarate

The active pharmaceutical ingredient (API), O-acetylpsilocin-fumarate, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the API is a solvate or hydrate, and to evaluate thermal stability. DVS data are used to evaluate hygroscopicity of the API and if hydrates can be formed at high relative humidity.

Figure 65:
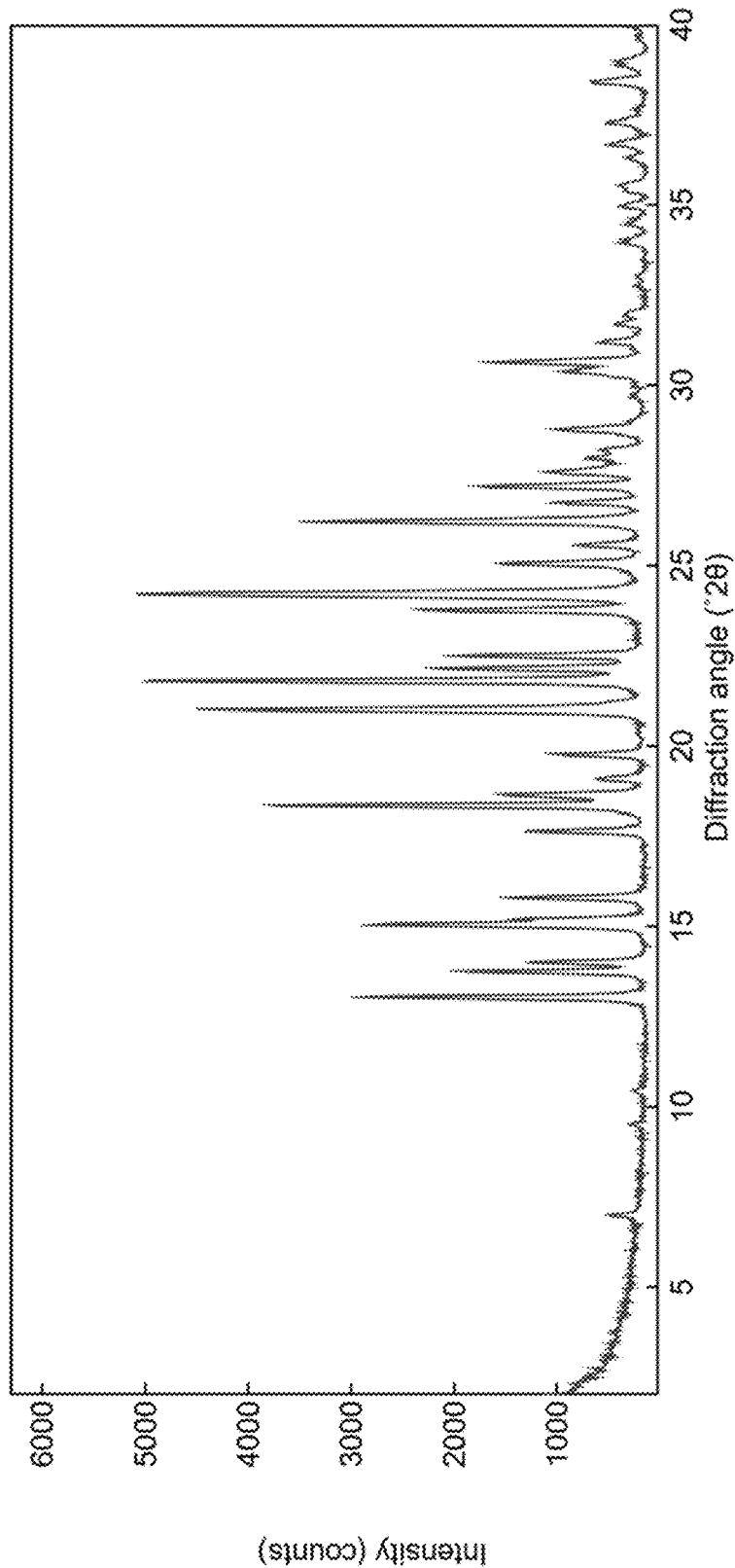
FIG. 65 provides an XRPD pattern of O-acetylpsilocin fumarate Form A.

XRPD characterization of a crystalline O-acetylpsilocin-fumarate produced by the present inventors resulted in the XRPD pattern illustrated in FIG. 65. The form characterized in FIG. 65 is designated as Form A herein. TGA of the Form A material showed only a negligible weight loss. A sharp, intense endotherm at 177° C. in the DSC thermogram is attributed to melting—decomposition is observed above about 180° C. Based on DVS data, Form A is non-hygroscopic as it exhibited approx. 0.1% water uptake in the range between 5-95% relative humidity and all the moisture is lost upon desorption.

About 10 to 15 solvents may be selected from the list below, based on their properties (polarity, dielectric constant and dipole moment).

TABLE 30

| Solvents | |
|---|---|
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |
| 2-ethoxyethanol (Cellusolve) | 1,1,1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water.

As above, Form A is further assessed for solubility: The experiments were carried out by adding the test solvent in aliquots to weighed portions of solid. Whether dissolution had occurred is judged by visual inspection after addition of each solvent aliquot. The results are shown in Table 31. Solubility is calculated by dividing the weight of the sample by the total amount of solvent used to dissolve the sample. As understood by those of skill in the art, the actual solubilities may be greater than the numbers calculated because of the use of solvent aliquots that were too large or because of slow dissolution rates. The solubility number is expressed as "less than" if dissolution did not occur during the experiment. The solubility number is expressed as "greater than or equal to" if dissolution occurred on addition of the first solvent aliquot. All solubility measurements were carried out at room temperature unless noted otherwise.

TABLE 31

| Solvent | Solubility(mg/mL) |
| --- | --- |
| acetone | <1 |
| acetonitrile (ACN) | <1 |
| dichloromethane (DCM) | <1 |
| 1,4-dioxane | <1 |
| ethanol (EtOH) | 2 |
| ethyl acetate (EtOAc) | <1 |
| hexanes | <1 |
| methanol (MeOH) | 2 |
| 2-propanol (2-PrOH) | 1 |
| tetrahydrofuran (THF) | 1 |
| toluene | <1 |
| water | 11 |
| 95:5 acetone: water | 10 |
| 95:5 ACN: water | 12 |
| 95:5 1,4-dioxane:water | 3 |
| 95:5 EtOH:water | 9 |
| 95:5 MeOH:water | >26 |
| 95:5 IPA:water | 4 |
| 95:5 THF:water | >17 |
| 70:30 acetone: water | >51 |
| 70:30 ACN: water | >75 |
| 50:50 MeOH: water | >33 |
| 50:50 THF: water | >55 |

The techniques used for the polymorph screen are chosen based on the solvent selected and properties of the API. The following techniques (or a combination of techniques) may be used for the polymorph screening:

API is dissolved in a solvent or mixture of solvents, and the solvents are evaporated at different rates (slow evaporation or fast evaporation) and at different temperatures (ambient or elevated).

API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling.

The solids formed will be recovered by filtration and dried (air dried or vacuum dried).

API is dissolved in a solvent or mixture of solvents, and an antisolvent is added to precipitate the salt. The solids formed will be recovered by filtration and dried (air dried or vacuum dried).

API is added to a solvent or mixture of solvents, where the API is not fully dissolved. The slurry will be agitated at different temperatures for a number of days. The solids formed will be recovered by filtration and (air dried or vacuum dried).

API is milled (by mechanical milling or by mortar and pestle), with a drop of solvent, or without any solvent.

API is melted and cooled (at different cooling rates, fast and slow, and cooled to different temperatures) to obtain solids.

API is suspended in a solvent or mixture of solvents, and the slurry is placed in a heating/cooling cycle for multiple cycles. The remaining solids after the final cooling cycle will be filtered and (air dried or vacuum dried).

API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.

API is exposed to elevated humidity (or elevated temperature, or combination thereof), or to solvent vapors for extended period of days.

Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).

API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Consistent with the polymorph screen described above, O-acetylpsilocin fumarate is mixed with various solvents under various conditions in attempts to generate polymorphs. The results from samples generated and analyzed are summarized in Table 32.

TABLE 32

| Method | Solvent | Conditions[a] | XRPD Pattern[b] |
| --- | --- | --- | --- |
| Input Material | | | A (FIG. 65) |
| Cooling | acetone | 60° C.→RT | A |
| | MeOH | 60° C.→RT | A |
| | EtOH | 60° C.→RT | A |
| | 2-propanol | 60° C.→RT | A |
| | THF | 60° C.→2° C. | A |
| Evaporation | acetone | Open vial, RT | A |
| | EtOH | Open vial, RT | A |
| | MeOH | Open vial, RT | A |

TABLE 32-continued

| Method | Solvent | Conditions[a] | XRPD Pattern[b] |
|---|---|---|---|
|  | 2-propanol | Open vial, RT | A |
|  | THF | Open vial, RT→oil. Added hexanes, SL, RT |  |
|  | water | Open vial, RT; | B (FIG. 66) |
|  |  | Reanalyzed after RT storage, 37 days; | B (FIG. 67) |
|  |  | Reanalyzed after RT storage, ~7 months | B |
|  |  | Open vial, RT; | A (PO) |
|  |  | VO, 4 days | A |
|  |  | Open vial, RT; | A (PO) |
|  |  | stressing at 94% RH/1 d | A |
|  |  | Open vial, RT; | A (PO) |
|  |  | seeded with Form B | A (PO) + weak peaks |
|  |  | "Flash" evaporation in a stream of dry air, seeded with Form B: single crystals | A + weak peaks |
|  |  | Soln stored capped RT/1 d → open vial: single crystals | A (PO) |
|  | 1,4-dioxane | Open vial, RT | A |
|  | 95:5 acetone:H2O | Vial covered with foil with pinholes, RT | A (PO) |
|  | 95:5 ACN:H2O | Vial covered with foil with pinholes, RT | A (PO) |
|  | 95:5 MeOH:H2O | Vial covered with foil with pinholes, RT | A (PO) |
|  | 95:5 THF:H2O | Vial covered with foil with pinholes, RT | A (PO) |
|  | Acetone/water (70:30) | Open vial, RT | A (PO) |
|  | ACN/water (70:30) | Open vial, RT | A (PO) |
|  | MeOH/water (50:50) | Open vial, RT | A (PO) |
|  | THF/water (50:50) | Open vial, RT | A (PO) |
| Slurry | DCM | RT, 7 days | A |
|  | ACN | RT, 7 days | A |
|  | hexanes | RT, 7 days | weak A pks + strong 18° pk |
|  | EtOAc | RT, 7 days | A |
|  | toluene | RT, 7 days | weak A pks + strong 18° pk |
|  | acetone | RT, 7 days | A |
|  | EtOH | RT, 7 days | A |
|  | MeOH | RT, 7 days | A |
|  | 2-propanol | RT, 7 days | A |
|  | THF | RT, 7 days | A |
|  | 1,4-dioxane | RT, 7 days | A |
|  | 1:1 EtOH:ACN | 50° C., 7 days | A |
|  | 95:5 1,4-dioxane:H2O | RT, 6 days | A |
|  | 95:5 EtOH:H2O | RT, 6 days | A |
|  | 95:5 IPA:H2O | RT, 6 days | A |
|  | 1:1 MeOH:DCE | 50° C.→RT, 6 days | A |
|  | 1:1 IPA:toluene | 50° C., 7 days | A |
|  | water | RT, 7 days | A |
| Grind | H2O | 30 min, 100% power | A |
|  | EtOH | 30 min, 100% power | A |
|  | Acetone | 30 min, 100% power | A |
|  | ACN | 30 min, 100% power | A |
| Antisolvent Precipitation | Water | RT→−15° C., ACN, no solids, FE: single crystals present | A (PO) |

Figure 66:
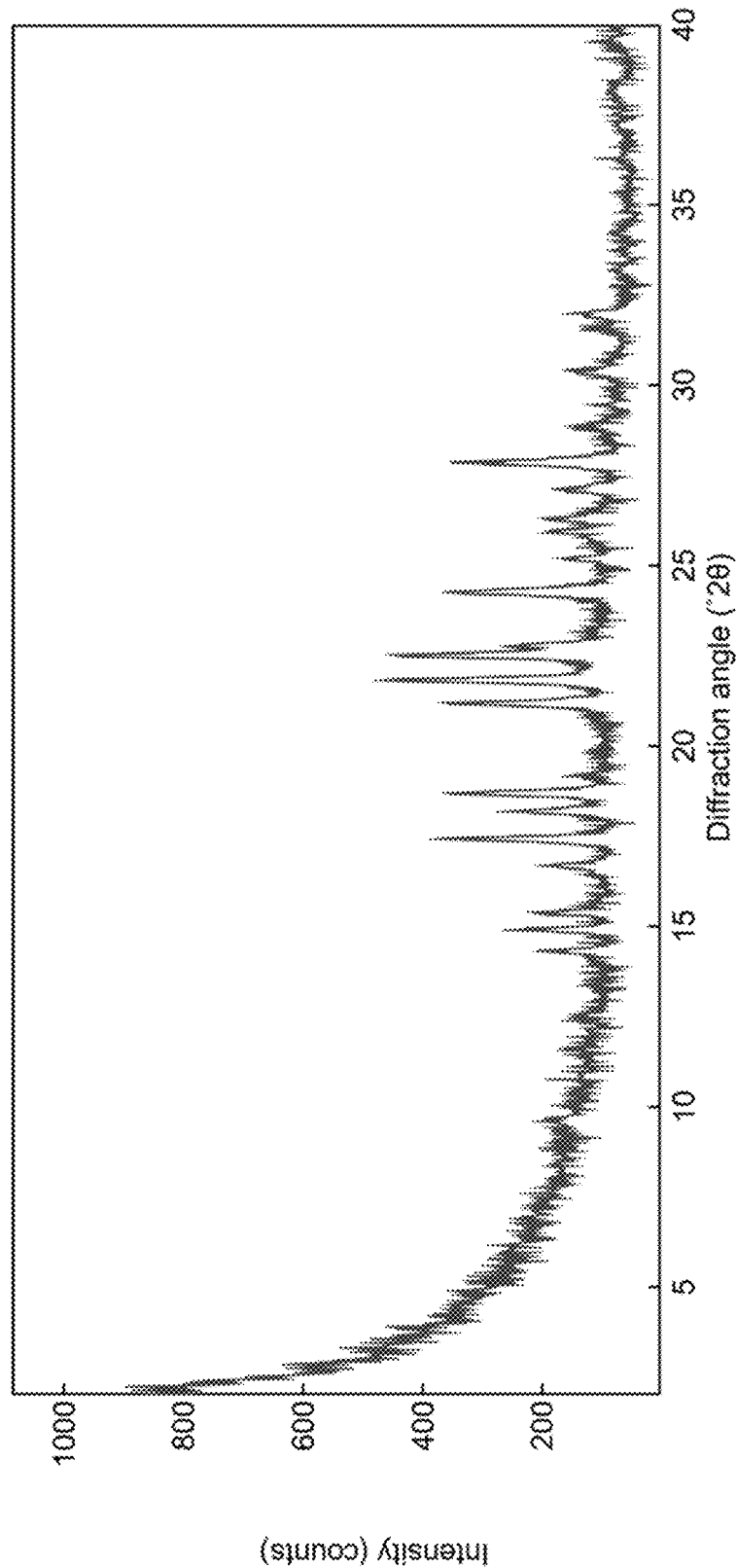
FIG. 66 provides an XRPD pattern of O-acetylpsilocin fumarate Form B.
Figure 67:
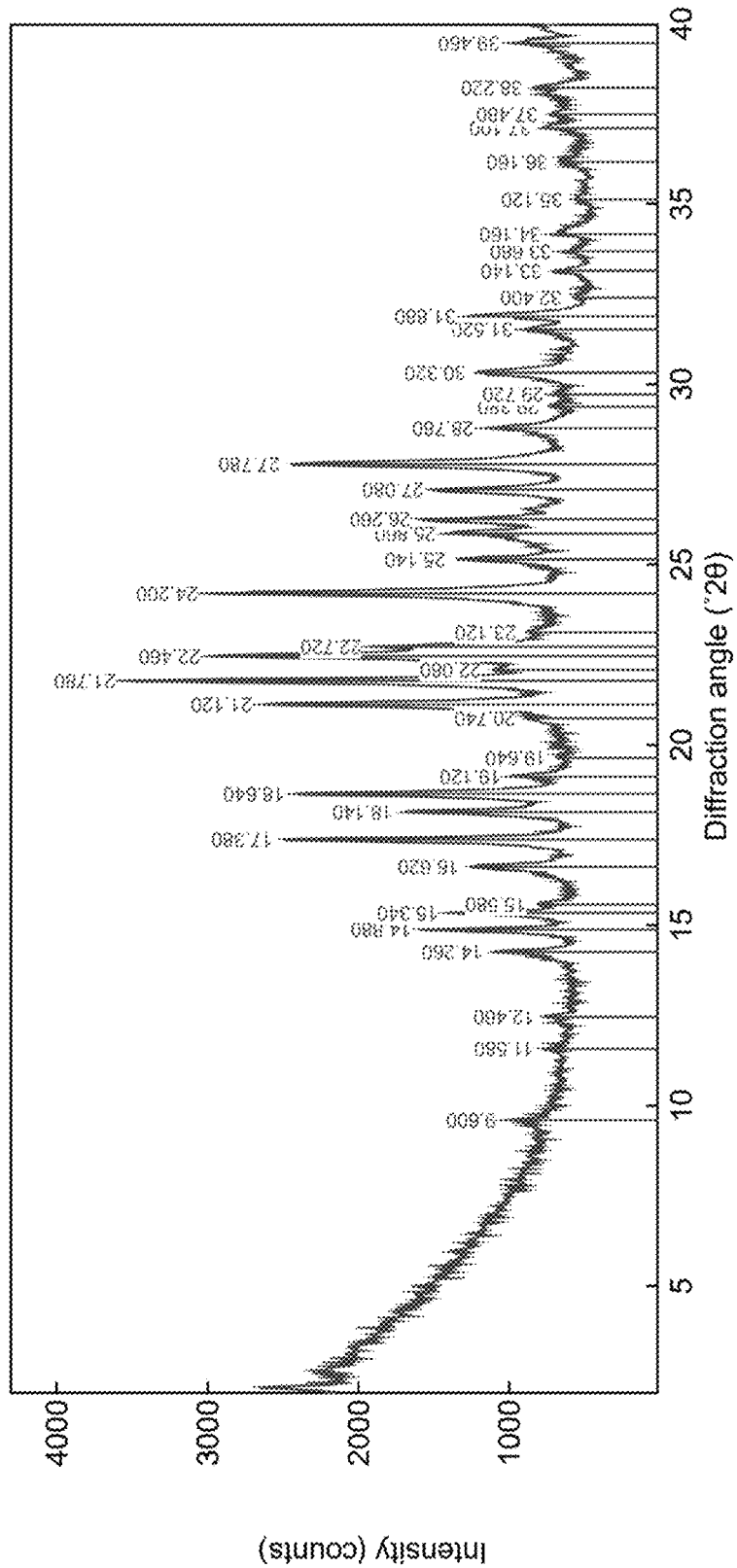
FIG. 67 provides an XRPD pattern of O-acetylpsilocin fumarate Form B.
Figure 68:
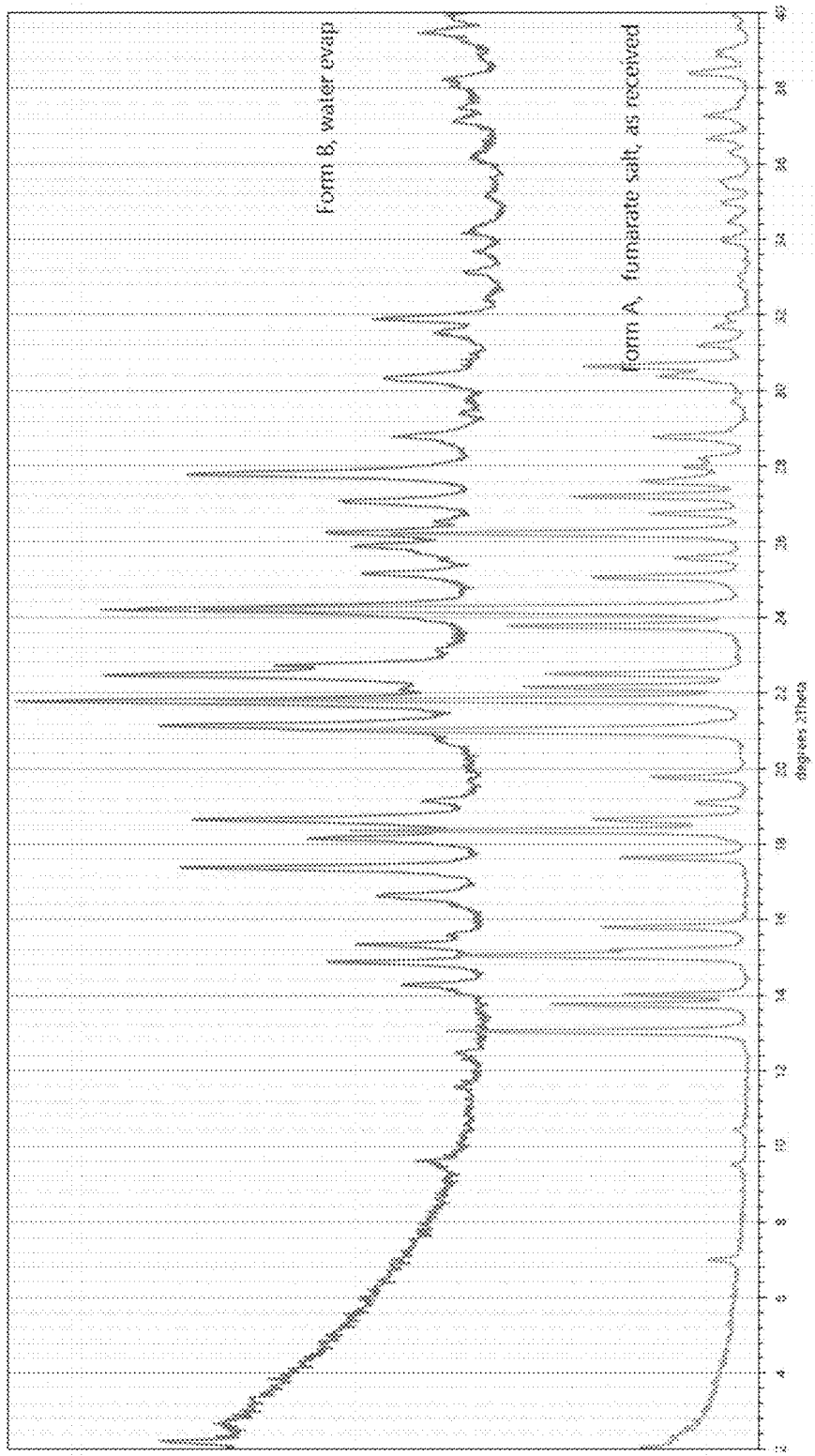
FIG. 68 provides an overlay of the XRPD patterns provided in FIG. 65 and FIG. 66, with the top pattern being from FIG. 66 and the bottom being from FIG. 65.
Figure 69:
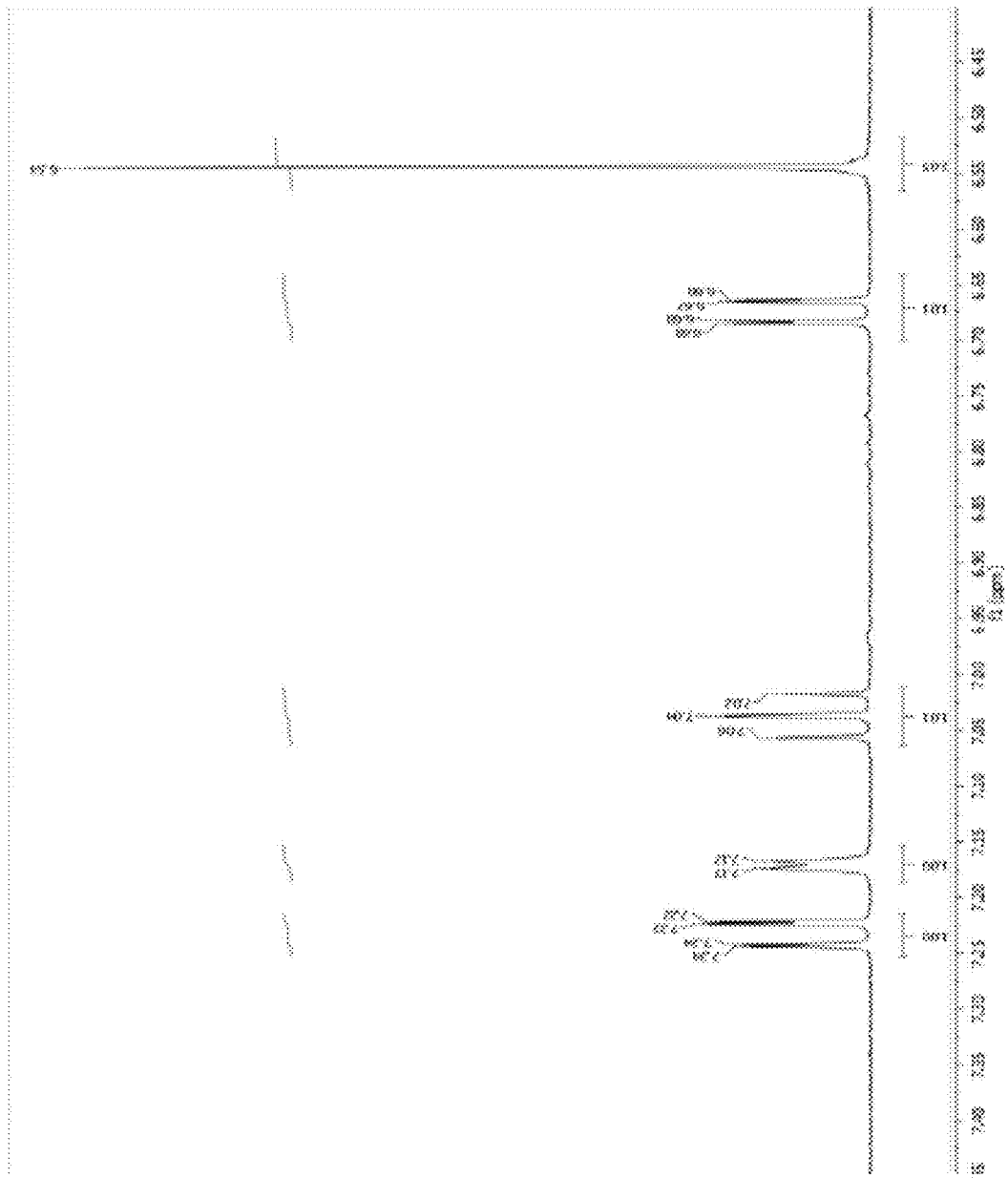
FIG. 69 provides a partial 1H NMR spectrum of O-acetylpsilocin fumarate Form B.
Figure 70:
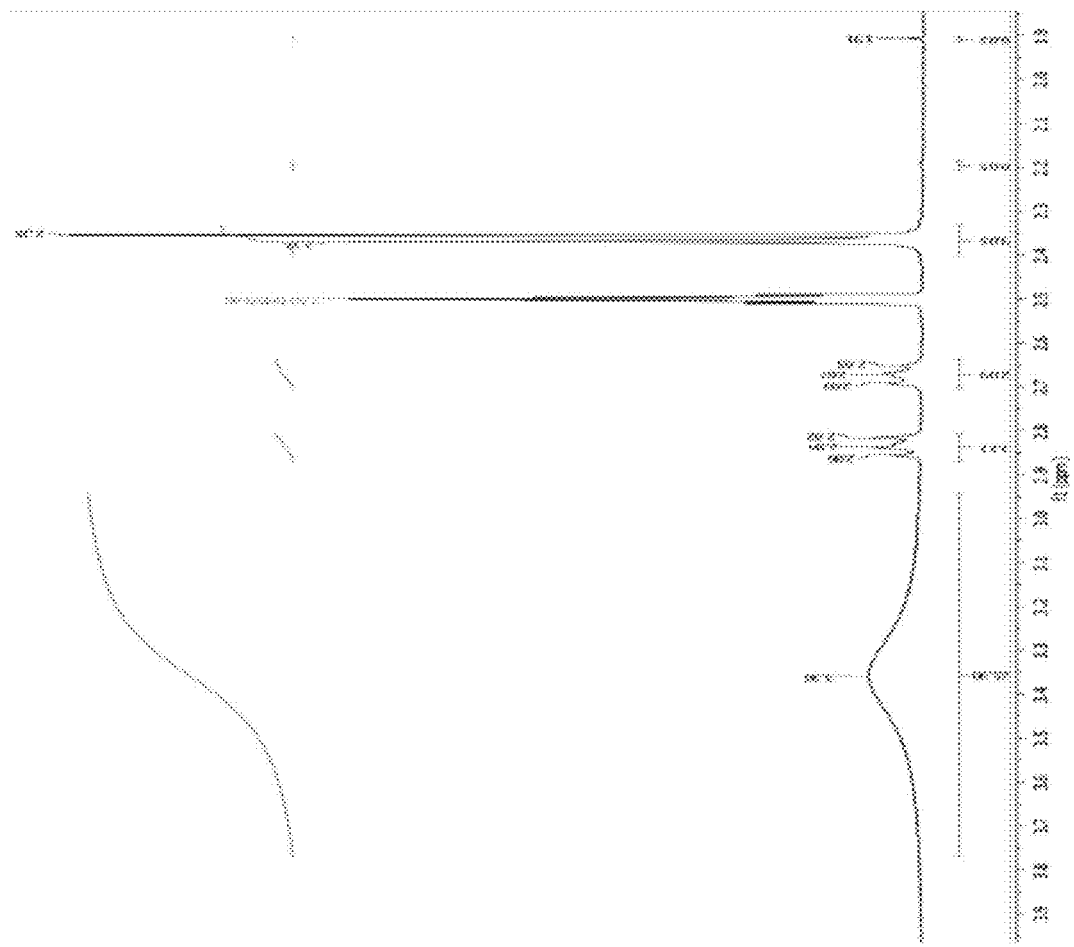
FIG. 70 provides a partial 1H NMR spectrum of O-acetylpsilocin fumarate Form B.

[a]ACN = acetonitrile;
FE = fast evaporation;
IS = insufficient solids;
RT = room temperature;
SL = slurry
[b]PO = preferred orientation;
pks = peaks As illustrated in the data provided above, two polymorphs of O-acetylpsilocin fumarate have been identified. They were designated as Form A (FIG. 65) and Form B (FIGS. 66-67). Form B was further characterized by proton NMR, which provided a spectrum consistent with O-acetylpsilocin fumarate. This spectrum is provided in FIGS. 69 and 70.

XRPD analysis of O-acetyl psilocin fumarate (Form A) (FIG. 65) shows characteristic peaks at 7.0±0.2° 2-Theta, 13.0±0.2° 2-Theta, and 13.8±0.2° 2-Theta; optionally with further characteristic peaks at 15.0±0.2° 2-Theta and 18.4±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) |
| --- | --- |
| 7.0 | 9.9 |
| 9.5 | 5.7 |
| 10.4 | 5.2 |
| 13.0 | 56.6 |
| 13.8 | 38.1 |
| 14.0 | 24.8 |
| 15.0 | 55.1 |
| 15.8 | 28.9 |
| 17.6 | 25.6 |
| 18.4 | 73.9 |
| 18.7 | 30.5 |
| 19.1 | 12.1 |
| 19.8 | 20.1 |
| 21.0 | 86.4 |
| 21.8 | 97.9 |
| 22.2 | 43.1 |
| 22.5 | 39.1 |
| 23.8 | 45.7 |
| 24.2 | 100.0 |
| 25.1 | 30.7 |
| 25.6 | 15.9 |
| 26.2 | 66.7 |
| 26.7 | 20.2 |
| 27.2 | 34.4 |
| 27.6 | 21.8 |
| 28.0 | 14.1 |
| 28.2 | 11.5 |
| 28.8 | 19.8 |
| 29.7 | 5.6 |
| 30.4 | 18.8 |
| 30.6 | 32.4 |
| 31.2 | 11.9 |
| 31.7 | 8.8 |
| 32.0 | 6.8 |
| 32.8 | 4.6 |
| 33.0 | 4.6 |
| 33.9 | 7.6 |
| 34.4 | 6.5 |
| 34.9 | 7.5 |
| 35.5 | 7.9 |
| 36.3 | 6.4 |
| 36.7 | 10.0 |
| 37.3 | 10.4 |
| 38.4 | 13.2 |
| 38.9 | 8.4 |
| 39.0 | 8.6 |

XRPD analysis of O-acetyl psilocin fumarate (Form B) (FIG. 66) shows characteristic peaks at 14.9±0.2° 2-Theta, 17.4±0.2° 2-Theta, and 18.7±0.2° 2-Theta; optionally with further characteristic peaks at 21.2±0.2° 2-Theta and 21.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) |
| --- | --- |
| 9.6 | 43.5 |
| 11.6 | 33.2 |
| 12.6 | 30.6 |
| 14.3 | 41.9 |
| 14.9 | 53.3 |
| 15.4 | 44.2 |
| 16.7 | 41.6 |
| 17.4 | 79.7 |
| 18.2 | 55.5 |
| 18.7 | 74.5 |
| 19.2 | 31.8 |
| 21.2 | 76.0 |
| 21.8 | 100.0 |
| 22.5 | 96.3 |
| 22.8 | 53.4 |
| 24.3 | 76.9 |
| 25.2 | 35.1 |
| 25.9 | 40.2 |
| 26.3 | 41.4 |
| 27.1 | 36.6 |
| 27.9 | 71.7 |
| 28.9 | 30.7 |
| 29.5 | 23.9 |
| 30.4 | 31.7 |
| 31.6 | 25.4 |
| 32.0 | 32.1 |
| 38.2 | 19.2 |
| 39.5 | 19.1 |

XRPD analysis of O-acetyl psilocin fumarate (Form B) (FIG. 67) shows characteristic peaks at 14.9±0.2° 2-Theta, 17.4±0.2° 2-Theta, and 18.6±0.2° 2-Theta; optionally with further characteristic peaks at 21.1±0.2° 2-Theta and 21.8±0.2° 2-Theta, as measured with Cu Kα radiation. A full list of peaks is found in the following table. The 2-Theta peak values that are provided for the XRPD are within ±0.2° 2-Theta.

| Angle 2-Theta (°) | Rel. Intensity (%) |
| --- | --- |
| 9.6 | 28.6 |
| 11.6 | 21.5 |
| 12.5 | 21.3 |
| 14.3 | 31.0 |
| 14.9 | 44.4 |
| 15.3 | 39.4 |
| 15.6 | 22.9 |
| 16.6 | 35.5 |
| 17.4 | 70.5 |
| 18.1 | 47.9 |
| 18.6 | 68.3 |
| 19.1 | 27.6 |
| 19.6 | 19.1 |
| 20.7 | 24.9 |
| 21.1 | 74.4 |
| 21.8 | 100.0 |
| 22.1 | 31.4 |
| 22.5 | 84.2 |
| 22.7 | 53.8 |
| 23.1 | 24.8 |
| 24.2 | 84.6 |
| 25.1 | 38.0 |
| 25.9 | 39.8 |
| 26.3 | 44.6 |
| 27.1 | 42.2 |
| 27.8 | 69.2 |
| 28.8 | 32.8 |
| 29.4 | 20.5 |
| 29.7 | 19.6 |
| 30.3 | 34.3 |
| 31.5 | 25.5 |
| 31.9 | 36.2 |
| 32.4 | 16.3 |
| 33.1 | 19.9 |
| 33.7 | 18.2 |
| 34.2 | 20.2 |
| 35.1 | 16.2 |
| 36.2 | 18.8 |
| 37.1 | 22.1 |
| 37.5 | 20.8 |
| 38.2 | 23.7 |
| 39.5 | 28.0 |

Instrumental Techniques

The data summarized above were gathered as follows:

Although the following diffractometers were used, other types of diffractometers could be used. Furthermore, other wavelengths could be used and converted to the Cu Kα.

"Characteristic peaks", to the extent they exist, are a subset of observed peaks and are used to differentiate one crystalline polymorph from another crystalline polymorph (polymorphs being crystalline forms having the same chemical composition). Characteristic peaks are determined by evaluating which observed peaks, if any, are present in one crystalline polymorph of a compound against all other known crystalline polymorphs of that compound to within +0.2° 2-Theta.

For X-ray Powder Diffraction (XRPD), a Rigaku Smart-Lab X-ray diffraction system is configured for reflection Bragg-Brentano geometry using a line source X-ray beam. The X-ray source is a Cu Long Fine Focus tube that is operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample is analyzed from 2 to 40° 2θ using a continuous scan of 6° 2θ per minute with an effective step size of 0.02° 2θ.

Differential Scanning Calorimetry (DSC) analyses were carried out using a TA Instruments Q2500 Discovery Series instrument. The instrument temperature calibration is performed using indium. The DSC cell is kept under a nitrogen purge of ~50 mL per minute during each analysis. The sample is placed in a standard, crimped, aluminum pan and is heated from approximately 25° C. to 350° C. at a rate of 10° C. per minute.

Thermogravimetric (TG) analysis is carried out using a TA Instruments Q5500 Discovery Series instrument. The instrument balance is calibrated using class M weights and the temperature calibration is performed using alumel. The nitrogen purge is ~40 mL per minute at the balance and ~60 mL per minute at the furnace. Each sample is placed into a pre-tared platinum pan and heated from approximately 25° C. to 350° C. at a rate of 10° C. per minute.

Dynamic Vapor Sorption (DVS) analysis is carried out using a TA Instruments Q5000 Dynamic Vapor Sorption analyzer. The instrument is calibrated with standard weights and a sodium bromide standard for humidity. Approximately 10-25 mg of sample is loaded into a metal-coated quartz pan for analysis. The sample is analyzed at 25° C. with a maximum equilibration time of one hour in 10% relative humidity (RH) steps from 5 to 95% RH (adsorption cycle) and from 95 to 5% RH (desorption cycle). The movement from one step to the next occurred either after satisfying the equilibrium criterion of 0.01% weight change or, if the equilibrium criterion is not met, after one hour. The percent weight change values is calculated using Microsoft Excel.

Nuclear Magnetic Resonance (1H NMR) spectra are acquired on a Bruker Avance II 400 spectrometer. Samples are prepared by dissolving material in DMSO-d6 or other suitable deuterated solvent, such as D20 or deuterated methanol. The solutions were filtered and placed into individual 5-mm NMR tubes for subsequent spectral acquisition. The temperature controlled (295K) 1H NMR spectra acquired on the Avance II 400 utilized a 5-mm cryoprobe operating at an observing frequency of 400.18 MHz.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50(TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45° 2θ with steps of 0.1°, and the measuring time is 1.0 second/step. All samples are ground to similar size before exposure to radiation. The powder samples are illuminated using CuKα radiation ($\lambda=1.54056$ Å) at 30 kV and 15 mA.

Variable temperature XRPD data are collected using a Huber Imaging Plate Guinier Camera 670 employing Ni-filtered CuK$_{\alpha1}$ radiation ($\lambda=1.5405981$ Å) produced at 40 kV and 20 mA by a Philips PW 1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005° 2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

The XRPD diffractograms provided as Figures herein were produced using the Rigaku Smart-Lab X-ray diffraction system was configured for reflection Bragg-Brentano geometry using a line source X-ray beam. The X-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40° 2θ using a continuous scan of 6° 2θ per minute with an effective step size of 0.02° 2θ.

The TG analysis described in this Example was carried out using a TA Instruments Q5500 Discovery Series instrument. The instrument balance was calibrated using class M weights and the temperature calibration was performed using alumel. The nitrogen purge was ~40 mL per minute at the balance and ~60 mL per minute at the furnace. Each sample was placed into a pre-tared platinum pan and heated from approximately 25° C. to 350° C. at a rate of 10° C. per minute.

Examples 13-21: Psychedelic and 5-HT$_{2A}$ Antagonist Studies

Hallucinogen-Induced Head Twitches

Mice administered the hallucinogen, LSD, were reported to respond with rapid and violent head shaking that does not occur in normal mice. See, Keller and Umbreit, Science, 1956, 124: 723). This response was found to be remarkably consistent when scored by different observers across laboratories. The head-shake response is elicited by a wide variety of known hallucinogens such as LSD, psilocybin, psilocin, N,N-dimethyltryptamine (DMT), and mescaline as well as serotonin-releasing agents and direct 5-HT2 agonists. See, Canal and Morgan, Drug Test Anal., 2012, 4, 556-576 2012. 2,5-dimethoxy-4-iodoamphetamine (DOI) has also been reported to elicit head shakes in rats (see Arnt and Hyttel Eur. J. Pharmacol., 1989, 161:45; also see Kennett et al., Br. J. Pharmacol., 1994, 111: 797-802) and head-twitches in mice (see Darmani et al., Pharmacol. Biochem. Behav., 1990, 36: 901-606), both of which were blocked by administration of the fairly selective 5-HT2A antagonist ketanserin. Later studies have confirmed 5-HT2A receptors are the primary, direct mediators of the response and that the headshake response in rats is essentially the same as head-twitches in mice, at least in regards to similarity in appearance and 5-HT2A receptor dependence. See, Canal and Morgan, Drug Test Anal., 2012, 4, 556-576 2012. The head twitch and head shake response in mice and rats have therefore been widely used to explore the effect of treatments on 5-HT$_{2A}$ receptors in vivo.

Animals for all Studies

Male C57BL/6J mice (approximately 25 g) were group housed. Animals were maintained under a 12 h light/dark cycle, at 23° C. with humidity controlled.

Example 13: Comparison of Psilocybin Induced Head Twitches in Mice with and without Administration of Volinanserin after T=8 Minutes Formulation Psilocybin was formulated in saline at a concentration of 0.4 mg/mL to give a dose of 2 mg/kg when administered i.p. in a 5 mL/kg dosing volume. Volinanserin HCl (91.1% free base content) was dissolved in Vehicle 1 (saline) at concentrations of 0.2 mg/ml to give a dose of 1 mg/kg when administered i.v. in a 5 mL/kg dosing volume.

Procedure

Figure 71A:
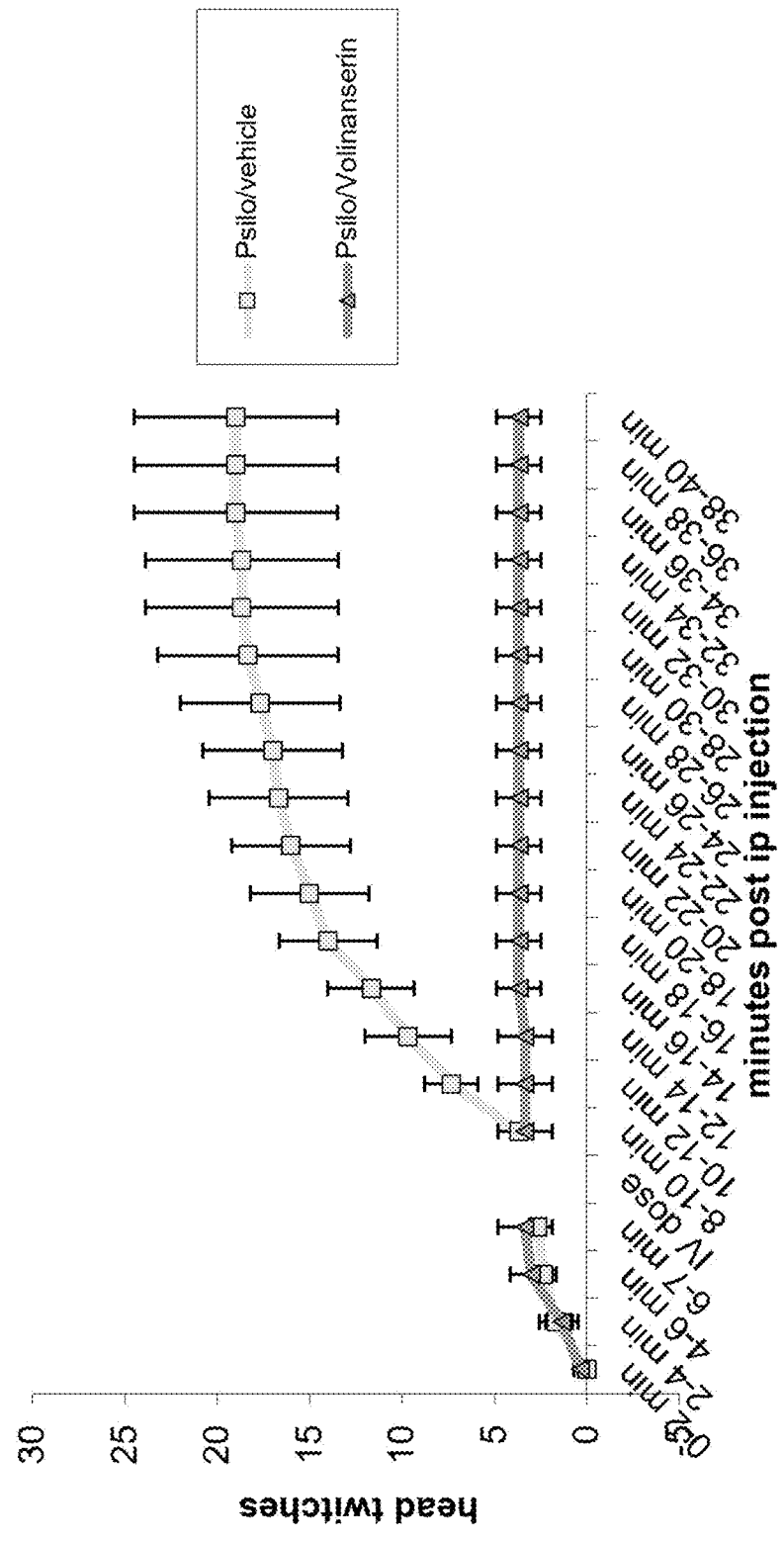
FIG. 71A illustrates comparison of psilocybin induced head twitches in mice with and without administration of volinanserin after T=7 minutes on average cumulative head twitches.
Figure 71B:
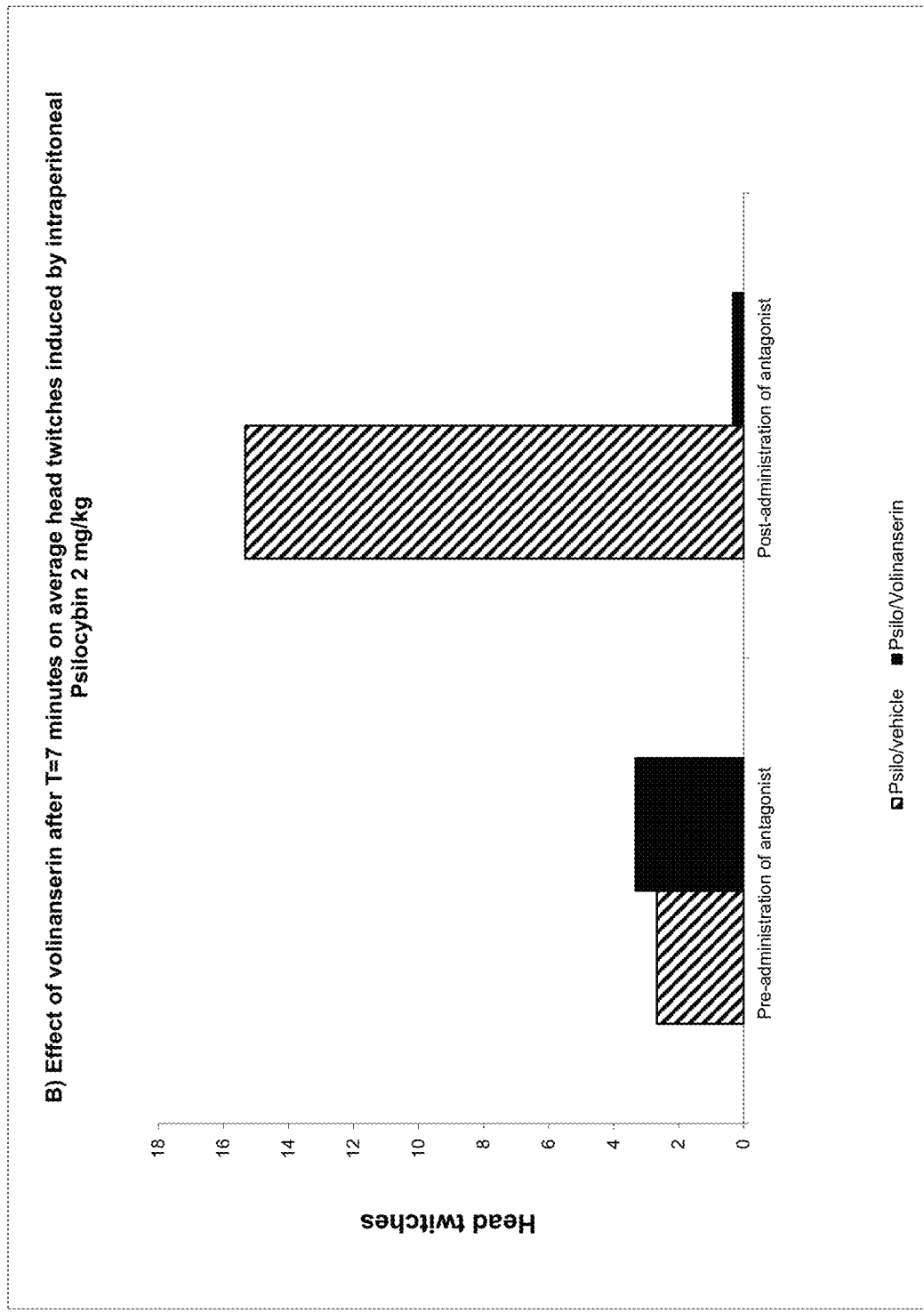
FIG. 71B illustrates the comparison of psilocybin induced head twitches in mice with and without administration of volinanserin after T=7 minutes on average head twitches.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with either vehicle 1 (saline) or volinanserin 1 mg/kg in 5 mL/kg dosing volumes. Mice were replaced into the observation cages and head twitch behavior were monitored until 40 min after agonist dosing. Cumulative head-twitches were measured every 2 minutes until 40 minutes after agonist dosing. As shown in FIG. 71, administration of volinanserin at this time point completely suppressed the head-twitch response. FIG. 71A shows a graph, FIG. 71B shows a bar chart illustrating that head twitches occurring before and after control or antagonist administration. Test condition groups of Example 13 are summarized in the following table.

| | | Synopsis of mouse twitch test pilot schedule | | | |
|---|---|---|---|---|---|
| Grp (n) | 60 min pre-test Place in test cage to habituate | T = −3 min Place in heated cage | T = 0 pretest Treatment i.p. (5 mL/kg saline) | T = 7 min Treatment i.v. (5 mL/kg) and replace in test cage | T = 0-40 min Assess number of head shakes 40 min per mouse |
| 3 | yes | Yes | Psilocybin 2 mg/kg | Vehicle 1 | Yes |
| 3 | yes | Yes | Psilocybin 2 mg/kg | Volinanserin 1 mg/kg | Yes |

Example 14: Effect of Intravenous Administration of Eplivanserin and Pimavanserin on Psilocybin Induced Head Twitches in Mice Formulation Psilocybin was formulated in saline at a concentration of 0.4 mg/mL to give a dose of 2 mg/kg when administered i.p. in a 5 mL/kg dosing volume. Eplivanserin was dissolved in Vehicle 1 (DMSO:HPCD [10:90]) at concentrations of 0.2 mg free base equivalents/ml to give a dose of 1 mg/kg when administered i.v. in a 5 mL/kg dosing volume. Pimavanserin Tartrate (85.07% free base content) was dissolved in Vehicle 1 (DMSO:HPCD=10:90) at concentrations of 0.2 mg free base equivalents/ml to give a dose of 1 mg/kg when administered i.v. in a 5 mL/kg dosing volume.

Procedure

Figure 72A:
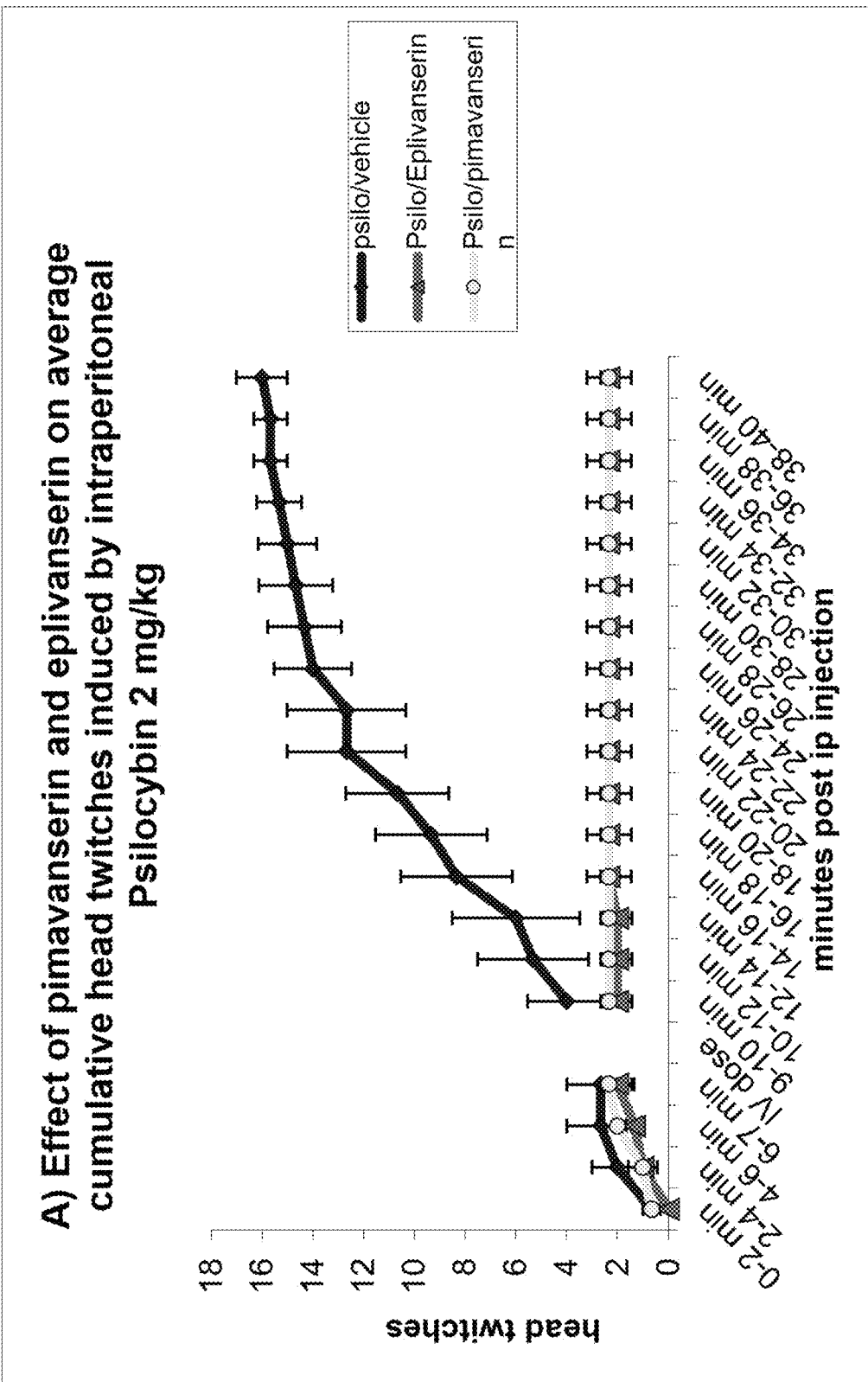
FIG. 72A illustrates effects of eplivanserin and pimavanserin administered after T=7 minutes on average cumulative psilocybin induced head twitches in mice.
Figure 72B:
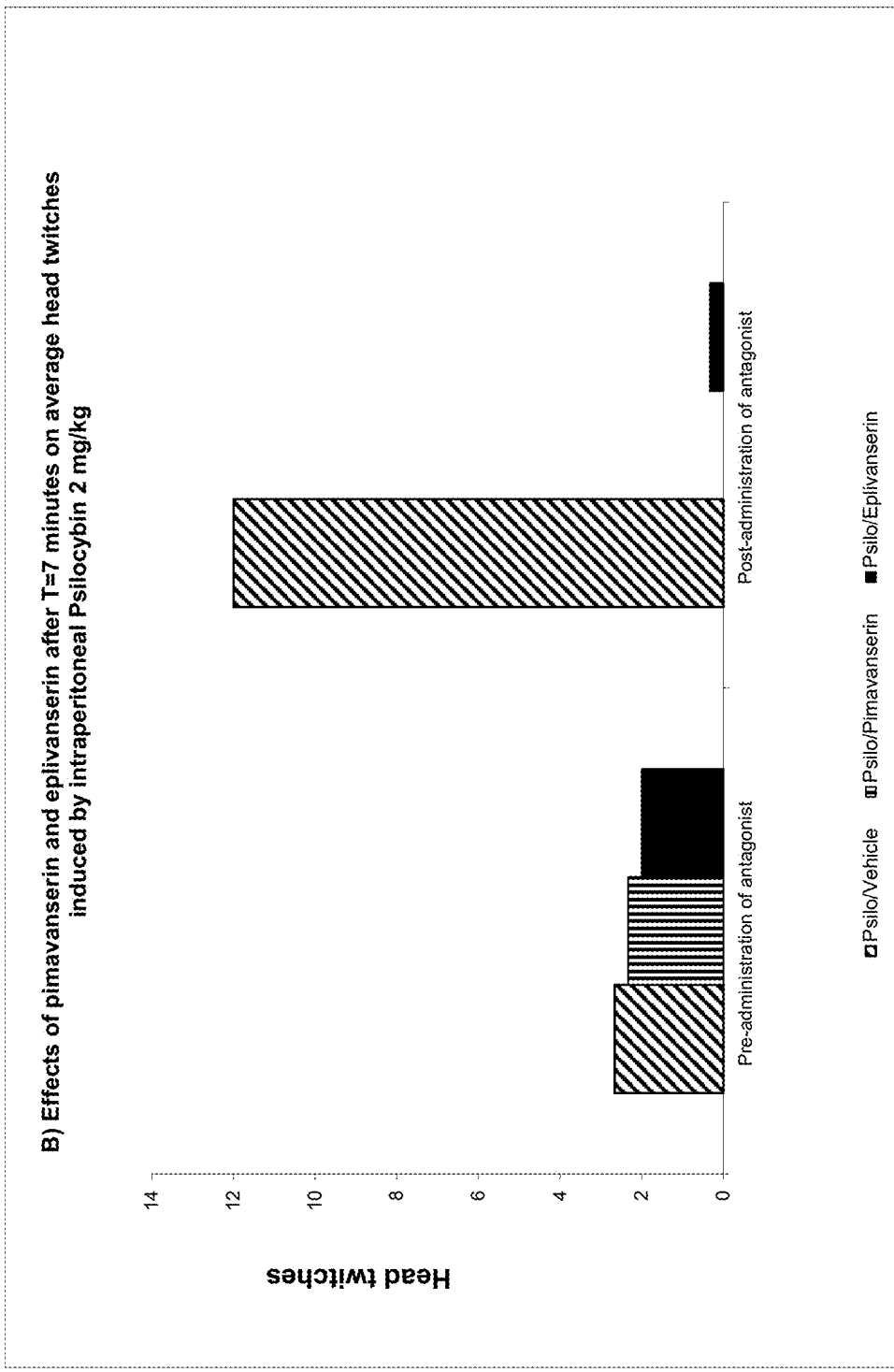
FIG. 72B illustrates effects of eplivanserin and pimavanserin administered after T=7 minutes on average psilocybin induced head twitches in mice.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with either vehicle 1 (DMSO:HPCD [10:90]) or eplivanserin 1 mg/kg or pimavanserin (1 mg/kg) in 5 mL/kg dosing volumes. Mice were replaced into the observation cages and head twitch behavior was monitored until 40 min after agonist dosing. Cumulative head-twitch behavior was measured every 2 minutes until 40 minutes after agonist dosing. As shown in FIG. 72, administration of eplivanserin and pimavanserin completely suppressed the head-twitch response. FIG. 72A shows a graph, FIG. 72B shows a bar chart showing head twitches occurring before and after control or antagonist administration. Test condition groups of Example 14 are summarized in the following table.

Example 15: Effect of Intravenous Administration of Risperidone and Pruvanserin on Psilocybin Induced Head Twitches in Mice Formulation Psilocybin was formulated in saline at a concentration of 0.4 mg/mL to give a dose of 2 mg/kg when administered i.p. in a 5 mL/kg dosing volume. Risperidone was dissolved in Vehicle 1 (DMSO:HPCD [10:90]) at concentrations of 0.2 mg free base equivalents/ml to give a dose of 1 mg/kg when administered i.v. in a 5 mL/kg dosing volume. Pruvanserin Tartrate (85.07% free base content) was dissolved in Vehicle 1 (DMSO:HPCD [10:90]) at concentrations of 0.2 mg free base equivalents/ml to give a dose of 1 mg/kg when administered i.v. in a 5 mL/kg dosing volume.

Procedure

Figure 73A:
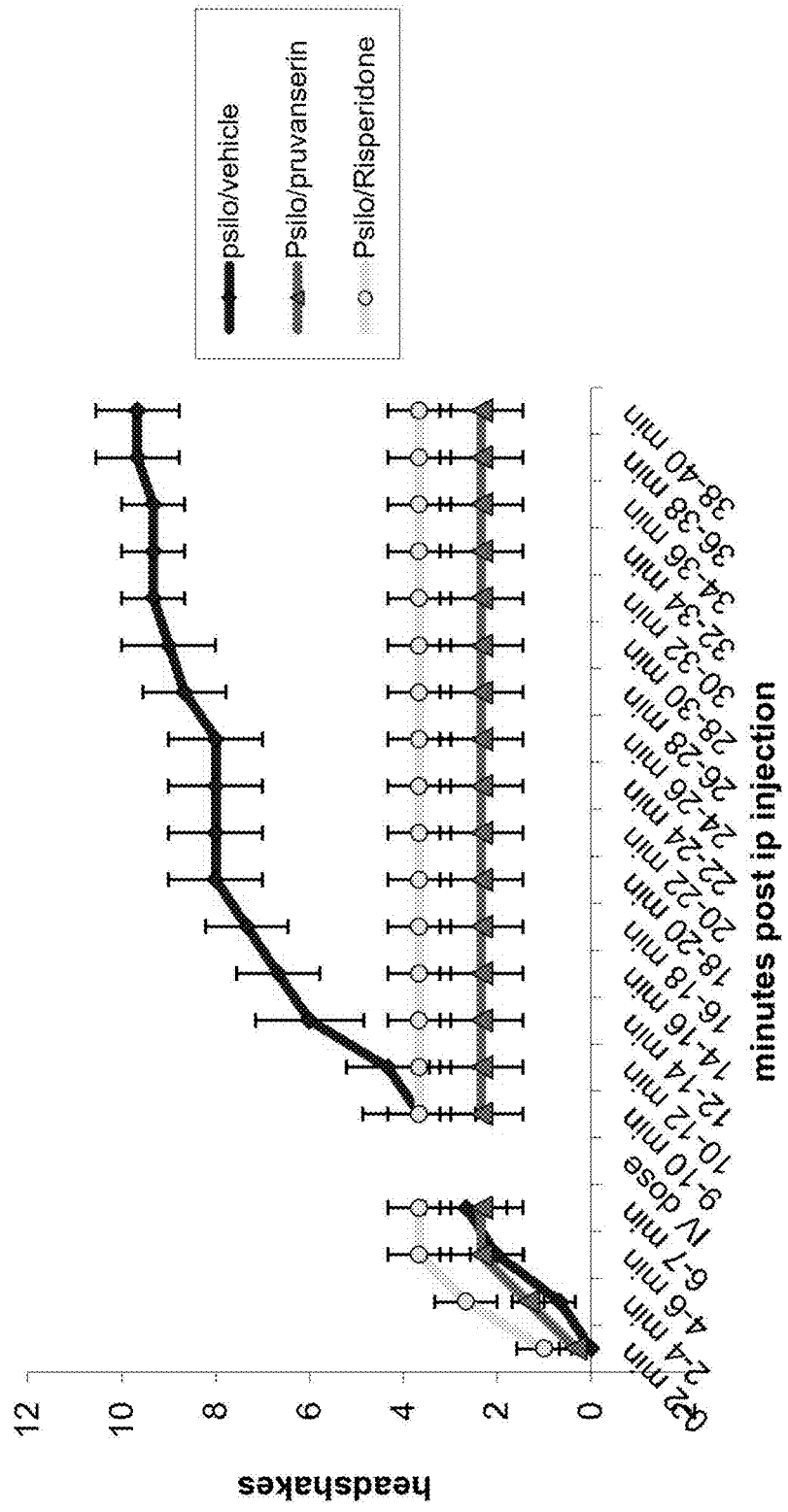
FIG. 73A illustrates effects of pruvanserin and risperidone administered after T=7 minutes on average cumulative psilocybin induced head twitches in mice.
Figure 73B:
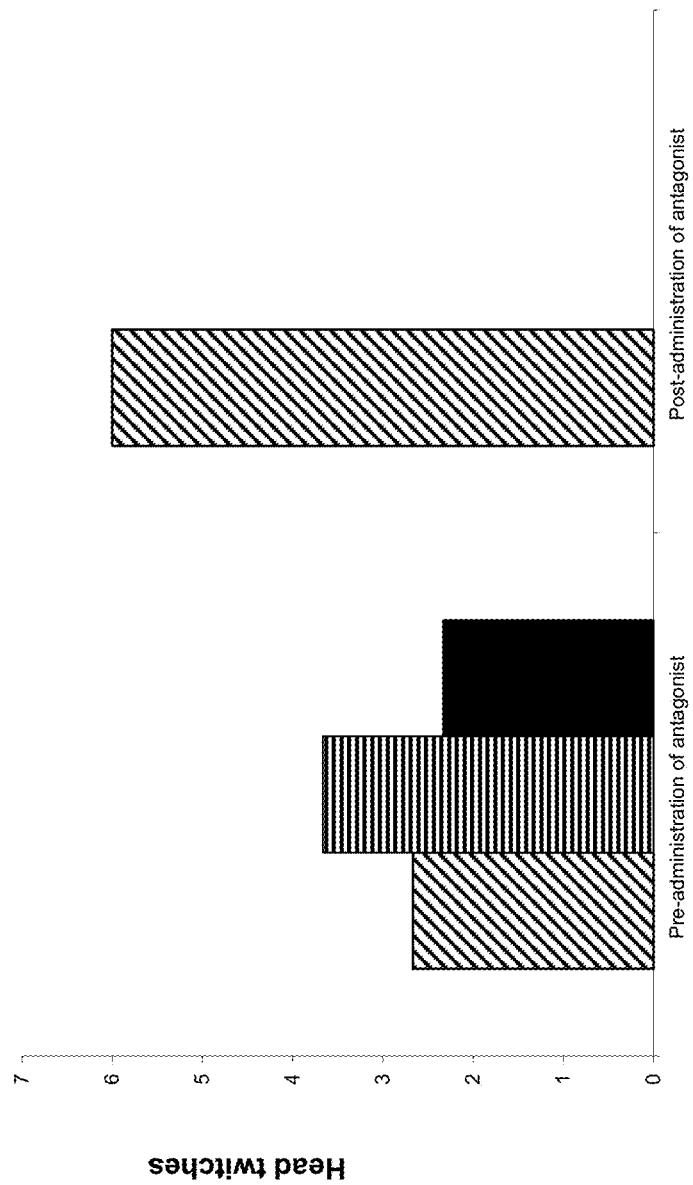
FIG. 73B illustrates effects of pruvanserin and risperidone administered after T=7 minutes on average psilocybin induced head twitches in mice.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with either vehicle 1 (DMSO:HPCD [10:90]) or risperidone 1 mg/kg or pruvanserin (1 mg/kg) in 5 mL/kg dosing volumes. Mice were replaced into the observation cages and head twitch behavior was monitored until 40 min after agonist dosing. Cumulative head-twitch behavior was measured every 2 minutes until 40 minutes after agonist dosing. As shown in FIG. 73, administration of pruvanserin and risperidone completely suppressed the head-twitch response. FIG. 73A shows a graph, FIG. 73B shows a bar chart showing head twitches occurring before and after control or antagonist administration. Test condition groups of Example 15 are summarized in the following table.

| | | | Synopsis of mouse twitch test pilot schedule | | |
|---|---|---|---|---|---|
| Group (n) | 60 min pre-test Place in test cage to habituate | T = −3 min Place in heated cage | T = 0 pretest Treatment i.p. (5 mL/kg saline) | T = 7 min Treatment i.v. (5 mL/kg) and replace in test cage | T = 0-40 min Assess number of head shakes 40 min per mouse |
| 3 | Yes | Yes | Psilocybin 2 mg/kg | Vehicle 1 | Yes |
| 3 | yes | yes | Psilocybin 2 mg/kg | Eplivanserin 1 mg/kg | Yes |
| 3 | yes | yes | Psilocybin 2 mg/kg | Pimavanserin 1 mg/kg | Yes |

Synopsis of mouse twitch test pilot schedule

| Group (n) | 60 min pre-test Place in test cage to habituate | T = −3 min Place in heated cage | T = 0 pretest Treatment i.p. (5 mL/kg saline) | T = 7 min Treatment i.v. (5 mL/kg) and replace in test cage | T = 0-40 min Assess number of head shakes 40 min per mouse |
|---|---|---|---|---|---|
| 3 | Yes | Yes | Psilocybin 2 mg/kg | Vehicle 1 | Yes |
| 3 | yes | yes | Psilocybin 2 mg/kg | Risperidone 1 mg/kg | Yes |
| 3 | yes | yes | Psilocybin 2 mg/kg | Pruvanserin 1 mg/kg | Yes |

Example 16: Effect of Intravenous Administration of Ritanserin, Nelotanserin and Olanzapine on Psilocybin Induced Head Twitches in Mice Formulation Psilocybin was formulated in saline at a concentration of 0.4 mg/mL to give a dose of 2 mg/kg when administered i.p. in a 5 mL/kg dosing volume. Ritanserin was dissolved in Vehicle 1 (DMSO:HPCD [10:90]) at concentrations of 0.2 mg free base equivalents/ml to give a dose of 1 mg/kg when administered i.v. in a 5 mL/kg dosing volume. Nelotanserin was dissolved in Vehicle 1 (DMSO:HPCD [10:90]) at concentrations of 0.2 mg free base equivalents/ml to give a dose of 1 mg/kg when administered i.v. in a 5 mL/kg dosing volume. Olanzapine was dissolved in Vehicle 1 (DMSO:HPCD [10:90]) at concentrations of 0.2 mg free base equivalents/ml to give a dose of 1 mg/kg when administered i.v. in a 5 mL/kg dosing volume.

Procedure

Figure 74A:
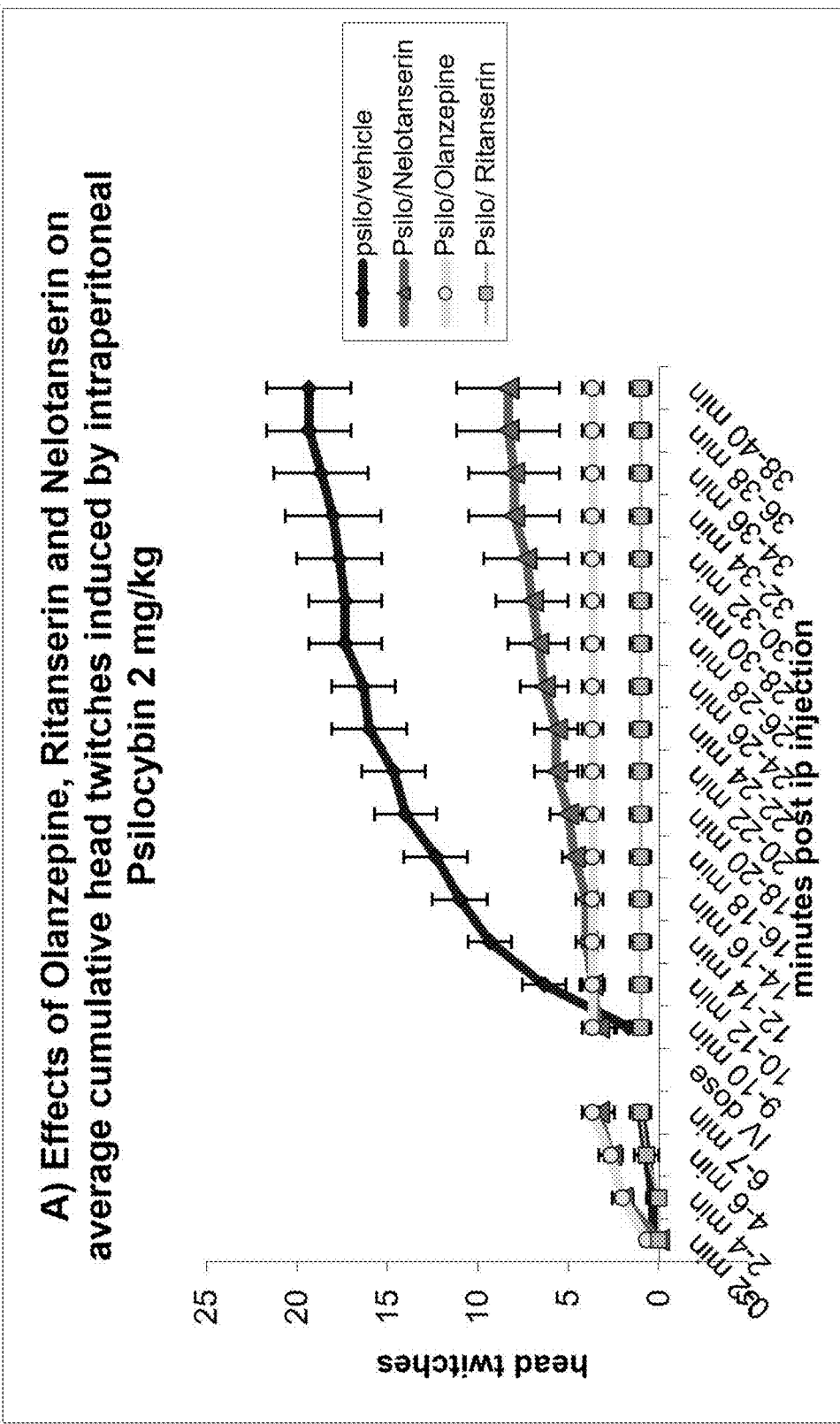
FIG. 74A illustrates effects of olanzapine, ritanserin, and nelotanserin administered after T=7 minutes on average cumulative psilocybin induced head twitches in mice.
Figure 74B:
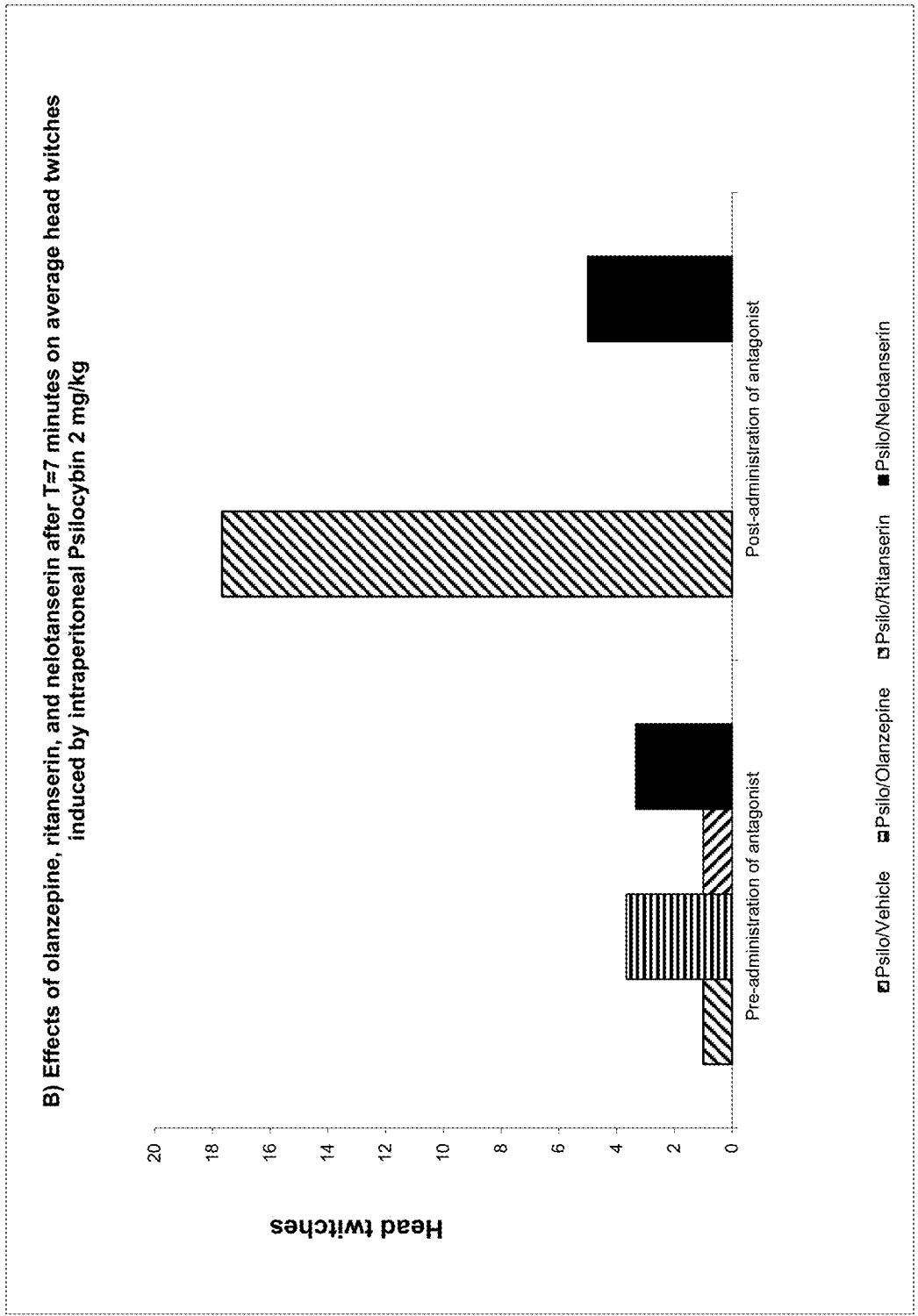
FIG. 74B illustrates effects of olanzapine, ritanserin, and nelotanserin administered after T=7 minutes on average psilocybin induced head twitches in mice.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with either vehicle 1 (DMSO:HPCD [10:90]) or ritanserin (1 mg/kg) or nelotanserin (1 mg/kg) or olanzapine (1 mg/kg) in 5 mL/kg dosing volumes. Mice were replaced into the observation cages and head twitch behavior was monitored until 40 min after agonist dosing. Cumulative head-twitch behavior was measured every 2 minutes until 40 minutes after agonist dosing. As shown in FIG. 74, administration of olanzapine and ritanserin completely suppressed the head-twitch response, and administration of nelotanserin partially suppressed the head-twitch response. FIG. 74A shows a graph, FIG. 74B shows a bar chart showing head twitches occurring before and after control or antagonist administration. Test condition groups of Example 16 are summarized in the following table.

Example 17: Effect of Intravenous Administration of Quetiapine on Psilocybin Induced Head Twitches in Mice Formulation Psilocybin (free base) was formulated in saline at a concentration of 0.4 mg/mL to give a dose of 2 mg/kg when administered i.p. in a 5 mL/kg dosing volume. Quetiapine was dissolved in Vehicle 1 (saline) at concentrations of 0.2 mg free base equivalents/ml to give a dose of 1 mg/kg when administered i.v. in a 5 mL/kg dosing volume.

Procedure

Figure 75A:
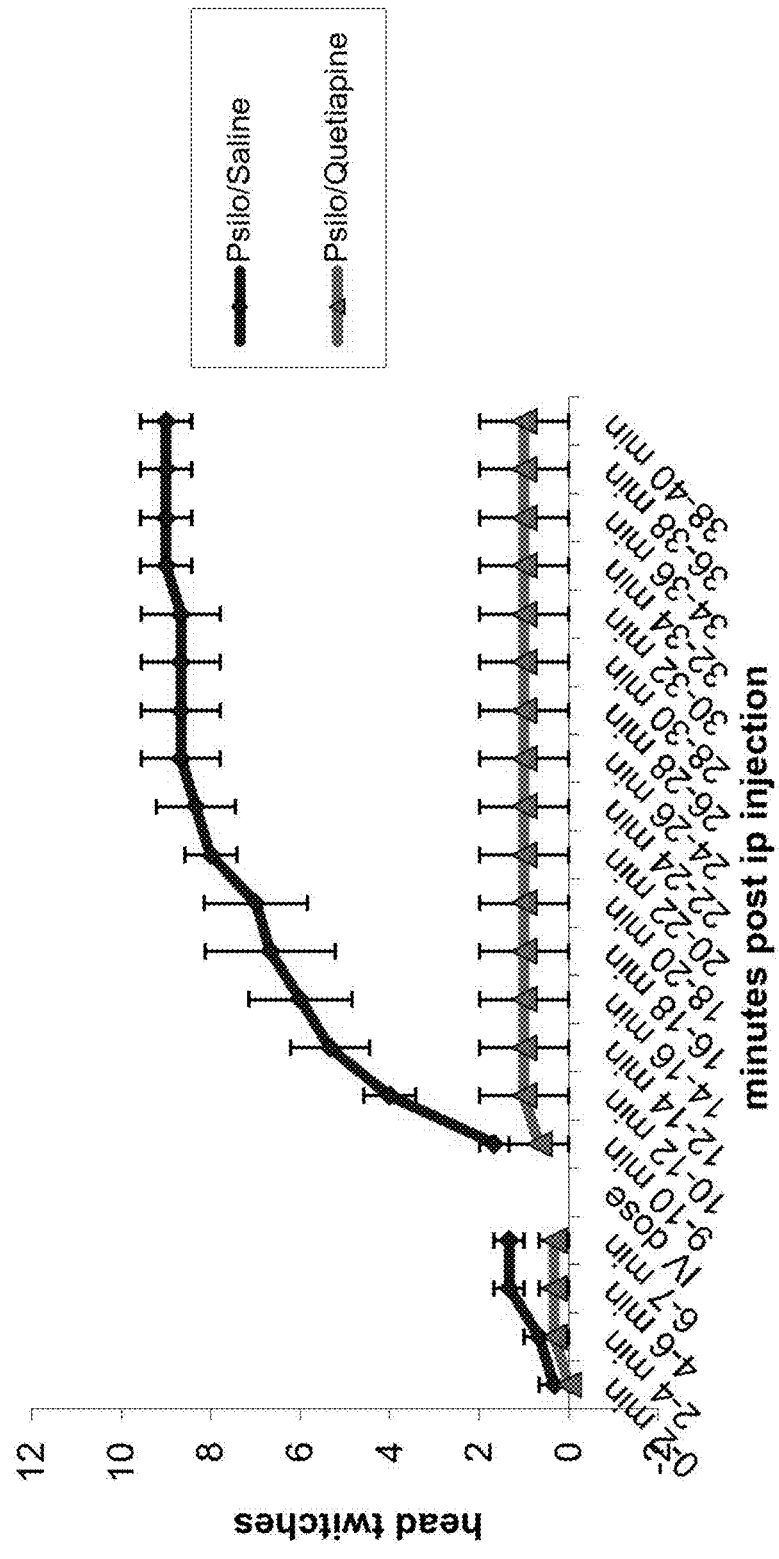
FIG. 75A illustrates effects of quetiapine administered after T=7 minutes on average cumulative psilocybin induced head twitches in mice.
Figure 75B:
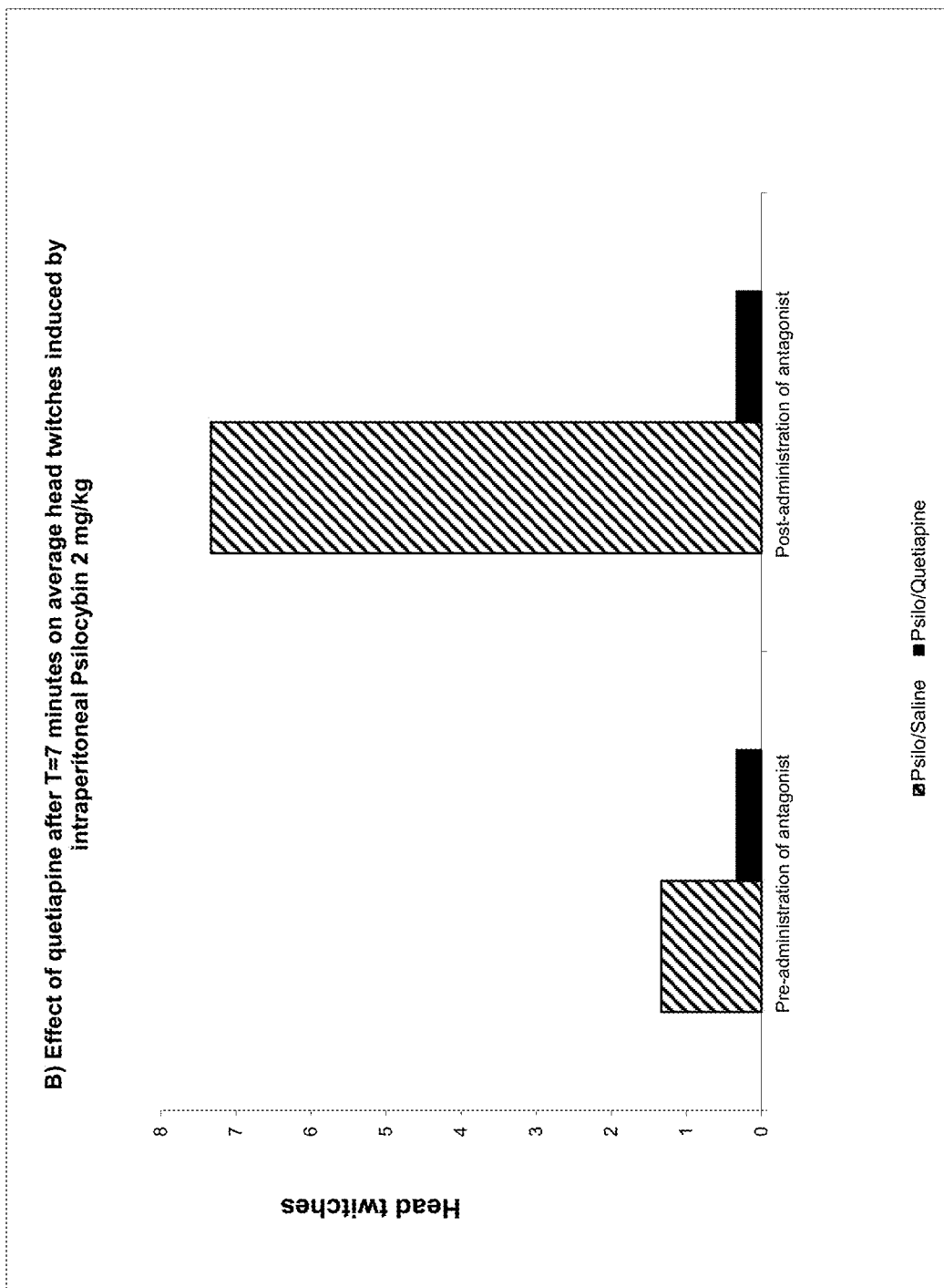
FIG. 75B illustrates effects of quetiapine administered after T=7 minutes on average psilocybin induced head twitches in mice.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with either vehicle 1 (saline) or quetiapine (1 mg/kg) in vehicle 1 in 5 mL/kg dosing volumes. Mice were replaced into the observation cages and head twitch behavior was monitored until 40 min after agonist dosing. Cumulative head-twitch behavior was measured every 2 minutes until 40 minutes after agonist dosing. As shown in FIG. 75, administration of quetiapine completely suppressed the head-twitch response. FIG. 75A shows a graph, FIG. 75B shows a bar chart showing head twitches occurring before and after control or antagonist administration. Test condition groups of Example 17 are summarized in the following table.

Synopsis of mouse twitch test pilot schedule

| Group (n) | 60 min pretest Place in test cage to habituate | T = −3 min Place in heated cage | T = 0 pretest Treatment i.p. (5 mL/kg saline) | T = 7 min Treatment i.v. (5 mL/kg) and replace in test cage | T = 0-40 min Assess number of head shakes 40 min per mouse |
|---|---|---|---|---|---|
| 3 | Yes | Yes | Psilocybin 2 mg/kg | Vehicle 1 | Yes |
| 3 | Yes | Yes | Psilocybin 2 mg/kg | Ritanserin 1 mg/kg | Yes |
| 3 | Yes | Yes | Psilocybin 2 mg/kg | Nelotanserin 1 mg/kg | Yes |
| 3 | Yes | Yes | Psilocybin 2 mg/kg | Olanzapine 1 mg/kg | Yes |

| Synopsis of mouse twitch test pilot schedule | | | | | |
|---|---|---|---|---|---|
| Group (n) | 60 min pre-test Place in test cage to habituate | T = −3 min Place in heated cage | T = 0 pretest Treatment i.p. (5 mL/kg saline) | T = 7 min Treatment i.v. (5 mL/kg) and replace in test cage | T = 0-40 min Assess no of head shakes/40 min per mouse |
| 3 | Yes | Yes | Psilocybin 2 mg/kg | Vehicle 1 (saline) | Yes |
| 3 | yes | yes | Psilocybin 2 mg/kg | Quetiapine 1 mg/kg | Yes |

Example 18: Effect of Intravenous Administration of Ketanserin on Psilocybin Induced Head Twitches in Mice Formulation Psilocybin (free base) was formulated in saline at a concentration of 0.4 mg/mL to give a dose of 2 mg/kg when administered i.p. in a 5 mL/kg dosing volume.

Ketanserin Tartrate (74.7% free base content) was dissolved in Vehicle 2 (DMSO:Cremophor EL:Hydroxypropyl-β-cyclodextrin (20% in water) [10:10:80]) at concentrations of 0.4 mg/ml to give a dose of 2 mg/kg when administered i.v. in a 5 mL/kg dosing volume.

Procedure

Figure 76A:
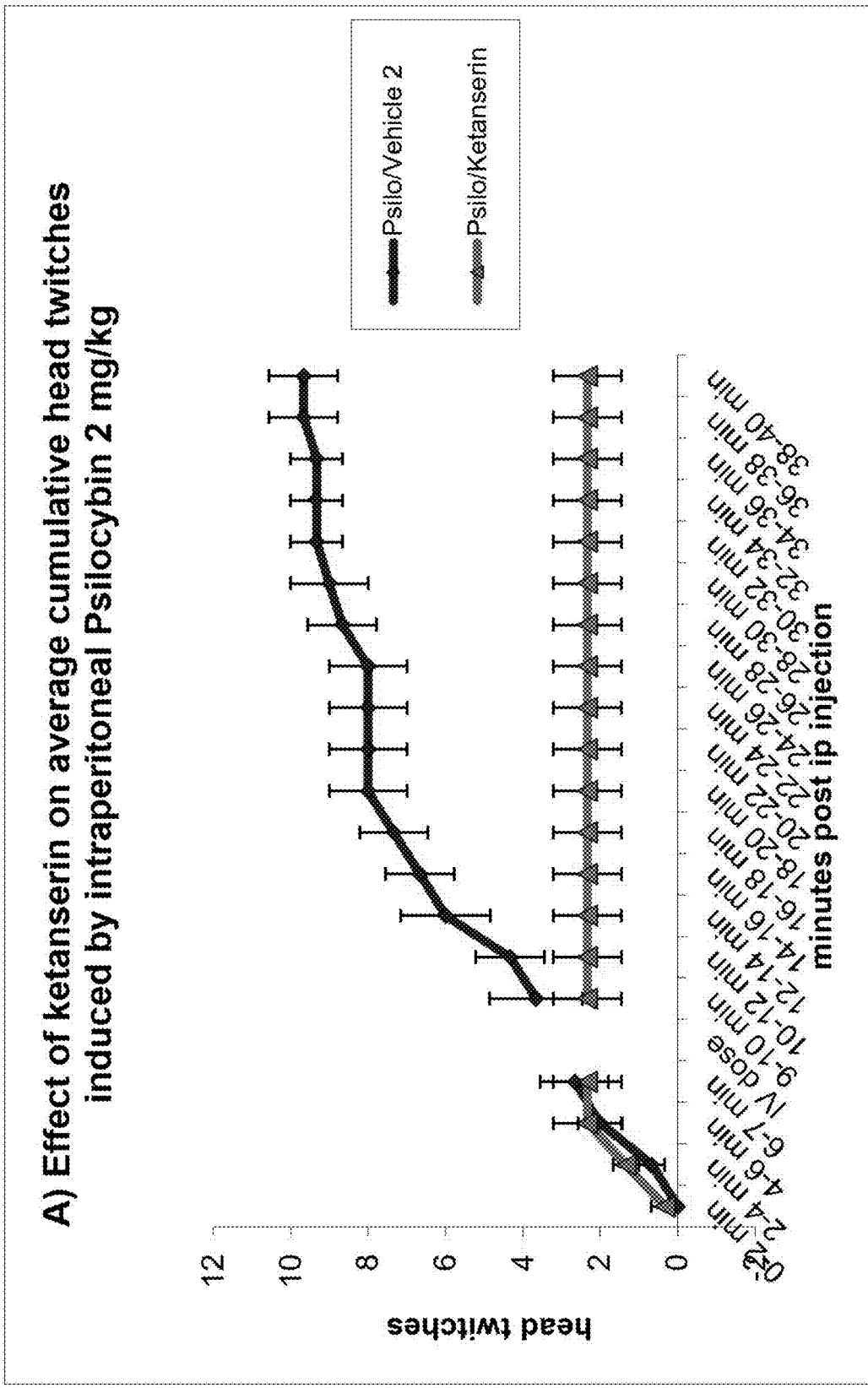
FIG. 76A illustrates comparison of average cumulative psilocybin induced head twitches in mice with and without administration of ketanserin after T=7 minutes.
Figure 76B:
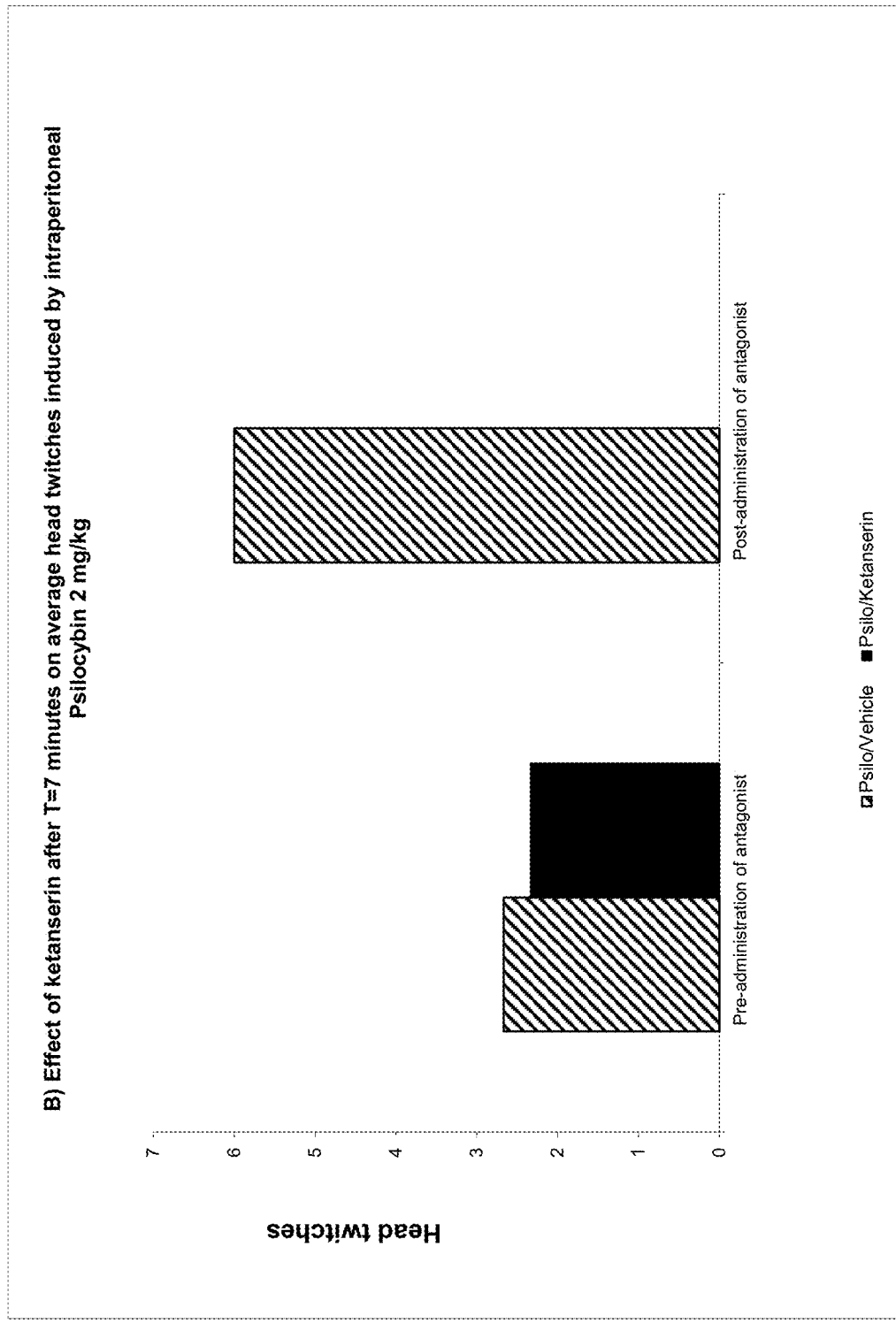
FIG. 76B illustrates comparison of average psilocybin induced head twitches in mice with and without administration of ketanserin after T=7 minutes.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with either Vehicle 2 (DMSO:cremophor:HPCD [10:10:80]) or ketanserin (2 mg/kg) in Vehicle 2 in 5 mL/kg dosing volumes. Mice were replaced into the observation cages and head twitch behavior was monitored until 40 min after agonist dosing. Cumulative head-twitch behavior was measured every 2 minutes until 40 minutes after agonist dosing. As shown in FIG. 76, administration of ketanserin completely suppressed the head-twitch response. FIG. 76A shows a graph, FIG. 76B shows a bar chart showing head twitches occurring before and after control or antagonist administration. Test condition groups of Example 18 are summarized in the following table.

Example 19: Effect of Intravenous Administration of AC-279 on Psilocybin-Induced Head Twitches in Mice Formulation Check AC-279 was assessed in up to 4 different formulations to identify a vehicle suitable for i.v. administration in which it forms a solution at a concentrations of 0.2 mg free base equivalents/ml to give a dose of 1 mg/kg when administered i.v. in a 5 mL/kg dosing volume.

Formulation

Psilocybin (free base) was formulated in Vehicle (saline) at a concentration of 0.4 mg/mL to give a dose of 2 mg/kg when administered i.p. in a 5 mL/kg dosing volume. AC-279 was dissolved in Vehicle 1 (10% DMSO:90% HPCD) at concentrations of 0.2 mg free base equivalents/ml to give a dose of 1 mg/kg when administered i.v. in a 5 mL/kg dosing volume.

Procedure 2: Psilocybin

Figure 77A:
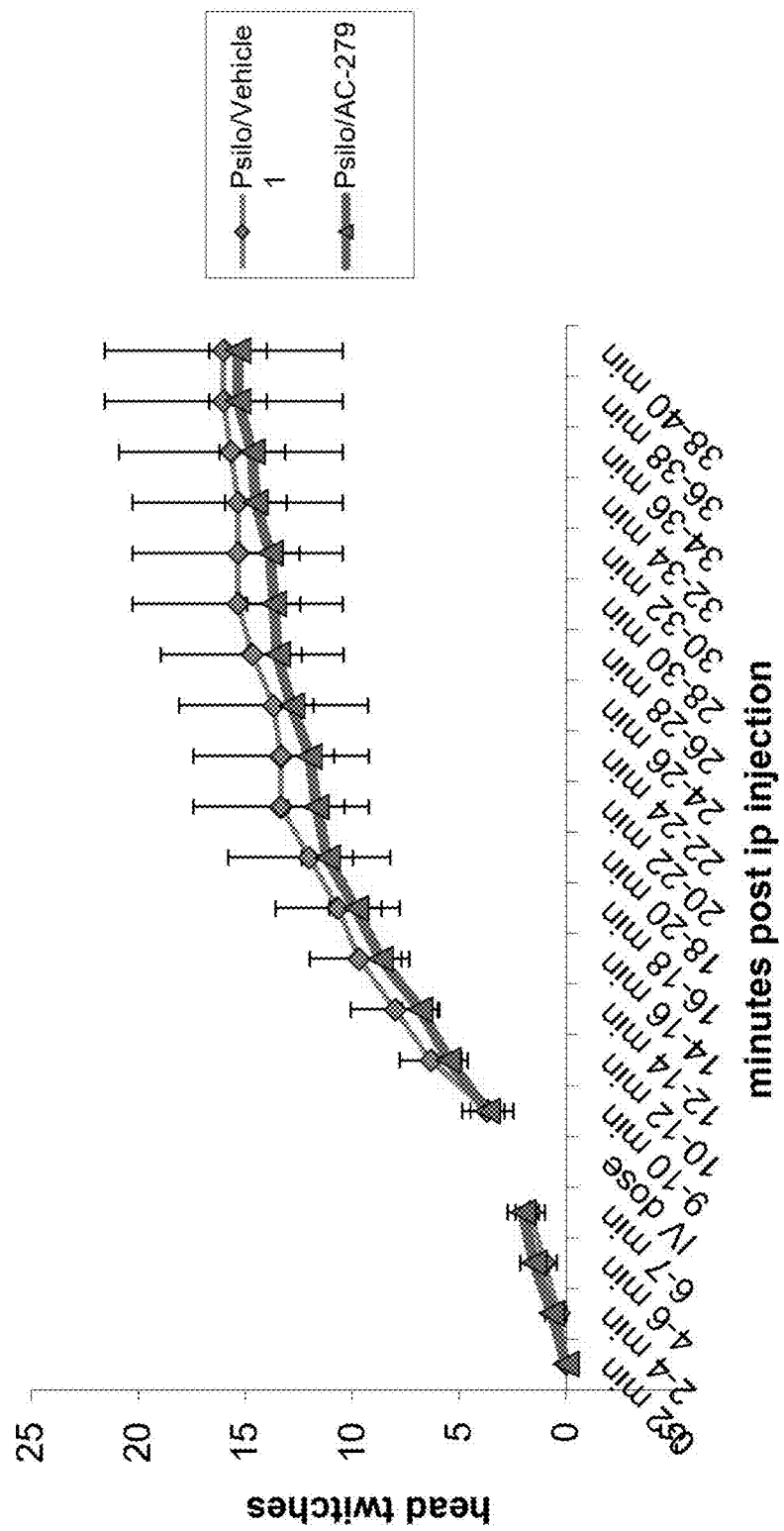
FIG. 77A illustrates effects of AC-279 administered after T=7 minutes on average cumulative psilocybin induced head twitches in mice.
Figure 77B:
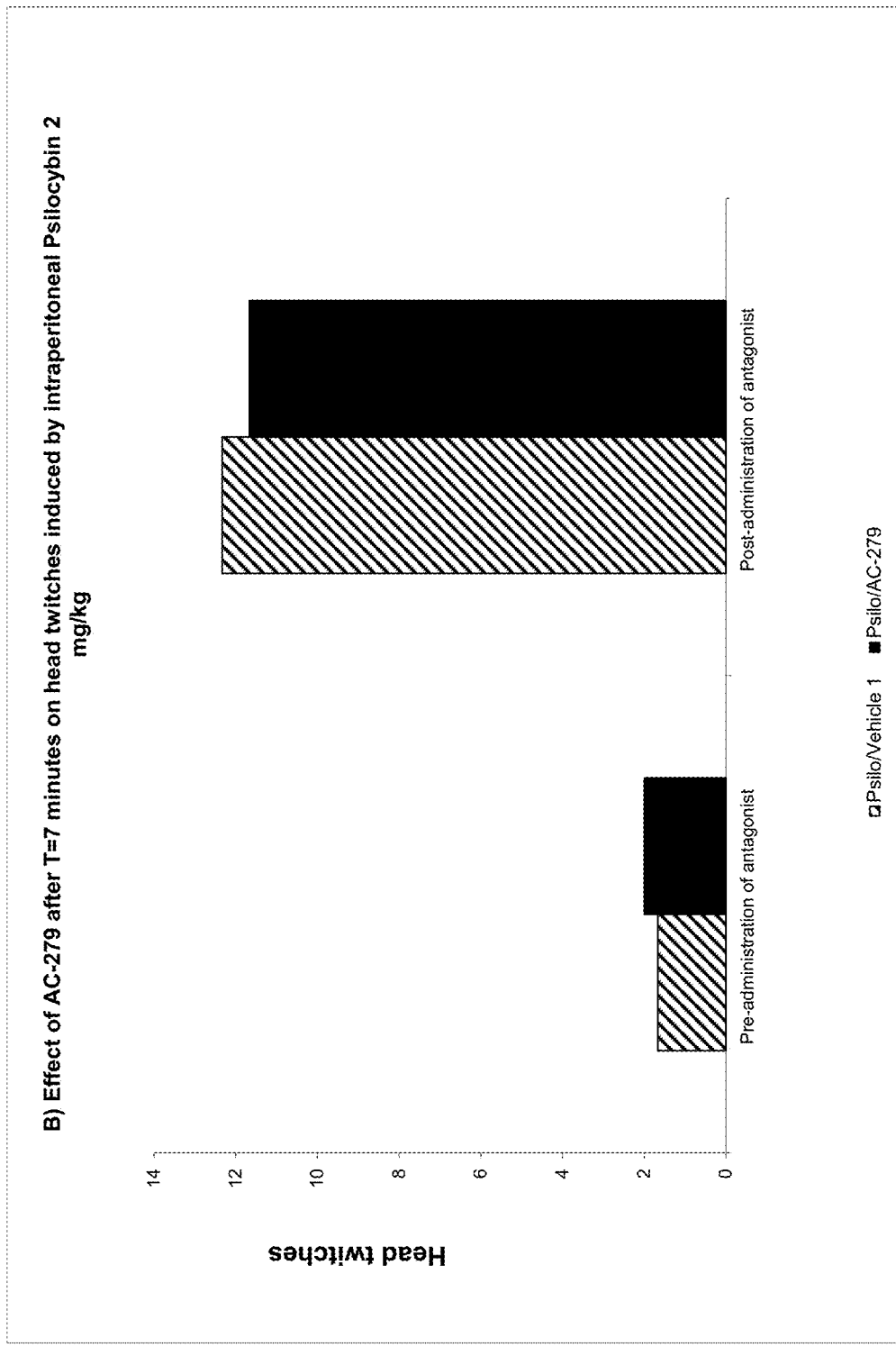
FIG. 77B illustrates effects of AC-279 administered after T=7 minutes on average psilocybin induced head twitches in mice.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with vehicle 1 (10% DMSO:90% HPCD) or AC-279 (1 mg/kg) in 5 mL/kg dosing volumes. Mice were replaced into the observation cages and head twitch behavior was monitored until 40 min after agonist dosing. Cumulative head-twitch behavior was measured every 2 minutes until 40 minutes after agonist dosing. As shown in FIG. 20, administration of AC-279 did not suppress the head-twitch response. FIG. 77A shows a graph, FIG. 77B shows a bar chart showing head twitches occurring before and after control or antagonist administration. Procedures 1 and 2 test condition groups of Example 19 are summarized in the following table.

| Synopsis of mouse twitch test pilot schedule | | | | | |
|---|---|---|---|---|---|
| Group (n) | 60 min pretest Place in test cage to habituate | T = −3 min Place in heated cage | T = 0 pretest Treatment i.p. (5 mL/kg saline) | T = 7 min Treatment i.v. (5 mL/kg) and replace in test cage | T = 0-40 min Assess no of head shakes/40 min per mouse |
| 3 | yes | yes | Psilocybin 2 mg/kg | Vehicle 2 (DMSO: Cremophor:HPCD) | Yes |
| 3 | yes | yes | Psilocybin 2 mg/kg | Ketanserin 2 mg/kg | Yes |

| | Synopsis of mouse twitch test study schedule | | | | |
|---|---|---|---|---|---|
| Group (n) | 60 min pretest Place in test cage to habituate 60 min pretest | T = −2 min Place in heated cage T = −3 min | T = 0 pretest Treatment i.p. (5 mL/kg saline) T = 0 pretest | T = 8 min Treatment i.v. (5 mL/kg) and replace in test cage T = 7 min | T = 0-40 min Assess no of head shakes/40 min per mouse T = 0-40 min |
| 3 | yes | yes | Psilocybin 2 mg/kg | Vehicle 1 (DMSO:HPCD) | Yes |
| 3 | yes | yes | Psilocybin 2 mg/kg | AC-279 1 mg/kg | Yes |

Example 20: Effect of Intravenous Administration of Flibanserin on Psilocybin-Induced Head Twitches in Mice Formulation Psilocybin (free base) was formulated in Vehicle 1 (saline) at a concentration of 0.4 mg/mL to give a dose of 2 mg/kg when administered i.p. in a 5 mL/kg dosing volume.

Flibanserin was dissolved in Vehicle 2 (DMSO:HPCD (20% w/v in water) [10:90]) at concentrations of 0.2 and 0.8 mg free base equivalents/ml to give doses of 1 and 4 mg/kg when administered i.v. in 5 mL/kg dosing volumes.

Procedure Psilocybin

Figure 78A:
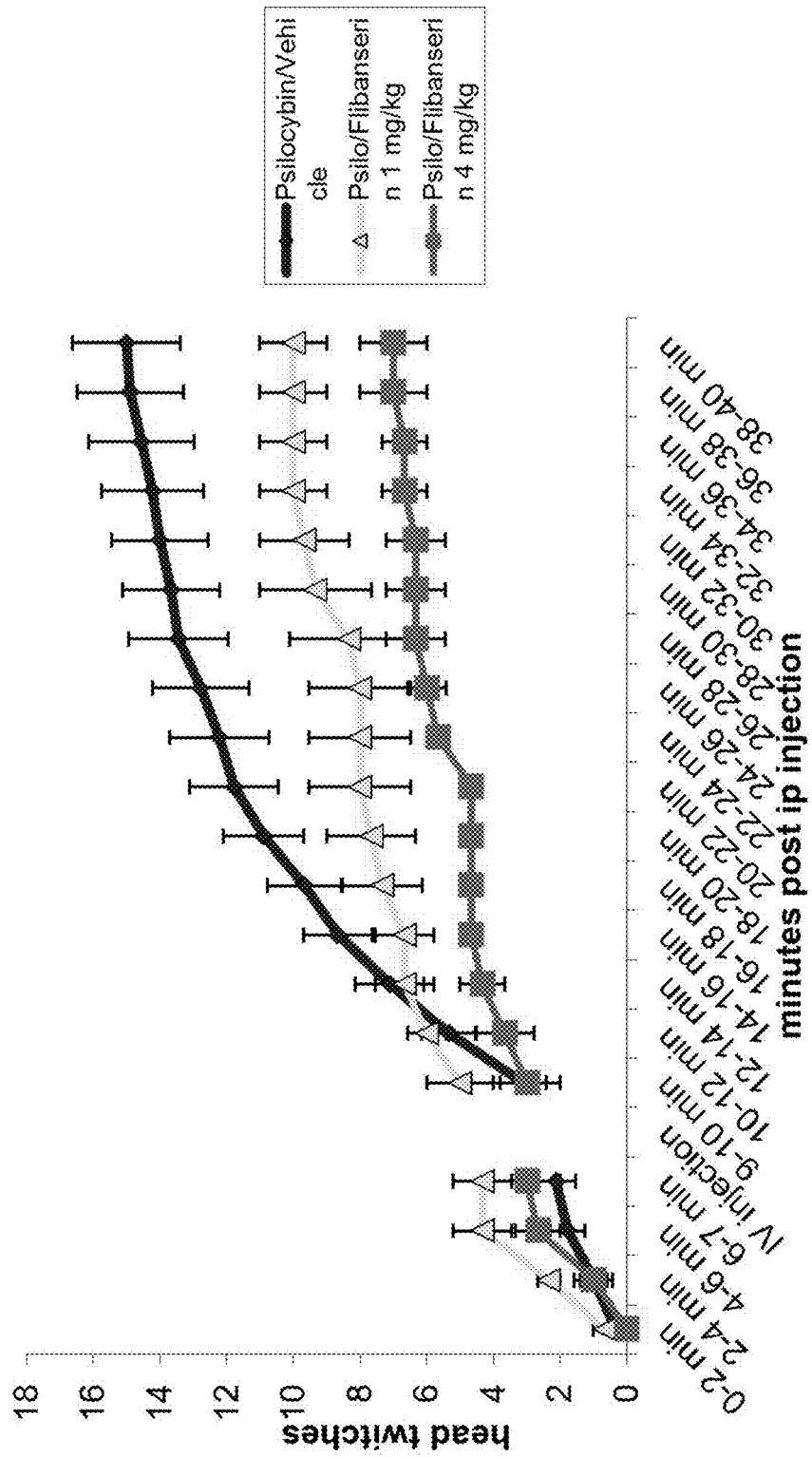
FIG. 78A illustrates effects of flibanserin administered after T=7 minutes on average cumulative psilocybin induced head twitches in mice.
Figure 78B:
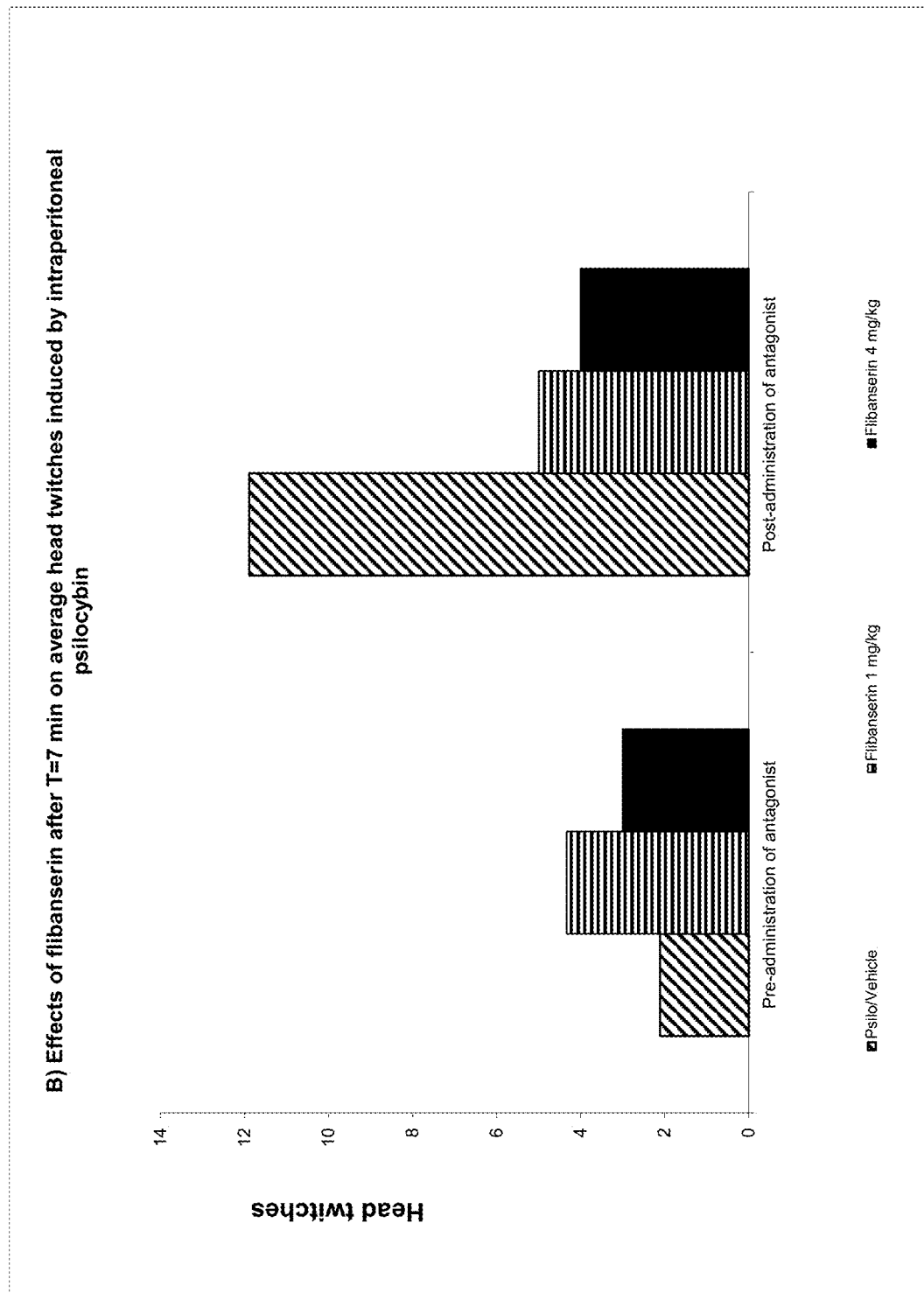
FIG. 78B illustrates effects of flibanserin administered after T=7 minutes on average psilocybin induced head twitches in mice.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with Flibanserin (1 or 4 mg/kg) in 5 mL/kg dosing volumes. Mice were then replaced into the observation cages and head twitch behavior was monitored until 40 min after agonist dosing. Since this combination of Psilocybin and vehicle had already been tested multiple times, a separate control group was not run concurrently to minimize the number of animals required for the study. Instead, the control groups from the other psilocybin and studies with the same vehicle 2 and dosing schedule were all averaged together. Cumulative head-twitch behavior was measured every 2 minutes until 40 minutes after agonist dosing. The average cumulative head twitches in mice dosed with psilocybin and then the same vehicle (DMSO:HPCD [10:90]) from the other studies is plotted for reference. As shown in FIG. 78, administration of flibanserin (1 mg/kg or 4 mg/kg) partially suppressed the head-twitch response. FIG. 78A shows a graph, FIG. 78B shows a bar chart showing head twitches occurring before and after control or antagonist administration. Test condition groups of Example 20 are summarized in the following table.

| | Synopsis of mouse twitch test study schedule | | | | |
|---|---|---|---|---|---|
| Group (n) | 60 min pre-test Place in test cage to habituate 60 min pre-test | T = −2 min Place in heated cage T = −3 min | T = 0 pretest Treatment i.p. (5 mL/kg saline) T = 0 pretest | T = 8 min Treatment i.v. (5 mL/kg) and replace in test cage T = 7 min | T = 0-40 min Assess no of head shakes/40 min per mouse T = 0-40 min |
| 9 | Yes | yes | Psilocybin 2 mg/kg | Vehicle 2 (DMSO: HPCD) | Yes |
| 3 | yes | yes | Psilocybin 2 mg/kg | Flibanserin 1 mg/kg | Yes |
| 3 | yes | yes | Psilocybin 2 mg/kg | Flibanserin 4 mg/kg | Yes |

Example 21: Effect of Intravenous Administration of Nelotanserin on Psilocybin Induced Head Twitches in Mice Formulation Psilocybin (free base) was formulated in saline at a concentration of 0.4 mg/mL to give a dose of 2 mg/kg when administered i.p. in a 5 mL/kg dosing volume. Nelotanserin (free base) was dissolved in Vehicle 1 (DMSO:Kolliphor: HPCD (20% in water) [10:10:80]) at concentrations of 0.8 mg free base equivalents/ml to give a dose of 4 mg/kg when administered i.v. in a 5 mL/kg dosing volume.

Procedure

Figure 79A:
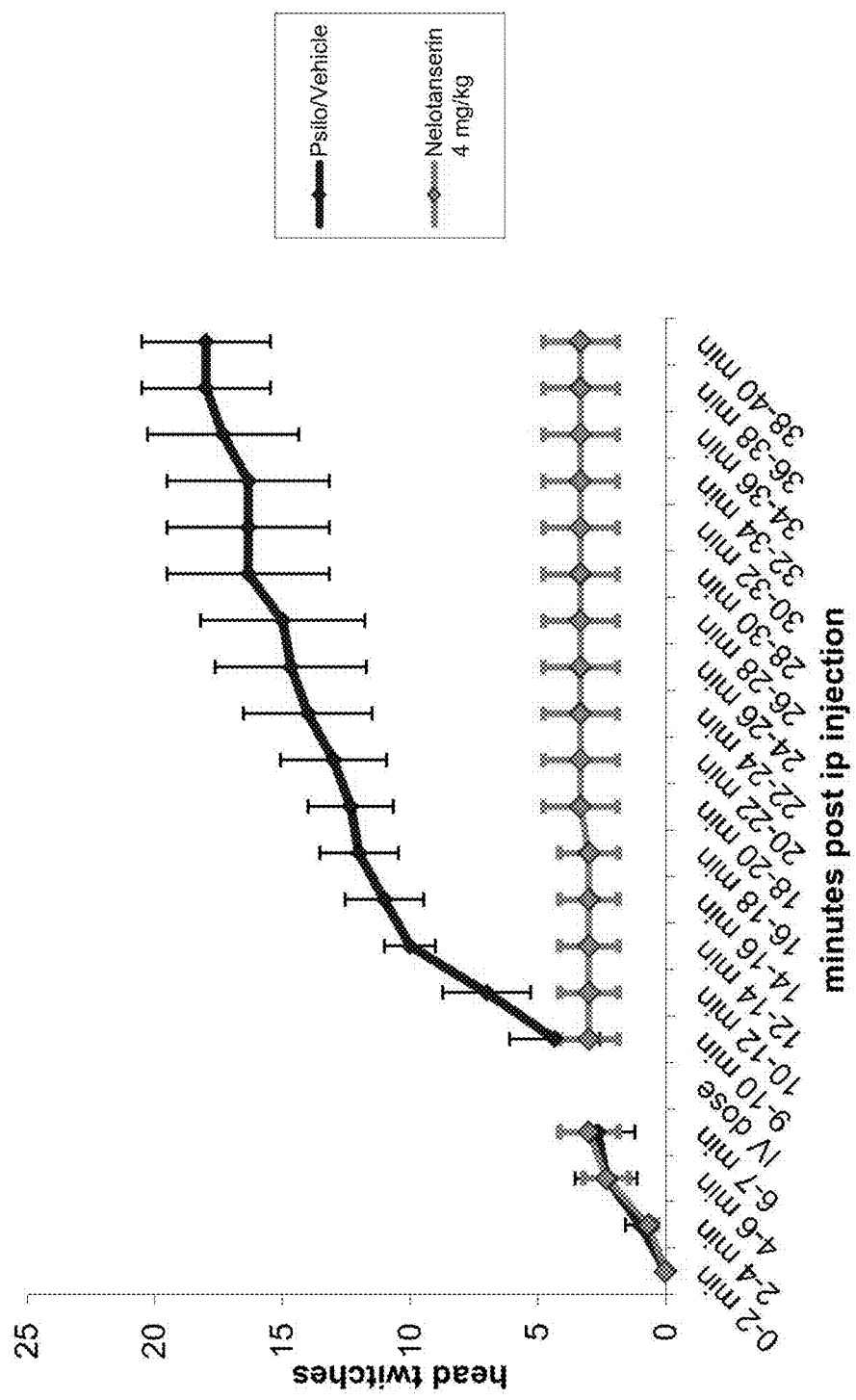
FIG. 79A illustrates effects of high dose nelotanserin administered after T=7 minutes on average cumulative psilocybin induced head twitches in mice.
Figure 79B:
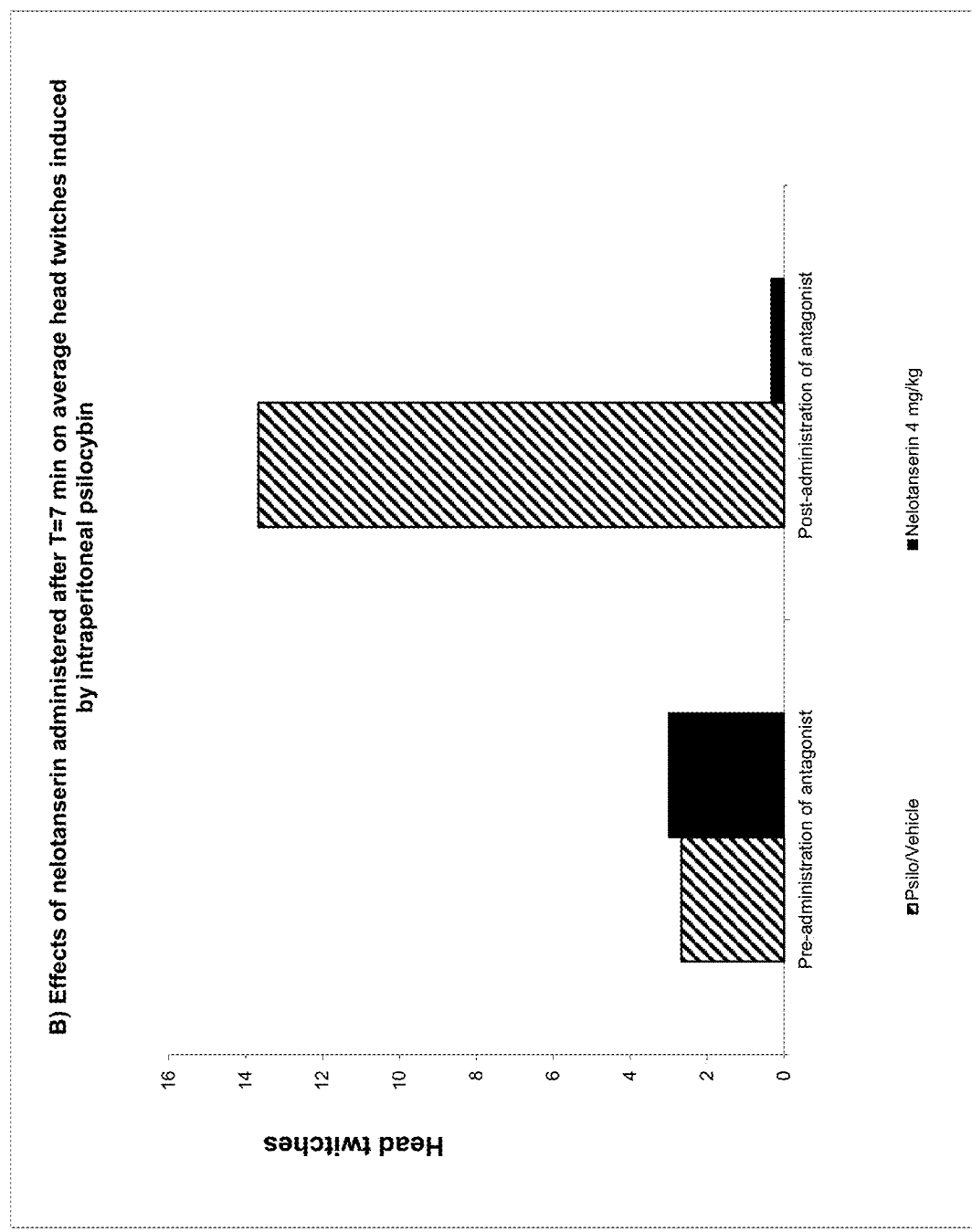
FIG. 79B illustrates effects of high dose nelotanserin administered after T=7 minutes on average psilocybin induced head twitches in mice.

At T=−60 min, C57BL/6J mice were individually housed into transparent observation cages with bedding removed and left to habituate. At T=−3 min, mice were placed into heated cages at 40° C. At T=0 h, groups of 3 mice were dosed intraperitoneally with psilocybin (2 mg/kg). Following dosing, mice were replaced into the heated cages and head-twitch responses continuously scored for 7 min. After 7 min, mice were intravenously dosed via the lateral tail vein with either vehicle 1 (DMSO:Kolliphor:HPCD) or nelotanserin (4 mg/kg) in 5 mL/kg dosing volumes. Mice were then replaced into the observation cages and head twitch behavior was monitored until 40 min after agonist dosing. Cumulative head-twitch behavior was measured every 2 minutes until 40 minutes after agonist dosing. As shown in FIG. 79, administration of higher dose nelotanserin (4 mg/kg) completely suppressed the head-twitch response. FIG. 79A shows a graph, FIG. 79B shows a bar chart showing head twitches occurring before and after control or antagonist administration.

Figure 80A:
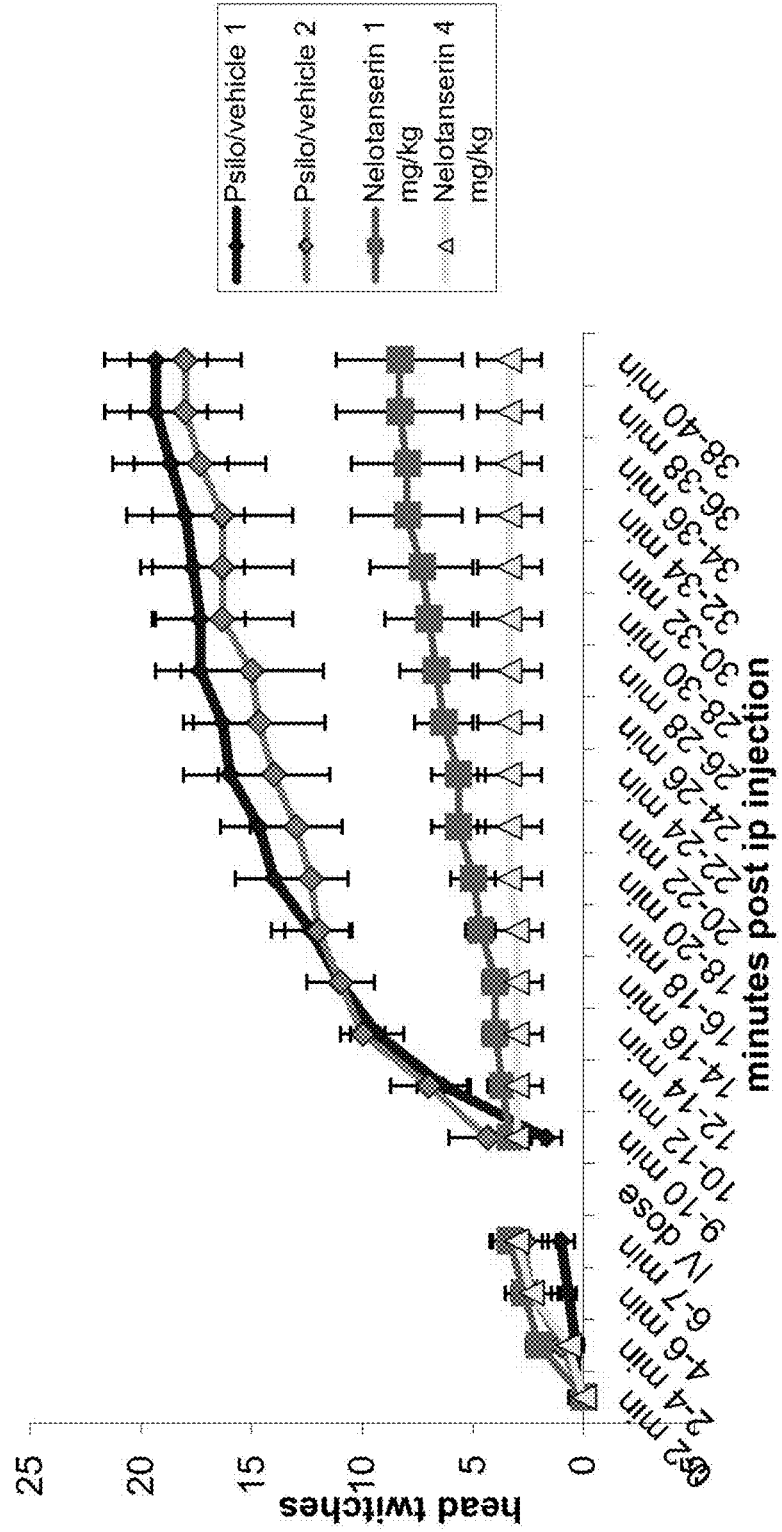
FIG. 80A illustrates effects of nelotanserin administered after T=7 minutes on average cumulative psilocybin induced head twitches in mice.
Figure 80B:
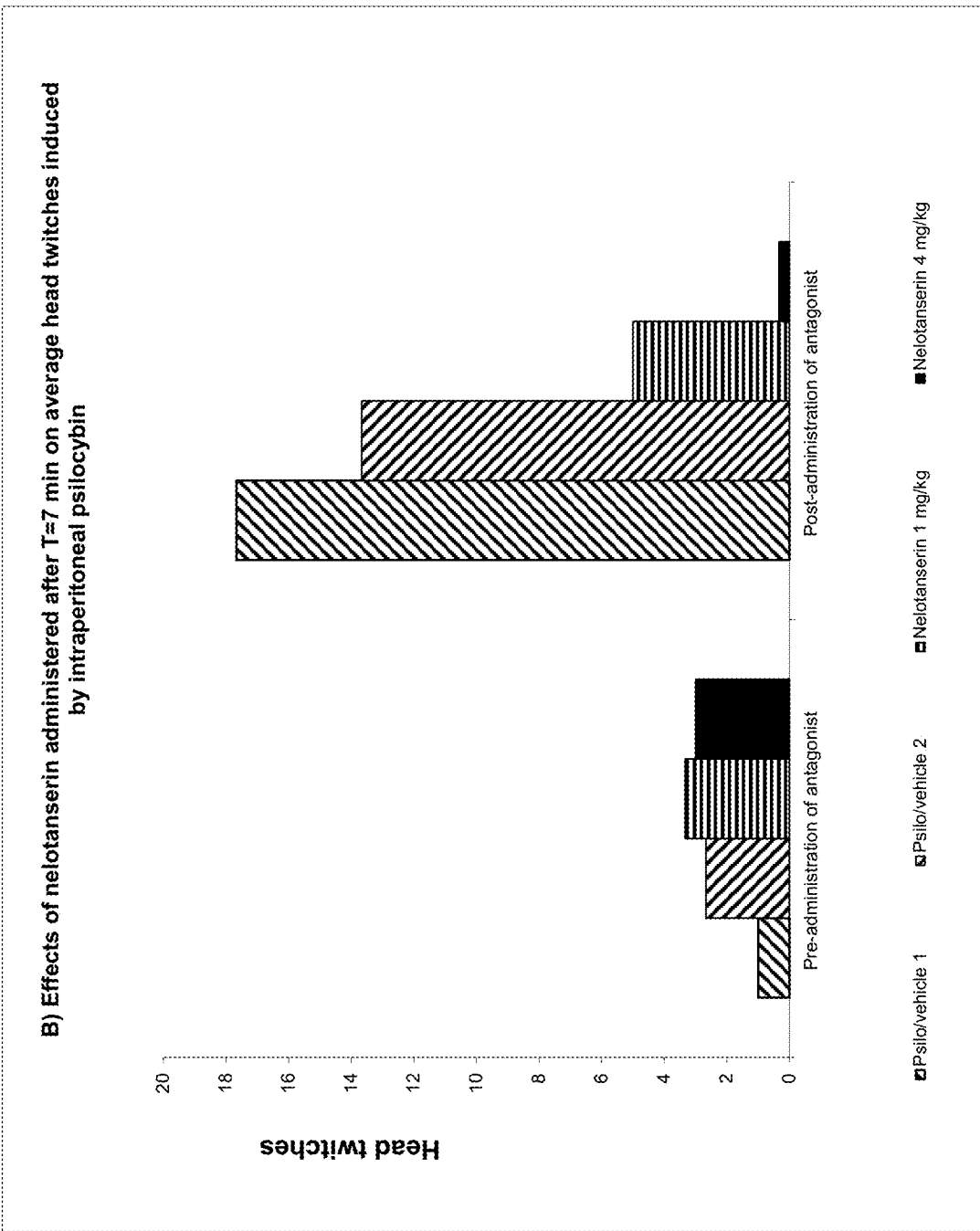
FIG. 80B illustrates effects of nelotanserin administered after T=7 minutes on average psilocybin induced head twitches in mice.

The results from Example 11 and Example 17 were analyzed in combination and graphed to illustrate the effects of nelotanserin dosage on cumulative head twitches induced by intraperitoneal psilocybin administration from the two protocols. Mice were dosed intraperitoneally with psilocybin (2 mg/kg) and head-twitch responses were continuously scored for 7 minutes. After 7 minutes, mice were intravenously dosed with either vehicle 1 (DMSO:HPCD [10:90]) or nelotanserin (1 mg/kg) in Example 11, or with either vehicle 2 (DMSO:Kolliphor:HPCD (20% in water)=10:10: 80) or nelotanserin (4 mg/kg) in Example 17. Cumulative head-twitch behavior was measured every 2 minutes until 40 minutes after agonist dosing. As shown in FIG. 80, administration of nelotanserin at 1 mg/kg partially suppressed the head-twitch response, and administration of nelotanserin at 4 mg/kg completed suppressed the response. This indicated a dose-responsive effect of nelotanserin in suppression of psilocybin-induced head twitches. FIG. 80A shows a graph, FIG. 80B shows a bar chart showing head twitches occurring before and after control or antagonist administration. Test condition groups of Example 21 are summarized in the following table.

| Synopsis of mouse twitch test pilot schedule | | | | | |
|---|---|---|---|---|---|
| Group (n) | 60 min pre-test Place in test cage to habituate | T = −3 min Place in heated cage | T = 0 pretest Treatment i.p. (5 mL/kg saline) | T = 7 min Treatment i.v. (5 mL/kg) and replace in test cage | T = 0-40 min Assess no of head shakes 40 min per mouse |
| 3 | Yes | Yes | Psilocybin 2 mg/kg | Vehicle 1 (DMSO: Kolliphor:HPCD) | Yes |
| 3 | yes | yes | Psilocybin 2 mg/kg | Nelotanserin 4 mg/kg | Yes |

Results of Examples 13-21

Table 33 is a list of all combinations tested of various 5HT-2A receptor antagonists with psilocybin-treated animals and a summary description of the results from the examples (Examples 13-21) above.

TABLE 33

| Psilocybin Combinations tested | | |
|---|---|---|
| Psychedelic | 5HT2A antagonist | Result |
| Psilocybin | Volinanserin | Full suppression of head twitch |
| Psilocybin | Eplivanserin | Full suppression of head twitch |
| Psilocybin | Pimavanserin | Full suppression of head twitch |
| Psilocybin | Pruvanserin | Full suppression of head twitch |
| Psilocybin | Nelotanserin | Partial suppression of head twitch, full suppression at high dose |
| Psilocybin | Ritanserin | Full suppression of head twitch |
| Psilocybin | Risperidone | Full suppression of head twitch |
| Psilocybin | Olanzapine | Full suppression of head twitch |
| Psilocybin | Quetiapine | Full suppression of head twitch |
| Psilocybin | AC-279 (N-Desmethyl Pimavanserin) | No suppression of head twitch |
| Psilocybin | Flibanserin | Partial suppression of head twitch |

Described in Table 34 are ranges of dosing of various 5HT-2A receptor antagonists in order to achieve a rapid ending of the hallucinogenic effects of a psychedelic trip.

TABLE 34

| Dosing for psychedelic trip ending | |
|---|---|
| Antagonist | Dose administered as a monotherapy in an oral or I.V. or intranasal dosage form to end or reduce the intensity of a psychedelic trip |
| Volinanserin | 1 mg to about 60 mg, or about 5 mg to about 20 mg |
| Pimavanserin | 1 mg to about 60 mg, or about 17 mg to about 34 mg |
| Ketanserin | about 10 mg to about 80 mg, about 30 mg to about 50 mg, or about 40 mg |
| Pruvanserin | 1 mg to about 40 mg, or about 3 mg to about 10 mg |
| Nelotanserin | 1 mg to about 80 mg, or about 40 mg to about 80 mg |
| Ritanserin | 1 mg to about 40 mg, or about 2.5 mg to about 10 mg |

TABLE 34-continued

Dosing for psychedelic trip ending

| Antagonist | Dose administered as a monotherapy in an oral or I.V. or intranasal dosage form to end or reduce the intensity of a psychedelic trip |
|---|---|
| Eplivanserin | 1 mg to about 40 mg, or about 5 mg to about 10 mg |
| Flibanserin | 10 mg to about 200 mg, or about 80 mg to about 120 mg, or about 100 mg |
| Risperidone | 0.5 mg to about 20 mg or about .5 mg, or about 1 mg, or about 2 mg, or about 3 mg or about 4 mg or about 5 mg or about 7.5 mg or about 10 mg or about 16 mg |
| Olanzapine | about 2.5 mg to about 30 mg, or about 5 mg or about 7.5 mg or about 10 mg, or about 15 mg or about 20 mg or about 25 mg |
| Quetiapine | about 25 mg to about 800 mg, or about 50 mg to about 100 mg, or about 150 mg or about 200 mg or about 250 mg or about 300 mg |
| extended-release of olanzapine (e.g., ZYPREXA RELPREVV ®) | 50 mg to about 450 mg, or about 150 mg or about 210 mg, or about 300 mg or about 405 mg |
| extended-release of quetiapine | 50 mg to about 300 mg, or about 50 mg or about 100 mg or about 200 mg, or about 300 mg |
| extended-release of risperidone (e.g., RISPERDAL CONSTA ®) | 12.5 mg, or about 25 mg, or about 37.5 mg, or about 50 mg |

Discussion of Results

As shown in the examples above and in Table 33, the selective 5HT2A antagonists volinanserin, eplivanserin, pimavanserin, and pruvanserin, and selective 5HT2A/5HT2C antagonist ritanserin resulted in full ending of psilocybin-induced head twitch compared to in vehicle-treated mice. Selective 5HT2A antagonists nelotanserin and flibanserin resulted in partial suppression of psilocybin's psychedelic effects when administered after psilocybin, indicating that nelotanserin and flibanserin reduced psilocybin-induced psychedelic effects. The active metabolite of pimavanserin, i.e., AC-279 (N-desmethyl Pimavanserin) did not have significant effects in reducing psilocybin-induced psychedelic effects. The atypical antipsychotics risperidone, olanzapine, and quetiapine resulted in full suppression of psilocybin induced head twitch. These results showed that the 5HT2A antagonists in Table 33, when administered after psilocybin could end or reduce the intensity of hallucinations induced by psilocybin.

The antagonists in Table 33 could be administered after Psilocybin, or to tailor the duration or intensity of psychedelic trips. Some of the benefits of administering the antagonists in Table 33 include tailoring psychedelic trips to durations that are suitable for psychedelic-assisted psychotherapy, ending bad trips, reducing the intensity of bad trips, treating psychosis induced by psychedelics, and treating overdose of psychedelics. The optimal duration of psychedelic assisted psychotherapy for a patient could be determined by a person of skilled in the art (e.g., a physician) to control the duration of the psychedelic effects to the optimal duration for each individual patient. This allows healthcare providers to tailor psychedelic trips for individual patients to minimize bad trips. By administering the antagonists in Table 33, each patient may receive a different and unique duration of therapy and a unique intensity of therapy that has been determined to be optimal for that patient. This allows personalized psychedelic assisted psychotherapy. Administration of the antagonists in Table 33 allows a new degree of control over the psychedelic experience by controlling both the duration and intensity of the psychedelic experience including controlling, visual hallucinations, auditory hallucinations, sensory hallucinations, depersonalization, delusions, ego loss, elation, feelings of being in other worlds, changes in the perception of time, altered perception of space, changes in the perception of bodily sensations, oceanic boundlessness, connections to higher powers, perception of inner peace, perception of love, altered perception of boundaries between self and surroundings, altered sense of memory, sensations of awe, and sensations of fear, Anxious ego dissolution, Visionary restructuralization, Vigilance reduction, Auditory alterations.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

Embodiments of the Invention

Embodiment 1. A solid form of psilocybin·HCl having at least one improved property compared to amorphous psilocybin·HCl. Embodiment 2. A solid form of psilocybin·HCl made by the method described in Example 1. Embodiment 3. The solid form of embodiment 2, having the XRPD diffractogram according to FIG. 2. Embodiment 4. The solid form of psilocybin·HCl according to embodiment 2 having at least one improved property compared to amorphous psilocybin·HCl and previously known crystalline forms ofpsilocybin·HCl. Embodiment 5. The solid form of psilocybin·HCl according to embodiment 1 or embodiment 4, wherein the at least one improved property comprises a physical property, chemical property, pharmacokinetic property, or a combination thereof. Embodiment 6. The solid form of psilocybin·HCl of embodiment 1 or embodiment 4, wherein the at least one improved property comprises melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof. Embodiment 7. The solid form of psilocybin·HCl according to any one of embodiments 1-6, wherein the solid form of psilocybin·HCl is a solvate. Embodiment 8. The solid form of psilocybin·HCl according to any one of embodiments 1, 2 or 4-7, wherein the solid form of psilocybin·HCl comprises a form having an XRPD diffractogram substantially according to FIG. 2.

Embodiment 9. A pharmaceutical composition, comprising a solid form of psilocybin·HCl according to any one of embodiments 1-8, and a pharmaceutically acceptable excipient.

Embodiment 10. A method, comprising administering to a subject an effective amount of a solid form of psilocybin·HCl according to any one of embodiments 1-8, or a pharmaceutical composition according to embodiment 9. Embodiment 11. The method of embodiment 10, wherein the subject has a neurological disorder, a psychiatric disorder, or both. Embodiment 12. The method of embodiment 11, wherein the neurological disorder is a neurodegenerative disorder. Embodiment 13. The method of embodiment 11, wherein the neurological disorder, psychiatric disorder, or both, comprises depression, addiction, anxiety, or a post-traumatic stress disorder. Embodiment 14. The method of embodiment 11, wherein the neurological disorder, psychiatric disorder, or both, comprises treatment resistant depression, suicidal ideation, major depressive disorder, bipolar disorder, schizophrenia, or substance use disorder. Embodiment 15. The method of embodiment 11, wherein the neurological disorder, psychiatric disorder, or both, comprises stroke, traumatic brain injury, or a combination thereof. Embodiment 16. The method of any one of embodiments 10-15, wherein administering comprises oral, parenteral, or topical administration. Embodiment 17. The method of any one of embodiments 10-15, wherein administering comprises oral administration. Embodiment 18. The method of any one of embodiments 10-15, wherein administering comprises administering by injection, inhalation, intraocular, intravaginal, intrarectal or transdermal routes. Embodiment 19. The method of any one of embodiments 10-18, wherein the psilocybin·HCl is administered, on a psilocybin basis, in a range about 10 milligram (mg) to 50 mg. Embodiment 20. The method of embodiment 19, wherein the psilocybin·HCl is administered, on a psilocybin basis, in a range of about 25 mg to about 30 mg.

Embodiment 21. A solid form of O-acetylpsilocin wherein the solid form is not O-acetylpsilocin fumarate. Embodiment 22. The solid form of embodiment 21, wherein the compound is a salt. Embodiment 23. The solid form of embodiment 22, wherein the salt is formed from an acid selected from galactaric (mucic) acid, naphthalene-1,5-disulfonic acid, citric acid, sulfuric acid, d-glucuronic acid, ethane-1,2-disulfonic acid, lactobionic acid, p-toluenesulfonic acid, D-glucoheptonic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, 2-hydroxyethanesulfonic acid (isethionic acid), glutaric acid, L-aspartic acid, cinnamic acid, maleic acid, adipic acid, phosphoric acid, sebacic acid, ethanesulfonic acid, (+)-camphoric acid, glutamic acid, acetic acid, hydrochloric acid, or a combination thereof. Embodiment 24. The solid form of embodiment 23, wherein the stoichiometric ratio of acid to O-acetylpsilocin is from about 0.4 molar equivalent to about 2.2 molar equivalents of the acid. Embodiment 25. The solid form of embodiment 23, wherein the stoichiometric ratio of acid to O-acetylpsilocin is from about 0.5 molar equivalent to about 2 molar equivalents of the acid. Embodiment 26. The solid form of embodiment 23, wherein the stoichiometric ratio of acid to O-acetylpsilocin is selected from about 0.5, 1 and 2 molar equivalents of the acid. Embodiment 27. The solid form of embodiment 21, wherein the solid form is a free base form of O-acetylpsilocin. Embodiment 28. The solid form of any one of embodiments 21-27, wherein the solid form is a crystalline solid. Embodiment 29. The solid form of embodiment 28, wherein the crystalline solid is a substantially single polymorph. Embodiment 30. The solid form of embodiment 29, wherein the polymorph is selected to have one or more desired properties. Embodiment 31. The solid form of embodiment 27, wherein the one or more desired properties are selected from physical properties, chemical properties, pharmacokinetic properties, or a combination thereof. Embodiment 32. The solid form of any of embodiments 21-27, wherein the solid form is a hydrate. Embodiment 33. The solid form of embodiment 30 or embodiment 31, wherein the one or more desired properties comprise melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

Embodiment 34. A pharmaceutical composition, comprising a solid form of a compound according to any one of embodiments 21-33, and a pharmaceutically acceptable excipient.

Embodiment 35. A method, comprising administering to a subject an effective amount of a solid form of a compound according to any one of embodiments 21-33, or a pharmaceutical composition according to embodiment 34. Embodiment 36. The method of embodiment 35, wherein the subject has a neurological disease or a psychiatric disorder, or both. Embodiment 37. The method of embodiment 36, wherein the neurological disorder is a neurodegenerative disorder. Embodiment 38. The method of embodiment 36, wherein the neurological disorder or psychiatric disorder, or both, comprises depression, addiction, anxiety, or a post-traumatic stress disorder. Embodiment 39. The method of embodiment 36, wherein the neurological disorder or psychiatric disorder, or both, comprises treatment resistant depression, suicidal ideation, major depressive disorder, bipolar disorder, schizophrenia, or substance use disorder. Embodiment 40. The method of embodiment 36, wherein the neurological disorder or psychiatric disorder, or both, comprises stroke, traumatic brain injury, or a combination thereof. Embodiment 41. The method of any one of embodiments 35-40, wherein administering comprises oral, parenteral, or topical administration. Embodiment 42. The method of any one of embodiments 35-40, wherein administering comprises oral administration. Embodiment 43. The method of embodiment 41, wherein administering comprises administering by injection, inhalation, intraocular, intravaginal, intrarectal or transdermal routes. Embodiment 44. The method of embodiment 36, further comprising administering to the subject an effective amount of an empathogenic agent. Embodiment 45. The method of embodiment 44, wherein the empathogenic agent is MDMA. Embodiment 46. The method of embodiment 36, further comprising administering a 5-HT2A antagonist to the subject. Embodiment 47. The method of embodiment 46, wherein the 5-HT2A antagonist is selected from MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, nelotanserin and lorcaserin.

Embodiment 48. A salt form of O-acetylpsilocin, wherein the salt form does not comprise O-acetylpsilocin fumarate. Embodiment 49. The salt form of embodiment 48, wherein the salt is an acid addition salt. Embodiment 50. The salt form of embodiment 49, wherein the acid is an inorganic acid. Embodiment 51. The salt form of embodiment 49, wherein the acid is an organic acid. Embodiment 52. The salt form of embodiment 48, wherein the salt form comprises a counterion selected from the group consisting of L-aspartate, benzene sulfonate, citrate, ethane sulfonate, gentisate, D-gluconate, L-glutamate, glycolate, chloride, xinafoate, lactate, malate, maleate, malonate, mesylate, mucate, phosphate, succinate, sulfate, tartrate, p-toluenesulfonate, and combinations thereof. Embodiment 53. The salt form of embodiment 48, wherein the salt form comprises a counterion selected from the group consisting of glycolate, chloride, malate, maleate, malonate, mesylate, mucate, phosphate, succinate, tartrate, p-toluenesulfonate, and combinations thereof. Embodiment 54. A pharmaceutical composition comprising a salt form of O-acetylpsilocin according to any one of embodiments 48-53.

Embodiment 55. A method, comprising administering to a subject an effective amount of a solid form of a compound according to any one of embodiments 48-53, or a pharmaceutical composition according to embodiment 54. Embodiment 56. The method of embodiment 55, wherein the subject has a neurological disorder, a psychiatric disorder, or both. Embodiment 57. The method of any one of embodiments 35-47 and 55-56, wherein the O-acetylpsilocin salt is administered, on an O-acetylpsilocin basis, in a range about 1 milligram (mg) to 50 mg. Embodiment 58. The method of embodiment 57, wherein the O-acetylpsilocin salt is administered, on an O-acetylpsilocin basis, in a range of about 20 mg to about 40 mg.

Embodiment 59. A solid form of psilocybin wherein the solid form is not psilocybin HCl. Embodiment 60. The solid form of embodiment 59, wherein the compound is a salt. Embodiment 61. The solid form of embodiment 60, wherein the salt is formed from an acid selected from galactaric (mucic) acid, naphthalene-1,5-disulfonic acid, citric acid, sulfuric acid, d-glucuronic acid, ethane-1,2-disulfonic acid, lactobionic acid, p-toluenesulfonic acid, D-glucoheptonic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, ethanesulfonic acid 2-hydroxy, glutaric acid, L-aspartic acid, cinnamic acid, maleic acid, adipic acid, phosphoric acid, sebacic acid, ethanesulfonic acid, (+)-camphoric acid, glutamic acid, acetic acid, or a combination thereof. Embodiment 62. The solid form of embodiment 60, wherein the salt is an ethane-1,2-disulfonic acid salt. Embodiment 63. The solid form of embodiment 61 or embodiment 62, wherein the stoichiometric ratio of acid to psilocybin is from about 0.4 molar equivalent to about 2.2 molar equivalents of the acid. Embodiment 64. The solid form of embodiment 61 or embodiment 62, wherein the stoichiometric ratio of acid to psilocybin is from about 0.5 molar equivalent to about 2 molar equivalents of the acid. Embodiment 65. The solid from of embodiment 61 or embodiment 62, wherein the stoichiometric ratio of acid to psilocybin is selected from about 0.5, 1 and 2 molar equivalents of the acid. Embodiment 66. The solid form of embodiment 59, wherein the solid form is a free base form of psilocybin. Embodiment 67. The solid form of embodiment 66, wherein the solid form is Form C. Embodiment 68. The solid form of embodiment 66, wherein the solid form has an XRPD spectrum and/or NMR spectrum corresponding to Form C in FIG. 24 and FIG. 25, respectively. Embodiment 69. The solid form of any of embodiments 59-68, wherein the solid form is a hydrate. Embodiment 70. The solid form of any one of embodiments 59-69, wherein the solid form is a crystalline solid. Embodiment 71. The solid form of embodiment 70, wherein the crystalline solid is a substantially single polymorph. Embodiment 72. The solid form of embodiment 71, wherein the polymorph is selected to have one or more desired properties. Embodiment 73. The solid form of embodiment 72, wherein the one or more desired properties are selected from physical properties, chemical properties, pharmacokinetic properties, or a combination thereof. Embodiment 74. The solid form of embodiment 72 or embodiment 73, wherein the one or more desired properties comprise melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof. Embodiment 75. A pharmaceutical composition, comprising a solid form of a compound according to any one of embodiments 59-74, and a pharmaceutically acceptable excipient.

Embodiment 76. A method, comprising administering to a subject an effective amount of a solid form of a compound according to any one of embodiments 59-74, or a pharmaceutical composition according to embodiment 75. Embodiment 77. The method of embodiment 76, wherein the subject has a neurological disease or a psychiatric disorder, or both. Embodiment 78. The method of embodiment 77, wherein the neurological disorder is a neurodegenerative disorder. Embodiment 79. The method of embodiment 77, wherein the neurological disorder or psychiatric disorder, or both, comprises depression, addiction, anxiety, or a post-traumatic stress disorder. Embodiment 80. The method of embodiment 77, wherein the neurological disorder or psychiatric disorder, or both, comprises treatment resistant depression, suicidal ideation, major depressive disorder, bipolar disorder, schizophrenia, or substance use disorder. Embodiment 81. The method of embodiment 77, wherein the neurological disorder or psychiatric disorder, or both, comprises stroke, traumatic brain injury, or a combination thereof. Embodiment 82. The method of any one of embodiments 76-81, wherein administering comprises oral, parenteral, or topical administration. Embodiment 83. The method of any one of embodiments 76-81, wherein administering comprises oral administration. Embodiment 84. The method of embodiment 82, wherein administering comprises administering by injection, inhalation, intraocular, intravaginal, intrarectal or transdermal routes.

Embodiment 85. A salt form of psilocybin wherein the salt form is not psilocybin HCl. Embodiment 86. The salt form of embodiment 85, wherein the salt form comprises psilocybin edisylate. Embodiment 87. The salt form of embodiment 85, wherein the salt form comprises psilocybin mesylate. Embodiment 88. The salt form of embodiment 86, wherein the salt form is crystalline. Embodiment 89. The salt form of embodiment 87, wherein the salt form is crystalline. Embodiment 90. A method, comprising administering to a subject an effective amount of a salt form of any one of embodiments 85-89. Embodiment 91. The method of embodiment 90, wherein the subject has a neurological disease, a psychiatric disorder, or both. Embodiment 92. The method of any one of embodiments 76-84, wherein the solid form of psilocybin is administered, on a psilocybin basis, in a range about 10 milligram (mg) to 50 mg. Embodiment 93. The method of embodiment 92, wherein the solid form of psilocybin is administered, on a psilocybin basis, in a range of about 25 mg to about 30 mg. Embodiment 94. The method of any one of embodiments 90-91, wherein the salt form of psilocybin is administered, on a psilocybin basis, in a range about 10 milligram (mg) to 50 mg. Embodiment 95. The method of embodiment 94, wherein the salt form of psilocybin is administered, on a psilocybin basis, in a range of about 25 mg to about 30 mg.

Embodiment 96. A solid form of O-acetylpsilocin fumarate having at least one improved property. Embodiment 97. A solid form of O-acetylpsilocin fumarate made by the method described in Example 12. Embodiment 98. The solid form of O-acetylpsilocin fumarate according to embodiment 97 having at least one improved property compared to amorphous O-acetylpsilocin fumarate. Embodiment 99. The solid form of O-acetylpsilocin fumarate according to any one of embodiments 96-98, wherein the at least one improved property comprises a physical property, chemical property, pharmacokinetic property, or a combination thereof. Embodiment 100. The solid form of O-acetylpsilocin fumarate of any one of embodiments 96-99, wherein the at least one improved property comprise melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof. Embodiment 101. The solid form of O-acetylpsilocin fumarate according to any one of embodiments 96-100, wherein the solid form of O-acetylpsilocin fumarate is a hydrate.

Embodiment 102. A pharmaceutical composition, comprising a solid form of O-acetylpsilocin fumarate according to any one of embodiments 96-101, and a pharmaceutically acceptable excipient.

Embodiment 103. A method, comprising administering to a subject an effective amount of a solid form of O-acetylpsilocin fumarate according to any one of embodiments 96-101, or a pharmaceutical composition according to embodiment 102. Embodiment 104. The method of embodiment 103, wherein the subject has a neurological disease or a psychiatric disorder, or both. Embodiment 105. The method of embodiment 104, wherein the neurological disorder is a neurodegenerative disorder. Embodiment 106. The method of embodiment 104, wherein the neurological disorder or psychiatric disorder, or both, comprises depression, addiction, anxiety, or a post-traumatic stress disorder. Embodiment 107. The method of embodiment 104, wherein the neurological disorder or psychiatric disorder, or both, comprises treatment resistant depression, suicidal ideation, major depressive disorder, bipolar disorder, schizophrenia, or substance use disorder. Embodiment 108. The method of embodiment 104, wherein the neurological disorder or psychiatric disorder, or both, comprises stroke, traumatic brain injury, or a combination thereof. Embodiment 109. The method of any one of embodiments 103-108, wherein administering comprises oral, parenteral, or topical administration. Embodiment 110. The method of any one of embodiments 103-108, wherein administering comprises oral administration. Embodiment 111. The method of embodiment 109, wherein administering comprises administering by injection, inhalation, intraocular, intravaginal, intrarectal or transdermal routes. Embodiment 112. The method of embodiment 104, further comprising administering to the subject an effective amount of an empathogenic agent. Embodiment 113. The method of embodiment 112, wherein the empathogenic agent is MDMA. Embodiment 114. The method of embodiment 104, further comprising administering a 5-HT2A antagonist to the subject. Embodiment 115. The method of embodiment 114, wherein the 5-HT2A antagonist is selected from MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, nelotanserin and lorcaserin.

Embodiment 116. The solid form of O-acetylpsilocin fumarate of any one of embodiments 96-99, comprising O-acetylpsilocin fumarate of Form A. Embodiment 117. The solid form of O-acetylpsilocin fumarate of any one of embodiments 96-99, comprising O-acetylpsilocin fumarate of Form B. Embodiment 118. The method of any one of embodiments 103-115, wherein the O-acetylpsilocin fumarate is administered, on an O-acetylpsilocin basis, in a range about 1 milligrams (mg) to 50 mg. Embodiment 119. The method of embodiment 118, wherein the O-acetylpsilocin fumarate is administered, on an O-acetylpsilocin basis, in a range of about 20 mg to about 40 mg.

What is claimed is:

1. A crystalline form of psilocybin edisylate (Form A) that is characterized as having:
   an X-ray powder diffraction (XRPD) diffractogram with characteristic peaks at 7.0±0.2° 2-Theta, 9.1±0.2° 2-Theta, 11.6±0.2° 2-Theta, 13.1±0.2° 2-Theta and 13.4±0.2° 2-Theta, as measured with Cu Kα radiation, or
   an XRPD diffractogram with characteristic peaks at 9.0±0.2° 2-Theta, 11.6±0.2° 2-Theta, 13.0±0.2° 2-Theta, 16.4±0.2° 2-Theta and 18.5±0.2° 2-Theta, as measured with Cu Kα radiation.

2. A crystalline form of psilocybin edisylate (Form A) that is characterized as having:
   an X-ray powder diffraction (XRPD) diffractogram with characteristic peaks at 7.0±0.2° 2-Theta, 9.1±0.2° 2-Theta, 11.6±0.2° 2-Theta, 13.1±0.2° 2-Theta and 13.4±0.2° 2-Theta, as measured with Cu Kα radiation.

3. A crystalline form of psilocybin edisylate (Form A) that is characterized as having:
   an XRPD diffractogram with characteristic peaks at 9.0±0.2° 2-Theta, 11.6±0.2° 2-Theta, 13.0±0.2° 2-Theta, 16.4±0.2° 2-Theta and 18.5±0.2° 2-Theta, as measured with Cu Kα radiation.

4. A pharmaceutical composition, comprising the crystalline form of psilocybin edisylate according to claim 1, and a pharmaceutically acceptable excipient.

5. A pharmaceutical composition, comprising the crystalline form of psilocybin edisylate according to claim 2, and a pharmaceutically acceptable excipient.

6. A pharmaceutical composition, comprising the crystalline form of psilocybin edisylate according to claim 3, and a pharmaceutically acceptable excipient.

7. A method of treating a neurological disorder, a psychiatric disorder, or both in a human subject comprising administering to the human subject in need thereof an amount of the crystalline form of psilocybin edisylate according to claim 1 that is equivalent to about 10 mg to about 50 mg of psilocybin, wherein the neurological disorder, psychiatric disorder, or both comprises depression, addiction, substance use disorder, anxiety, post-traumatic stress disorder, suicidal ideation, bipolar disorder, schizophrenia, stroke, traumatic brain injury, or a combination thereof.

8. The method of claim 7, wherein the neurological disorder, psychiatric disorder, or both comprises treatment resistant depression.

9. The method of claim 7, wherein the neurological disorder, psychiatric disorder, or both comprises major depressive disorder.

10. The method of claim 7, wherein the method comprises orally administering about 10 mg, about 15 mg, about 20 mg, about 25 mg, about 30 mg, about 35 mg, about 40 mg, about 45 mg, or about 50 mg of the crystalline form of psilocybin edisylate according to claim 1 to the human subject in need thereof.

11. A method of treating a neurological disorder, a psychiatric disorder, or both in a human subject comprising administering to the human subject in need thereof an amount of the crystalline form of psilocybin edisylate according to claim 2 that is equivalent to about 10 mg to about 50 mg of psilocybin, wherein the neurological disorder, psychiatric disorder, or both comprises depression, addiction, substance use disorder, anxiety, post-traumatic stress disorder, suicidal ideation, bipolar disorder, schizophrenia, stroke, traumatic brain injury, or a combination thereof.

12. The method of claim 11, wherein the neurological disorder, psychiatric disorder, or both comprises treatment resistant depression.

13. The method of claim 11, wherein the neurological disorder, psychiatric disorder, or both comprises major depressive disorder.

14. The method of claim 11, wherein the method comprises orally administering to the human subject in need thereof an amount of the crystalline form of psilocybin edisylate according to claim 5 that is equivalent to about 10 mg, about 15 mg, about 20 mg, about 25 mg, about 30 mg, about 35 mg, about 40 mg, about 45 mg, or about 50 mg of psilocybin.

15. A method of treating a neurological disorder, a psychiatric disorder, or both in a human subject comprising administering to the human subject in need thereof an amount of the crystalline form of psilocybin edisylate according to claim 3 that is equivalent to about 10 mg to about 50 mg of psilocybin, wherein the neurological disorder, psychiatric disorder, or both comprises depression, addiction, substance use disorder, anxiety, post-traumatic stress disorder, suicidal ideation, bipolar disorder, schizophrenia, stroke, traumatic brain injury, or a combination thereof.

16. The method of claim 15, wherein the neurological disorder, psychiatric disorder, or both comprises treatment resistant depression.

17. The method of claim 15, wherein the neurological disorder, psychiatric disorder, or both comprises major depressive disorder.

18. The method of claim 15, wherein the method comprises orally administering to the human subject in need thereof an amount of the crystalline form of psilocybin edisylate according to claim 5 that is equivalent to about 10 mg, about 15 mg, about 20 mg, about 25 mg, about 30 mg, about 35 mg, about 40 mg, about 45 mg, or about 50 mg of psilocybin.

\* \* \* \* \*